US010774327B2

(12) United States Patent
Khvorova et al.

(10) Patent No.: US 10,774,327 B2
(45) Date of Patent: Sep. 15, 2020

(54) OLIGONUCLEOTIDE COMPOUNDS FOR TARGETING HUNTINGTIN MRNA

(71) Applicant: UNIVERSITY OF MASSACHUSETTS, Boston, MA (US)

(72) Inventors: Anastasia Khvorova, Westborough, MA (US); Neil Aronin, Newtonville, MA (US); Julia Alterman, Worcester, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 0 days.

(21) Appl. No.: 16/263,200

(22) Filed: Jan. 31, 2019

(65) Prior Publication Data

US 2019/0225965 A1  Jul. 25, 2019

Related U.S. Application Data

(63) Continuation of application No. 15/697,120, filed on Sep. 6, 2017, which is a continuation of application No. 15/089,319, filed on Apr. 1, 2016, now Pat. No. 9,809,817.

(60) Provisional application No. 62/289,274, filed on Jan. 31, 2016, provisional application No. 62/142,731, filed on Apr. 3, 2015.

(51) Int. Cl.
  *C12N 15/113* (2010.01)
  *A61K 31/713* (2006.01)
  *A61K 9/00* (2006.01)

(52) U.S. Cl.
  CPC .......... *C12N 15/113* (2013.01); *A61K 9/0085* (2013.01); *A61K 31/713* (2013.01); *C12N 2310/14* (2013.01); *C12N 2310/315* (2013.01); *C12N 2310/343* (2013.01); *C12N 2310/344* (2013.01); *C12N 2310/346* (2013.01); *C12N 2310/3515* (2013.01); *C12N 2310/3517* (2013.01); *C12N 2310/3519* (2013.01); *C12N 2310/52* (2013.01); *C12N 2320/11* (2013.01); *C12N 2320/30* (2013.01); *C12N 2320/32* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,328,470 A | 7/1994 | Nabel et al. | |
| 5,684,143 A | 11/1997 | Gryaznov et al. | |
| 5,814,014 A | 9/1998 | Elsberry et al. | |
| 5,858,988 A | 1/1999 | Wang | |
| 6,093,180 A | 7/2000 | Elsberry | |
| 6,107,094 A | 8/2000 | Crooke | |
| 6,168,587 B1 | 1/2001 | Bellhouse et al. | |
| 6,177,403 B1 | 1/2001 | Stedman | |
| 6,194,389 B1 | 2/2001 | Johnston et al. | |
| 6,291,438 B1 | 9/2001 | Wang | |
| 6,471,996 B1 | 10/2002 | Sokoll et al. | |
| 6,472,375 B1 | 10/2002 | Hoon et al. | |
| 7,250,496 B2 | 7/2007 | Bentwich | |
| 7,459,547 B2 | 12/2008 | Zamore et al. | |
| 7,691,997 B2* | 4/2010 | Khvorova ............ A61K 31/713 536/24.5 |
| 7,732,593 B2 | 6/2010 | Zamore et al. | |
| 7,750,144 B2 | 7/2010 | Zamore et al. | |
| 7,772,203 B2 | 8/2010 | Zamore et al. | |
| 8,304,530 B2 | 11/2012 | Zamore et al. | |
| 8,309,704 B2 | 11/2012 | Zamore et al. | |
| 8,309,705 B2 | 11/2012 | Zamore et al. | |
| 8,329,892 B2 | 12/2012 | Zamore et al. | |
| 8,431,544 B1 | 4/2013 | Agrawal et al. | |
| 9,809,817 B2 | 11/2017 | Khvorova et al. | |
| 9,862,952 B2 | 1/2018 | Khvorova et al. | |
| 2003/0143732 A1 | 7/2003 | Fosnaugh et al. | |
| 2005/0096284 A1 | 5/2005 | McSwiggen et al. | |
| 2005/0220766 A1 | 10/2005 | Amalfitano et al. | |
| 2006/0078542 A1 | 4/2006 | Mah et al. | |
| 2006/0094032 A1 | 5/2006 | Fougerolles et al. | |
| 2007/0099860 A1 | 5/2007 | Sah et al. | |
| 2007/0191273 A1 | 8/2007 | Ambati et al. | |
| 2007/0259827 A1 | 11/2007 | Aronin et al. | |
| 2008/0039415 A1 | 2/2008 | Stewart et al. | |
| 2008/0119427 A1 | 5/2008 | Bhat et al. | |
| 2008/0269149 A1 | 10/2008 | Bowles et al. | |
| 2009/0143322 A1 | 6/2009 | Burkoth et al. | |
| 2010/0186103 A1 | 7/2010 | Gao et al. | |

(Continued)

FOREIGN PATENT DOCUMENTS

CN 101199858 A 6/2008
EP 2853597 A1 4/2015

(Continued)

OTHER PUBLICATIONS

Alexopoulou et al. (2001) "Recognition of double-stranded RNA and activation of NF-κB by Toll-like receptor 3," Nature. 413:732-738.

Allerson et al. (2005) "Fully 2'-Modified Oligonucleotide Duplexes with Improved in Vitro Potency and Stability Compared to Unmodified Small Interfering RNA," J. Med. Chem. 48(4):901-904.

Alterman et al. (Dec. 12, 2015) "Hydrophobically Modified siRNAs Silence Huntingtin mRNA in Primary Neurons and Mouse Brain," Mol. Ther.: Nucleic Acids. 4(12):e266. pp. 1-12.

Altschul et al. (1997) "Gapped BLAST and PSI-BLAST: a new generation of protein database search programs," Nucleic Acids Res. 25(17):3389-3402.

(Continued)

*Primary Examiner* — Tracy Vivlemore
(74) *Attorney, Agent, or Firm* — Lathrop GPM LLP; James H. Velema, Esq.

(57) ABSTRACT

This disclosure relates to novel huntingtin targets. Novel oligonucleotides for the treatment of Huntington's disease are also provided.

20 Claims, 146 Drawing Sheets

Specification includes a Sequence Listing.

(56) References Cited

U.S. PATENT DOCUMENTS

| | | |
|---|---|---|
| 2013/0131141 A1 | 5/2013 | Khvorova et al. |
| 2014/0296486 A1 | 10/2014 | Gao et al. |
| 2015/0209441 A1 | 7/2015 | Carell |
| 2016/0319278 A1 | 11/2016 | Khvorova et al. |
| 2016/0355808 A1 | 12/2016 | Khvorova et al. |
| 2016/0355826 A1 | 12/2016 | Khvorova et al. |
| 2017/0043024 A1 | 2/2017 | Khvorova et al. |
| 2017/0312367 A1 | 11/2017 | Khvorova et al. |
| 2017/0369882 A1 | 12/2017 | Khvorova et al. |

FOREIGN PATENT DOCUMENTS

| | | |
|---|---|---|
| WO | 2003/029459 A2 | 4/2003 |
| WO | 2004/008946 A2 | 1/2004 |
| WO | 2004/044136 A2 | 5/2004 |
| WO | 2006/019430 A2 | 2/2006 |
| WO | WO 2007022470 A2 | 2/2007 |
| WO | WO 2007022506 A2 | 2/2007 |
| WO | 2007/051045 A2 | 5/2007 |
| WO | 2007/094218 A1 | 8/2007 |
| WO | 2007/112414 A2 | 10/2007 |
| WO | 2008/154482 A2 | 12/2008 |
| WO | 2009/054551 A2 | 4/2009 |
| WO | 2009/099991 A2 | 8/2009 |
| WO | 2010/033247 A2 | 3/2010 |
| WO | 2012/005898 A2 | 1/2012 |
| WO | 2012/118911 A1 | 9/2012 |
| WO | 2013/165816 A2 | 11/2013 |
| WO | 2014/076195 A1 | 5/2014 |
| WO | 2015/161184 A1 | 10/2015 |
| WO | 2016/161374 A1 | 10/2016 |
| WO | 2017/015555 A1 | 1/2017 |

OTHER PUBLICATIONS

Ameres et al. (2007) "Molecular basis for target RNA recognition and cleavage by human RISC," Cell. 130:101-112.

Anderson et al. (2008) "Experimental validation of the importance of seed complement frequency to siRNA specificity," RNA. 14:853-861.

Anderson et al. (2008) "Identifying siRNA-induced off-targets by microarray analysis," Ch.4 In; Methods in Molecular Biology. 442:45-63.

Bagella et al. (1998) "Cloning of murine CDK9/PITALRE and its tissue-specific expression in development," J. Cell. Physiol. 177:206-213.

Bartlett (2006) "Insights into the kinetics of siRNA-mediated gene silencing from live-cell and live-animal bioluminescent imaging," Nucleic Acids Research. 34:322-333.

Behlke et al. (2008) "Chemical modification of siRNAs for in vivo use," Oligonucleotides. 18:305-320.

Billy et al. (2001) "Specific interference with gene expression induced by long, double-stranded RNA in mouse embryonal teratocarcinoma cell lines," Proc Natl Acad Sci USA. 98(25)14428-14433.

Birmingham et al. (2006) "3' UTR seed matches, but not overall identity, are associated with RNAi off-targets," Nat. Methods. 3:199-204.

Birmingham et al. (2007) "A protocol for designing siRNAs with high functionality and specificity," Nature Protocols. 2:2068-2078.

Braasch et al. (2003) "RNA Interference in Mammalian Cells by Chemically-Modified RNA," Biochemistry 42:7967-7975.

Brennecke et al. (2003) "Towards a complete description of the microRNA complement of animal genomes," Genome Biol. 4(9):228.

Brummelkamp et al. (2002) "A system for stable expression of short interfering RNAs in mammalian cells," Science. 296:550-553.

Burchard et al. (2009) "MicroRNA-like off-target transcript regulation by siRNAs is species specific," RNA. 15:308-315.

Byrne et al. (Nov. 1, 2013) "Novel hydrophobically modified asymmetric RNAi compounds (sd-rxRNA) demonstrate robust efficacy in the eye," Journal of Ocular Pharmacology and Therapeutics. 29:855-864.

Calegari et al. (2002) "Tissue-specific RNA interference in postimplantation mouse embryos with endoribonuclease-prepared short interfering RNA," Proc. Natl. Acad. Sci. USA. 99(22):14236-14240.

Charrier et al. (May 3, 2012) "Inhibition of SRGAP2 function by its human-specific paralogs induces neoteny during spine maturation," Cell. 149(4):923-935.

Cho et al. (Feb. 13, 2012) "Vascular endothelial growth factor receptor 1 morpholino decreases angiogenesis in a murine corneal suture model," Invest. Opthamol. Visual Sci. 53(2):685-692.

Choe et al. (2005) "Crystal structure of human toll-like receptor 3 (TLR3) ectodomain," Science. 309:581-585.

Coelho et al. (Aug. 29, 2013) "Safety and efficacy of RNAi therapy for transthyretin amyloidosis," The New England Journal of Medicine. 369:819-829.

Deleavey et al. (Jan. 5, 2013) "The 5' binding MID domain of human Argonaute2 tolerates chemically modified nucleotide analogues" Nucleic Acid Therapeutics. 23:81-87.

Difiglia et al. (2007) "Therapeutic silencing of mutant huntingtin with siRNA attenuates striatal and cortical neuropathology and behavioral deficits," Proc. Natl. Acad. Sci. USA. 104(43):17204-17209.

Doench et al. (2003) "siRNAs can function as miRNAs," Genes Dev. 17(4):438-442.

Eckstein (2000) "Phosphorothioate Oligodeoxynucleotides: What Is Their Origin and What Is Unique About Them?" Antisense Nucleic Acid Drug Dev. 10(2):117-121.

Elmen et al. (2005) "Locked nucleic acid (LNA) mediated improvements in siRNA stability and functionality," Nucleic Acids Res. 33(1):439-447.

Fan et al. (Oct. 20, 2014) "Endometrial VEGF induces placental sFLT1 and leads to pregnancy complications," J. Clin. Inves. 124(11):4941-4952.

Federov et al. (2006) "Off-target effects by siRNA can induce toxic phenotype," RNA. 12:1188-1196.

Felber et al. (Sep. 2012) "The interactions of amphiphilic antisense oligonucleotides with serum proteins and their effects on in vitro silencing activity," Biomaterials. 33(25):5955-5965.

Frazier (Nov. 9, 2015) "Antisense Oligonucleotide Therapies: The Promise and the Challenges from a Toxicologic Pathologist's Perspective," Toxicologic Pathology. 43:78-89.

Gaglione et al. (2010) "Recent progress in chemically modified siRNAs," Mini Rev. Med. Chem. 10(7):578-595.

Godard et al. (1995) "Antisense Effects of Cholesterol-Oligodeoxynucleotide Conjugates Associated with Poly(alkylcyanoacrylate) Nanoparticles," Eur. J. Biochem. 232(2):404-410.

Grad et al. (2003) "Computational and experimental identification of C. elegans microRNAs," Mol. Cell. 11(5):1253-1263.

Griffiths-Jones (2004) "The microRNA Registry," Nuc. Acids Res. 32(Database Issue):D109-D111.

Grimm et al. (2006) "Fatality in mice due to oversaturation of cellular microRNA/short hairpin RNA pathways," Nature. 441:537-541.

Herdewijn (2000) "Heterocyclic modifications of oligonucleotides and antisense technology," Antisense Nucleic Acid Drug Dev. 10(4):297-310.

Heydarian et al. (2009) "Novel splice variants of sFlt1 are upregulated in preeclampsia," Placenta. 30:250-255.

Heyer et al. (Dec. 12, 2014) "An optimized kit-free method for making strand-specific deep sequencing libraries from RNA fragments," Nucleic Acids Res. 43(1):e2. pp. 1-14.

Hutvagner et al. (2002) "A microRNA in a multiple-turnover RNAi enzyme complex," Science. 297 (5589):2056-2060.

Jackson et al. (2006) "Position-specific chemical modification of siRNAs reduces 'off-target' transcript silencing," RNA. 12:1197-1205.

Jackson et al. (2010) "Recognizing and avoiding siRNA off-target effects for target identification and therapeutic application," Nature Reviews in Drug Discovery. 9:57-67.

Jacque et al. (2002) "Modulation of HIV-1 replication by RNA interference," Nature. 418:435-438.

(56) References Cited

OTHER PUBLICATIONS

Judge et al. (2006) "Design of Noninflammatory Synthetic siRNA Mediating Potent Gene Silencing in Vivo," Molecular Therapy. 13:494-505.
Karlin et al. (1990) "Methods for assessing the statistical significance of molecular sequence features by using general scoring schemes," Proc. Natl. Acad. Sci. USA. 87:2264-2268.
Karlin et al. (1993) "Applications and statistics for multiple high-scoring segments in molecular sequences," Proc. Natl. Acad. Sci. USA 90:5873-5877.
Kenski et al. (2012) "siRNA-optimized Modifications for Enhanced In Vivo Activity," Mol. Ther. Nucleic Acids. 1:e5. pp. 1-8.
Khvorova et al. (2003) "Functional siRNAs and miRNAs Exhibit Strand Bias," Cell. 115:209-216.
Khvorova et al. (Mar. 15, 2016) "Abstract IA27: Advances in oligonucleotide chemistry for the treatment of neurodegenerative disorders and brain tumors," Cancer Res. 76(6) Abstract No. IA27.
Yu et al. (2002) "RNA interference by expression of short-interfering RNAs and hairpin RNAs in mammalian cells," Proc Natl Acad Sci USA. 99:6047-6052.
Yu et al. (Aug. 31, 2012) "Single-stranded RNAs use RNAi to potently and allele-selectively inhibit mutant huntingtin expression," Cell. 150(5):895-908.
Zeng et al. (2002) "Both natural and designed micro RNAs can inhibit the expression of cognate mRNAs when expressed in human cells," Mol. Cell. 9(6):1327-1333.
Zeng et al. (2003) "Sequence requirements for micro RNA processing and function in human cells," RNA. 9(1):112-123.
International Search Report with Written Opinion corresponding to International Patent Application No. PCT/US2016/025722, dated Aug. 12, 2016.
International Search Report with Written Opinion corresponding to International Patent Application No. PCT/US2016/025731, dated Sep. 9, 2016.
International Search Report with Written Opinion corresponding to International Patent Application No. PCT/US2016/025753, dated Sep. 14, 2016.
International Search Report with Written Opinion corresponding to International Patent Application No. PCT/US2016/046810, dated Nov. 29, 2016.
Raouane et al. (2012) "Lipid Conjugated Oligonucleotides: A Useful Strategy for Delivery," Bioconjugate Chemistry, 23(6):1091-1104.
Nikan et al. (2016) "Docosahexaenoic Acid 1-20 Conjugation Enhances Distribution and Safety of siRNA upon Local Administration in Mouse Brain—Supplementary Figures and Table S1," Molecular Therapy—Nucleic Acids, 5(1):e344.
Extended European Search Report for European Application No. 16837593.9, dated Mar. 20, 2019 (13 pages).
Lagos-Quintana et al. (2001) "Identification of novel genes coding for small expressed RNAs," Science. 294 (5543):853-858.
Lai et al. (2003) "Computational identification of *Drosophila* microRNA genes," Genome Biol. 4(7):R42. pp. 1-20.
Lau et al. (2001) "An abundant class of tiny RNAs with probable regulatory roles in Caenorhabditis elegans," Science. 294(5543):858-862.
Lau et al. (2006) "Characterization of the piRNA complex from rat testes," Science. 313(5785):363-367.
Lee et al. (2001) "An extensive class of small RNAs in Caenorhabditis elegans," Science. 294(5543):862-864.
Lee et al. (2002) "Expression of small interfering RNAs targeted against HIV-1 rev transcripts in human cells," Nat. Biotechnol. 20:500-505.
Lim et al. (2003) "The microRNAs of Caenorhabditis elegans," Genes Dev. 17(8):991-1008.
Lim et al. (2003) "Vertebrate microRNA genes," Science. 299(5612):1540.
Lima et al. (Aug. 31, 2012) "Single-stranded siRNAs activate RNAi in animals," Cell. 150:883-894.
Lorenz et al. (2004) "Steroid and lipid conjugates of siRNAs to enhance cellular uptake and gene silencing in liver cells," Bioorg. Med. Chem. Lett. 14:4975-4977.
Luo et al. (Jun. 18, 2013) "Photoreceptor avascular privilege is shielded by soluble VEGF receptor-1," eLife. 6: e19456. pp. 1-22.
McCaffrey et al. (2002) "RNA interference in adult mice," Nature. 418(6893):38-39.
McManus et al. (2002) "Gene silencing using micro-RNA designed hairpins," RNA. 8:842-850.
Miyagishi et al. (2002) "U6 promoter-driven siRNAs with four uridine 3' overhangs efficiently suppress targeted gene expression in mammalian cells," Nat. Biotechnol. 20:497-500.
Molitoris et al. (2009) "siRNA Targeted to p53 Attenuates Ischemic and Cisplatin-Induced Acute Kidney Injury," Journal of the American Society of Nephrology. 20:1754-1764.
Myers et al. (1988) "Optimal alignments in linear space," Comput. Appl. Biosci. 4(1):11-17.
Nair et al. (Dec. 10, 2014) "Multivalent N-Acetylgalactosamine-Conjugated siRNA Localizes in Hepatocytes and Elicits Robust RNAi-Mediated Gene Silencing," J. Am. Chem. Soc. 136(49):16958-16961.
Nielsen et al. (2001) "Sequence-selective recognition of DNA by strand displacement with a thymine-substituted polyamide," Science. 254:1497-1500.
Nikan et al. (Aug. 9, 2016) "Docosahexaenoic Acid Conjugation Enhances Distribution and Safety of siRNA upon Local Administration in Mouse Brain," Mol. Ther. Nucleic Acids. 5(8):e344. pp. 1-11.
Owen et al. (Mar. 15, 2012) "Morpholino-mediated increase in soluble Flt-1 expression results in decreased ocular and tumor neovascularization," PloS One. 7(3):e33576. pp. 1-9.
Addison et al. (2002) "Short hairpin RNAs (shRNAs) induce sequence-specific silencing in mammalian cells," Gene Dev. 16:948-958.
Pasquinelli et al. (2000) "Conservation of the sequence and temporal expression of let-7 heterochronic regulatory RNA," Nature. 408(6808):86-89.
Paul et al. (2002) "Effective expression of small interfering RNA in human cells," Nature Biotechnol. 20:505-508.
Peel et al. (Feb. 12, 2015) "Conjugation and Evaluation of Small Hydrophobic Molecules to Triazole-Linked siRNAs," ACS Med. Chem. Lett. 6(2):117-122.
Petersen et al. (2003) "LNA: a versatile tool for therapeutics and genomics," Trends Biotechnol 21:74-81.
Putnam (1996) "Antisense strategies and therapeutic applications," Am. J. Health Syst. Pharm. 53(2):151-160.
Reinhart et al. (2002) "Small RNAs correspond to centromere heterochromatic repeats," Science. 297(5588):1831.
Rigo et al. (Apr. 20, 2014) "Pharmacology of a central nervous system delivered 2'-O-methoxyethyl-modified survival of motor neuron splicing oligonucleotide in mice and nonhuman primates," The Journal of Pharmacology and Experimental Therapeutics. 350:46-55.
Rodriguez-Lebron et al. (2005) "Intrastriatal rAAV-mediated delivery of anti-huntingtin shRNAs induces partial reversal of disease progression in R6/1 Huntington's disease transgenic mice," Mol. Ther. 12(4):618-633.
Rusckowski et al. (2000) "Biodistribution and metabolism of a mixed backbone oligonucleotide (GEM 231) following single and multiple dose administration in mice," Antisense Nucleic Acid Drug Dev. 10(5):333-345.
Schirle et al. (Oct. 31, 2014) "Gene Regulation. Structural basis for microRNA targeting," Science. 346:608-613.
Schwab et al. (1994) "An approach for new anticancer drugs: oncogene-targeted antisense DNA," Ann. Oncol. 5(Suppl 4):55-58.
Schwarz et al. (2003) Asymmetry in the Assembly of the RNAi Enzyme Complex. Cell 115:199-208.
Song et al. (2003) "Sustained Small Interfering RNA-Mediated Human Immunodeficiency Virus Type 1 Inhibition in Primary Macrophages," Journal of Virology. 77:7174-7181.
Soutschek et al. (2004) "Therapeutic silencing of an endogenous gene by systemic administration of modified siRNAs," Nature. 432:173-178.

(56) References Cited

OTHER PUBLICATIONS

Stalder et al. (Mar. 19, 2013) "The rough endoplasmatic reticulum is a central nucleation site of siRNA-mediated RNA silencing," EMBO J. 32:1115-1127.

Stein (2001) "Inhibition of Vesivirus infections in mammalian tissue culture with antisense morpholiro oligomers," Antisense Nucleic Acid Drug Dev. 11(5):317-25.

Stokman et al. (2010) "Application of siRNA in targeting protein expression in kidney disease," Advanced Drug Delivery Reviews. 62:1378-1389.

Sui et al. (2002) "A DNA vector-based RNAi technology to suppress gene expression in mammalian cells," Proc Natl Acad Sci USA. 99:5515-5520.

Tabernero et al. (Apr. 2013) "First-in-humans trial of an RNA interference therapeutic targeting VEGF and KSP in cancer patients with liver involvement," Cancer Discovery. 3:406-417.

Thomas et al. (2009) "A recently evolved novel trophoblast-enriched secreted form of fms-lice tyrosine kinase-1 variant is up-regulated in hypoxia and preeclampsia," J. Clin. Endocrinol. Metabol. 94:2524-2530.

Tuschl (2002) "Expanding small RNA interference," Nat. Biotechnol. 20(5):446-448.

Tuschl et al. (May 6, 2004) "The siRNA User Guide," Accessible on the Internet at URL: http://diyhpl.us/~bryan/irc/protocol-online/protocol-cache/sima.html. [Last Accessed Aug. 11, 2016].

Vaught et al. (2004) "T7 RNA Polymerase Transcription with 5-Position Modified UTP Derivatives," J. Am. Chem. Soc. 126:11231-11237.

Vorobjev et al. (2001) "Nuclease resistance and RNase H sensitivity of oligonucleotides bridged by oligomethylenediol and oligoethylene glycol linkers," Antisense Nucleic Acid Drug Dev. 11(2):77-85.

Watanabe et al. (2008) "Endogenous siRNAs from naturally formed dsRNAs regulate transcripts in mouse oocytes," Nature. 453(7194):539-543.

Wooddell et al. (Feb. 26, 2013) "Hepatocyte-targeted RNAi Therapeutics for the Treatment of Chronic Hepatitis B Virus Infection," Molecular Therapy. 21:973-985.

Xia et al. (2002) "siRNA-mediated gene silencing in vitro and in vivo," Nature Biotechnol. 20(10):1006-1010.

Young et al. (2010) "Pathogenesis of preeclampsia," Annual Review of Pathology. 5:173-192.

Younis et al. (2013) "Overview of the Nonclinical Development Strategies and Class-Effects of Oligonucleotide-Based Therapeutics," Ch. 26 In; A Comprehensive Guide to Toxicology in Preclinical Drug Development. Ed.: Faqi. Academic Press. pp. 647-664.

* cited by examiner

- ⊖ 2'-O-Methyl RNA
- ⊚ 2'-Fluoro RNA
- ○ Sense strand
- ⊘ Antisense strand
- ⊛ Cholesterol
- ⊘ TEG linker
- ⊘ Phosphorothioate
- ⊘ 5'-Phosphate

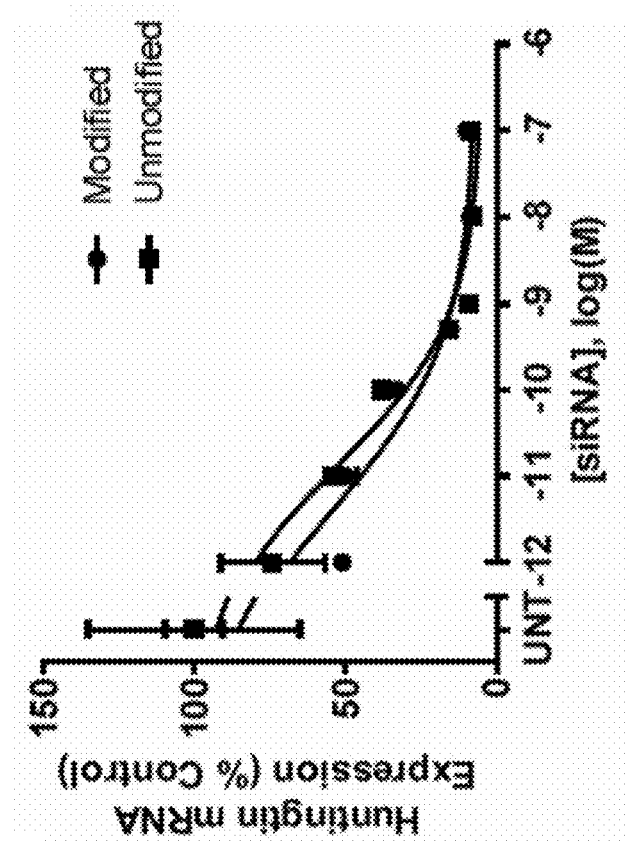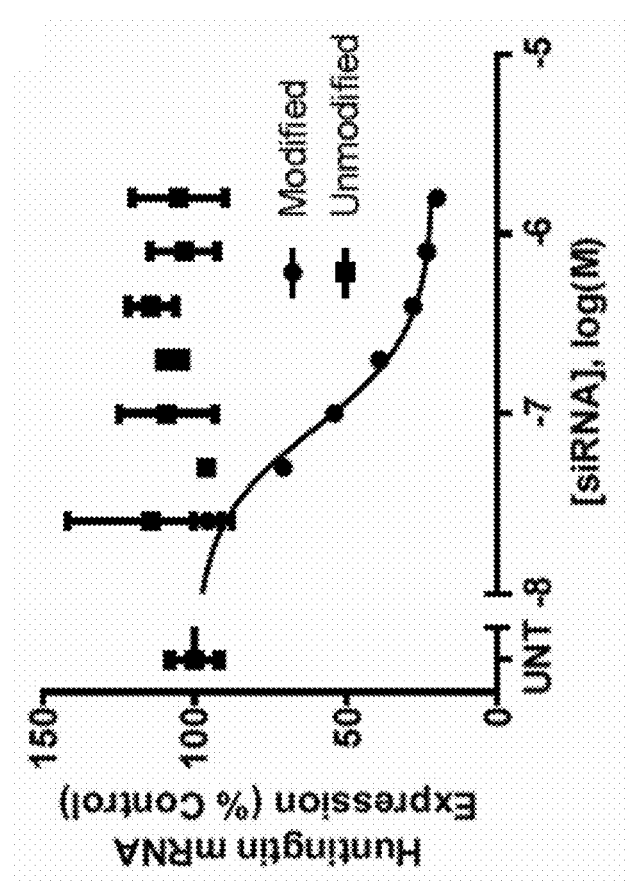
Fig. 3A  Fig. 3B  Fig. 3C

| Gene | Active hsiRNAs | | | Strand Modifications | | Homology | | | Primary Screen Huntingtin mRNA Expression (% control) | IC50 (nM) | |
|---|---|---|---|---|---|---|---|---|---|---|---|
| | Accession Number | Position | Target Sequence | Sense Strand | Antisense Strand | H. sapien | M. musculus | M. mulatta | | Passive Uptake | Lipid-Mediated Uptake |
| HTT | NM_002111.6 | 1214 | GGUUUAUGA ACUGAC | mG.mG.mU.mU.mU.A. mU.G.A.A.mC.mU.G# mA#mAtegChol | PmU.fU.fC.A.G.fU.fU. fC.A.fU.A.A.mA.fC#f C#fU#G#G#mA#C | yes | yes | yes | 34.3 | 197.4 | N/A |
| HTT | NM_002111.6 | 1218 | UAUGAACUG ACGUUA | mU.mA.mU.G.A.A.mC .mU.G.A.mC.G.mU#m U#mAtegChol | PmU.A.A.fC.G.fU.fC. A.G.fU.fU.fC.A.fU#A# A#mA#fC#fC#U | yes | | yes | 44.8 | 293.2 | N/A |
| HTT | NM_002111.6 | 1219 | AUGAACUGA CGUUAC | mA.mU.G.A.A.mC.mU .G.A.mC.G.mU.mU#n A#mAtegChol | PmU.fU.A.A.fC.G.fU.f C.A.G.fU.fU.fC.A#fU# A#A#mA#fC#C | yes | | yes | 29.6 | 163.6 | 0.053 |
| HTT | NM_002111.6 | 1257 | AAUGUUGUG ACCGGA | mA.mA.mU.G.mU.mU. G.mU.G.A.mC.mC.G# mG#mAtegChol | PmU.fC.C.G.G.fU.fC. A.fC.A.fC.A.fU#fU#fU #G#fU#G#G#U | yes | yes | yes | 28.5 | 156.7 | N/A |
| HTT | NM_002111.6 | 1894 | UAGACGGUA CCGACA | mU.mA.G.A.mC.G.G. mU.A.mC.mC.G.A#m C#mAtegChol | PmU.G.fU.fC.G.G.fU. A.fC.fC.G.fU.fC.fU.fA #A#fC#A#fC#A | yes | yes | yes | 23.7 | 95.53 | 0.048 |
| HTT | NM_002111.6 | 1907 | CAACCAGUA UUUGGG | mC.mA.A.mC.mC.A.G .mU.A.mU.mU.mU.G# mG#mAtegChol | PmU.fC.fC.A.A.mA.f U.A.fC.fU.G.G.fU.fU# G#fU#fC#G#G#U | yes | | yes | 39.3 | 217.9 | N/A |
| HTT | NM_002111.6 | 2866 | UGCUCAAUA AUGUUG | mU.mG.mC.mU.mC.A. A.mU.A.A.mU.G.mU# mU#mAtegChol | PmU.A.A.fC.A.fU.fU. A.fU.fU.G.A.mG.fC#A #fC#fU#fC#G#U | yes | yes | yes | 35.3 | 191.7 | 0.091 |
| HTT | NM_002111.6 | 4041 | UCCUGCUUU AGUCGA | mU.mC.mC.mU.G.mC. mU.mU.mU.A.G.mU.m C#mG#mAtegChol | PmU.fC.G.A.fC.fU.A. A.mA.G.fC.A.G.mG# A#fU#fU#fU#fC#A | yes | yes | yes | 53.5 | 765.7 | N/A |
| HTT | NM_002111.6 | 4049 | UAGUCGAGA ACCAAU | mU.mA.G.mU.mC.G.A .mG.A.A.mC.mC.mA#m A#mAtegChol | PmU.fU.fU.G.G.fU.fU. fC.fU.fC.G.A.fC.fU#A #A#mA#G#fC#A | yes | yes | | 41.2 | 217.8 | N/A |
| HTT | NM_002111.6 | 5301 | AGUACUUCA ACGCUA | mA.mG.fC.G.fU.fU. G.A.mA.G.fU.A.fC#fU #G#fU#fC#fC#fU#U | PmU.A.G.fC.G.fU.fU. G.A.mA.G.fU.A.fC#fU #G#fU#fC#fC#fU#U | | | | | | |

Fig. 8

| Gene | Active hsiRNAs | | | Strand Modifications | | Homology | | | Primary Screen | IC50 (nM) | |
|---|---|---|---|---|---|---|---|---|---|---|---|
| | Accession Number | Position | Target Sequence | Sense Strand | Antisense Strand | H. sapien | M. musculus | M. mulatta | Huntingtin mRNA Expression (% control) | Passive Uptake | Lipid-Mediated Uptake |
| HTT | NM_002111.6 | 6016 | UUCAGUCUCGUUGUG | mU.mU.mC.A.G.mU.mC.mU.mC.G.mU.mU.G#mU#fU#G#fC#C | PmU.A.fC.A.A.fC.G.A.mG.A.fC.fU.G.A#mA#fU#fU#G#fC#C | yes | | yes | 26.4 | 147.9 | N/A |
| HTT | NM_002111.6 | 6579 | CUAGCUCCAUGCUUA | mC.mU.A.G.mC.mU.mC.mC.A.mU.G.mC.mU#mU#mAtegChol | PmU.A.A.mG.fC.A.fU.G.G.mA.G.fC.fU.A#G#fC#A#G#mG#C | yes | yes | yes | 28.3 | 89.8 | 0.056 |
| HTT | NM_002111.6 | 8603 | CUGCGUGAACAUUCA | mC.mU.G.mC.G.mU.G.A.A.mC.A.mU.mU#m C#mAtegChol | PmU.G.A.mA.fU.G.fU.fU.fC.A.fC.G.fC.A#G#fU#G#mG#mG#C | yes | yes | yes | 40.0 | 236.1 | N/A |
| HTT | NM_002111.6 | 10125 | CUCAGGAUUUAAAAU (SEQ ID NO:3) | mC.mU.mC.A.G.G.A.mU.mU.mU.A.A.A#mA#mAtegChol | PmU.fU.fU.fU.fU.A.A.fU.fC.fC.fU.G.A#mG#A#A#mG#A#A | yes | | yes | 31.1 | 158.7 | 0.059 |
| HTT | NM_002111.6 | 10146 | AUAUCAGUAAAGAGA (SEQ ID NO:2) | mA.mU.A.mU.mC.A.G.mU.A.A.A.G.A#mG#mAtegChol | PmU.fC.fC.fU.fC.fU.fU.f U.A.fC.fU.G.A.fU.A#fU#A#fU#U#A | yes | yes | yes | 25.9 | 217.7 | 0.052 |
| HTT | NM_002111.6 | 10150 | CAGUAAAGAGAUUAA (SEQ ID NO:1) | mC.mA.G.mU.A.A.A.G.A.G.A.mU.mU#m A#mAtegChol | PmU.fU.A.A.fU.fU.fC.fU.fC.fU.fU.fU.A.fC.fU#G#A#fU#A#fU#A | yes | yes | yes | 28.6 | 82.2 | 0.004 |
| HTT | NM_002111.6 | 424 | CAGCUACCAAGAAAG | mC.mA.G.mC.mU.A.mC.mU.A.m C.mA.A.G.A.A#mA#mAtegChol | PmU.fU.fU.fU.fU.fC.fU.fU.G.G.fU.A.G.fC.fU#G#A#mA#A#G#U | yes | | yes | 67.4 | N/A | N/A |
| HTT | NM_002111.6 | 456 | CUGACAAUAUGUGAA | mC.mU.G.A.mC.A.A.mU.A.mU.G.mU.G#m A#mAtegChol | PmU.fU.fC.A.fC.A.fU.A.fU.fU.G.fU.fC.A#fU#C#A#A#U | yes | | yes | 51.5 | N/A | N/A |
| HTT | NM_002111.6 | 522 | GGCAUCGCUAUGGAA | mG.mC.mG.mC.mU.A.mU.G.mC.mU.A.mU.G.G#mA#mAtegChol | PmU.fU.fC.fC.A.fU.A.G.fC.G.A.fU.G.fC#fC#A#G#mA#A | yes | | yes | 68.2 | N/A | N/A |
| HTT | NM_002111.6 | 527 | CGCUAUGGAACUUUU | mC.mC.mG.mC.mU.A.mU.G.G.mA.A.mC.mU.mU#mU#mAtegChol | PmU.A.A.mA.G.fU.fU.fC.fC.A.fU.A.G.fC#G#A#fU#G#fC | yes | | yes | 45.5 | N/A | N/A |

Fig. 8 (cont.)

| Gene | Active hsiRNAs | | | Strand Modifications | | Homology | | | Primary Screen | IC50 (nM) | |
|---|---|---|---|---|---|---|---|---|---|---|---|
| | Accession Number | Position | Target Sequence | Sense Strand | Antisense Strand | H. sapien | M. musculus | M. mulatta | Huntingtin mRNA Expression (% control) | Passive Uptake | Lipid-Mediated Uptake |
| HTT | NM_002111.6 | 878 | UGACAAUGAAAUUAA | mU.mG.A.mC.A.A.mU.G.A.mA.A.mU.mU#mA#mAtegChol | PmU.fU.A.A.fU.fU.fU.fC.A.fU.G.fU.fC#A#fU#fU#fU#G#C | yes | | yes | 64.8 | N/A | N/A |
| HTT | NM_002111.6 | 879 | GACAAUGAAAUUAAG | mG.A.mC.A.A.mU.G.A.mA.A.mU.mU.A#mA#mAtegChol | PmU.fU.A.A.fU.fU.fU.fU.fC.A.fU.fU.G.fU#fC#A#fU#fU#fU#G | yes | | yes | 51.5 | N/A | N/A |
| HTT | NM_002111.6 | 908 | CUUCAUAGCGAACCU | mC.mU.mU.mC.A.mU.A.G.mC.G.A.A.mC#mC#mAtegChol | PmU.G.G.fU.fU.fC.G.fC.fU.A.fU.G.A.A.mG#fC#fC#fU#U | yes | | yes | 99.6 | N/A | N/A |
| HTT | NM_002111.6 | 1024 | AUGUGCUCUUAGGCU | mA.mU.G.mU.G.mC.mU.mC.mU.mU.A.G.G#mC#mAtegChol | PmU.G.fC.fC.fC.fC.A.fU.A.A.mG.A.G.fC.A#fU#fU#fU#A#G#U | yes | | yes | 52.9 | N/A | N/A |
| HTT | NM_002111.6 | 1165 | UGACAAGGAAAGAAA | mU.mG.A.mC.A.A.G.G.A.A.A.G.A.A#A#mAtegChol | PmU.fU.fU.fC.fU.fU.fU.fC.fC.fU.fU.G.fU.fC#A#fU#fU#fC#fC#G | yes | yes | yes | 77.0 | N/A | N/A |
| HTT | NM_002111.6 | 1207 | UUGUCCAGGUUUAUG | mU.mU.G.mU.mC.mC.A.G.G.mU.mU.mU.A#mU#mAtegChol | PmU.A.fU.A.A.mA.fC.fC.fU.G.G.mA.fC.A#A#mG#fC#fU#G#C | yes | yes | yes | 109.5 | N/A | N/A |
| HTT | NM_002111.6 | 1212 | CAGGUUUAUGAACUG | mC.mA.G.G.mU.mU.mU.A.mU.G.A.A.mC#mU#mAtegChol | PmU.A.G.fU.fU.fC.A.fU.A.A.mA.fC.fC.fU#G#mA#fC#A#A | yes | yes | yes | 74.9 | N/A | N/A |
| HTT | NM_002111.6 | 1217 | UUAUGAACUGACGUU | mU.mU.A.mU.G.A.A.mC.mU.G.A.mC.G#mU#mAtegChol | PmU.A.fC.G.fU.fC.A.fU.A#A#mA#fC#fC#fU#G | yes | | yes | 104.0 | N/A | N/A |
| HTT | NM_002111.6 | 1220 | UGAACUGACGUUACA | mU.mG.A.A.mC.mU.G.A.mC.G.fU.mU.A#mA#mAtegChol | PmU.G.fU.A.A.fC.G.fU.fC.A.G.fU.fU.fC#A#fU#A#A#mC | yes | | yes | 83.9 | N/A | N/A |
| HTT | NM_002111.6 | 1223 | ACUGACGUUACAUCA | mA.mC.mU.G.A.mC.G.mU.mU.A.mC.A.mU#mC#mAtegChol | PmU.G.A.fU.G.fU.A.A.fC.G.fU.fC.A.G#fU#fU#A#A | yes | | yes | 92.2 | N/A | N/A |

Fig. 8 (cont.)

| Gene | Active hsiRNAs | | | Strand Modifications | | Homology | | | Primary Screen | IC50 (nM) | |
|---|---|---|---|---|---|---|---|---|---|---|---|
| | Accession Number | Position | Target Sequence | Sense Strand | Antisense Strand | H. sapien | M. musculus | M. mulatta | Huntingtin mRNA Expression (% control) | Passive Uptake | Lipid-Mediated Uptake |
| HTT | NM_002111.6 | 1227 | ACGUUACAU CAUACA | mA.mC.G.mU.mU.A.mC.A.mU.mC.A.mU.A#mC#mAtegChol | PmU.G.fU.A.fU.G.A.fU.G.fU.A.A.fC.G#fU#fC#A#G#fU#U | yes | | yes | 81.4 | N/A | N/A |
| HTT | NM_002111.6 | 1229 | GUUACAUCA UACACA | mG.mU.mU.A.mC.A.mU.mC.A.mU.A.mC.A#mC#mAtegChol | PmU.G.fU.G.fU.A.fU.G.A.fU.G.fU.A.A.fC#G#fU#fC#A#G | yes | | yes | 82.2 | N/A | N/A |
| HTT | NM_002111.6 | 1260 | GUUGUGACC GGAGCC | mG.mU.mU.G.mU.G.A.mC.mC.G.mG.A.G#mC#mAtegChol | PmU.G.fC.fU.fC.fC.G.G.fU.fC.A.fC.A.A.G#fC#A#fU#fU#G#U | yes | | yes | 108.4 | N/A | N/A |
| HTT | NM_002111.6 | 1403 | UAUUGUGGA ACUUAU | mU.mA.mU.mU.G.mU.G.G.A.A.mC.mU.mU.A#mU#mAtegChol | PmU.fU.A.A.mG.fU.U.fC.A.fU.C.A.A.fU.A#fC#fC#fC#C | yes | | yes | 138.6 | N/A | N/A |
| HTT | NM_002111.6 | 1470 | AAAGUGCUC UUAGGA | mA.mA.A.G.mU.G.mU.mU.mU.A.A.G.G#mC#mAtegChol | PmU.fC.fC.fU.A.A.mG.A.G.fC.A.fC.fU.fU.m#fU#G#fC#fC#fU#U | yes | yes | yes | 85.6 | N/A | N/A |
| HTT | NM_002111.6 | 1901 | UACCGACAA CCAGUA | mU.mA.mC.mC.mC.G.A.mC.mA.A.mC.mC.A.G#mU#mAtegChol | PmU.A.fC.fU.G.G.fU.fU.G.fU.fC.G.G#fU#A#fC#fC#G#fU#C | yes | | yes | 81.4 | N/A | N/A |
| HTT | NM_002111.6 | 1903 | CCGACAACC AGUAUU | mC.mC.G.A.mC.A.A.mC.mC.A.G.mU.A#mU#mAtegChol | PmU.A.fU.A.fC.fU.G.G.fU.fU.G.fU.fC.G#G#fU#A#fC#fC#G | yes | | yes | 72.7 | N/A | N/A |
| HTT | NM_002111.6 | 2411 | CUACAUCGA UCAUGG | mC.mU.A.mC.A.mU.mC.G.A.fU.fC.A.fU.G.fU.A.#G#fU#fU.A.#G#U#fU#fC#A#A | PmU.fC.A.fU.G.A.fU.C.G.A.fU.G.A.#G#fU#fU.A.#G#U#fU#fC#A#A | yes | | yes | 53.0 | N/A | N/A |
| HTT | NM_002111.6 | 2412 | UACAUCGAU CAUGGA | mU.mA.mC.A.mU.mC.G.A.mU.mC.A.mU.G#mC#mAtegChol | PmU.fC.fC.A.fU.G.A.fU.fC.G.A.fU.G#fU#fU#fC#A | yes | | yes | 57.1 | N/A | N/A |
| HTT | NM_002111.6 | 2865 | GUGCUCAAU AAUGUU | mG.mU.G.mC.mU.mC.A.A.mU.A.A.mU.G#mU#mAtegChol | PmU.A.fC.A.fU.fU.A.fU.fU.G.A.mG.fC.A.#fC#fU#fC#G#fU#U | yes | | yes | 83.1 | N/A | N/A |

| Gene | Active hsiRNAs | | | Strand Modifications | | Homology | | | Primary Screen Huntingtin mRNA Expression (% control) | IC50 (nM) | |
|---|---|---|---|---|---|---|---|---|---|---|---|
| | Accession Number | Position | Target Sequence | Sense Strand | Antisense Strand | H. sapien | M. musculus | M. mulatta | | Passive Uptake | Lipid-Mediated Uptake |
| HTT | NM_002111.6 | 3801 | GUUACAAACAAGUAAA | mG.mU.mU.A.mC.A.A.mC.A.A.G.mU.A#mA#mAtegChol | PmU.fU.fU.A.fC.fU.fU.G.fU.fU.G.fU.A.A.#fC#A#G#mG#A#C | yes | | yes | 48.9 | N/A | N/A |
| HTT | NM_002111.6 | 4040 | AUCCUGCUUUAGUCG | mA.mU.mC.mC.mU.G.mC.mU.mU.mU.A.G.m U#mU#fU#fC#A#G | PmU.G.A.fC.fU.A.A.mA.G.fC.A.G.mG.A#f U#fU#fU#fC#A#G | yes | yes | yes | 56.2 | N/A | N/A |
| HTT | NM_002111.6 | 4048 | UUAGUCGAGAACCAA | mU.mU.A.G.mU.C.G.A.mG.A.A.fC.mC#m A#mAtegChol | PmU.fU.G.G.fU.fU.fC.fU.fC.G.A.fC.fU.A#A# mA#G#fC#A#G | yes | yes | yes | 72.2 | N/A | N/A |
| HTT | NM_002111.6 | 4052 | UCGAGAACCAAUGAU | mU.mC.G.A.mG.A.A. mC.mC.A.A.mU.G#m A#mAtegChol | PmU.fU.fC.A.fU.fU.G. G.fU.fU.fC.fU.fC.G#A #fC#fU#A#A#A | yes | yes | yes | 90.8 | N/A | N/A |
| HTT | NM_002111.6 | 4055 | AGAACCAAUGAUGGC | mA.mG.A.A.mC.mC.A .A.mU.G.A.mU.G#mG #mAtegChol | PmU.fC.fC.A.fU.fU.fC. fU.fU.G.G.fU.fU.fU#f U#fC#G#A#fC#U | yes | yes | yes | 37.2 | N/A | N/A |
| HTT | NM_002111.6 | 4083 | CAACAAUUGUUGAAG | mC.mA.A.mC.A.A.mU. mU.G.mU.mU.G.A#m A#mAtegChol | PmU.fU.fU.fC.A.A.fC. A.A.fU.fU.G.fU.fU#G# A#mA#fC#A#C | yes | | yes | 91.7 | N/A | N/A |
| HTT | NM_002111.6 | 4275 | AACAUGGUGCAGGCG | mA.mA.mC.A.mU.G.G .mU.G.mC.A.G.G#mC #mAtegChol | PmU.G.fC.fC.fC.fU.G.fC. A.fC.fC.A.fU.G.fU#fU #fC#fC#fU#fC#A | yes | yes | yes | 77.2 | N/A | N/A |
| HTT | NM_002111.6 | 4372 | CAAAGAACCGUGCAG | mC.mA.A.A.G.A.A.mC .mC.G.mU.G.mC#mA# mAtegChol | PmU.fU.G.fC.A.fC.G. G.fU.fU.fC.fU.fU.fU# G#fU#G#A#fC#A | yes | | yes | 44.5 | N/A | N/A |
| HTT | NM_002111.6 | 4374 | AAGAACCGUGCAGAU | mA.mA.G.A.A.mC.mC .G.mU.G.mC.A.G#mA #mAtegChol | PmU.fU.fC.fU.G.fU.fC.A. fC.G.G.fU.fU.fC.fU#f U#fU#G#fU#G#A | yes | | yes | 97.5 | N/A | N/A |
| HTT | NM_002111.6 | 4376 | GAACCGUGCAGAUAA | mG.mA.A.mC.mC.G.m U.G.mC.A.G.A.mU#m A#mAtegChol | PmU.fU.A.fU.fC.fU.G. fC.A.fC.G.G.fU.fU#fC #fU#fU#G#U | yes | | yes | 64.1 | N/A | N/A |

| Gene | Active hsiRNAs | | | Strand Modifications | | Homology | | | Primary Screen Huntingtin mRNA Expression (% control) | IC50 (nM) | |
|---|---|---|---|---|---|---|---|---|---|---|---|
| | Accession Number | Position | Target Sequence | Sense Strand | Antisense Strand | H. sapien | M. musculus | M. mulatta | | Passive Uptake | Lipid-Mediated Uptake |
| HTT | NM_002111.6 | 4425 | CCUCUUGUU AUAAAA | mC.mC.mU.mC.mU.m U.G.mU.mU.A.mU.A.A #mA#mAtegChol | PmU.fU.fU.fU.A.fU.A. AfC.A.A.A.mG.A.G#m G#fU#fU##fC#A#A | yes | yes | yes | 44.6 | N/A | N/A |
| HTT | NM_002111.6 | 4562 | UGGCUUUGU AUUGAA | mU.mG.G.mC.mU.mU. mU.G.mU.A.mU.mU.G #mA#mAtegChol | PmU.fU.fC.A.A.fU.A.f C.A.A.mA.G.fC.fC#A #A#fU#A#A#A | yes | | yes | 102.1 | N/A | N/A |
| HTT | NM_002111.6 | 4692 | GGAAUUCCU AAAAUC | mG.mG.A.A.mU.mU.m C.mC.mU.A.A.A.A#m U#mAtegChol | PmU.A.fU.fU.fU.fU.A. G.mG.A.A.A.fU.fC#f C#A#A#fU#G#A | yes | yes | yes | 53.8 | N/A | N/A |
| HTT | NM_002111.6 | 4721 | UGGCAUCAU GGCCAG | mU.mG.G.mC.A.mU.m C.A.mU.G.G.mC.mC# mA#mAtegChol | PmU.fU.G.G.fC.fC.A.f U.G.A.fU.G.fC.fC#A#f U#fC#A#fC#A | yes | | yes | 124.2 | N/A | N/A |
| HTT | NM_002111.6 | 5200 | CCCAGUCAA CUGAAG | mC.mC.mC.A.G.mU.m C.A.A.mC.mU.G.A#m A#mAtegChol | PmU.fU.fU.fC.A.G.fU. fU.G.A.fC.fU.G.G#m G#A#A#mA#fU#C | yes | yes | | 43.8 | N/A | N/A |
| HTT | NM_002111.6 | 5443 | AGCAGCAAC AUACUU | mA.mG.mC.A.G.mC.A .A.mC.A.mU.A.mC#m U#mAtegChol | PmU.A.G.fU.A.fU.G.f U.fU.G.fC.fU.G.fC#fU #fC#A#fC#fU#C | yes | yes | yes | 48.9 | N/A | N/A |
| HTT | NM_002111.6 | 5515 | GAAUGUUCC GGAGAA | mG.mA.A.mU.G.mU.m U.mC.mC.G.G.A.G#m A#mAtegChol | PmU.fU.fC.fU.fC.fC.G .G.mA.A.fC.A.fU.fU#f C#fC#A#G#mA#C | yes | yes | yes | 62.0 | N/A | N/A |
| HTT | NM_002111.6 | 8609 | GAACAUUCA CAGCCA | mG.mA.A.mC.A.mU.m U.mC.A.mC.A.G.mC# mC#mAtegChol | PmU.G.G.fC.fU.G.fU. G.A.mA.fU.G.fU.fU#f C#A#fC#G#fC#A | yes | yes | yes | 47.4 | N/A | N/A |
| HTT | NM_002111.6 | 10130 | GAUUUAAAA UUUAAU | mG.mA.A.A.mU.mU. A.A.A.mU.mU.mU.A# mA#mAtegChol | PmU.fU.fU.A.A.mA.f U.fU.fU.A.A.mA.fU #fC#fC#fU#G#A#G | yes | | yes | 49.6 | N/A | N/A |
| HTT | NM_002111.6 | 10134 | UAAAAUUUA AUUAUA | mU.mA.A.A.A.mU.mU. mU.A.A.mU.mU.A#mU #mAtegChol | PmU.A.fU.A.A.fU.fU. A.A.mA.fU.fU.fU.fU# A#A#mA#fU##fC#C | yes | yes | yes | 113.7 | N/A | N/A |

Fig. 8 (cont.)

| Gene | Active hsiRNAs | | | Strand Modifications | | Homology | | | Primary Screen Huntingtin mRNA Expression (% control) | IC50 (nM) | |
| --- | --- | --- | --- | --- | --- | --- | --- | --- | --- | --- | --- |
| | Accession Number | Position | Target Sequence | Sense Strand | Antisense Strand | H. sapien | M. musculus | M. mulatta | | Passive Uptake | Lipid-Mediated Uptake |
| HTT | NM_002111.6 | 10142 | AAUUAUAUC AGUAAA | mA.mA.mU.mU.A.mU.A.mU.mC.A.G.mU.A#mA#mU#U | PmU.fU.fU.A.fC.fU.G.A.fU.A.fU.A.A.fU#U#A#A#mA#fU#U | yes | yes | yes | 78.0 | N/A | N/A |
| HTT | NM_002111.6 | 10169 | AACGUAACU CUUUCU | mA.mA.mC.G.mU.A.A.mC.mU.mC.mU.mU.mU#U#A#A#mA#fU | PmU.G.A.mA.A.G.mA.G.fU.fU.A.fC.G.fU#fU#A#A#mA#A#U | yes | yes | | 69.0 | N/A | N/A |
| HTT | NM_002111.6 | 10182 | CUAUGCCCG UGUAAA | mC.mU.A.mU.G.mC.mC.mC.G.mU.G.mU.A#mA#mA#mU | PmU.fU.fU.A.fC.A.fC.G.G.mG.fC.A.fU.A#G#mA#A#mG#A | yes | yes | yes | 100.1 | N/A | N/A |
| HTT | NM_002111.6 | 10186 | GCCCGUGUA AAGUAU | mG.mC.mC.mC.G.mU.G.mU.A.A.G.mU#m A#mU#U#A#G | PmU.fU.A.fC.fU.fU.A.fC.A.fC.G.G.mG#fC#A#fU#A#G | yes | | yes | 83.5 | N/A | N/A |
| HTT | NM_002111.6 | 10809 | AGUCAGGAG AGUGCA | mA.mG.mU.mC.A.G.G.A.G.A.G.mU.G#mC#A | PmU.G.fC.A.fC.fU.fC.fU.fC.fC.fU.G.A.fC#U#A#A#mA#A#G | yes | | | 101.7 | N/A | N/A |
| HTT | NM_002111.6 | 11116 | UGGGUAUUG AAUGUG | mU.mG.G.G.mU.A.mU.mU.G.A.A.mU.G#mU# | PmU.A.fC.A.fU.fU.fC.A.A.fU.A.fC.fC#A#A#fC#A | yes | | | 90.0 | N/A | N/A |
| HTT | NM_002111.6 | 11129 | UGGUAAGUG GAGGAA | mU.mG.G.mU.A.A.G.mU.G#mA#m A | PmU.fU.fC.fC.fU.fC.fC.f.C.A.fC.fU.fU.A.fC.fC#A#fC#A#fU#C | yes | | | 105.9 | N/A | N/A |
| HTT | NM_002111.6 | 11134 | AGUGGAGGA AAUGUU | mA.mC.mU.G.G.A.G.G.A.A.A.mU.G#mU#U | PmU.A.fC.A.fU.fU.fU.fC.fC.fU.fC.fC.A.fC#U#A#fC#U#A | yes | | | 85.1 | N/A | N/A |
| HTT | NM_002111.6 | 11147 | UUGGAACUC UGUGCA | mU.mU.mC.mC.mU.mU.G.mU#mC#A | PmU.G.fC.A.fC.A.G.A.G.mA.G.fU.fC.A#fC#A#fU#U | yes | | | 109.9 | N/A | N/A |
| HTT | NM_002111.6 | 11412 | UGAGGAGGC CCUUAA | mU.mG.A.G.G.mA.G.G.mC.mC.mC.mU#U#A#A | PmU.fU.A.A.mG.G.G.fC.fC.fC.fU.fC#A#U#C | yes | | | 122.0 | N/A | N/A |

Fig. 8 (cont.)

| Gene | Active hsiRNAs | | | Strand Modifications | | Homology | | | Primary Screen | IC50 (nM) | |
|---|---|---|---|---|---|---|---|---|---|---|---|
| | Accession Number | Position | Target Sequence | Sense Strand | Antisense Strand | H. sapien | M. musculus | M. mulatta | Huntingtin mRNA Expression (% control) | Passive Uptake | Lipid-Mediated Uptake |
| HTT | NM_002111.6 | 1142 6 | AGGGAAGCU ACUGAA | mA.mC.G.G.A.A.G.m C.mU.A.mC.mU.G#m A#mA#mG#Chol | PmU.fU.fC.A.G.fU.A. G.fC.fU.fU.fC.fC.fC#f U#fU#A#A#mG#G | yes | | | 106.3 | N/A | N/A |
| HTT | NM_002111.6 | 1144 3 | AUAACACGU AAGAAA | mA.mU.A.A.mC.A.mC. G.mU.A.A.G.A#mA#m A#mAtegChol | PmU.fU.fU.fC.fU.fU.A .fC.G.fU.G.fU.fU.A#f U#A#A#fU#fU#C | yes | yes | | 91.7 | N/A | N/A |
| HTT | NM_002111.6 | 1165 9 | UACAUUGU AAGAAA | mU.mA.mC.A.mU.mU. mU.G.mU.A.A.G.A#m A#mA#mfC#A#U | PmU.fU.fU.fC.fU.fU.A .fC.A.A.mA.fU.G.fU# A#A#mA#fC#A#U | yes | | | 80.7 | N/A | N/A |
| HTT | NM_002111.6 | 1166 6 | GUAAGAAAU AACACU | mG.mU.A.A.G.mA.A. mU.A.A.mC.A#mC#m AtegChol | PmU.G.fU.G.fU.fU.A.f U.fU.fC.fU.fU.A#f C#A#A#mA#fU#G | yes | | | 98.5 | N/A | N/A |
| HTT | NM_002111.6 | 1167 7 | CACUGUGAA UGUAAA | mC.mA.mC.mU.G.mU. G.A.A.mU.G.mU.A#m A#mA#mAtegChol | PmU.fU.fU.A.fC.A.fU. fU.fC.A.fC.A.G.fU#G# fU#fU#A#fU#U | yes | | | 87.8 | N/A | N/A |
| HTT | NM_002111.6 | 1186 3 | GAGCUCAUU AGUAAA | mG.mA.G.mC.mU.mC. A.mU.mU.A.G.mU.A# mA#mAtegChol | PmU.fU.fU.A.fC.fU.A. A.fU.G.A.mG.fC.fU#f C#A#fU#A#fU#U | yes | | | 77.4 | N/A | N/A |
| HTT | NM_002111.6 | 1189 0 | CACGCAUAU ACAUAA | mC.mA.mC.G.mC.A.m U.A.mU.A.mC.A.mU# mA#mAtegChol | PmU.fU.A.fU.G.fU.A.f U.A.fU.G.fC.G.fU#G# G#mG#fU#G#A | yes | | | 114.3 | N/A | N/A |
| HTT | NM_002111.6 | 1192 7 | GACACAUCU AUAAUU | mG.mA.mC.A.mC.A.m U.mC.mU.A.mU.A.A# mU#mAtegChol | PmU.A.fU.fU.A.fU.A. G.mA.fU.G.fU.G.fU# C#fU#A#fU#A#U | yes | | | 113.3 | N/A | N/A |
| HTT | NM_002111.6 | 1194 7 | CACACACCU CUCAAG | mC.mC.mU.mC.mU.mC. C.mC.mU.mC.mU.mC. A#mU#mAtegChol | PmU.fU.fU.G.A.mG.A .G.mG.fU.G.fU.G.fU# G#fU#G#fU#A#A | yes | | | 99.8 | N/A | N/A |
| HTT | NM_002111.6 | 1216 3 | UAUCAUGUU CCUAAA | mU.fU.mU.mC.A.mU. G.mU.mU.mC.mC.mU. A#mA#mA#mAtegChol | PmU.fU.fU.A.fU.G.A.mG.A .A.fC.A.fU.G.A.fU#A# A#mA#G#fU#C | yes | | | 70.7 | N/A | N/A |

Fig. 8 (cont.)

| Gene | Active hsiRNAs | | | Strand Modifications | | Homology | | | Primary Screen | IC50 (nM) | |
| --- | --- | --- | --- | --- | --- | --- | --- | --- | --- | --- | --- |
| | Accession Number | Position | Target Sequence | Sense Strand | Antisense Strand | H. sapien | M. musculus | M. mulatta | Huntingtin mRNA Expression (% control) | Passive Uptake | Lipid-Mediated Uptake |
| HTT | NM_002111.6 | 12218 | GCAAAUGUGAUUAAU | mG.mC.A.A.A.mU.G.mU.G.A.mU.mU.A#mA#mAtegChol | PmU.fU.fU.A.A.fU.fC.A.fC.A.fU.fU.fU.G#fC#A#A#fC#A#A | yes | | | 115.3 | N/A | N/A |
| HTT | NM_002111.6 | 12223 | UGUGAUUAAUUUGGU | mU.mG.mU.G.A.mU.mU.A.A.mU.mU.mU.G#mC#mAtegChol | PmU.fC.fC.A.A.mA.fU.fU.A.A.fU.fC.A.fC#A#fU#fU#fU#G#C | yes | | | 114.6 | N/A | N/A |
| HTT | NM_002111.6 | 12235 | GGUGUCAAGUUUUG | mG.mG.mU.G.mU.mC.A.A.G.mU.mU.mU#mU#mAtegChol | PmU.A.mA.A.fC.fU.fU.G.A.fC.A.A.fC#fC#A#A#mA#fU#U | yes | | | 108.3 | N/A | N/A |
| HTT | NM_002111.6 | 12279 | UUUCCUGCUGGUAAU | mU.mU.mU.mC.mC.mU.G.mC.mU.G.G.mU.A#mA#mC#mAtegChol | PmU.fU.fU.A.fC.fC.A.G.fC.A.G.mG.A.A.A#A#fC#A#A#A | yes | | | 83.9 | N/A | N/A |
| HTT | NM_002111.6 | 12282 | CCUGCUGGUAAUAUC | mC.mC.mU.G.mC.mU.G.G.mU.A.A.mU.A#mA#mAtegChol | PmU.A.fU.A.fU.fU.A.fC.fC.A.G.fC.A.G#mG#A#A#mA#C | yes | | | 89.9 | N/A | N/A |
| HTT | NM_002111.6 | 12297 | GGGAAAGAUUUUAAU | mG.mG.G.A.A.A.G.A.mU.mU.mU.mU.A#mA#mAtegChol | PmU.fU.fU.A.A.A.mA.fU.fC.fU.fU.fU.fC.fC#G#A#fU#A#fU | yes | | | 82.9 | N/A | N/A |
| HTT | NM_002111.6 | 12309 | AAUGAAACCAGGGUA | mA.mA.mU.G.A.A.A.mC.mC.A.G.G.G#mU#mAtegChol | PmU.A.fC.fC.fC.fU.G.G.fU.fU.fU.fC.A.fU#f U#A#A#mA#A#fU | yes | | | 73.4 | N/A | N/A |
| HTT | NM_002111.6 | 12313 | AAACCAGGGUAGAAU | mA.mA.A.mC.mC.A.G.G.G.mU.A.G.A.A#mA#mAtegChol | PmU.fU.fU.fC.fU.fC.fC.fU.A.fC.fC.fC.fU.G.G.fU.fU#fU#U#fC#A#fU#fU#A | yes | | | 89.8 | N/A | N/A |
| HTT | NM_002111.6 | 12331 | UUGGCAAUGCACUGA | mU.mU.G.G.mC.A.A.mU.G.mC.A.mC.mU.mG.A#mA#mAtegChol | PmU.fC.A.G.fU.G.fU.fC.fC.A.G.fU.fU.G.fC.fC.A#mA#fC#A#A#U | yes | | | 109.9 | N/A | N/A |
| HTT | NM_002111.6 | 13136 | CAGUGUUUCUAAGA | mC.mA.G.mU.G.mU.mU.mU.mC.mU.A.A.G.A#mG#mAtegChol | PmU.fC.fU.fU.A.G.fU.fU.fC.A.A.fC.fU#G#A#mG#G#G | yes | | | 113.2 | N/A | N/A |

Fig. 8 (cont.)

| Gene | Active hsiRNAs | | | Strand Modifications | | Homology | | | Primary Screen | IC50 (nM) | |
|---|---|---|---|---|---|---|---|---|---|---|---|
| | Accession Number | Position | Target Sequence | Sense Strand | Antisense Strand | H. sapien | M. musculus | M. mul atta | Huntingtin mRNA Expression (% control) | Passive Uptake | Lipid-Mediated Uptake |
| HTT | NM_002111.6 | 13398 | GACGAGAGAUGUAUA | mG.mA.mC.G.A.G.A.G.A.mU.G.mU.A#mU#mAtegChol | PmU.A.fU.A.fC.A.fU.f C.fU.fC.fU.fC.G.fU#f C#A#G#fU#fC#C | yes | | | 102.1 | N/A | N/A |
| HTT | NM_002111.6 | 13403 | GAGAUGUAUAUUUAA | mG.mA.G.A.mU.G.mU .A.mU.A.mU.mU.mU# mA#mAtegChol | PmU.fU.A.A.mA.fU.A .fU.A.fC.A.fU.fC.fU#f C#fU#fC#G#fU#C | yes | | | 84.1 | N/A | N/A |
| HTT | NM_002111.6 | 13423 | UAACUGCUGCAAACA | mU.mA.A.mC.mU.G.m C.mU.G.mC.A.A.A#m C#mAtegChol | PmU.G.fU.fU.fU.G.fC. A.G.fC.A.G.fU.fU#A# A#mA#A#A | yes | | | 124.8 | N/A | N/A |
| HTT | NM_002111.6 | 13428 | GCUGCAAACAUUGUA | mG.mC.mU.G.mC.A.A .A.mC.A.mU.mU.G#m U#mAtegChol | PmU.A.fC.A.A.fU.G.f U.fU.G.fC.A.G.#fC# A#G#fU#fU#A | yes | | | 114.1 | N/A | N/A |
| NTC | N/A | N/A | ACAAAUACG AUUA | mA.mC.A.A.A.mU.A.m C.G.A.mU#mU#mA#te gChol | P.mU.A.A.fU.fC.G.fU. A.fU.fU.GU.mU#mC#A #A#mU#mC#A | yes | | | 102.0 | N/A | N/A |

Fig. 8 (cont.)

| Target | Accession Number | Position | Targeting region (20 mer) | Targeting Region (30 mer) |
|---|---|---|---|---|
| HTT | NM_002111.6 | 1214 | GUCCAGGUUAUGAACUGAC | AGCUGUCCAGGUUAUGAACUGACGUAAC |
| HTT | NM_002111.6 | 1218 | AGGUUAUGAACUGACGUUA | UGUCCAGGUUAUGAACUGACGUUACAUCA |
| HTT | NM_002111.6 | 1219 | GGUUAUGAACUGACGUUAC | GUCCAGGUUAUGAACUGACGUUACAUCAU |
| HTT | NM_002111.6 | 1257 | ACCACAAUGUUGUAGCGGA | CCAAGACCAAUGUUGUAGCGGAGCCCU |
| HTT | NM_002111.6 | 1894 | UGUGUAGCGGUAACGGACA | GAAAUGUGUAGCGGUAACGGACGAACCAAG |
| HTT | NM_002111.6 | 1907 | ACCGUACAACCAGUAUUGGG | ACGUACCGUACAACCAGUAUUGGGCCUGC |
| HTT | NM_002111.6 | 2866 | ACGAUGUCUCAAUAAUGUUG | CAAGAACCGAGUCUCAAUAAUGUUGUCAUC |
| HTT | NM_002111.6 | 4041 | UGAAAUCCUGUUUAGUCGA | AUACCUGAAAUCCUGUUUAGUCGAGAACC |
| HTT | NM_002111.6 | 4049 | UGCUUUAGUCGGAACCAAU | AAUCCUGUUUAGUCGGAACCUAGAAUGG |
| HTT | NM_002111.6 | 5301 | GGGACAGUACUUCAACGUA | AGAUGGGACAGUACUUCAACGUAGAAAC |
| HTT | NM_002111.6 | 6018 | GGGACAAUUCAGUCUCAUGUUA | AUCCAGGGACAAUUCAGUCUCAUGUAAGC |
| HTT | NM_002111.6 | 8579 | GCCUGCUCGUCCAUGGAA | CCUAAGCCUGCUCGUCCAUGAACAGCC |
| HTT | NM_002111.6 | 8803 | GCCCACUGCUGACAUUCA | GGAUGGCCCACUGCUGGAACACAUUAAAU |
| HTT | NM_002111.6 | 10125 | UUCUCUCAGGAUUUAAAAU | CUCUUUCUCUCAGGAUUAAAAUUAAU |
| HTT | NM_002111.6 | 10146 | UAAUUAUAUCAGUAAGAGA | AAAUUAAUAUCAGUAAAGAGAUUAAUUAAU |
| HTT | NM_002111.6 | 10150 | UAUAUCAGUAAAGAGAUUA | UUAAUUAUAUCAGUAAAGAGAUUAAUUUA |
| HTT | NM_002111.6 | 424 | ACUUGAGCUACCAAGAAG | AAAACUUGAGCUACCAAGAAUGAACCGU |
| HTT | NM_002111.6 | 456 | AUUGUCUGACAAUAUGGAA | GAAUCAUUGUCUGACAAUAUGUGAAACAU |
| HTT | NM_002111.6 | 522 | UUCUGGGCAUGGGAA | UUCUGGGCAUGGAAUCGAUCUUUUUCGC |
| HTT | NM_002111.6 | 527 | GGCAUCGGUAUGGAACUUU | GGCAUCGGUAUGGAACUUUAAGAAGUU |
| HTT | NM_002111.6 | 878 | GCAAAGACAAUGAAAUUAA | AUUUGCAAAGACAAUGAAAUUAAGGUUU |
| HTT | NM_002111.6 | 879 | CAAAGACAAUGAAAUAAG | UUUGCAAAGACAAUGAAAUUAAGGUUUU |
| HTT | NM_002111.6 | 908 | AAGGCCUUCAAUGUAGCAACU | UGUAAGGCCUUCAAUGUAGCGAAGU |
| HTT | NM_002111.6 | 1024 | ACUAAAUGUGCUUAGGCU | UGGCUAAAUGUGCUUAGGCUAGGCUAUCC |

Fig. 21

| Target | Accession Number | Position | Targeting region (20 mer) | Targeting Region (30 mer) |
|---|---|---|---|---|
| HTT | NM_002111.6 | 1165 | CGGAGUGACAAGGAAGAAA | AGCUUCGGAGUGACAAGGAAGAAAUGGAA |
| HTT | NM_002111.6 | 1207 | GCAGCUGUCCAGGUUAUG | GCAGAGCAGCUGUCCAGGUUAUGAACUG |
| HTT | NM_002111.6 | 1212 | UGUCCAGGUUAUGAACUG | GCAGCUGUCCAGGUUAUGAACUGACUG |
| HTT | NM_002111.6 | 1217 | CAGGUUAUGAACUGACGUU | UGUCCAGGUUAUGAACUGACGUACGUU |
| HTT | NM_002111.6 | 1220 | GUUAUGAACUGACGUACA | UCCAGGUUAUGAACUGACGUACAUCAUA |
| HTT | NM_002111.6 | 1223 | UAUGAACUGACGUACAUCA | AGGUUAUGAACUGACGUACAUCAUACA |
| HTT | NM_002111.6 | 1227 | AACUGACGUACAUCAUACA | UUAUGAACUGACGUACAUCAUACACAGCA |
| HTT | NM_002111.6 | 1229 | CUGACGUUACAUCAUACACA | AUGAACUGACGUACAUCAUACACAGCACC |
| HTT | NM_002111.6 | 1260 | ACAAUGUUGUGCGGAGCC | AGACCAAUGUUGUGCGGAGCCCUGGA |
| HTT | NM_002111.6 | 1403 | GGGAGUAUUGUGGAACUUAU | GUAGUGGGAGUAUUGUGGAACUUAUAGCUG |
| HTT | NM_002111.6 | 1470 | AAGGCAAAGUGCUCUAGGA | ACAAAAAGGCAAAGUGCUCUAGGAAGA |
| HTT | NM_002111.6 | 1901 | GACGGUACCGACAACCAGUA | UGUUAGACGGUACCGACAACCAGUAUUGGG |
| HTT | NM_002111.6 | 1903 | CGGUACCGACAACCAGUAUU | UUUGACGGUACCGACAACCAGUAUUGGGC |
| HTT | NM_002111.6 | 2411 | UGAACUGACGUGAUCUGG | ACAUUGAACUGACUACAUCGAUCGGACC |
| HTT | NM_002111.6 | 2412 | UGAACUGACUACAUCGAUCGGA | CAUUGAACUGACUACAUCGAUCGGAGACCC |
| HTT | NM_002111.6 | 2865 | AAGCUGCUCAAUAAUGGU | GCAAGAACGAGUGCUCAAUAAUGUGUCAU |
| HTT | NM_002111.6 | 3801 | GUCUGUUAAACAAGUAA | CUCAGGUCCUGUUAACAAGUAAAUCCUC |
| HTT | NM_002111.6 | 4040 | CUGAAAUCCUGCUUAAGGUCG | GAUACCUGAAAUCCUGCUUAGUCGAGAAC |
| HTT | NM_002111.6 | 4048 | CUGCUUUAGUCGAGAACCAA | AAUCCUGCUUAGUCGAGAACCAAUGAAUG |
| HTT | NM_002111.6 | 4052 | UUUAGUCGAGAACCAAUGAU | CCUGCUUUAGUCGAGAACCAAUGAUGCAA |
| HTT | NM_002111.6 | 4055 | AGUCGAGAACCAAUGAUGGC | GCUUAGUCGAGAACCAAUGAUGGCAACUG |
| HTT | NM_002111.6 | 4083 | GUGUCAACAAUUGUUGAAG | UGUUGUGUCAACAAUUGUUGAAGAUCU |
| HTT | NM_002111.6 | 4275 | UGAGGAACAUGGUGCAGGCG | CAGCUGAGGAACAUGGUGCAGGCGGAGCA |
| HTT | NM_002111.6 | 4372 | UGUCACAAAGAACCGUGCAG | ACGAGUGUCACAAAGAACCGUGCAGAUAAG |
| HTT | NM_002111.6 | 4374 | UCACAAAGAACCGUGCAGAU | GAGUGUCACAAAGAACCGUGCAGAUAAGAA |

Fig. 21 cont.

| Target | Accession Number | Position | Targeting region (20 mer) | Targeting Region (30 mer) |
|---|---|---|---|---|
| HTT | NM_002111.6 | 4376 | ACAAAGAACCGUGCAGAUAA | GUGUCACAAAGAACCGUGCAGAUAAGAAUG |
| HTT | NM_002111.6 | 4425 | UUGAACUCUGUAUAAAA | UUGUUUGAACUCUGUAUAAAGCUU |
| HTT | NM_002111.6 | 4562 | UUGAUUGGCUUUGUAUUGAA | AGGUGUUUAUUGGCUUUGUAUUGAAACAGU |
| HTT | NM_002111.6 | 4692 | UCAUUGGAAUCCUAAAAUC | ACAGAUCAUUGGAAUCCUAAAAUCAUUCA |
| HTT | NM_002111.6 | 4721 | UGGAUGGCAUCAUGGCCAG | AGCUCUGUGAUGGCAUCAUGGCCAGUGGAA |
| HTT | NM_002111.6 | 5200 | GAUUCCCAGUCAACUGAAG | GUUCUGAUUCCCAGUCAACUGAAGACUGAU |
| HTT | NM_002111.6 | 5443 | GAGUGAGCAGCAACAUACUU | GAAAUGAGUGAGCAGCAACAUACUUUCUAU |
| HTT | NM_002111.6 | 5515 | GUCUGGAAUGUUCGGGAGAA | UUCAAGUCUGGAAUGUUCGGGAGAAUCACA |
| HTT | NM_002111.6 | 8609 | UGCGUGAACAUUCACAGCCA | CCCACUGCGUGAACAUUCACAGCCAGCAGC |
| HTT | NM_002111.6 | 10130 | CUCAGGAUUAAAAUUUAAU | UUCUUCAGGAUUAAAAUUUAAUUAUAUAU |
| HTT | NM_002111.6 | 10134 | GGAUUAAAAUUUAAUUAUA | UCUCAGGAUUAAAAUUUAAUUAUAUCAGU |
| HTT | NM_002111.6 | 10142 | AAUUAAUUAUAUCAGUAAA | UUUAAAAUUUAAUUAUAUCAGUAAAGAGAU |
| HTT | NM_002111.6 | 10169 | AUUUUUACGUAACUCUUUCU | GAUUAAAUUUUACGUAACUCUUUCUAUGCC |
| HTT | NM_002111.6 | 10182 | UCUUUCUAUGCCCGUGUAA | GUAACUCUUUCUAUGCCCGUGUAAAGUAUG |
| HTT | NM_002111.6 | 10186 | UCUAUGCCCGUGUAAAGUAU | CUCUUUCUAUGCCCGUGUAAAGUAUGAA |
| HTT | NM_002111.6 | 10809 | CUUUAUGUCAGGAGAGUGCA | GACCCUUUAUGUCAGGAGAGUGCAGAUCU |
| HTT | NM_002111.6 | 11116 | UGUUUGGUAUUGAAUGGAAG | GUCGAUGUUUGGUAUUGAAUGGAAG |
| HTT | NM_002111.6 | 11129 | GAAUGGGUAAGUGGAGGAA | GUAUUGAAUGGGUAAGUGGAGGAAAUUGG |
| HTT | NM_002111.6 | 11134 | UGGUAAGUGGAGGAAAUGUU | GAAUGGGUAAGUGGAGGAAAUGUUGGAAC |
| HTT | NM_002111.6 | 11147 | AAAUGUUGGAACUCUGUGCA | GGAGGAAAUGUUGGAACUCUGUGCAGGUGC |
| HTT | NM_002111.6 | 11412 | AUGUUUGA GGAGGCCCUUAA | GUCCGAUGUUUGAGGAGGCCCUUAAGGGAA |
| HTT | NM_002111.6 | 11426 | CCUUAAGGGAAGCUACUGAA | GAGGCCCUUAAGGGAAGCUACUGAAGAAA |
| HTT | NM_002111.6 | 11443 | GAAUUAUAACGUUAAGAAAA | CUACUGAAUUAUAACGUUAAGAAAAAUCAC |
| HTT | NM_002111.6 | 11659 | AUGUUUACAUUUGUAAGAAA | GCUUACAUGUUUACAUUUGUAAGAAAUACA |
| HTT | NM_002111.6 | 11666 | CAUUUGUAAGAAAUACACACU | GUUUACAUUUGUAAGAAAUACACUGUGAA |
| HTT | NM_002111.6 | 11677 | AAUAACACUGUGAAUGUAAA | UAAGAAAUACACUGUGAAAUAAACAGA |

Fig. 21 cont.

| Target | Accession Number | position | Targeting region (20 mer) | Targeting Region (30 mer) |
|---|---|---|---|---|
| HTT | NM_002111.6 | 11863 | AAUAUGAGCUCAUAGUAAA | AGAUGAAUAUGAGCUCAUAGUAAAAUGA |
| HTT | NM_002111.6 | 11890 | UCACCCAGGAUAUACAUAA | UGACUUCACCCAGGAUAUACAUAAAGUAU |
| HTT | NM_002111.6 | 11927 | AUAUAGACACUAUCUAAUU | UGUGCAUAUAGACACUAUCUAAUUUUACA |
| HTT | NM_002111.6 | 11947 | UUACACACACCUCUCAAG | UAAUUUACACACACCUCUCAAGACGGA |
| HTT | NM_002111.6 | 12163 | GACUUUAUCAUGUUCCUAAA | AGGAAGACUUUAUCAUGUUCCUAAAAUCU |
| HTT | NM_002111.6 | 12218 | UUGUGUCAAAUGUAAUUUGU | AAAUUUGUGUCAAAUGUAAUUUGGUUGU |
| HTT | NM_002111.6 | 12223 | GCAAAUGUAAUUGGUUUGGU | UUGUGUCAAAUGUAAUUGGUUGGGGUCA |
| HTT | NM_002111.6 | 12235 | AAUUGGUUGUCAAGUUUG | UGAAUAAUUGGUUGUCAAGUUUGGGGGU |
| HTT | NM_002111.6 | 12279 | UUUGUUUCCUGUGUAAUAU | UUGCUUUGUUUCCUGUGUAAUAUCGG |
| HTT | NM_002111.6 | 12282 | GUUUCCUGUGUAAUAUC | CUUUGUUUCCUGUGUAAUAUCCGGAA |
| HTT | NM_002111.6 | 12297 | AUAUCGGGAAAGAUUUAAU | UGGUAAUAUCGGGAAAGAUUUAAUGAAAC |
| HTT | NM_002111.6 | 12309 | AUUUAAUGAAAACCAGGGUA | GAAAGAUUUAAUGAAAACCAGGGUAGAAUU |
| HTT | NM_002111.6 | 12313 | UAAUGAAACCAGGGUAGAAU | GAUUUAAUGAAACCAGGGUAGAAUUGUU |
| HTT | NM_002111.6 | 12331 | AUUGUUGGCAAUGCACUGA | GUAGAAUUGUUGGCAAUGCACUGAAGCGU |
| HTT | NM_002111.6 | 13136 | CCCUCAGUUGUUUCUAAGA | GCCUUCCCUCAGUUGUUUCUAAGAGAGA |
| HTT | NM_002111.6 | 13398 | GGACUGACUGAGAUGUAUA | GGAAGACUGACUGAGAUGUAUAUUAAUU |
| HTT | NM_002111.6 | 13403 | GACGAGAGAUGUAUAUUAA | GGACUGACGAGAGAUGUAUAUUAAUUUU |
| HTT | NM_002111.6 | 13423 | UUUUUAACUGUCAAACAUGUA | UUUUUAACUGUCAAACAUGUUACAUGUA |
| HTT | NM_002111.6 | 13428 | UAACUGCUUCAAACAUGUA | UUUUUAACUGCUUCAAACAUGUACAUCC |
| HTT | NM_002111.6 | 152 | ACCUGGAAAAGCUGAUGAA | UGGCGACCCUGGAAAAGCUGAUGAAGGCCU |
| HTT | NM_002111.6 | 170 | AAGGCCUUCGAGUCCCUCAA | UGAUGAAGGCCUUCGAGUCCCUCAAGUCCU |
| HTT | NM_002111.6 | 402 | CGCUGGACCGACCAAAGAA | GGACGCCUGCACCGACCAAAGAAGAACU |
| HTT | NM_002111.6 | 420 | AAGAACUUCAGCUACCAAG | AAAGAAGAACUUCAGCUACCAAGAAAGA |
| HTT | NM_002111.6 | 430 | AGCUACCAAGAAAGACCGUG | CUUUCAGCUACCAAGAAAGACCGUGAAU |
| HTT | NM_002111.6 | 446 | CGUGAAUCAUGUCUGUAC | AAGACCGUGAAUCAUGUCUGACAAUAU |
| HTT | NM_002111.6 | 454 | UCAUGUCUGACAAUAUGUG | GUGAAUCAUGUCUGACAAUAUGUGAAAAC |
| HTT | NM_002111.6 | 462 | UGACAAUAUGUGAAAACAU | UUGUCUGACAAUAUGUGAAAACAUAGUGGCC |
| HTT | NM_002111.6 | 467 | AUAAUGUGAAAACAUAGUGC | UGACAAUAUGUGAAAACAUAGUGGCACAGU |
| HTT | NM_002111.6 | 211 | GCAGCAGCAGCAGCAGC | CAGCAGCAGCAGCAGCAGCAGCAGCAG |

| Sense strand (P1) | Antisense Strand (P1) |
|---|---|
| fCmUfGmAfGmAfGmAfCmAfGmAfCmAfG#mA#fA-linkerX | P-mUfUmUfCmUfUmUfCmUfUmUfCmUfCmUfCmA#fmA#fC#mL#fG#mC#fG |
| fGmXfCfAmGfCmUfGmJfUmUfCmAfG#mrA#fC#mrA#fA-linkerX | P-mUfAmUfAmAfAmCfGmCfGmCfAmCfA#mA#fG#mC#fU#mG#fC |
| fUmUfGmAfGmUfUmUfCmAfGmUfAmAfCmCfA#mU#fmU#fA-linkerX | P-mUfGmAfGmAfUmUfCmAfUmUfGmJfA#mC#fA#mC#fA#mA#fA |
| fGmAfGmUfUmUfAmUfGmAfUmAfGmUfA#mC#fmL#fA-linkerX | P-mUfGmUfAmCfAmUfCmAfUmAfA#mA#fA#mC#fU#mC#fA |
| fUmUfGmJfUmUfAmUfCmAfCmUfUmCfCmAfA#mU#fmL#fA-linkerX | P-mUfUmGfGmAfAmGfUmGfAmUfAmA#fC#mA#fC#mA#fA#fA |
| fGmGfCmUfGmUfUmAfGmUfCmCfA#mC#fA#mU#fA-linkerX | P-mUfGmUfGmGfAmCfUmAfAmCfA#mGfCmC#mA#fA#fU |
| fGmUfAmCfAmCfAmGfAmAfUmAfGmAfA#mU#fA-linkerX | P-mUfUmCfGmUfAmUfCmUfAmUfUmCfUmG#tUmG#fU |
| fAmAfGmJfAmCfAmAfAmCfAmAfCmCfA#mU#fA-linkerX | P-mUfGmAfUmGfGmJfUmGfUmUfCmUfU#mAfC#fU |
| fAmAfGmJfAmCfAmAfGmUfAmUfCmUfA#mA#fC#fA-linkerX | P-mUfGmUfUmAfGmJfAmCfAmCfUmUfA#mA#fC#tU |
| fAmAfCmAfCmUfCmCfAmAfCmAfAmAfA#mL#fA-linkerX | P-mUfGmCfUmUfGmUfUmGfUmGfAmGfU#mU#fU#fU |
| fGmUfAmCfAmGfGmAfUmGfGmCfA#mU#fmL#fA-linkerX | P-mUfGmUfAmGfUmGfAmUfUmGfA#mC#fA#fU |
| fCmUfGmJfAmCfGmAfCmUfAmUfGmAfA#mC#fA-linkerX | P-mUfGmJfGmJfAmAfUmGfGmAfUmAfA#mG#fC#fG |
| fUmUfGmCfAmCfGmAfAmAfGmAfA#mC#fA-linkerX | P-mUfGmJfAmCfGmAfAmGfA#mA#fC#tU#mA#fG |
| fCmAfGmAfAmCfGmAfAmAfA#mU#fmL#fA-linkerX | P-mUfUmUfAmAfGmCfAmUfAmAfA#mG#fG#fA |
| fAmAfAmCfAmGfGmJfAmCfAmCfA#mU#fA-linkerX | P-mUfGmAfAmAfAmCfUmAfGmUfAmCfA#mG#fC |
| fGmAfAmCfAmCfAmCfAmGfAmJfAmAfA#mC#fA-linkerX | P-mUfUmAfAmJfAmJfUmCfUmUfAmGfU#mG#fA#fU |
| fUmGfCmUfUmAfAmAfGmJfAmGfAmAfA#mC#fA-linkerX | P-mUfUmAfGmJfAmGfUmGfA#mC#fAmC#fU#mC#fU |
| fAmAfCmAfCmUfGmCfAmAfGmJfAmAfA#mC#fA-linkerX | P-mUfUmAfCmUfAmAfCmAfUmAfA#mA#fC#mC#fU |
| fUmUfGmJfAmAfAmGfGmAfAmAfA#mC#fA-linkerX | P-mUfAmUfUmCfGmAfCmGfAmCfA#mC#fU#mU#fU |

| Sense strand (P2) | Antisense Strand (P2) | H. sapien | M. musculus | M. mulatta | Huntingtin mRNA Expression (% control) | Passive Uptake | Lipid-Mediated Uptake |
|---|---|---|---|---|---|---|---|
| fGfmnUfCmCfAmfEfGmUfUmUfAmUfGmnAfUmUfCfAmnUfCmnAfA-linkerX | P:-mUfmUfmCfAmrG3fUmJfCmnAfUmnAfCfGmCfGmnAfA-linkerX | yes | yes | yes | 34.3 | 197.4 | N/A |
| fAfmUfGmnUfUmfUfAmUfGmtAmfc2UfmnGfmA-linkerX | P:-mUfmUfmCfAmrG3fUmJfCmnAfUmnAfCfGmCfGmnAfU | yes | | yes | 44.8 | 293.2 | N/A |
| fGfmnGfHUfmlJfUmnAfUmnCfAmfCfmJfGfmAfffA-linkerX | P:-mUfmUfmCfAmrG3fUmJfCmnAfUmnAfCfGmCfGmnAfC | yes | | yes | 29.6 | 163.6 | 0.053 |
| fAfmfCfmnAfCfmnAfCmfAfCmJfUmfCfmJfUmCfAfmnA-linkerX | P:-mUfmUfmCfAmrG3fUmJfCmnAfUmnAfCfGmCfGmnAfU | yes | | yes | 28.5 | 156.7 | N/A |
| fUfmnGfUmmGfCmGfAmCfmCfmJfAfmnUfAfmA-linkerX | P:-mUfmUfmCfAmrG3fUmJfCmnAfUmnAfCfGmCfGmnAfC | yes | | yes | 23.7 | 95.53 | 0.048 |
| fAfmCfmnGfCmnAfAmCfmCfAfmCfmfUfmfAffA-linkerX | P:-mUfmUfmCfAmrG3fUmJfCmnAfUmnAfCfGmCfGmnAfU | yes | | yes | 39.3 | 217.9 | N/A |
| fAfmJfmnGfmnAfGmCfAmnUfmCmnCfmJfUmCmAf-linkerX | P:-mUfmUfmCfAmrG3fUmJfCmnAfUmnAfCfGmCfGmnAfU | yes | | yes | 35.3 | 191.7 | 0.091 |
| fUfmnGfmCfmnJfUmCfGmAfCfmCfUmCfUmAfUmfA-linkerX | P:-mUfmUfmCfAmrG3fUmJfCmnAfUmnAfCfGmCfGmnAfA | yes | yes | yes | 53.5 | 765.7 | N/A |
| fUfmnCfmUfmnJfUmfAfmnGfUmfCfGfmA-linkerX | P:-mUfmUfmCfAmrG3fUmJfCmnAfUmnAfCfGmCfGmnAfA | yes | yes | yes | 41.2 | 217.8 | N/A |
| fGfmCfmnGfmnCfmAfmfAmnCfUmfCfmfGfCmfGfmnA-linkerX | P:-mUfmUfmCfAmrG3fUmJfCmnAfUmnAfCfGmCfGmnAfC | yes | | yes | 35.6 | 230.2 | 0.080 |
| fGfmCfmnGfmnCfmAfmGfmCnCfmCfmnCfmfAfmA-linkerX | P:-mUfmUfmCfAmrG3fUmJfCmnAfUmnAfCfGmCfGmnAfC | yes | | yes | 25.4 | 147.9 | N/A |
| fGfmCfmnGfmnCfmAfmfAfGmnCfUmfCfmfAfCmfCfmnA-linkerX | P:-mUfmUfmCfAmrG3fUmJfCmnAfUmnAfCfGmCfGmnAfC | yes | | yes | 28.3 | 89.8 | 0.056 |
| fUfmnGfmCfmnJfUmfAfmfCfAmfUfCmUfmfUmAfmfA-linkerX | P:-mUfmUfmCfAmrG3fUmJfCmnAfUmnAfCfGmCfGmnAfC | yes | yes | yes | 45.0 | 236.1 | N/A |
| fUfmnGfmCfmnJfUmfCfmfCfAmfUfCmfUmfUmAfmfA-linkerX | P:-mUfmUfmCfAmrG3fUmJfCmnAfUmnAfCfGmCfGmnAfA | yes | yes | yes | 31.1 | 156.7 | 0.059 |
| fUfmnGfmCfmnJfUmfAfmGfmnAfUmfCmUmfAmfmA-linkerX | P:-mUfmUfmCfAmrG3fUmJfCmnAfUmnAfCfGmCfGmnAfA | yes | yes | yes | 25.9 | 217.7 | 0.052 |
| fUfmnGfmJfmnAfmfAfCfmmAfGmnCfUmfCfGmfAmA-linkerX | P:-mUfmUfmCfAmrG3fUmJfCmnAfUmnAfCfGmCfGmnAfA | yes | | yes | 28.6 | 82.2 | 0.004 |
| fUfmnGfmCfUmCfAmfCfGmfAmfCfmJfCmfCmmfAfmA-linkerX | P:-mUfmUfmCfAmrG3fUmJfCmnAfUmnAfCfGmCfGmnGfU | yes | | yes | 67.4 | N/A | N/A |
| fUfmnGfmGfmCnAmfGfCmnfAmfAmfGfUfCfmfCfmfAfmA-linkerX | P:-mUfmUfmCfAmrG3fUmJfCmnAfUmnAfCfGmCfGmnAfA | yes | | yes | 51.5 | N/A | N/A |
| fUfmnGfmCfmCfmfAfmnCfmCfAmfGfCmfCfmJfCmmfAfmA-linkerX | P:-mUfmUfmCfAmrG3fUmJfCmnAfUmnAfCfGmCfGmnAfC | yes | | yes | 68.2 | N/A | N/A |
| fGfmnCfmAfmnAfmfAfmnCfmfAmfCmfAfmfUfmfAfmfA-linkerX | P:-mUfmUfmCfAmrG3fUmJfCmnAfUmnAfCfGmCfGmnAfU | yes | | yes | 45.5 | N/A | N/A |
| fCfmnCfmnAfmfGfmfUmfGfmCfAmfAfCmfGfmJfAfmfA-linkerX | P:-mUfmUfmCfAmrG3fUmJfCmnAfUmnAfCfGmCfGmnAfG | yes | | yes | 64.8 | N/A | N/A |
| fAfmnAfmnAfmfGfUmfUmfGfmCfAmfAfCmfGfmJfAfmfA-linkerX | P:-mUfmUfmCfAmrG3fUmJfCmnAfUmnAfCfGmCfGmnAfU | yes | | yes | 51.5 | N/A | N/A |
| fAfmnGfmnUfUmfAmfCfmAfmfUfmfGfmCfmJfUmAfmA-linkerX | P:-mUfmUfmCfAmrG3fUmJfCmnAfUmnAfCfGmCfGmnAfU | yes | | yes | 52.9 | N/A | N/A |

| hsiRNA ID | hsiRNA Structure | IC50 (Passive Uptake) | IC50 (Lipid-mediated Uptake) |
|---|---|---|---|
| hsiRNA<sup>FLT1</sup> | | 169 nM | 7.3 pM |
| FM.1-hsiRNA<sup>FLT1</sup> | | 70 nM | 2.3 pM |
| Fluoro tail-hsiRNA<sup>FLT1</sup> | | 222 nM | 2.9 pM |
| Fluoro AS-hsiRNA<sup>FLT1</sup> | | 251 nM | 6.4 pM |
| FM-hsiRNA-mismatch<sup>FLT1</sup> | | 135 nM | 3.4 pM |
| Fluoro AS-hsiRNA-mismatch<sup>FLT1</sup> | | 273 nM | 29 pM |

○ 2'-OH   ● 2'-O-Methyl   ◐ 2'-F   ⊗ 2'-F Mismatch   — Phosphodiester   ▬ Phosphorothioate

Fig. 36A

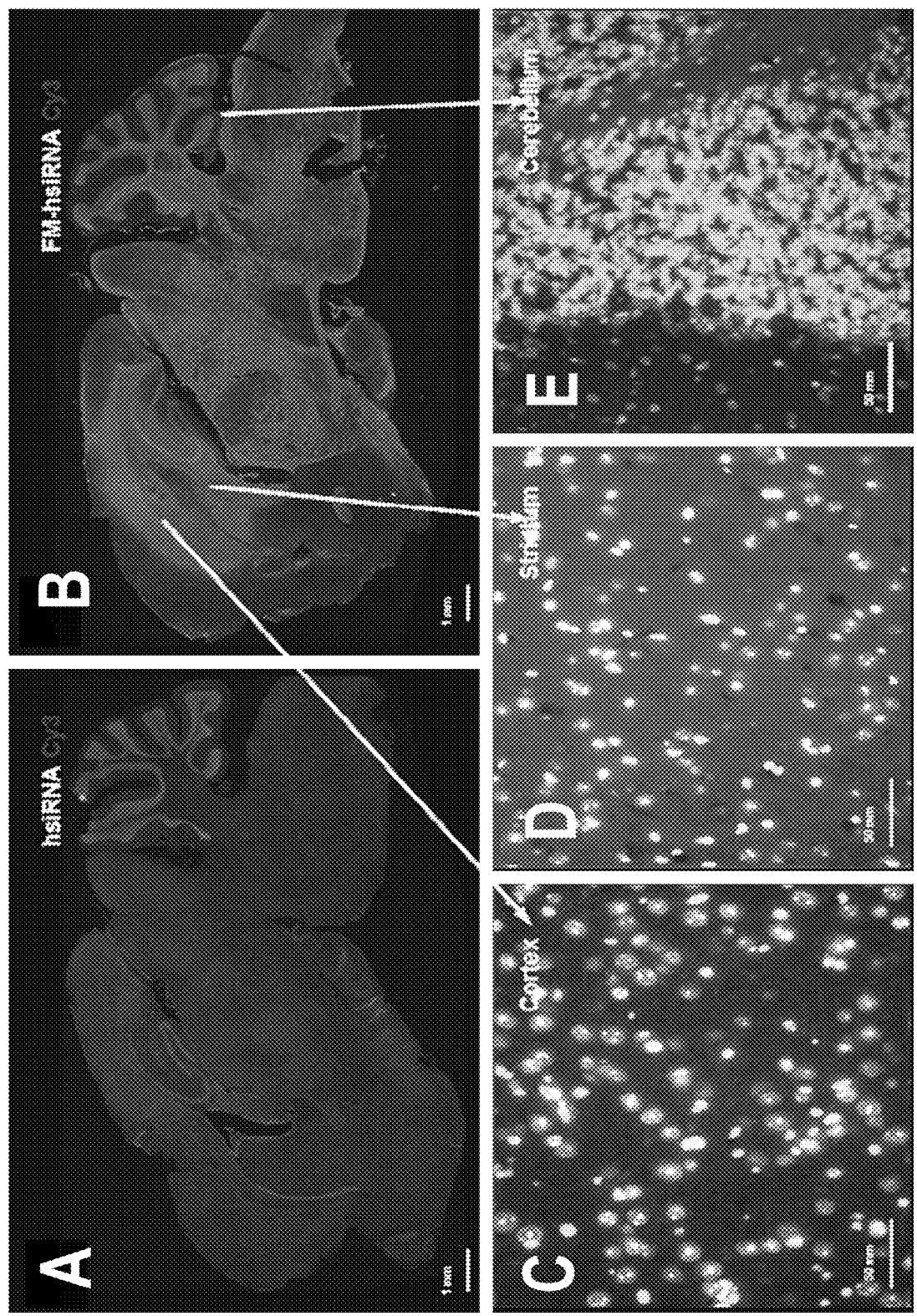
Fig. 38A-E

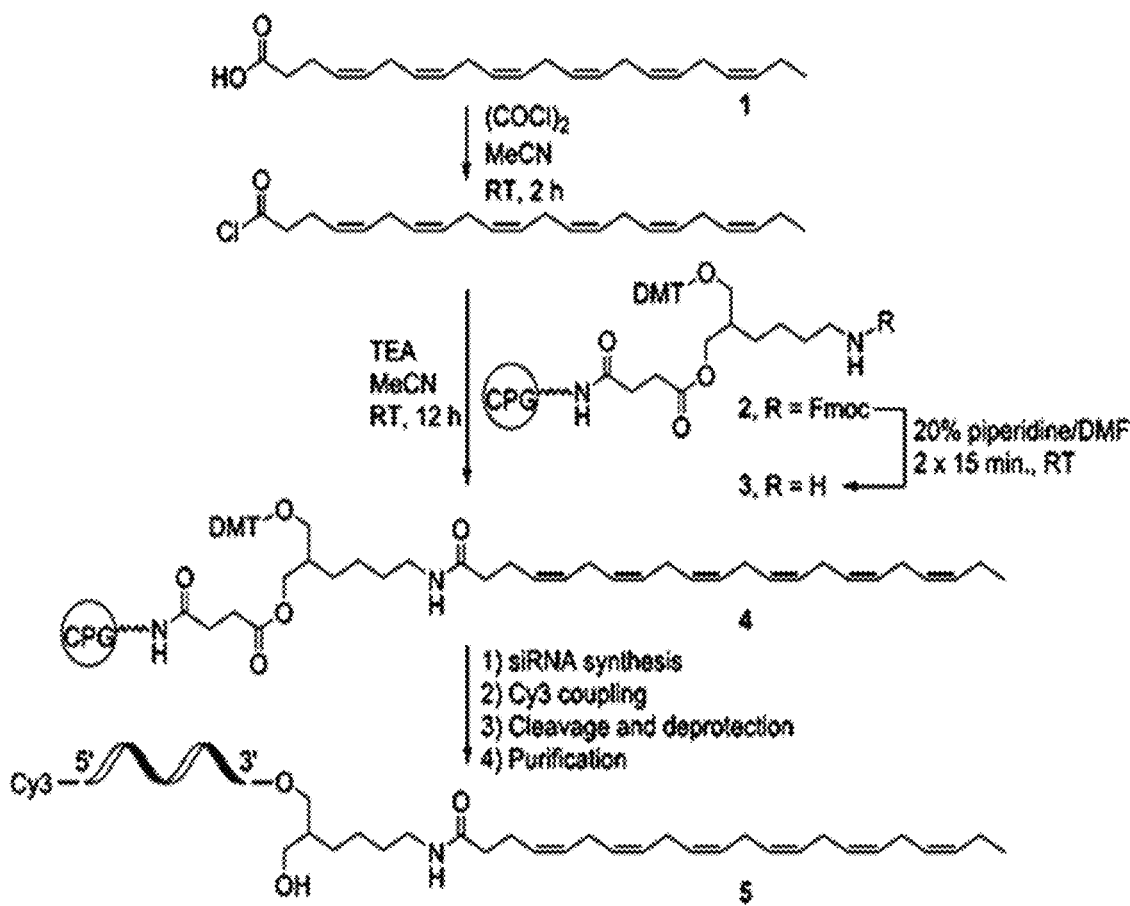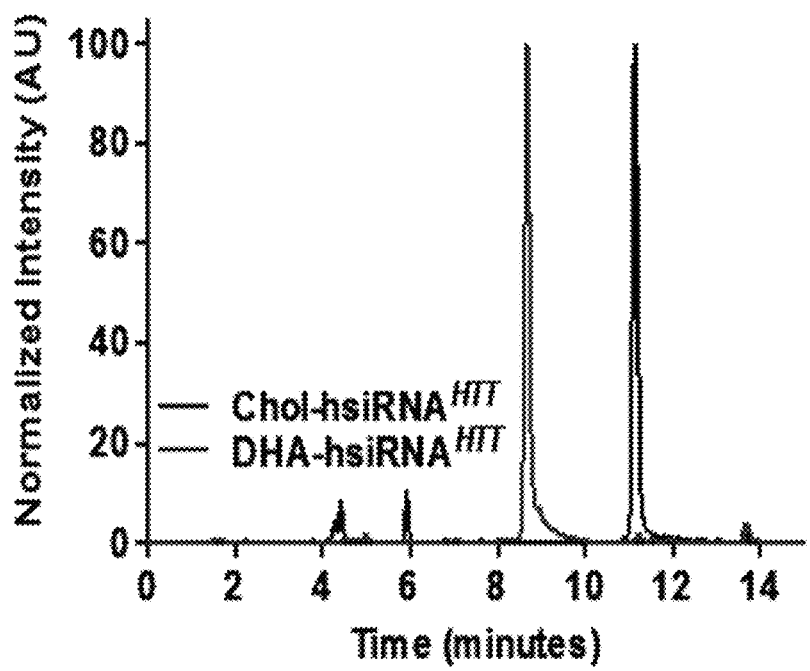
Fig. 42

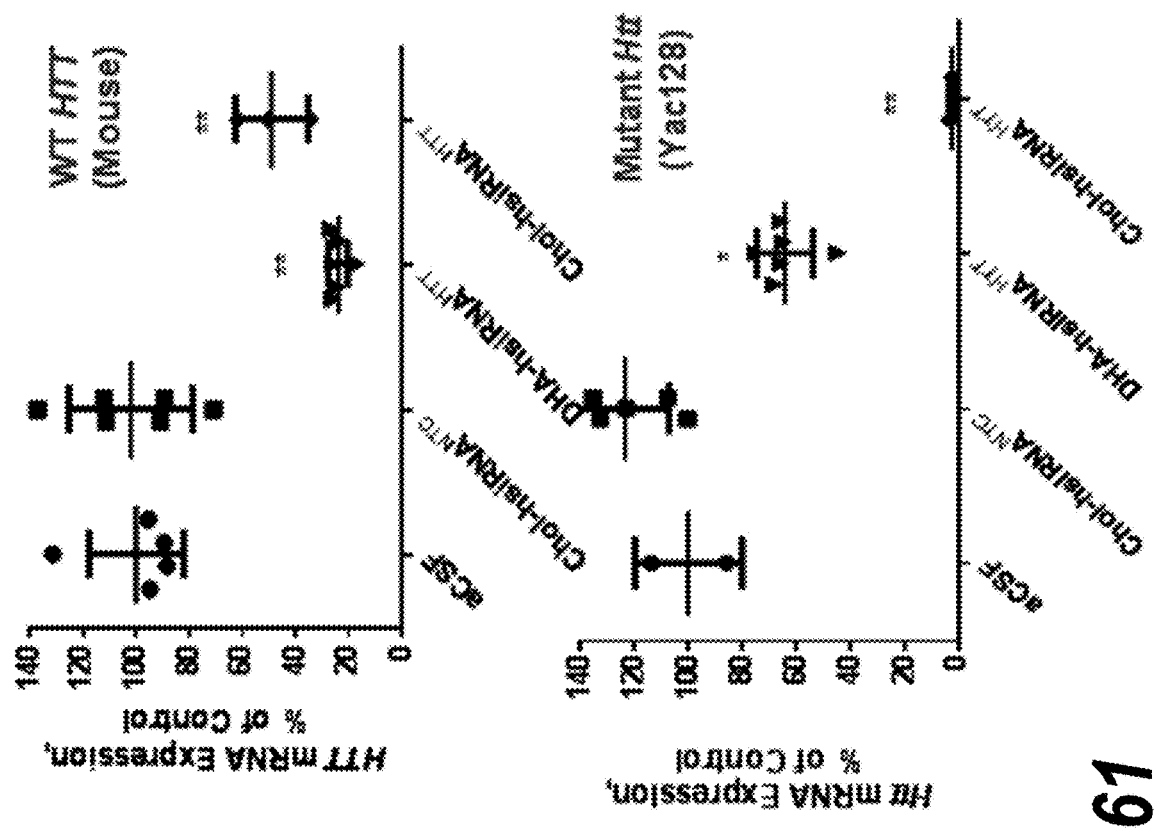
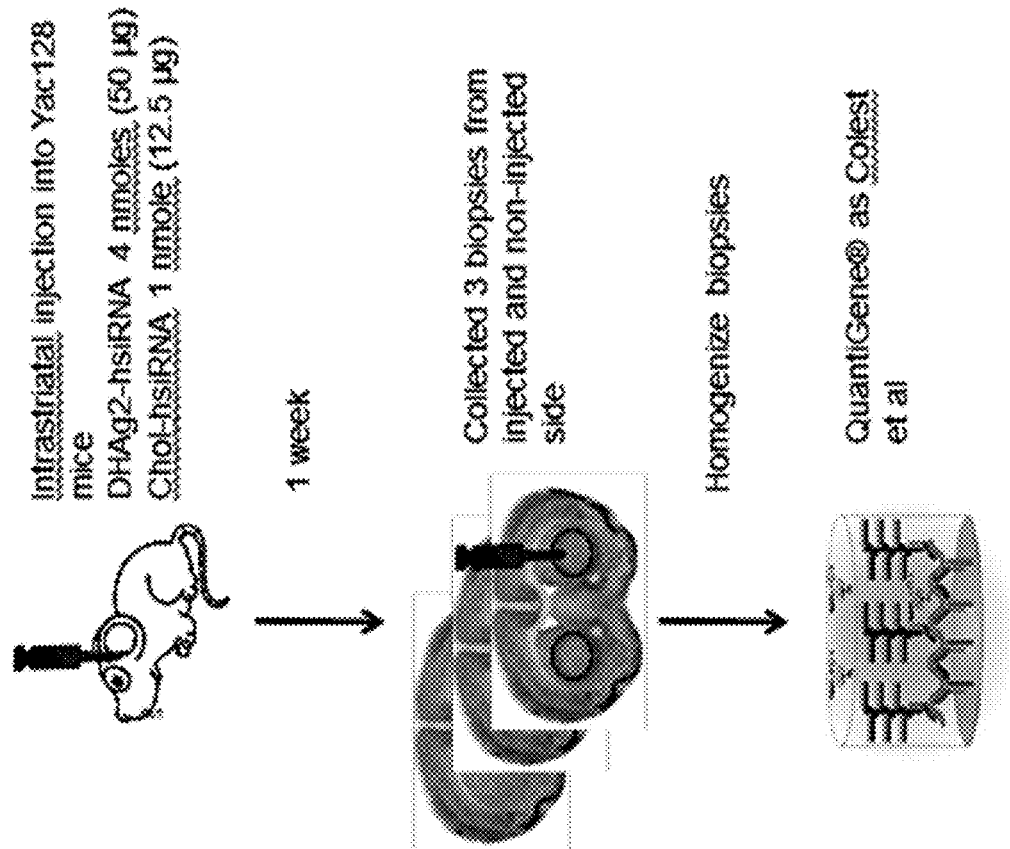
Fig. 61

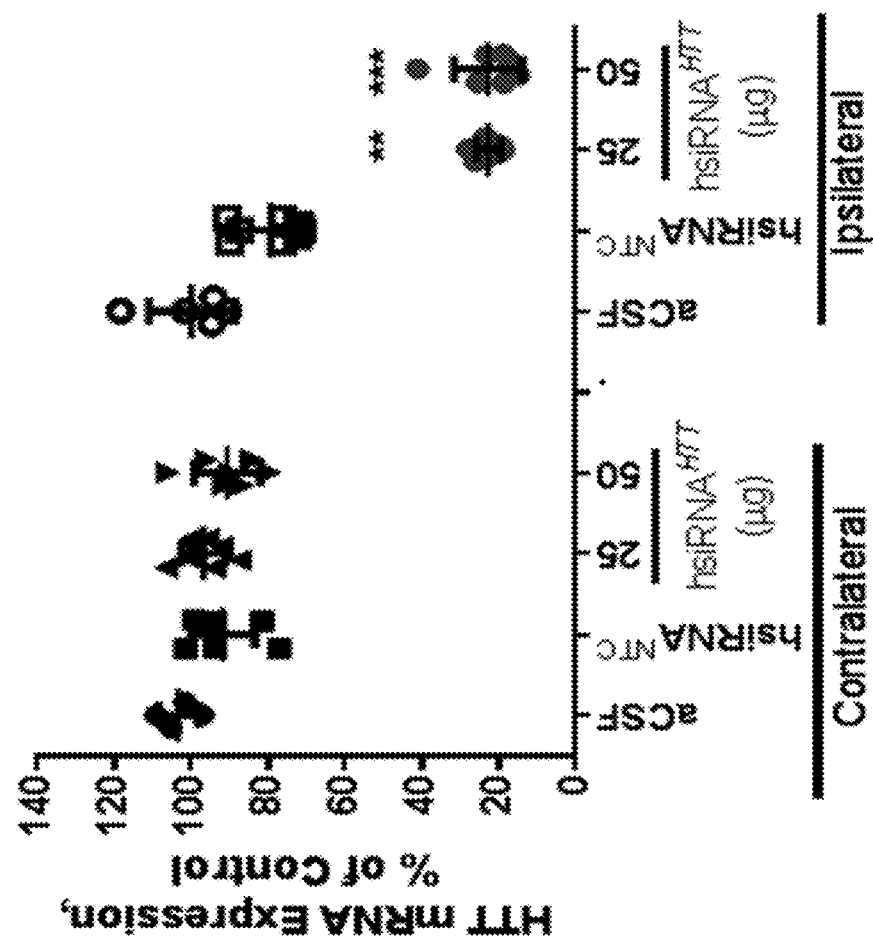
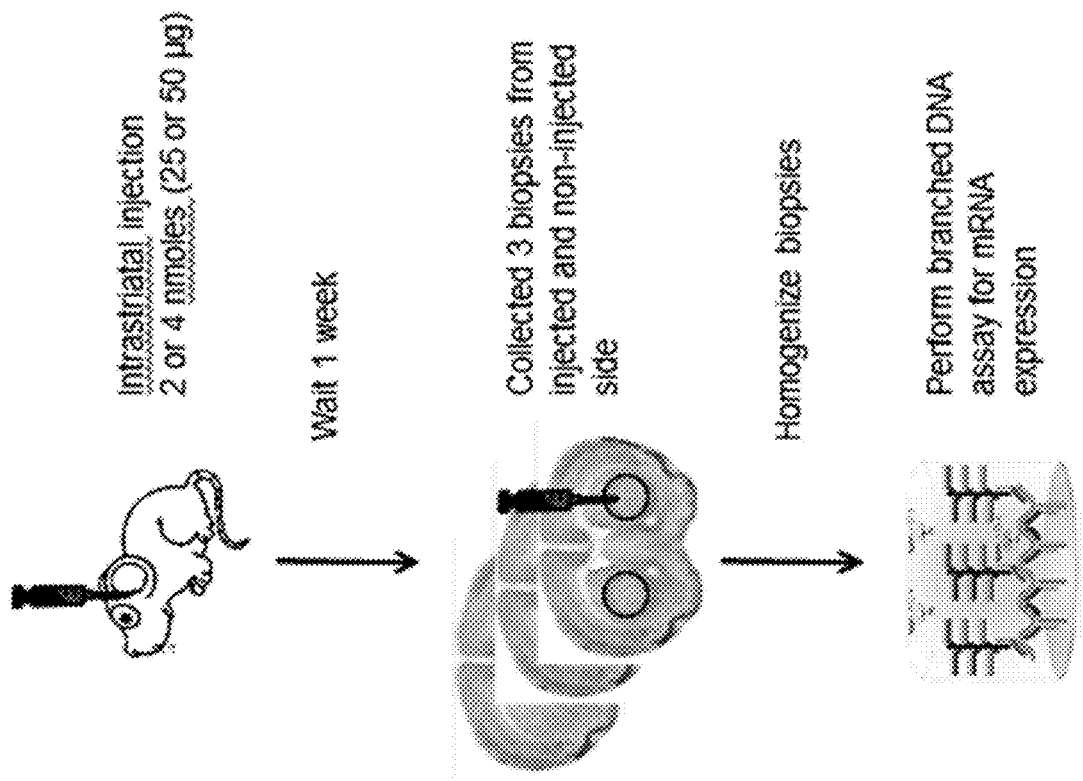
Fig. 66

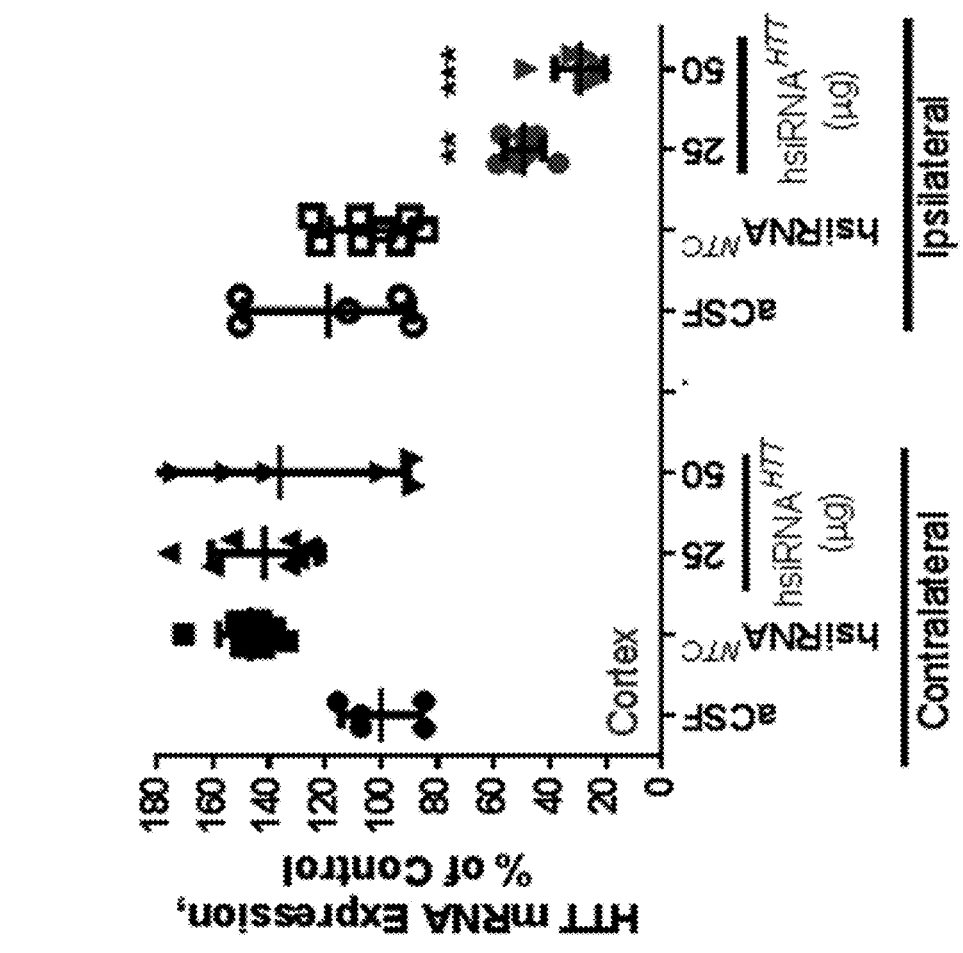
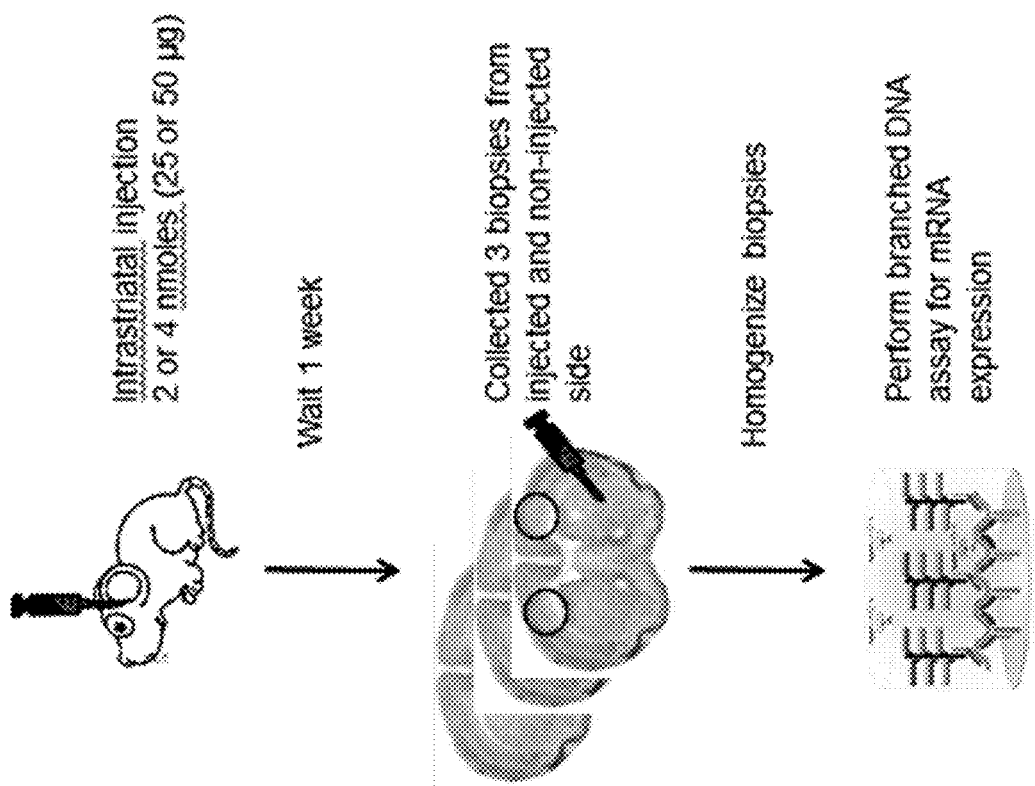
Fig. 67

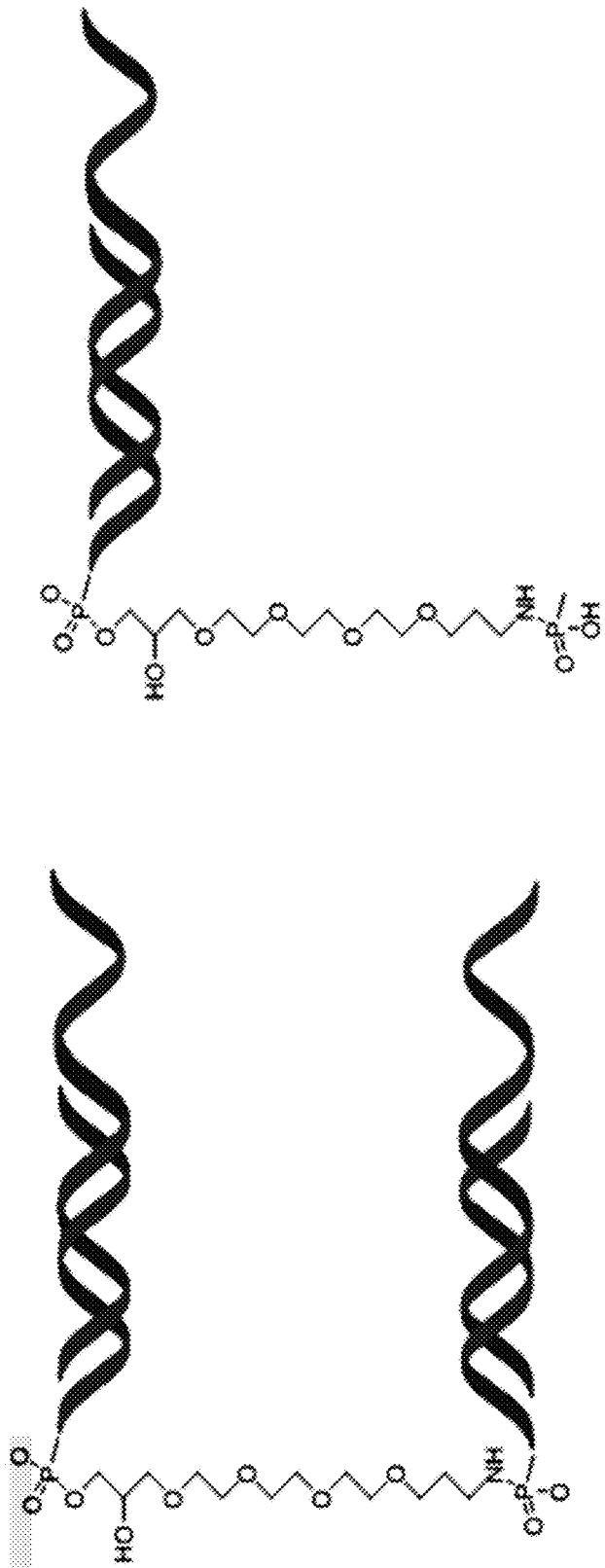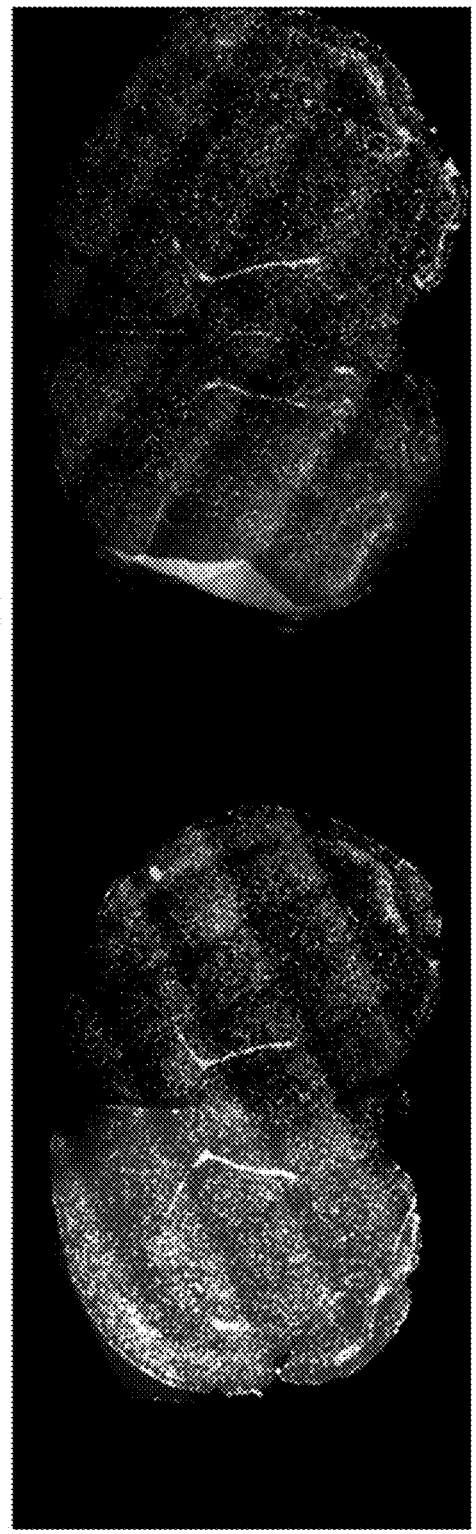
Fig. 70

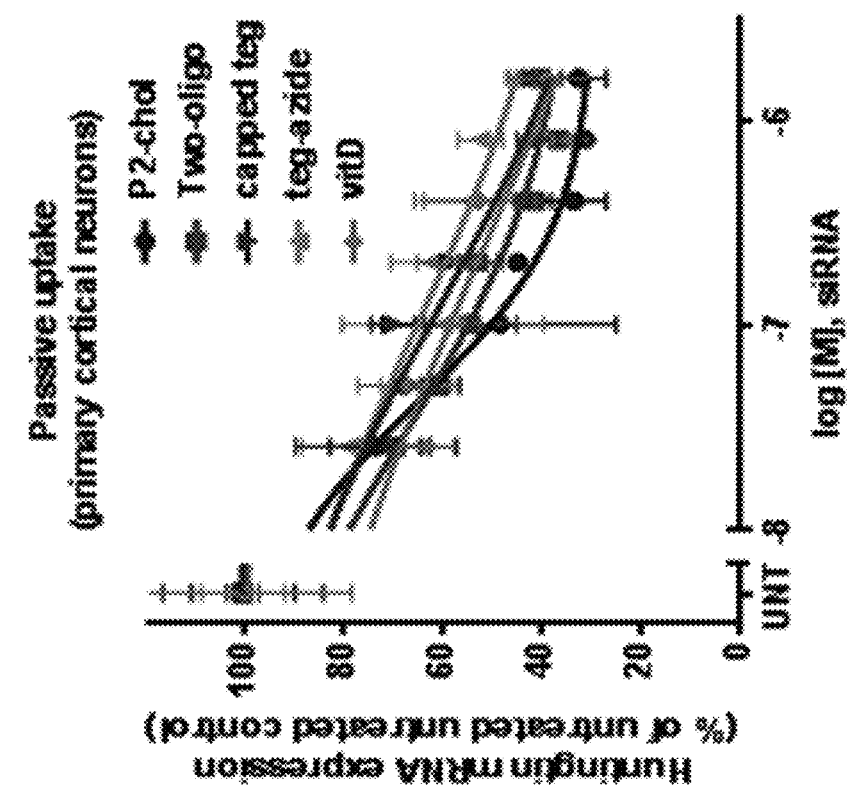
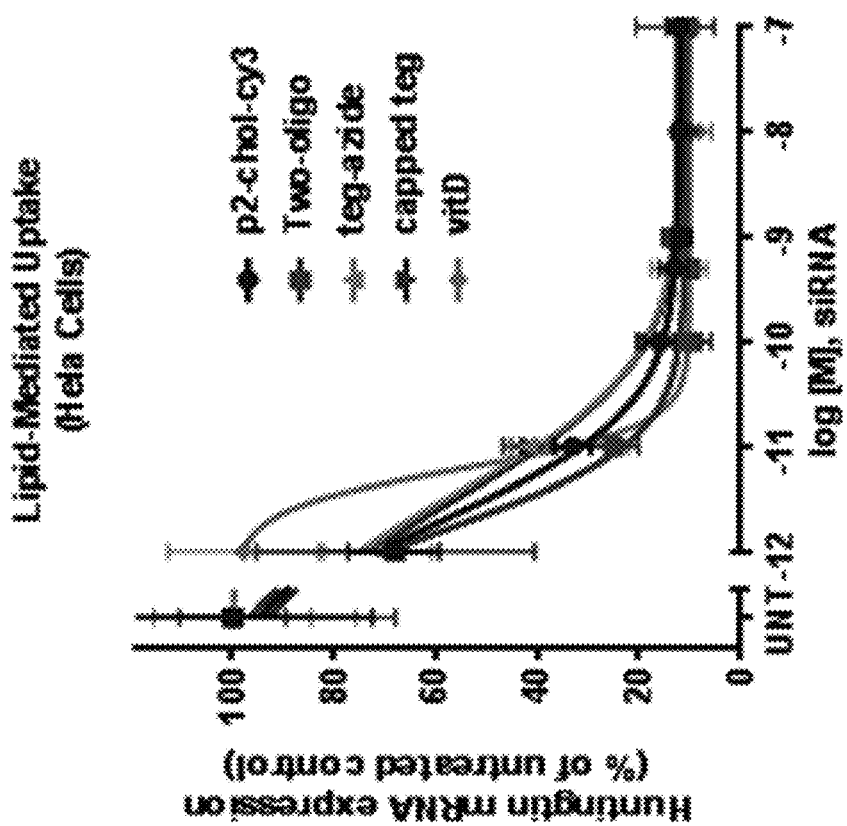
Fig. 80

$R^1R^3\underline{U}=A-\underline{A}-U-\underline{C}-U-\underline{C}-U-\underline{U}-U-\underline{A}-C-\underline{U}=G=\underline{A}=U=\underline{A}=UR^3\underline{A}$ (5'-3')

. . . . . . . . . . . . . . . . . .

$-\underline{A}R^3\underline{A}=\underline{U}-U-\underline{A}-G-\underline{A}-G-\underline{A}-A-\underline{A}-U-\underline{G}=AR^3\underline{C}$ (3'-5')

L $R^1=\underline{U}=A-\underline{A}-U-\underline{C}-U-\underline{C}-U-\underline{U}-U-\underline{A}-C-\underline{U}=G=\underline{A}=U=\underline{A}=U=\underline{A}$ (5'-3')

. . . . . . . . . . . . . . . . .

$-\underline{A}=\underline{A}=\underline{U}-U-\underline{A}-G-\underline{A}-G-\underline{A}-A-\underline{A}-U-\underline{G}=A=\underline{C}$ (3'-5')

Legend

<u>X</u>- 2'-deoxy-2'-fluoro
X̄- 2'-O-methyl

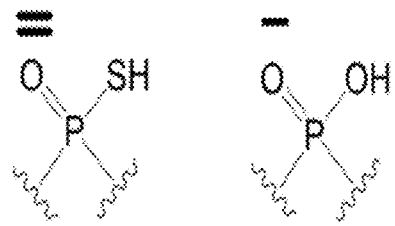

Fig. 81

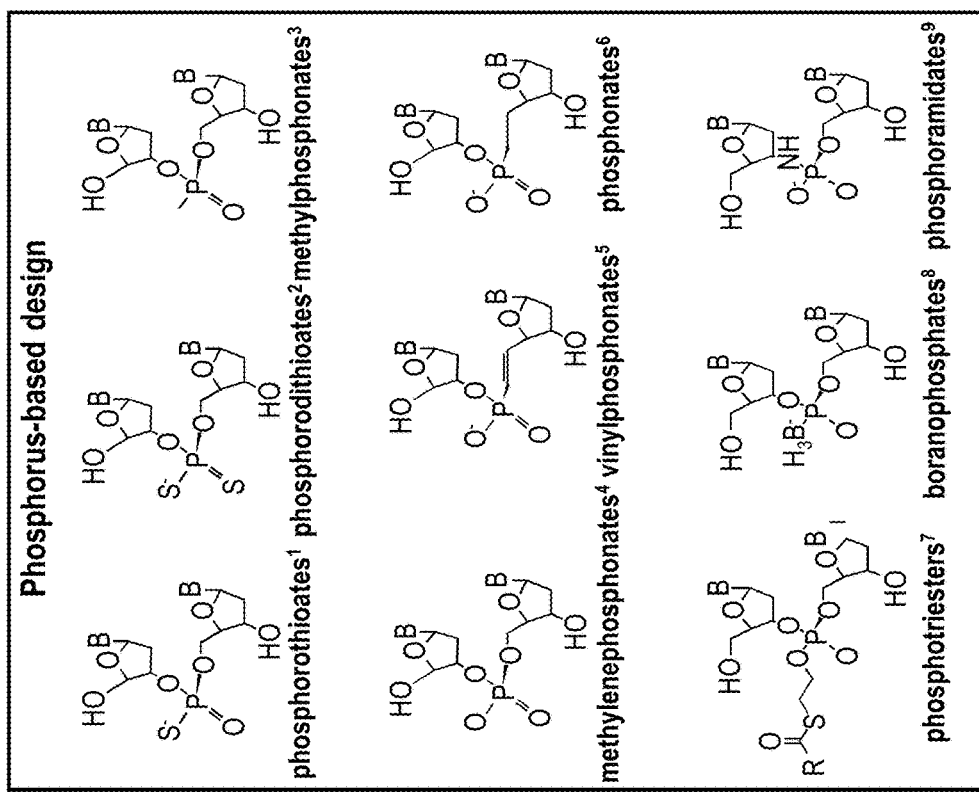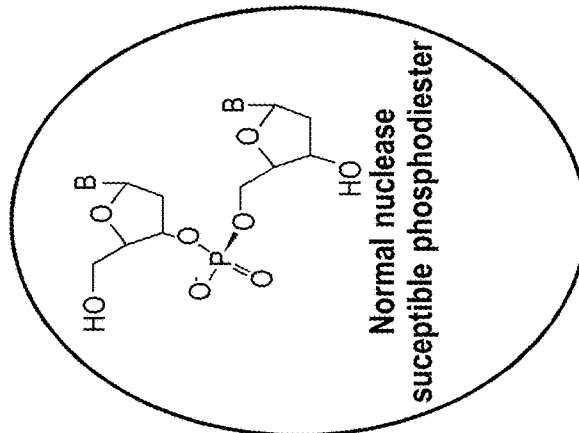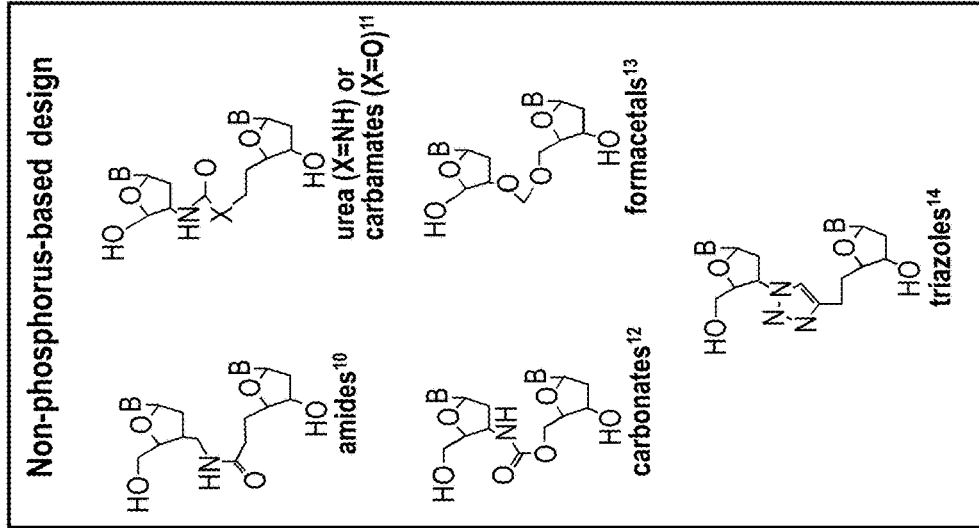
Fig. 82

```
R¹=U=A-A-U-C-U-C-U-U-U-A-C-U=G=A=U=A=U=A    (5'-3')
     . . . . . . . . . . . . . . . . .
  ┌── A=A-U-U-A-G-A-G-A-A-A-U-G=A=C          (3'-5')
  │
L │
  │ R¹=U=A-A-U-C-U-C-U-U-U-A-C-U=G=A=U=A=U=A  (5'-3')
  │  . . . . . . . . . . . . . . . . .
  └── A=A-U-U-A-G-A-G-A-A-A-U-G=A=C          (3'-5')
```
*Fig. 83*
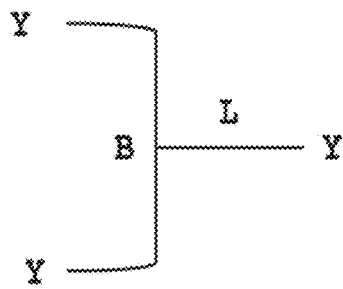
```
Y=    R¹R³U=A-A-U-C-U-C-U-U-U-A-C-U=G=A=U=A=UR³A   (5'-3')
         . . . . . . . . . . . . . . . . .
      AR³A=U-U-A-G-A-G-A-A-A-U-G=AR³C              (3'-5')
```
Legend
X - 2'-deoxy-2'-fluoro
X - 2'-O-methyl
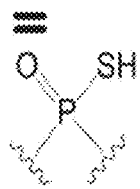 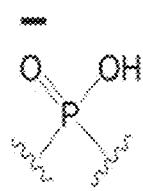
*Fig. 84*

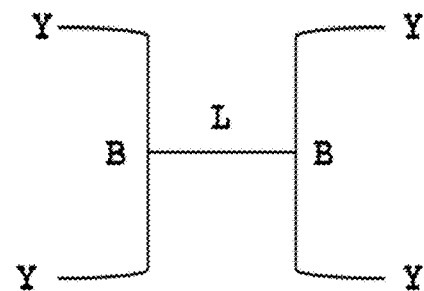
Y= 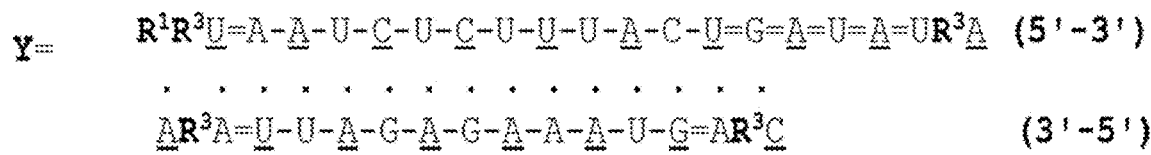
Legend
X̲- 2'-deoxy-2'-fluoro
X̳- 2'-O-methyl
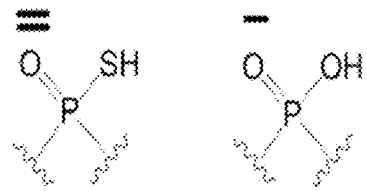
Fig. 85
Y= 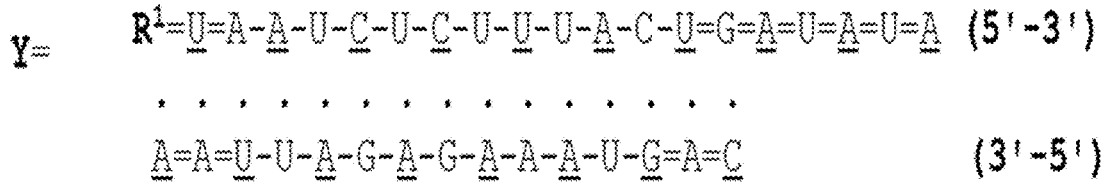
Fig. 86

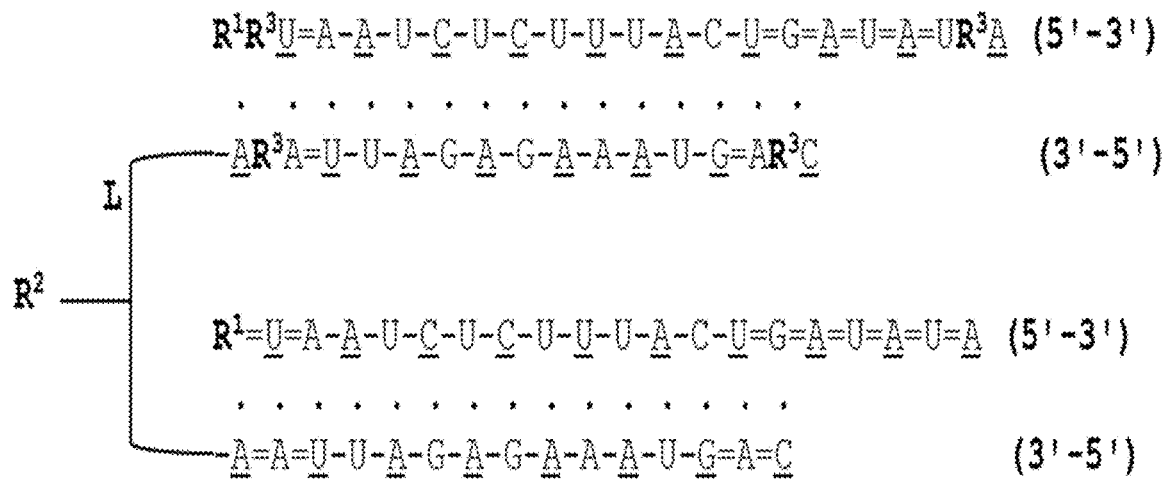
Legend
X- 2'-deoxy-2'-fluoro
X- 2'-O-methyl
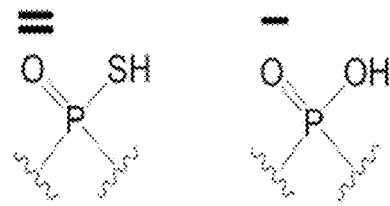
Fig. 87
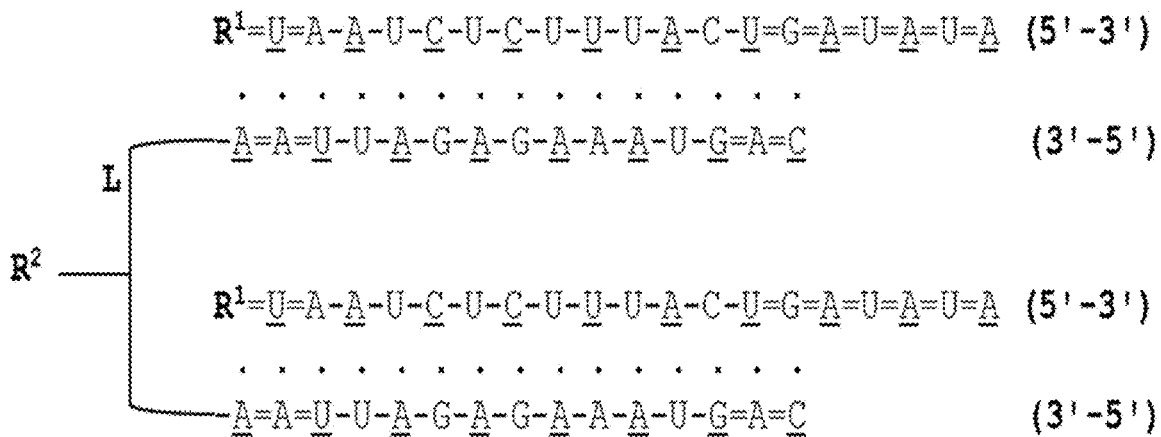
Fig. 88

(5'-3')  R¹R³U=A-A-U-C-U-C-U-U-U-A-C-U=G=A=U=A=UR³A
(3'-5')  R²-AR³A=U-U-A-G-A-G-A-A-A-U-G=AR³C
Legend
X- 2'-deoxy-2'-fluoro
X- 2'-O-methyl
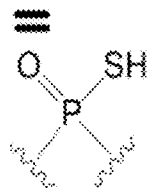  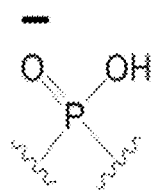
*Fig. 89*
(5'-3')  R¹=U=A-A-U-C-U-C-U-U-U-A-C-U=G=A=U=A=U=A
(3'-5')  R²-A=A=U-U-A-G-A-G-A-A-A-U-G=A=C
*Fig. 90*

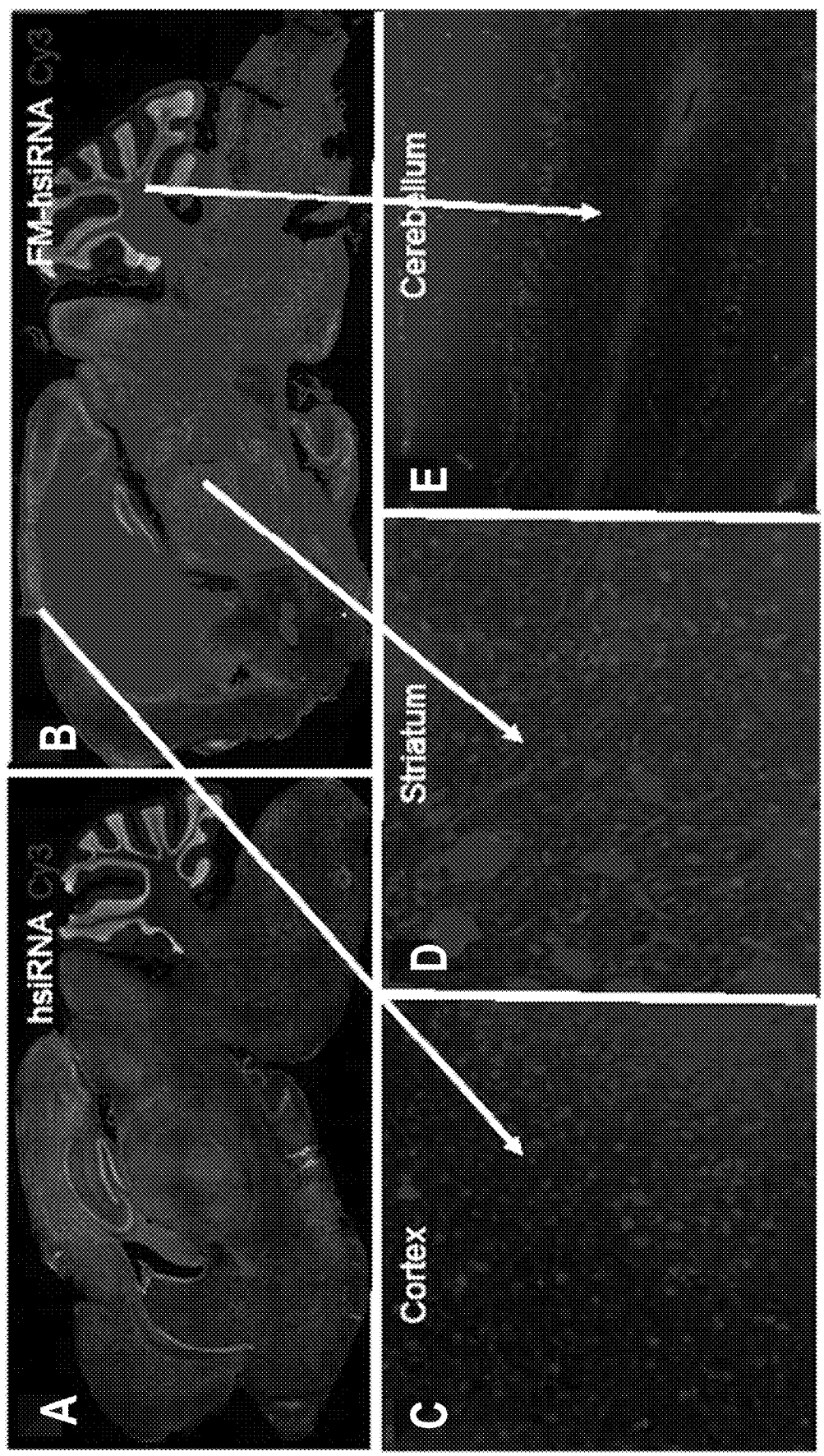
Fig. 111A-E

OLIGONUCLEOTIDE COMPOUNDS FOR TARGETING HUNTINGTIN MRNA

RELATED APPLICATIONS

This application is a continuation of U.S. patent application Ser. No. 15/697,120, filed Sep. 6, 2017, which is a continuation of U.S. patent application Ser. No. 15/089,319, filed Apr. 1, 2016, now U.S. Pat. No. 9,809,817, which claims priority to U.S. Provisional Patent Application Ser. No. 62/289,274, filed Jan. 31, 2016, and U.S. Provisional Patent Application Ser. No. 62/142,731, filed Apr. 3, 2015. The entire contents of these applications are herein incorporated by reference.

STATEMENT REGARDING FEDERALLY SPONSORED RESEARCH OR DEVELOPMENT

This invention was made with government support under grant numbers NS038194 and TR000888 awarded by the National Institutes of Health. The Government has certain rights in the invention.

SEQUENCE LISTING

[002.1] The instant application contains a Sequence Listing which has been submitted electronically in ASCII format and is hereby incorporated by reference in its entirety. Said ASCII copy, created on Jan. 30, 2019, is named 607857_UM9-203CON2_Sequence_Listing.txt and is 310,927 bytes in size.

FIELD OF THE INVENTION

This disclosure relates to novel huntingtin targets and novel oligonucleotides for the treatment of Huntington's disease.

BACKGROUND

Neurological disorders including Huntington's disease, Parkinson's disease and Alzheimer's disease represent a major unmet medical need. In some cases, these diseases are monogenic, making them ideal targets for oligonucleotide therapeutic intervention, e.g., RNA interference (RNAi). RNAi is a fundamental mechanism involving short double stranded RNA fragments that can be used to reprogram cellular machinery and silence and degrade targeted mRNA on demand. This technology is clinically advanced and has revolutionized the field of human functional genetics.

Many different technologies have been explored for mRNA knockdown both as therapeutics and as tools for functional study, including viral based delivery of short hairpin RNAs (shRNAs), antisense oligonucleotides (ASOs), and naked or slightly modified siRNAs (Sah, D. W. Y. & Aronin, N. Oligonucleotide therapeutic approaches for Huntington disease. *J. Clin. Invest.* 121, 500-507 (2011); DiFiglia, M. et al. Therapeutic silencing of mutant huntingtin with siRNA attenuates striatal and cortical neuropathology and behavioral deficits. *Proceedings of the National Academy of Sciences of the United States of America* 104, 17204-17209 (2007)).

ASOs have also shown to be a promising approach. This technology exhibits efficient delivery to cells without a delivery vehicle and has been administered to brain for the treatment of Huntington's disease for successful knockdown in both rodent and non-human primate brains (Mantha, N., Das, S. K. & Das, N. G. RNAi-based therapies for Huntington's disease: delivery challenges and opportunities. *Therapeutic delivery* 3, 1061-1076 (2012); Kordasiewicz, H. B. et al. Sustained Therapeutic Reversal of Huntington's Disease by Transient Repression of Huntingtin Synthesis. *NEURON* 74, 1031-1044 (2012)). Unfortunately, current studies show that a 700 µg cumulative dose administrated over two weeks is required to see just 50% silencing (Kordasiewicz, Supra).

Unmodified siRNA ("naked siRNA") has been difficult to deliver to more sensitive cell lines and in vivo to tissue in the past. Although transfection reagents such as Lipofectamine can be used, there is a very narrow window within which it is efficacious and non-toxic, and it must be optimized independently for different batches of neurons to determine siRNA to lipid ratios necessary for comparable levels of silencing (Bell, H., Kimber, W. L., Li, M. & Whittle, I. R. Liposomal transfection efficiency and toxicity on glioma cell lines: in vitro and in vivo studies. *NeuroReport* 9, 793-798 (1998); Dass, C. R. Cytotoxicity issues pertinent to lipoplex-mediated gene therapy in-vivo. *Journal of Pharmacy and Pharmacology* 1-9 (2010); Masotti, A. et al. Comparison of different commercially available cationic liposome-DNA lipoplexes: Parameters influencing toxicity and transfection efficiency. *Colloids and Surfaces B: Biointerfaces* 68, 136-144 (2009); Zou, L. L. et al. Liposome-mediated NGF gene transfection following neuronal injury: potential therapeutic applications. *Gene Ther* 6, 994-1005 (1999)). Hydrophobically modified siRNAs have also been used as an alternative for cellular and brain delivery (Sah, Supra; Soutschek, J. et al. Therapeutic silencing of an endogenous gene by systemic administration of modified siRNAs. *Nature* 432, 173-178 (2004); Cheng, K., Ye, Z., Guntaka, R. V. & Mahato, R. I. Enhanced hepatic uptake and bioactivity of type alpha1(I) collagen gene promoter-specific triplex-forming oligonucleotides after conjugation with cholesterol. *Journal of Pharmacology and Experimental Therapeutics* 317, 797-805 (2006); Byrne, M. et al. Novel Hydrophobically Modified Asymmetric RNAi Compounds (sd-rxRNA) Demonstrate Robust Efficacy in the Eye. *Journal of Ocular Pharmacology and Therapeutics* 29, 855-864 (2013)), and some of these compounds have even made it to clinic, but ensuring both chemical stability and minimal toxicity while maximizing delivery remains a difficult task. Current hurdles in RNAi technology limit its ability to be used for both functional genomics studies and therapeutics, providing an opportunity for improvement to their design as it applies to the area of neuroscience both in vitro and in vivo.

SUMMARY

Accordingly, provided herein are novel huntingtin target sequences. Also provided herein are novel RNA molecules (e.g., siRNAs) that target the novel huntingtin target sequences. Said novel RNA molecules (e.g., siRNAs) demonstrate efficacy and potency in both primary neurons in vitro, and in vivo in mouse brain subsequent to a single, low dose injection.

In one aspect, an RNA molecule is provided that is between 15 and 30 bases in length or between 15 and 35 bases in length, comprising a region of complementarity which is substantially complementary to 5' CAGUAAAGA-GAUUAA 3' (SEQ ID NO: 1).

In certain embodiments, the RNA molecule is single stranded (ss) RNA or double stranded (ds) RNA. In certain embodiments, the dsRNA comprises a sense strand and an antisense strand, wherein the antisense strand comprises the region of complementarity which is substantially complementary to 5' CAGUAAAGAGAUUAA 3' (SEQ ID NO: 1).

In certain embodiments, the dsRNA is between 30 and 35 base pairs in length. In certain embodiments the region of complementarity is complementary to at least 10, 11, 12 or 13 contiguous nucleotides of SEQ ID NO:1. In certain embodiments, the region of complementarity contains no more than 3 mismatches with SEQ ID NO:1. In certain embodiments, the region of complementarity is fully complementary to SEQ ID NO: 1.

In certain embodiments, the dsRNA is blunt-ended. In certain embodiments, the dsRNA comprises at least one single stranded nucleotide overhang. In certain embodiments, the dsRNA comprises naturally occurring nucleotides.

In certain embodiments, the dsRNA comprises at least one modified nucleotide. In certain embodiments, the modified nucleotide is chosen from the group of: a 2'-O-methyl modified nucleotide, a nucleotide comprising a 5'phosphorothioate group, and a terminal nucleotide linked to a cholesteryl derivative or dodecanoic acid bisdecylamide group. In certain embodiments, the modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. In certain embodiments, the dsRNA comprises at least one 2'-O-methyl modified nucleotide and at least one nucleotide comprising a 5'phosphorothioate group.

In certain embodiments, the RNA molecule comprises a 5' end, a 3' end and has complementarity to a target, wherein: (1) the RNA molecule comprises alternating 2'-methoxy-ribonucleotides and 2'-fluoro-ribonucleotides; (2) the nucleotides at positions 2 and 14 from the 5' end are not 2'-methoxy-ribonucleotides; (3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In certain embodiments, the dsRNA has a 5' end, a 3' end and complementarity to a target, and comprises a first oligonucleotide and a second oligonucleotide, wherein: (1) the first oligonucleotide comprises a sequence set forth as SEQ ID NO:1; (2) a portion of the first oligonucleotide is complementary to a portion of the second oligonucleotide; (3) the second oligonucleotide comprises alternating 2'-methoxy-ribonucleotides and 2'-fluoro-ribonucleotides; (4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In certain embodiments, the second oligonucleotide is linked to a hydrophobic molecule at the 3' end of the second oligonucleotide. In certain embodiments, the linkage between the second oligonucleotide and the hydrophobic molecule comprises polyethylene glycol or triethylene glycol. In certain embodiments, the nucleotides at positions 1 and 2 from the 3' end of second oligonucleotide are connected to adjacent nucleotides via phosphorothioate linkages. In certain embodiments, the nucleotides at positions 1 and 2 from the 3' end of second oligonucleotide, and the nucleotides at positions 1 and 2 from the 5' end of second oligonucleotide, are connected to adjacent ribonucleotides via phosphorothioate linkages.

In certain aspects, a pharmaceutical composition for inhibiting the expression of the HTT gene in an organism, comprising a dsRNA and a pharmaceutically acceptable carrier is provided. The dsRNA comprises a sense strand and an antisense strand. The dsRNA is between 15 and 35 base pairs in length and the antisense strand comprises a region of complementarity which is substantially complementary to 5' CAGUAAAGAGAUUAA 3' (SEQ ID NO: 1).

In certain embodiments, the dsRNA comprises a cholesterol moiety.

In certain aspects, a method for inhibiting expression of HTT gene in a cell is provided. The method includes the steps of introducing into the cell a double-stranded ribonucleic acid (dsRNA) comprising a sense strand and an antisense strand, the dsRNA is between 15 and 35 base pairs in length and the antisense strand comprises a region of complementarity which is substantially complementary to 5' CAGUAAAGAGAUUAA 3' (SEQ ID NO:1), and maintaining the cell produced in step (a) for a time sufficient to obtain degradation of the mRNA transcript of the HTT gene, thereby inhibiting expression of the HTT gene in the cell.

In certain aspects, a method of treating or managing Huntington's disease comprising administering to a patient in need of such treatment or management a therapeutically effective amount of a dsRNA is provided. The dsRNA comprises a sense strand and an antisense strand, and is between 15 and 35 base pairs in length, and the antisense strand comprises a region of complementarity which is substantially complementary to 5' CAGUAAAGA-GAUUAA 3' (SEQ ID NO: 1).

In certain embodiments, the dsRNA is administered to the brain of the patient. In certain embodiments, the dsRNA is administered by any of intrastriatal, intracerebroventricular and/or intrathecal infusion and/or pump. In certain embodiments, administering the dsRNA to the brain causes a decrease in HTT gene mRNA in the striatum. In certain embodiments, administering the dsRNA to the brain causes a decrease in HTT gene mRNA in the cortex.

In certain aspects, a vector for inhibiting the expression of HTT gene in a cell is provided. The vector comprising a regulatory sequence operably linked to a nucleotide sequence that encodes an RNA molecule substantially complementary to 5' CAGUAAAGAGAUUAA 3' (SEQ ID NO:1), wherein said RNA molecule is between 15 and 35 bases in length, and wherein said RNA molecule, upon contact with a cell expressing said HTT gene, inhibits the expression of said HTT gene by at least 20%.

In certain embodiments, the RNA molecule is ssRNA or dsRNA. In certain embodiments, the dsRNA comprises a sense strand and an antisense strand, wherein the antisense strand comprises the region of complementarity which is substantially complementary to 5' CAGUAAAGA-GAUUAA 3' (SEQ ID NO: 1).

In certain aspects, a cell comprising a vector for inhibiting the expression of HTT gene in a cell is provided. The vector comprising a regulatory sequence operably linked to a nucleotide sequence that encodes an RNA molecule substantially complementary to 5' CAGUAAAGAGAUUAA 3' (SEQ ID NO:1), wherein said RNA molecule is between 15 and 35 bases in length, and wherein said RNA molecule, upon contact with a cell expressing said HTT gene, inhibits the expression of said HTT gene by at least 20%.

In certain embodiments, the RNA molecule is ssRNA or dsRNA. In certain embodiments, the dsRNA comprises a sense strand and an antisense strand, wherein the antisense strand comprises the region of complementarity which is substantially complementary to 5' CAGUAAAGA-GAUUAA 3' (SEQ ID NO: 1).

In one aspect, an RNA molecule is provided that is between 15 and 35 bases in length, comprising a region of complementarity which is substantially complementary to 5' AUAUCAGUAAAGAGA 3' (SEQ ID NO:2) or 5' CUCAGGAUUUAAAAU 3' (SEQ ID NO:3).

In certain embodiments, the RNA molecule is single stranded (ss) RNA or double stranded (ds) RNA. In certain embodiments, the dsRNA comprises a sense strand and an antisense strand, wherein the antisense strand comprises the region of complementarity which is substantially complementary to 5' CAGUAAAGAGAUUAA 3' (SEQ ID NO: 1).

In certain embodiments, the dsRNA is between 30 and 35 base pairs in length. In certain embodiments the region of complementarity is complementary to at least 10, 11, 12 or 13 contiguous nucleotides of SEQ ID NO:2 or 3. In certain embodiments, the region of complementarity contains no more than 3 mismatches with SEQ ID NO:1. In certain embodiments, the region of complementarity is fully complementary to SEQ ID NO:2 or 3.

In certain embodiments, the dsRNA is blunt-ended. In certain embodiments, the dsRNA comprises at least one single stranded nucleotide overhang. In certain embodiments, the dsRNA comprises naturally occurring nucleotides.

In certain embodiments, the dsRNA comprises at least one modified nucleotide. In certain embodiments, the modified nucleotide is chosen from the group of: a 2'-O-methyl modified nucleotide, a nucleotide comprising a 5'phosphorothioate group, and a terminal nucleotide linked to a cholesteryl derivative or dodecanoic acid bisdecylamide group. In certain embodiments, the modified nucleotide is chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. In certain embodiments, the dsRNA comprises at least one 2'-O-methyl modified nucleotide and at least one nucleotide comprising a 5'phosphorothioate group.

In certain embodiments, the RNA molecule comprises a 5' end, a 3' end and has complementarity to a target, wherein: (1) the RNA molecule comprises alternating 2'-methoxy-ribonucleotides and 2'-fluoro-ribonucleotides; (2) the nucleotides at positions 2 and 14 from the 5' end are not 2'-methoxy-ribonucleotides; (3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In certain embodiments, the dsRNA has a 5' end, a 3' end and complementarity to a target, and comprises a first oligonucleotide and a second oligonucleotide, wherein: (1) the first oligonucleotide comprises a sequence set forth as SEQ ID NO:1; (2) a portion of the first oligonucleotide is complementary to a portion of the second oligonucleotide; (3) the second oligonucleotide comprises alternating 2'-methoxy-ribonucleotides and 2'-fluoro-ribonucleotides; (4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In certain embodiments, the second oligonucleotide is linked to a hydrophobic molecule at the 3' end of the second oligonucleotide. In certain embodiments, the linkage between the second oligonucleotide and the hydrophobic molecule comprises polyethylene glycol or triethylene glycol. In certain embodiments, the nucleotides at positions 1 and 2 from the 3' end of second oligonucleotide are connected to adjacent nucleotides via phosphorothioate linkages. In certain embodiments, the nucleotides at positions 1 and 2 from the 3' end of second oligonucleotide, and the nucleotides at positions 1 and 2 from the 5' end of second oligonucleotide, are connected to adjacent ribonucleotides via phosphorothioate linkages.

In certain aspects, a pharmaceutical composition for inhibiting the expression of the HTT gene in an organism, comprising a dsRNA and a pharmaceutically acceptable carrier is provided. The dsRNA comprises a sense strand and an antisense strand. The dsRNA is between 15 and 35 base pairs in length and the antisense strand comprises a region of complementarity which is substantially complementary to 5' AUAUCAGUAAAGAGA 3' (SEQ ID NO:2) or 5' CUCAGGAUUUAAAAU 3' (SEQ ID NO:3).

In certain embodiments, the dsRNA comprises a cholesterol moiety.

In certain aspects, a method for inhibiting expression of HTT gene in a cell is provided. The method includes the steps of introducing into the cell a double-stranded ribonucleic acid (dsRNA) comprising a sense strand and an antisense strand, the dsRNA is between 15 and 35 base pairs in length and the antisense strand comprises a region of complementarity which is substantially complementary to 5' AUAUCAGUAAAGAGA 3' (SEQ ID NO:2) or 5' CUCAGGAUUUAAAAU 3' (SEQ ID NO:3), and maintaining the cell produced in step (a) for a time sufficient to obtain degradation of the mRNA transcript of the HTT gene, thereby inhibiting expression of the HTT gene in the cell.

In certain aspects, a method of treating or managing Huntington's disease comprising administering to a patient in need of such treatment or management a therapeutically effective amount of a dsRNA is provided. The dsRNA comprises a sense strand and an antisense strand, and is between 15 and 35 base pairs in length, and the antisense strand comprises a region of complementarity which is substantially complementary to 5' AUAUCAGUAAAGAGA 3' (SEQ ID NO:2) or 5' CUCAGGAUUUAAAAU 3' (SEQ ID NO:3).

In certain embodiments, the dsRNA is administered to the brain of the patient. In certain embodiments, the dsRNA is administered by intrastriatal infusion. In certain embodiments, administering the dsRNA to the brain causes a decrease in HTT gene mRNA in the striatum. In certain embodiments, administering the dsRNA to the brain causes a decrease in HTT gene mRNA in the cortex.

In certain aspects, a vector for inhibiting the expression of HTT gene in a cell is provided. The vector comprising a regulatory sequence operably linked to a nucleotide sequence that encodes an RNA molecule substantially complementary to 5' AUAUCAGUAAAGAGA 3' (SEQ ID NO:2) or 5' CUCAGGAUUUAAAAU 3' (SEQ ID NO:3), wherein said RNA molecule is between 15 and 35 bases in length, and wherein said RNA molecule, upon contact with a cell expressing said HTT gene, inhibits the expression of said HTT gene by at least 20%.

In certain embodiments, the RNA molecule is ssRNA or dsRNA. In certain embodiments, the dsRNA comprises a sense strand and an antisense strand, wherein the antisense strand comprises the region of complementarity which is substantially complementary to 5' AUAUCAGUAAAGAGA 3' (SEQ ID NO:2) or 5' CUCAGGAUUUAAAAU 3' (SEQ ID NO:3).

In certain aspects, a cell comprising a vector for inhibiting the expression of HTT gene in a cell is provided. The vector comprising a regulatory sequence operably linked to a nucleotide sequence that encodes an RNA molecule substantially complementary to 5' AUAUCAGUAAAGAGA 3' (SEQ ID NO:2) or 5' CUCAGGAUUUAAAAU 3' (SEQ ID NO:3), wherein said RNA molecule is between 15 and 35 bases in length, and wherein said RNA molecule, upon contact with a cell expressing said HTT gene, inhibits the expression of said HTT gene by at least 20%.

In certain embodiments, the RNA molecule is ssRNA or dsRNA. In certain embodiments, the dsRNA comprises a sense strand and an antisense strand, wherein the antisense strand comprises the region of complementarity which is substantially complementary to 5' AUAUCA-GUAAAGAGA 3' (SEQ ID NO:2) or 5' CUCAG-GAUUUAAAAU 3' (SEQ ID NO:3).

In certain aspects, an RNA molecule that is between 15 and 35 bases in length is provided. The RNA molecule comprises a region of complementarity which is substantially complementary to 5' CAGUAAAGAGAUUAA 3' (SEQ ID NO: 1), 5' AUAUCAGUAAAGAGA 3' (SEQ ID NO:2) or 5' CUCAGGAUUUAAAAU 3' (SEQ ID NO:3), and the RNA molecule targets a 3' untranslated region (UTR) of HTT gene short mRNA.

The 3' UTR of the HTT gene short mRNA is as follows:

(SEQ ID NO: 4)
AGCGCCAUGGUGGGAGAGACUGUGAGGCGGCAGCUGGGGCCGGAGCCUUU

GGAAGUCUGCGCCCUUGUGCCCUGCCUCCACCGAGCCAGCUUGGUCCCUA

UGGGCUUCCGCACAUGCCGCGGGCGGCCAGGCAACGUGCGUGUCUCUGCC

AUGUGGCAGAAGUGCUCUUUGUGGCAGUGGCCAGGCAGGGAGUGUCUGCA

GUCCUGGUGGGGCUGAGCCUGAGGCCUUCCAGAAAGCAGGAGCAGCUGUG

CUGCACCCCAUGUGGGUGACCAGGUCCUUUCUCCUGAUAGUCACCUGCUG

GUUGUUGCCAGGUUGCAGCUGCUCUUGCAUCUGGGCCAGAAGUCCUCCCU

CCUGCAGGCUGGCUGUUGGCCCCUCUGCUGUCCUGCAGUAGAAGGUGCCG

UGAGCAGGCUUUGGGAACACUGGCCUGGGUCUCCCUGGUGGGGUGUGCAU

GCCACGCCCCGUGUCUGGAUGCACAGAUGCCAUGGCCUGUGCUGGGCCAG

UGGCUGGGGGUGCUAGACACCCGGCACCAUUCUCCCUUCUCUCUUUUCUU

CUCAGGAUUUAAAAUUUAAUUAUAUCAGUAAAGAGAUUAAUUUUAACGUA

ACUCUUUCUAUGCCCGUGUA

In certain embodiments, the RNA molecule is ssRNA or dsRNA. In certain embodiments, the dsRNA comprises a sense strand and an antisense strand, wherein the antisense strand comprises the region of complementarity which is substantially complementary to 5' CAGUAAAGA-GAUUAA 3' (SEQ ID NO:1), 5' AUAUCAGUAAAGAGA 3' (SEQ ID NO:2) or 5' CUCAGGAUUUAAAAU 3' (SEQ ID NO:3).

In certain aspects, a dsRNA molecule that is between 15 and 35 bases in length, comprising a region of complementarity which is substantially complementary to 5' CAGUAAAGAGAUUAA 3' (SEQ ID NO:1), 5' AUAUCA-GUAAAGAGA 3' (SEQ ID NO:2) or 5' CUCAG-GAUUUAAAAU 3' (SEQ ID NO:3), wherein the RNA molecule targets an HTT mRNA and comprises at least one modified nucleotide is provided. In certain embodiments, the modified nucleotide is a terminal nucleotide linked to a phosphatidylcholine derivative.

In certain aspects, a di-branched RNA compound comprising two RNA molecules that are between 15 and 35 bases in length, comprising a region of complementarity which is substantially complementary to 5' CAGUAAAGA-GAUUAA 3' (SEQ ID NO:1), 5' AUAUCAGUAAAGAGA 3' (SEQ ID NO:2) or 5' CUCAGGAUUUAAAAU 3' (SEQ ID NO:3), wherein the two RNA molecules are connected to one another by one or more moieties independently selected from a linker, a spacer and a branching point, is provided.

In any of the aspects described herein, the RNA molecule is an antisense molecule (e.g., ASO) or a GAPMER molecule. In certain embodiments, the antisense molecule enhances degradation of the region of complementarity. In certain embodiments, the degradation is nuclease degradation (e.g., RNase H).

BRIEF DESCRIPTION OF THE DRAWINGS

The foregoing and other features and advantages of the present invention will be more fully understood from the following detailed description of illustrative embodiments taken in conjunction with the accompanying drawings. The patent or application file contains at least one drawing executed in color. Copies of this patent or patent application publication with color drawing(s) will be provided by the Office upon request and payment of the necessary fee.

FIGS. 3A-3C depict concentration-dependent silencing of huntingtin mRNA by HTT10150, in both passive (A) and lipid-mediated delivery (B). Chemical modifications enable passive uptake without negative impact on siRNA RISC (RNA Induced Silencing Complex) entry. HeLa cells were incubated with modified (containing both hydrophobic and base chemical modifications) or unmodified HTT10150 at concentrations shown in the absence (A) and presence (B) of RNAIMAX. Level of huntingtin mRNA was measured using QUANTIGENE (Affymetrix) at 72 hours normalized to housekeeping gene, PPIB (cyclophillin B), and presented as percent of untreated control (n=3, mean+/−SD). UNT—untreated cells. IC50 values calculated as described herein. (C) Is a table summarizing these results.

FIG. 8 depicts target sequences (SEQ ID NOS 1045-1057, 3, 2, 1 and 1061-1139, respectively, in order of appearance), modified oligonucleotides ("Sense Strand" sequences disclosed as SEQ ID NOS 1140-1231 and "Antisense Strand" sequences disclosed as SEQ ID NOS 1232-1326, all respectively, in order of appearance) and their efficacy according to certain embodiments.

FIG. 21 depicts additional target sequences (SEQ ID NOS 5-212, respectively, in order of columns) along with chemical modifications and structural scaffolds according to certain embodiments of the invention ("Sense Naked" sequences disclosed as SEQ ID NOS 213-316, "Anstisense Naked" sequences disclosed as SEQ ID NOS 317-420, "Sense Strand (P0)" sequences disclosed as SEQ ID NOS 421-524, "Antisense Strand (P0)" sequences disclosed as SEQ ID NOS 525-628, "Sense Strand (P1)" sequences disclosed as SEQ ID NOS 629-732, "Antisense Strand (P1)" sequences disclosed as SEQ ID NOS 733-836, "Sense Strand (P2)" sequences disclosed as SEQ ID NOS 837-940, and "Antisense Strand (P2)" sequences disclosed as SEQ ID NOS 941-1044, all respectively, in order of columns).

FIGS. 36A-36C depict full metabolic stabilization of hsiRNAs.

FIGS. 38A-38E depict fully metabolically stabilized hsiRNA (FM-hsiRNA) enhancement of local delivery and distribution.

FIG. 42 depicts docosahexaenoic acid (DHA) hsiRNA synthesis.

FIG. 61 shows that each of PC-DHA-hsiRNA and chol-hsiRNA silence mutant and wild-type htt mRNA.

FIG. 66 shows approximately 80% silencing in mouse striatum after a single IS injection PC-DHA-hsiRNA.

FIG. 67 shows approximately 60% silencing in mouse cortex after a single IS injection PC-DHA-hsiRNA.

FIG. 70 depicts effect of branching on brain distribution.

FIG. 80 depicts the efficacy of vitamin D synthesis on htt mRNA expression.

FIG. 81 depicts a chemical Formula of a compound provided herein. Fig. discloses SEQ ID NOS 1327, 1328, 1327, and 1328, respectively, in order of appearance.

FIG. 82 depicts examples of internucleotide linkages of $R^3$.

FIG. 83 depicts an embodiment of the chemical Formula of FIG. 81. Fig. discloses SEQ ID NOS 1327, 1328, 1327, and 1328, respectively, in order of appearance.

FIG. 84 depicts a chemical Formula of a compound provided herein. Fig. discloses SEQ ID NOS 1327-1328, respectively, in order of appearance.

FIG. 85 depicts a chemical Formula of a compound provided herein. Fig. discloses SEQ ID NOS 1327-1328, respectively, in order of appearance.

FIG. 86 depicts an embodiment of the Y moiety of FIG. 84 or FIG. 85. Fig. discloses SEQ ID NOS 1327-1328, respectively, in order of appearance.

FIG. 87 depicts a chemical Formula of a compound provided herein. Fig. discloses SEQ ID NOS 1327, 1328, 1327, and 1328, respectively, in order of appearance.

FIG. 88 depicts an embodiment of the chemical Formula of FIG. 87. Fig. discloses SEQ ID NOS 1327, 1328, 1327, and 1328, respectively, in order of appearance.

FIG. 89 depicts a chemical Formula of a compound provided herein. Fig. discloses SEQ ID NOS 1327-1328, respectively, in order of appearance.

FIG. 90 depicts an embodiment of the chemical Formula of FIG. 89. Fig. discloses SEQ ID NOS 1327-1328, respectively, in order of appearance.

FIGS. 111A-111G show that fully modified hsiRNAs are broadly distributed throughout the brain and demonstrate higher potency and longer duration of silencing upon local administration. hsiRNATT (A) and FM-hsiRNATT(B, C, D, E) were injected ICV, distribution through the sagittal section of the brain after 48 hours is shown. Nuclei stained with DAPI (blue). Cy3-hsiRNA (red). (F, G) hsiRNATT and FM-hsiRNATT were unilaterally injected into the striatum and level of HTT mRNA was measured using QuantiGene® (Affymetrix) after (F) 5 days or (G) 7, 14 and 28 days, normalized to housekeeping gene, PPIB, and presented as percent of untreated control (n=8 mice, mean+SD). NTC=non-targeting control; CSF=artificial cerebrospinal fluid All error bars represent mean+SD. , P<0.01; *, P<0.001; ****, P<0.0001.

DETAILED DESCRIPTION OF CERTAIN EXEMPLARY EMBODIMENTS

Figure 1A:
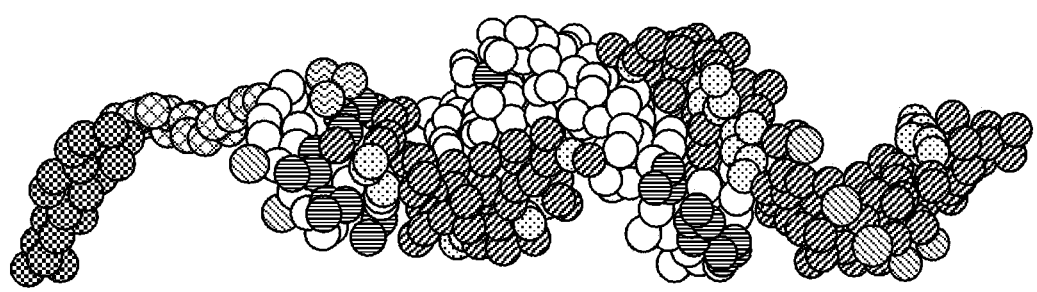
FIGS. 1A-1B depict hydrophobic siRNA structural and chemical composition and efficient internalization in primary cortical neurons. A) Schematic of the hydrophobically modified and stabilized siRNAs (hsiRNAs) B) Cy3-HTT10150 hsiRNA (red), 0.5 µM, was added to primary cortical neurons. Imaged on Zeiss confocal microscope, 63×, nuclei stained with Hoechst dye (blue).

Novel huntingtin target sequences are provided. Also provided are novel siRNAs that target the novel huntingtin target sequences of the invention.

Generally, nomenclature used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

So that the invention may be more readily understood, certain terms are first defined.

The term "nucleoside" refers to a molecule having a purine or pyrimidine base covalently linked to a ribose or deoxyribose sugar. Exemplary nucleosides include adenosine, guanosine, cytidine, uridine and thymidine. Additional exemplary nucleosides include inosine, 1-methyl inosine, pseudouridine, 5,6-dihydrouridine, ribothymidine, 2N-methylguanosine and 2,2N,N-dimethylguanosine (also referred to as "rare" nucleosides). The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester or phosphorothioate linkage between 5' and 3' carbon atoms.

The term "RNA" or "RNA molecule" or "ribonucleic acid molecule" refers to a polymer of ribonucleotides (e.g., 2, 3, 4, 5, 10, 15, 20, 25, 30, or more ribonucleotides). The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, a siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs). The term "short" siRNA refers to a siRNA comprising about 21 nucleotides (or nucleotide analogs), for example, 19, 20, 21 or 22 nucleotides. The term "long" siRNA refers to a siRNA comprising about 24-25 nucleotides, for example, 23, 24, 25 or 26 nucleotides. Short siRNAs may, in some instances, include fewer than 19 nucleotides, e.g., 16, 17 or 18 nucleotides, provided that the shorter siRNA retains the ability to mediate RNAi. Likewise, long siRNAs may, in some instances, include more than 26 nucleotides, provided that the longer siRNA retains the ability to mediate RNAi absent further processing, e.g., enzymatic processing, to a short siRNA.

The term "nucleotide analog" or "altered nucleotide" or "modified nucleotide" refers to a non-standard nucleotide, including non-naturally occurring ribonucleotides or deoxyribonucleotides. Exemplary nucleotide analogs are modified at any position so as to alter certain chemical properties of the nucleotide yet retain the ability of the nucleotide analog to perform its intended function. Examples of positions of the nucleotide which may be derivatized include the 5 position, e.g., 5-(2-amino)propyl uridine, 5-bromo uridine, 5-propyne uridine, 5-propenyl uridine, etc.; the 6 position, e.g., 6-(2-amino)propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other hetero-cyclically modified nucleotide analogs such as those described in Herdewijn, Antisense Nucleic Acid Drug Dev., 2000 Aug. 10(4):297-310.

Nucleotide analogs may also comprise modifications to the sugar portion of the nucleotides. For example the 2' OH-group may be replaced by a group selected from H, OR, R, F, Cl, Br, I, SH, SR, $NH_2$, NHR, $NR_2$, COOR, or OR, wherein R is substituted or unsubstituted $C_1$-$C_6$ alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2):117-21, Rusckowski et al. Antisense Nucleic Acid Drug Dev. 2000 Oct. 10(5):333-45, Stein, Antisense Nucleic Acid Drug Dev. 2001 Oct. 11(5): 317-25, Vorobjev et al. Antisense Nucleic Acid Drug Dev. 2001 Apr. 11(2): 77-85, and U.S. Pat. No. 5,684,143. Certain of the above-referenced modifications (e.g., phosphate group modifications) preferably decrease the rate of hydrolysis of, for example, polynucleotides comprising said analogs in vivo or in vitro.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

An RNAi agent, e.g., an RNA silencing agent, having a strand which is "sequence sufficiently complementary to a target mRNA sequence to direct target-specific RNA interference (RNAi)" means that the strand has a sequence sufficient to trigger the destruction of the target mRNA by the RNAi machinery or process.

As used herein, the term "isolated RNA" (e.g., "isolated siRNA" or "isolated siRNA precursor") refers to RNA molecules which are substantially free of other cellular material, or culture medium when produced by recombinant techniques, or substantially free of chemical precursors or other chemicals when chemically synthesized.

As used herein, the term "RNA silencing" refers to a group of sequence-specific regulatory mechanisms (e.g. RNA interference (RNAi), transcriptional gene silencing (TGS), post-transcriptional gene silencing (PTGS), quelling, co-suppression, and translational repression) mediated by RNA molecules which result in the inhibition or "silencing" of the expression of a corresponding protein-coding gene. RNA silencing has been observed in many types of organisms, including plants, animals, and fungi.

The term "discriminatory RNA silencing" refers to the ability of an RNA molecule to substantially inhibit the expression of a "first" or "target" polynucleotide sequence while not substantially inhibiting the expression of a "second" or "non-target" polynucleotide sequence," e.g., when both polynucleotide sequences are present in the same cell. In certain embodiments, the target polynucleotide sequence corresponds to a target gene, while the non-target polynucleotide sequence corresponds to a non-target gene. In other embodiments, the target polynucleotide sequence corresponds to a target allele, while the non-target polynucleotide sequence corresponds to a non-target allele. In certain embodiments, the target polynucleotide sequence is the DNA sequence encoding the regulatory region (e.g. promoter or enhancer elements) of a target gene. In other embodiments, the target polynucleotide sequence is a target mRNA encoded by a target gene.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

As used herein, the term "transgene" refers to any nucleic acid molecule, which is inserted by artifice into a cell, and becomes part of the genome of the organism that develops from the cell. Such a transgene may include a gene that is partly or entirely heterologous (i.e., foreign) to the transgenic organism, or may represent a gene homologous to an endogenous gene of the organism. The term "transgene" also means a nucleic acid molecule that includes one or more selected nucleic acid sequences, e.g., DNAs, that encode one or more engineered RNA precursors, to be expressed in a transgenic organism, e.g., animal, which is partly or entirely heterologous, i.e., foreign, to the transgenic animal, or homologous to an endogenous gene of the transgenic animal, but which is designed to be inserted into the animal's genome at a location which differs from that of the natural gene. A transgene includes one or more promoters and any other DNA, such as introns, necessary for expression of the selected nucleic acid sequence, all operably linked to the selected sequence, and may include an enhancer sequence.

A gene "involved" in a disease or disorder includes a gene, the normal or aberrant expression or function of which effects or causes the disease or disorder or at least one symptom of said disease or disorder.

The term "gain-of-function mutation" as used herein, refers to any mutation in a gene in which the protein encoded by said gene (i.e., the mutant protein) acquires a function not normally associated with the protein (i.e., the wild type protein) causes or contributes to a disease or disorder. The gain-of-function mutation can be a deletion, addition, or substitution of a nucleotide or nucleotides in the gene which gives rise to the change in the function of the encoded protein. In one embodiment, the gain-of-function mutation changes the function of the mutant protein or causes interactions with other proteins. In another embodiment, the gain-of-function mutation causes a decrease in or removal of normal wild-type protein, for example, by interaction of the altered, mutant protein with said normal, wild-type protein.

As used herein, the term "target gene" is a gene whose expression is to be substantially inhibited or "silenced." This silencing can be achieved by RNA silencing, e.g., by cleaving the mRNA of the target gene or translational repression of the target gene. The term "non-target gene" is a gene whose expression is not to be substantially silenced. In one embodiment, the polynucleotide sequences of the target and non-target gene (e.g. mRNA encoded by the target and non-target genes) can differ by one or more nucleotides. In another embodiment, the target and non-target genes can differ by one or more polymorphisms (e.g., Single Nucleotide Polymorphisms or SNPs). In another embodiment, the target and non-target genes can share less than 100% sequence identity. In another embodiment, the non-target gene may be a homologue (e.g. an orthologue or paralogue) of the target gene.

A "target allele" is an allele (e.g., a SNP allele) whose expression is to be selectively inhibited or "silenced." This silencing can be achieved by RNA silencing, e.g., by cleaving the mRNA of the target gene or target allele by a siRNA. The term "non-target allele" is a allele whose expression is not to be substantially silenced. In certain embodiments, the target and non-target alleles can correspond to the same target gene. In other embodiments, the target allele corresponds to, or is associated with, a target gene, and the non-target allele corresponds to, or is associated with, a non-target gene. In one embodiment, the polynucleotide sequences of the target and non-target alleles can differ by one or more nucleotides. In another embodiment, the target and non-target alleles can differ by one or more allelic polymorphisms (e.g., one or more SNPs). In another embodiment, the target and non-target alleles can share less than 100% sequence identity.

The term "polymorphism" as used herein, refers to a variation (e.g., one or more deletions, insertions, or substitutions) in a gene sequence that is identified or detected when the same gene sequence from different sources or subjects (but from the same organism) are compared. For example, a polymorphism can be identified when the same gene sequence from different subjects are compared. Identification of such polymorphisms is routine in the art, the methodologies being similar to those used to detect, for example, breast cancer point mutations. Identification can be made, for example, from DNA extracted from a subject's lymphocytes, followed by amplification of polymorphic regions using specific primers to said polymorphic region. Alternatively, the polymorphism can be identified when two alleles of the same gene are compared. In particular embodiments, the polymorphism is a single nucleotide polymorphism (SNP).

A variation in sequence between two alleles of the same gene within an organism is referred to herein as an "allelic polymorphism." In certain embodiments, the allelic polymorphism corresponds to a SNP allele. For example, the allelic polymorphism may comprise a single nucleotide variation between the two alleles of a SNP. The polymorphism can be at a nucleotide within a coding region but, due to the degeneracy of the genetic code, no change in amino acid sequence is encoded. Alternatively, polymorphic sequences can encode a different amino acid at a particular position, but the change in the amino acid does not affect protein function. Polymorphic regions can also be found in non-encoding regions of the gene. In exemplary embodiments, the polymorphism is found in a coding region of the gene or in an untranslated region (e.g., a 5' UTR or 3' UTR) of the gene.

As used herein, the term "allelic frequency" is a measure (e.g., proportion or percentage) of the relative frequency of an allele (e.g., a SNP allele) at a single locus in a population of individuals. For example, where a population of individuals carry n loci of a particular chromosomal locus (and the gene occupying the locus) in each of their somatic cells, then the allelic frequency of an allele is the fraction or percentage of loci that the allele occupies within the population. In particular embodiments, the allelic frequency of an allele (e.g., an SNP allele) is at least 10% (e.g., at least 15%, 20%, 25%, 30%, 35%, 40% or more) in a sample population.

As used herein, the term "sample population" refers to a population of individuals comprising a statistically significant number of individuals. For example, the sample population may comprise 50, 75, 100, 200, 500, 1000 or more individuals. In particular embodiments, the sample population may comprise individuals which share at least on common disease phenotype (e.g., a gain-of-function disorder) or mutation (e.g., a gain-of-function mutation).

As used herein, the term "heterozygosity" refers to the fraction of individuals within a population that are heterozygous (e.g., contain two or more different alleles) at a particular locus (e.g., at a SNP). Heterozygosity may be calculated for a sample population using methods that are well known to those skilled in the art.

The term "polyglutamine domain," as used herein, refers to a segment or domain of a protein that consist of a consecutive glutamine residues linked to peptide bonds. In one embodiment the consecutive region includes at least 5 glutamine residues.

The term "expanded polyglutamine domain" or "expanded polyglutamine segment," as used herein, refers to a segment or domain of a protein that includes at least 35 consecutive glutamine residues linked by peptide bonds. Such expanded segments are found in subjects afflicted with a polyglutamine disorder, as described herein, whether or not the subject has shown to manifest symptoms.

The term "trinucleotide repeat" or "trinucleotide repeat region" as used herein, refers to a segment of a nucleic acid sequence e.g.) that consists of consecutive repeats of a particular trinucleotide sequence. In one embodiment, the trinucleotide repeat includes at least 5 consecutive trinucleotide sequences. Exemplary trinucleotide sequences include, but are not limited to, CAG, CGG, GCC, GAA, CTG and/or CGG.

The term "trinucleotide repeat diseases" as used herein, refers to any disease or disorder characterized by an expanded trinucleotide repeat region located within a gene, the expanded trinucleotide repeat region being causative of the disease or disorder. Examples of trinucleotide repeat diseases include, but are not limited to spino-cerebellar ataxia type 12 spino-cerebellar ataxia type 8, fragile X syndrome, fragile XE mental retardation, Friedreich's ataxia and myotonic dystrophy. Exemplary trinucleotide repeat diseases for treatment according to the present invention are those characterized or caused by an expanded trinucleotide repeat region at the 5' end of the coding region of a gene, the gene encoding a mutant protein which causes or is causative of the disease or disorder. Certain trinucleotide diseases, for example, fragile X syndrome, where the mutation is not associated with a coding region may not be suitable for treatment according to the methodologies of the present invention, as there is no suitable mRNA to be targeted by RNAi. By contrast, disease such as Friedreich's ataxia may be suitable for treatment according to the methodologies of the invention because, although the causative mutation is not within a coding region (i.e., lies within an intron), the mutation may be within, for example, an mRNA precursor (e.g., a pre-spliced mRNA precursor).

The term "polyglutamine disorder" as used herein, refers to any disease or disorder characterized by an expanded of a (CAG)n repeats at the 5' end of the coding region (thus encoding an expanded polyglutamine region in the encoded protein). In one embodiment, polyglutamine disorders are characterized by a progressive degeneration of nerve cells.

Examples of polyglutamine disorders include but are not limited to: Huntington's disease, spino-cerebellar ataxia type 1, spino-cerebellar ataxia type 2, spino-cerebellar ataxia type 3 (also known as Machado-Joseph disease), and spinocerebellar ataxia type 6, spino-cerebellar ataxia type 7 and dentatoiubral-pallidoluysian atrophy.

The phrase "examining the function of a gene in a cell or organism" refers to examining or studying the expression, activity, function or phenotype arising therefrom.

As used herein, the term "RNA silencing agent" refers to an RNA which is capable of inhibiting or "silencing" the expression of a target gene. In certain embodiments, the RNA silencing agent is capable of preventing complete processing (e.g., the full translation and/or expression) of a mRNA molecule through a post-transcriptional silencing mechanism. RNA silencing agents include small (<50 b.p.), noncoding RNA molecules, for example RNA duplexes comprising paired strands, as well as precursor RNAs from which such small noncoding RNAs can be generated. Exemplary RNA silencing agents include siRNAs, miRNAs, siRNA-like duplexes, antisense oligonucleotides, GAPMER molecules, and dual-function oligonucleotides as well as precursors thereof. In one embodiment, the RNA silencing agent is capable of inducing RNA interference. In another embodiment, the RNA silencing agent is capable of mediating translational repression.

As used herein, the term "rare nucleotide" refers to a naturally occurring nucleotide that occurs infrequently, including naturally occurring deoxyribonucleotides or ribonucleotides that occur infrequently, e.g., a naturally occurring ribonucleotide that is not guanosine, adenosine, cytosine, or uridine. Examples of rare nucleotides include, but are not limited to, inosine, 1-methyl inosine, pseudouridine, 5,6-dihydrouridine, ribothymidine, $^2$N-methylguanosine and $^{2,2}$N,N-dimethylguanosine.

The term "engineered," as in an engineered RNA precursor, or an engineered nucleic acid molecule, indicates that the precursor or molecule is not found in nature, in that all or a portion of the nucleic acid sequence of the precursor or molecule is created or selected by a human. Once created or selected, the sequence can be replicated, translated, transcribed, or otherwise processed by mechanisms within a cell. Thus, an RNA precursor produced within a cell from a transgene that includes an engineered nucleic acid molecule is an engineered RNA precursor.

As used herein, the term "microRNA" ("miRNA"), also referred to in the art as "small temporal RNAs" ("stRNAs"), refers to a small (10-50 nucleotide) RNA which are genetically encoded (e.g., by viral, mammalian, or plant genomes) and are capable of directing or mediating RNA silencing. An "miRNA disorder" shall refer to a disease or disorder characterized by an aberrant expression or activity of an miRNA.

As used herein, the term "dual functional oligonucleotide" refers to a RNA silencing agent having the formula T-L-µ, wherein T is an mRNA targeting moiety, L is a linking moiety, and µ is a miRNA recruiting moiety. As used herein, the terms "mRNA targeting moiety," "targeting moiety," "mRNA targeting portion" or "targeting portion" refer to a domain, portion or region of the dual functional oligonucleotide having sufficient size and sufficient complementarity to a portion or region of an mRNA chosen or targeted for silencing (i.e., the moiety has a sequence sufficient to capture the target mRNA). As used herein, the term "linking moiety" or "linking portion" refers to a domain, portion or region of the RNA-silencing agent which covalently joins or links the mRNA.

As used herein, the term "antisense strand" of an RNA silencing agent, e.g., an siRNA or RNA silencing agent, refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process (RNAi interference) or complementarity sufficient to trigger translational repression of the desired target mRNA.

The term "sense strand" or "second strand" of an RNA silencing agent, e.g., an siRNA or RNA silencing agent, refers to a strand that is complementary to the antisense strand or first strand. Antisense and sense strands can also be referred to as first or second strands, the first or second strand having complementarity to the target sequence and the respective second or first strand having complementarity to said first or second strand. miRNA duplex intermediates or siRNA-like duplexes include a miRNA strand having sufficient complementarity to a section of about 10-50 nucleotides of the mRNA of the gene targeted for silencing and a miRNA* strand having sufficient complementarity to form a duplex with the miRNA strand.

As used herein, the term "guide strand" refers to a strand of an RNA silencing agent, e.g., an antisense strand of an siRNA duplex or siRNA sequence, that enters into the RISC complex and directs cleavage of the target mRNA.

As used herein, the term "asymmetry," as in the asymmetry of the duplex region of an RNA silencing agent (e.g., the stem of an shRNA), refers to an inequality of bond strength or base pairing strength between the termini of the RNA silencing agent (e.g., between terminal nucleotides on a first strand or stem portion and terminal nucleotides on an opposing second strand or stem portion), such that the 5' end of one strand of the duplex is more frequently in a transient unpaired, e.g., single-stranded, state than the 5' end of the complementary strand. This structural difference determines that one strand of the duplex is preferentially incorporated into a RISC complex. The strand whose 5' end is less tightly paired to the complementary strand will preferentially be incorporated into RISC and mediate RNAi.

As used herein, the term "bond strength" or "base pair strength" refers to the strength of the interaction between pairs of nucleotides (or nucleotide analogs) on opposing strands of an oligonucleotide duplex (e.g., an siRNA duplex), due primarily to H-bonding, van der Waals interactions, and the like between said nucleotides (or nucleotide analogs).

As used herein, the "5' end," as in the 5' end of an antisense strand, refers to the 5' terminal nucleotides, e.g., between one and about 5 nucleotides at the 5' terminus of the antisense strand. As used herein, the "3' end," as in the 3' end of a sense strand, refers to the region, e.g., a region of between one and about 5 nucleotides, that is complementary to the nucleotides of the 5' end of the complementary antisense strand.

As used herein the term "destabilizing nucleotide" refers to a first nucleotide or nucleotide analog capable of forming a base pair with second nucleotide or nucleotide analog such that the base pair is of lower bond strength than a conventional base pair (i.e., Watson-Crick base pair). In certain embodiments, the destabilizing nucleotide is capable of forming a mismatch base pair with the second nucleotide. In other embodiments, the destabilizing nucleotide is capable of forming a wobble base pair with the second nucleotide. In yet other embodiments, the destabilizing nucleotide is capable of forming an ambiguous base pair with the second nucleotide.

As used herein, the term "base pair" refers to the interaction between pairs of nucleotides (or nucleotide analogs) on opposing strands of an oligonucleotide duplex (e.g., a duplex formed by a strand of a RNA silencing agent and a target mRNA sequence), due primarily to H-bonding, van der Waals interactions, and the like between said nucleotides (or nucleotide analogs). As used herein, the term "bond strength" or "base pair strength" refers to the strength of the base pair.

As used herein, the term "mismatched base pair" refers to a base pair consisting of non-complementary or non-Watson-Crick base pairs, for example, not normal complementary G:C, A:T or A:U base pairs. As used herein the term "ambiguous base pair" (also known as a non-discriminatory base pair) refers to a base pair formed by a universal nucleotide.

As used herein, term "universal nucleotide" (also known as a "neutral nucleotide") include those nucleotides (e.g. certain destabilizing nucleotides) having a base (a "universal base" or "neutral base") that does not significantly discriminate between bases on a complementary polynucleotide when forming a base pair. Universal nucleotides are predominantly hydrophobic molecules that can pack efficiently into antiparallel duplex nucleic acids (e.g., double-stranded DNA or RNA) due to stacking interactions. The base portion of universal nucleotides typically comprise a nitrogen-containing aromatic heterocyclic moiety.

As used herein, the terms "sufficient complementarity" or "sufficient degree of complementarity" mean that the RNA silencing agent has a sequence (e.g. in the antisense strand, mRNA targeting moiety or miRNA recruiting moiety) which is sufficient to bind the desired target RNA, respectively, and to trigger the RNA silencing of the target mRNA.

As used herein, the term "translational repression" refers to a selective inhibition of mRNA translation. Natural translational repression proceeds via miRNAs cleaved from shRNA precursors. Both RNAi and translational repression are mediated by RISC. Both RNAi and translational repression occur naturally or can be initiated by the hand of man, for example, to silence the expression of target genes.

Various methodologies of the instant invention include step that involves comparing a value, level, feature, characteristic, property, etc. to a "suitable control," referred to interchangeably herein as an "appropriate control." A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNA silencing agent of the invention into a cell or organism.

In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and example are illustrative only and not intended to be limiting.

Various aspects of the invention are described in further detail in the following subsections.

I. Polyglutamine Disorders

Polyglutamine disorders are a class of disease or disorders characterized by a common genetic mutation. In particular, the disease or disorders are characterized by an expanded repeat of the trinucleotide CAG which gives rise, in the encoded protein, to an expanded stretch of glutamine residues. Polyglutamine disorders are similar in that the diseases are characterized by a progressive degeneration of nerve cells. Despite their similarities, polyglutamine disorders occur on different chromosomes and thus occur on entirely different segments of DNA. Examples of polyglutamine disorders include Huntington's disease, Dentatorubropallidoluysian Atrophy, Spinobulbar Muscular atrophy, Spinocerebellar Ataxia Type 1, Spinocerebellar Ataxia Type 2, Spinocerebellar Ataxia Type 3, Spinocerebellar Ataxia Type 6 and Spinocerebellar Ataxia Type 7.

Polyglutamine disorders of the invention are characterized by, e.g., domains having between about 30 to 35 glutamine residues, between about 35 to 40 glutamine residues, between about 40 to 45 glutamine residues or having about 45 or more glutamine residues. The polyglutamine domain typically contains consecutive glutamine residues (Q n>36).

II. Huntington Disease

In some embodiments, the RNA silencing agents of the invention are designed to target polymorphisms (e.g. single nucleotide polymorphisms) in the mutant human huntingtin protein (htt) for the treatment of Huntington's disease.

Huntington's disease, inherited as an autosomal dominant disease, causes impaired cognition and motor disease. Patients can live more than a decade with severe debilitation, before premature death from starvation or infection. The disease begins in the fourth or fifth decade for most cases, but a subset of patients manifest disease in teenage years. The genetic mutation for Huntington's disease is a lengthened CAG repeat in the huntingtin gene. CAG repeats vary in number from 8 to 35 in normal individuals (Kremer et al., 1994). The genetic mutation e.g., an increase in length of the CAG repeats from normal (less than 36 in the huntingtin gene to greater than 36 in the disease) is associated with the synthesis of a mutant Huntingtin protein, which has greater than 36 polyglutamates (Aronin et al., 1995). In general, individuals with 36 or more CAG repeats will develop Huntington's disease. Prototypic for as many as twenty other diseases with a lengthened CAG as the underlying mutation, Huntington's disease still has no effective therapy. A variety of interventions, such as interruption of apoptotic pathways, addition of reagents to boost mitochondrial efficiency, and blockade of NMDA receptors, have shown promise in cell cultures and mouse model of Huntington's disease. However, at best these approaches reveal a short prolongation of cell or animal survival.

Huntington's disease complies with the central dogma of genetics: a mutant gene serves as a template for production of a mutant mRNA; the mutant mRNA then directs synthesis of a mutant protein (Aronin et al., 1995; DiFiglia et al., 1997). Without intending to be bound by scientific theory, it is thought that mutant huntingtin protein accumulates in selective neurons in the striatum and cortex, disrupts as yet determined cellular activities, and causes neuronal dysfunction and death (Aronin et al., 1999; Laforet et al., 2001). Because a single copy of a mutant gene suffices to cause Huntington's disease, the most parsimonious treatment would render the mutant gene ineffective. Theoretical approaches might include stopping gene transcription of mutant huntingtin, destroying mutant mRNA, and blocking translation. Each has the same outcome: loss of mutant huntingtin.

III. Huntingtin Gene

The disease gene linked to Huntington's disease is termed Huntingtin or (htt). The huntingtin locus is large, spanning 180 kb and consisting of 67 exons. The huntingtin gene is widely expressed and is required for normal development. It is expressed as 2 alternatively polyadenylated forms displaying different relative abundance in various fetal and adult tissues. The larger transcript is approximately 13.7 kb and is expressed predominantly in adult and fetal brain whereas the smaller transcript of approximately 10.3 kb is more widely expressed. The two transcripts differ with respect to their 3' untranslated regions (Lin et al., 1993). Both messages are predicted to encode a 348 kilodalton protein containing 3144 amino acids. The genetic defect leading to Huntington's disease is believed to confer a new property on the mRNA or alter the function of the protein.

The present invention targets huntingtin (e.g., wild-type and/or mutant huntingtin) using RNA interference (Hutvagner et al., 2002). One strand of double-stranded RNA (siRNA) complements a target sequence within the huntingtin mRNA. After introduction of siRNA into neurons, the siRNA partially unwinds, binds to polymorphic region within the huntingtin mRNA in a site-specific manner, and activates an mRNA nuclease. This nuclease cleaves the huntingtin mRNA, thereby halting translation of the huntingtin (e.g., wild-type and/or mutant huntingtin). Cells rid themselves of partially digested mRNA, thus precluding translation, or cells digest partially translated proteins. In certain embodiments, neurons survive on the wild-type huntingtin from the normal allele, preventing the ravages of mutant huntingtin by eliminating its production.

In embodiments of the invention, RNA silencing agents of the invention are capable of targeting one or more of the target sequences listed in FIG. 8. In certain exemplary embodiments, RNA silencing agents of the invention are capable of targeting one or more of the target sequences at one or more target sequences listed at gene positions selected from the group consisting of 1214, 1218, 1219, 1257, 1894, 1907, 2866, 4041, 4049, 5301, 6016, 6579, 8603, 10125, 10146, 10150, 424, 456, 522, 527, 878, 879, 908, 1024, 1165, 1207, 1212, 1217, 1220, 1223, 1227, 1229, 1260, 1403, 1470, 1901, 1903, 2411, 2412, 2865, 3801, 4040, 4048, 4052, 4055, 4083, 4275, 4372, 4374, 4376, 4425, 4562, 4692, 4721, 5200, 5443, 5515, 8609, 10130, 10134, 10142, 10169, 10182, 10186, 10809, 11116, 11129, 11134, 11147, 11412, 11426, 11443, 11659, 11666, 11677, 11863, 11890, 11927, 11947, 12163, 12218, 12223, 12235, 12279, 12282, 12297, 12309, 12313, 12331, 13136, 13398, 13403, 13423, 13428 of the human htt gene (as set forth at FIG. 8). In certain exemplary embodiments, RNA silencing agents of the invention are capable of targeting one or more of the target sequences at one or more target sequences listed at gene positions selected from the group consisting of 5301, 10125, 10146, 10150, 424, 878, 879, 4083, 4275, 4562, 4721, 5200, 10130, 10134, 10142, 11116, 11129, 11134, 11147, 11412, 11426, 11443, 11659, 11666, 11677, 11863, 11890, 11927, 11947, 12163, 12218, 12223, 12235, 12279, 12282, 12297, 12331, 13136, 13423 and 13428 of the human htt gene (as set forth at FIG. 8). Particularly exemplary target sequences of the human htt gene can be found at positions 10150 (5' CAGUAAAGAGAUUAA 3' (SEQ ID NO:1)), 10146 (5' AUAUCAGUAAAGAGA 3' (SEQ ID NO:2)) and 10125 (5' CUCAGGAUUUAAAAU 3' (SEQ ID NO:3)). Genomic sequence for each target sequence can be found in, for example, the publically available database maintained by the NCBI.

Figure 21:
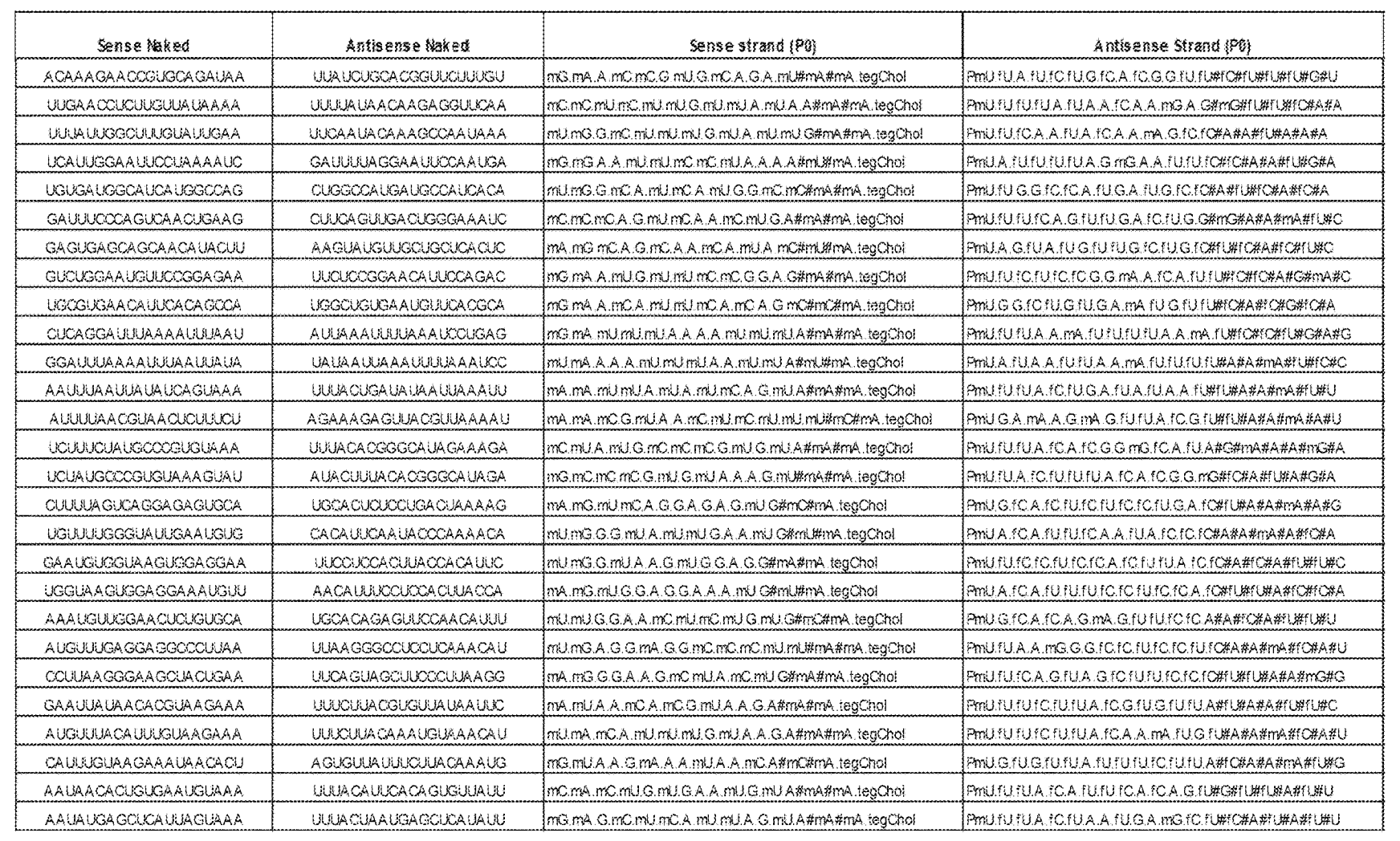
Figure 21:
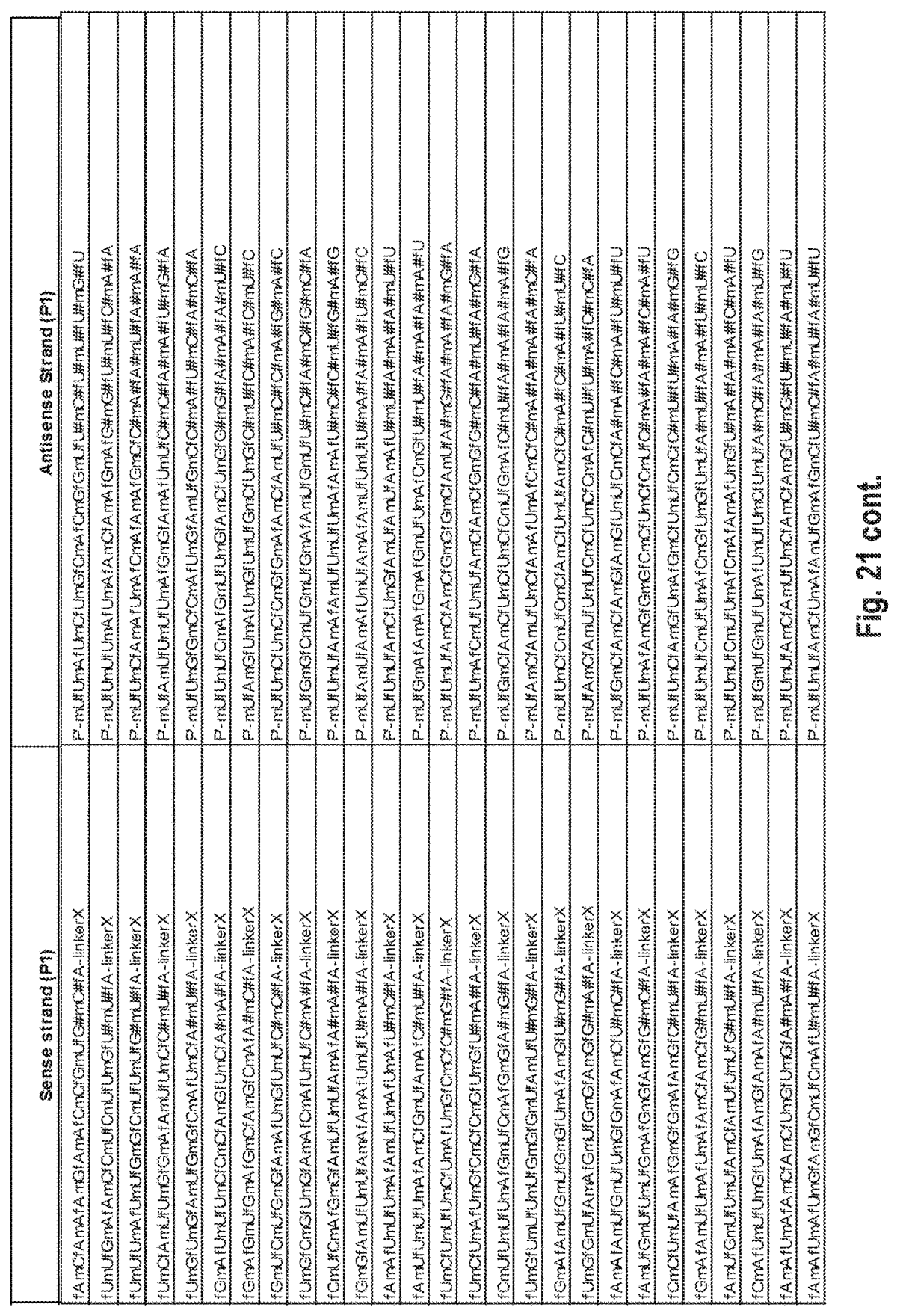
Figure 21:
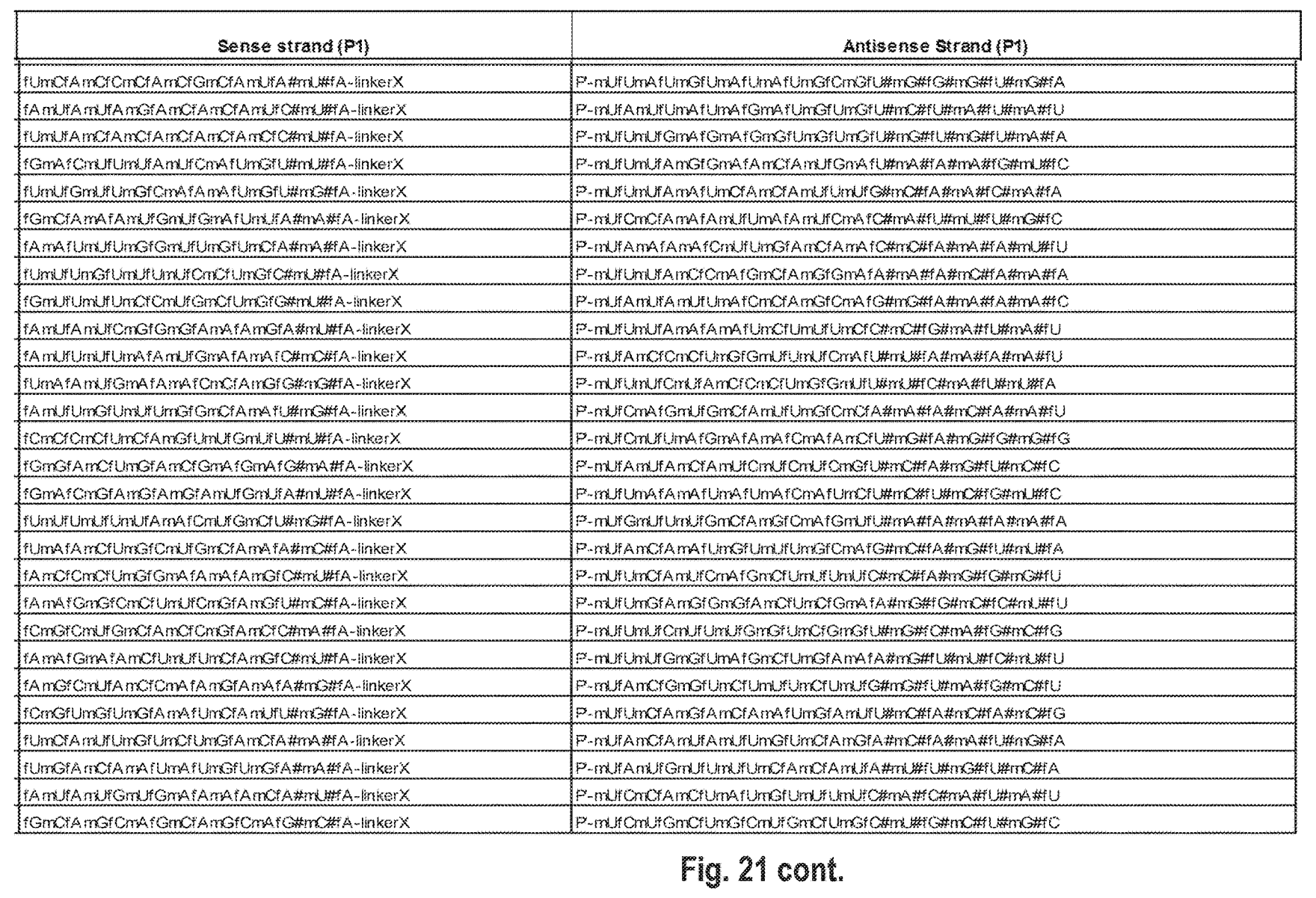
Figure 21:
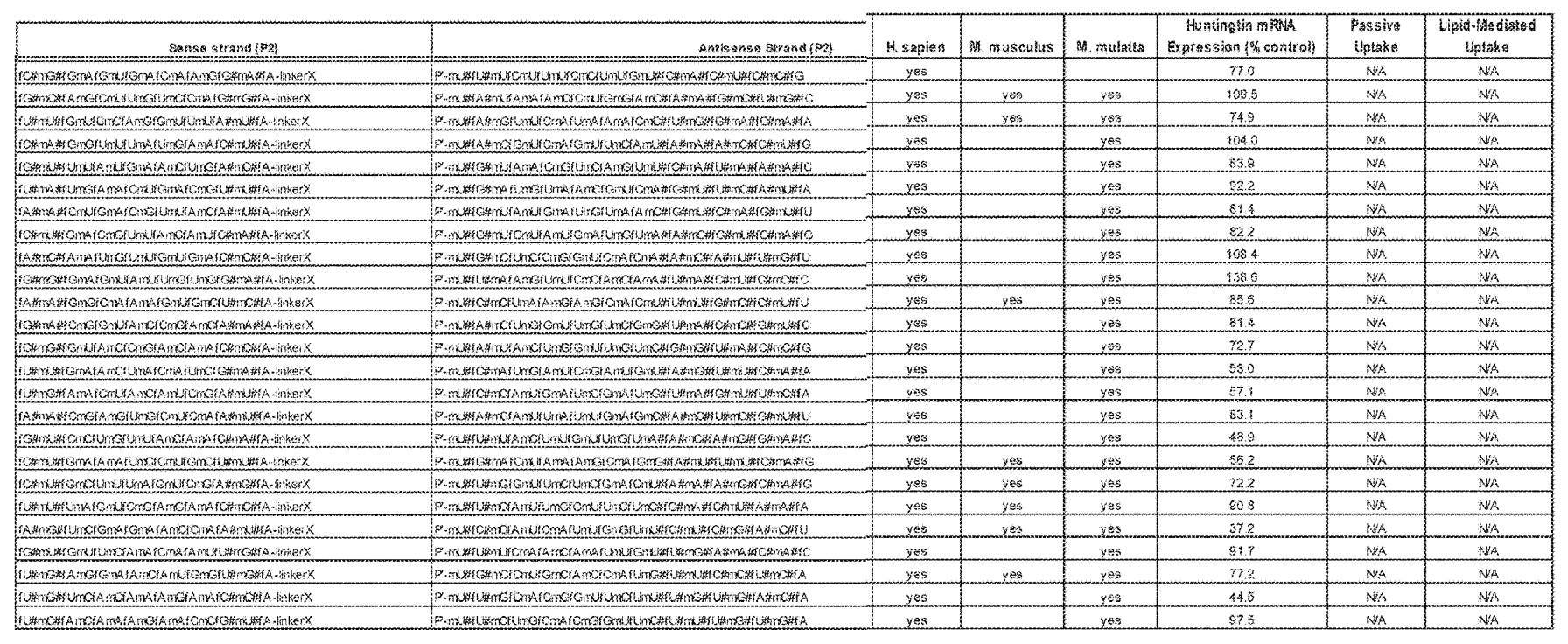
Figure 21:
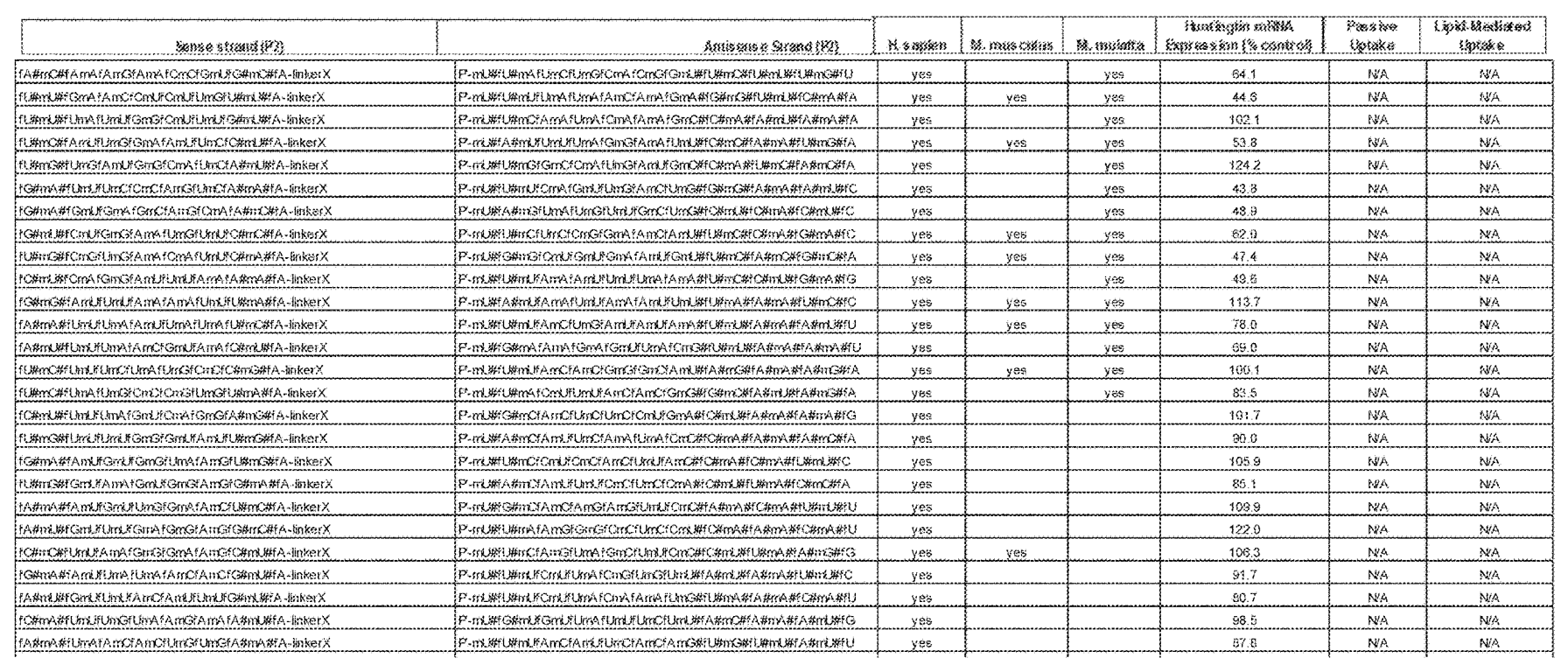
Figure 21:
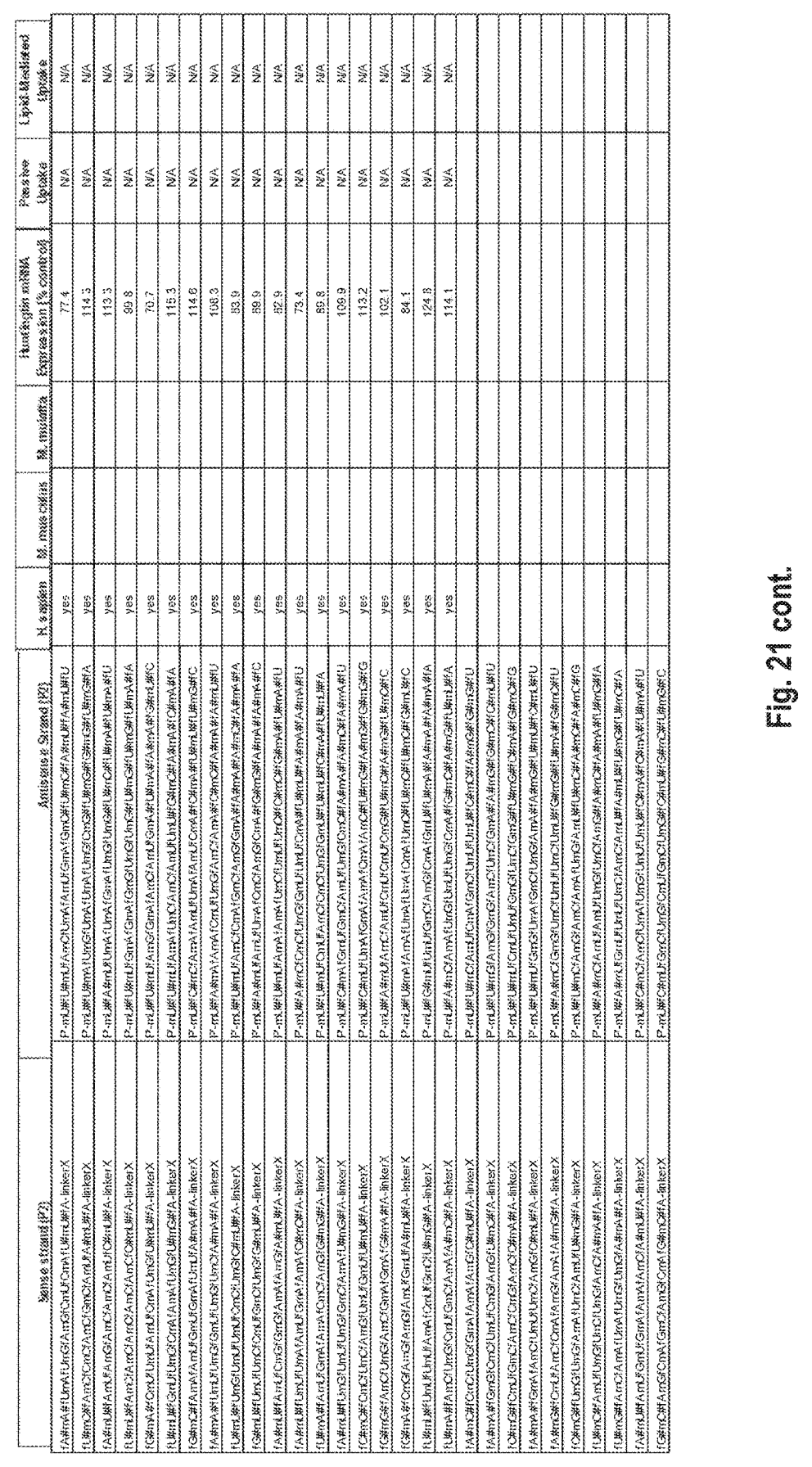

In certain exemplary embodiments, RNA silencing agents of the invention that are capable of targeting one or more of the target sequences at one or more target sequences are set forth in Table 1, below, and in FIG. 21 (which also includes exemplary modifications).

TABLE 1

Additional target sequences according to certain embodiments of the invention (SEQ ID NOS 5-212, respectively, in order of columns).

| GCUGCCGGGF | Accession Number | Position | Targeting region (20 mer) | Targeting Region (30 mer) |
|---|---|---|---|---|
| HTT | NM_002111.6 | 1214 | GUCCAGGUUUAUGAACUGAC | AGCUUGUCCAGGUUUAUGAACUGACGUUAC |
| HTT | NM_002111.6 | 1218 | AGGUUUAUGAACUGACGUUA | UGUCCAGGUUUAUGAACUGACGUUACAUCA |
| HTT | NM_002111.6 | 1219 | GGUUUAUGAACUGACGUUAC | GUCCAGGUUUAUGAACUGACGUUACAUCAU |
| HTT | NM_002111.6 | 1257 | ACCACAAUGUUGUGACCGGA | CCAAGACCACAAUGUUGUGACCGGAGCCCU |
| HTT | NM_002111.6 | 1894 | UGUGUUAGACGGUACCGACA | GAAAUUGUGUUAGACGGUACCGACAACCAG |
| HTT | NM_002111.6 | 1907 | ACCGACAACCAGUAUUUGGG | ACGGUACCGACAACCAGUAUUUGGGCCUGC |
| HTT | NM_002111.6 | 2866 | ACGAGUGCUCAAUAAUGUUG | CAAGAACGAGUGCUCAAUAAUGUUGUCAUC |
| HTT | NM_002111.6 | 4041 | UGAAAUCCUGCUUUAGUCGA | AUACCUGAAAUCCUGCUUUAGUCGAGAACC |
| HTT | NM_002111.6 | 4049 | UGCUUUAGUCGAGAACCAAU | AAUCCUGCUUUAGUCGAGAACCAAUGAUGG |
| HTT | NM_002111.6 | 5301 | GGGACAGUACUUCAACGCUA | AGAUGGGACAGUACUUCAACGCUAGAAGA |
| HTT | NM_002111.6 | 6016 | GGCAAUUCAGUCUCGUUGUG | AUCCAGGCAAUUCAGUCUCGUUGUGAAAAC |
| HTT | NM_002111.6 | 6579 | GCCUGCUAGCUCCAUGCUUA | CCUAAGCCUGCUAGCUCCAUGCUUAAGCCU |
| HTT | NM_002111.6 | 8603 | GCCCACUGCGUGAACAUUCA | GGAUCGCCCACUGCGUGAACAUUCACAGCC |
| HTT | NM_002111.6 | 10125 | UUCUUCUCAGGAUUUAAAAU | CUCUUUUCUUCUCAGGAUUUAAAAUUUAAU |
| HTT | NM_002111.6 | 10146 | UAAUUAUAUCAGUAAAGAGA | AAAUUUAAUUAUAUCAGUAAAGAGAUUAAU |
| HTT | NM_002111.6 | 10150 | UAUAUCAGUAAAGAGAUUAA | UUAAUUAUAUCAGUAAAGAGAUUAAUUUUA |
| HTT | NM_002111.6 | 424 | ACUUUCAGCUACCAAGAAAG | AAAGAACUUUCAGCUACCAAGAAAGACCGU |
| HTT | NM_002111.6 | 456 | AUUGUCUGACAAUAUGUGAA | GAAUCAUUGUCUGACAAUAUGUGAAAACAU |
| HTT | NM_002111.6 | 522 | UUCUGGGCAUCGCUAUGGAA | |
| HTT | NM_002111.6 | 527 | GGCAUCGCUAUGGAACUUUU | UUCUGGGCAUCGCUAUGGAACUUUUCUGC |
| HTT | NM_002111.6 | 878 | GCAAAUGACAAUGAAAUUAA | AUUUGCAAAUGACAAUGAAAUUAAGGUUU |
| HTT | NM_002111.6 | 879 | CAAAUGACAAUGAAAUUAAG | UUUGCAAAUGACAAUGAAAUUAAGGUUUU |
| HTT | NM_002111.6 | 908 | AAGGCCUUCAUAGCGAACCU | UGUAAAGGCCUUCAUAGCGAACCUGAAGU |
| HTT | NM_002111.6 | 1024 | ACUAAAUGUGCUCUUAGGCU | UGGCUACUAAAUGUGCUCUUAGGCUUACUC |
| HTT | NM_002111.6 | 1165 | CGGAGUGACAAGGAAAGAAA | AGCUUCGGAGUGACAAGGAAAGAAAUGGAA |
| HTT | NM_002111.6 | 1207 | GCAGCUUGUCCAGGUUUAUG | GCAGAGCAGCUUGUCCAGGUUUAUGAACUG |
| HTT | NM_002111.6 | 1212 | UUGUCCAGGUUUAUGAACUG | GCAGCUUGUCCAGGUUUAUGAACUGACGUU |
| HTT | NM_002111.6 | 1217 | CAGGUUUAUGAACUGACGUU | UUGUCCAGGUUUAUGAACUGACGUUACAUC |

TABLE 1-continued

Additional target sequences according to certain embodiments of the
invention (SEQ ID NOS 5-212, respectively, in order of columns).

| GCUGCCGGGF | Accession Number | Position | Targeting region (20 mer) | Targeting Region (30 mer) |
|---|---|---|---|---|
| HTT | NM_002111.6 | 1220 | GUUUAUGAACUGACGUUACA | UCCAGGUUUAUGAACUGACGUUACAUCAUA |
| HTT | NM_002111.6 | 1223 | UAUGAACUGACGUUACAUCA | AGGUUUAUGAACUGACGUUACAUCAUACAC |
| HTT | NM_002111.6 | 1227 | AACUGACGUUACAUCAUACA | UUAUGAACUGACGUUACAUCAUACACAGCA |
| HTT | NM_002111.6 | 1229 | CUGACGUUACAUCAUACACA | AUGAACUGACGUUACAUCAUACACAGCACC |
| HTT | NM_002111.6 | 1260 | ACAAUGUUGUGACCGGAGCC | AGACCACAAUGUUGUGACCGGAGCCCUGGA |
| HTT | NM_002111.6 | 1403 | GGGAGUAUUGUGGAACUUAU | GUAGUGGGAGUAUUGUGGAACUUAUAGCUG |
| HTT | NM_002111.6 | 1470 | AAGGCAAAGUGCUCUUAGGA | ACAAAAGGCAAAGUGCUCUUAGGAGAAGA |
| HTT | NM_002111.6 | 1901 | GACGGUACCGACAACCAGUA | UGUUAGACGGUACCGACAACCAGUAUUUGG |
| HTT | NM_002111.6 | 1903 | CGGUACCGACAACCAGUAUU | UUAGACGGUACCGACAACCAGUAUUUGGGC |
| HTT | NM_002111.6 | 2411 | UUGAACUACAUCGAUCAUGG | ACAUCUUGAACUACAUCGAUCAUGGAGACC |
| HTT | NM_002111.6 | 2412 | UGAACUACAUCGAUCAUGGA | CAUCUUGAACUACAUCGAUCAUGGAGACCC |
| HTT | NM_002111.6 | 2865 | AACGAGUGCUCAAUAAUGUU | GCAAGAACGAGUGCUCAAUAAUGUUGUCAU |
| HTT | NM_002111.6 | 3801 | GUCCUGUUACAACAAGUAAA | CUCAGGUCCUGUUACAACAAGUAAAUCCUC |
| HTT | NM_002111.6 | 4040 | CUGAAAUCCUGCUUUAGUCG | GAUACCUGAAAUCCUGCUUUAGUCGAGAAC |
| HTT | NM_002111.6 | 4048 | CUGCUUUAGUCGAGAACCAA | AAAUCCUGCUUUAGUCGAGAACCAAUGAUG |
| HTT | NM_002111.6 | 4052 | UUUAGUCGAGAACCAAUGAU | CCUGCUUUAGUCGAGAACCAAUGAUGGCAA |
| HTT | NM_002111.6 | 4055 | AGUCGAGAACCAAUGAUGGC | GCUUUAGUCGAGAACCAAUGAUGGCAACUG |
| HTT | NM_002111.6 | 4083 | GUGUUCAACAAUUGUUGAAG | UGUUUGUGUUCAACAAUUGUUGAAGACUCU |
| HTT | NM_002111.6 | 4275 | UGAGGAACAUGGUGCAGGCG | CAGCCUGAGGAACAUGGUGCAGGCGGAGCA |
| HTT | NM_002111.6 | 4372 | UGUCACAAAGAACCGUGCAG | ACGAGUGUCACAAAGAACCGUGCAGAUAAG |
| HTT | NM_002111.6 | 4374 | UCACAAAGAACCGUGCAGAU | GAGUGUCACAAAGAACCGUGCAGAUAAGAA |
| HTT | NM_002111.6 | 4376 | ACAAAGAACCGUGCAGAUAA | GUGUCACAAAGAACCGUGCAGAUAAGAAUG |
| HTT | NM_002111.6 | 4425 | UUGAACCUCUUGUUAUAAAA | UUUGUUUGAACCUCUUGUUAUAAAAGCUUU |
| HTT | NM_002111.6 | 4562 | UUUAUUGGCUUUGUAUUGAA | AGGUGUUUAUUGGCUUUGUAUUGAAACAGU |
| HTT | NM_002111.6 | 4692 | UCAUUGGAAUUCCUAAAAUC | ACAGAUCAUUGGAAUUCCUAAAAUCAUUCA |
| HTT | NM_002111.6 | 4721 | UGUGAUGGCAUCAUGGCCAG | AGCUCUGUGAUGGCAUCAUGGCCAGUGGAA |
| HTT | NM_002111.6 | 5200 | GAUUUCCCAGUCAACUGAAG | GUUCUGAUUUCCCAGUCAACUGAAGAUAUU |
| HTT | NM_002111.6 | 5443 | GAGUGAGCAGCAACAUACUU | GAAAUGAGUGAGCAGCAACAUACUUUCUAU |
| HTT | NM_002111.6 | 5515 | GUCUGGAAUGUUCCGGAGAA | UUCAAGUCUGGAAUGUUCCGGAGAAUCACA |
| HTT | NM_002111.6 | 8609 | UGCGUGAACAUUCACAGCCA | CCCACUGCGUGAACAUUCACAGCCAGCAGC |
| HTT | NM_002111.6 | 10130 | CUCAGGAUUUAAAAUUUAAU | UUCUUCUCAGGAUUUAAAAUUUAAUUAUAU |
| HTT | NM_002111.6 | 10134 | GGAUUUAAAAUUUAAUUAUA | UCUCAGGAUUUAAAAUUUAAUUAUAUCAGU |
| HTT | NM_002111.6 | 10142 | AAUUUAAUUAUAUCAGUAAA | UUUAAAAUUUAAUUAUAUCAGUAAAGAGAU |
| HTT | NM_002111.6 | 10169 | AUUUUAACGUAACUCUUUCU | GAUUAAUUUAACGUAACUCUUUCUAUGCC |
| HTT | NM_002111.6 | 10182 | UCUUUCUAUGCCCGUGUAAA | GUAACUCUUUCUAUGCCCGUGUAAAGUAUG |
| HTT | NM_002111.6 | 10186 | UCUAUGCCCGUGUAAAGUAU | CUCUUUCUAUGCCCGUGUAAAGUAUGUGAA |
| HTT | NM_002111.6 | 10809 | CUUUUAGUCAGGAGAGUGCA | GACCCCUUUUAGUCAGGAGAGUGCAGAUCU |
| HTT | NM_002111.6 | 11116 | UGUUUGGGUAUUGAAUGUG | GUCGAUGUUUGGGUAUUGAAUGUGGUAAG |

TABLE 1-continued

Additional target sequences according to certain embodiments of the
invention (SEQ ID NOS 5-212, respectively, in order of columns).

| GCUGCCGGGF | Accession Number | Position | Targeting region (20 mer) | Targeting Region (30 mer) |
|---|---|---|---|---|
| HTT | NM_002111.6 | 11129 | GAAUGUGGUAAGUGGAGGAA | GUAUUGAAUGUGGUAAGUGGAGGAAAUGUU |
| HTT | NM_002111.6 | 11134 | UGGUAAGUGGAGGAAAUGUU | GAAUGUGGUAAGUGGAGGAAAUGUUGGAAC |
| HTT | NM_002111.6 | 11147 | AAAUGUUGGAACUCUGUGCA | GGAGGAAAUGUUGGAACUCUGUGCAGGUGC |
| HTT | NM_002111.6 | 11412 | AUGUUUGAGGAGGCCCUUAA | GUCCGAUGUUUGAGGAGGCCCUUAAGGGAA |
| HTT | NM_002111.6 | 11426 | CCUUAAGGGAAGCUACUGAA | GAGGCCCUUAAGGGAAGCUACUGAAUUAUA |
| HTT | NM_002111.6 | 11443 | GAAUUAUAACACGUAAGAAA | CUACUGAAUUAUAACACGUAAGAAAAUCAC |
| HTT | NM_002111.6 | 11659 | AUGUUUACAUUUGUAAGAAA | GCUAGAUGUUUACAUUUGUAAGAAAUAACA |
| HTT | NM_002111.6 | 11666 | CAUUUGUAAGAAAUAACACU | GUUUACAUUUGUAAGAAAUAACACUGUGAA |
| HTT | NM_002111.6 | 11677 | AAUAACACUGUGAAUGUAAA | UAAGAAAUAACACUGUGAAUGUAAAACAGA |
| HTT | NM_002111.6 | 11863 | AAUAUGAGCUCAUUAGUAAA | AGAUGAAUAUGAGCUCAUUAGUAAAAAUGA |
| HTT | NM_002111.6 | 11890 | UCACCCACGCAUAUACAUAA | UGACUUCAOCCACGCAUAUACAUAAAGUAU |
| HTT | NM_002111.6 | 11927 | AUAUAGACACAUCUAUAAUU | UGUGCAUAUAGACACAUCUAUAAUUUUACA |
| HTT | NM_002111.6 | 11947 | UUACACACACACCUCUCAAG | UAAUUUUACACACACACCUCUCAAGACGGA |
| HTT | NM_002111.6 | 12163 | GACUUUAUCAUGUUCCUAAA | AGGAAGACUUUAUCAUGUUCCUAAAAAUCU |
| HTT | NM_002111.6 | 12218 | UUGUUGCAAAUGUGAUUAAU | AAAUUUGUUGCAAAUGUGAUUAAUUUGGU |
| HTT | NM_002111.6 | 12223 | GCAAAUGUGAUUAAUUUGGU | UUGUUGCAAAUGUGAUUAAUUUGGUUGUCA |
| HTT | NM_002111.6 | 12235 | AAUUUGGUUGUCAAGUUUUG | UGAUUAAUUUGGUUGUCAAGUUUUGGGGGU |
| HTT | NM_002111.6 | 12279 | UUUGUUUUCCUGCUGGUAAU | UUGCUUUUGUUUUCCUGCUGGUAAUAUCGG |
| HTT | NM_002111.6 | 12282 | GUUUUCCUGCUGGUAAUAUC | CUUUUGUUUUCCUGCUGGUAAUAUCGGGAA |
| HTT | NM_002111.6 | 12297 | AUAUCGGGAAAGAUUUUAAU | UGGUAAUAUCGGGAAAGAUUUUAAUGAAAC |
| HTT | NM_002111.6 | 12309 | AUUUUAAUGAAACCAGGGUA | GAAAGAUUUUAAUGAAACCAGGGUAGAAUU |
| HTT | NM_002111.6 | 12313 | UAAUGAAACCAGGGUAGAAU | GAUUUUAAUGAAACCAGGGUAGAAUUGUUU |
| HTT | NM_002111.6 | 12331 | AUUGUUUGGCAAUGCACUGA | GUAGAAUUGUUUGGCAAUGCACUGAAGCGU |
| HTT | NM_002111.6 | 13136 | CCCCUCAGUUGUUUCUAAGA | GCCUUCCCCUCAGUUGUUUCUAAGAGCAGA |
| HTT | NM_002111.6 | 13398 | GGACUGACGAGAGAUGUAUA | GGGAAGGACUGACGAGAGAUGUAUAUUUAA |
| HTT | NM_002111.6 | 13403 | GACGAGAGAUGUAUAUUUAA | GGACUGACGAGAGAUGUAUAUUUAAUUUUU |
| HTT | NM_002111.6 | 13423 | UUUUUUAACUGCUGCAAACA | UUUAAUUUUUUAACUGCUGCAAACAUUGUA |
| HTT | NM_002111.6 | 13428 | UAACUGCUGCAAACAUUGUA | UUUUUUAACUGCUGCAAACAUUGUACAUCC |
| HTT | NM_002111.6 | 152 | ACCCUGGAAAAGCUGAUGAA | UGGCGAOCCUGGAAAAGCUGAUGAAGGCCU |
| HTT | NM_002111.6 | 170 | AAGGCCUUCGAGUCCCUCAA | UGAUGAAGGCCUUCGAGUCCCUCAAGUCCU |
| HTT | NM_002111.6 | 402 | CGCUGCACCGACCAAAGAAA | GGAGCCGCUGCACCGACCAAAGAAAGAACU |
| HTT | NM_002111.6 | 420 | AAGAACUUUCAGCUACCAAG | AAAGAAAGAACUUUCAGCUACCAAGAAAGA |
| HTT | NM_002111.6 | 430 | AGCUACCAAGAAAGACCGUG | CUUUCAGCUACCAAGAAAGACCGUGUGAAU |
| HTT | NM_002111.6 | 446 | CGUGUGAAUCAUUGUCUGAC | AAGACCGUGUGAAUCAUUGUCUGACAAUAU |
| HTT | NM_002111.6 | 454 | UCAUUGUCUGACAAUAUGUG | GUGAAUCAUUGUCUGACAAUAUGUGAAAAC |
| HTT | NM_002111.6 | 462 | UGACAAUAUGUGAAAACAUA | UUGUCUGACAAUAUGUGAAAACAUAGUGGC |

TABLE 1-continued

Additional target sequences according to certain embodiments of the
invention (SEQ ID NOS 5-212, respectively, in order of columns).

| GCUGCCGGGF | Accession Number | Position | Targeting region (20 mer) | Targeting Region (30 mer) |
|---|---|---|---|---|
| HTT | NM_002111.6 | 467 | AUAUGUGAAAACAUAGUGGC | UGACAAUAUGUGAAAACAUAGUGGCACAGU |
| HTT | NM_002111.6 | 211 | GCAGCAGCAGCAGCAGCAGC | CAGCAGCAGCAGCAGCAGCAGCAGCAGCAG |

IV. siRNA Design

In some embodiments, siRNAs are designed as follows. First, a portion of the target gene (e.g., the htt gene), e.g., one or more of the target sequences set forth at FIG. 8, is selected, e.g., 10150, 10146 and/or 10125 from the 5' untranslated region of a target gene. Cleavage of mRNA at these sites should eliminate translation of corresponding mutant protein. Sense strands were designed based on the target sequence. (See FIG. 8.) Preferably the portion (and corresponding sense strand) includes about 19 to 25 nucleotides, e.g., 19, 20, 21, 22, 23, 24 or 25 nucleotides. More preferably, the portion (and corresponding sense strand) includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNAi agents have been demonstrated to elicit an interferon or PKR response in certain mammalian cells which may be undesirable. Preferably, the RNAi agents of the invention do not elicit a PKR response (i.e., are of a sufficiently short length). However, longer RNAi agents may be useful, for example, in cell types incapable of generating a PRK response or in situations where the PKR response has been down-regulated or dampened by alternative means.

The sense strand sequence is designed such that the target sequence is essentially in the middle of the strand. Moving the target sequence to an off-center position may, in some instances, reduce efficiency of cleavage by the siRNA. Such compositions, i.e., less efficient compositions, may be desirable for use if off-silencing of the wild-type mRNA is detected.

The antisense strand is routinely the same length as the sense strand and includes complementary nucleotides. In one embodiment, the strands are fully complementary, i.e., the strands are blunt-ended when aligned or annealed. In another embodiment, the strands comprise align or anneal such that 1-, 2-, 3-, 4-, 5-, 6- or 7-nucleotide overhangs are generated, i.e., the 3' end of the sense strand extends 1, 2, 3, 4, 5, 6 or 7 nucleotides further than the 5' end of the antisense strand and/or the 3' end of the antisense strand extends 1, 2, 3, 4, 5, 6 or 7 nucleotides further than the 5' end of the sense strand. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material.

To facilitate entry of the antisense strand into RISC (and thus increase or improve the efficiency of target cleavage and silencing), the base pair strength between the 5' end of the sense strand and 3' end of the antisense strand can be altered, e.g., lessened or reduced, as described in detail in U.S. Pat. Nos. 7,459,547, 7,772,203 and 7,732,593, entitled "Methods and Compositions for Controlling Efficacy of RNA Silencing" (filed Jun. 2, 2003) and U.S. Pat. Nos. 8,309,704, 7,750,144, 8,304,530, 8,329,892 and 8,309,705, entitled "Methods and Compositions for Enhancing the Efficacy and Specificity of RNAi" (filed Jun. 2, 2003), the contents of which are incorporated in their entirety by this reference. In one embodiment of these aspects of the invention, the base-pair strength is less due to fewer G:C base pairs between the 5' end of the first or antisense strand and the 3' end of the second or sense strand than between the 3' end of the first or antisense strand and the 5' end of the second or sense strand. In another embodiment, the base pair strength is less due to at least one mismatched base pair between the 5' end of the first or antisense strand and the 3' end of the second or sense strand. In certain exemplary embodiments, the mismatched base pair is selected from the group consisting of G:A, C:A, C:U, G:G, A:A, C:C and U:U. In another embodiment, the base pair strength is less due to at least one wobble base pair, e.g., G:U, between the 5' end of the first or antisense strand and the 3' end of the second or sense strand. In another embodiment, the base pair strength is less due to at least one base pair comprising a rare nucleotide, e.g., inosine (I). In certain exemplary embodiments, the base pair is selected from the group consisting of an I:A, I:U and I:C. In yet another embodiment, the base pair strength is less due to at least one base pair comprising a modified nucleotide. In certain exemplary embodiments, the modified nucleotide is selected from the group consisting of 2-amino-G, 2-amino-A, 2,6-diamino-G, and 2,6-diamino-A.

The design of siRNAs suitable for targeting the htt target sequences set forth at FIG. 8 is described in detail below. siRNAs can be designed according to the above exemplary teachings for any other target sequences found in the htt gene. Moreover, the technology is applicable to targeting any other target sequences, e.g., non-disease causing target sequences.

To validate the effectiveness by which siRNAs destroy mRNAs (e.g., huntingtin mRNA), the siRNA can be incubated with cDNA (e.g., huntingtin cDNA) in a *Drosophila*-based in vitro mRNA expression system. Radiolabeled with $^{32}$P, newly synthesized mRNAs (e.g., huntingtin mRNA) are detected autoradiographically on an agarose gel. The presence of cleaved mRNA indicates mRNA nuclease activity. Suitable controls include omission of siRNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Sites of siRNA-mRNA complementation are selected which result in optimal mRNA specificity and maximal mRNA cleavage.

While the instant invention primarily features targeting specific target sequences of a gene (e.g., in htt) distinct from the expanded CAG region mutation, the skilled artisan will appreciate that targeting the mutant region may have applicability as a therapeutic strategy in certain situations. Targeting the mutant region can be accomplished using siRNA that complements CAG in series. The siRNA$^{cag}$ would bind to mRNAs with CAG complementation, but might be expected to have greater opportunity to bind to an extended CAG series. Multiple siRNA$^{cag}$ would bind to the mutant huntingtin mRNA (as opposed to fewer for the wild type huntingtin mRNA); thus, the mutant huntingtin mRNA is more likely to be cleaved. Successful mRNA inactivation using this approach would also eliminate normal or wild-type huntingtin mRNA. Also inactivated, at least to some extent, could be other normal genes (approximately 70) which also have CAG repeats, where their mRNAs could interact with the siRNA. This approach would thus rely on an attrition strategy—more of the mutant huntingtin mRNA would be destroyed than wild-type huntingtin mRNA or the other approximately 69 mRNAs that code for polyglutamines.

V. RNAi Agents

The present invention includes siRNA molecules designed, for example, as described above. The siRNA molecules of the invention can be chemically synthesized, or can be transcribed in vitro from a DNA template, or in vivo from e.g., shRNA, or by using recombinant human DICER enzyme, to cleave in vitro transcribed dsRNA templates into pools of 20-, 21- or 23-bp duplex RNA mediating RNAi. The siRNA molecules can be designed using any method known in the art.

In one aspect, instead of the RNAi agent being an interfering ribonucleic acid, e.g., an siRNA or shRNA as described above, the RNAi agent can encode an interfering ribonucleic acid, e.g., an shRNA, as described above. In other words, the RNAi agent can be a transcriptional template of the interfering ribonucleic acid. Thus, RNAi agents of the present invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21-23 nucleotides (Brummelkamp et al., 2002; Lee et al., 2002, Supra; Miyagishi et al., 2002; Paddison et al., 2002, supra; Paul et al., 2002, supra; Sui et al., 2002 supra; Yu et al., 2002, supra. More information about shRNA design and use can be found on the internet at the following addresses: katandin.cshl.org:9331/RNAi/docs/B seRI-BamHI_Strategy.pdf and katandin.cshl.org:9331/RNAi/docs/Web_version_of PCR_strategy1.pdf).

Expression constructs of the present invention include any construct suitable for use in the appropriate expression system and include, but are not limited to, retroviral vectors, linear expression cassettes, plasmids and viral or virally-derived vectors, as known in the art. Such expression constructs can include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct. (Tuschl, T., 2002, Supra).

Synthetic siRNAs can be delivered into cells by methods known in the art, including cationic liposome transfection and electroporation. To obtain longer term suppression of the target genes (i.e., htt genes) and to facilitate delivery under certain circumstances, one or more siRNA can be expressed within cells from recombinant DNA constructs. Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl, T., 2002, supra) capable of expressing functional double-stranded siRNAs; (Bagella et al., 1998; Lee et al., 2002, supra; Miyagishi et al., 2002, supra; Paul et al., 2002, supra; Yu et al., 2002), supra; Sui et al., 2002, supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998; Lee et al., 2002, supra; Miyagishi et al., 2002, supra; Paul et al., 2002, supra; Yu et al., 2002), supra; Sui et al., 2002, supra). Constructs containing siRNA sequence under the control of T7 promoter also make functional siRNAs when cotransfected into the cells with a vector expressing T7 RNA polymerase (Jacque et al., 2002, supra). A single construct may contain multiple sequences coding for siRNAs, such as multiple regions of the gene encoding htt, targeting the same gene or multiple genes, and can be driven, for example, by separate PolIII promoter sites.

Animal cells express a range of noncoding RNAs of approximately 22 nucleotides termed micro RNA (miRNAs) which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with sequence complementary to the target mRNA, a vector construct that expresses the engineered precursor can be used to produce siRNAs to initiate RNAi against specific mRNA targets in mammalian cells (Zeng et al., 2002, supra). When expressed by DNA vectors containing polymerase III promoters, micro-RNA designed hairpins can silence gene expression (McManus et al., 2002, supra). MicroRNAs targeting polymorphisms may also be useful for blocking translation of mutant proteins, in the absence of siRNA-mediated gene-silencing. Such applications may be useful in situations, for example, where a designed siRNA caused off-target silencing of wild type protein.

Viral-mediated delivery mechanisms can also be used to induce specific silencing of targeted genes through expression of siRNA, for example, by generating recombinant adenoviruses harboring siRNA under RNA Pol II promoter transcription control (Xia et al., 2002, supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. Id. In an animal model, whole-embryo electroporation can efficiently deliver synthetic siRNA into post-implantation mouse embryos (Calegari et al., 2002). In adult mice, efficient delivery of siRNA can be accomplished by "high-pressure" delivery technique, a rapid injection (within 5 seconds) of a large volume of siRNA containing solution into animal via the tail vein (Liu et al., 1999, supra; McCaffrey et al., 2002, supra; Lewis et al., 2002. Nanoparticles and liposomes can also be used to deliver siRNA into animals. In certain exemplary embodiments, recombinant adeno-associated viruses (rAAVs) and their associated vectors can be used to deliver one or more siRNAs into cells, e.g., neural cells (e.g., brain cells) (US Patent Applications 2014/0296486, 2010/0186103, 2008/0269149, 2006/0078542 and 2005/0220766).

The nucleic acid compositions of the invention include both unmodified siRNAs and modified siRNAs as known in the art, such as crosslinked siRNA derivatives or derivatives having non nucleotide moieties linked, for example to their 3' or 5' ends. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. The RNA precursors are typically nucleic acid molecules that individually encode either one strand of a dsRNA or encode the entire nucleotide sequence of an RNA hairpin loop structure.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability and/or half-life. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

The nucleic acid molecules of the present invention can also be labeled using any method known in the art. For instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the siRNA can be radiolabeled, e.g., using $^{3}H$, $^{32}P$ or other appropriate isotope.

Moreover, because RNAi is believed to progress via at least one single-stranded RNA intermediate, the skilled artisan will appreciate that ss-siRNAs (e.g., the antisense strand of a ds-siRNA) can also be designed (e.g., for chemical synthesis) generated (e.g., enzymatically generated) or expressed (e.g., from a vector or plasmid) as described herein and utilized according to the claimed methodologies. Moreover, in invertebrates, RNAi can be triggered effectively by long dsRNAs (e.g., dsRNAs about 100-1000 nucleotides in length, preferably about 200-500, for example, about 250, 300, 350, 400 or 450 nucleotides in length) acting as effectors of RNAi. (Brondani et al., Proc Natl Acad Sci USA. 2001 Dec. 4; 98(25):14428-33. Epub 2001 Nov. 27.)

VI. Anti-Htt RNA Silencing Agents

The present invention features anti-huntingtin RNA silencing agents (e.g., siRNA and shRNAs), methods of making said RNA silencing agents, and methods (e.g., research and/or therapeutic methods) for using said improved RNA silencing agents (or portions thereof) for RNA silencing of huntingtin protein (e.g., mutant huntingtin protein). The RNA silencing agents comprise an antisense strand (or portions thereof), wherein the antisense strand has sufficient complementary to a heterozygous single nucleotide polymorphism to mediate an RNA-mediated silencing mechanism (e.g. RNAi).

In certain embodiments, siRNA compounds are provided having one or any combination of the following properties: (1) fully chemically-stabilized (i.e., no unmodified 2'-OH residues); (2) asymmetry; (3) 11-16 base pair duplexes; (4) alternating pattern of chemically-modified nucleotides (e.g., 2'-fluoro and 2'-methoxy modifications); and (5) single-stranded, fully phosphorothioated tails of 5-8 bases. The number of phosphorothioate modifications is critical. This number is varied from 6 to 17 total in different embodiments.

In certain embodiments, the siRNA compounds described herein can be conjugated to a variety of targeting agents, including, but not limited to, cholesterol, DHA, phenyltropanes, cortisol, vitamin A, vitamin D, GalNac, and gangliozides. The cholesterol-modified version showed 5-10 fold improvement in efficacy in vitro versus previously used chemical stabilization patterns (e.g., wherein all purine but not purimidines are modified) in wide range of cell types (e.g., HeLa, neurons, hepatocytes, trophoblasts).

Certain compounds of the invention having the structural properties described above and herein may be referred to as "hsiRNA-ASP" (hydrophobically-modified, small interfering RNA, featuring an advanced stabilization pattern). In addition, this hsiRNA-ASP pattern showed a dramatically improved distribution through the brain, spinal cord, delivery to liver, placenta, kidney, spleen and several other tissues, making them accessible for therapeutic intervention.

In liver hsiRNA-ASP delivery specifically to endothelial and kupper cells, but not hepatocytes, making this chemical modification pattern complimentary rather than competitive technology to GalNac conjugates.

The compounds of the invention can be described in the following aspects and embodiments.

In a first aspect, provided herein is oligonucleotide of at least 16 contiguous nucleotides, said oligonucleotide having a 5' end, a 3' end and complementarity to a target, wherein: (1) the oligonucleotide comprises alternating 2'-methoxy-ribonucleotides and 2'-fluoro-ribonucleotides; (2) the nucleotides at positions 2 and 14 from the 5' end are not 2'-methoxy-ribonucleotides; (3) the nucleotides are connected via phosphodiester or phosphorothioate linkages; and (4) the nucleotides at positions 1-6 from the 3' end, or positions 1-7 from the 3' end, are connected to adjacent nucleotides via phosphorothioate linkages.

In a second aspect, provided herein is a double-stranded, chemically-modified nucleic acid, comprising a first oligonucleotide and a second oligonucleotide, wherein: (1) the first oligonucleotide is an oligonucleotide described herein (e.g., comprising SEQ ID Nos:1, 2, 3 or 4); (2) a portion of the first oligonucleotide is complementary to a portion of the second oligonucleotide; (3) the second oligonucleotide comprises alternating 2'-methoxy-ribonucleotides and 2'-fluoro-ribonucleotides; (4) the nucleotides at positions 2 and 14 from the 3' end of the second oligonucleotide are 2'-methoxy-ribonucleotides; and (5) the nucleotides of the second oligonucleotide are connected via phosphodiester or phosphorothioate linkages.

In a third aspect, provided herein is oligonucleotide having the structure:

wherein: X is a 5' phosphate group; A, for each occurrence, independently is a 2'-methoxy-ribonucleotide; B, for each occurrence, independently is a 2'-fluoro-ribonucleotide; L, for each occurrence independently is a phosphodiester or phosphorothioate linker; S is a phosphorothioate linker; and R is selected from hydrogen and a capping group (e.g., an acyl such as acetyl); j is 4, 5, 6 or 7; r is 2 or 3; and t is 0 or 1.

In a fourth aspect, provided herein is a double-stranded, chemically-modified nucleic acid comprising a first oligonucleotide and a second oligonucleotide, wherein: (1) the first oligonucleotide is selected from the oligonucleotides of the third aspect; (2) a portion of the first oligonucleotide is complementary to a portion of the second oligonucleotide; and (3) the second oligonucleotide has the structure:

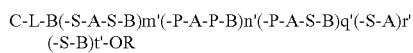

wherein: C is a hydrophobic molecule; A, for each occurrence, independently is a 2'-methoxy-ribonucleotide; B, for each occurrence, independently is a 2'-fluoro-ribonucleotide; L is a linker comprising one or more moiety selected from the group consisting of: 0-4 repeat units of ethyleneglycol, a phosphodiester, and a phosphorothioate; S is a phosphorothioate linker; P is a phosphodiester linker; R is selected from hydrogen and a capping group (e.g., an acyl such as acetyl); m' is 0 or 1; n' is 4, 5 or 6; q' is 0 or 1; r' is 0 or 1; and t' is 0 or 1.

a) Design of Anti-Htt siRNA Molecules

An siRNA molecule of the invention is a duplex consisting of a sense strand and complementary antisense strand, the antisense strand having sufficient complementary to an htt mRNA to mediate RNAi. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is sufficiently complementary to a target region. Preferably, the strands are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 16-30, e.g., 16, 17, 18, 19, 20, 21, 22, 23, 24, 25, 26, 27, 28, 29, or 30 nucleotides in each strand, wherein one of the strands is substantially complementary to a target sequence, and the other strand is identical or substantially identical to the first strand.

Generally, siRNAs can be designed by using any method known in the art, for instance, by using the following protocol:

1. The siRNA should be specific for a target sequence, e.g., a target sequence set forth in FIG. 8. In one embodiment, a target sequence is found in a mutant huntingtin (htt) allele, but not a wild-type huntingtin allele. In another embodiment, a target sequence is found in both a mutant huntingtin (htt) allele, and a wild-type huntingtin allele. In another embodiment, a target sequence is found in a wild-type huntingtin allele. The first strand should be complementary to the target sequence, and the other strand is substantially complementary to the first strand. (See FIG. 8 for exemplary sense and antisense strands.) In one embodiment, the target sequence is outside the expanded CAG repeat of the mutant huntingin (htt) allele. In another embodiment, the target sequence is outside a coding region of the target gene. Exemplary target sequences are selected from the 5' untranslated region (5'-UTR) of a target gene. Cleavage of mRNA at these sites should eliminate translation of corresponding mutant protein. Target sequences from other regions of the htt gene are also suitable for targeting. A sense strand is designed based on the target sequence. Further, siRNAs with lower G/C content (35-55%) may be more active than those with G/C content higher than 55%. Thus in one embodiment, the invention includes nucleic acid molecules having 35-55% G/C content.

2. The sense strand of the siRNA is designed based on the sequence of the selected target site. Preferably the sense strand includes about 19 to 25 nucleotides, e.g., 19, 20, 21, 22, 23, 24 or 25 nucleotides. More preferably, the sense strand includes 21, 22 or 23 nucleotides. The skilled artisan will appreciate, however, that siRNAs having a length of less than 19 nucleotides or greater than 25 nucleotides can also function to mediate RNAi. Accordingly, siRNAs of such length are also within the scope of the instant invention provided that they retain the ability to mediate RNAi. Longer RNA silencing agents have been demonstrated to elicit an interferon or Protein Kinase R (PKR) response in certain mammalian cells which may be undesirable. Preferably the RNA silencing agents of the invention do not elicit a PKR response (i.e., are of a sufficiently short length). However, longer RNA silencing agents may be useful, for example, in cell types incapable of generating a PRK response or in situations where the PKR response has been down-regulated or dampened by alternative means.

The siRNA molecules of the invention have sufficient complementarity with the target sequence such that the siRNA can mediate RNAi. In general, siRNA containing nucleotide sequences sufficiently identical to a target sequence portion of the target gene to effect RISC-mediated cleavage of the target gene are preferred. Accordingly, in a preferred embodiment, the sense strand of the siRNA is designed have to have a sequence sufficiently identical to a portion of the target. For example, the sense strand may have 100% identity to the target site. However, 100% identity is not required. Greater than 80% identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% identity, between the sense strand and the target RNA sequence is preferred. The invention has the advantage of being able to tolerate certain sequence variations to enhance efficiency and specificity of RNAi. In one embodiment, the sense strand has 4, 3, 2, 1, or 0 mismatched nucleotide(s)

with a target region, such as a target region that differs by at least one base pair between a wild-type and mutant allele, e.g., a target region comprising the gain-of-function mutation, and the other strand is identical or substantially identical to the first strand. Moreover, siRNA sequences with small insertions or deletions of 1 or 2 nucleotides may also be effective for mediating RNAi. Alternatively, siRNA sequences with nucleotide analog substitutions or insertions can be effective for inhibition.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=number of identical positions/total number of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) Proc. Natl. Acad. Sci. USA 87:2264-68, modified as in Karlin and Altschul (1993) Proc. Natl. Acad. Sci. USA 90:5873-77. Such an algorithm is incorporated into the BLAST programs (version 2.0) of Altschul, et al. (1990) J. Mol. Biol. 215:403-10.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) Nucleic Acids Res. 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

3. The antisense or guide strand of the siRNA is routinely the same length as the sense strand and includes complementary nucleotides. In one embodiment, the guide and sense strands are fully complementary, i.e., the strands are blunt-ended when aligned or annealed. In another embodiment, the strands of the siRNA can be paired in such a way as to have a 3' overhang of 1 to 7 (e.g., 2, 3, 4, 5, 6 or 7), or 1 to 4, e.g., 2, 3 or 4 nucleotides. Overhangs can comprise (or consist of) nucleotides corresponding to the target gene sequence (or complement thereof). Alternatively, overhangs can comprise (or consist of) deoxyribonucleotides, for example dTs, or nucleotide analogs, or other suitable non-nucleotide material. Thus in another embodiment, the nucleic acid molecules may have a 3' overhang of 2 nucleotides, such as TT. The overhanging nucleotides may be either RNA or DNA. As noted above, it is desirable to choose a target region wherein the mutant:wild type mismatch is a purine:purine mismatch.

4. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website.

5. Select one or more sequences that meet your criteria for evaluation.

Further general information about the design and use of siRNA may be found in "The siRNA User Guide," available at The Max-Plank-Institut fur Biophysikalishe Chemie website.

Alternatively, the siRNA may be defined functionally as a nucleotide sequence (or oligonucleotide sequence) that is capable of hybridizing with the target sequence (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, Tm (° C.)=2(# of A+T bases)+4(# of G+C bases). For hybrids between 18 and 49 base pairs in length, Tm(° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al., eds., John Wiley & Sons, Inc., sections 2.10 and 6.3-6.4, incorporated herein by reference.

Negative control siRNAs should have the same nucleotide composition as the selected siRNA, but without significant sequence complementarity to the appropriate genome. Such negative controls may be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

6. To validate the effectiveness by which siRNAs destroy target mRNAs (e.g., wild-type or mutant huntingtin mRNA), the siRNA may be incubated with target cDNA (e.g., huntingtin cDNA) in a *Drosophila*-based in vitro mRNA expression system. Radiolabeled with $^{32}$P, newly synthesized target mRNAs (e.g., huntingtin mRNA) are detected autoradiographically on an agarose gel. The presence of cleaved target mRNA indicates mRNA nuclease activity. Suitable controls include omission of siRNA and use of non-target cDNA. Alternatively, control siRNAs are selected having the same nucleotide composition as the selected siRNA, but without significant sequence complementarity to the appropriate target gene. Such negative controls can be designed by randomly scrambling the nucleotide sequence of the selected siRNA. A homology search can be performed to ensure that the negative control lacks homology to any other gene in the appropriate genome. In addition, negative control siRNAs can be designed by introducing one or more base mismatches into the sequence.

Anti-htt siRNAs may be designed to target any of the target sequences described supra. Said siRNAs comprise an antisense strand which is sufficiently complementary with the target sequence to mediate silencing of the target sequence. In certain embodiments, the RNA silencing agent is a siRNA.

In certain embodiments, the siRNA comprises a sense strand comprising a sequence set forth at FIG. 8, and an antisense strand comprising a sequence set forth at FIG. 8.

Sites of siRNA-mRNA complementation are selected which result in optimal mRNA specificity and maximal mRNA cleavage.

b) siRNA-Like Molecules siRNA-like molecules of the invention have a sequence (i.e., have a strand having a sequence) that is "sufficiently complementary" to a target sequence of a htt mRNA to direct gene silencing either by RNAi or translational repression. siRNA-like molecules are designed in the same way as siRNA molecules, but the degree of sequence identity between the sense strand and target RNA approximates that observed between an miRNA and its target. In general, as the degree of sequence identity between a miRNA sequence and the corresponding target gene sequence is decreased, the tendency to mediate post-transcriptional gene silencing by translational repression rather than RNAi is increased. Therefore, in an alternative embodiment, where post-transcriptional gene silencing by translational repression of the target gene is desired, the miRNA sequence has partial complementarity with the target gene sequence. In certain embodiments, the miRNA sequence has partial complementarity with one or more short sequences (complementarity sites) dispersed within the target mRNA (e.g. within the 3'-UTR of the target mRNA) (Hutvagner and Zamore, Science, 2002; Zeng et al., Mol. Cell, 2002; Zeng et al., RNA, 2003; Doench et al., Genes & Dev., 2003). Since the mechanism of translational repression is cooperative, multiple complementarity sites (e.g., 2, 3, 4, 5, or 6) may be targeted in certain embodiments.

The capacity of a siRNA-like duplex to mediate RNAi or translational repression may be predicted by the distribution of non-identical nucleotides between the target gene sequence and the nucleotide sequence of the silencing agent at the site of complementarity. In one embodiment, where gene silencing by translational repression is desired, at least one non-identical nucleotide is present in the central portion of the complementarity site so that duplex formed by the miRNA guide strand and the target mRNA contains a central "bulge" (Doench J G et al., Genes & Dev., 2003). In another embodiment 2, 3, 4, 5, or 6 contiguous or non-contiguous non-identical nucleotides are introduced. The non-identical nucleotide may be selected such that it forms a wobble base pair (e.g., G:U) or a mismatched base pair (G:A, C:A, C:U, G:G, A:A, C:C, U:U). In a further preferred embodiment, the "bulge" is centered at nucleotide positions 12 and 13 from the 5' end of the miRNA molecule.

c) Short Hairpin RNA (shRNA) Molecules

In certain featured embodiments, the instant invention provides shRNAs capable of mediating RNA silencing of an htt target sequence with enhanced selectivity. In contrast to siRNAs, shRNAs mimic the natural precursors of micro RNAs (miRNAs) and enter at the top of the gene silencing pathway. For this reason, shRNAs are believed to mediate gene silencing more efficiently by being fed through the entire natural gene silencing pathway.

miRNAs are noncoding RNAs of approximately 22 nucleotides which can regulate gene expression at the post transcriptional or translational level during plant and animal development. One common feature of miRNAs is that they are all excised from an approximately 70 nucleotide precursor RNA stem-loop termed pre-miRNA, probably by Dicer, an RNase III-type enzyme, or a homolog thereof. Naturally-occurring miRNA precursors (pre-miRNA) have a single strand that forms a duplex stem including two portions that are generally complementary, and a loop, that connects the two portions of the stem. In typical pre-miRNAs, the stem includes one or more bulges, e.g., extra nucleotides that create a single nucleotide "loop" in one portion of the stem, and/or one or more unpaired nucleotides that create a gap in the hybridization of the two portions of the stem to each other. Short hairpin RNAs, or engineered RNA precursors, of the invention are artificial constructs based on these naturally occurring pre-miRNAs, but which are engineered to deliver desired RNA silencing agents (e.g., siRNAs of the invention). By substituting the stem sequences of the pre-miRNA with sequence complementary to the target mRNA, a shRNA is formed. The shRNA is processed by the entire gene silencing pathway of the cell, thereby efficiently mediating RNAi.

The requisite elements of a shRNA molecule include a first portion and a second portion, having sufficient complementarity to anneal or hybridize to form a duplex or double-stranded stem portion. The two portions need not be fully or perfectly complementary. The first and second "stem" portions are connected by a portion having a sequence that has insufficient sequence complementarity to anneal or hybridize to other portions of the shRNA. This latter portion is referred to as a "loop" portion in the shRNA molecule. The shRNA molecules are processed to generate siRNAs. shRNAs can also include one or more bulges, i.e., extra nucleotides that create a small nucleotide "loop" in a portion of the stem, for example a one-, two- or three-nucleotide loop. The stem portions can be the same length, or one portion can include an overhang of, for example, 1-5 nucleotides. The overhanging nucleotides can include, for example, uracils (Us), e.g., all Us. Such Us are notably encoded by thymidines (Ts) in the shRNA-encoding DNA which signal the termination of transcription.

In shRNAs (or engineered precursor RNAs) of the instant invention, one portion of the duplex stem is a nucleic acid sequence that is complementary (or anti-sense) to the htt target sequence. Preferably, one strand of the stem portion of the shRNA is sufficiently complementary (e.g., antisense) to a target RNA (e.g., mRNA) sequence to mediate degradation or cleavage of said target RNA via RNA interference (RNAi). Thus, engineered RNA precursors include a duplex stem with two portions and a loop connecting the two stem portions. The antisense portion can be on the 5' or 3' end of the stem. The stem portions of a shRNA are preferably about 15 to about 50 nucleotides in length. Preferably the two stem portions are about 18 or 19 to about 21, 22, 23, 24, 25, 30, 35, 37, 38, 39, or 40 or more nucleotides in length. In preferred embodiments, the length of the stem portions should be 21 nucleotides or greater. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). In fact, a stem portion can include much larger sections complementary to the target mRNA (up to, and including the entire mRNA).

The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 nucleotides. The overhanging nucleotides can include, for example, uracils (Us), e.g., all Us. The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop in the shRNAs or engineered RNA precursors can be 2, 3, 4, 5, 6, 7, 8, 9, or more, e.g., 15 or 20, or more nucleotides in length.

The loop in the shRNAs or engineered RNA precursors may differ from natural pre-miRNA sequences by modifying the loop sequence to increase or decrease the number of paired nucleotides, or replacing all or part of the loop sequence with a tetraloop or other loop sequences. Thus, the loop portion in the shRNA can be about 2 to about 20 nucleotides in length, i.e., about 2, 3, 4, 5, 6, 7, 8, 9, or more, e.g., 15 or 20, or more nucleotides in length. A preferred loop consists of or comprises a "tetraloop" sequences. Exemplary tetraloop sequences include, but are not limited to, the sequences GNRA, where N is any nucleotide and R is a purine nucleotide, GGGG, and UUUU.

In certain embodiments, shRNAs of the invention include the sequences of a desired siRNA molecule described supra. In other embodiments, the sequence of the antisense portion of a shRNA can be designed essentially as described above or generally by selecting an 18, 19, 20, 21 nucleotide, or longer, sequence from within the target RNA (e.g., htt mRNA), for example, from a region 100 to 200 or 300 nucleotides upstream or downstream of the start of translation. In general, the sequence can be selected from any portion of the target RNA (e.g., mRNA) including the 5' UTR (untranslated region), coding sequence, or 3' UTR, provided said portion is distant from the site of the gain-of-function mutation. This sequence can optionally follow immediately after a region of the target gene containing two adjacent AA nucleotides. The last two nucleotides of the nucleotide sequence can be selected to be UU. This 21 or so nucleotide sequence is used to create one portion of a duplex stem in the shRNA. This sequence can replace a stem portion of a wild-type pre-miRNA sequence, e.g., enzymatically, or is included in a complete sequence that is synthesized. For example, one can synthesize DNA oligonucleotides that encode the entire stem-loop engineered RNA precursor, or that encode just the portion to be inserted into the duplex stem of the precursor, and using restriction enzymes to build the engineered RNA precursor construct, e.g., from a wild-type pre-miRNA.

Engineered RNA precursors include in the duplex stem the 21-22 or so nucleotide sequences of the siRNA or siRNA-like duplex desired to be produced in vivo. Thus, the stem portion of the engineered RNA precursor includes at least 18 or 19 nucleotide pairs corresponding to the sequence of an exonic portion of the gene whose expression is to be reduced or inhibited. The two 3' nucleotides flanking this region of the stem are chosen so as to maximize the production of the siRNA from the engineered RNA precursor and to maximize the efficacy of the resulting siRNA in targeting the corresponding mRNA for translational repression or destruction by RNAi in vivo and in vitro.

In certain embodiments, shRNAs of the invention include miRNA sequences, optionally end-modified miRNA sequences, to enhance entry into RISC. The miRNA sequence can be similar or identical to that of any naturally occurring miRNA (see e.g. The miRNA Registry; Griffiths-Jones S, Nuc. Acids Res., 2004). Over one thousand natural miRNAs have been identified to date and together they are thought to comprise about 1% of all predicted genes in the genome. Many natural miRNAs are clustered together in the introns of pre-mRNAs and can be identified in silico using homology-based searches (Pasquinelli et al., 2000; Lagos-Quintana et al., 2001; Lau et al., 2001; Lee and Ambros, 2001) or computer algorithms (e.g. MiRScan, MiRSeeker) that predict the capability of a candidate miRNA gene to form the stem loop structure of a pri-mRNA (Grad et al., Mol. Cell., 2003; Lim et al., Genes Dev., 2003; Lim et al., Science, 2003; Lai E C et al., Genome Bio., 2003). An online registry provides a searchable database of all published miRNA sequences (The miRNA Registry at the Sanger Institute website; Griffiths-Jones S, Nuc. Acids Res., 2004). Exemplary, natural miRNAs include lin-4, let-7, miR-10, mirR-15, miR-16, miR-168, miR-175, miR-196 and their homologs, as well as other natural miRNAs from humans and certain model organisms including *Drosophila melanogaster, Caenorhabditis elegans*, zebrafish, *Arabidopsis thalania, Mus musculus*, and *Rattus norvegicus* as described in International PCT Publication No. WO 03/029459.

Naturally-occurring miRNAs are expressed by endogenous genes in vivo and are processed from a hairpin or stem-loop precursor (pre-miRNA or pri-miRNAs) by Dicer or other RNAses (Lagos-Quintana et al., Science, 2001; Lau et al., Science, 2001; Lee and Ambros, Science, 2001; Lagos-Quintana et al., Curr. Biol., 2002; Mourelatos et al., Genes Dev., 2002; Reinhart et al., Science, 2002; Ambros et al., Curr. Biol., 2003; Brennecke et al., 2003; Lagos-Quintana et al., RNA, 2003; Lim et al., Genes Dev., 2003; Lim et al., Science, 2003). miRNAs can exist transiently in vivo as a double-stranded duplex, but only one strand is taken up by the RISC complex to direct gene silencing. Certain miRNAs, e.g., plant miRNAs, have perfect or near-perfect complementarity to their target mRNAs and, hence, direct cleavage of the target mRNAs. Other miRNAs have less than perfect complementarity to their target mRNAs and, hence, direct translational repression of the target mRNAs. The degree of complementarity between an miRNA and its target mRNA is believed to determine its mechanism of action. For example, perfect or near-perfect complementarity between a miRNA and its target mRNA is predictive of a cleavage mechanism (Yekta et al., Science, 2004), whereas less than perfect complementarity is predictive of a translational repression mechanism. In particular embodiments, the miRNA sequence is that of a naturally-occurring miRNA sequence, the aberrant expression or activity of which is correlated with an miRNA disorder.

d) Dual Functional Oligonucleotide Tethers

In other embodiments, the RNA silencing agents of the present invention include dual functional oligonucleotide tethers useful for the intercellular recruitment of a miRNA. Animal cells express a range of miRNAs, noncoding RNAs of approximately 22 nucleotides which can regulate gene expression at the post transcriptional or translational level. By binding a miRNA bound to RISC and recruiting it to a target mRNA, a dual functional oligonucleotide tether can repress the expression of genes involved e.g., in the arteriosclerotic process. The use of oligonucleotide tethers offer several advantages over existing techniques to repress the expression of a particular gene. First, the methods described herein allow an endogenous molecule (often present in abundance), an miRNA, to mediate RNA silencing. Accordingly, the methods described herein obviate the need to introduce foreign molecules (e.g., siRNAs) to mediate RNA silencing. Second, the RNA-silencing agents and, in particular, the linking moiety (e.g., oligonucleotides such as the 2'-O-methyl oligonucleotide), can be made stable and resistant to nuclease activity. As a result, the tethers of the present invention can be designed for direct delivery, obviating the need for indirect delivery (e.g. viral) of a precursor molecule or plasmid designed to make the desired agent within the cell. Third, tethers and their respective moieties, can be designed to conform to specific mRNA sites and specific miRNAs. The designs can be cell and gene product specific. Fourth, the methods disclosed herein leave the mRNA intact, allowing one skilled in the art to block protein synthesis in short pulses using the cell's own machinery. As a result, these methods of RNA silencing are highly regulatable.

The dual functional oligonucleotide tethers ("tethers") of the invention are designed such that they recruit miRNAs (e.g., endogenous cellular miRNAs) to a target mRNA so as to induce the modulation of a gene of interest. In preferred embodiments, the tethers have the formula T-L-µ, wherein T is an mRNA targeting moiety, L is a linking moiety, and µ is an miRNA recruiting moiety. Any one or more moiety may be double stranded. Preferably, however, each moiety is single stranded.

Moieties within the tethers can be arranged or linked (in the 5' to 3' direction) as depicted in the formula T-L-µt (i.e., the 3' end of the targeting moiety linked to the 5' end of the linking moiety and the 3' end of the linking moiety linked to the 5' end of the miRNA recruiting moiety). Alternatively, the moieties can be arranged or linked in the tether as follows: µ-T-L (i.e., the 3' end of the miRNA recruiting moiety linked to the 5' end of the linking moiety and the 3' end of the linking moiety linked to the 5' end of the targeting moiety).

The mRNA targeting moiety, as described above, is capable of capturing a specific target mRNA. According to the invention, expression of the target mRNA is undesirable, and, thus, translational repression of the mRNA is desired. The mRNA targeting moiety should be of sufficient size to effectively bind the target mRNA. The length of the targeting moiety will vary greatly depending, in part, on the length of the target mRNA and the degree of complementarity between the target mRNA and the targeting moiety. In various embodiments, the targeting moiety is less than about 200, 100, 50, 30, 25, 20, 19, 18, 17, 16, 15, 14, 13, 12, 11, 10, 9, 8, 7, 6, or 5 nucleotides in length. In a particular embodiment, the targeting moiety is about 15 to about 25 nucleotides in length.

The miRNA recruiting moiety, as described above, is capable of associating with a miRNA. According to the invention, the miRNA may be any miRNA capable of repressing the target mRNA. Mammals are reported to have over 250 endogenous miRNAs (Lagos-Quintana et al. (2002) Current Biol. 12:735-739; Lagos-Quintana et al. (2001) Science 294:858-862; and Lim et al. (2003) Science 299:1540). In various embodiments, the miRNA may be any art-recognized miRNA.

The linking moiety is any agent capable of linking the targeting moieties such that the activity of the targeting moieties is maintained. Linking moieties are preferably oligonucleotide moieties comprising a sufficient number of nucleotides such that the targeting agents can sufficiently interact with their respective targets. Linking moieties have little or no sequence homology with cellular mRNA or miRNA sequences. Exemplary linking moieties include one or more 2'-O-methylnucleotides, e.g., 2'-β-methyladenosine, 2'-O-methylthymidine, 2'-O-methylguanosine or 2'-O-methyluridine.

e) Gene Silencing Oligonucleotides

In certain exemplary embodiments, gene expression (i.e., htt gene expression) can be modulated using oligonucleotide-based compounds comprising two or more single stranded antisense oligonucleotides that are linked through their 5'-ends that allow the presence of two or more accessible 3'-ends to effectively inhibit or decrease htt gene expression. Such linked oligonucleotides are also known as Gene Silencing Oligonucleotides (GSOs). (See, e.g., U.S. Pat. No. 8,431,544 assigned to Idera Pharmaceuticals, Inc., incorporated herein by reference in its entirety for all purposes.)

The linkage at the 5' ends of the GSOs is independent of the other oligonucleotide linkages and may be directly via 5', 3' or 2' hydroxyl groups, or indirectly, via a non-nucleotide linker or a nucleoside, utilizing either the 2' or 3' hydroxyl positions of the nucleoside. Linkages may also utilize a functionalized sugar or nucleobase of a 5' terminal nucleotide.

GSOs can comprise two identical or different sequences conjugated at their 5'-5' ends via a phosphodiester, phosphorothioate or non-nucleoside linker. Such compounds may comprise 15 to 27 nucleotides that are complementary to specific portions of mRNA targets of interest for antisense down regulation of gene product. GSOs that comprise identical sequences can bind to a specific mRNA via Watson-Crick hydrogen bonding interactions and inhibit protein expression. GSOs that comprise different sequences are able to bind to two or more different regions of one or more mRNA target and inhibit protein expression. Such compounds are comprised of heteronucleotide sequences complementary to target mRNA and form stable duplex structures through Watson-Crick hydrogen bonding. Under certain conditions, GSOs containing two free 3'-ends (5'-5'-attached antisense) can be more potent inhibitors of gene expression than those containing a single free 3'-end or no free 3'-end.

In some embodiments, the non-nucleotide linker is glycerol or a glycerol homolog of the formula HO—$(CH_2)_o$—CH(OH)—$(CH_2)_p$—OH, wherein o and p independently are integers from 1 to about 6, from 1 to about 4 or from 1 to about 3. In some other embodiments, the non-nucleotide linker is a derivative of 1,3-diamino-2-hydroxypropane. Some such derivatives have the formula HO—$(CH_2)_m$—C(O)NH—$CH_2$—CH(OH)—$CH_2$—NHC(O)—$(CH_2)_m$—OH, wherein m is an integer from 0 to about 10, from 0 to about 6, from 2 to about 6 or from 2 to about 4.

Some non-nucleotide linkers permit attachment of more than two GSO components. For example, the non-nucleotide linker glycerol has three hydroxyl groups to which GSO components may be covalently attached. Some oligonucleotide-based compounds of the invention, therefore, comprise two or more oligonucleotides linked to a nucleotide or a non-nucleotide linker. Such oligonucleotides according to the invention are referred to as being "branched."

In certain embodiments, GSOs are at least 14 nucleotides in length. In certain exemplary embodiments, GSOs are 15 to 40 nucleotides long or 20 to 30 nucleotides in length. Thus, the component oligonucleotides of GSOs can independently be 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

These oligonucleotides can be prepared by the art recognized methods such as phosphoramidate or H-phosphonate chemistry which can be carried out manually or by an automated synthesizer. These oligonucleotides may also be modified in a number of ways without compromising their ability to hybridize to mRNA. Such modifications may include at least one internucleotide linkage of the oligonucleotide being an alkylphosphonate, phosphorothioate, phosphorodithioate, methylphosphonate, phosphate ester, alkylphosphonothioate, phosphoramidate, carbamate, carbonate, phosphate hydroxyl, acetamidate or carboxymethyl ester or a combination of these and other internucleotide linkages between the 5' end of one nucleotide and the 3' end of another nucleotide in which the 5' nucleotide phosphodiester linkage has been replaced with any number of chemical groups.

VII. Modified Anti-Htt RNA Silencing Agents

In certain aspects of the invention, an RNA silencing agent (or any portion thereof) of the invention as described supra may be modified such that the activity of the agent is further improved. For example, the RNA silencing agents described in Section II supra may be modified with any of the modifications described infra. The modifications can, in part, serve to further enhance target discrimination, to enhance stability of the agent (e.g., to prevent degradation), to promote cellular uptake, to enhance the target efficiency, to improve efficacy in binding (e.g., to the targets), to improve patient tolerance to the agent, and/or to reduce toxicity.

1) Modifications to Enhance Target Discrimination

In certain embodiments, the RNA silencing agents of the invention may be substituted with a destabilizing nucleotide to enhance single nucleotide target discrimination (see U.S. application Ser. No. 11/698,689, filed Jan. 25, 2007 and U.S. Provisional Application No. 60/762,225 filed Jan. 25, 2006, both of which are incorporated herein by reference). Such a modification may be sufficient to abolish the specificity of the RNA silencing agent for a non-target mRNA (e.g. wild-type mRNA), without appreciably affecting the specificity of the RNA silencing agent for a target mRNA (e.g. gain-of-function mutant mRNA).

In preferred embodiments, the RNA silencing agents of the invention are modified by the introduction of at least one universal nucleotide in the antisense strand thereof. Universal nucleotides comprise base portions that are capable of base pairing indiscriminately with any of the four conventional nucleotide bases (e.g. A, G, C, U). A universal nucleotide is preferred because it has relatively minor effect on the stability of the RNA duplex or the duplex formed by the guide strand of the RNA silencing agent and the target mRNA. Exemplary universal nucleotide include those having an inosine base portion or an inosine analog base portion selected from the group consisting of deoxyinosine (e.g. 2'-deoxyinosine), 7-deaza-2'-deoxyinosine, 2'-aza-2'-deoxyinosine, PNA-inosine, morpholino-inosine, LNA-inosine, phosphoramidate-inosine, 2'-O-methoxyethyl-inosine, and 2'-OMe-inosine. In particularly preferred embodiments, the universal nucleotide is an inosine residue or a naturally occurring analog thereof.

In certain embodiments, the RNA silencing agents of the invention are modified by the introduction of at least one destabilizing nucleotide within 5 nucleotides from a specificity-determining nucleotide (i.e., the nucleotide which recognizes the disease-related polymorphism). For example, the destabilizing nucleotide may be introduced at a position that is within 5, 4, 3, 2, or 1 nucleotide(s) from a specificity-determining nucleotide. In exemplary embodiments, the destabilizing nucleotide is introduced at a position which is 3 nucleotides from the specificity-determining nucleotide (i.e., such that there are 2 stabilizing nucleotides between the destabilizing nucleotide and the specificity-determining nucleotide). In RNA silencing agents having two strands or strand portions (e.g. siRNAs and shRNAs), the destabilizing nucleotide may be introduced in the strand or strand portion that does not contain the specificity-determining nucleotide. In preferred embodiments, the destabilizing nucleotide is introduced in the same strand or strand portion that contains the specificity-determining nucleotide. 2) Modifications to Enhance Efficacy and Specificity In certain embodiments, the RNA silencing agents of the invention may be altered to facilitate enhanced efficacy and specificity in mediating RNAi according to asymmetry design rules (see U.S. Pat. Nos. 8,309,704, 7,750,144, 8,304,530, 8,329,892 and 8,309,705). Such alterations facilitate entry of the antisense strand of the siRNA (e.g., a siRNA designed using the methods of the invention or an siRNA produced from a shRNA) into RISC in favor of the sense strand, such that the antisense strand preferentially guides cleavage or translational repression of a target mRNA, and thus increasing or improving the efficiency of target cleavage and silencing. Preferably the asymmetry of an RNA silencing agent is enhanced by lessening the base pair strength between the antisense strand 5' end (AS 5') and the sense strand 3' end (S 3') of the RNA silencing agent relative to the bond strength or base pair strength between the antisense strand 3' end (AS 3') and the sense strand 5' end (S'5) of said RNA silencing agent.

In one embodiment, the asymmetry of an RNA silencing agent of the invention may be enhanced such that there are fewer G:C base pairs between the 5' end of the first or antisense strand and the 3' end of the sense strand portion than between the 3' end of the first or antisense strand and the 5' end of the sense strand portion. In another embodiment, the asymmetry of an RNA silencing agent of the invention may be enhanced such that there is at least one mismatched base pair between the 5' end of the first or antisense strand and the 3' end of the sense strand portion. Preferably, the mismatched base pair is selected from the group consisting of G:A, C:A, C:U, G:G, A:A, C:C and U:U. In another embodiment, the asymmetry of an RNA silencing agent of the invention may be enhanced such that there is at least one wobble base pair, e.g., G:U, between the 5' end of the first or antisense strand and the 3' end of the sense strand portion. In another embodiment, the asymmetry of an RNA silencing agent of the invention may be enhanced such that there is at least one base pair comprising a rare nucleotide, e.g., inosine (I). Preferably, the base pair is selected from the group consisting of an I:A, I:U and I:C. In yet another embodiment, the asymmetry of an RNA silencing agent of the invention may be enhanced such that there is at least one base pair comprising a modified nucleotide. In preferred embodiments, the modified nucleotide is selected from the group consisting of 2-amino-G, 2-amino-A, 2,6-diamino-G, and 2,6-diamino-A.

3) RNA Silencing Agents with Enhanced Stability

The RNA silencing agents of the present invention can be modified to improve stability in serum or in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features RNA silencing agents that include first and second strands wherein the second strand and/or first strand is modified by the substitution of internal nucleotides with modified nucleotides, such that in vivo stability is enhanced as compared to a corresponding unmodified RNA silencing agent. As defined herein, an "internal" nucleotide is one occurring at any position other than the 5' end or 3' end of nucleic acid molecule, polynucleotide or oligonucleotide. An internal nucleotide can be within a single-stranded molecule or within a strand of a duplex or double-stranded molecule. In one embodiment, the sense strand and/or antisense strand is modified by the substitution of at least one internal nucleotide. In another embodiment, the sense strand and/or antisense strand is modified by the substitution of at least 2, 3, 4, 5, 6, 7, 8, 9, 10, 11, 12, 13, 14, 15, 16, 17, 18, 19, 20, 21, 22, 23, 24, 25 or more internal nucleotides. In another embodiment, the sense strand and/or antisense strand is modified by the substitution of at least 5%, 10%, 15%, 20%, 25%, 30%, 35%, 40%, 45%, 50%, 55%, 60%, 65%, 70%, 75%, 80%, 85%, 90%, 95% or more of the internal nucleotides. In yet another embodiment, the sense strand and/or antisense strand is modified by the substitution of all of the internal nucleotides.

In a preferred embodiment of the present invention, the RNA silencing agents may contain at least one modified nucleotide analogue. The nucleotide analogues may be located at positions where the target-specific silencing activity, e.g., the RNAi mediating activity or translational repression activity is not substantially effected, e.g., in a region at the 5'-end and/or the 3'-end of the siRNA molecule. Particularly, the ends may be stabilized by incorporating modified nucleotide analogues.

Exemplary nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In exemplary backbone-modified ribonucleotides, the phosphoester group connecting to adjacent ribonucleotides is replaced by a modified group, e.g., of phosphothioate group. In exemplary sugar-modified ribonucleotides, the 2' OH-group is replaced by a group selected from H, OR, R, halo, SH, SR, NH$_2$, NHR, NR$_2$ or ON, wherein R is C$_1$-C$_6$ alkyl, alkenyl or alkynyl and halo is F, Cl, Br or I.

In particular embodiments, the modifications are 2'-fluoro, 2'-amino and/or 2'-thio modifications. Particularly preferred modifications include 2'-fluoro-cytidine, 2'-fluoro-uridine, 2'-fluoro-adenosine, 2'-fluoro-guanosine, 2'-amino-cytidine, 2'-amino-uridine, 2'-amino-adenosine, 2'-amino-guanosine, 2,6-diaminopurine, 4-thio-uridine, and/or 5-amino-allyl-uridine. In a particular embodiment, the 2'-fluoro ribonucleotides are every uridine and cytidine. Additional exemplary modifications include 5-bromo-uridine, 5-iodo-uridine, 5-methyl-cytidine, ribo-thymidine, 2-aminopurine, 2'-amino-butyryl-pyrene-uridine, 5-fluoro-cytidine, and 5-fluoro-uridine. 2'-deoxy-nucleotides and 2'-Ome nucleotides can also be used within modified RNA-silencing agents moities of the instant invention. Additional modified residues include, deoxy-abasic, inosine, N3-methyl-uridine, N6,N6-dimethyl-adenosine, pseudouridine, purine ribonucleoside and ribavirin. In a particularly preferred embodiment, the 2' moiety is a methyl group such that the linking moiety is a 2'-O-methyl oligonucleotide.

In an exemplary embodiment, the RNA silencing agent of the invention comprises Locked Nucleic Acids (LNAs). LNAs comprise sugar-modified nucleotides that resist nuclease activities (are highly stable) and possess single nucleotide discrimination for mRNA (Elmen et al., Nucleic Acids Res., (2005), 33(1): 439-447; Braasch et al. (2003) Biochemistry 42:7967-7975, Petersen et al. (2003) Trends Biotechnol 21:74-81). These molecules have 2'-0,4'-C-ethylene-bridged nucleic acids, with possible modifications such as 2'-deoxy-2"-fluorouridine. Moreover, LNAs increase the specificity of oligonucleotides by constraining the sugar moiety into the 3'-endo conformation, thereby pre-organizing the nucleotide for base pairing and increasing the melting temperature of the oligonucleotide by as much as 10° C. per base.

In another exemplary embodiment, the RNA silencing agent of the invention comprises Peptide Nucleic Acids (PNAs). PNAs comprise modified nucleotides in which the sugar-phosphate portion of the nucleotide is replaced with a neutral 2-amino ethylglycine moiety capable of forming a polyamide backbone which is highly resistant to nuclease digestion and imparts improved binding specificity to the molecule (Nielsen, et al., Science, (2001), 254: 1497-1500).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

In other embodiments, cross-linking can be employed to alter the pharmacokinetics of the RNA silencing agent, for example, to increase half-life in the body. Thus, the invention includes RNA silencing agents having two complementary strands of nucleic acid, wherein the two strands are crosslinked. The invention also includes RNA silencing agents which are conjugated or unconjugated (e.g., at its 3' terminus) to another moiety (e.g. a non-nucleic acid moiety such as a peptide), an organic compound (e.g., a dye), or the like). Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

Other exemplary modifications include: (a) 2' modification, e.g., provision of a 2' OMe moiety on a U in a sense or antisense strand, but especially on a sense strand, or provision of a 2' OMe moiety in a 3' overhang, e.g., at the 3' terminus (3' terminus means at the 3' atom of the molecule or at the most 3' moiety, e.g., the most 3' P or 2' position, as indicated by the context); (b) modification of the backbone, e.g., with the replacement of an O with an S, in the phosphate backbone, e.g., the provision of a phosphorothioate modification, on the U or the A or both, especially on an antisense strand; e.g., with the replacement of a O with an S; (c) replacement of the U with a C5 amino linker; (d) replacement of an A with a G (sequence changes are preferred to be located on the sense strand and not the antisense strand); and (d) modification at the 2', 6', 7', or 8' position. Exemplary embodiments are those in which one or more of these modifications are present on the sense but not the antisense strand, or embodiments where the antisense strand has fewer of such modifications. Yet other exemplary modifications include the use of a methylated P in a 3' overhang, e.g., at the 3' terminus; combination of a 2' modification, e.g., provision of a 2' O Me moiety and modification of the backbone, e.g., with the replacement of a O with an S, e.g., the provision of a phosphorothioate modification, or the use of a methylated P, in a 3' overhang, e.g., at the 3' terminus; modification with a 3' alkyl; modification with an abasic pyrrolidone in a 3' overhang, e.g., at the 3' terminus; modification with naproxen, ibuprofen, or other moieties which inhibit degradation at the 3' terminus.

4) Modifications to Enhance Cellular Uptake

In other embodiments, RNA silencing agents may be modified with chemical moieties, for example, to enhance cellular uptake by target cells (e.g., neuronal cells). Thus, the invention includes RNA silencing agents which are conjugated or unconjugated (e.g., at its 3' terminus) to another moiety (e.g. a non-nucleic acid moiety such as a peptide), an organic compound (e.g., a dye), or the like. The conjugation can be accomplished by methods known in the art, e.g., using the methods of Lambert et al., Drug Deliv. Rev.: 47(1), 99-112 (2001) (describes nucleic acids loaded to polyalkylcyanoacrylate (PACA) nanoparticles); Fattal et al., J. Control Release 53(1-3):137-43 (1998) (describes nucleic acids bound to nanoparticles); Schwab et al., Ann. Oncol. 5 Suppl. 4:55-8 (1994) (describes nucleic acids linked to intercalating agents, hydrophobic groups, polycations or PACA nanoparticles); and Godard et al., Eur. J. Biochem. 232(2):404-10 (1995) (describes nucleic acids linked to nanoparticles).

In a particular embodiment, an RNA silencing agent of invention is conjugated to a lipophilic moiety. In one embodiment, the lipophilic moiety is a ligand that includes a cationic group. In another embodiment, the lipophilic moiety is attached to one or both strands of an siRNA. In an exemplary embodiment, the lipophilic moiety is attached to one end of the sense strand of the siRNA. In another exemplary embodiment, the lipophilic moiety is attached to the 3' end of the sense strand. In certain embodiments, the lipophilic moiety is selected from the group consisting of cholesterol, vitamin E, vitamin K, vitamin A, folic acid, or a cationic dye (e.g., Cy3). In an exemplary embodiment, the lipophilic moiety is a cholesterol. Other lipophilic moieties include cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, 03-(oleoyl)lithocholic acid, 03-(oleoyl) cholenic acid, dimethoxytrityl, or phenoxazine.

5) Tethered Ligands

Other entities can be tethered to an RNA silencing agent of the invention. For example, a ligand tethered to an RNA silencing agent to improve stability, hybridization thermodynamics with a target nucleic acid, targeting to a particular tissue or cell-type, or cell permeability, e.g., by an endocytosis-dependent or -independent mechanism. Ligands and associated modifications can also increase sequence specificity and consequently decrease off-site targeting. A tethered ligand can include one or more modified bases or sugars that can function as intercalators. These are preferably located in an internal region, such as in a bulge of RNA silencing agent/target duplex. The intercalator can be an aromatic, e.g., a polycyclic aromatic or heterocyclic aromatic compound. A polycyclic intercalator can have stacking capabilities, and can include systems with 2, 3, or 4 fused rings. The universal bases described herein can be included on a ligand. In one embodiment, the ligand can include a cleaving group that contributes to target gene inhibition by cleavage of the target nucleic acid. The cleaving group can be, for example, a bleomycin (e.g., bleomycin-A5, bleomycin-A2, or bleomycin-B2), pyrene, phenanthroline (e.g., O-phenanthroline), a polyamine, a tripeptide (e.g., lys-tyr-lys tripeptide), or metal ion chelating group. The metal ion chelating group can include, e.g., an Lu(III) or EU(III) macrocyclic complex, a Zn(II) 2,9-dimethylphenanthroline derivative, a Cu(II) terpyridine, or acridine, which can promote the selective cleavage of target RNA at the site of the bulge by free metal ions, such as Lu(III). In some embodiments, a peptide ligand can be tethered to a RNA silencing agent to promote cleavage of the target RNA, e.g., at the bulge region. For example, 1,8-dimethyl-1,3,6,8,10, 13-hexaazacyclotetradecane (cyclam) can be conjugated to a peptide (e.g., by an amino acid derivative) to promote target RNA cleavage. A tethered ligand can be an aminoglycoside ligand, which can cause an RNA silencing agent to have improved hybridization properties or improved sequence specificity. Exemplary aminoglycosides include glycosylated polylysine, galactosylated polylysine, neomycin B, tobramycin, kanamycin A, and acridine conjugates of aminoglycosides, such as Neo-N-acridine, Neo-S-acridine, Neo-C-acridine, Tobra-N-acridine, and KanaA-N-acridine. Use of an acridine analog can increase sequence specificity. For example, neomycin B has a high affinity for RNA as compared to DNA, but low sequence-specificity. An acridine analog, neo-5-acridine has an increased affinity for the HIV Rev-response element (RRE). In some embodiments the guanidine analog (the guanidinoglycoside) of an aminoglycoside ligand is tethered to an RNA silencing agent. In a guanidinoglycoside, the amine group on the amino acid is exchanged for a guanidine group. Attachment of a guanidine analog can enhance cell permeability of an RNA silencing agent. A tethered ligand can be a poly-arginine peptide, peptoid or peptidomimetic, which can enhance the cellular uptake of an oligonucleotide agent.

Exemplary ligands are coupled, preferably covalently, either directly or indirectly via an intervening tether, to a ligand-conjugated carrier. In exemplary embodiments, the ligand is attached to the carrier via an intervening tether. In exemplary embodiments, a ligand alters the distribution, targeting or lifetime of an RNA silencing agent into which it is incorporated. In exemplary embodiments, a ligand provides an enhanced affinity for a selected target, e.g., molecule, cell or cell type, compartment, e.g., a cellular or organ compartment, tissue, organ or region of the body, as, e.g., compared to a species absent such a ligand.

Exemplary ligands can improve transport, hybridization, and specificity properties and may also improve nuclease resistance of the resultant natural or modified RNA silencing agent, or a polymeric molecule comprising any combination of monomers described herein and/or natural or modified ribonucleotides. Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics. Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, mucin carbohydrate, multivalent lactose, multivalent galactose, N-acetyl-galactosamine, N-acetyl-glucosamine, multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic. Other examples of ligands include dyes, intercalating agents (e.g. acridines and substituted acridines), cross-linkers (e.g. psoralene, mitomycin C), porphyrins (TPPC4, texaphyrin, Sapphyrin), polycyclic aromatic hydrocarbons (e.g., phenazine, dihydrophenazine, phenanthroline, pyrenes), lys-tyr-lys tripeptide, aminoglycosides, guanidium aminoglycodies, artificial endonucleases (e.g. EDTA), lipophilic molecules, e,g, cholesterol (and thio analogs thereof), cholic acid, cholanic acid, lithocholic acid, adamantane acetic acid, 1-pyrene butyric acid, dihydrotestosterone, glycerol (e.g., esters (e.g., mono, bis, or tris fatty acid esters, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ fatty acids) and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, stearic acid (e.g., glyceryl distearate), oleic acid, myristic acid, 03-(oleoyl)lithocholic acid, 03-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, naproxen, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the RNA silencing agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin. The ligand can increase the uptake of the RNA silencing agent into the cell by activating an inflammatory response, for example. Exemplary ligands that would have such an effect include tumor necrosis factor alpha (TNFα), interleukin-1 beta, or gamma interferon. In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA. A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney. In a preferred embodiment, the lipid based ligand binds HSA. A lipid-based ligand can bind HSA with a sufficient affinity such that the conjugate will be preferably distributed to a non-kidney tissue. However, it is preferred that the affinity not be so strong that the HSA-ligand binding cannot be reversed. In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the RNA silencing agent, such as by enhancing cellular recognition and absorption. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. The peptide moiety can be an L-peptide or D-peptide.

In another alternative, the peptide moiety can include a hydrophobic membrane translocation sequence (MTS). A peptide or peptidomimetic can be encoded by a random sequence of DNA, such as a peptide identified from a phage-display library, or one-bead-one-compound (OBOC) combinatorial library (Lam et al., *Nature* 354:82-84, 1991). In exemplary embodiments, the peptide or peptidomimetic tethered to an RNA silencing agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. 6) Compounds In one aspect, provided herein is a compound of the Formula shown in FIG. 81, or a pharmaceutically acceptable salt thereof, wherein $R^1$ is selected from the group consisting of:

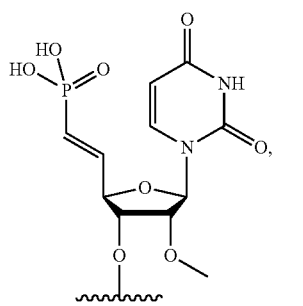

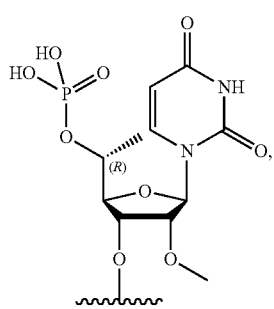

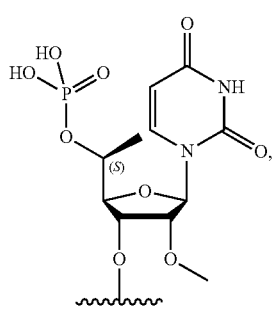

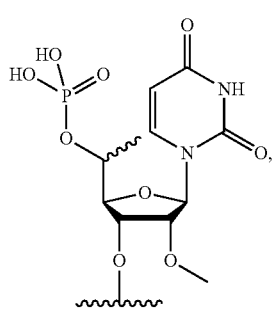

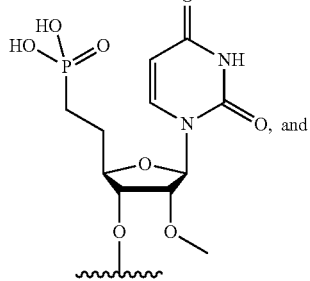

-continued

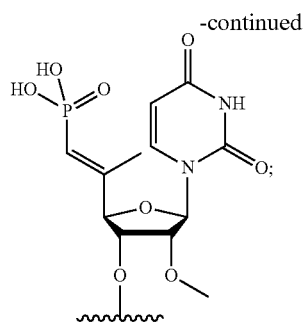

R³ is independently selected at each occurrence from the group consisting of an internucleotide linker as shown in FIG. 82; and L is a linker connecting two moieties, wherein the linker is selected from the group consisting of an ethylene glycol chain, an alkyl chain, a peptide, an RNA, a DNA,

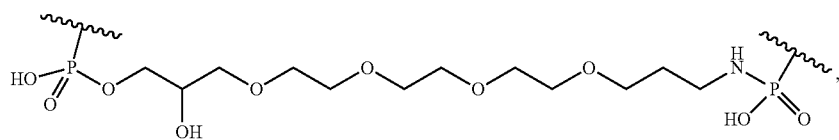 [SMILES: *P(=O)(O)NCCCOCCOCCOCCOCC(O)COP(*)(=O)O]

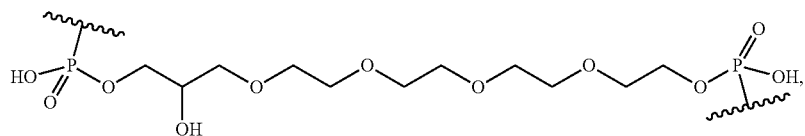 [SMILES: *P(=O)(O)OCCOCCOCCOCCOCC(O)COP(*)(=O)O]

or a combination thereof.

In one embodiment, R¹ is selected from the group consisting of

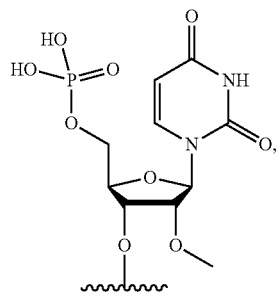

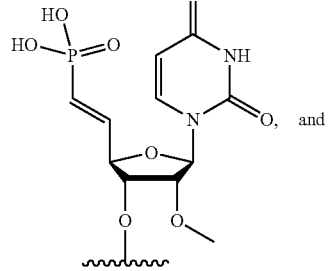

and

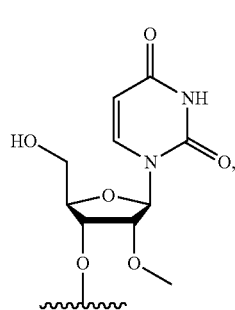

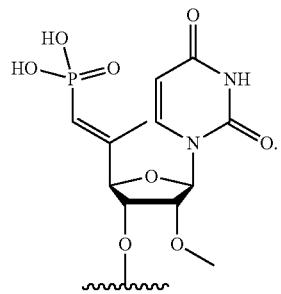

In another embodiment, $R^1$ is

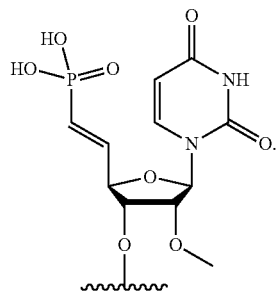

In another embodiment, $R^3$ is an internucleotide linker independently selected at each occurrence from the group consisting of a phosphorothioate, a phosphorodithioate, a methylphosphonate, a methylenephosphonate, a phosphotriester, and a boranophosphate.

In another embodiment, $R^3$ is an internucleotide linker independently selected at each occurrence from the group consisting of a phosphorothioate, a phosphorodithioate, and a boranophosphate.

In another embodiment, $R^3$ is a phosphorothioate.

In another embodiment, L is selected from the group consisting of an ethylene glycol chain, an alkyl chain, and a peptide.

In another embodiment, L is selected from an ethylene glycol chain or a peptide.

In yet another embodiment, L is

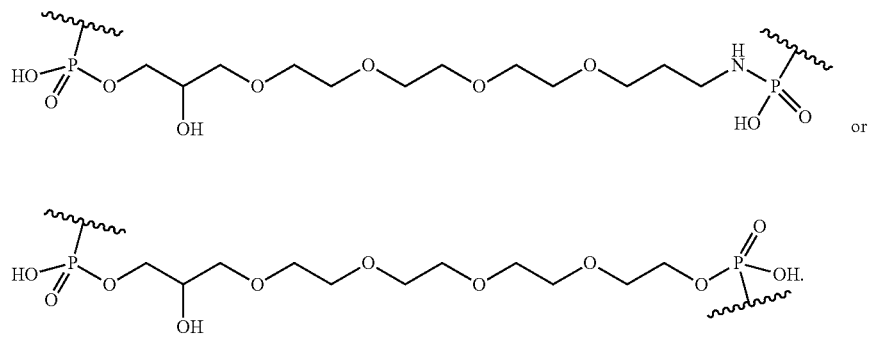

In still another embodiment, L is

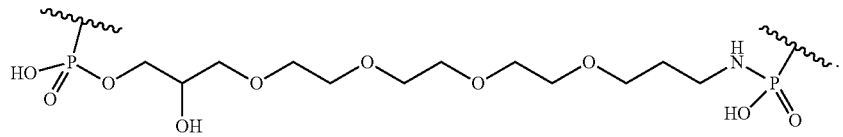 [SMILES: *P(=O)(O)NCCCOCCOCCOCCOCC(O)COP(*)(=O)O]

In another embodiment, L is

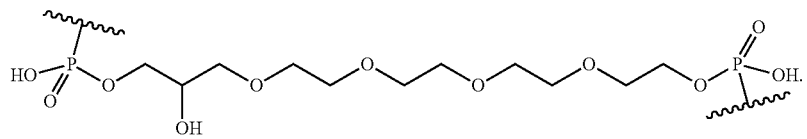 [SMILES: *P(=O)(O)OCCOCCOCCOCCOCC(O)COP(*)(=O)O]

In one embodiment, the compound of the Formula shown in FIG. 81 is a compound the Formula shown in FIG. 83.

In another embodiment, the compound of the Formula shown in FIG. 81 is a compound of the Formula shown in FIG. 83, or a pharmaceutically acceptable salt thereof, wherein
$R^1$ is

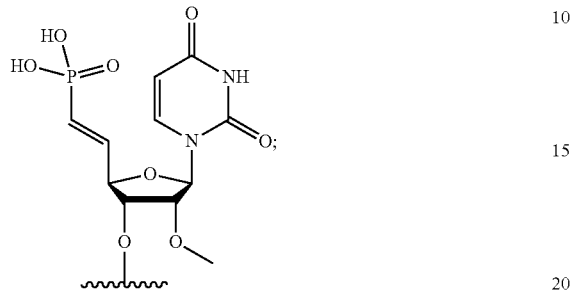

L is

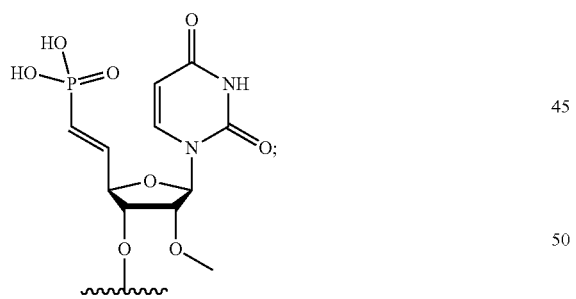

In another embodiment, the compound of the Formula shown in FIG. 81 is a compound of the Formula shown in FIG. 83, or a pharmaceutically acceptable salt thereof, wherein
$R^1$ is

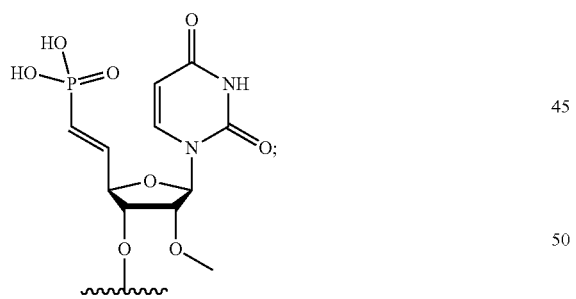

L is

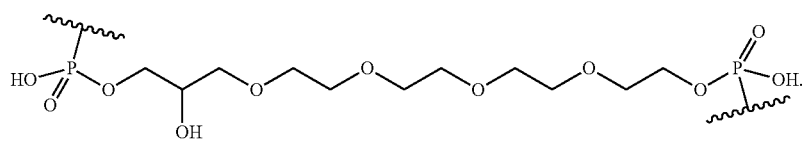

In another aspect, provided herein is a compound of the Formula shown in FIG. 84, or a pharmaceutically acceptable salt thereof, wherein
R¹ is selected from the group consisting of

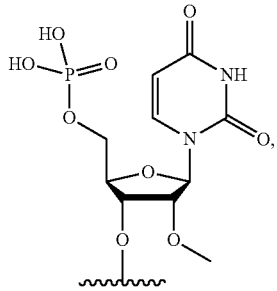

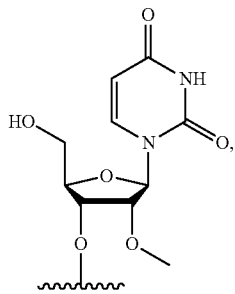

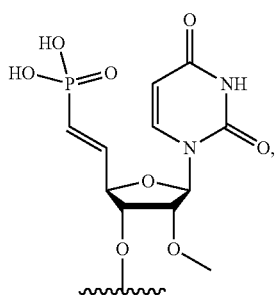

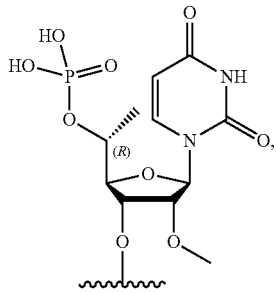

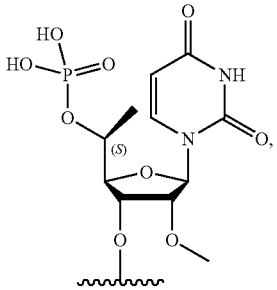

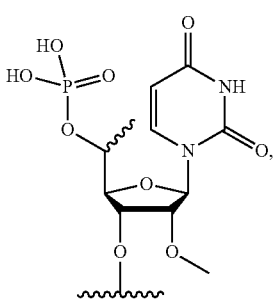

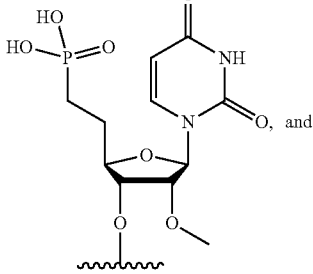

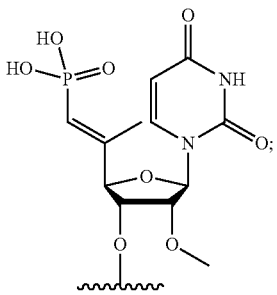

R³ is independently selected at each occurrence from the group consisting of an internucleotide linker as shown in FIG. 82;

L is a linker connecting two moieties, wherein the linker is selected from the group consisting of an ethylene glycol chain, an alkyl chain, a peptide, an RNA, a DNA,

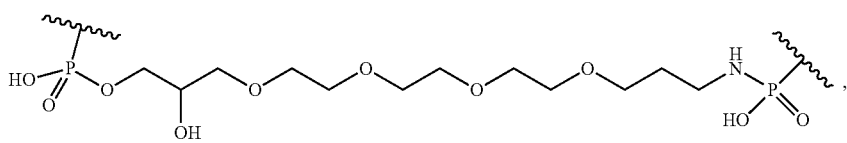 [SMILES: *P(=O)(O)NCCCOCCOCCOCCOCC(O)COP(*)(=O)O]

or a combination thereof; and

B is a branch point between two or more linkers, wherein the branch point is selected from the group consisting of a glycol, an amino acid, or any poly-valent organic species.

In one embodiment, $R^1$ is selected from the group consisting of

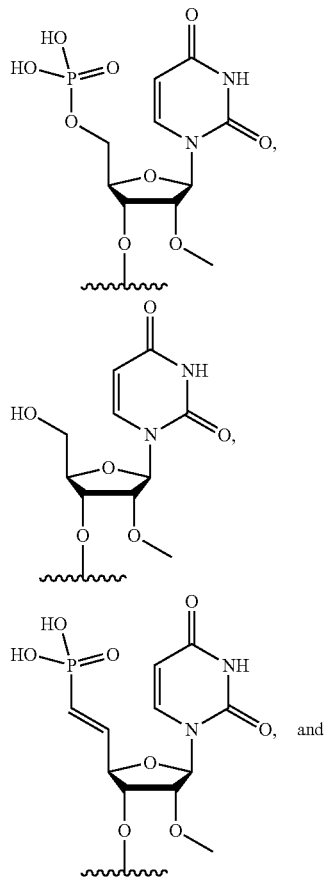

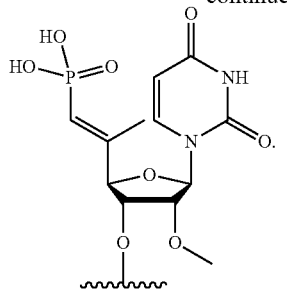

In one embodiment, $R^1$ is

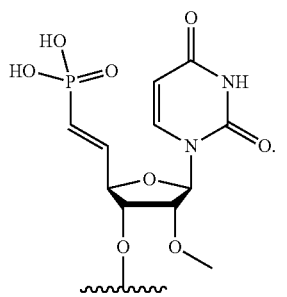

In another embodiment, $R^3$ is an internucleotide linker independently selected at each occurrence from the group consisting of a phosphorothioate, a phosphorodithioate, a methylphosphonate, a methylenephosphonate, a phosphotriester, and a boranophosphate.

In another embodiment, $R^3$ is an internucleotide linker independently selected at each occurrence from the group consisting of a phosphorothioate, a phosphorodithioate, and a boranophosphate.

In another embodiment, $R^3$ is a phosphorothioate.

In another embodiment, L is selected from the group consisting of an ethylene glycol chain, an alkyl chain, and a peptide.

In another embodiment, L is selected from an ethylene glycol chain or a peptide.

In yet another embodiment, L is

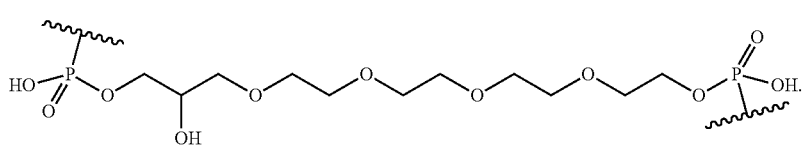

In still another embodiment, L is

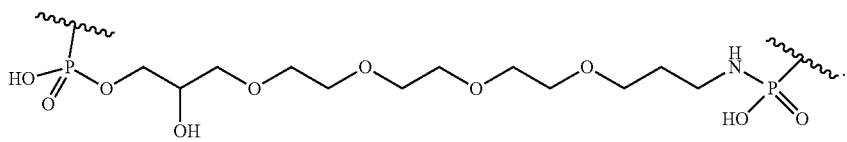 [SMILES: *P(=O)(O)NCCCOCCOCCOCCOCC(O)COP(*)(=O)O]

In another embodiment, L is

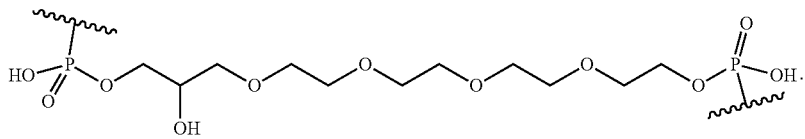

In one embodiment, B is a branch point between two or more linkers, wherein the branch point is selected a glycol or an amino acid. In another embodiment, the branch point is a glycol.

In another embodiment, the branch point is an amino acid.

In another embodiment of the compound of the Formula shown in FIG. 84, Y is defined as shown in FIG. 86.

In another aspect, provided herein is a compound of the Formula shown in FIG. 85, or a pharmaceutically acceptable salt thereof, wherein $R^1$ is selected from the group consisting of

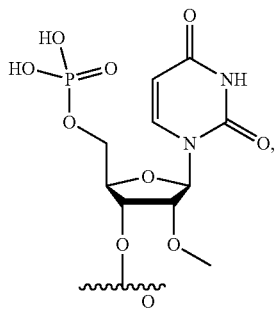

,

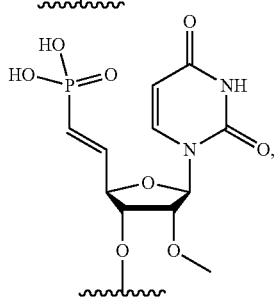

,

-continued

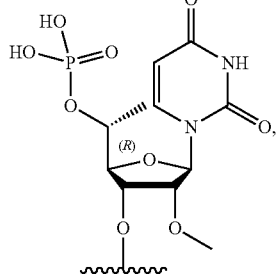

,

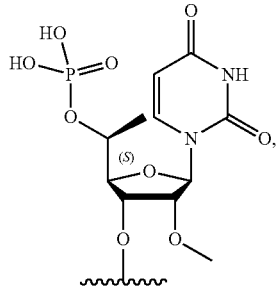

,

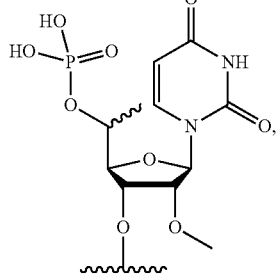

,

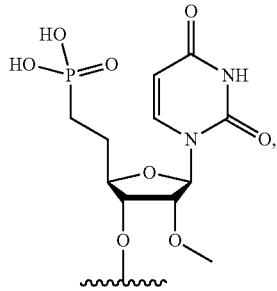

and

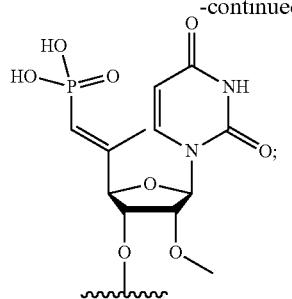

R³ is independently selected at each occurrence from the group consisting of an internucleotide linker as shown in FIG. 82; L is a linker connecting two moieties, wherein the linker is selected from the group consisting of an ethylene glycol chain, an alkyl chain, a peptide, an RNA, a DNA,

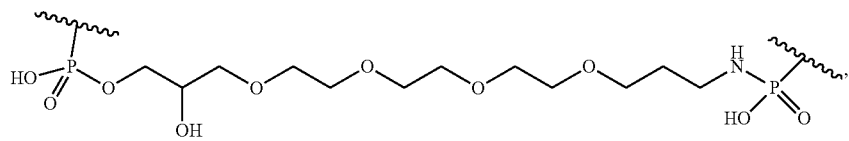

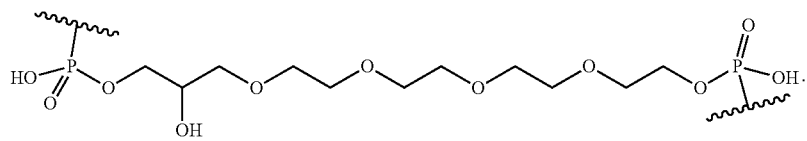 [SMILES: *P(=O)(O)OCCOCCOCCOCCOCC(O)COP(*)(=O)O]

or a combination thereof; and

B is a branch point between two or more linkers, wherein the branch point is selected from the group consisting of a glycol, an amino acid, or any polyvalent organic species.

In one embodiment, R¹ is selected from the group consisting of

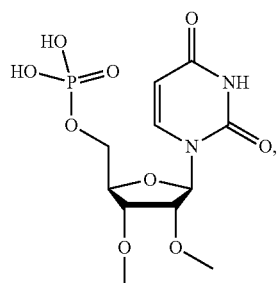

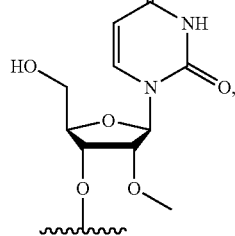

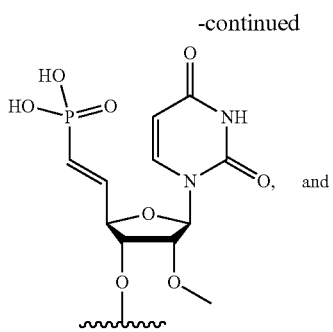

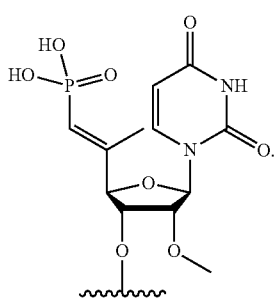

In another embodiment, R¹ is

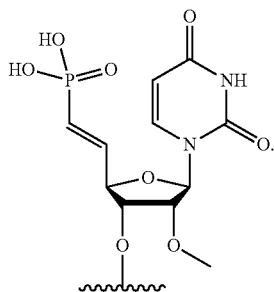

In another embodiment, R³ is an internucleotide linker independently selected at each occurrence from the group consisting of a phosphorothioate, a phosphorodithioate, a methylphosphonate, a methylenephosphonate, a phosphotriester, and a boranophosphate.

In another embodiment, R³ is an internucleotide linker independently selected at each occurrence from the group consisting of a phosphorothioate, a phosphorodithioate, and a boranophosphate.

In another embodiment, R³ is a phosphorothioate.

In another embodiment, L is selected from the group consisting of an ethylene glycol chain, an alkyl chain, and a peptide.

In another embodiment, L is selected from an ethylene glycol chain or a peptide.

In yet another embodiment, L is

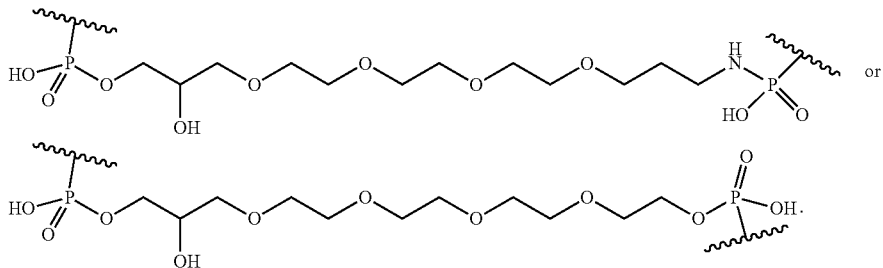

In still another embodiment, L is

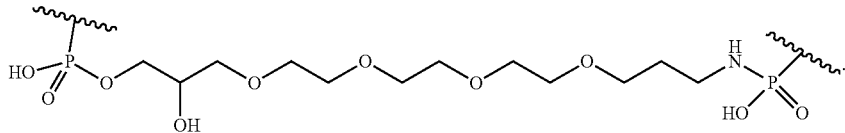 [SMILES: *P(=O)(O)NCCCOCCOCCOCCOCC(O)COP(*)(=O)O]

In another embodiment, L is

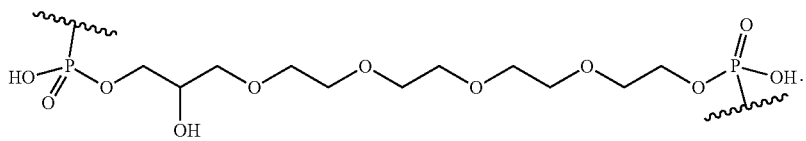 [SMILES: *P(=O)(O)OCCOCCOCCOCCOCC(O)COP(*)(=O)O]

In one embodiment, B is a branch point between two or more linkers, wherein the branch point is selected a glycol or an amino acid. In another embodiment, the branch point is a glycol. In another embodiment, the branch point is an amino acid.

In one embodiment of the compound of the Formula shown in FIG. 85, Y is defined as shown in FIG. 86.

In another aspect, provided herein is a compound of the Formula shown in FIG. 87, or a pharmaceutically acceptable salt thereof, wherein R¹ is selected from the group consisting of

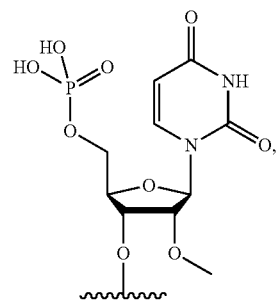

75
-continued
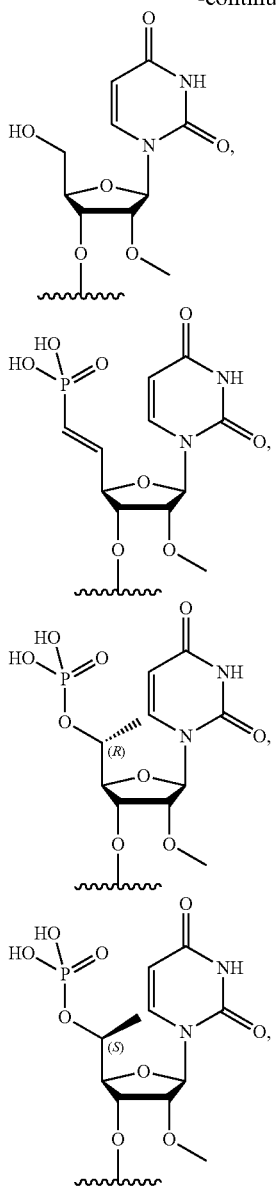
76
-continued
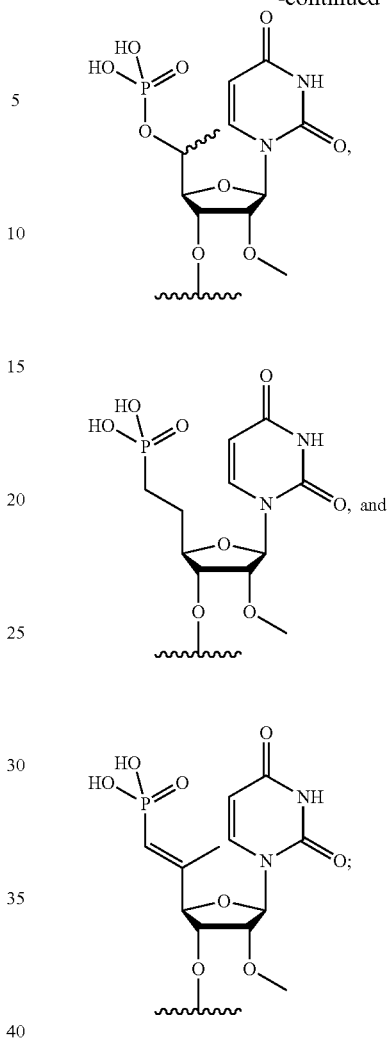
R³ is independently selected at each occurrence from the group consisting of an internucleotide linker as shown in FIG. 82;
L is a linker connecting two moieties, wherein the linker is selected from the group consisting of an ethylene glycol chain, an alkyl chain, a peptide, an RNA, a DNA,
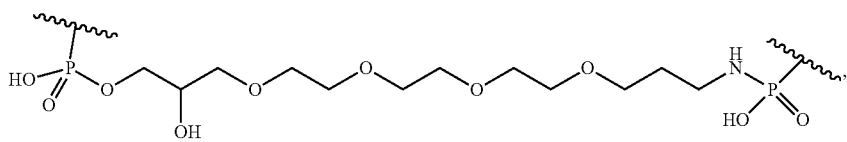 [SMILES: *P(=O)(O)NCCCOCCOCCOCCOCC(O)COP(*)(=O)O]
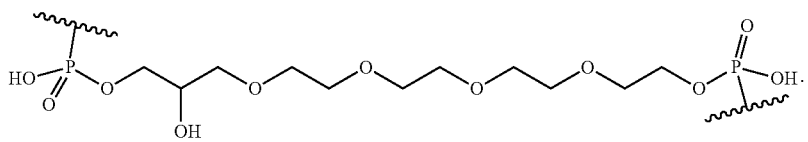 [SMILES: *P(=O)(O)OCCOCCOCCOCCOCC(O)COP(*)(=O)O]

or a combination thereof; and
$R^2$ is selected from the group consisting of an alkyl chain (e.g., $C_{1-6}$, $C_{1-10}$, $C_{1-20}$, $C_{1-30}$, or $C_{1-40}$), a vitamin, a ligand, a peptide, a bioactive conjugate (including, but not limited to glycosphingolipids, polyunsaturated fatty acids, secosteroids, steroid hormones, or sterol lipids),
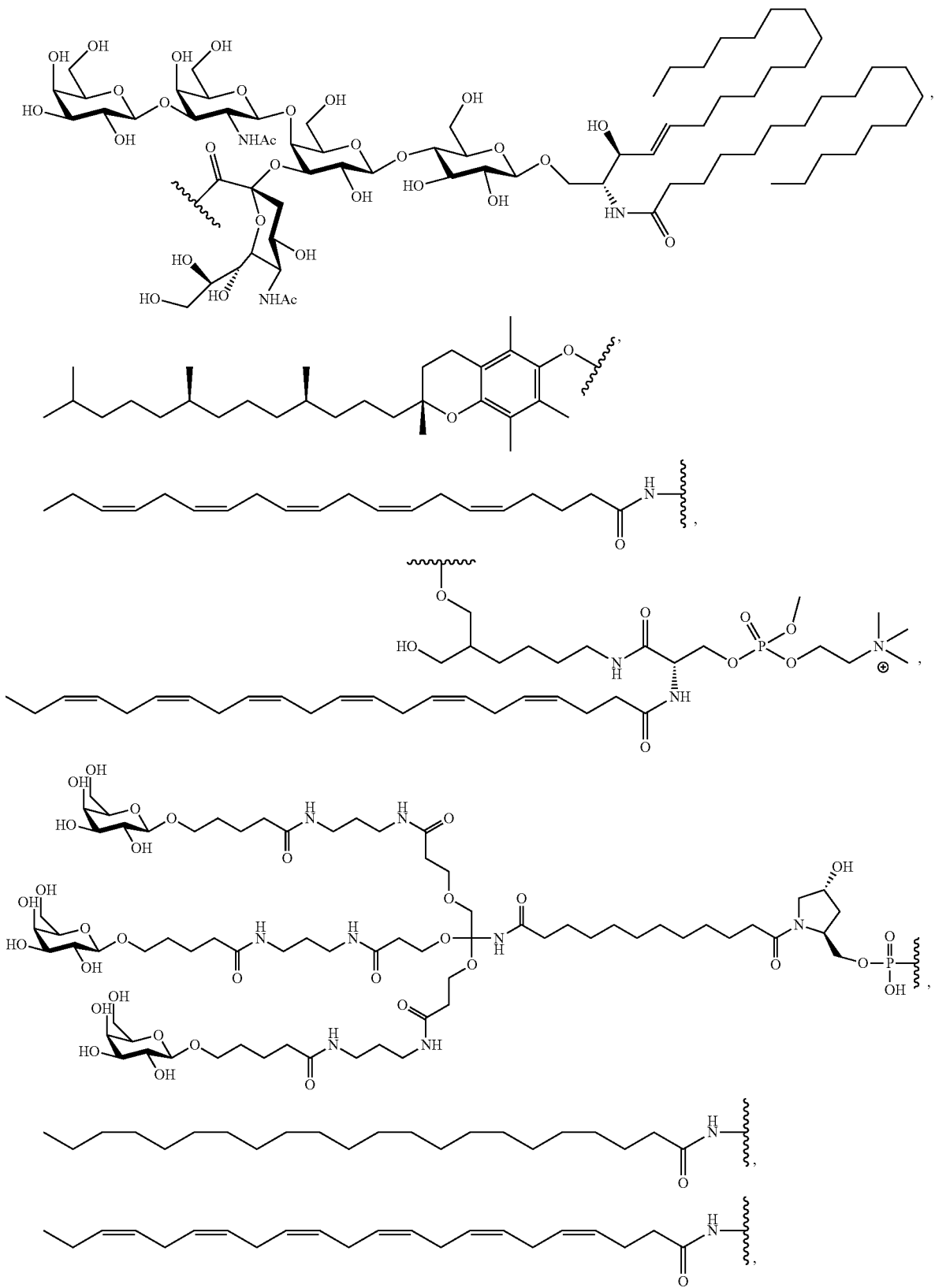

-continued
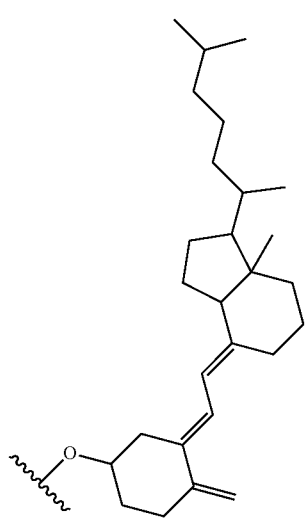
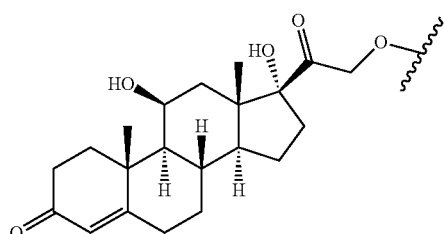
, and
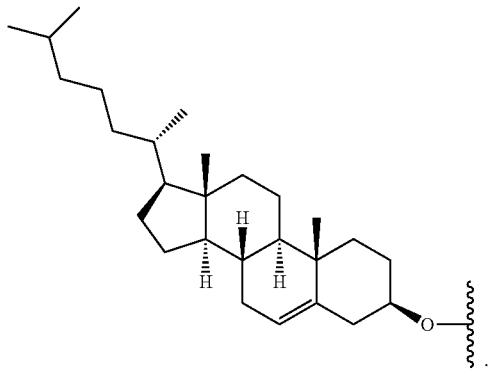
.
In one embodiment, R¹ is selected from the group consisting of
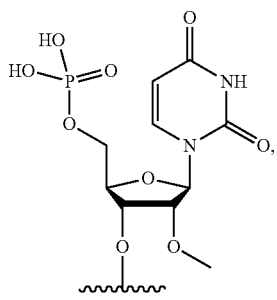
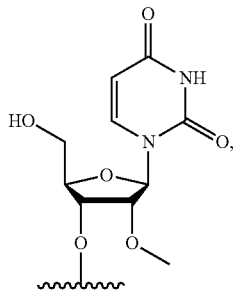
,
-continued
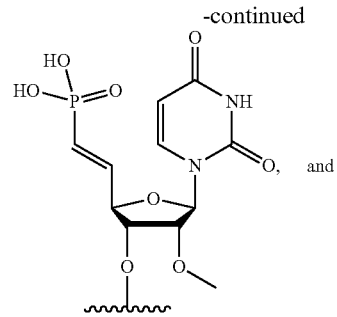
, and
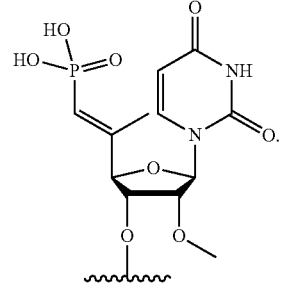
.

In another embodiment, $R^1$ is
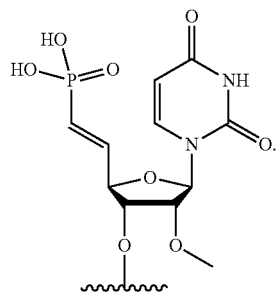
In another embodiment, $R^2$ is selected from the group consisting of
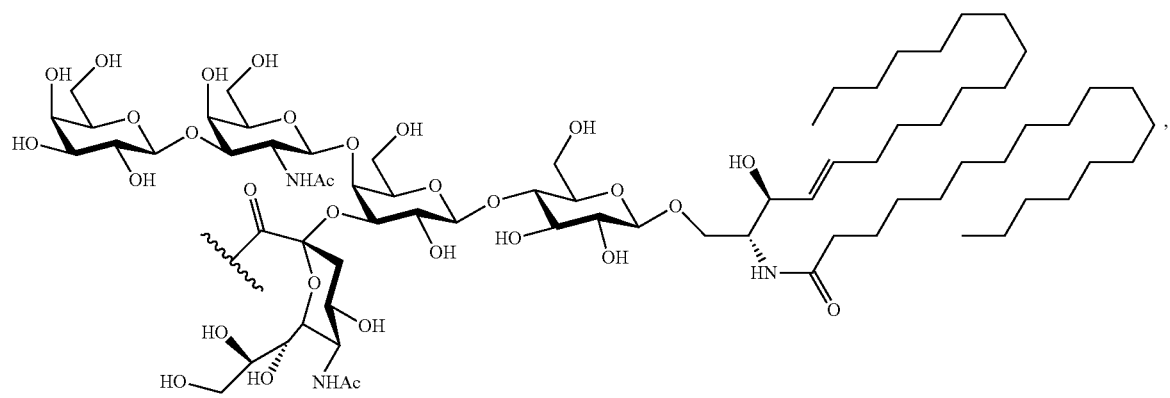
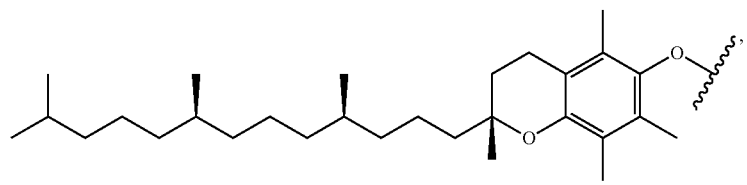
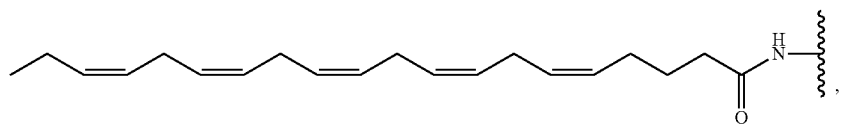
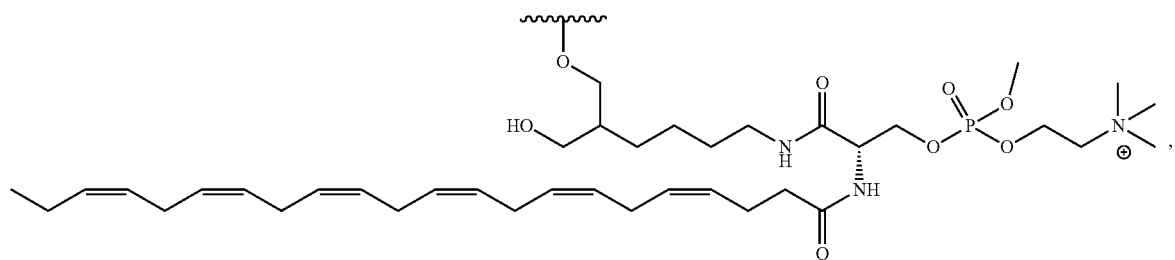

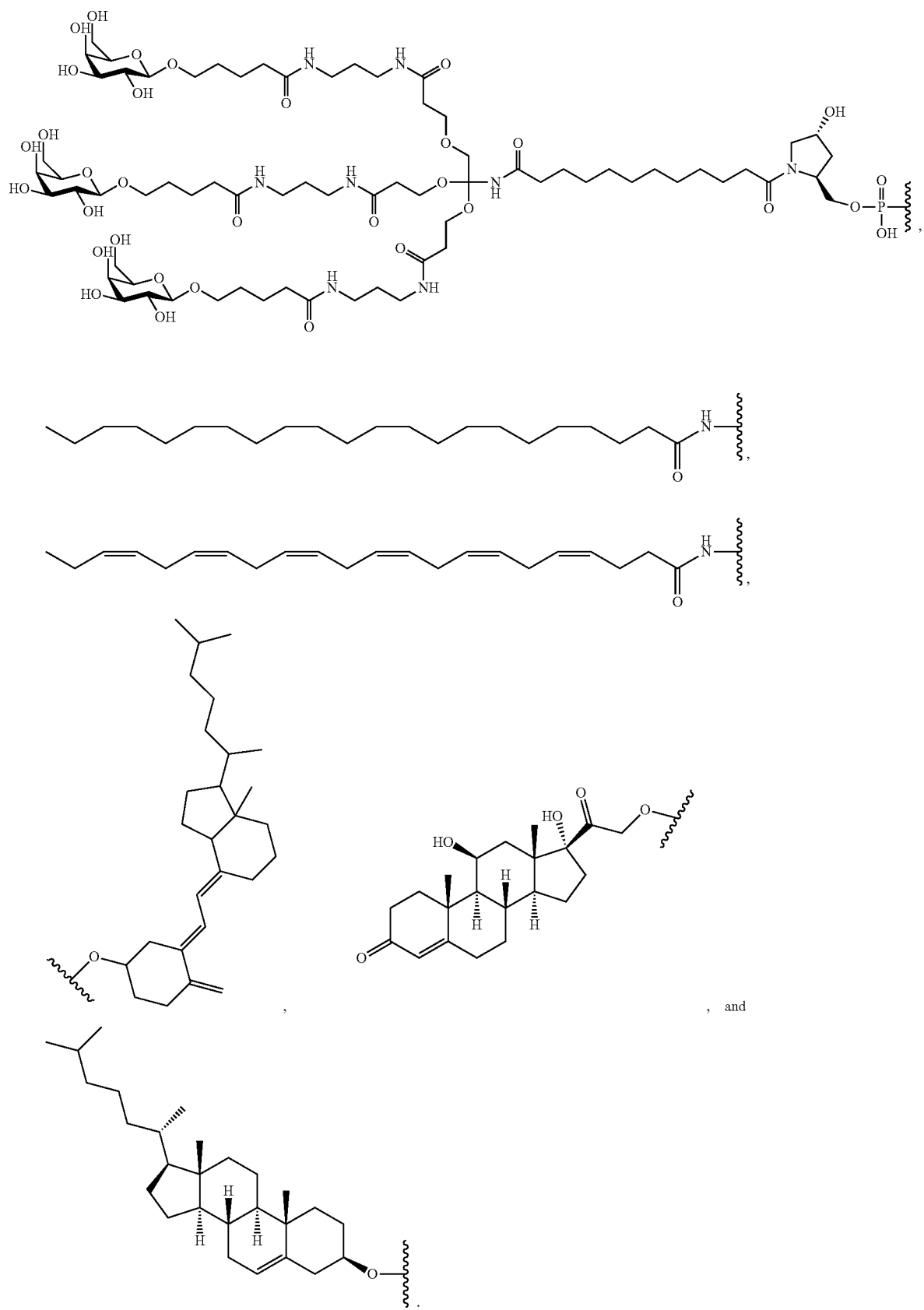

In another embodiment, $R^3$ is an internucleotide linker independently selected at each occurrence from the group consisting of a phosphorothioate, a phosphorodithioate, a methylphosphonate, a methylenephosphonate, a phosphotriester, and a boranophosphate.

In another embodiment, $R^3$ is an internucleotide linker independently selected at each occurrence from the group consisting of a phosphorothioate, a phosphorodithioate, and a boranophosphate.

In another embodiment, $R^3$ is a phosphorothioate.

In another embodiment, L is selected from the group consisting of an ethylene glycol chain, an alkyl chain, and a peptide.

In another embodiment, L is selected from an ethylene glycol chain or a peptide.

In yet another embodiment, L is

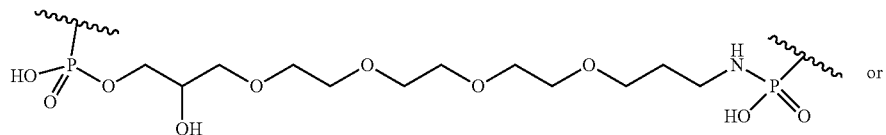 or

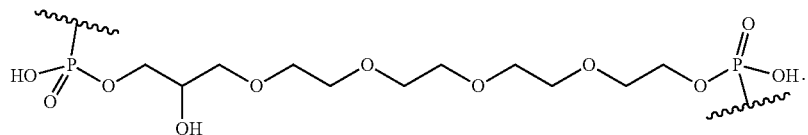

In still another embodiment, L is

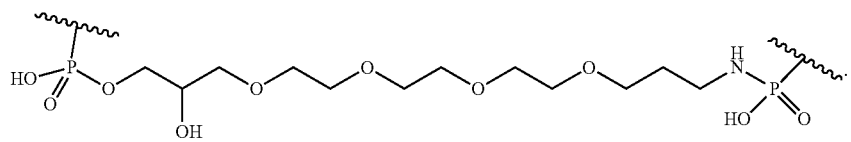

In another embodiment, L is

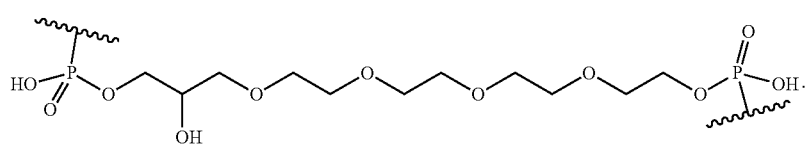

In one embodiment, the compound of the Formula shown in FIG. 87 is a compound the Formula shown in FIG. 88.

In another embodiment, the compound of the Formula shown in FIG. 87, is a compound of the Formula shown in FIG. 88, or a pharmaceutically acceptable salt thereof, wherein
R¹ is

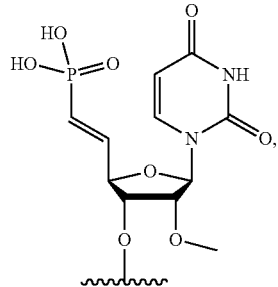

and
R² is

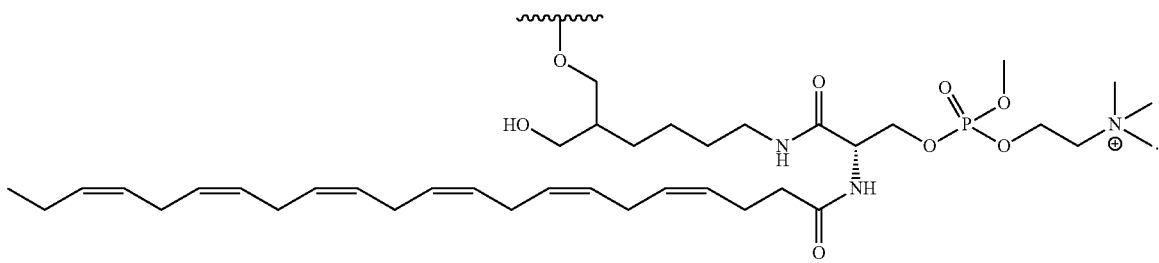 [SMILES: *OCC(CO)CCCCNC(=O)[C@H](COP(=O)(OC)OCC[N+](C)(C)C)NC(=O)CC/C=C\C/C=C\C/C=C\C/C=C\C/C=C\C/C=C\CC]

In another aspect, provided herein is a compound of the Formula shown in FIG. 89, or a pharmaceutically acceptable salt thereof, wherein
R¹ is selected from the group consisting of

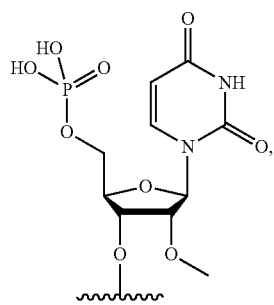

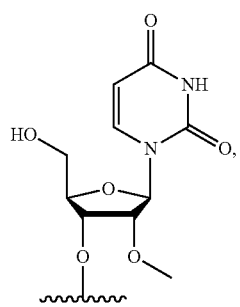

-continued

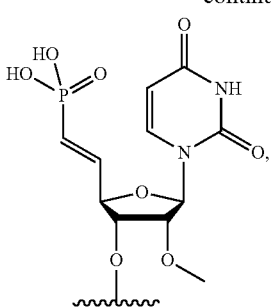

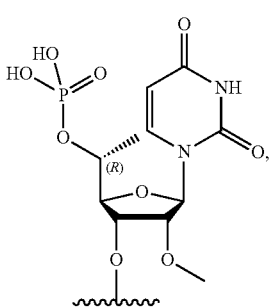

89

-continued

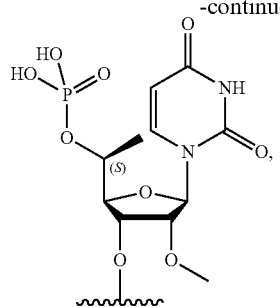

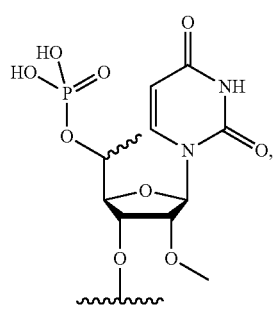

90

-continued

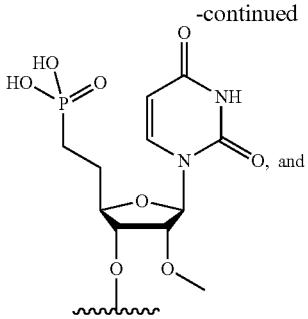

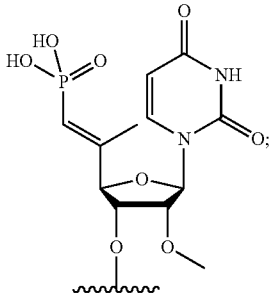

$R^3$ is independently selected at each occurrence from the group consisting of an internucleotide linker as shown in FIG. 82; and $R^2$ is selected from the group consisting of an alkyl chain (e.g., $C_{1-6}$, $C_{1-10}$, $C_{1-20}$, $C_{1-30}$, or $C_{1-40}$), a vitamin, a ligand, a peptide, a bioactive conjugate (including, but not limited to glycosphingolipids, polyunsaturated fatty acids, secosteroids, steroid hormones, or sterol lipids),

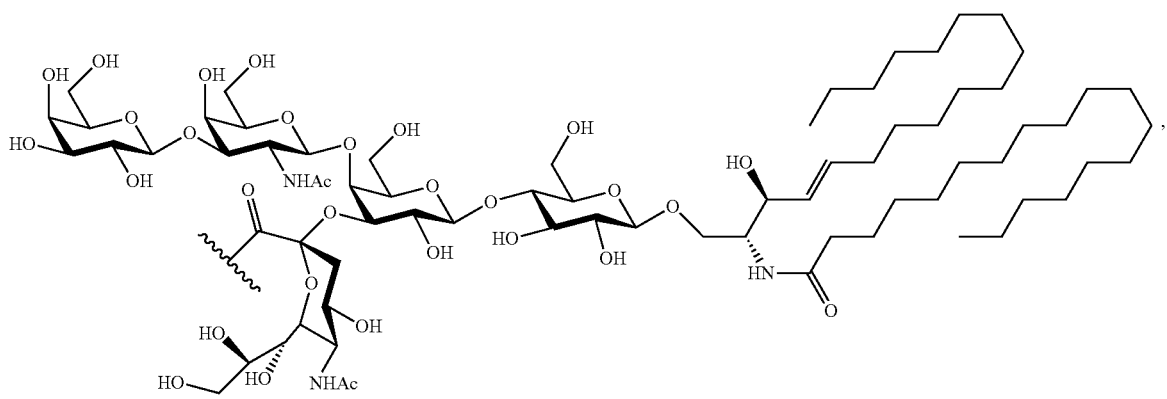

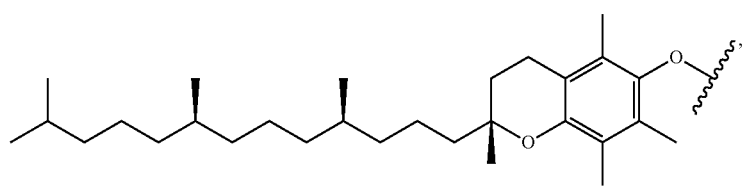

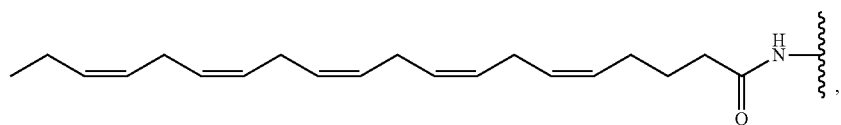

-continued
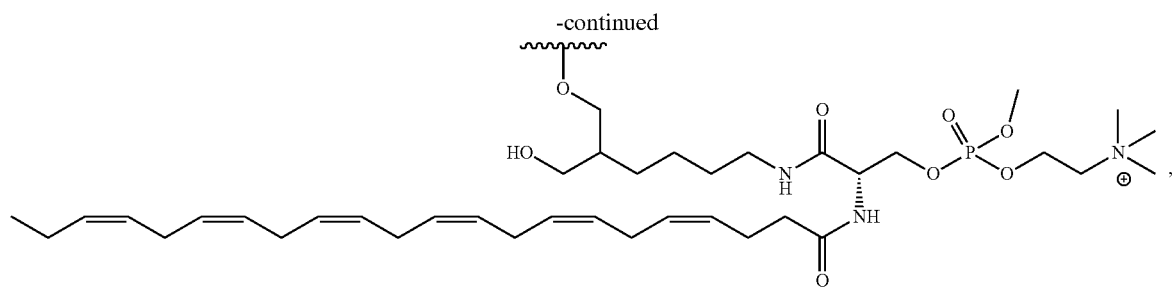
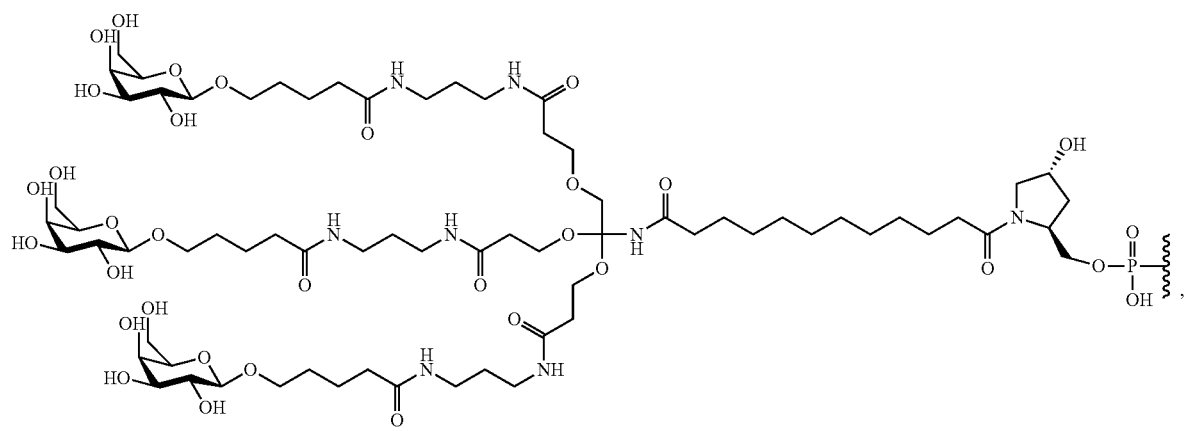
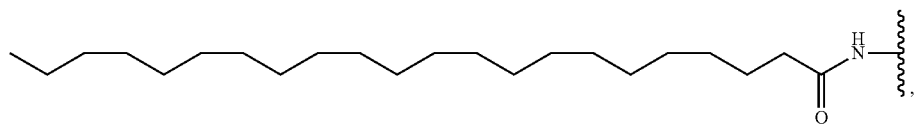
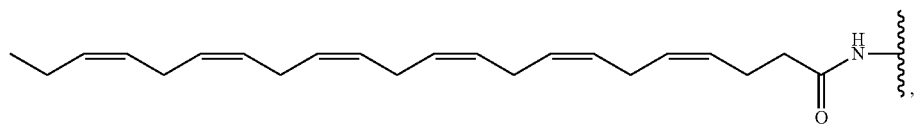
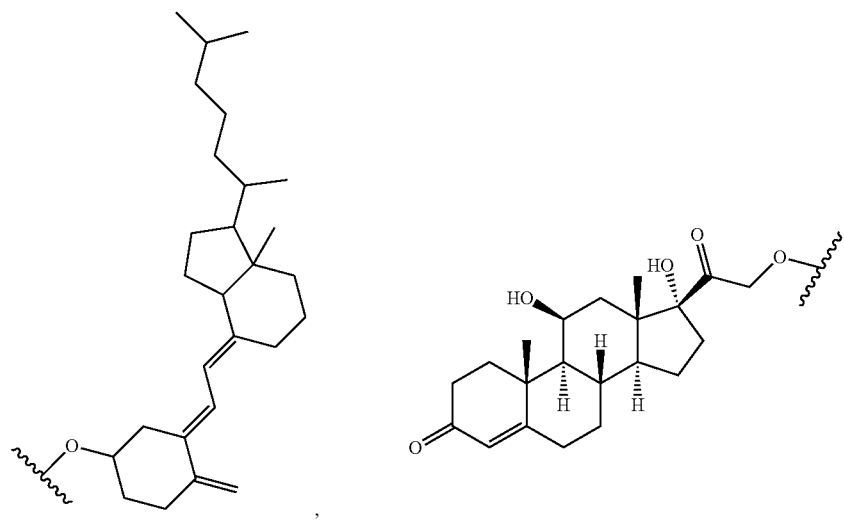
, and

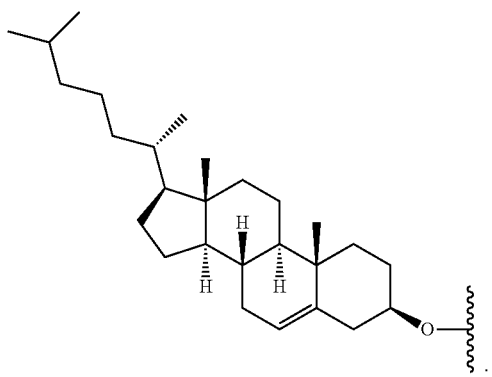
In one embodiment, R¹ is selected from the group consisting of
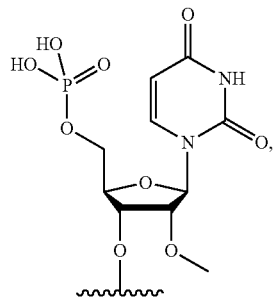
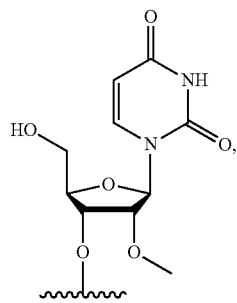
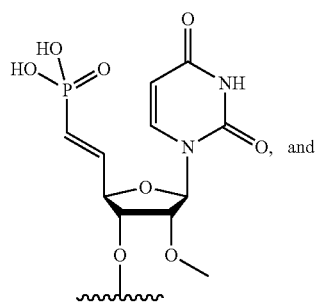
-continued
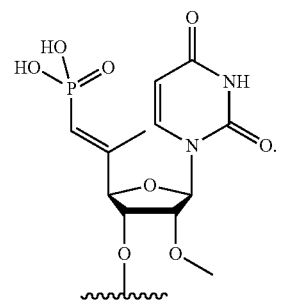
In another embodiment, R¹ is
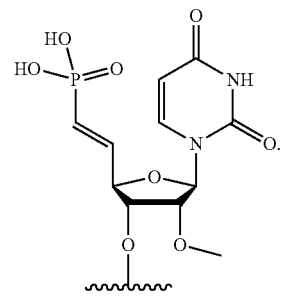
In another embodiment, R² is selected from the group consisting of

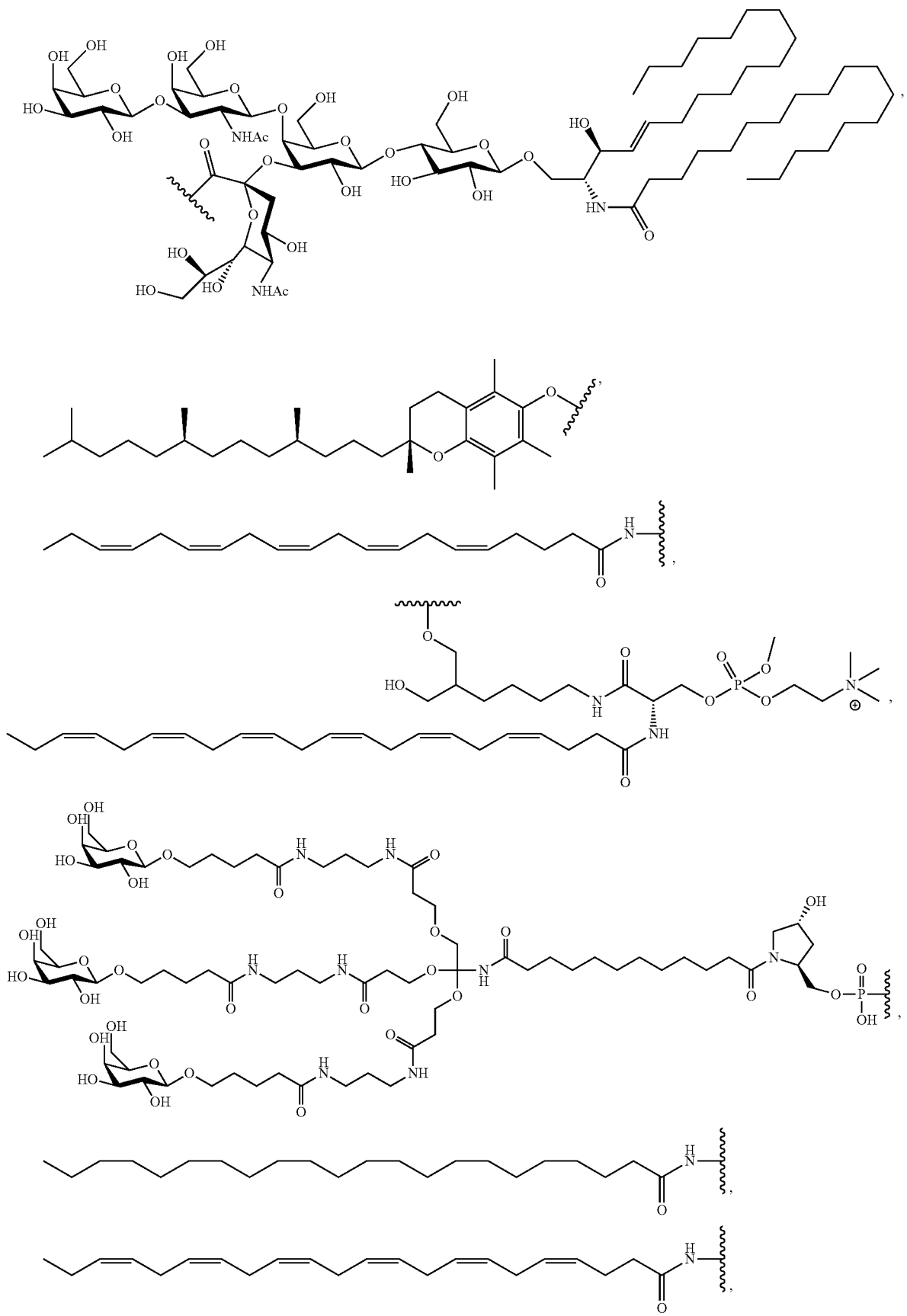

-continued

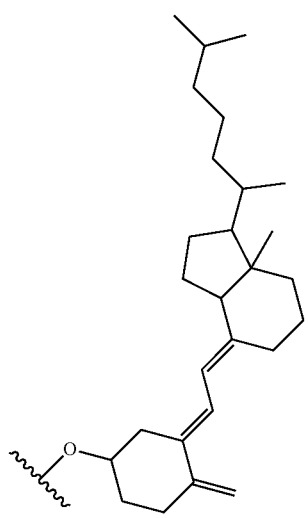

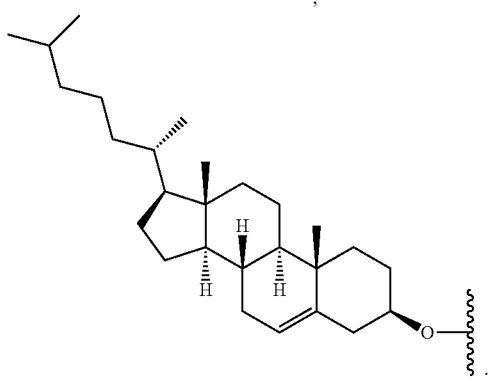

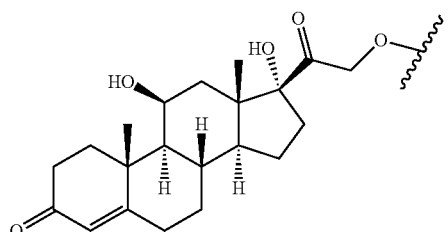

, and

In another embodiment, $R^3$ is an internucleotide linker independently selected at each occurrence from the group consisting of a phosphorothioate, a phosphorodithioate, a methylphosphonate, a methylenephosphonate, a phosphotriester, and a boranophosphate.

In another embodiment, $R^3$ is an internucleotide linker independently selected at each occurrence from the group consisting of a phosphorothioate, a phosphorodithioate, and a boranophosphate.

In another embodiment, $R^3$ is a phosphorothioate.

In one embodiment, the compound of the Formula shown in FIG. 89 is a compound of the Formula shown in FIG. 90.

In one embodiment, the compound of the Formula shown in FIG. 89, is a compound of the Formula shown in FIG. 90, or a pharmaceutically acceptable salt thereof, wherein $R^1$ is

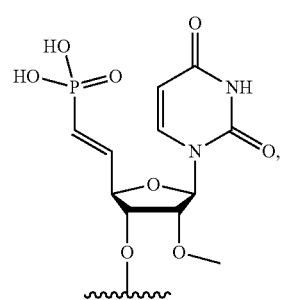

and
$R^2$ is

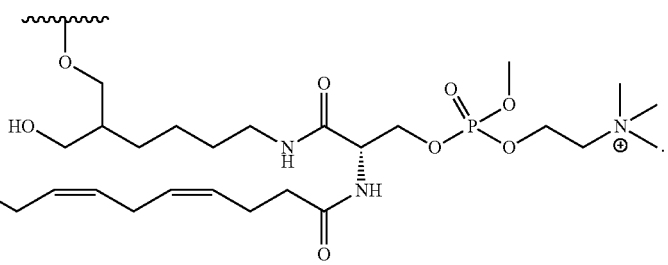

In one embodiment, the compound of the Formula shown in FIG. 89, is a compound of the Formula shown in FIG. 90, or a pharmaceutically acceptable salt thereof, wherein R[1] is
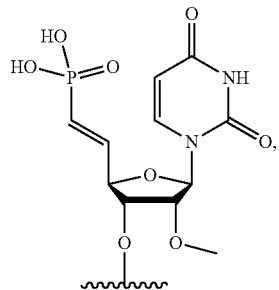
and R[2] is
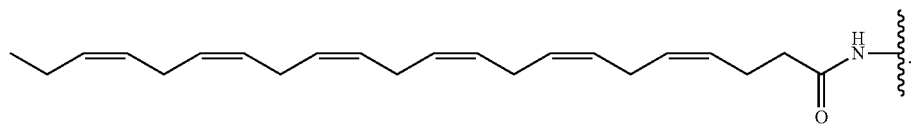 [SMILES: *NC(=O)CC/C=C\C/C=C\C/C=C\C/C=C\C/C=C\C/C=C\CC]
In one embodiment, the compound of the Formula shown in FIG. 89, is a compound of the Formula shown in FIG. 90, or a pharmaceutically acceptable salt thereof, wherein R[1] is
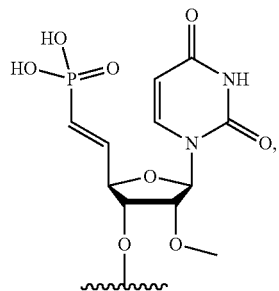
and R[2] is
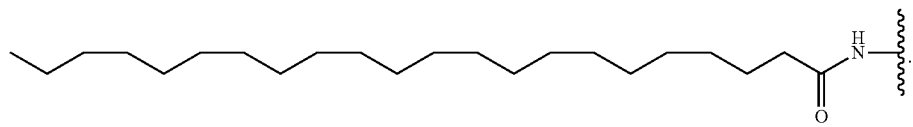 [SMILES: *NC(=O)CCCCCCCCCCCCCCCCCCCCC]

In one embodiment, the compound of the Formula shown in FIG. 89, is a compound of the Formula shown in FIG. 90, or a pharmaceutically acceptable salt thereof, wherein $R^1$ is
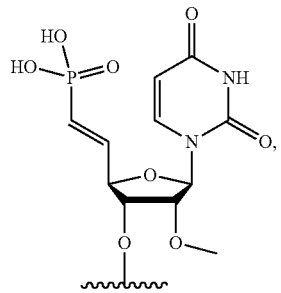
$R^2$ is
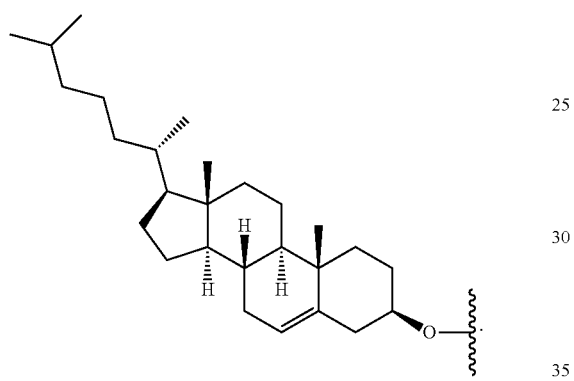
In one embodiment, the compound of the Formula shown in FIG. 89, is a compound of the Formula shown in FIG. 90, or a pharmaceutically acceptable salt thereof, wherein $R^1$ is
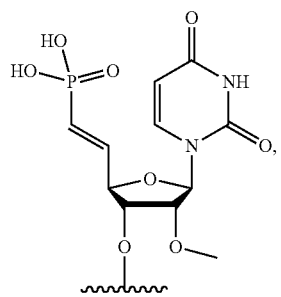
and
$R^2$ is
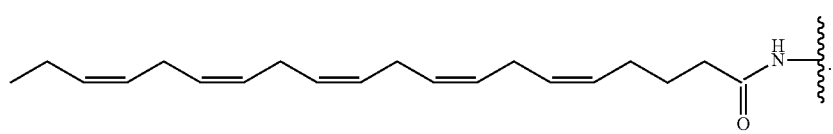

In one embodiment, the compound of the Formula shown in FIG. 89, is a compound of the Formula shown in FIG. 90, or a pharmaceutically acceptable salt thereof, wherein $R^1$ is

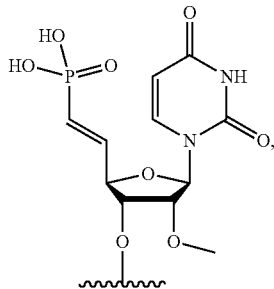

and
$R^2$ is

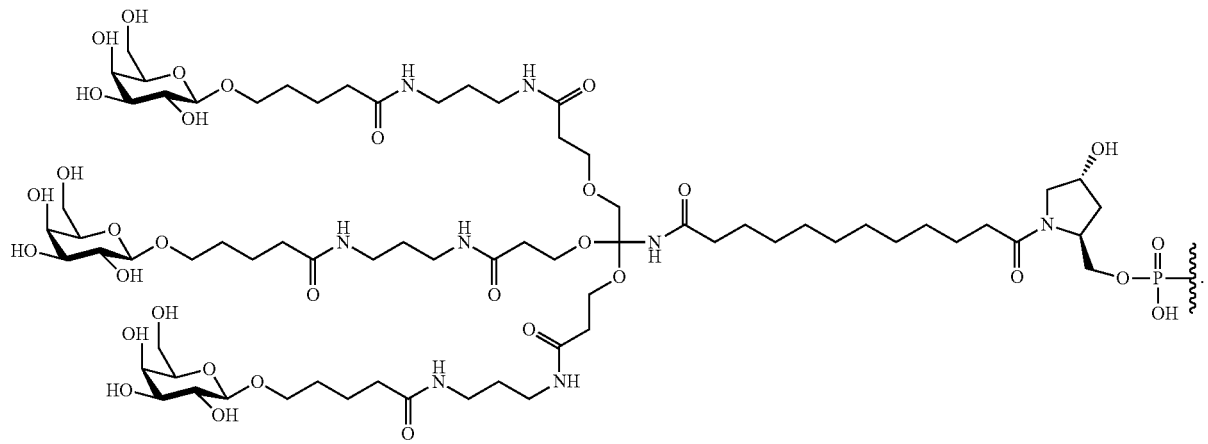

VIII. Methods of Introducing Nucleic Acids, Vectors and Host Cells

RNA silencing agents of the invention may be directly introduced into the cell (e.g., a neural cell) (i.e., intracellularly); or introduced extracellularly into a cavity, interstitial space, into the circulation of an organism, introduced orally, or may be introduced by bathing a cell or organism in a solution containing the nucleic acid. Vascular or extravascular circulation, the blood or lymph system, and the cerebrospinal fluid are sites where the nucleic acid may be introduced.

The RNA silencing agents of the invention can be introduced using nucleic acid delivery methods known in art including injection of a solution containing the nucleic acid, bombardment by particles covered by the nucleic acid, soaking the cell or organism in a solution of the nucleic acid, or electroporation of cell membranes in the presence of the nucleic acid. Other methods known in the art for introducing nucleic acids to cells may be used, such as lipid-mediated carrier transport, chemical-mediated transport, and cationic liposome transfection such as calcium phosphate, and the like. The nucleic acid may be introduced along with other components that perform one or more of the following activities: enhance nucleic acid uptake by the cell or otherwise increase inhibition of the target gene.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, inhibit annealing of single strands, stabilize the single strands, or other-wise increase inhibition of the target gene.

RNA may be directly introduced into the cell (i.e., intracellularly); or introduced extracellularly into a cavity, interstitial space, into the circulation of an organism, introduced orally, or may be introduced by bathing a cell or organism in a solution containing the RNA. Vascular or extravascular circulation, the blood or lymph system, and the cerebrospinal fluid are sites where the RNA may be introduced.

The cell having the target gene may be from the germ line or somatic, totipotent or pluripotent, dividing or non-dividing, parenchyma or epithelium, immortalized or transformed, or the like. The cell may be a stem cell or a differentiated cell. Cell types that are differentiated include adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes, and cells of the endocrine or exocrine glands.

Depending on the particular target gene and the dose of double stranded RNA material delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, Enzyme Linked ImmunoSorbent Assay (ELISA), Western blotting, RadioImmunoAssay (RIA), other immunoassays, and Fluorescence Activated Cell Sorting (FACS).

For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentarnycin, hygromycin, kanamycin, lincomycin, methotrexate, phosphinothricin, puromycin, and tetracyclin. Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of RNAi agent may result in inhibition in a smaller fraction of cells (e.g., at least 10%, 20%, 50%, 75%, 90%, or 95% of targeted cells). Quantization of gene expression in a cell may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNA may be introduced in an amount which allows delivery of at least one copy per cell. Higher doses (e.g., at least 5, 10, 100, 500 or 1000 copies per cell) of material may yield more effective inhibition; lower doses may also be useful for specific applications.

In an exemplary aspect, the efficacy of an RNAi agent of the invention (e.g., an siRNA targeting an htt target sequence) is tested for its ability to specifically degrade mutant mRNA (e.g., htt mRNA and/or the production of huntingtin protein) in cells, in particular, in neurons (e.g., striatal or cortical neuronal clonal lines and/or primary neurons). Also suitable for cell-based validation assays are other readily transfectable cells, for example, HeLa cells or COS cells. Cells are transfected with human wild type or mutant cDNAs (e.g., human wild type or mutant huntingtin cDNA). Standard siRNA, modified siRNA or vectors able to produce siRNA from U-looped mRNA are co-transfected. Selective reduction in target mRNA (e.g., huntingtin mRNA) and/or target protein (e.g., huntingtin protein) is measured. Reduction of target mRNA or protein can be compared to levels of target mRNA or protein in the absence of an RNAi agent or in the presence of an RNAi agent that does not target htt mRNA. Exogenously-introduced mRNA or protein (or endogenous mRNA or protein) can be assayed for comparison purposes. When utilizing neuronal cells, which are known to be somewhat resistant to standard transfection techniques, it may be desirable to introduce RNAi agents (e.g., siRNAs) by passive uptake.

Recombinant Adeno-Associated Viruses and Vectors

In certain exemplary embodiments, recombinant adeno-associated viruses (rAAVs) and their associated vectors can be used to deliver one or more siRNAs into cells, e.g., neural cells (e.g., brain cells). AAV is able to infect many different cell types, although the infection efficiency varies based upon serotype, which is determined by the sequence of the capsid protein. Several native AAV serotypes have been identified, with serotypes 1-9 being the most commonly used for recombinant AAV. AAV-2 is the most well-studied and published serotype. The AAV-DJ system includes serotypes AAV-DJ and AAV-DJ/8. These serotypes were created through DNA shuffling of multiple AAV serotypes to produce AAV with hybrid capsids that have improved transduction efficiencies in vitro (AAV-DJ) and in vivo (AAV-DJ/8) in a variety of cells and tissues.

In particular embodiments, widespread central nervous system (CNS) delivery can be achieved by intravascular delivery of recombinant adeno-associated virus 7 (rAAV7), RAAV9 and rAAV10, or other suitable rAAVs (Zhang et al. (2011) Mol. Ther. 19(8):1440-8. doi: 10.1038/mt.2011.98. Epub 2011 May 24). rAAVs and their associated vectors are well-known in the art and are described in US Patent Applications 2014/0296486, 2010/0186103, 2008/0269149, 2006/0078542 and 2005/0220766, each of which is incorporated herein by reference in its entirety for all purposes.

rAAVs may be delivered to a subject in compositions according to any appropriate methods known in the art. An rAAV can be suspended in a physiologically compatible carrier (i.e., in a composition), and may be administered to a subject, i.e., a host animal, such as a human, mouse, rat, cat, dog, sheep, rabbit, horse, cow, goat, pig, guinea pig, hamster, chicken, turkey, a non-human primate (e.g., Macaque) or the like. In certain embodiments, a host animal is a non-human host animal.

Delivery of one or more rAAVs to a mammalian subject may be performed, for example, by intramuscular injection or by administration into the bloodstream of the mammalian subject. Administration into the bloodstream may be by injection into a vein, an artery, or any other vascular conduit. In certain embodiments, one or more rAAVs are administered into the bloodstream by way of isolated limb perfusion, a technique well known in the surgical arts, the method essentially enabling the artisan to isolate a limb from the systemic circulation prior to administration of the rAAV virions. A variant of the isolated limb perfusion technique, described in U.S. Pat. No. 6,177,403, can also be employed by the skilled artisan to administer virions into the vasculature of an isolated limb to potentially enhance transduction into muscle cells or tissue. Moreover, in certain instances, it may be desirable to deliver virions to the central nervous system (CNS) of a subject. By "CNS" is meant all cells and tissue of the brain and spinal cord of a vertebrate. Thus, the term includes, but is not limited to, neuronal cells, glial cells, astrocytes, cerebrospinal fluid (CSF), interstitial spaces, bone, cartilage and the like. Recombinant AAVs may be delivered directly to the CNS or brain by injection into, e.g., the ventricular region, as well as to the striatum (e.g., the caudate nucleus or putamen of the striatum), spinal cord and neuromuscular junction, or cerebellar lobule, with a needle, catheter or related device, using neurosurgical techniques known in the art, such as by stereotactic injection (see, e.g., Stein et al., J Virol 73:3424-3429, 1999; Davidson et al., PNAS 97:3428-3432, 2000; Davidson et al., Nat. Genet. 3:219-223, 1993; and Alisky and Davidson, Hum. Gene Ther. 11:2315-2329, 2000).

The compositions of the invention may comprise an rAAV alone, or in combination with one or more other viruses (e.g., a second rAAV encoding having one or more different transgenes). In certain embodiments, a composition comprises 1, 2, 3, 4, 5, 6, 7, 8, 9, 10 or more different rAAVs each having one or more different transgenes.

An effective amount of an rAAV is an amount sufficient to target infect an animal, target a desired tissue. In some embodiments, an effective amount of an rAAV is an amount sufficient to produce a stable somatic transgenic animal model. The effective amount will depend primarily on factors such as the species, age, weight, health of the subject, and the tissue to be targeted, and may thus vary among animal and tissue. For example, an effective amount of one or more rAAVs is generally in the range of from about 1 ml to about 100 ml of solution containing from about $10^9$ to $10^{16}$ genome copies. In some cases, a dosage between about $10^{11}$ to $10^{12}$ rAAV genome copies is appropriate. In certain embodiments, $10^{12}$ rAAV genome copies is effective to target heart, liver, and pancreas tissues. In some cases, stable transgenic animals are produced by multiple doses of an rAAV.

In some embodiments, rAAV compositions are formulated to reduce aggregation of AAV particles in the composition, particularly where high rAAV concentrations are present (e.g., about $10^{13}$ genome copies/mL or more). Methods for reducing aggregation of rAAVs are well known in the art and, include, for example, addition of surfactants, pH adjustment, salt concentration adjustment, etc. (See, e.g., Wright et al. (2005) Molecular Therapy 12:171-178, the contents of which are incorporated herein by reference.)

"Recombinant AAV (rAAV) vectors" comprise, at a minimum, a transgene and its regulatory sequences, and 5' and 3' AAV inverted terminal repeats (ITRs). It is this recombinant AAV vector which is packaged into a capsid protein and delivered to a selected target cell. In some embodiments, the transgene is a nucleic acid sequence, heterologous to the vector sequences, which encodes a polypeptide, protein, functional RNA molecule (e.g., siRNA) or other gene product, of interest. The nucleic acid coding sequence is operatively linked to regulatory components in a manner which permits transgene transcription, translation, and/or expression in a cell of a target tissue.

The AAV sequences of the vector typically comprise the cis-acting 5' and 3' inverted terminal repeat (ITR) sequences (See, e.g., B. J. Carter, in "Handbook of Parvoviruses", ed., P. Tijsser, CRC Press, pp. 155 168 (1990)). The ITR sequences are usually about 145 basepairs in length. In certain embodiments, substantially the entire sequences encoding the ITRs are used in the molecule, although some degree of minor modification of these sequences is permissible. The ability to modify these ITR sequences is within the skill of the art. (See, e.g., texts such as Sambrook et al, "Molecular Cloning. A Laboratory Manual", 2d ed., Cold Spring Harbor Laboratory, New York (1989); and K. Fisher et al., J Virol., 70:520 532 (1996)). An example of such a molecule employed in the present invention is a "cis-acting" plasmid containing the transgene, in which the selected transgene sequence and associated regulatory elements are flanked by the 5' and 3' AAV ITR sequences. The AAV ITR sequences may be obtained from any known AAV, including mammalian AAV types described further herein.

IX. Methods of Treatment

The present invention provides for both prophylactic and therapeutic methods of treating a subject at risk of (or susceptible to) a disease or disorder caused, in whole or in part, by a gain of function mutant protein. In one embodiment, the disease or disorder is a trinucleotide repeat disease or disorder. In another embodiment, the disease or disorder is a polyglutamine disorder. In a preferred embodiment, the disease or disorder is a disorder associated with the expression of huntingtin and in which alteration of huntingtin, especially the amplification of CAG repeat copy number, leads to a defect in huntingtin gene (structure or function) or huntingtin protein (structure or function or expression), such that clinical manifestations include those seen in Huntington's disease patients.

"Treatment," or "treating," as used herein, is defined as the application or administration of a therapeutic agent (e.g., a RNA agent or vector or transgene encoding same) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an RNAi agent or vector or transgene encoding same). Subjects at risk for the disease can be identified by, for example, any or a combination of diagnostic or prognostic assays as described herein. Administration of a prophylactic agent can occur prior to the manifestation of symptoms characteristic of the disease or disorder, such that the disease or disorder is prevented or, alternatively, delayed in its progression.

Another aspect of the invention pertains to methods treating subjects therapeutically, i.e., alter onset of symptoms of the disease or disorder. In an exemplary embodiment, the modulatory method of the invention involves contacting a cell expressing a gain-of-function mutant with a therapeutic agent (e.g., a RNAi agent or vector or transgene encoding same) that is specific for a target sequence within the gene (e.g., SEQ ID NOs:1, 2 or 3), such that sequence specific interference with the gene is achieved. These methods can be performed in vitro (e.g., by culturing the cell with the agent) or, alternatively, in vivo (e.g., by administering the agent to a subject).

With regards to both prophylactic and therapeutic methods of treatment, such treatments may be specifically tailored or modified, based on knowledge obtained from the field of pharmacogenomics. "Pharmacogenomics," as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

Therapeutic agents can be tested in an appropriate animal model. For example, an RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent. For example, an agent can be used in an animal model to determine the efficacy, toxicity, or side effects of treatment with such an agent.

Alternatively, an agent can be used in an animal model to determine the mechanism of action of such an agent.

A pharmaceutical composition containing an RNA silencing agent of the invention can be administered to any patient diagnosed as having or at risk for developing a neurological disorder, such as Huntington's disease. In one embodiment, the patient is diagnosed as having a neurological disorder, and the patient is otherwise in general good health. For example, the patient is not terminally ill, and the patient is likely to live at least 2, 3, 5 or more years following diagnosis. The patient can be treated immediately following diagnosis, or treatment can be delayed until the patient is experiencing more debilitating symptoms, such as motor fluctuations and dyskinesis in Parkinson's disease patients. In another embodiment, the patient has not reached an advanced stage of the disease.

An RNA silencing agent modified for enhance uptake into neural cells can be administered at a unit dose less than about 1.4 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA silencing agent per kg of bodyweight. The unit dose, for example, can be administered by injection (e.g., intravenous or intramuscular, intrathecally, or directly into the brain), an inhaled dose, or a topical application. Particularly preferred dosages are less than 2, 1, or 0.1 mg/kg of body weight.

Delivery of an RNA silencing agent directly to an organ (e.g., directly to the brain) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ. The dosage can be an amount effective to treat or prevent a neurological disease or disorder, e.g., Huntington's disease. In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time. In one embodiment, the effective dose is administered with other traditional therapeutic modalities.

In one embodiment, a subject is administered an initial dose, and one or more maintenance doses of an RNA silencing agent. The maintenance dose or doses are generally lower than the initial dose, e.g., one-half less of the initial dose. A maintenance regimen can include treating the subject with a dose or doses ranging from 0.01 µg to 1.4 mg/kg of body weight per day, e.g., 10, 1, 0.1, 0.01, 0.001, or 0.00001 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. In one embodiment, a pharmaceutical composition includes a plurality of RNA silencing agent species. In another embodiment, the RNA silencing agent species has sequences that are non-overlapping and non-adjacent to another species with respect to a naturally occurring target sequence. In another embodiment, the plurality of RNA silencing agent species is specific for different naturally occurring target genes. In another embodiment, the RNA silencing agent is allele specific. In another embodiment, the plurality of RNA silencing agent species target two or more target sequences (e.g., two, three, four, five, six, or more target sequences).

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

The concentration of the RNA silencing agent composition is an amount sufficient to be effective in treating or preventing a disorder or to regulate a physiological condition in humans. The concentration or amount of RNA silencing agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an RNA silencing agent can include a single treatment or, preferably, can include a series of treatments. It will also be appreciated that the effective dosage of an RNA silencing agent for treatment may increase or decrease over the course of a particular treatment. Changes in dosage may result and become apparent from the results of diagnostic assays as described herein. For example, the subject can be monitored after administering an RNA silencing agent composition. Based on information from the monitoring, an additional amount of the RNA silencing agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA, e.g., an RNA expressed in a neural cell. The transgenic animal can be deficient for the corresponding endogenous RNA. In another embodiment, the composition for testing includes an RNA silencing agent that is complementary, at least in an internal region, to a sequence that is conserved between the target RNA in the animal model and the target RNA in a human.

X. Pharmaceutical Compositions and Methods of Administration

The invention pertains to uses of the above-described agents for prophylactic and/or therapeutic treatments as described Infra. Accordingly, the modulators (e.g., RNAi agents) of the present invention can be incorporated into pharmaceutical compositions suitable for administration. Such compositions typically comprise the nucleic acid molecule, protein, antibody, or modulatory compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. In certain exemplary embodiments, a pharmaceutical composition of the invention is delivered to the cerebrospinal fluid (CSF) by a route of administration that includes, but is not limited to, intrastriatal (IS) administration, intracerebroventricular (ICV) administration and intrathecal (IT) administration (e.g., via a pump, an infusion or the like). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous, IS, ICV and/or IT administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives.

Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

The RNA silencing agents can also be administered by transfection or infection using methods known in the art, including but not limited to the methods described in McCaffrey et al. (2002), Nature, 418(6893), 38-9 (hydrodynamic transfection); Xia et al. (2002), Nature Biotechnol., 20(10), 1006-10 (viral-mediated delivery); or Putnam (1996), Am. J. Health Syst. Pharm. 53(2), 151-160, erratum at Am. J. Health Syst. Pharm. 53(3), 325 (1996).

The RNA silencing agents can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al. (1998), Clin. Immunol. Immunopathol., 88(2), 205-10. Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack or dispenser together with optional instructions for administration.

As defined herein, a therapeutically effective amount of a RNA silencing agent (i.e., an effective dosage) depends on the RNA silencing agent selected. For instance, if a plasmid encoding shRNA is selected, single dose amounts in the range of approximately 1 µg to 1000 mg may be administered; in some embodiments, 10, 30, 100 or 1000 µg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into expression constructs, e.g., viral vectors, retroviral vectors, expression cassettes, or plasmid viral vectors, e.g., using methods known in the art, including but not limited to those described in Xia et al., (2002), Supra. Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

The nucleic acid molecules of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides. Brummelkamp et al. (2002), Science, 296, 550-553; Lee et al, (2002). supra; Miyagishi and Taira (2002), Nature Biotechnol., 20, 497-500; Paddison et al. (2002), supra; Paul (2002), supra; Sui (2002) supra; Yu et al. (2002), supra.

The expression constructs may be any construct suitable for use in the appropriate expression system and include, but are not limited to retroviral vectors, linear expression cassettes, plasmids and viral or virally-derived vectors, as known in the art. Such expression constructs may include one or more inducible promoters, RNA Pol III promoter systems such as U6 snRNA promoters or H1 RNA polymerase III promoters, or other promoters known in the art. The constructs can include one or both strands of the siRNA. Expression constructs expressing both strands can also include loop structures linking both strands, or each strand can be separately transcribed from separate promoters within the same construct. Each strand can also be transcribed from a separate expression construct, Tuschl (2002), Supra.

In certain exemplary embodiments, a composition that includes an RNA silencing agent of the invention can be delivered to the nervous system of a subject by a variety of routes. Exemplary routes include intrathecal, parenchymal (e.g., in the brain), nasal, and ocular delivery. The composition can also be delivered systemically, e.g., by intravenous, subcutaneous or intramuscular injection, which is particularly useful for delivery of the RNA silencing agents to peripheral neurons. A preferred route of delivery is directly to the brain, e.g., into the ventricles or the hypothalamus of the brain, or into the lateral or dorsal areas of the brain. The RNA silencing agents for neural cell delivery can be incorporated into pharmaceutical compositions suitable for administration.

For example, compositions can include one or more species of an RNA silencing agent and a pharmaceutically acceptable carrier. The pharmaceutical compositions of the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, intrathecal, or intraventricular (e.g., intracerebroventricular) administration. In certain exemplary embodiments, an RNA silencing agent of the invention is delivered across the Blood-Brain-Barrier (BBB) suing a variety of suitable compositions and methods described herein.

The route of delivery can be dependent on the disorder of the patient. For example, a subject diagnosed with Huntington's disease can be administered an anti-htt RNA silencing agent of the invention directly into the brain (e.g., into the globus pallidus or the corpus striatum of the basal ganglia, and near the medium spiny neurons of the corpus striatum). In addition to an RNA silencing agent of the invention, a patient can be administered a second therapy, e.g., a palliative therapy and/or disease-specific therapy. The secondary therapy can be, for example, symptomatic (e.g., for alleviating symptoms), neuroprotective (e.g., for slowing or halting disease progression), or restorative (e.g., for reversing the disease process). For the treatment of Huntington's disease, for example, symptomatic therapies can include the drugs haloperidol, carbamazepine, or valproate. Other therapies can include psychotherapy, physiotherapy, speech therapy, communicative and memory aids, social support services, and dietary advice.

An RNA silencing agent can be delivered to neural cells of the brain. Delivery methods that do not require passage of the composition across the blood-brain barrier can be utilized. For example, a pharmaceutical composition containing an RNA silencing agent can be delivered to the patient by injection directly into the area containing the disease-affected cells. For example, the pharmaceutical composition can be delivered by injection directly into the brain. The injection can be by stereotactic injection into a particular region of the brain (e.g., the substantia nigra, cortex, hippocampus, striatum, or globus pallidus). The RNA silencing agent can be delivered into multiple regions of the central nervous system (e.g., into multiple regions of the brain, and/or into the spinal cord). The RNA silencing agent can be delivered into diffuse regions of the brain (e.g., diffuse delivery to the cortex of the brain).

In one embodiment, the RNA silencing agent can be delivered by way of a cannula or other delivery device having one end implanted in a tissue, e.g., the brain, e.g., the substantia nigra, cortex, hippocampus, striatum or globus pallidus of the brain. The cannula can be connected to a reservoir of RNA silencing agent. The flow or delivery can be mediated by a pump, e.g., an osmotic pump or minipump, such as an Alzet pump (Durect, Cupertino, Calif.). In one embodiment, a pump and reservoir are implanted in an area distant from the tissue, e.g., in the abdomen, and delivery is effected by a conduit leading from the pump or reservoir to the site of release. Devices for delivery to the brain are described, for example, in U.S. Pat. Nos. 6,093,180, and 5,814,014.

An RNA silencing agent of the invention can be further modified such that it is capable of traversing the blood brain barrier. For example, the RNA silencing agent can be conjugated to a molecule that enables the agent to traverse the barrier. Such modified RNA silencing agents can be administered by any desired method, such as by intraventricular or intramuscular injection, or by pulmonary delivery, for example.

In certain embodiments, exosomes are used to deliver an RNA silencing agent of the invention. Exosomes can cross the BBB and deliver siRNAs, antisense oligonucleotides, chemotherapeutic agents and proteins specifically to neurons after systemic injection (See, Alvarez-Erviti L, Seow Y, Yin H, Betts C, Lakhal S, Wood M J. (2011). Delivery of siRNA to the mouse brain by systemic injection of targeted exosomes. Nat Biotechnol. 2011 April; 29(4):341-5. doi: 10.1038/nbt.1807; El-Andaloussi S, Lee Y, Lakhal-Littleton S, Li J, Seow Y, Gardiner C, Alvarez-Erviti L, Sargent I L, Wood M J. (2011). Exosome-mediated delivery of siRNA in vitro and in vivo. Nat Protoc. 2012 December; 7(12):2112-26. doi: 10.1038/nprot.2012.131; E L Andaloussi S, Mager I, Breakefield X O, Wood M J. (2013). Extracellular vesicles: biology and emerging therapeutic opportunities. Nat Rev Drug Discov. 2013 May; 12(5):347-57. doi: 10.1038/nrd3978; El Andaloussi S, Lakhal S, Mager I, Wood M J. (2013). Exosomes for targeted siRNA delivery across biological barriers. Adv Drug Deliv Rev. 2013 March; 65(3):391-7. doi: 10.1016/j.addr.2012.08.008).

In certain embodiments, one or more lipophilic molecules are used to allow delivery of an RNA silencing agent of the invention past the BBB (Alvarez-Ervit (2011)). The RNA silencing agent would then be activated, e.g., by enzyme degradation of the lipophilic disguise to release the drug into its active form.

In certain embodiments, one or more receptor-mediated permeablizing compounds can be used to increase the permeability of the BBB to allow delivery of an RNA silencing agent of the invention. These drugs increase the permeability of the BBB temporarily by increasing the osmotic pressure in the blood which loosens the tight junctions between the endothelial cells ((El-Andaloussi (2012)). By loosening the tight junctions normal intravenous injection of an RNA silencing agent can be performed.

In certain embodiments, nanoparticle-based delivery systems are used to deliver an RNA silencing agent of the invention across the BBB. As used herein, "nanoparticles" refer to polymeric nanoparticles that are typically solid, biodegradable, colloidal systems that have been widely investigated as drug or gene carriers (S. P. Egusquiaguirre, M. Igartua, R. M. Hernandez, and J. L. Pedraz, "Nanoparticle delivery systems for cancer therapy: advances in clinical and preclinical research," Clinical and Translational Oncology, vol. 14, no. 2, pp. 83-93, 2012). Polymeric nanoparticles are classified into two major categories, natural polymers and synthetic polymers. Natural polymers for siRNA delivery include, but are not limited to, cyclodextrin, chitosan, and atelocollagen (Y. Wang, Z. Li, Y. Han, L. H. Liang, and A. Ji, "Nanoparticle-based delivery system for application of siRNA in vivo," Current Drug Metabolism, vol. 11, no. 2, pp. 182-196, 2010). Synthetic polymers include, but are not limited to, polyethyleneimine (PEI), poly(dl-lactide-co-glycolide) (PLGA), and dendrimers, which have been intensively investigated (X. Yuan, S. Naguib, and Z. Wu, "Recent advances of siRNA delivery by nanoparticles," Expert Opinion on Drug Delivery, vol. 8, no. 4, pp. 521-536, 2011). For a review of nanoparticles and other suitable delivery systems, See Jong-Min Lee, Tae-Jong Yoon, and Young-Seok Cho, "Recent Developments in Nanoparticle-Based siRNA Delivery for Cancer Therapy," BioMed Research International, vol. 2013, Article ID 782041, 10 pages, 2013. doi:10.1155/2013/782041 (incorporated by reference in its entirety.)

An RNA silencing agent of the invention can be administered ocularly, such as to treat retinal disorder, e.g., a retinopathy. For example, the pharmaceutical compositions can be applied to the surface of the eye or nearby tissue, e.g., the inside of the eyelid. They can be applied topically, e.g., by spraying, in drops, as an eyewash, or an ointment. Ointments or droppable liquids may be delivered by ocular delivery systems known in the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The pharmaceutical composition can also be administered to the interior of the eye, and can be introduced by a needle or other delivery device which can introduce it to a selected area or structure. The composition containing the RNA silencing agent can also be applied via an ocular patch.

In general, an RNA silencing agent of the invention can be administered by any suitable method. As used herein, topical delivery can refer to the direct application of an RNA silencing agent to any surface of the body, including the eye, a mucous membrane, surfaces of a body cavity, or to any internal surface. Formulations for topical administration may include transdermal patches, ointments, lotions, creams, gels, drops, sprays, and liquids. Conventional pharmaceutical carriers, aqueous, powder or oily bases, thickeners and the like may be necessary or desirable. Topical administration can also be used as a means to selectively deliver the RNA silencing agent to the epidermis or dermis of a subject, or to specific strata thereof, or to an underlying tissue.

Compositions for intrathecal or intraventricular (e.g., intracerebroventricular) administration may include sterile aqueous solutions which may also contain buffers, diluents and other suitable additives. Compositions for intrathecal or intraventricular administration preferably do not include a transfection reagent or an additional lipophilic moiety besides, for example, the lipophilic moiety attached to the RNA silencing agent.

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

An RNA silencing agent of the invention can be administered to a subject by pulmonary delivery. Pulmonary delivery compositions can be delivered by inhalation of a dispersion so that the composition within the dispersion can reach the lung where it can be readily absorbed through the alveolar region directly into blood circulation. Pulmonary delivery can be effective both for systemic delivery and for localized delivery to treat diseases of the lungs. In one embodiment, an RNA silencing agent administered by pulmonary delivery has been modified such that it is capable of traversing the blood brain barrier.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver drugs that may be readily formulated as dry powders. An RNA silencing agent composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The types of pharmaceutical excipients that are useful as carriers include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, trehalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

An RNA silencing agent of the invention can be administered by oral and nasal delivery. For example, drugs administered through these membranes have a rapid onset of action, provide therapeutic plasma levels, avoid first pass effect of hepatic metabolism, and avoid exposure of the drug to the hostile gastrointestinal (GI) environment. Additional advantages include easy access to the membrane sites so that the drug can be applied, localized and removed easily. In one embodiment, an RNA silencing agent administered by oral or nasal delivery has been modified to be capable of traversing the blood-brain barrier.

In one embodiment, unit doses or measured doses of a composition that include RNA silencing agents are dispensed by an implanted device. The device can include a sensor that monitors a parameter within a subject. For example, the device can include a pump, such as an osmotic pump and, optionally, associated electronics.

An RNA silencing agent can be packaged in a viral natural capsid or in a chemically or enzymatically produced artificial capsid or structure derived therefrom.

XI. Kits

In certain other aspects, the invention provides kits that include a suitable container containing a pharmaceutical formulation of an RNA silencing agent, e.g., a double-stranded RNA silencing agent, or sRNA agent, (e.g., a precursor, e.g., a larger RNA silencing agent which can be processed into a sRNA agent, or a DNA which encodes an RNA silencing agent, e.g., a double-stranded RNA silencing agent, or sRNA agent, or precursor thereof). In certain embodiments the individual components of the pharmaceutical formulation may be provided in one container. Alternatively, it may be desirable to provide the components of the pharmaceutical formulation separately in two or more containers, e.g., one container for an RNA silencing agent preparation, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

It will be readily apparent to those skilled in the art that other suitable modifications and adaptations of the methods described herein may be made using suitable equivalents without departing from the scope of the embodiments disclosed herein. Having now described certain embodiments in detail, the same will be more clearly understood by reference to the following example, which is included for purposes of illustration only and is not intended to be limiting.

EXAMPLES

Example 1. Reduction of Huntingtin in Both Primary Neurons and Mouse Brain with Unformulated, Stabilized, Hydrophobic siRNAs The use of hydrophobically modified ASO-siRNA hybrids, which have the potential to offer both better efficacy and distribution in vivo and knockdown in primary neurons in vitro, was explored. The huntingtin gene was used as a target for mRNA knockdown. Huntington's disease is monogenic (Mangiarini, L. et al. Exon 1 of the HTT gene with an expanded CAG repeat is sufficient to cause a progressive neurological phenotype in transgenic mice. *Cell* 87, 493-506 (1996)) with a number of cellular mechanisms leading to disease pathology (Zuccato, C., Valenza, M. & Cattaneo, E. Molecular Mechanisms and Potential Therapeutical Targets in Huntington's Disease. *Physiological Reviews* 90, 905-981 (2010)) making it an excellent candidate for possible future oligonucleotide therapeutics.

A panel of hydrophobically modified siRNAs targeting the Huntingtin gene was developed. Efficacy and potency in was observed both in primary neurons in vitro, and in vivo in mouse brain upon a single low dose injection without any formulation for delivery. These compounds combine a number of different chemical and structural modifications found both in earlier model siRNAs and hsiRNAs, as well as in ASOs. These properties, which include stabilizing base modifications, cholesterol conjugation, and a fully phosphorothioated single stranded tail, make these hsiRNAs excellent tools for studying gene function in hard-to-target primary cells and organs that can be adapted for use in a number of different biologically relevant systems.

Figure 1B:
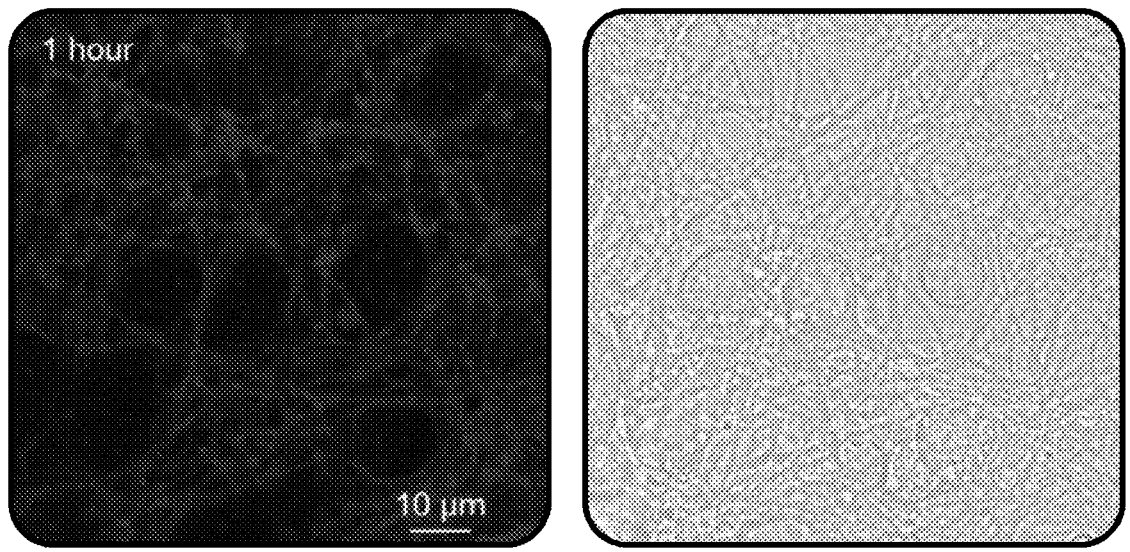
Figure 9:
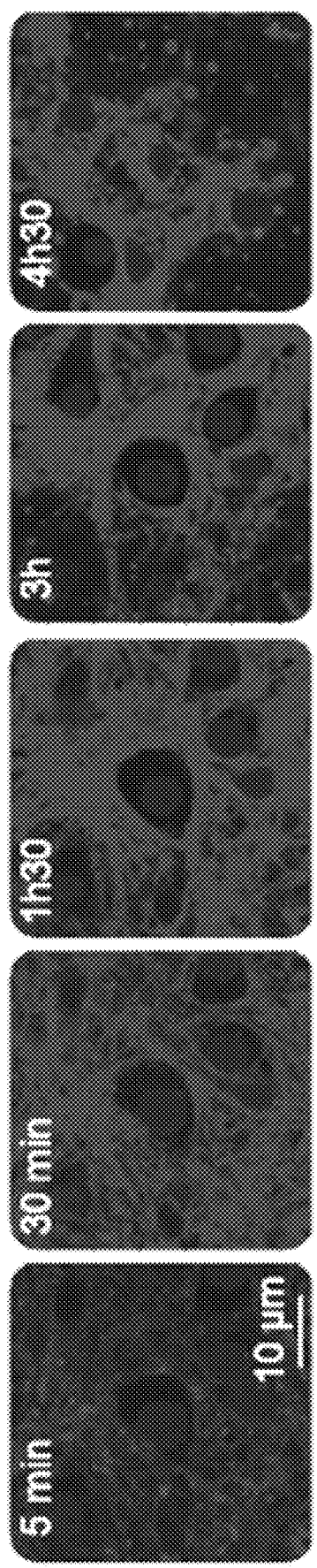
FIG. 9 depicts efficient uptake and internalization of hsiRNA in primary cortical neurons over time. Cy3-HTT10150 hsiRNA (red), 0.5 M, was added to primary cortical neurons. Imaged on Zeiss confocal microscope, 63×, nuclei stained with Hoechst dye (blue).

1.1 hsiRNA—Hydrophobically Modified siRNA/Antisense Hybrids were Efficiently Internalized by Primary Neurons The hsiRNAs were asymmetric compounds, with a short duplex region (15 basepairs) and single-stranded fully phosphorothioated tail. All pyrimidines in these compounds were 2'-Fluoro and 2'-O-Methyl modified (providing stabilization), and the 3' end of the passenger strand was conjugated to TEG-Cholesterol (FIG. 1A, FIG. 8) 13. The cholesterol conjugate enabled quick membrane association, while the single stranded phosphorothioated tail was necessary for cellular internalization by a mechanism similar to the one used by conventional antisense oligonucleotides. Addition of Cy3-labeled hsiRNA to primary cortical neurons resulted in immediate (within minutes) cellular association (FIG. 1B). Interestingly, the uptake was first observed preferentially in dendrites, followed by re-localization to the cellular body (FIG. 9). The uptake was uniform across all cells in the dish, affirming efficient internalization.

1.2 Identification of hsiRNAs Targeting Huntingtin

Figure 10A:
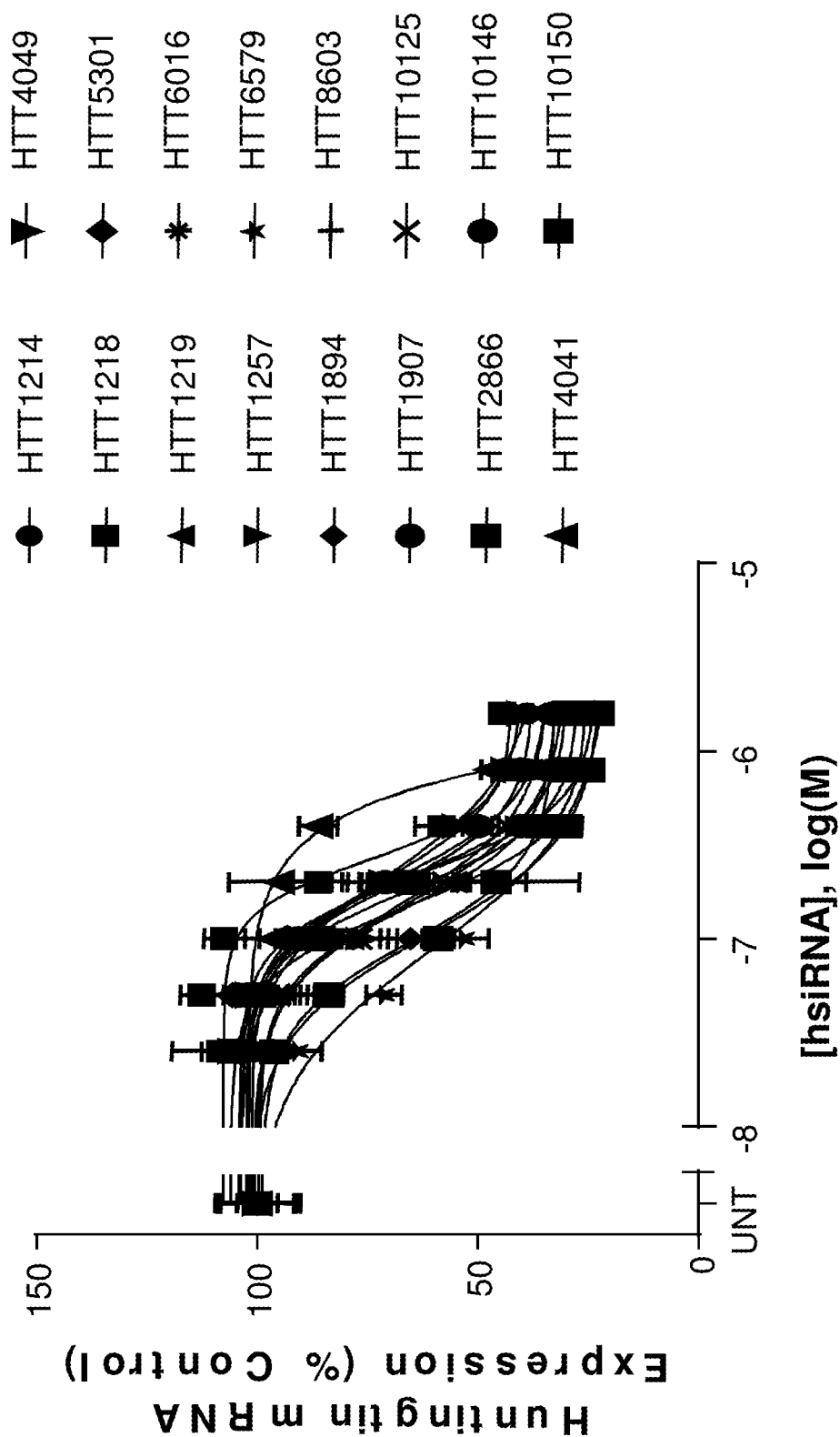
FIGS. 10A-10B graphically depict concentration-dependent silencing of huntingtin mRNA by HTT10150 in HeLa cells. Level of huntingtin mRNA was measured using QUANTIGENE (Affymetrix) at 72 hours normalized to housekeeping gene, PPIB (cyclophillin B), and presented as percent of untreated control (n=3, mean+/−SD). UNT—untreated cells, NTC—non-targeting control. A) Dose response of 16 active sequences in passive uptake (no formulation). B) Dose response of eight selected sequences in lipid-mediated uptake (using Invitrogen LIPOFECTAMINE RNAIMAX Transfection Reagent). Dose response data was fitted using GraphPad Prism 6.03.
Figure 10B:
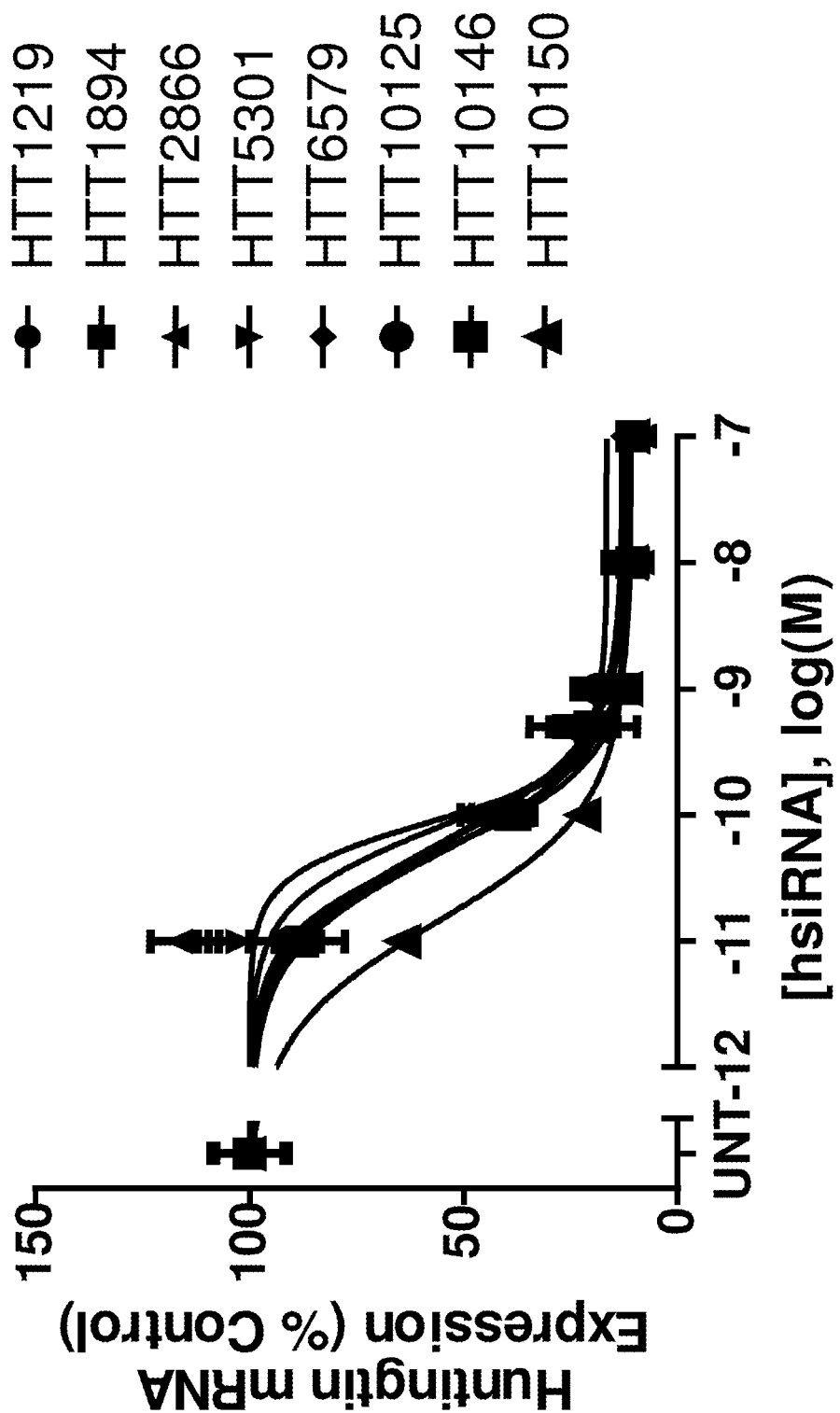

A panel of 94 hsiRNA compounds (FIG. 8) targeting huntingtin mRNA was designed and synthesized. These sequences spanned the gene and were selected to comply with standard siRNA design parameters (Birmingham, A. et al. A protocol for designing siRNAs with high functionality and specificity. *Nat Protoc* 2, 2068-2078 (2007)) including assessment of GC content, specificity and low seed compliment frequency (Anderson, E. M. et al. Experimental validation of the importance of seed complement frequency to siRNA specificity. *RNA* 14, 853-861 (2008)), elimination of sequences containing miRNA seeds, and examination of thermodynamic bias (Khvorova, A., Reynolds, A. & Jayasena, S. D. Functional siRNAs and miRNAs Exhibit Strand Bias. *Cell* 115, 209-216 (2003); Schwarz, D. S. et al. Asymmetry in the Assembly of the RNAi Enzyme Complex. *Cell* 115, 199-208 (2003)). More than 50% of bases were chemically modified, to provide in vivo stability and minimization of immune response (Judge, A., Bola, G., Lee, A. & MacLachlan, I. Design of Noninflammatory Synthetic siRNA Mediating Potent Gene Silencing in Vivo. *Molecular Therapy* 13, 494-505 (2006)). The modifications imposed additional restrictions on sequence space, reducing the hit rate. Impact on Huntingtin mRNA expression was measured after 72 hours exposure to 1.5 µM hsiRNA (passive uptake, no formulation) in HeLa cells by QUANTIGENE assay (FIG. 2), with 7% of sequences showing more than 70% silencing. Functional target sites were spread across the gene with the exception of the distal part of the 3'UTR, later explained by preferential expression of the shorter htt isoform in HeLa cells (Li, S. H. et al. Huntington's disease gene (IT15) is widely expressed in human and rat tissues. *NEURON* 11, 985-993 (1993)). IC50 values were identified for sixteen active sequences, selected based on primary screen activity and cross-species conservation (FIG. 10). IC50 values ranged from 90 to 766 nM in passive uptake (no formulation) and from 4 to 91 µM in lipid-mediated uptake (FIG. 8). Fully chemically-optimized active compounds were readily identified, indicating that a much smaller library should be sufficient in future screens for other genes, although hit rate is likely to be variable from target to target. The hsiRNA targeting position 10150 (HTT10150 (i.e., 5' CAGUAAAGAGAUUAA 3' (SEQ ID NO:1))) was used for further studies. To ensure that the hsiRNA chemical scaffold did not negatively impact efficacy and potency of HTT10150, the modified and unmodified versions of the compound were tested in both passive and lipid-mediated silencing assays (FIG. 3). As expected, only the modified sequence was successful at cellular delivery and Htt silencing by passive uptake (IC50=82.2 nM), while both the modified and unmodified compounds showed similar IC50 values in lipid mediated delivery (4 µM and 13 µM respectively) suggesting that the hsiRNA scaffold modifications did not interfere with RNA-Induced Silencing Complex (RISC) loading.

Figure 4A:
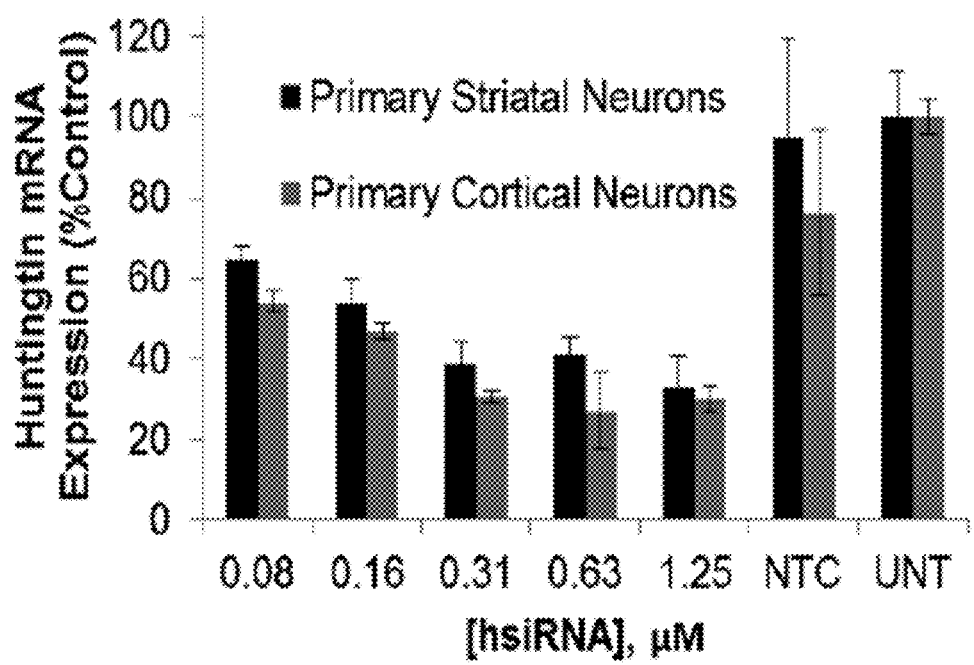
FIGS. 4A-4B graphically depict concentration-dependent silencing of huntingtin mRNA and protein by HTT10150 in primary neurons (passive uptake). Primary neurons were incubated with HTT10150 at concentrations shown. Level of huntingtin mRNA was measured using QUANTIGENE (Affymetrix) normalized to housekeeping gene, PPIB (cyclophillin B), and presented as percent of untreated control (n=3, mean+/−SD). UNT—untreated cells. A) In primary cortical and striatal neurons, 1 week. B) Huntingtin protein levels after one week incubation with HTT10150 were detected by western blot and normalized to β-Tubulin.
Figure 4B:
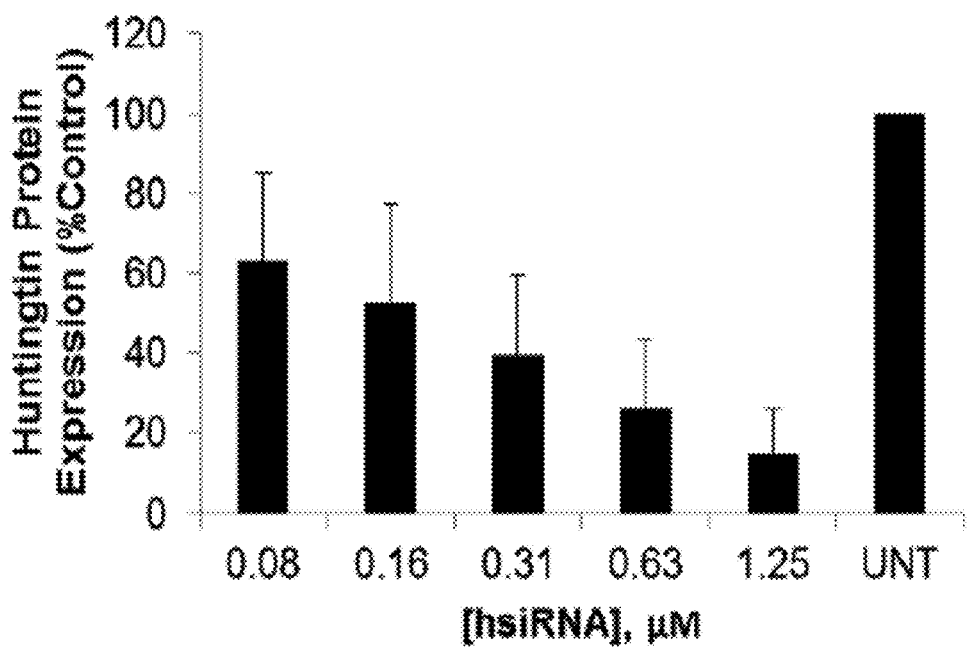
Figure 14:
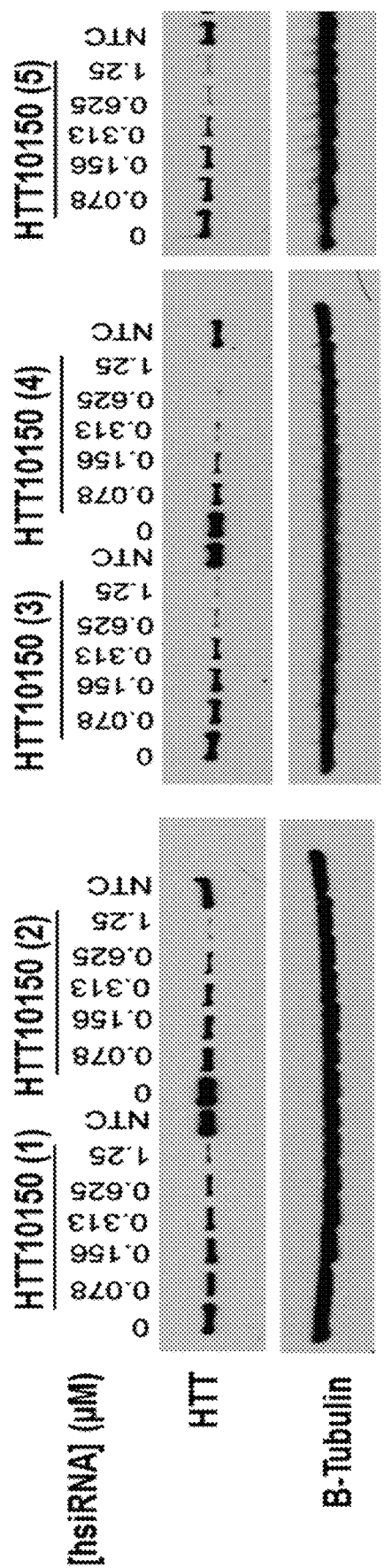
FIG. 14 depicts representative Western blots of Htt reduction in primary cortical neurons. Primary cortical neurons were cultured from five individual pups (#1-5) and incubated with HTT10150 at concentrations shown for one week. Huntingtin protein levels were detected by Western blot using antibody AB 1.

1.3 Potent and Specific Gene Silencing with Unformulated hsiRNAs in Primary Neurons HTT10150 was further tested for mRNA silencing in primary neurons isolated from FVBN mice. Efficacy was seen at both 72 hours and one week following simple unformulated compound addition to cortical neurons (FIG. 4A) with maximum silencing (70%) observed at the 1.25 M concentration. HTT10150 also showed similar silencing in primary striatal neurons (FIG. 4B). Protein levels were measured after one week by Western blot (FIG. 14), confirming mRNA data with 85% reduction of protein upon treatment with 1.25 M of compound (FIG. 4C). The housekeeping genes (PPIB, GAPDH) and overall cell viability, measured by ALAMARBLUE Assay (FIGS. 11B and 14), were not affected at these concentrations. In other experiments, a slight impact on cell viability was observed at 3 µM.

To evaluate duration of effect upon a single HTT10150 treatment, the silencing was measured at one week, two week, and three week intervals (FIG. 4D). The half-life of the loaded RISC complex was weeks (Song, E. et al. Sustained Small Interfering RNA-Mediated Human Immunodeficiency Virus Type 1 Inhibition in Primary Macrophages. *Journal of Virology* 77, 7174-7181 (2003)), and silencing was expected to be long lasting in non-dividing cells. Indeed, single treatment with hsiRNAs was sufficient to induce htt silencing at all times tested. Three weeks was the longest the primary neurons could be maintained in culture. Other systems will be used for longer-term experiments.

Figure 11A:
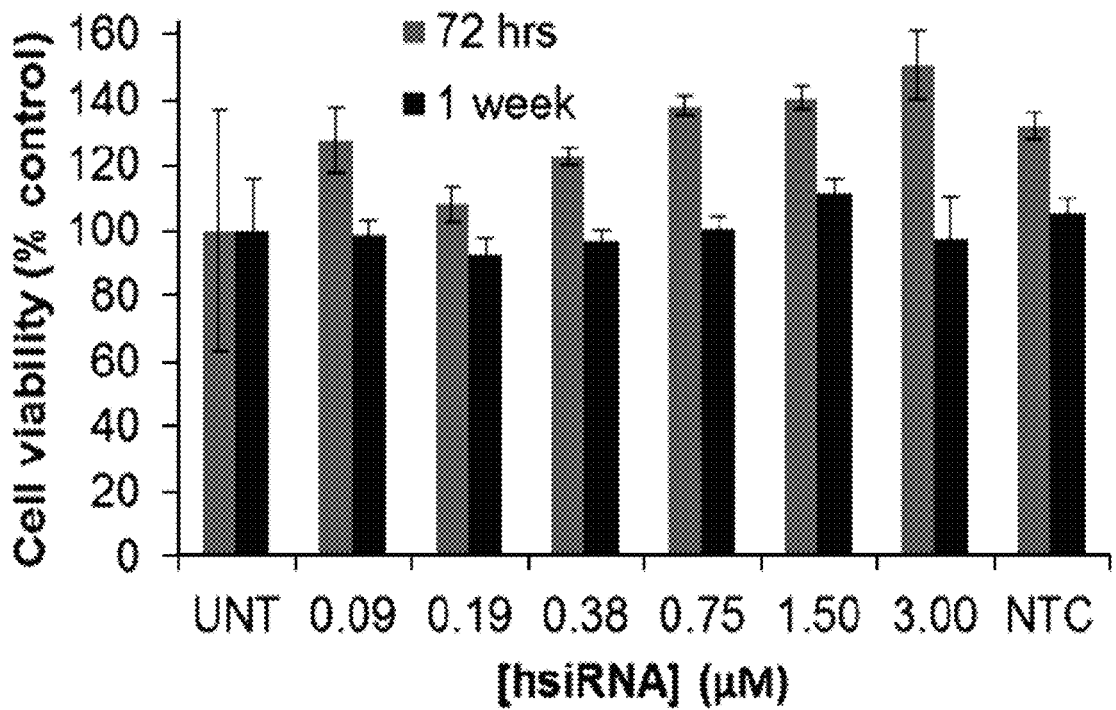
FIGS. 11A-11B graphically depict huntingtin mRNA levels. A) Cell viability was tested using ALAMAR BLUE (Life Technologies) after incubation of HTT10150 and NTC with primary cortical neurons for 72 hours and one week. B) Primary cortical neurons were incubated with three HTT hsiRNA sequences HTT10150, HTT10146, and HTT1215 at concentrations shown. Level of huntingtin mRNA was measured using QUANTIGENE (Affymetrix) normalized to housekeeping gene, PPIB (cyclophillin B), and presented as percent of untreated control (n=3, mean+/−SD). UNT—untreated cells.
Figure 11B:
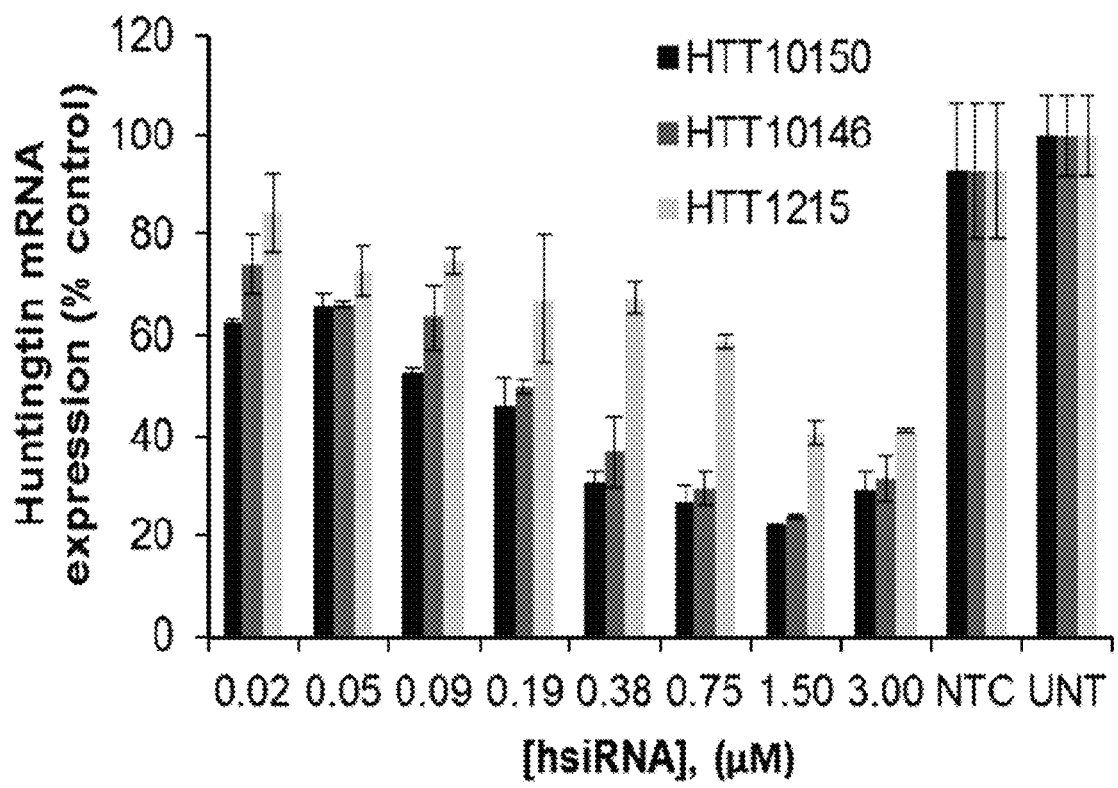
Figure 12A:
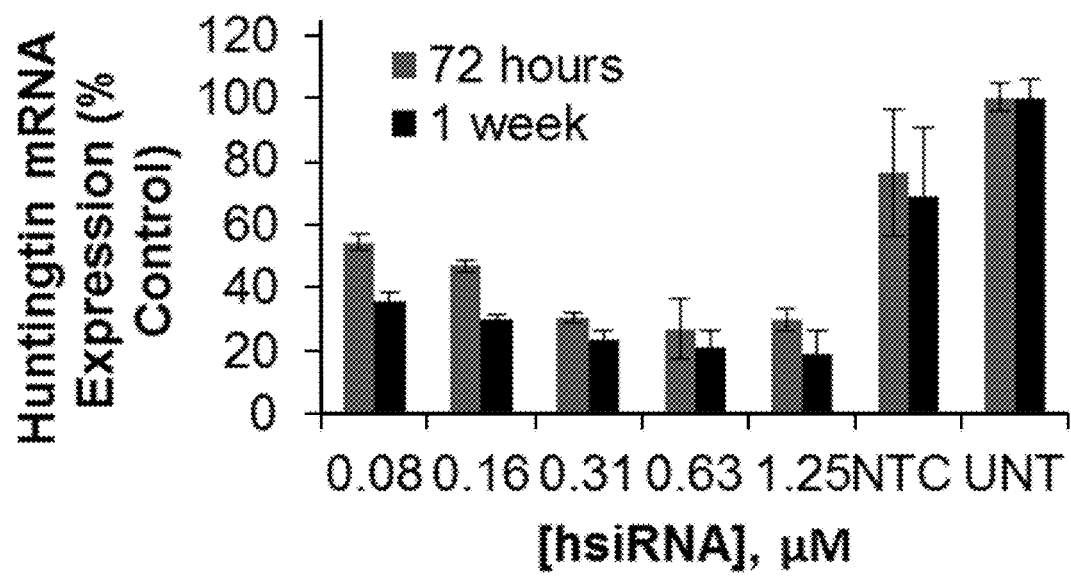
FIGS. 12A-12B graphically depict concentration-dependent silencing of huntingtin mRNA by HTT10150 in primary neurons (passive uptake). Primary neurons were incubated with HTT10150 at concentrations shown. Level of huntingtin mRNA was measured using QUANTIGENE (Affymetrix) normalized to housekeeping gene, PPIB (cyclophillin B), and presented as percent of untreated control (n=3, mean+/−SD). UNT—untreated cells. A) For 72 hours and 1 week. B) For 1, 2 and 3 weeks.
Figure 12B:
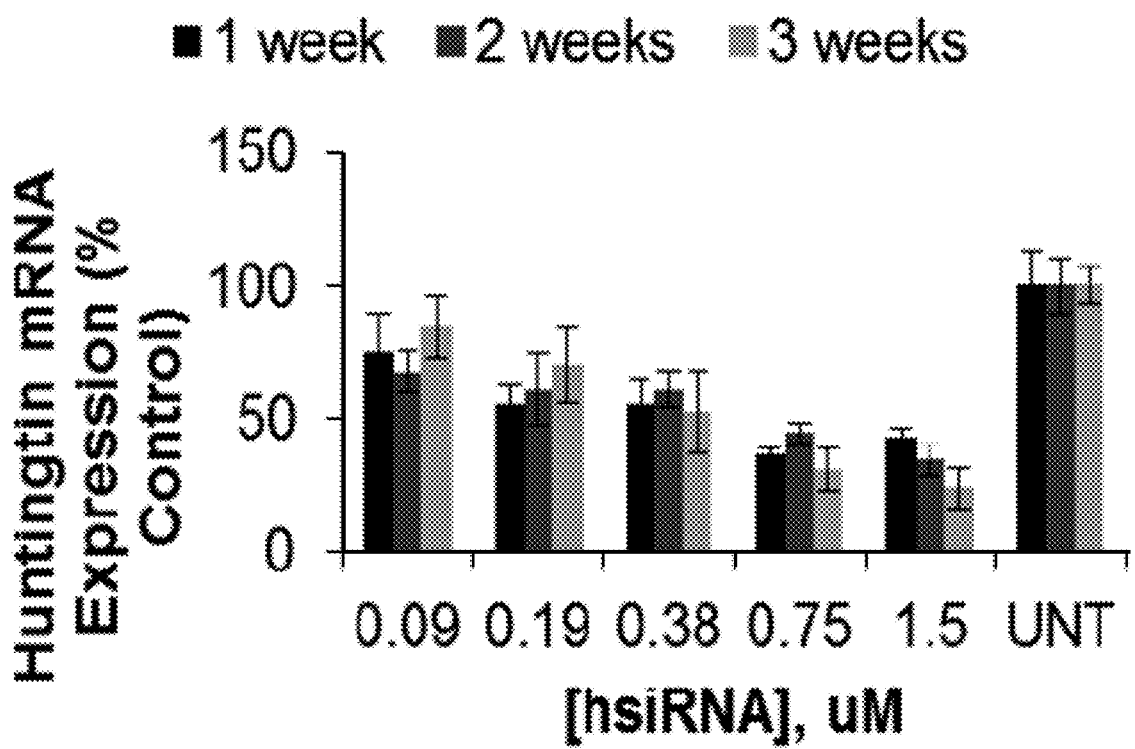
Figure 13:
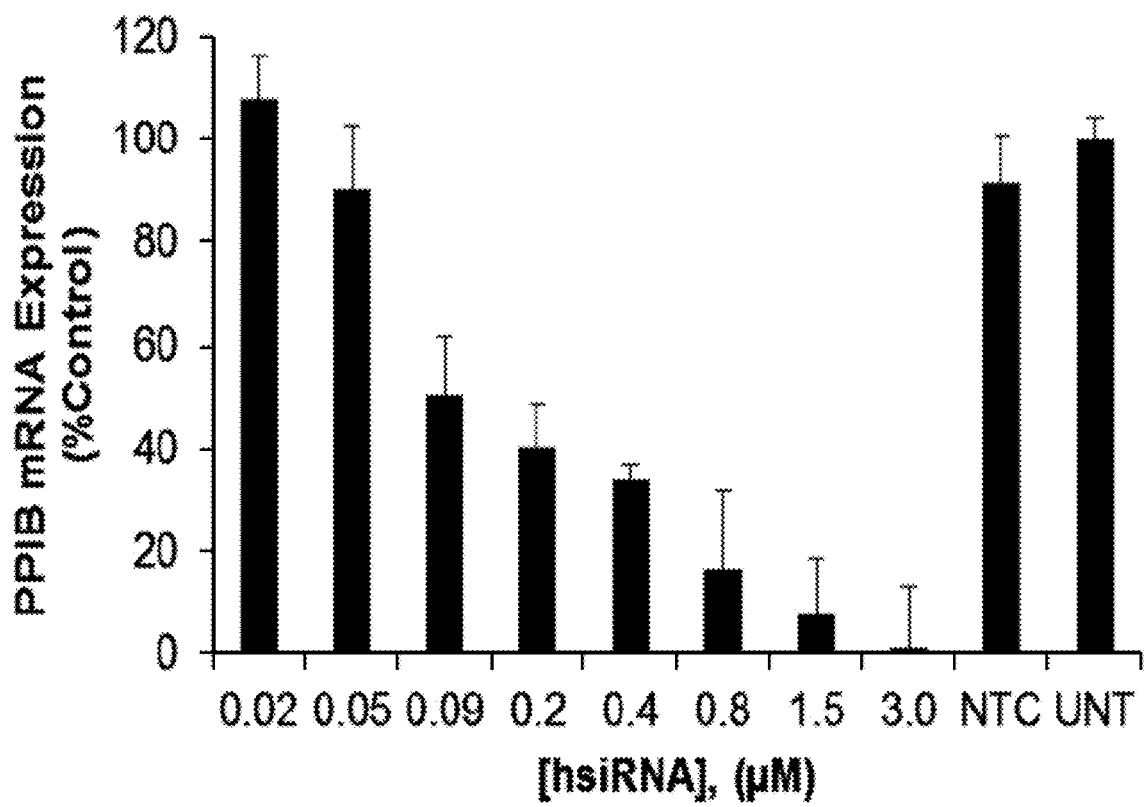
FIG. 13 graphically depicts efficacy of hsiRNA against cyclophilin B (PPIB) in primary cortical neurons. Primary neurons were incubated with hsiRNA targeting PPIB at concentrations shown. Level of PPIB mRNA was measured using QUANTIGENE (Affymetrix) normalized to housekeeping gene, HTT and presented as percent of untreated control (n=3, mean+/−SD). UNT—untreated cells for 1 week.

To demonstrate the general applicability of hsiRNAs as a tool for neuronal gene silencing, and to confirm this chemistry scaffold as valid for neuronal delivery, similar experiments were performed with several other hsiRNAs targeting HTT and with one targeting the house-keeping gene PPIB (Cyclophilin B) (FIGS. 11A and 13). Silencing as high as 70 and 90% was achieved with HTT and PPIB, respectively.

In summary, these data demonstrate that hydrophobically modified siRNA is a simple and straightforward approach for gene silencing in primary neurons, and can be adapted for multiple gene targets.

1.4 hsiRNA Distribution In Vivo in Mouse Brain Upon Single Injection hsiRNAs are efficiently internalized by different types of neurons in vitro. The selected hsiRNA, HTT10150, was further evaluated for its potential to silence gene expression in the brain in vivo. To determine the distribution profile of HTT10150 upon in vivo administration, 12.5 µg of Cy3 labelled hsiRNA (See FIG. 8 for sequence) was injected intrastriatally and, after 24 hours, the brain was perfused, sectioned, and oligonucleotide distribution was visualized by fluorescence microscopy (Leica DM5500—DFC365FX). The artificial CSF injected samples processed concurrently were used to set up microscopic imaging settings to control for background tissue epifluorescence.

Figures 5A, 5B, 5C, 5D, 5E, 5F, 5G, 5H:
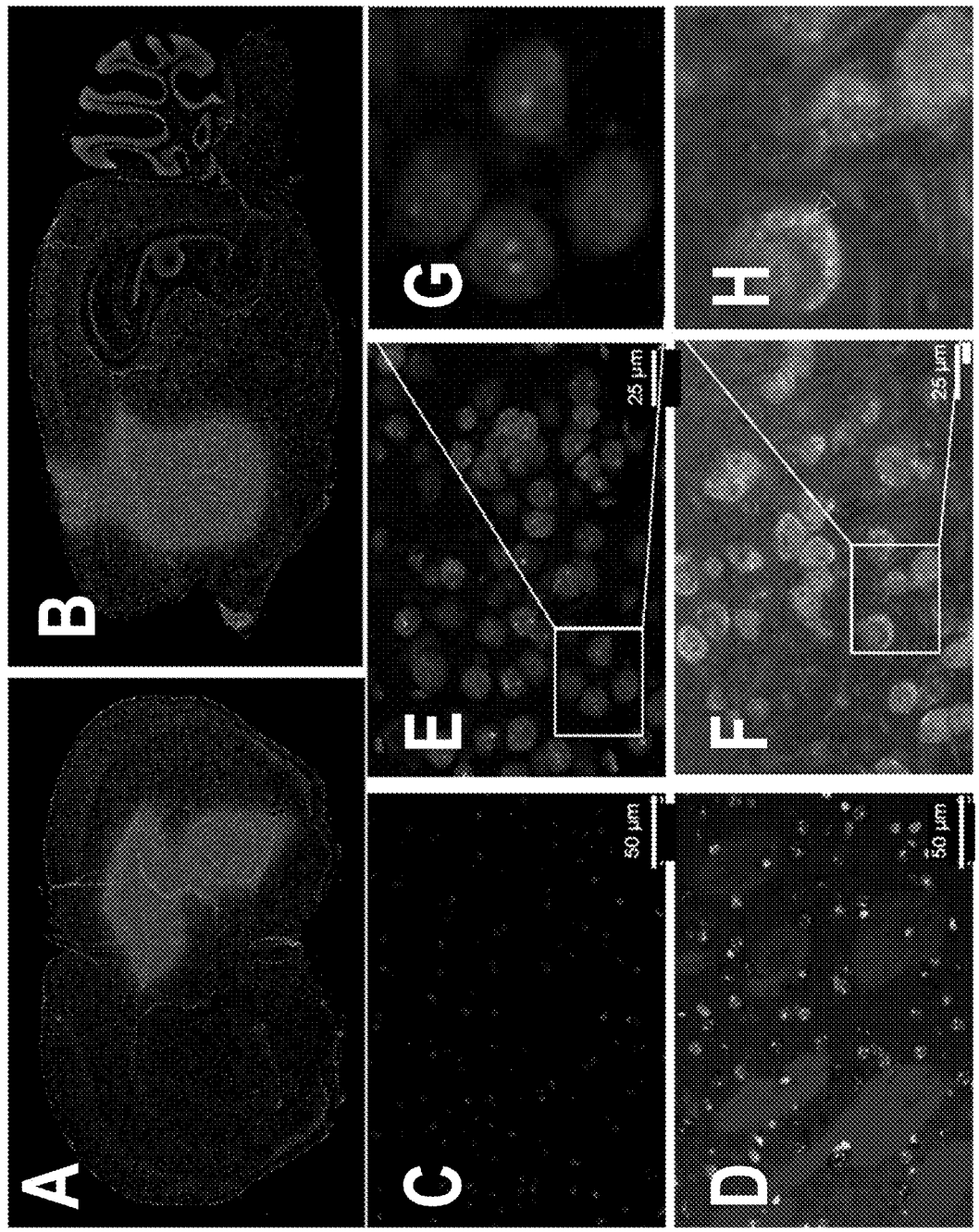
FIGS. 5A-5H depict a single intrastriatal injection of HTT10150 is localized to neurons and fiber tracts ipsilateral to the injection site after 24 hours. 1 nmol CY3-HTT10150 (Red) was unilaterally injected into the striatum of WT (FVBNj) mice. Brains were collected after 24 hours, paraffin imbedded and sectioned and sectioned. (A) Tiled image of coronal brain section (16×). Majority of HTT10150 was localized at site of injection with sharp gradient of diffusion. (B) Tiled image of sagittal brain section (16×), injected side. (C) Image of coronal brain section (40×), non-injected side. (D) Image of coronal brain section (40×), injected side. (E, G) NueN stained neurons from non-injected side (60×). (F, H) NueN stained neurons from injected side (60×).

The majority of compound showed a steep gradient of diffusion away from the injection site, with most of the ipsilateral striatum being covered (FIG. 5A, 5B). Interestingly, hsiRNAs were detected on the non-injected side (contralateral) side of the brain (both cortex and striatum), although relative concentrations appeared much lower. Higher magnification images showed significant association of hsiRNA with fiber tracks, most likely due to the presence of a hydrophobic modification. This aspect of hsiRNA may make it useful as a labelling reagent to visualize brain signalling architecture (FIGS. 5C, 5D). In addition to fiber tracks and neurite labelling, hsiRNA could be detected as punctate staining in the perinuclear space of different cell types, including neurons, as evident from co-localization with NeuN (neuronal marker) stained cells (FIG. 5E) only 24 hours after injection.

Figure 79:
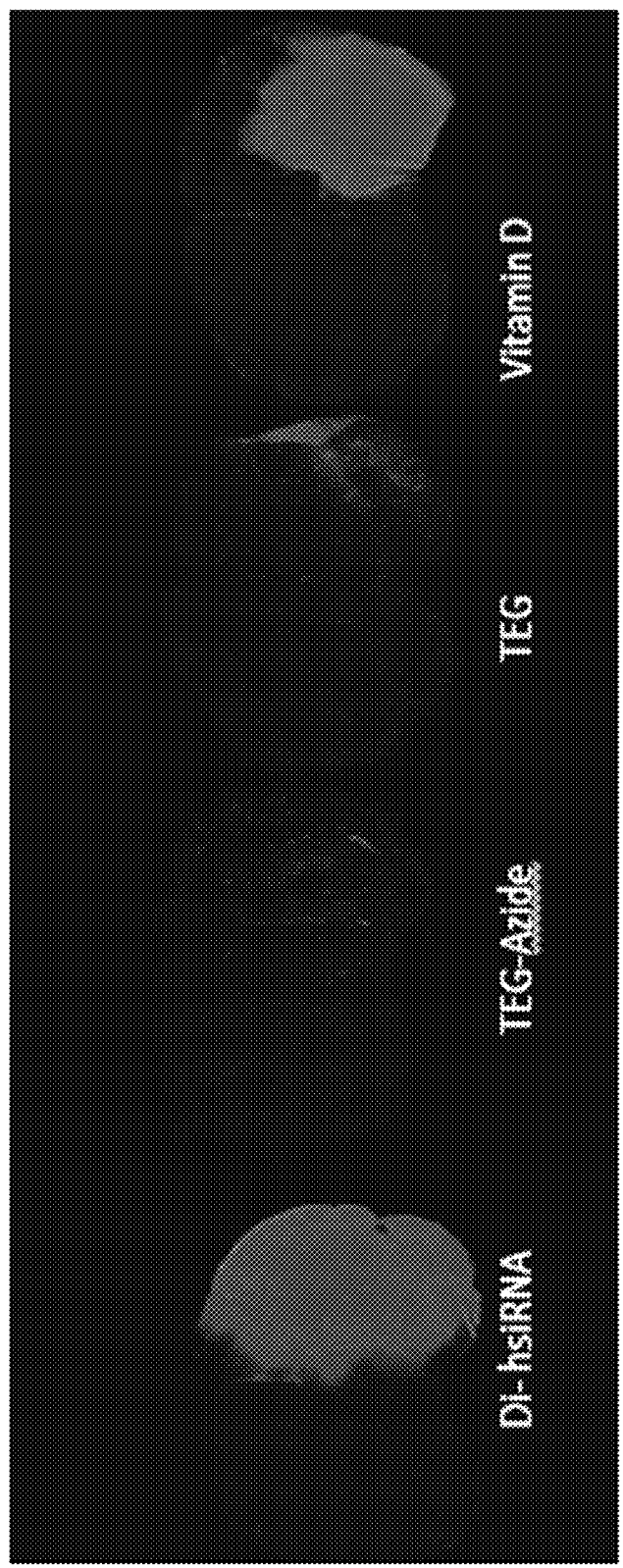
FIG. 79 depicts brain distribution of di-hsiRNA, TEG-azide, TEG and vitamin D after 48 hours. 2 nmole injected IS, N=2 mice per conjugate, brains collected 48 hours later.
Figure 91A:
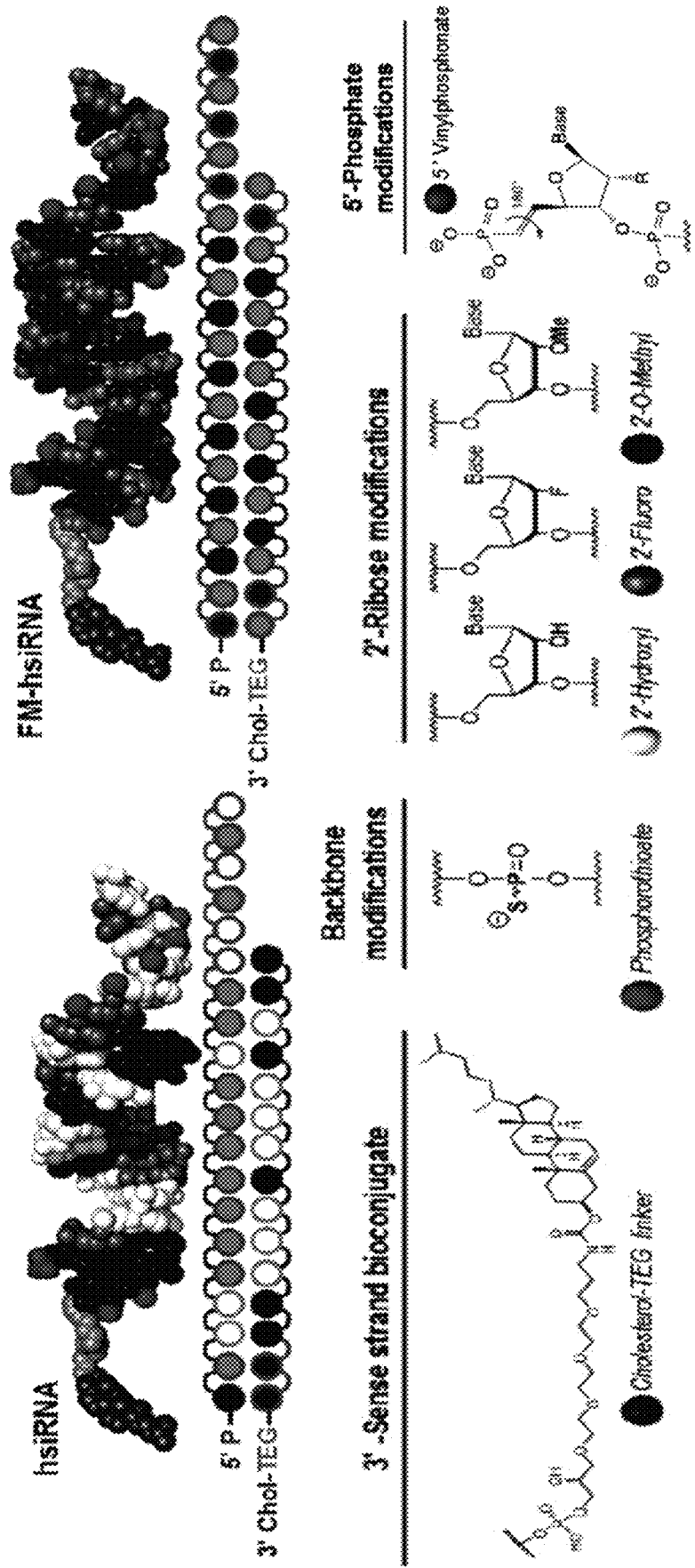
FIGS. 91A-91D depict the development of fully metabolically stabilized hsiRNAs (FM-hsiRNAs). (A) Schematics of partially and fully modified hsiRNAs. (B) hsiRNA and FM-hsiRNA have equal ability to enter RISC (HeLa, 72 hours). (C) Metabolically stable 5'-E-VP is as active as 5'-P. (D) 5'-E-VP enables sustained delivery to distant tissues (7 days post injection, PNA assay).
Figure 91B:
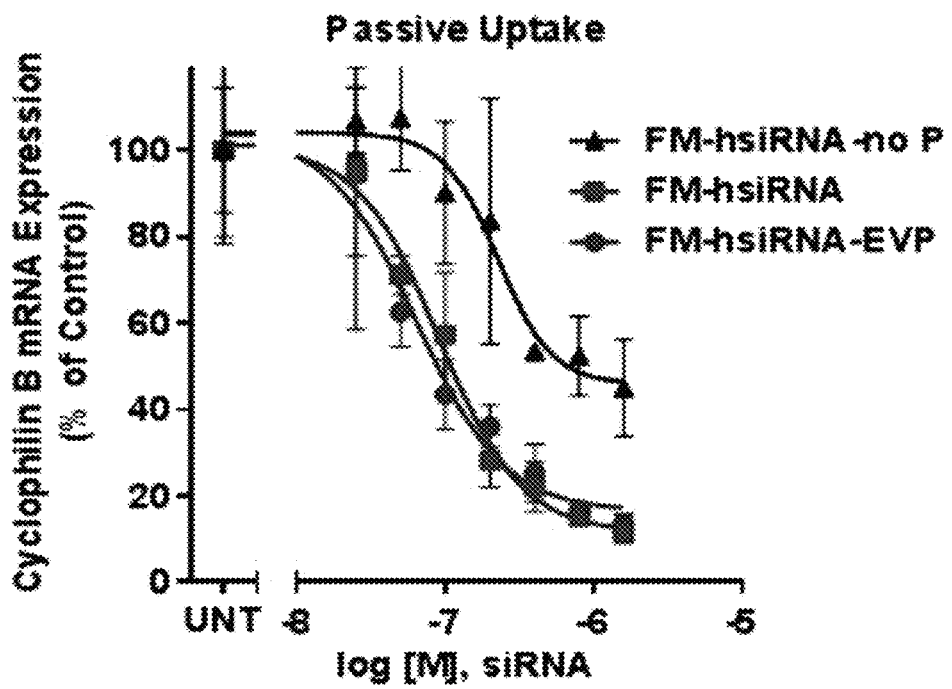
Figure 91C:
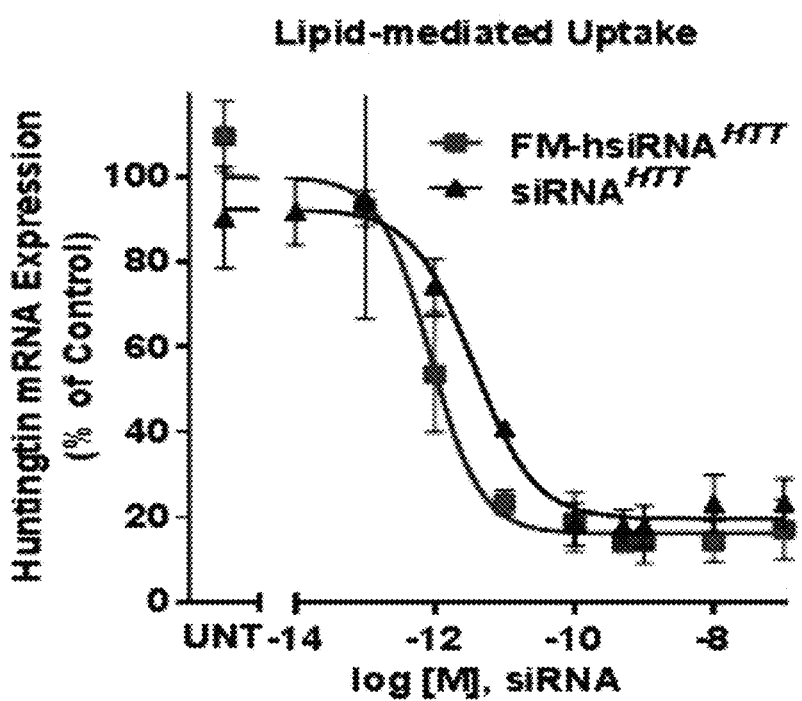
Figure 91D:
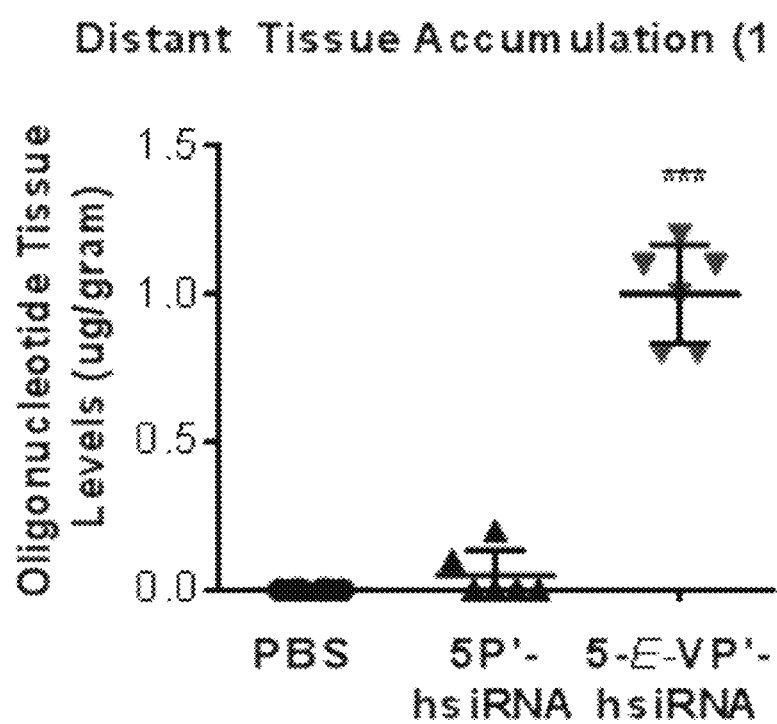

The effect of vitamin D on hsiRNA distribution is depicted in FIGS. 79 and 80.

1.5 hsiRNA Efficacy In Vivo in Mouse Brain Upon Single Injection

To determine HTT10150 efficacy in vivo, wild type FVBN mice were dosed intrastriatally with a single injection of between 3 and 25 µg (0.1-0.9 mg/kg) of compound and mRNA silencing was examined both ipsilateral and contralateral to the injection site. Eight animals were dosed per treatment group and three individual punches were taken from each side of the striatum for mRNA and protein quantification. Level of huntingtin expression were measured by QUANTIGENE Assay and normalized to a housekeeping gene (details in Online methods).

Figure 6:
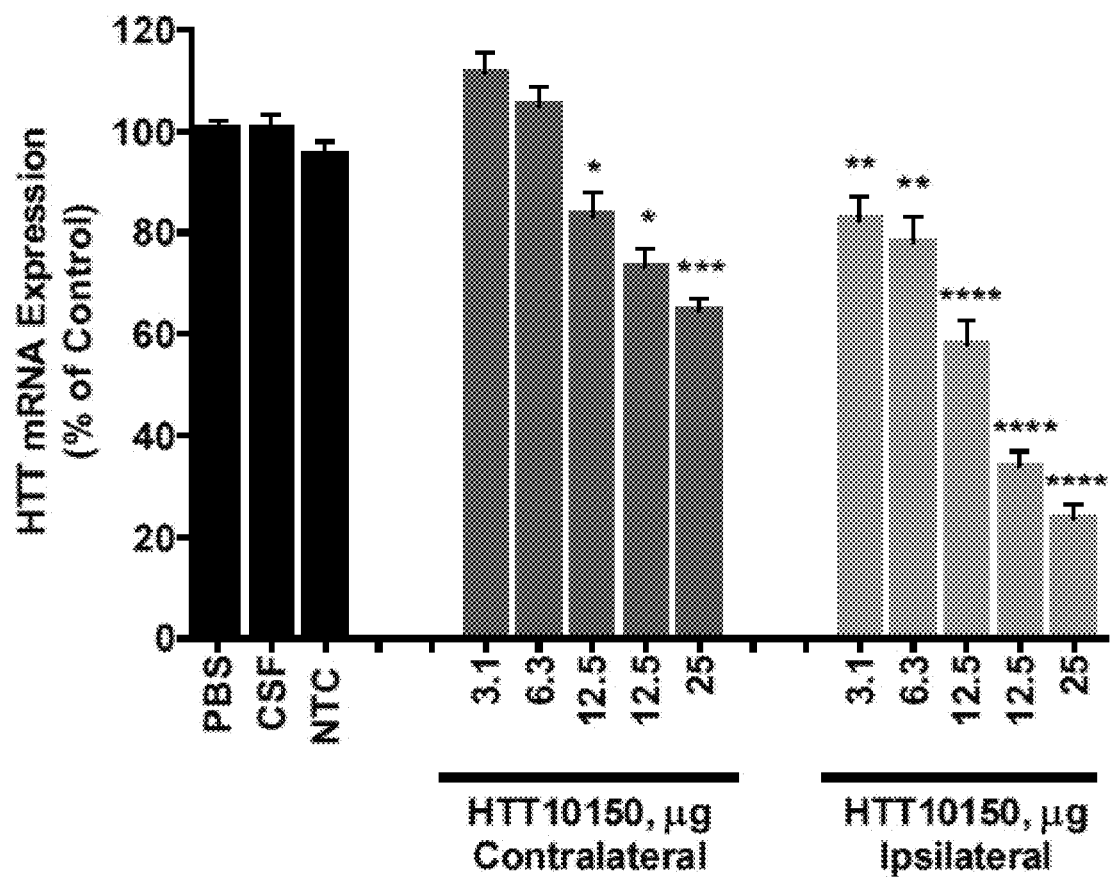
FIG. 6 graphically depicts evaluation of HTT10150 efficacy in vivo. HTT10150 was unilaterally injected into the striatum of WT (FVB) mice (2 µl). Mice were sacrificed at 120 hours. Brains were sliced into 300 m sections and six—2 mm punch biopsies of the striatum were collected from both Ipsilateral and Contralateral sides. Level of huntingtin mRNA was measured using QUANTIGENE (Affymetrix) normalized to housekeeping gene, PPIB (cyclophillin B), and presented as percent of untreated control (n=24, mean+/−SEM, 8 animals, 3 biopsies per region).
Figure 15A:
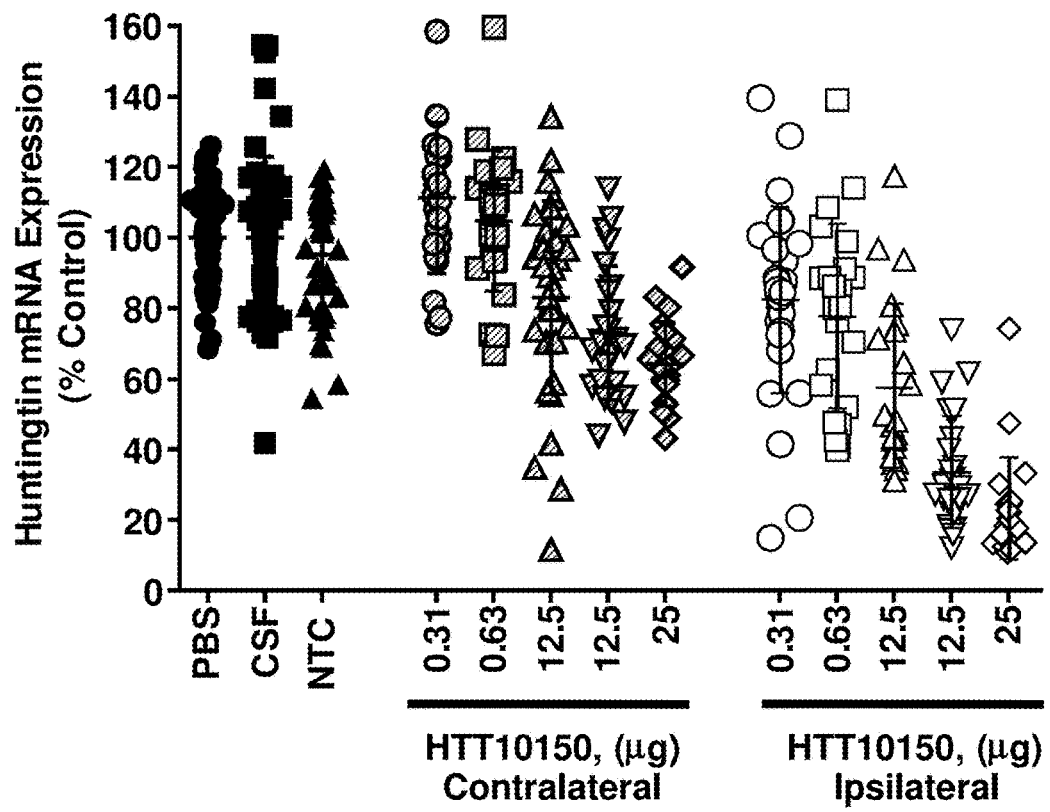
FIGS. 15A-15B graphically depict evaluation of HTT10150 efficacy in vivo. A) HTT10150 was unilaterally injected into the striatum of WT (FVB) mice (2 µl). Mice were sacrificed at 120 hours. Brains were sliced into 300 m sections and six 2 mm punch biopsies of the striatum were collected from both ipsilateral and contralateral sides. Level of huntingtin mRNA was measured using QUANTIGENE (Affymetrix) normalized to housekeeping gene, PPIB (cyclophilin B), and presented as percent of untreated control (n=8 animals, mean+/−SD). B) Quantification of huntingtin protein silencing by Western blot.
Figure 15B:
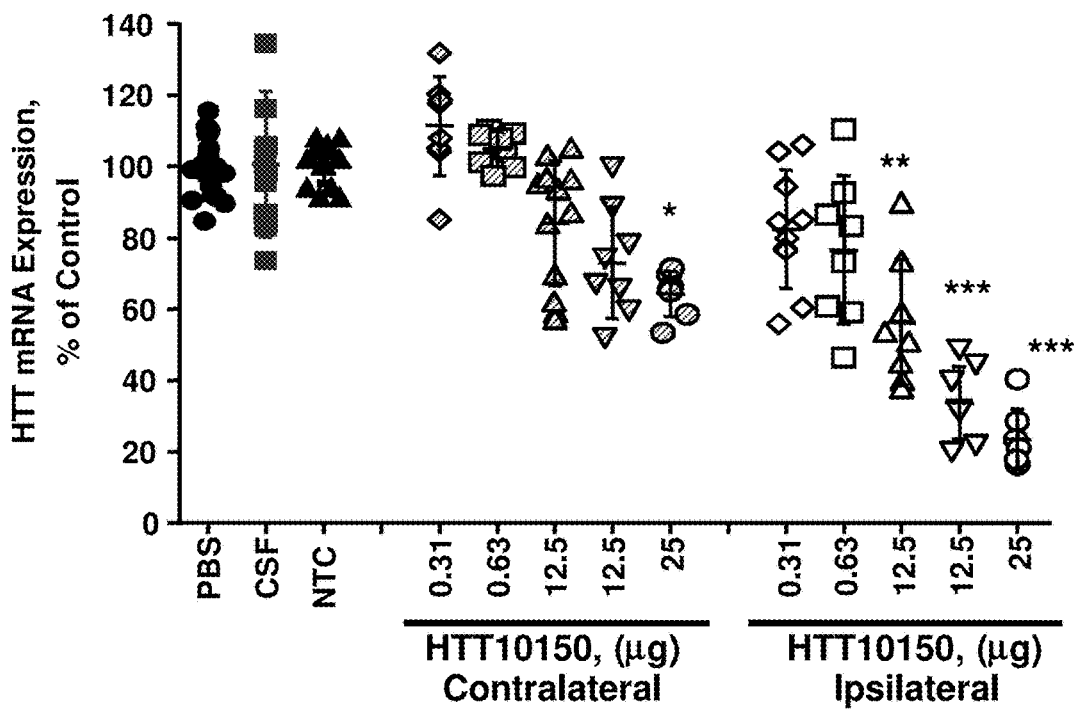

Statistical analysis was performed by one-way ANOVA comparison against CSF or PBS control with Bonferroni corrections for repeat measures using GraphPad Prism (Online methods for details). All groups induced silencing that was significant against CSF, PBS, and non-targeting control treated animals. Raw Data from the 24 individual punches per treatment group (8 animals, 3 punches per animal) can be seen in FIG. 15. At the site of administration (ipsilateral side), dose-dependent silencing reaching statistical significance was observed at all concentrations. The 25 µg treatment induced 77% silencing (p<0.0001), and the 12.5 µg treatment was repeated with two groups of animals on different days and showed statistically significant silencing of 66% and 42% (FIG. 6).

While initial distribution studies showed a steep gradient of diffusion away from the injection site with a minimal amount of compound migrating to the contralateral side, treatment with the higher doses of 25 µg and 12.5 µg resulted in statistically significant silencing (p<0.0001) on the non-injected side. However, the level of silencing was significantly less (only 36% for the 25 µg group) than on the treated side of the brain.

In summary, these data show that a single intrastriatal injection of hsiRNA is sufficient to induce potent gene silencing around the site of administration. This effect was reproducible across different treatment groups and independent experiments.

1.6 Neuronal Viability Following Single hsiRNA Injection in Mouse Brain

Cholesterol modification of non-modified, naked siRNA has previously been used for improvement of siRNA brain distribution, with toxicity at high doses being identified as a potential limitation. To evaluate the degree of non-specific chemistry related effects on the brain, DARPP32 expression, an established marker for dopamine receptor expression on medium spiny neurons in the striatum and representative of neuronal viability, was investigated. Additionally, potential induction of an immune response was performed by assessing the extent of microglia activation upon hsiRNA injection.

Figure 7A:
FIGS. 7A-7E depict that HTT10150 shows no toxicity in DARPP-32 positive neurons around the site of injection. HTT10150 was unilaterally injected into the striatum of WT (FVB) mice. Brains were collected after 5 days fixed, sectioned, and stained with antibodies against DARPP-32 (A-D). Representative image of striatum after injection of ACSF, full brain scan and 60× magnification (A, B) or 12.5 g HTT10150, full brain scan and 60× magnification (C, D). Quantification of DARPP-32 positive neurons (E) (n=3 animals, mean+/−SD).
Figure 7B:
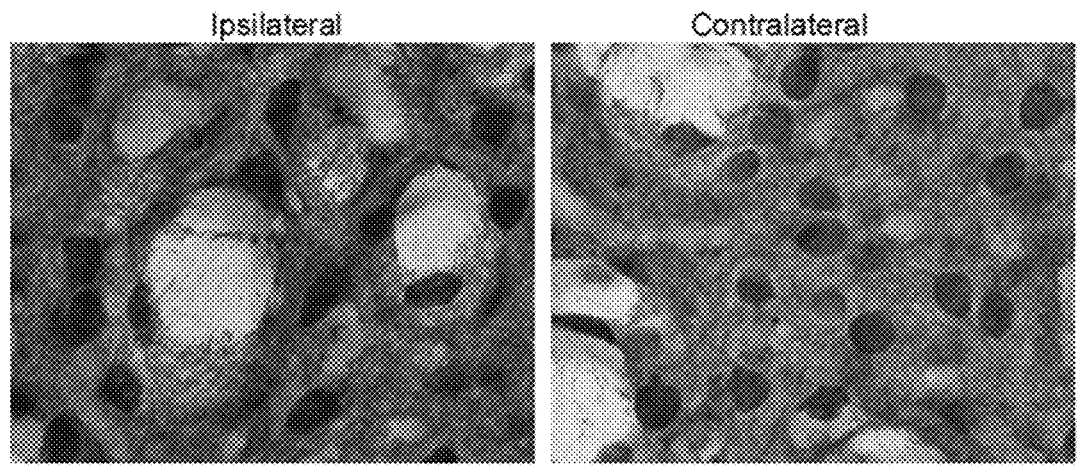
Figure 7C:
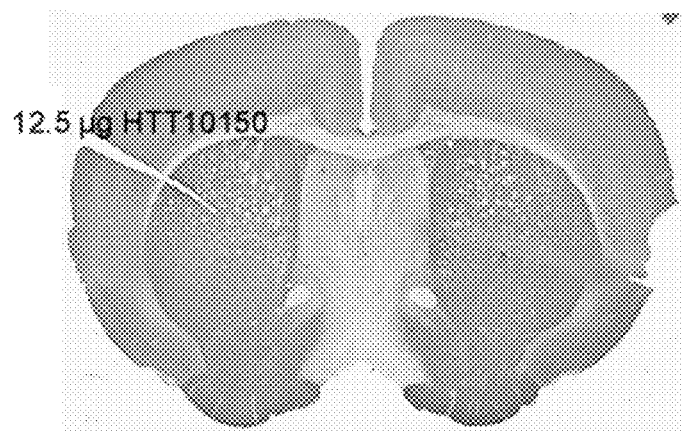
Figure 7D:
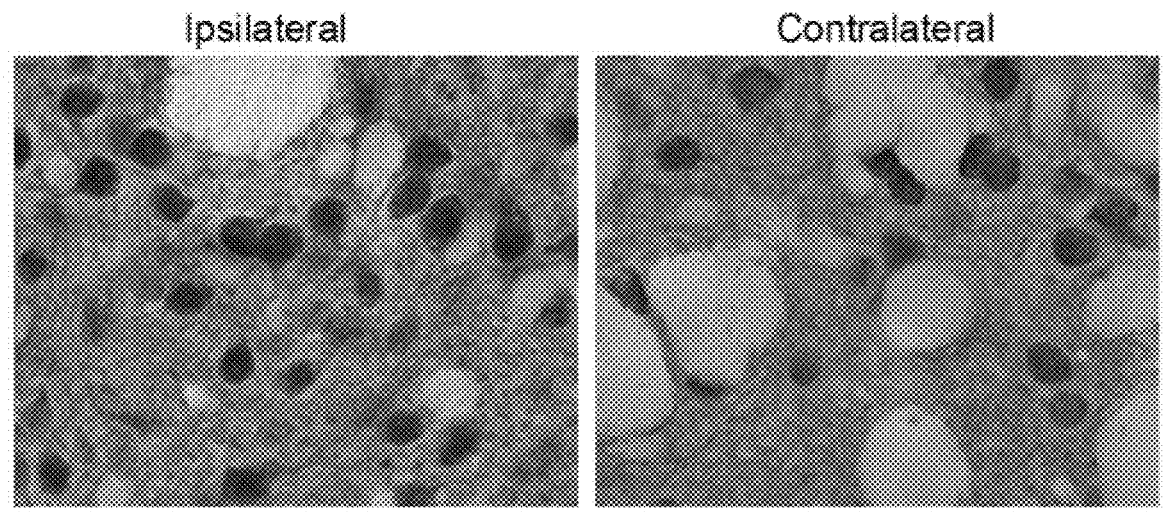
Figure 7E:
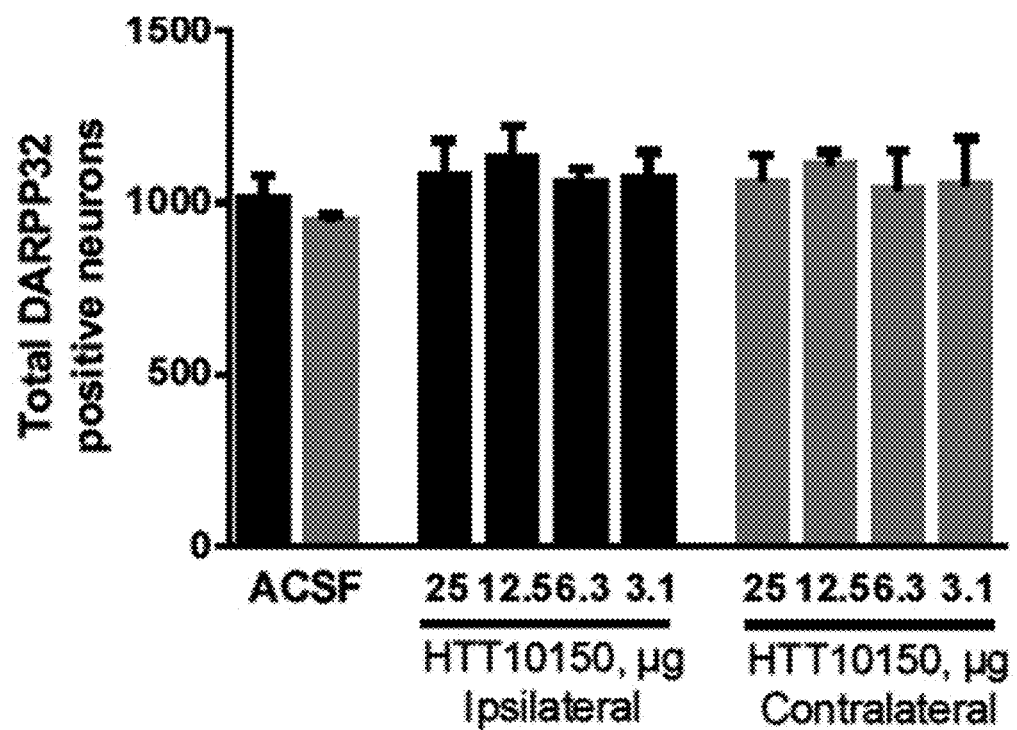
Figure 16:
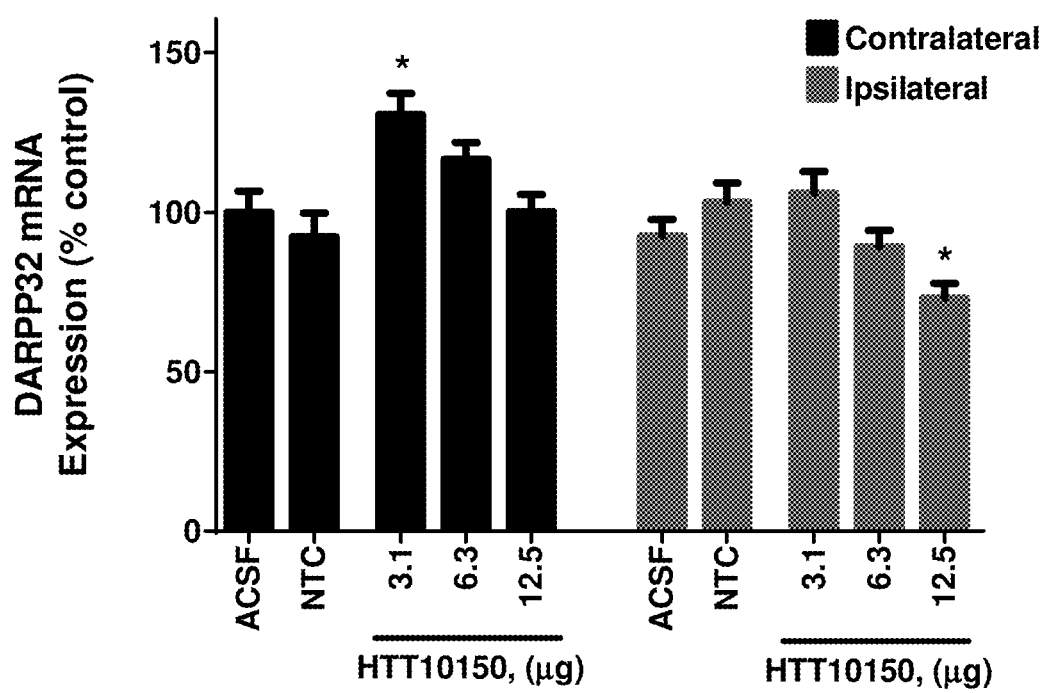
FIG. 16 graphically depicts evaluation of HTT10150 cytotoxicity in vivo. DARPP32 neuronal marker was minimally affected by HTT10150 injection, indicating no major impact on neuronal health. HTT10150 was unilaterally injected into the striatum of wild-type (FVB) mice at doses shown. Mice were sacrificed at 120 hours. Brains were sliced into 300 m sections and six punch biopsies (2 mm) of the striatum were collected from both ipsilateral and contralateral sides. Level of DARPP32 mRNA expression was measured using QUANTIGENE (Affymetrix) normalized to housekeeping gene, PPIB (cyclophilin B), and presented as percent of untreated control (n=24, mean+/−SD).
Figure 17B:
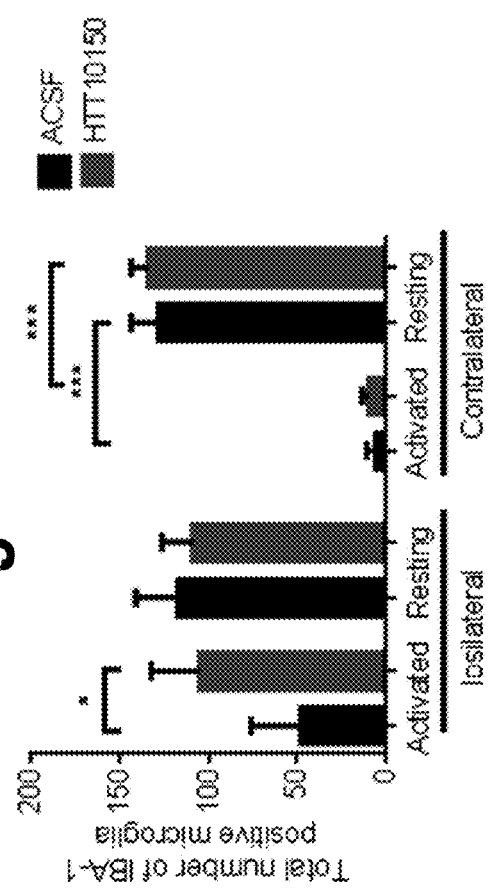
FIGS. 17A-17C depict that HTT10150 showed a two-fold increase in microglial activation at the site of injection. HTT10150 was unilaterally injected into the striatum of WT (FVB) mice. Brains were collected after 6 hours (b) and 5 days (a and c) fixed, sectioned, and stained with antibodies against IBA-1. (A) Representative images of activated (black arrowhead) and resting (open arrowhead) after injection of 1 nmol HTT10150 and ACSF 5 days post injection. 40× magnification. (B) Quantification of activated and resting microglia 6 hrs post-injection of ACSF (n=6) and 1 nmol HTT10150 (n=3). (C) Quantification of activated and resting microglia 5 days post-injection of ACSF (n=4) and 1 nmol HTT10150 (n=3).
Figure 17C:
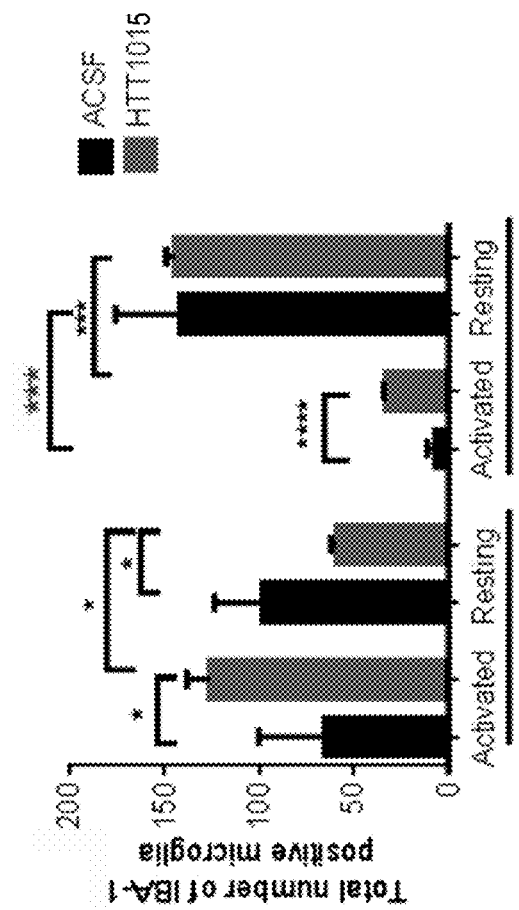
Figure 17A:
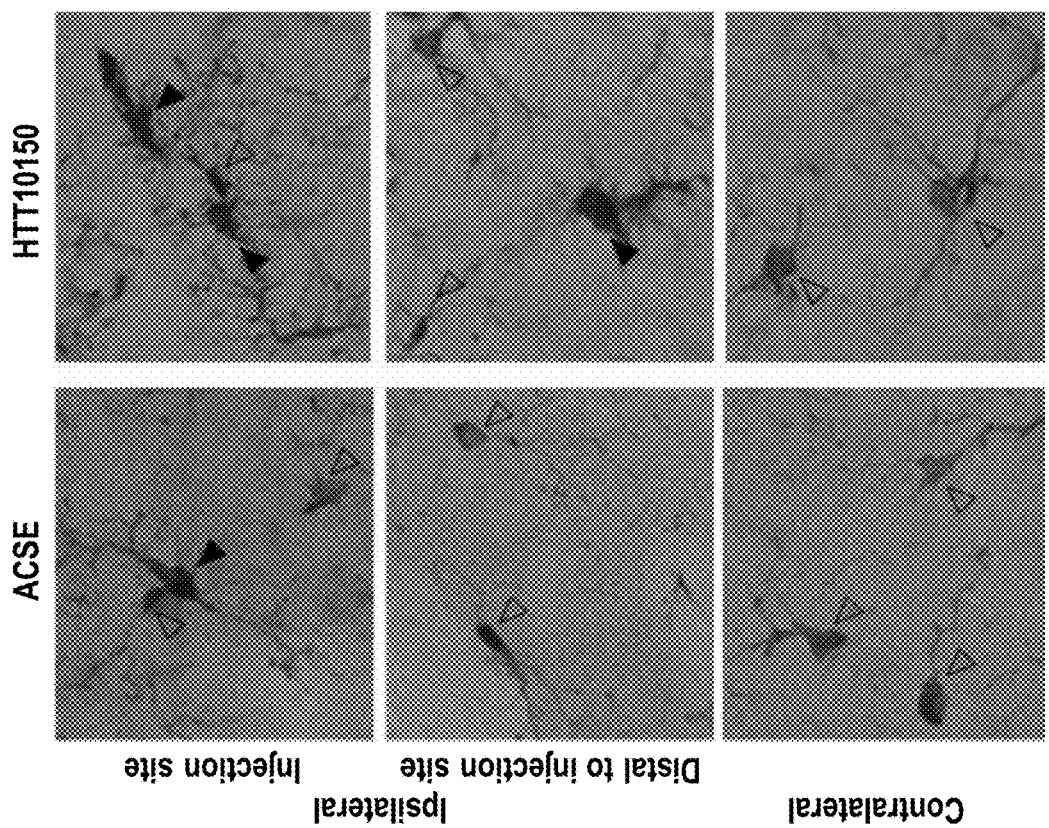
Figure 18A:
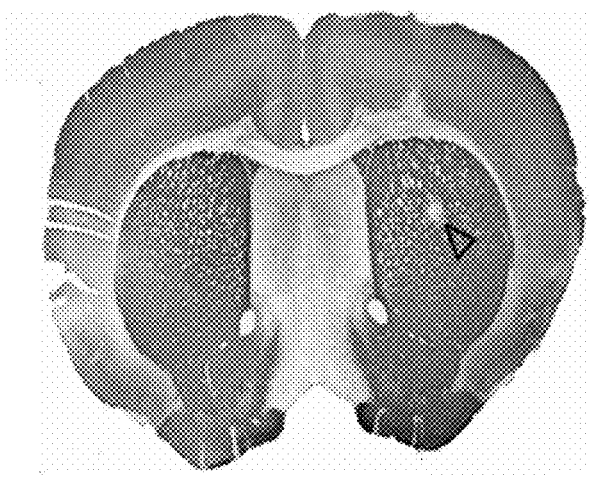
FIGS. 18A-18C depict that HTT10150 showed limited toxicity at the site of injection at the 25 µg dose. HTT10150 was unilaterally injected into the striatum of WT (FVB) mice. Brains were collected after 5 days fixed, sectioned, and stained with antibodies against DARPP-32. Representative image of striatum after injection of 25 μg, full brain scan (A), 10× magnification at injections site (B), 20× magnification at injection site (C), and 60× magnification.
Figure 18B:
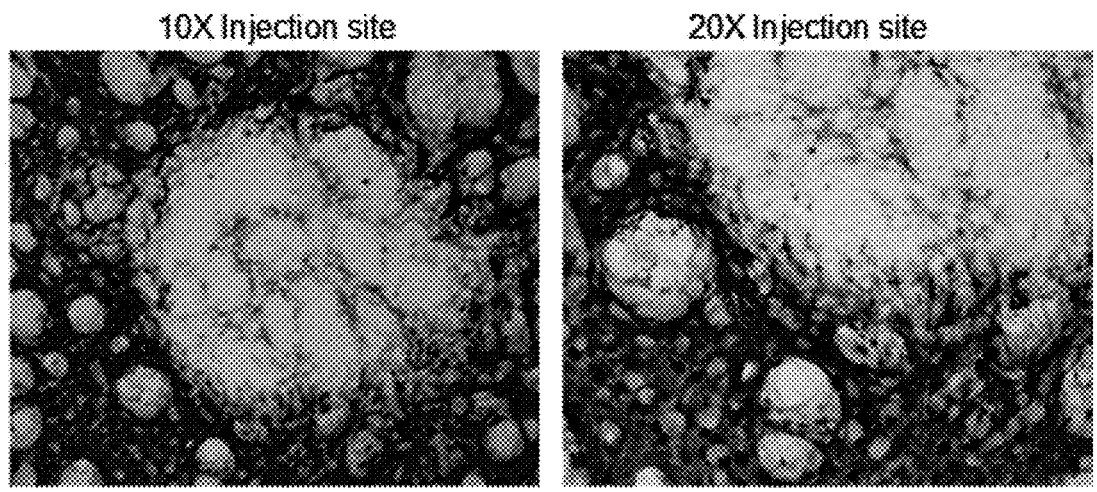
Figure 18C:
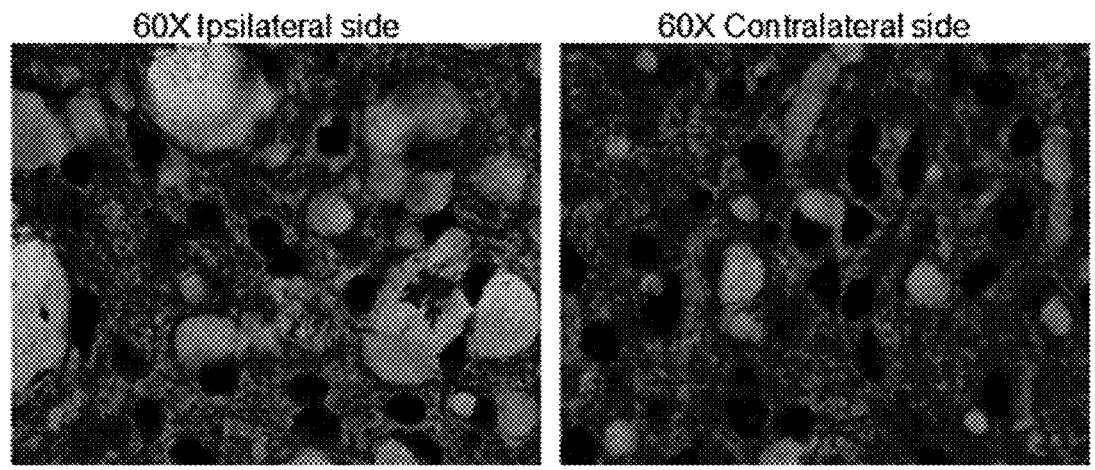
Figure 19:
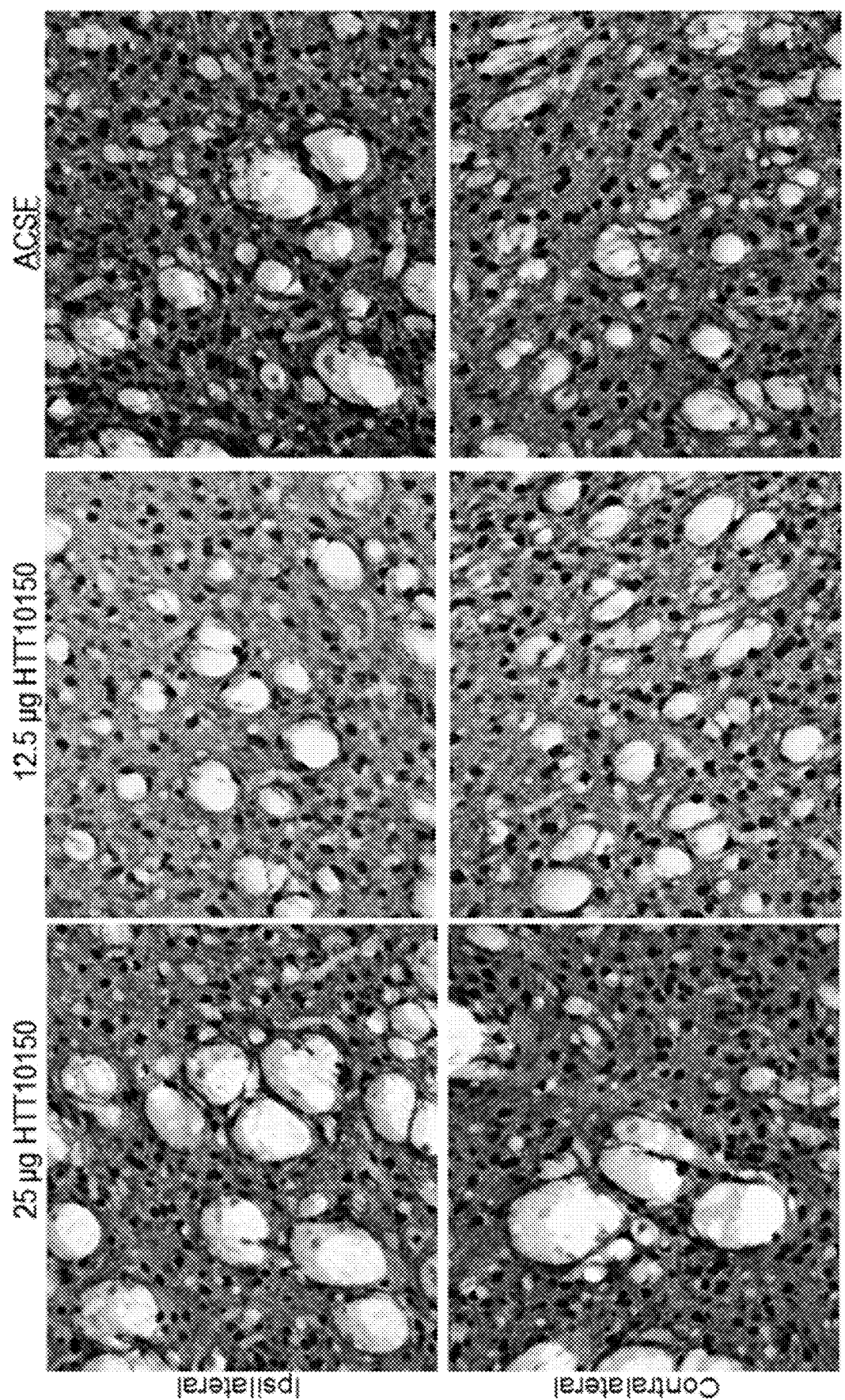
FIG. 19 depicts that HTT10150 showed no toxicity to Darpp32 positive neurons at lower concentrations. HTT10150 was unilaterally injected into the striatum of WT (FVB) mice. Brains were collected after 5 days fixed, sectioned, and stained with antibodies against DARPP-32. Representative image of striatum after injection of 25 μg, 12.5 μg, and ACSF (20× magnification) ipsilateral and contralateral to the site of injection.
Figure 20A:
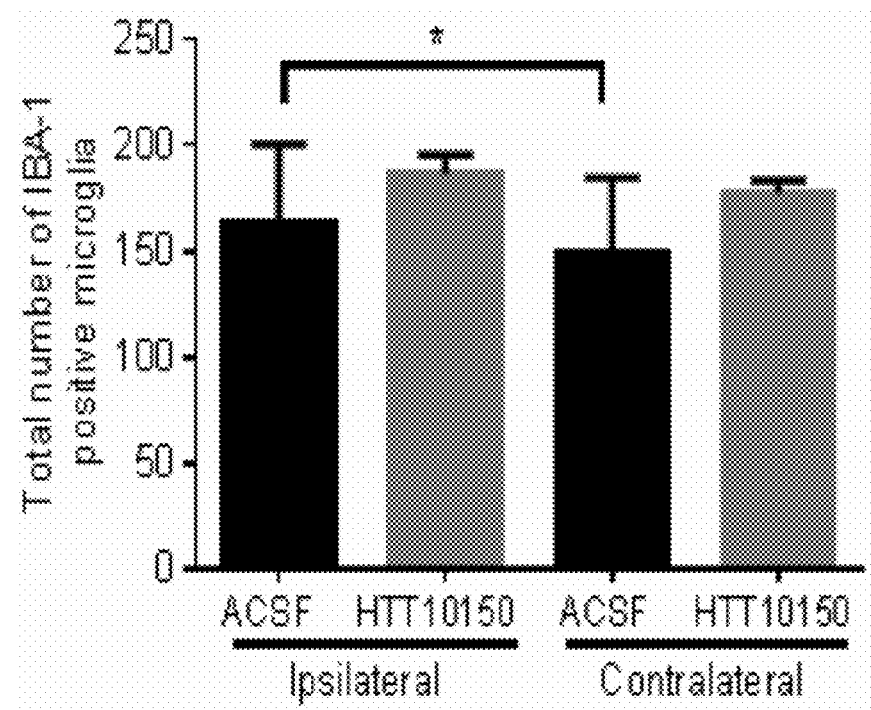
FIGS. 20A-20B depict that HTT10150 caused a slight increase in total resting microglia 5 days post injection. HTT10150 was unilaterally injected into the striatum of WT (FVB) mice. Brains were collected after 6 hours and 5 days fixed, sectioned, and stained with antibodies against IBA-1. Quantification of total microglia 6 hrs (A) and 5 days (B) post-injection of ACSF (n=6, A) (n=4, B) and 12.5 μg HTT10150 (n=3, A, B).
Figure 20B:
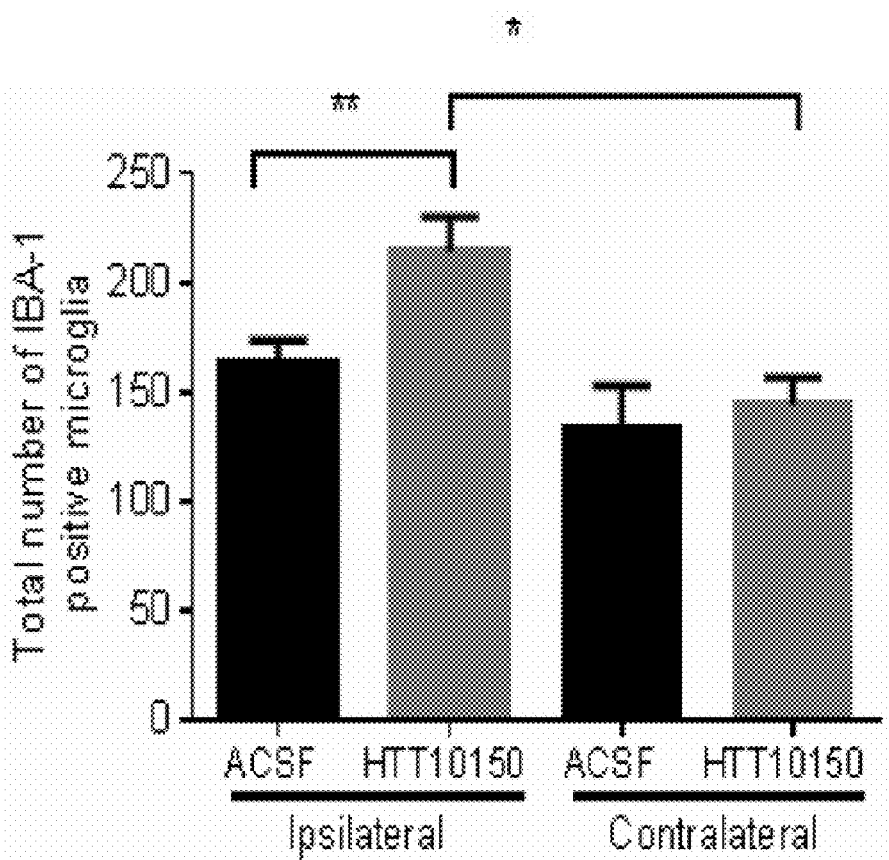
Figure 22:
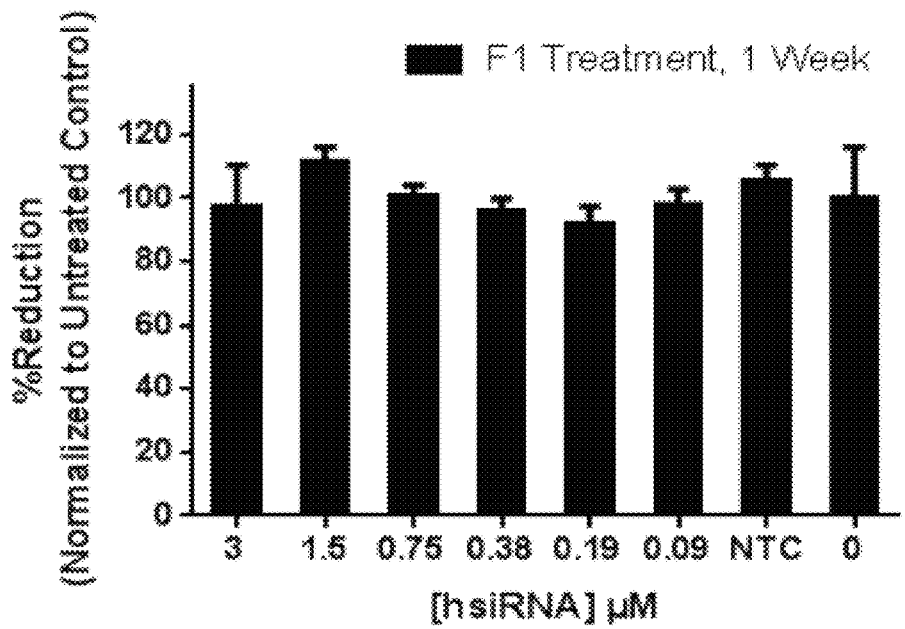
FIG. 22 depicts hsiRNA$^{HTT}$ efficacy in primary cortical neurons (cell viability) after one week using QUANTIGENE and ALAMAR BLUE. NTC=non-targeting control.
Figure 23:
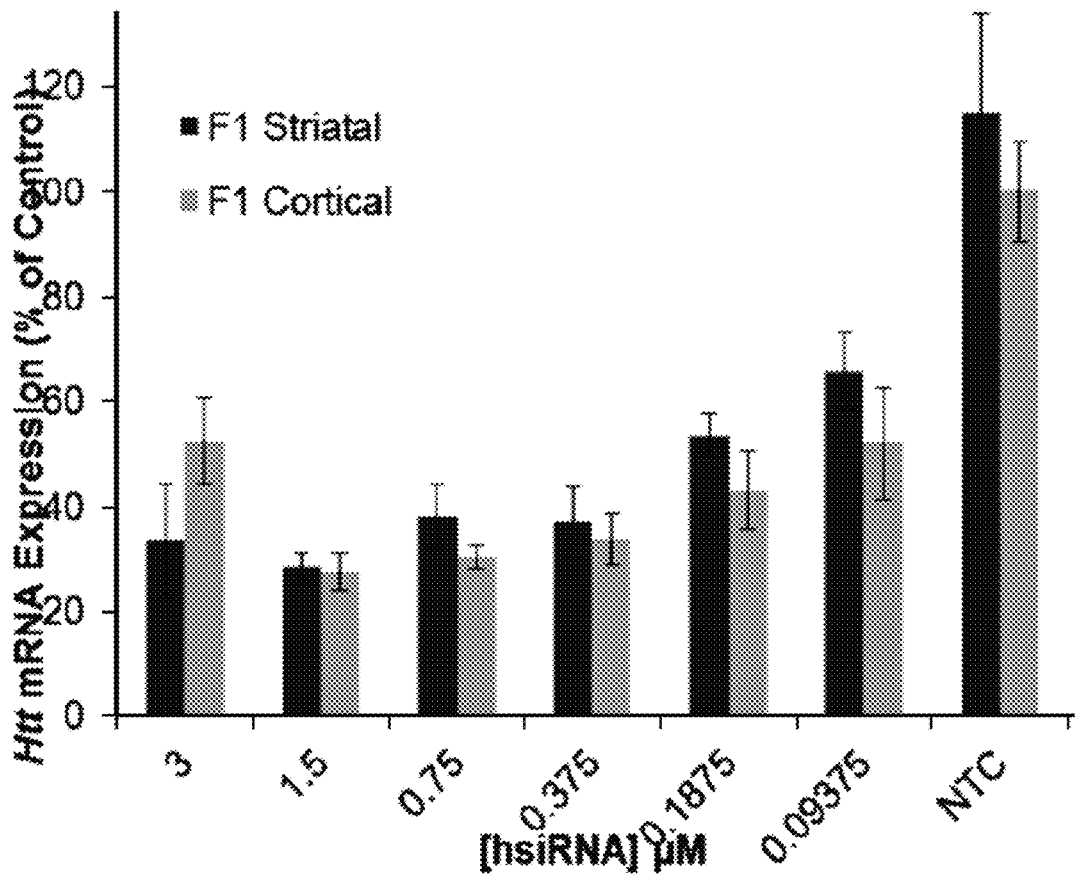
FIG. 23 depicts HTT hsiRNA efficacy in wild-type primary striatal neurons and primary cortical neurons after one week using QUANTIGENE. NTC=non-targeting control.

No significant impact on DARPP32 expression was observed for doses up to 12.5 g suggesting persistent neuronal viability (FIGS. 7A, 7B, 16). Similarly, minimal microglial activation was visualized at the 12.5 µg dose (FIGS. 7C, 7D) indicative of a limited immune response in the presence of the modified hsiRNA. The 25 µg dose did induce some reduction in DARPP32 just around the site of injection indicative of toxicity and establishing the maximum dose levels for this chemical scaffold upon the indicated route of administration. A 10-12.5 µg single administration of hsiRNA efficiently silenced HTT mRNA in three, well powered, independent studies with robust silencing of 62, 42 and 52% without toxicity. These data indicate that this technology can be widely used for functional studies of other neurologically significant targets.

1.7 Further Characterization in Neurons

Figure 24:
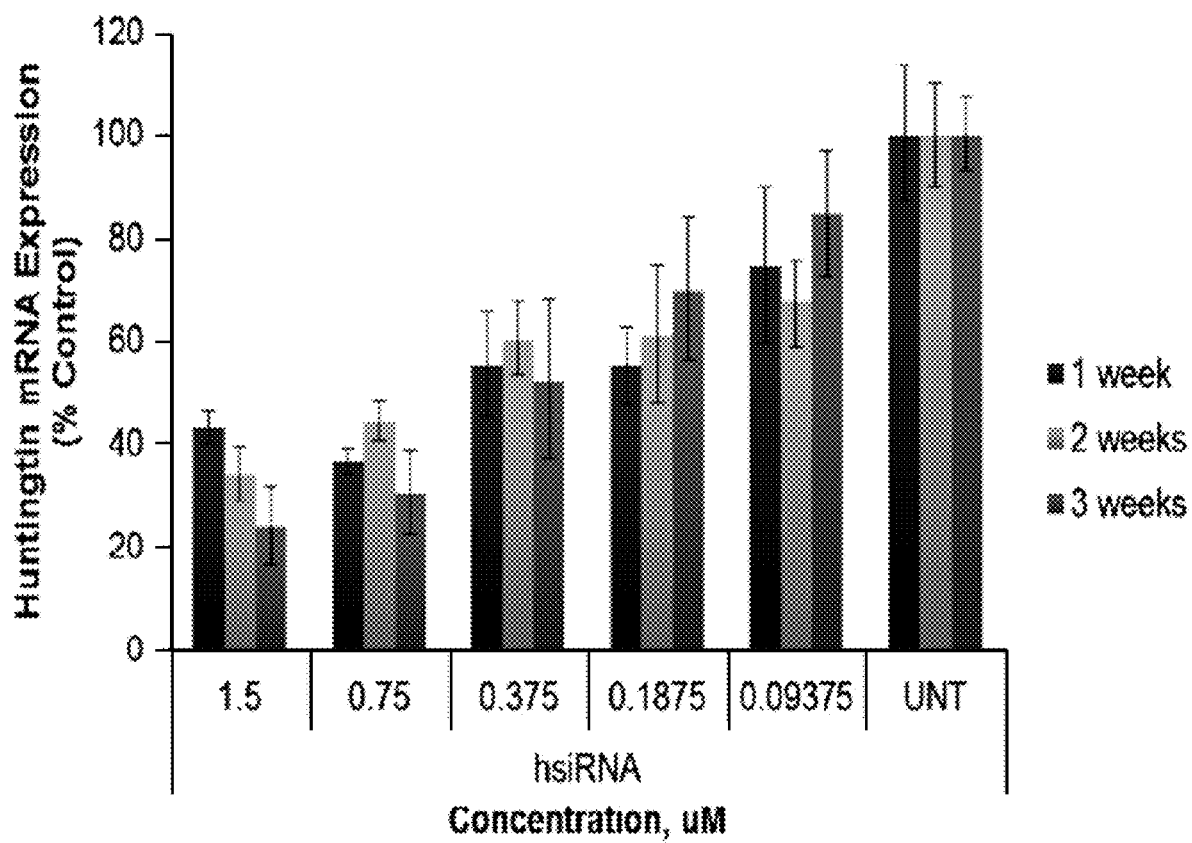
FIG. 24 depicts HTT hsiRNA efficacy in primary neurons (duration of effect) from one to three weeks post-treatment via passive uptake. HTT expression was normalized to PPIB. Data is shown is an approximate percentage of non-targeting control. UNT=untreated.
Figure 25:
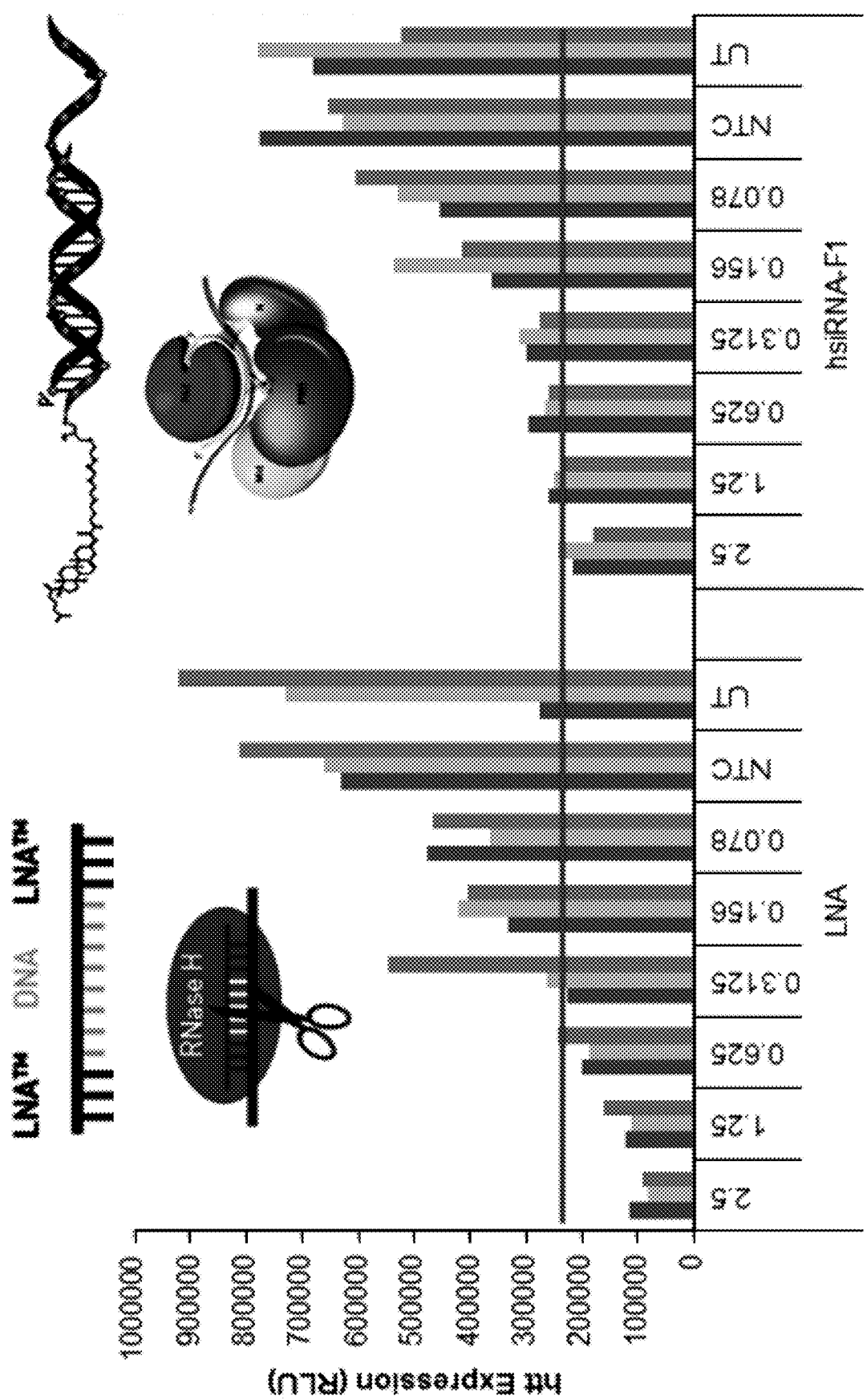
FIG. 25 graphically depicts that hsiRNA$^{HTT}$ but not LNA-GAPMER exhibits a silencing plateau in cortical neurons after 72 hours using QUANTIGENE. N=3.
Figure 26:
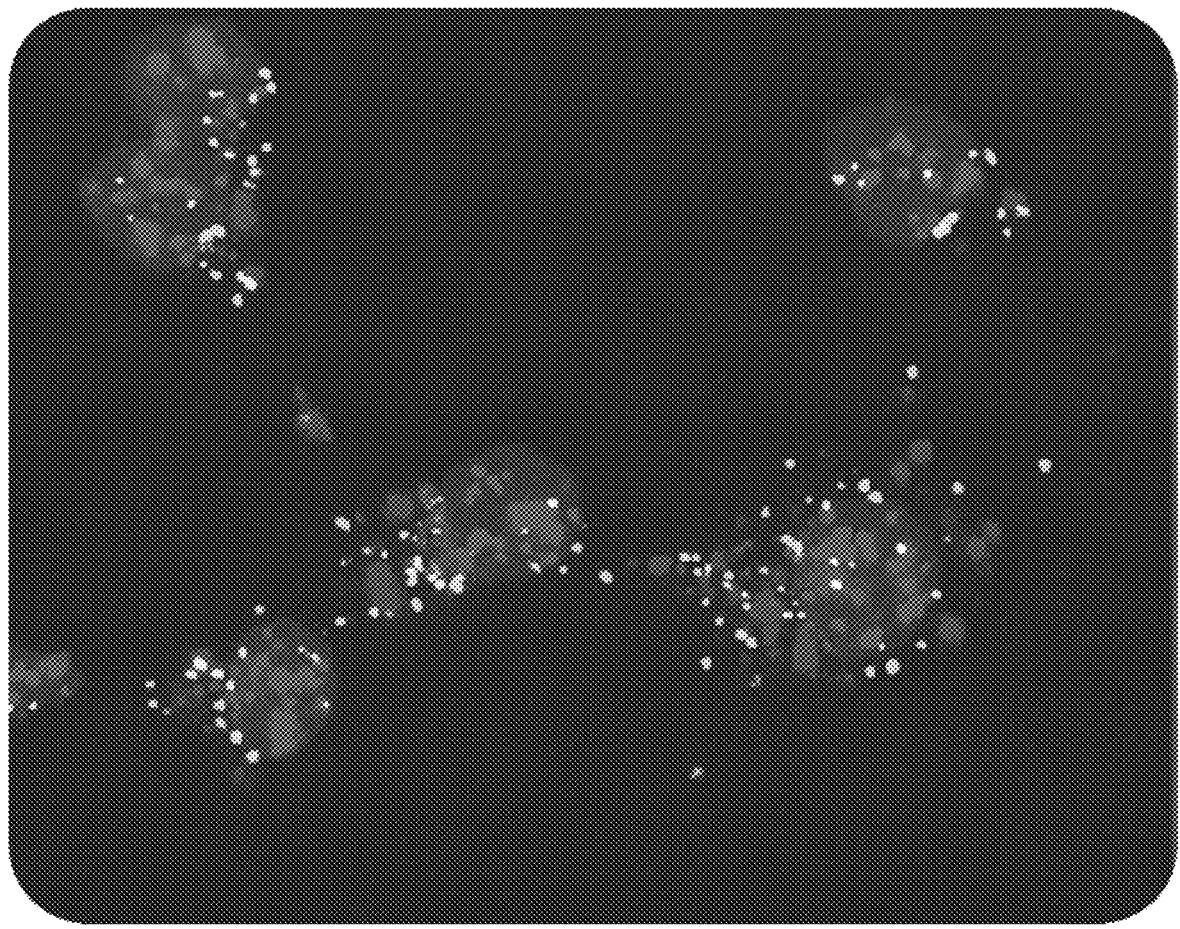
FIG. 26 shows intracellular localization of htt and ppib in primary cortical neurons using RNA-SCOPE. Htt mRNA, red; ppib mRNA, green; nuclei (DAPI), blue.

Sustained silencing was achieved for 21 days in terminally-differentiated neurons (FIG. 24). A silencing plateau was observed with RNAi (cytoplasmic) but not RNaseH (predominantly nuclear) compounds (FIG. 25). The observed plateau was specific to the htt gene. Approximately 60% of htt mRNA localized in the nuclei (FIG. 26).

Figure 27:
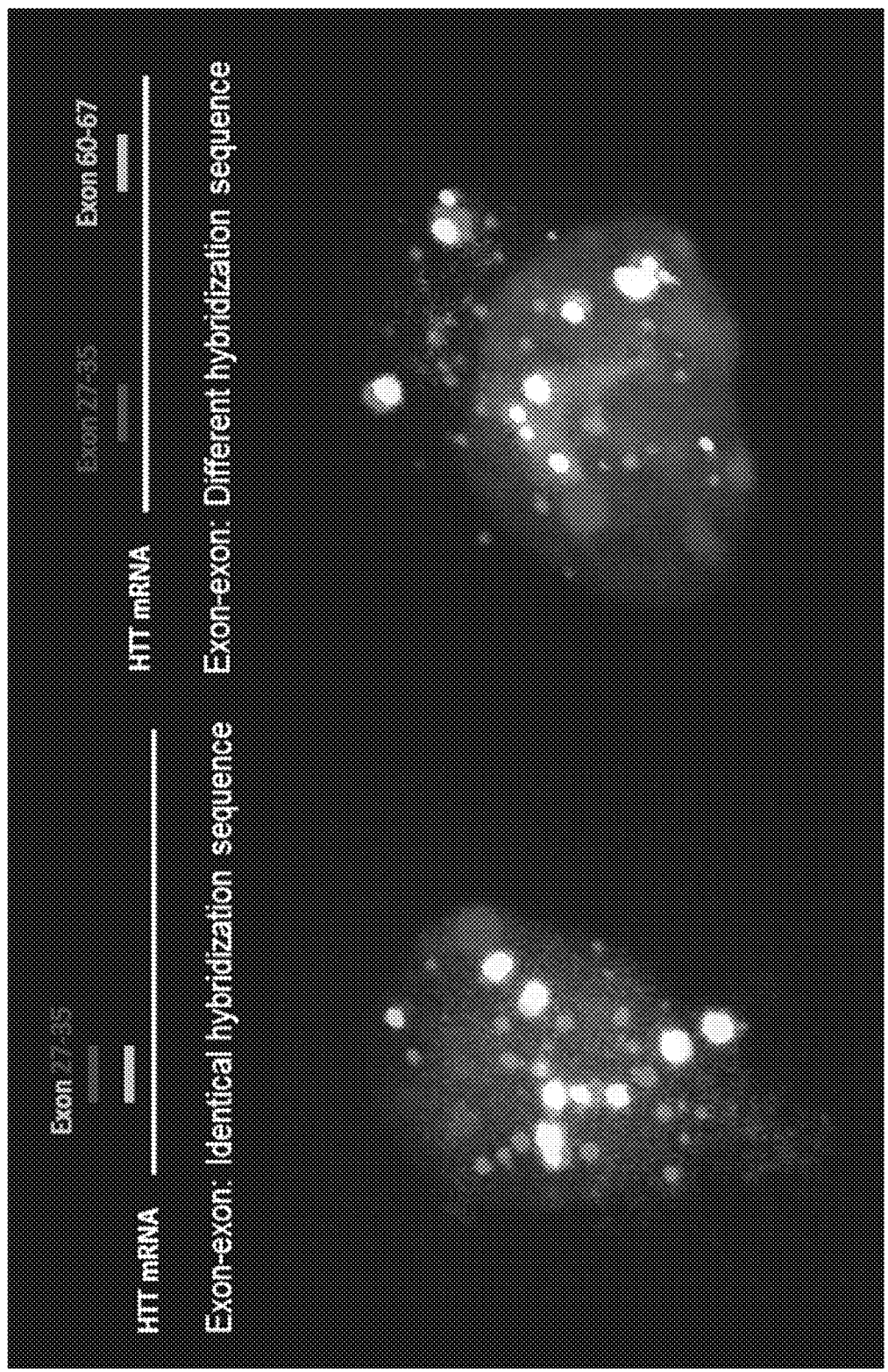
FIG. 27 validates in neurons an htt detection probe set, affirming specificity.

Probe sets were validated in neurons (FIG. 27). A majority of the detected signal was specific to htt mRNA. A high fraction of yellow (co-localized staining) areas were observed. Without intending to be bound by scientific theory, the high degree of red signal may be related to uneven concentrations of the two probed sets.

Figure 28:
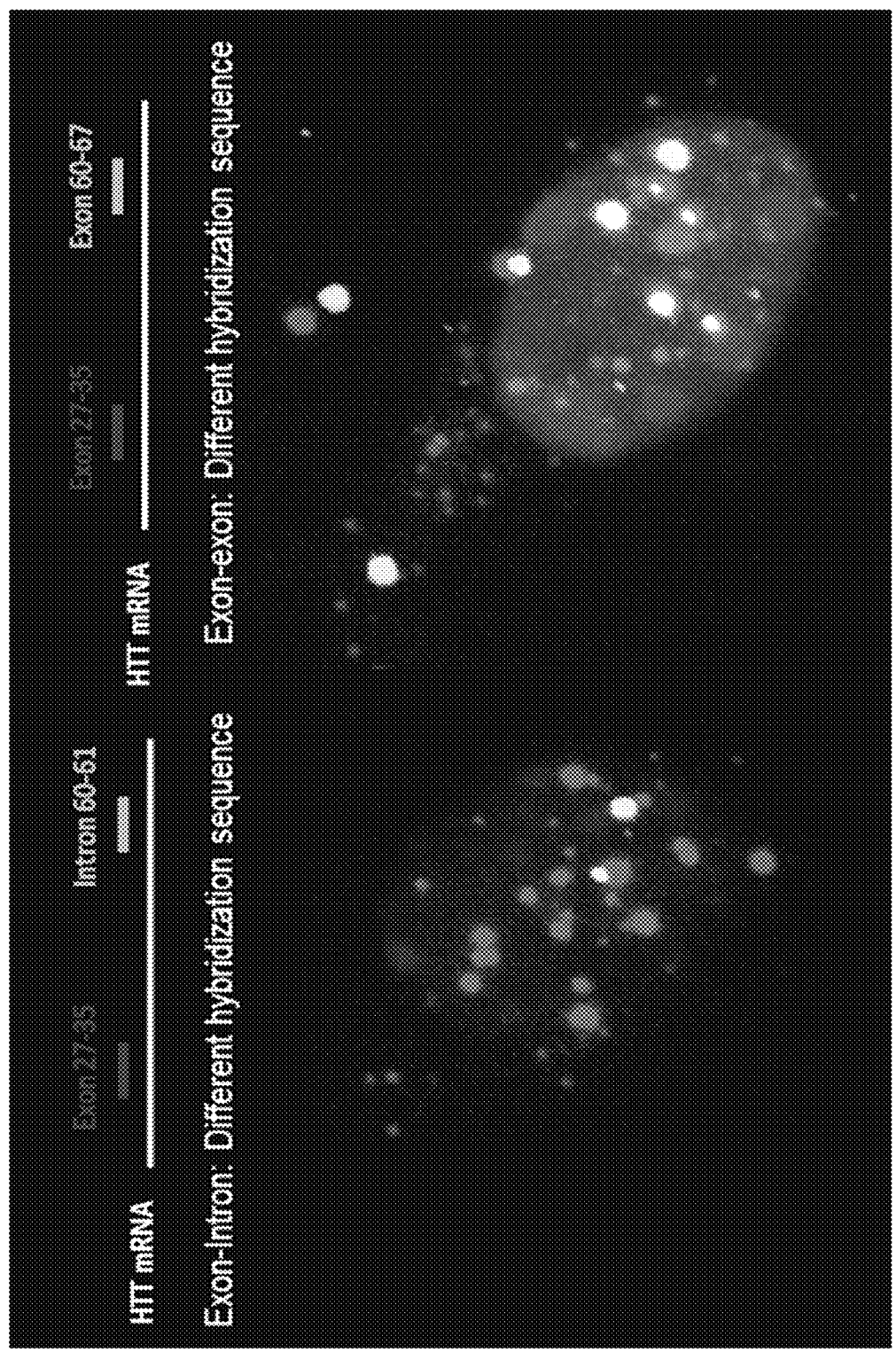
FIG. 28 validates in neurons an htt detection probe set, showing that the signal is not intron-specific (validated for intron 60-61).

Additional probe sets were validated for intron 60-61 in neurons (FIG. 28). Intron-specific probes showed one to two yellow dots in the nuclei specific to transcription sites. Exon-specific probes showed a higher degree of overlap.

Figure 29:
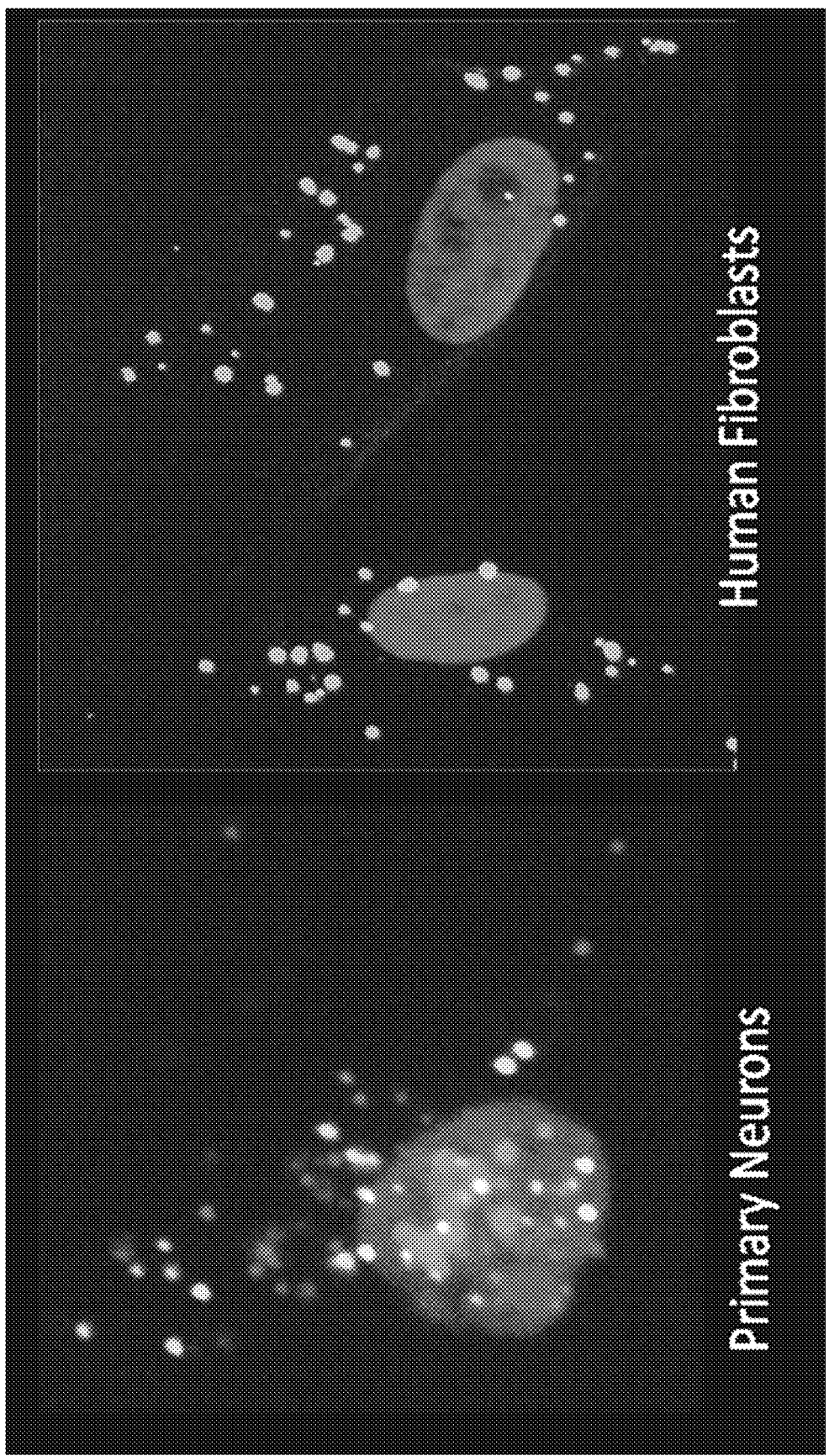
FIG. 29 depicts that htt mRNA nuclear localization is specific to neurons only. Left panel depicts primary neurons; ppib mRNA, green; htt mRNA, red, nuclei, blue.
Figure 30:
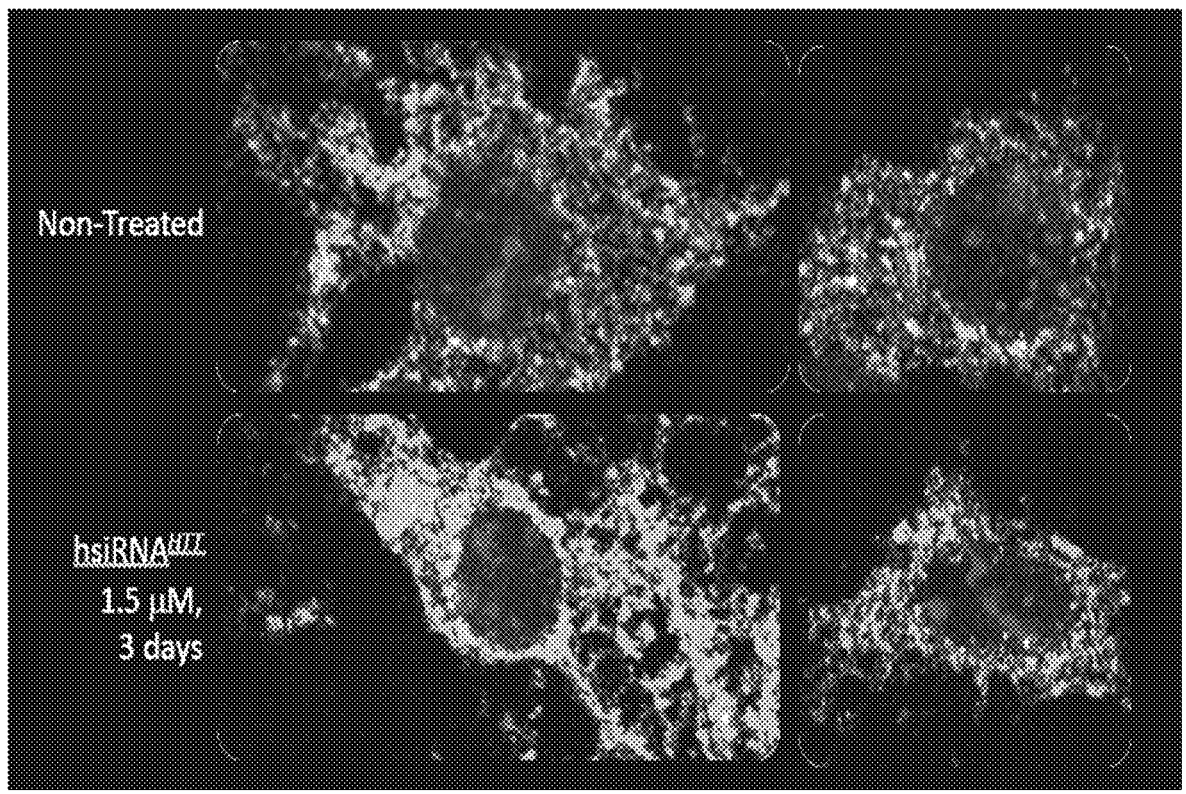
FIG. 30 depicts that hsiRNA$^{HTT}$ treatment of cortical neurons preferentially eliminates cytoplasmic htt mRNA. Ppib mRNA, green; htt mRNA, red; nuclei, blue. Top panel: non-treated. Bottom panel, treated with 1.5 μM hsiRNA$^{HTT}$ for three days.
Figure 31:
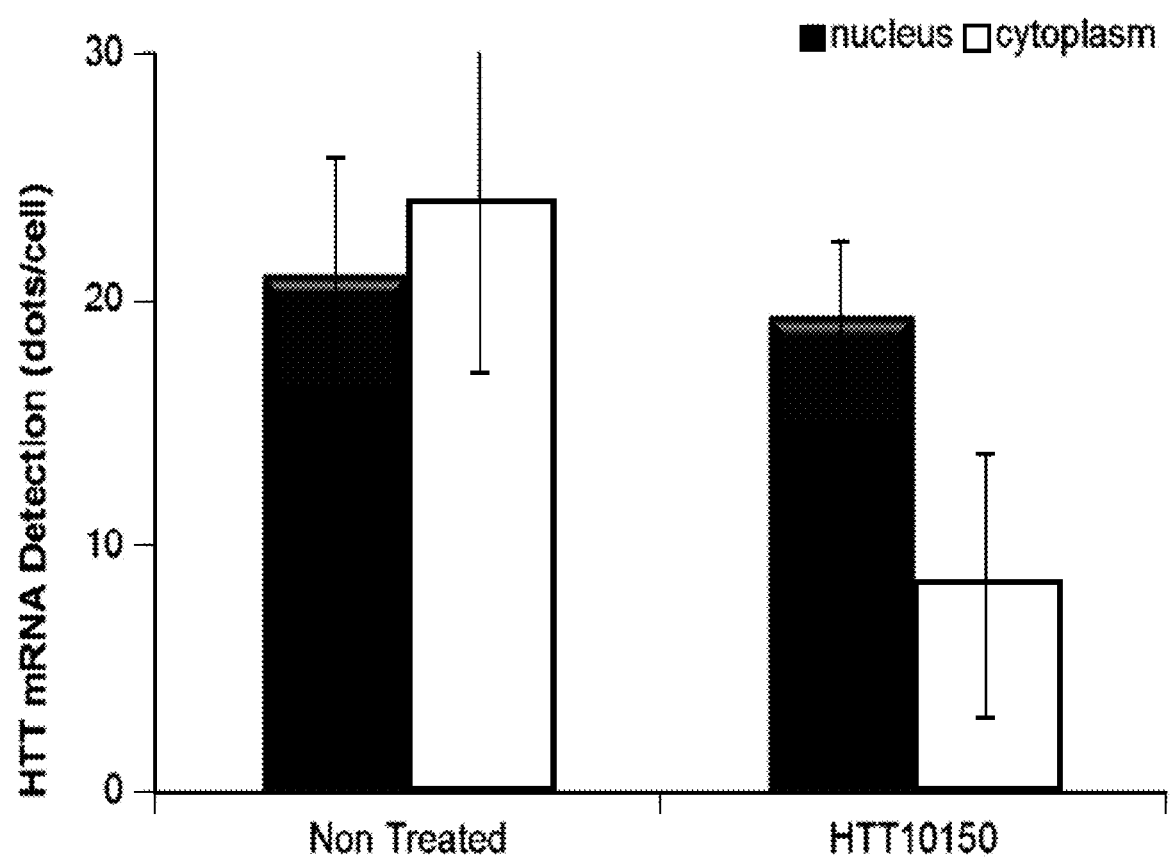
FIG. 31 graphically depicts that hsiRNA$^{HTT}$ treatment of cortical neurons preferentially eliminates cytoplasmic htt mRNA.

Htt mRNA nuclear localization was specific to neurons and not to fibroblasts (FIG. 29). HsiRNA$^{HTT}$ treatment of cortical neurons preferentially eliminated cytoplasmic htt mRNA (FIGS. 30 and 31).

Figure 32:
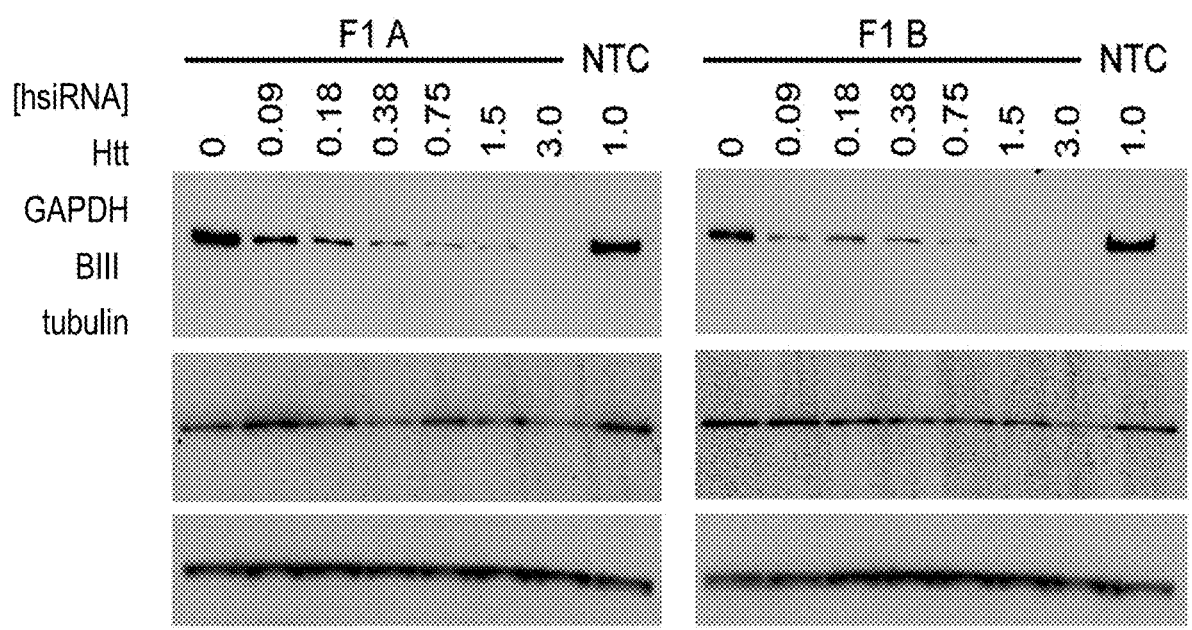
FIG. 32 depicts a Western blot showing HTT protein silencing in wild-type primary cortical neurons. hsiRNA htt-10150; NTC=non-targeting control, 1 week.

Close to complete HTT protein silencing was observed in primary cortical neurons (FIG. 32).

Figure 33:
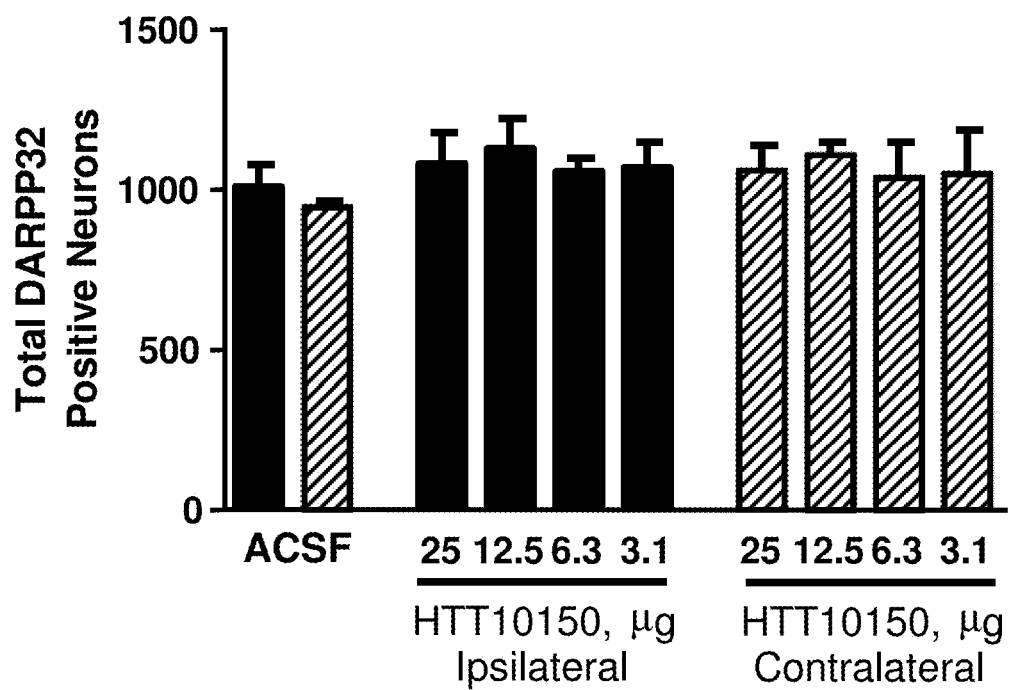
FIG. 33 graphically depicts the results of HTT10150 direct injection. No effects on neuronal viability were observed.
Figure 34:
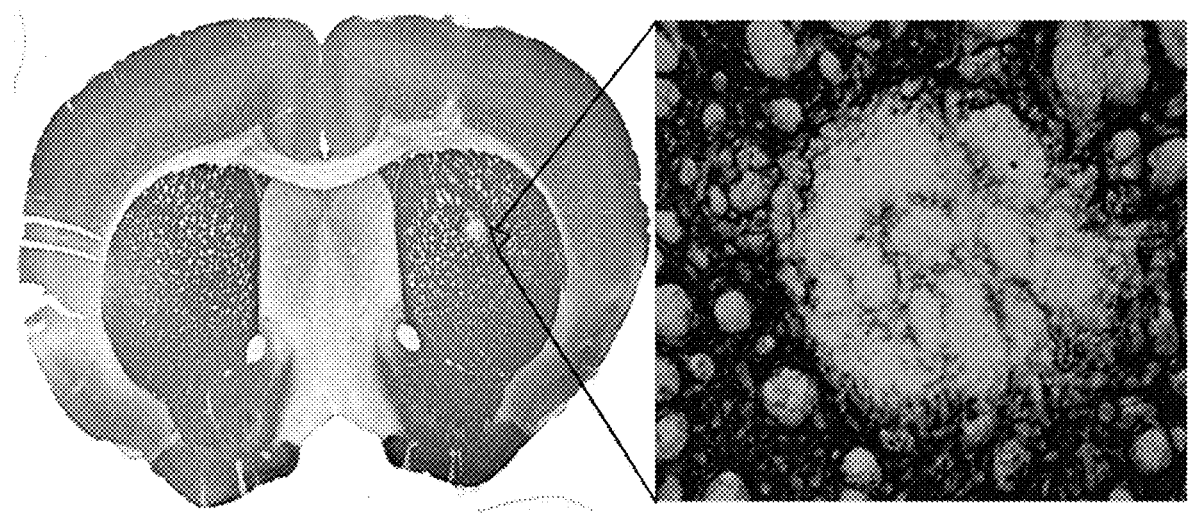
FIG. 34 depicts toxicity adjacent to the injection site following cholesterol-hsiRNA administration.

Direct injection of HTT10150 caused no detectable changes in neuronal numbers (FIG. 33). Cholesterol-hsiRNA exhibited a small area of toxicity adjacent to the injection site (FIG. 34).

Figure 58:
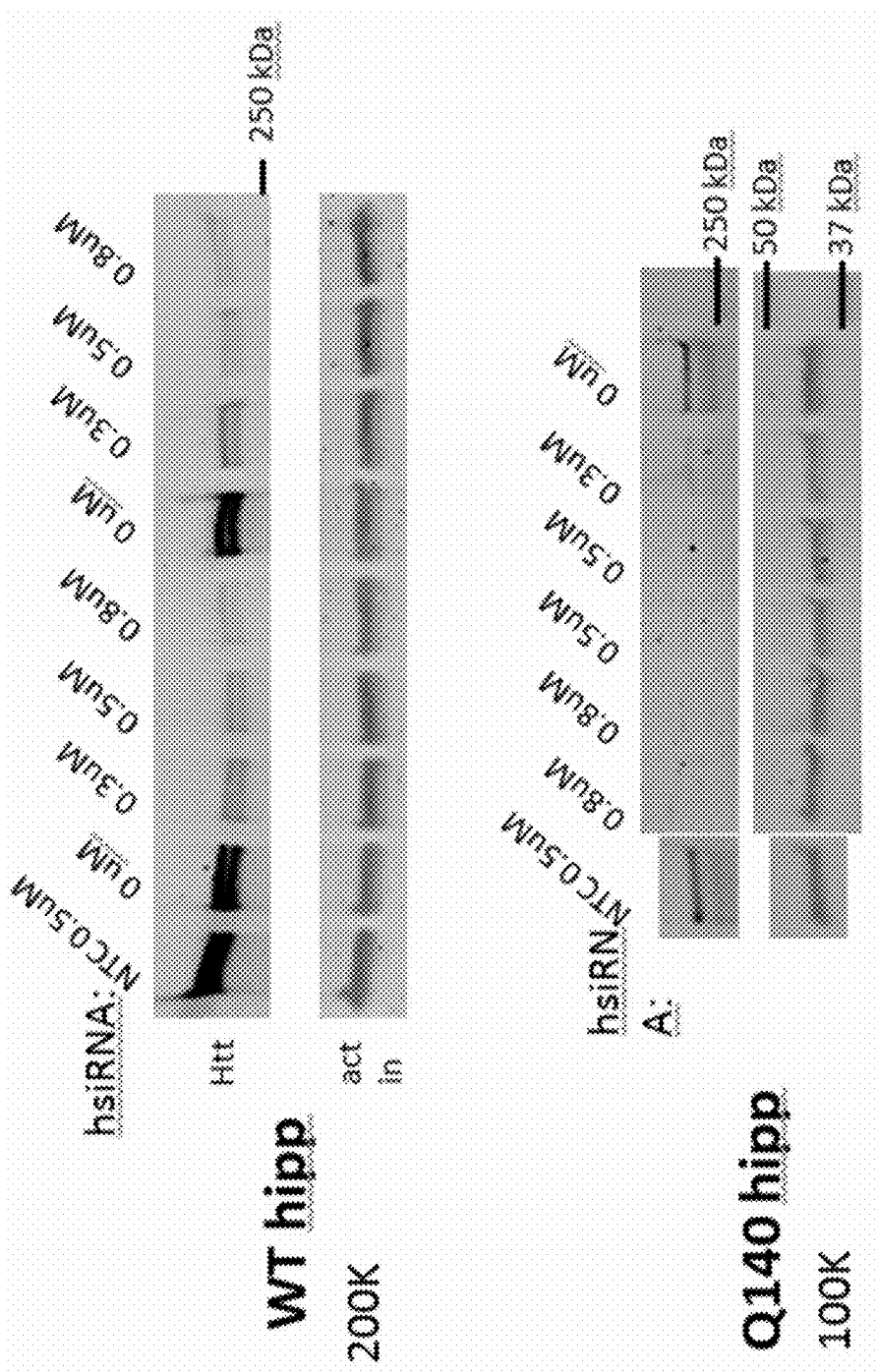
FIG. 58 shows hsiRNA efficacy in wild-type primary hippocampal neurons and Q140 primary hippocampal neurons. 16% gel.
Figure 59:
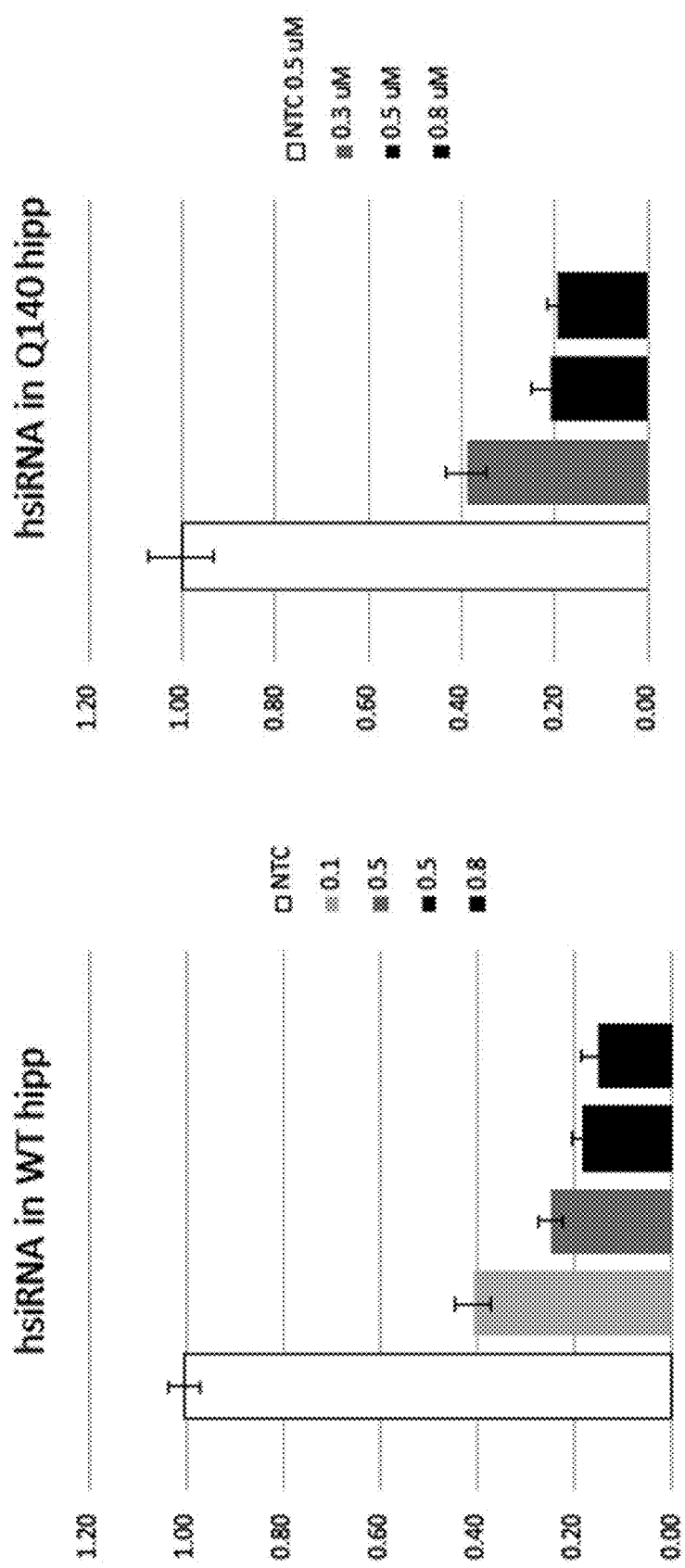
FIG. 59 graphically depicts hsiRNA efficacy in wild-type primary hippocampal neurons and Q140 primary hippocampal neurons.
Figure 60:
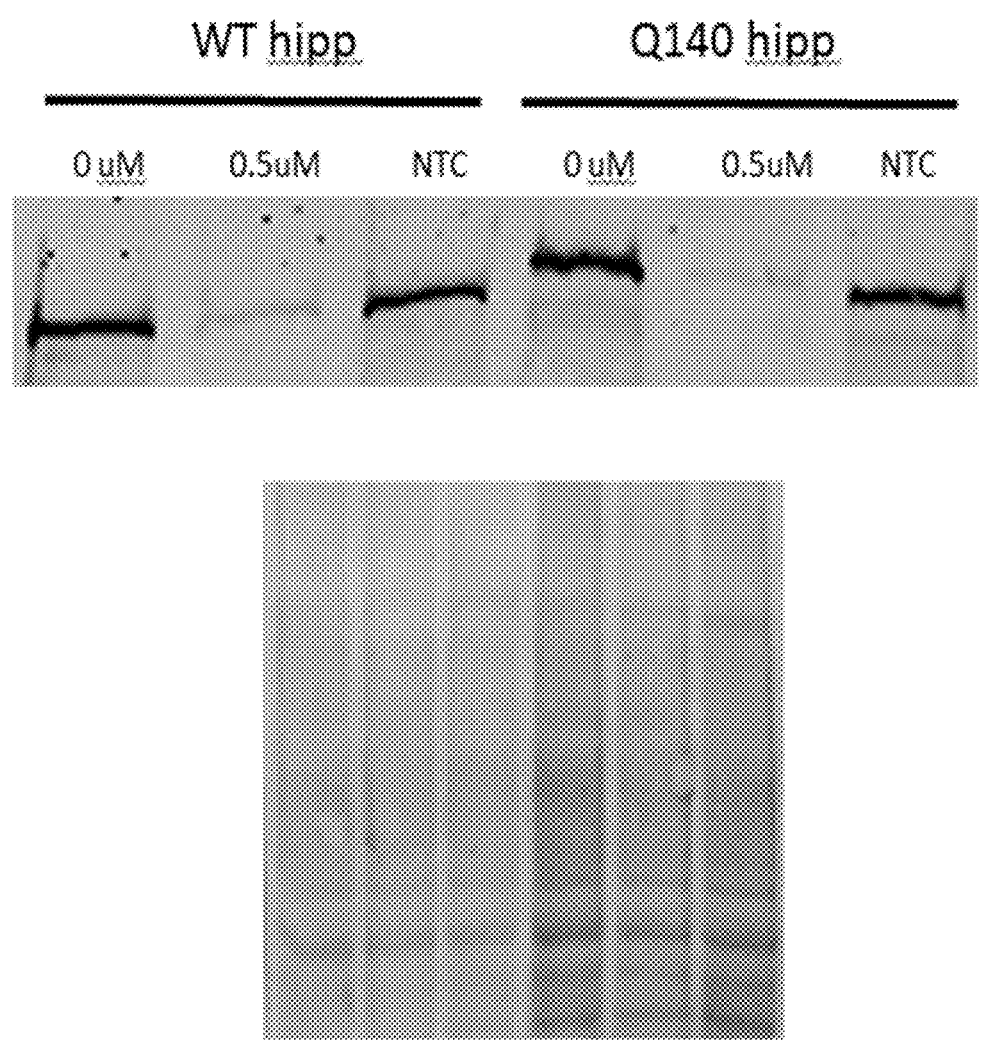
FIG. 60 shows hsiRNA efficacy in wild-type primary hippocampal neurons and Q140 primary hippocampal neurons. 7.5% gel.

FIGS. 58-60 disclose hsiRNA efficacy in wild-type and Q140 primary hippocampal neurons.

1.8 Discussion

This study demonstrates that the use of hydrophobically modified siRNA for delivery to primary cells is a valuable tool to enable functional and genomic studies of neuronal pathways and neurological disorders.

The ability to cause gene silencing in primary neurons without the use of toxic formulation has a significant impact on neuroscience research, facilitating a more in depth study of neurological disorders in the context of primary cell lines, and ultimately providing a more relevant understanding of in vivo function and pathology. Most neuronal studies are done in stable cell lines due to ease of delivery and cell maintenance, but using artificial cell systems can lead to artifacts in the data that can be attributed to manipulation of these cell lines, a problem that can be avoided by using primary cells (Cheung, Y.-T. et al. Effects of all-trans-retinoic acid on human SH-SY5Y neuroblastoma as in vitro model in neurotoxicity research. *NeuroToxicology* 30, 127-135 (2009); Gilany, K. et al. The proteome of the human neuroblastoma cell line SH-SY5Y: An enlarged proteome. *Biochimica et Biophysica Acta (BBA)—Proteins and Proteomics* 1784, 983-985 (2008); Lopes, F. M. et al. Comparison between proliferative and neuron-like SH-SY5Y cells as an in vitro model for Parkinson disease studies. *Brain Research* 1337, 85-94 (2010); Zhang, W. et al. Cyclohexane 1,3-diones and their inhibition of mutant SOD1-dependent protein aggregation and toxicity in PC12 cells. *BIOORGANIC &MEDICINAL CHEMISTRY* 1-17 (2011). doi:10.1016/j.bmc.2011.11.039). Current methods for delivering siRNA to primary neurons include the use of lentiviral vectors, Adeno-Associated Viruses (AAV), or Lipofectamine™-mediated transfection (Karra, D. & Dahm, R. Transfection Techniques for Neuronal Cells. *Journal of Neuroscience* 30, 6171-6177 (2010)). By conjugating a hydrophobic moiety such as cholesterol directly to the siRNA itself and by utilizing an additional single stranded phosphorothioated tail for enhanced uptake, it has been demonstrated herein that, not only can siRNA be delivered efficiently into primary neurons in vitro with minimal toxicity, but also remains a potent silencer of mRNA.

Without intending to be bound by scientific theory, one of the major advantages of RNAi over antisense technology is that the loaded RISC is expected to remain active for a long period of time in non-dividing cells (Bartlett, D. W. Insights into the kinetics of siRNA-mediated gene silencing from live-cell and live-animal bioluminescent imaging. *Nucleic Acids Research* 34, 322-333 (2006)). Additionally, a limited number of loaded RISCs are sufficient for the induction of RNAi-mediated silencing (Stalder, L. et al. The rough endoplasmatic reticulum is a central nucleation site of siRNA-mediated RNA silencing. *The EMBO Journal* 32, 1115-1127 (2013)). The data presented herein demonstrates silencing for up to three weeks in vitro in primary cortical neurons upon a single treatment with hsiRNA, supporting the notion that RNAi-mediated silencing can be both efficient and long lasting. The data presented herein also shows that these compounds can be used to target multiple regions in two different genes, which demonstrates the adaptability of hsiRNA for the study of alternative neurological pathways and diseases.

While a single intra-striatal injection of hsiRNA resulted in potent gene silencing near the injection site in vivo, the effect was not evenly spread throughout the brain. Although limited, spread to other areas of the brain (demonstrated by in vivo efficacy studies) could be happening through a number of mechanisms. These include movement in the CSF, spread via fiber tracts which were shown to have a large visual density of Cy3-labeled hsiRNA in distribution studies, or possibly through retrograde transport (Stewart, G. R. & Sah, D. Retrograde Transport of siRNA and Therapeutic Uses to Treat Neurological Disorders. United States Patent Application Publication US 2008/0039415 A1, 1-18 (2008)), although further studies will be conducted to determine the actual mechanism.

The technology presented herein is useful for understanding functional genomics of particular brain regions, as well as for studying relationships between brain regions. Additionally, the study of some neurological disorders (for example memory disorders (Samuelson, K. W. Post-traumatic stress disorder and declarative memory functioning: a review. *Dialogues in Clinical Neuroscience* 13, 346-351 (2011))) can benefit from limited and regionally targeted distribution and silencing. However, due to its distribution profile, hsiRNA as it currently exists is not a viable therapeutic for general neurological disorders like Huntington's disease. Multiple injections may work to increase overall silencing in small rodents, but in order to adapt this technology for use in larger animal brains and humans, and to achieve even and widespread distribution, other chemical modifications and therapeutic methods of delivery will be utilized. There are a number of ways in which this might be approached. First, chemical adjustments to the hsiRNA composition itself can be made. These include conjugating it to a different lipid, supplementing the backbone with additional phosphorothioate groups, or by addition of hydrophobic moieties to the nucleotides themselves (Vaught, J. D., Dewey, T. & Eaton, B. E. T7 RNA Polymerase Transcription with 5-Position Modified UTP Derivatives. *J. Am. Chem. Soc.* 126, 11231-11237 (2004)). All of these modifications could support a range of hydrophobicities that would allow for more improved distribution across a larger distance. Increased bioavailability could also be achieved with different modes of injection such as into the CSF instead of intrastriatally, increasing the likelihood of exposure to the whole brain. However, delivery via the CSF could favor localization of hsiRNA to brain regions other than the striatum, making it a less than ideal delivery method for the treatment of Huntington's disease. Another possibility is formulated delivery by packaging these hydrophobically modified siRNAs into exosomes and liposomes (less toxic than current Lipofectamine™ formulations) and using these natural and synthetic nanocarriers to deliver cargo in a more evenly distributed fashion (Alvarez-Erviti, L. et al. Delivery of siRNA to the mouse brain by systemic injection of targeted exosomes. *Nat Biotechnol* 1-7 (2011). doi:10.1038/nbt.1807; Marcus, M. & Leonard, J. FedExosomes: Engineering Therapeutic Biological Nanoparticles that Truly Deliver. *Pharmaceuticals* 6, 659-680 (2013)). However, potency and efficacy of the delivered hsiRNA still needs to be validated for these methods.

In conclusion, HTT10150 was efficient for targeting huntingtin mRNA in primary neurons in vitro and locally in the mouse brain in vivo. This compound did not require any formulation for delivery to primary cells and enabled gene functional studies for huntingtin as well as other targets, making it a very useful tool for the study of neurological disorders. Potential advances to this technology should allow for hsiRNA to function as a therapeutic treatment for Huntington's disease as well as other neurological diseases in the future.

1.9 Methods

Cell Culture

HeLa cells were maintained in DMEM (Corning Cellgro) supplemented with 10% fetal bovine serum (Gibco) and 100 U/mL penicillin/streptomycin (Invitrogen) and grown at 37° C. and 5% $CO_2$. Cells were split every 2-5 days up to passage 15 and then discarded.

Cell Culture for Passive Uptake

Cells were plated in DMEM with 6% FBS at 10,000 cells/well in 96-well tissue culture treated plates. hsiRNA was diluted in OptiMEM (Gibco) to 2× final concentration and 50 µL diluted hsiRNA was added to 50 µL of cells for 3% FBS final. Cells were incubated for 72 hours at 37° C. and 5% $CO_2$.

Cell Culture for Lipid-Mediated Uptake

Cells were plated in DMEM with 6% FBS at 10,000 cells/well in 96-well tissue culture treated plates. hsiRNA was diluted in OptiMEM to 4× final concentration. LIPOFECTAMINE RNAIMAX Transfection Reagent (Invitrogen #13778150) was diluted to 4× final concentration (final=0.3 µL/25 µL/well). RNAIMAX and hsiRNA were mixed 1:1 and 50 µL was added to 50 µL of cells for 3% FBS final. Cells were incubated for 72 hours at 37° C. and 5% $CO_2$.

Preparation of Primary Neurons

Primary cortical neurons were obtained from E15.5 mouse embryos of WT (FVBN) mice. Pregnant females were anesthetized by IP injection of Avertin (250 mg/kg weight) followed by cervical dislocation. Embryos were removed and transferred into a Petri dish with ice-cold DMEM/F12 medium (Invitrogen). Brains were removed and meninges were carefully detached. Cortices were isolated and transferred into a 1.5-ml tube with pre-warmed papain solution for 25 minutes at 37° C. and 5% $CO_2$ to dissolve tissue. Papain solution was prepared as follows: papain (Worthington #54N15251) was dissolved in 2 mL HibernateE (Brainbits) and 1 mL EBSS (Worthington). Separately, DNase (Worthington #54M15168) was re-suspended in 0.5 mL HibernateE. Then, 0.25 mL of re-suspended DNase was transferred to re-suspended papain for the final solution. After the 25 minute incubation, papain solution was removed and 1 mL NbActiv4 (Brainbits) supplemented with 2.5% FBS was added to the tissue. The cortices were then dissociated by pipetting up and down with a fire polished, glass Pasteur pipet. Cortical neurons were counted and plated at $1 \times 10^6$ cells/ml. For live-cell imaging studies, culture plates were pre-coated with poly-L-lysine (Sigma # P4707) and $2 \times 10^5$ cells were added to the glass center of each dish. For silencing assays, neurons were plated on poly-L-lysine pre-coated 96-well plates (BD BIOCOAT #356515) at $1 \times 10^5$ cells per well. After overnight incubation at 37° C. and 5% $CO_2$ an equal volume of NbActiv4 (Brainbits) supplemented with anti-mitotics, 0.484 µL/mL of 5'UtP (Sigma # U6625) and 0.2402 µL/mL of 5'FdU (Sigma # F3503), to prevent the growth of non-neuronal cells, was added to neuronal cultures. Half of the volume of media was replaced every 48 hours (with new NbActiv4 with anti-mitotics) until the neurons were treated with siRNA. Once the cells were treated, media was not removed, only added. All subsequent media additions contained anti-mitotics.

mRNA Quantification mRNA was quantified using the QuantiGene 2.0 Assay (Affymetrix # QS0011). Cells were lysed in 250 µL diluted lysis mixture (Affymetrix #13228), 1 part lysis mixture, 2 parts $H_2O$, with 0.167 µg/µL proteinase K (Affymetrix # QS0103) for 30 minutes at 55° C. Cell lysates were mixed thoroughly and 40 µL (approximately 8000 cells) of lysate were added to the capture plate along with 40 µL additional diluted lysis mixture without proteinase K. Probe sets were diluted as specified in the Affymetrix protocol. For HeLa cells, 20 µL of human HTT or PPIB probe set (Affymetrix # SA-50339, # SA-10003) was added to appropriate wells for a final volume of 100 µL. For primary neurons, 20 µL of mouse HTT or PPIB probe set (Affymetrix # SB-14150, # SB-10002) was used.

Tissues were treated similarly, using 300 µL of Homogenizing Buffer (Affymetrix #10642) with 2 µg/L proteinase K for a 5 mg tissue punch. Tissues were then homogenized in 96-well plate format on the QIAGEN TissueLyser II and 40 µL were added to the capture plate. Probe sets were diluted as specified in the Affymetrix protocol and 60 µL of either HTT or PPIB probe sets (Affymetrix # SB-14150, #

SB-10002) were added to each well of the capture plate for a final volume of 100 μL. For DARPP32 quantification, only 10 μL of tissue sample and 30 μL of homogenizing buffer were added to each well with 60 μL of mouse Ppp1r1b probe set (Affymetrix # SB-21622). Signal was amplified according to the Affymetrix protocol. Luminescence was detected on either the Veritas Luminometer or the Tecan M 1000.

Live Cell Staining

To monitor live cell hsiRNA uptake, cells were plated at a density of $2 \times 10^5$ cells per 35 mm glass-bottom dish as described in the preparation of primary neurons above. Prior to imaging, cell nuclei were stained in phenol red free NbActiv4 using NUCBLUE (Molecular Probes by Life Technologies # R37605) as indicated by the manufacturer. Imaging was performed in phenol red free NbActiv4. Cells were treated with 0.5 μM of Cy3-labeled hsiRNA, and live cell imaging was performed over time. All live cell confocal images were acquired with a Zeiss confocal microscope and images were processed using ImageJ (1.47v) software.

Immunohistochemistry/Immunofluorescence

For distribution studies, brains were injected with 1 nmol (12.5 μg) of Cy3-labeled hsiRNA. After 24 hours, mice were sacrificed and brains were removed and sent to the DERC Morphology Core at UMASS Medical School to be embedded in paraffin and sliced into 4 μm sections and mounted on glass slides. Sections were de-parafinized for 8 minutes in xylene two times. Sections were then rehydrated with serial ethanol dilutions (100%, 95%, 80%) for 4 minutes each, then washed twice for two minutes with PBS. For NueN staining, slides were boiled for 5 minutes in antigen retrieval buffer and then left to sit at room temperature for 20 minutes, followed by a 5-minute wash with PBS. Slides were then blocked with 5% normal goat serum in PBS+0.05% Tween20 for 1 hour and washed once with PBS+0.05% Tween20 for 5 minutes. Primary antibody (1:1000 dilution in PBS+0.05% Tween20) was added to slides for a 1 hour incubation followed by three 5-minute washes with PBS+0.05% Tween20. Secondary antibody (1:1000 dilution in PBS+0.05% Tween20) was added to slides for a 30-minute incubation in the dark followed by three 5-minute washes with PBS+0.05% Tween20. Slides were then stained with DAPI (Molecular Probes by Life Technologies # D3571), diluted to 250 ng/mL in PBS, for one minute followed by three 1-minute washes with PBS. Mounting media and coverslips were applied to slides and left to dry over night before imaging on Leica DM5500—DFC365FX microscope at indicated magnification.

For toxicity and microglia activation studies extracted, perfused brains were sliced into 40 μm sections on the Leica 2000T Vibratome in ice cold PBS. Immunohistochemistry was performed on every 6th section against DARPP32 (Millipore, 1:10,000 dilution) and IBA-1 (Millipore, 1:500 dilution). Sections were mounted and visualized by light microscopy. Four images were taken at 20× in the striatum of both injected and non-injected sides of each section. The number of DARPP32 positive neurons was quantified using ImageJ. Activated microglia was quantified by morphology of stained cells for IBA-1.

Animals, Stereotaxic Injections

Wild-type (FVBN) mice received microinjections by stereotactic placement into the right striata (coordinates (relative to bregma) were 1.0 mm anterior, 2.0 mm lateral, and 3.0 mm ventral). Animals were deeply anesthetized prior to injection with 1.2% Avertin. For both toxicity (DARPP32) and efficacy studies, mice received injections of either PBS or artificial cerebrospinal fluid (2 μL per striata, N=8 mice), 12.5 μg of NTC hsiRNA (2 μL of 500 μM stock solution per striata, N=8 mice), 25 ptg of HTT10150 hsiRNA (2 μL of 1 mM stock solution per striata, N=8 mice), 12.5 ptg of HTT10150 hsiRNA (2 μL of 500 pLM stock solution per striata, N=16 mice total, two sets of 8 mice on two different days), 6.3 μg of HTT10150 hsiRNA (2 μL of 250 μM stock solution per striata, N=8 mice), or 3.1 μg of HTT10150 hsiRNA (2 μL of 125 pLM stock solution per striata, N=8 mice) and euthanized 5 days later. Brains were harvested and three 300 μm coronal sections were made. One 2 mm punch was taken per side (injected and non-injected) for each section and placed in RNAlater (Ambion # AM7020) for 24 hours at 4° C. Each punch was processed as an individual sample for the QuantiGene assay analysis. All animal procedures were approved by the University of Massachusetts Medical School Institutional Animal Care and Use Committee (IACUC, protocol number A-2411).

Statistical Analysis

Data analyses were done using GraphPad Prism 6 version 6.04 software (GraphPad Software, Inc., San Diego, Calif.). For concentration dependent curve IC50s, a curve was fitted using log(inhibitor) vs. response—variable slope (four parameters). The bottom of the curve was set to be no less than zero and the top of the curve was set to be no greater than 100. For each independent mouse experiment, the level of knockdown at each dose was normalized to the mean of the control group, which was the non-injected side of the PBS or artificial CSF groups, so that all data were expressed as a proportion of the control. In vivo data were analyzed using the Kruskal-Wallis test (one-way ANOVA) with Bonferroni corrections for multiple comparisons. Differences in all comparisons were considered significant at P-values less than 0.05.

Cell Culture for Passive Uptake (Primary Screen and Dose Response)

Cells were plated in DMEM (Gibco) with 6% FBS (Gibco) at 10,000 cells/well in 96-well tissue culture treated plates. HsiRNA was diluted in OptiMEM (Gibco) to 2× final concentration and 50 uL diluted hsiRNA was added to 50 μL of cells for 3% FBS final. Cells were incubated for 72 hours at 37 C and 5% $CO_2$.

Cell Culture for Lipid-Mediated Uptake

Cells were plated in DMEM (Gibco) with 6% FBS (Gibco) at 10,000 cells/well in 96-well tissue culture treated plates. HsiRNA was diluted in OptiMEM (Gibco) to 4× final concentration. LIPOFECTAMINE RNAIMAX Transfection Reagent (Invitrogen CAT #13778150) was diluted to 4× final concentration (final=0.3 μL/25 μL/well). RNAIMAX and hsiRNA were mixed 1:1 and 50 μL was added to 50 uL of cells for 3% FBS final. Cells were incubated for 72 hours at 37 C and 5% $CO_2$.

mRNA Quantification mRNA was quantified using the QuantiGene 2.0 Assay (Affymetrix QS0011). Cells were lysed in 250 μL diluted lysis mixture, 1 part lysis mixture, 2 parts H2O, with 0.167 μg/μL proteinase K (Affymetrix QS0103) for 30 minutes at 55 C. Cell lysates were mixed thoroughly and 40 μL (~8000 cells) of lysate were added to capture plate along with 40 μL additional diluted lysis mixture without proteinase K. Tissues were treated similarly, using 300 μL of Homoginizing Buffer (Affymetrix) with 2 μg/μL proteinase K for a 5 mg tissue punch. Tissues were then homogenized in 96-well plate format on Qaigen TissueLyzer and 40 μL were added to capture plate. Probe sets were diluted as specified in Affymetrix protocol and 20 μL of either HTT or PPIB probes (Affymetrix: SA-50339, SA-10003) were added to each well of capture plate for final volume of 100 μL. Signal was amplified according to manufacture protocol. Luminescence was detected on either the Veritas Luminometer or the Tecan M 1000.

Live Cell Staining and Brain Sections Immunostaining

For live cell uptake monitoring, cells were plated at a density of 2×10$^5$ cells per 35 mm glass-bottom dish and grown overnight. Prior to imaging, cell organelles were stained in HBSS (Gibco) using staining reagents purchased from Life Technologies unless specified: cell nuclei, endoplasmic reticulum and lysosomes were respectively stained using the NUCBLUE Live READYPROBE, ER-TRACKER Green (Bodipy FL Glibenclamide) and LYSOTRACKER Deep Red reagents as indicated by the manufacturer. Imaging was performed in non-supplemented DMEM without phenol red (Invitrogen). Cells were treated with 0.5 µM of Cy3-labeled hsiRNA, and live cell imaging was performed over time.

Confocal Imaging

All confocal images were acquired with a CSU10B Spinning Disk Confocal System scan head (Solamere Technology Group) mounted on a TE-200E2 inverted microscope (Nikon) with a 60× Plan/APO oil lens and a Coolsnap HQ2 camera (Roper). Images were processed using ImageJ (1.47v) software. Number of neurons without or with hsiRNA was counted using ImageJ software. Brain sections images were acquired with a z-axis spacing of 1 µm.

Example 2. hsiRNA Retention and Distribution is Directly Related to Hydrophobicity Although FM-hsiRNAs showed improved retention and accumulation in brain and spinal cord and induce maximal silencing at 10-fold lower doses than partially stabilized hsiRNAs, they were largely retained near the injection site (FIG. 102; Chol-hsiRNA). It was hypothesized that the limited distribution of hsiRNAs could result from preferential binding of hsiRNA to lipid-enriched myelin and myelinated structures due to the strong hydrophobicity of the cholesterol conjugate, and that tuning the hydrophobicity of the hsiRNA conjugates would improve distribution through the spinal cord and brain. To test the idea, a panel of naturally occurring, hydrophobic molecules capable of active neuronal trafficking, was screened including: (i) neuroactive steroids, i.e., endogenous steroids that traverse the blood-brain barrier and bind a variety of gated-ion channels and neuronal-expressed receptors (Rupprecht R. Neuroactive steroids: mechanisms of action and neuropsychopharmacological properties. *Psychoneuroendocrinology.* 2003; 28:139-68. PMID: 12510009), including GABA (Lan N C, Gee K W. Neuroactive steroid actions at the GABAA receptor. Hormones and behavior. 1994; 28:537-44. PMID: 7729823); (ii) gangliosides-neuroprotective glycolipids critical for neuronal plasticity and repair (Aureli M, Mauri L, Ciampa M G, Prinetti A, Toffano G, Secchieri C, Sonnino S. GM1 Ganglioside: Past Studies and Future Potential. *Molecular neurobiology.* 2015. PMID: 25762012); and (iii) endocannabinoid-like long-chain polyunsaturated fatty acids-neuromodulatory lipids recognized by receptors involved in appetite, pain, mood, and memory (Dyall S C. Long-chain omega-3 fatty acids and the brain: a review of the independent and shared effects of EPA, DPA and DHA. *Frontiers in aging neuroscience.* 2015; 7:52. PMID: 25954194; PMCID: PMC4404917; Janssen C I, Kiliaan A J. Long-chain polyunsaturated fatty acids (LCPUFA) from genesis to senescence: the influence of LCPUFA on neural development, aging, and neurodegeneration. *Progress in lipid research.* 2014; 53:1-17. PMID: 24334113; Figueroa J D, De Leon M. Neurorestorative targets of dietary long-chain omega-3 fatty acids in neurological injury. *Molecular neurobiology.* 2014; 50:197-213. PMID: 24740740; PMCID: PMC4183712).

Figure 98A:
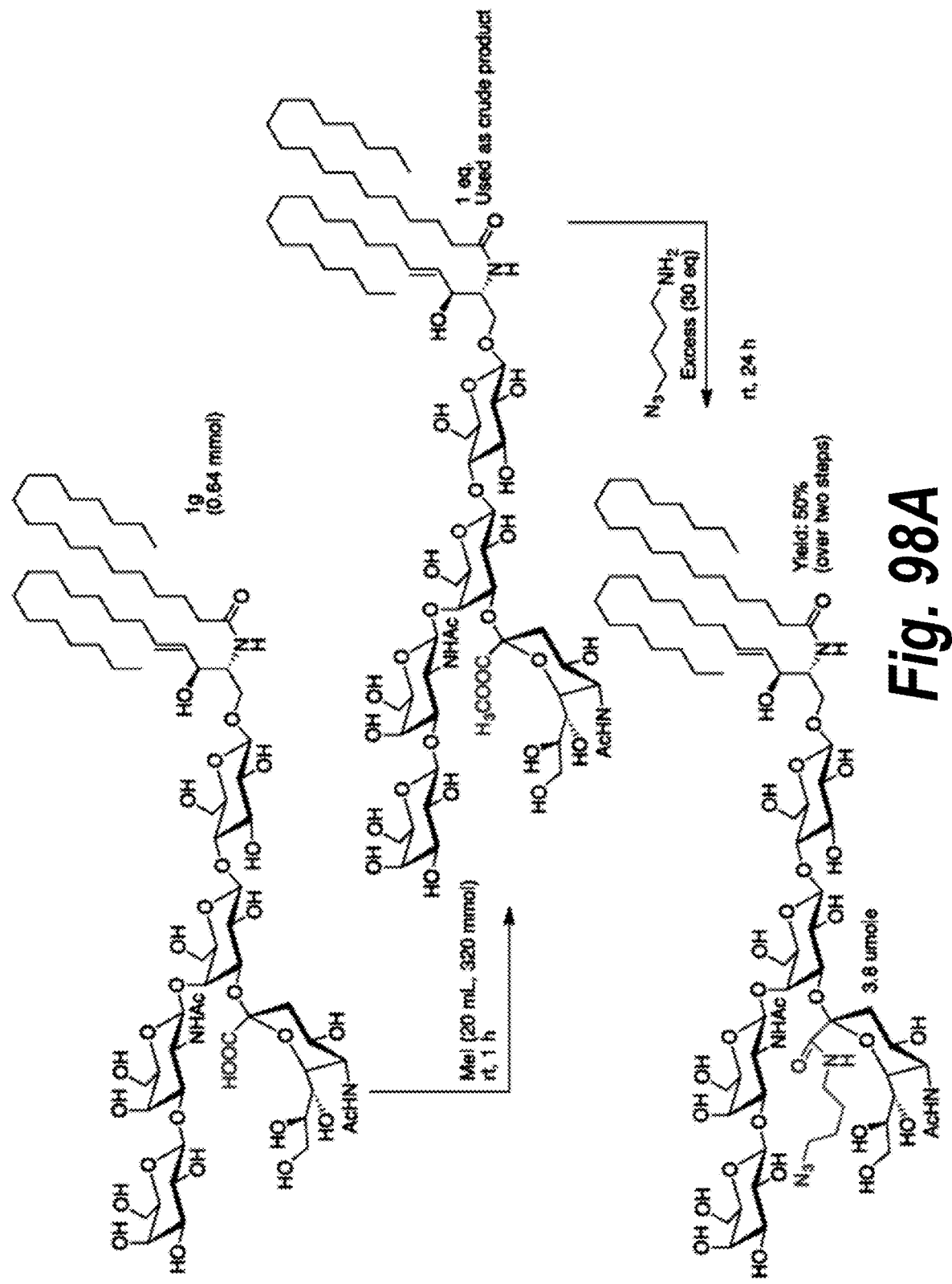
FIG. 98A-98B depicts a solution-phase synthetic protocol for a GM1-conjugated hsiRNA.
Figure 98B:
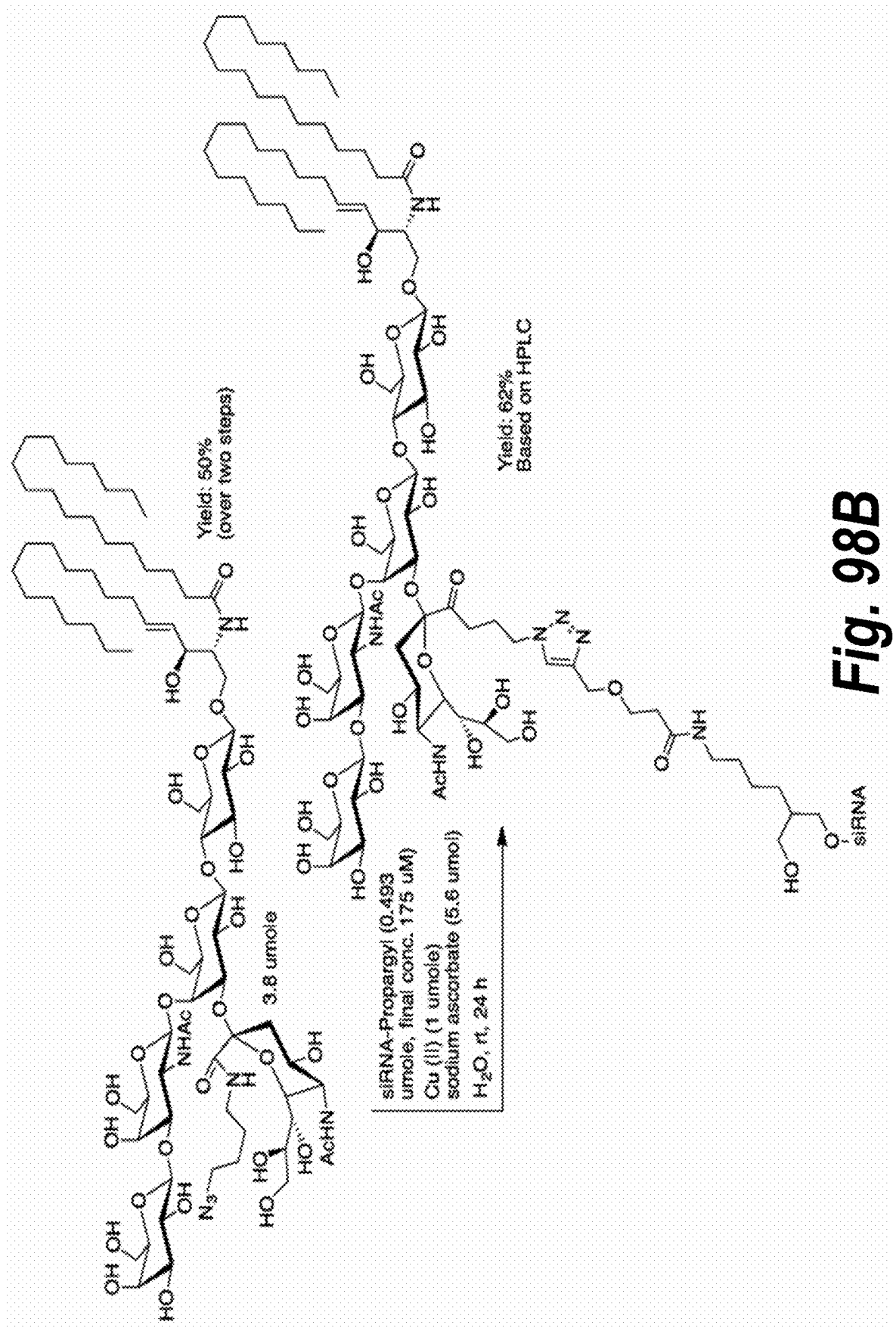
Figure 99:
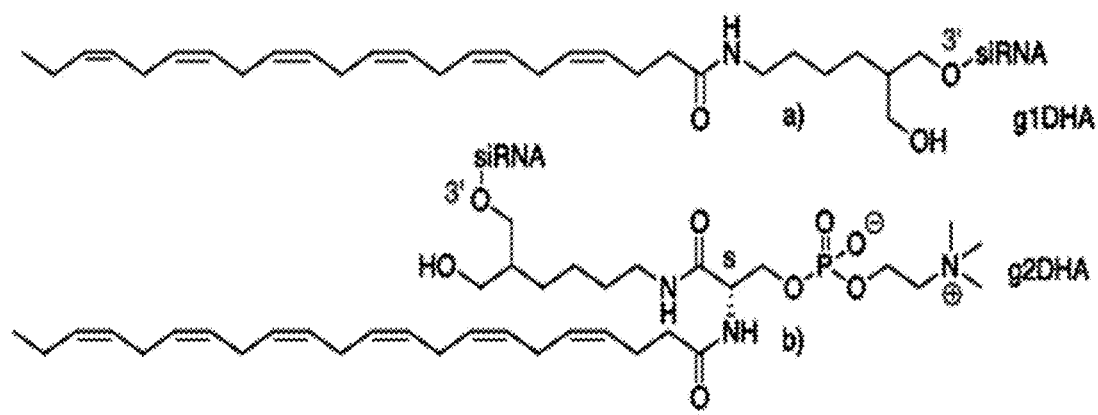
FIG. 99 depicts chemical structures for DHA-conjugates (g1DHA) and PC-DHA hsiRNA conjugates (g2DHA).

The most robust approach for synthesis of oligonucleotide conjugates was to attach the activated conjugate to an amino-modified support. The structure and length of the linker were varied (e.g., branched) and the support was functionalized whenever feasible. Variations of the synthetic approaches outlined in FIGS. 93 and 94 were used to synthesize hsiRNAs conjugated to cortisol, docosahexaenoic acid (DHA), calciferol, cholesterol, and GM1 ganglioside (FIGS. 98 and 99). All compounds were HPLC-purified and their identities were confirmed by mass spectrometry. The calciferol-functionalized support was unstable, resulting in a mixture of several variants that were tested in vivo (described infra).

As expected, the compounds showed different degrees of hydrophobicity based on retention time during reverse phase chromatography. Injection of Cy3-labeled hsiRNA conjugates into striata or ICV (FIG. 92) of wild-type mice revealed varying degrees of hsiRNA distribution and retention that strongly correlated with hydrophobicity. Non-conjugated or linker-only hsiRNAs showed minimal retention in the brain (similar to that of antisense oligonucleotides) and the most hydrophobic compounds, cholesterol and GM1, were primarily retained near the site of injection. Optimal retention/distribution was achieved with DHA and calciferol conjugates (infra), which have intermediate hydrophobicity profiles. DHA-hsiRNA was studied in detail and showed great efficacy and unprecedented safety (therapeutic index >20-fold) (Nikan et al., 2016; Molecular Therapy, in revision, see Appendix). In summary, the data presented herein show that tuning the hydrophobicity of conjugates is a valid strategy to identify conjugates that support optimal retention, distribution, and safety in brain tissues.

Figure 108:
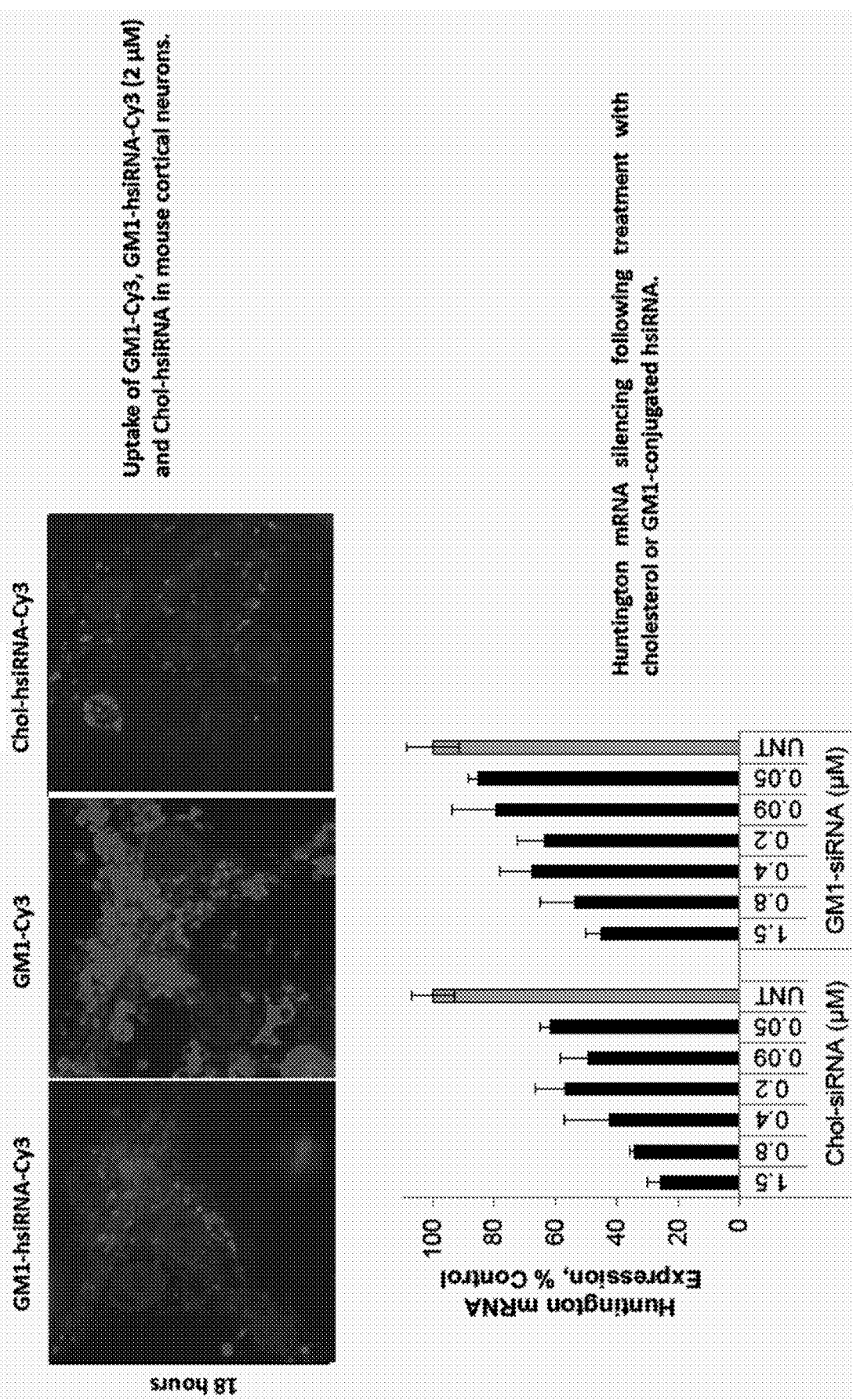
FIG. 108 depicts GM1-hsiRNA internalization and GM1-hsiRNA-mediated htt mRNA silencing.
Figure 109:
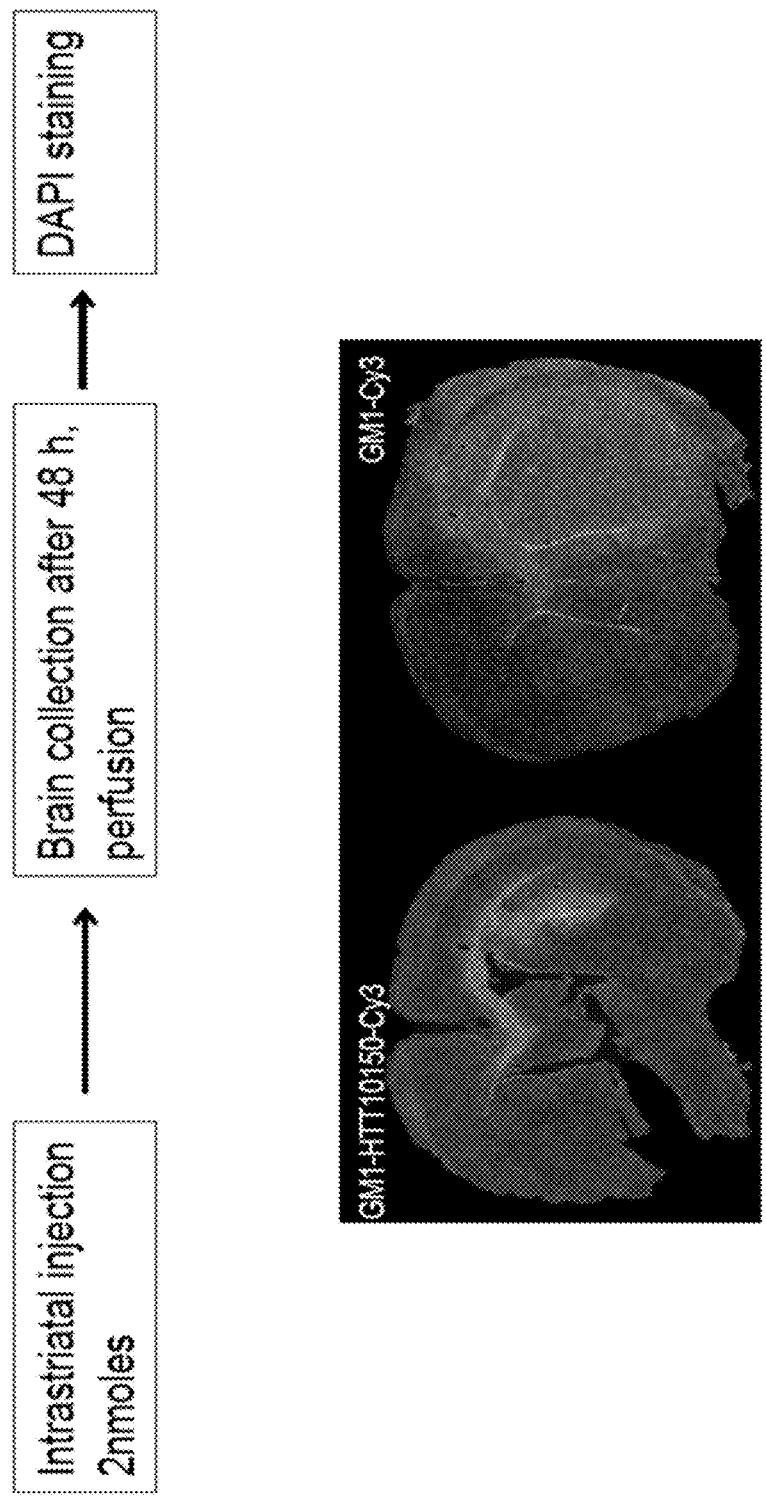
FIG. 109 depicts GM1-hsiRNA brain distribution.
Figure 110A:
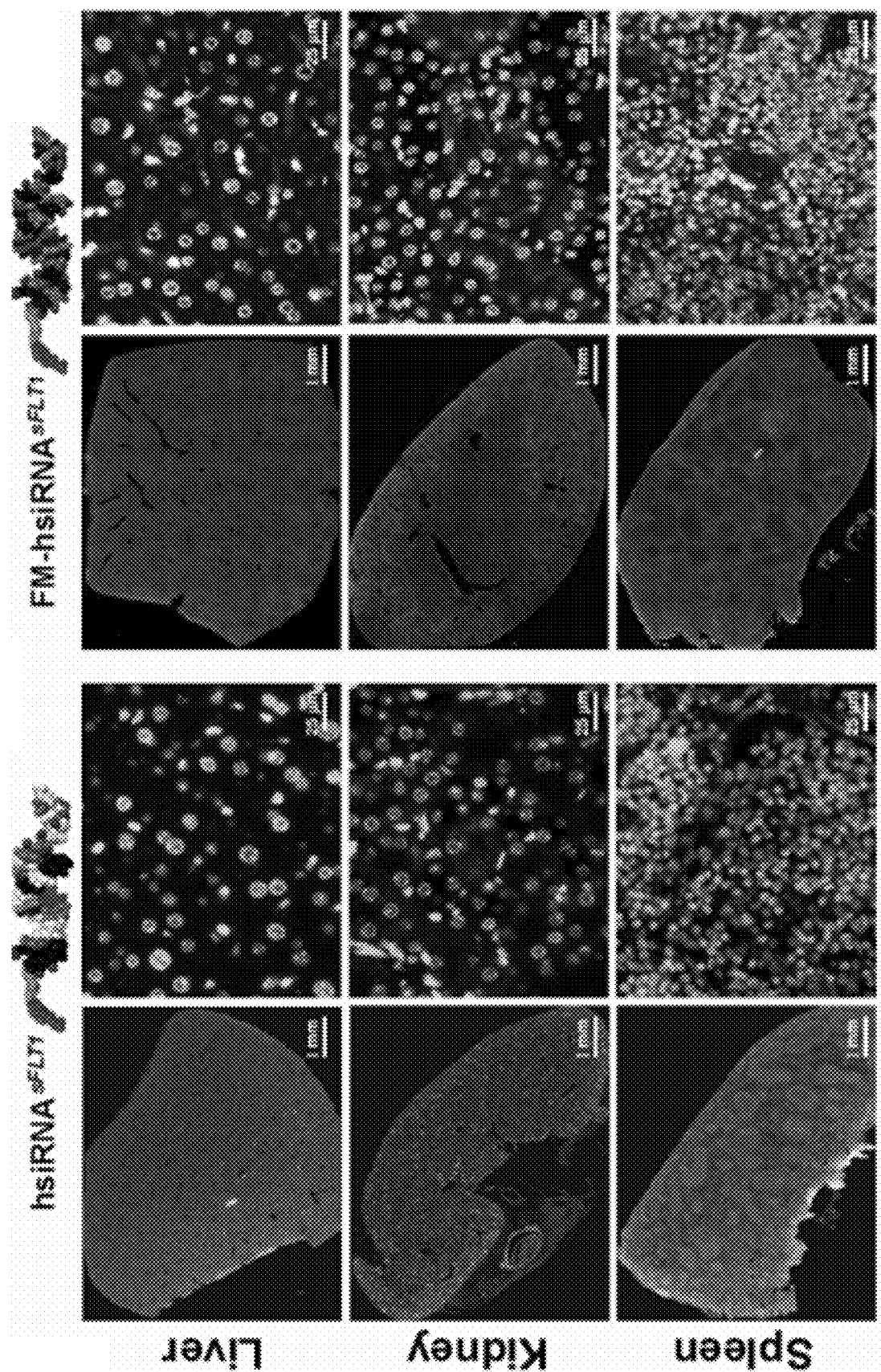
FIGS. 110A-110G show that systemically-administered fully modified (FM) hsiRNA exhibits dramatically enhanced tissue distribution and efficacy in vivo. (A) Tissue distribution of Cy3-hsiRNA and Cy3-FM-hsiRNAsFLT1 (red) 10 mg/kg IV injection. Nuclei stained with DAPI (blue). All images were acquired at identical settings. (B-E) Guide strand quantification by PNA hybridization-based assay (B) 10 mg/kg, IV, 24 hours (C) 10 mg/kg, SC, 24 hours (D) 2×20 mg/kg, IV, 120 hours, (n=7) (E) 2×15 mg/kg, IV, 120 hours, (n=12). (F, G) Quantification of sFLT1 mRNA silencing after (F) 2×20 mg/kg, C57B6 mice, (n=3, PBS; n=7, FM-hsiRNAsFLT), (G) 2×15 mg/kg, CD1 mice. (n=12, for PBS; n=6, NTC; n=12, FM-hsiRNAsFLT1). mRNA levels were measured 120 hours after injection with QuantiGene® (Affymetrix) assay, normalized to housekeeping gene FLT1, and presented as percent of PBS treated control. All error bars represent mean+SD. *, P<0.001; **, P<0.0001.
Figure 110B:
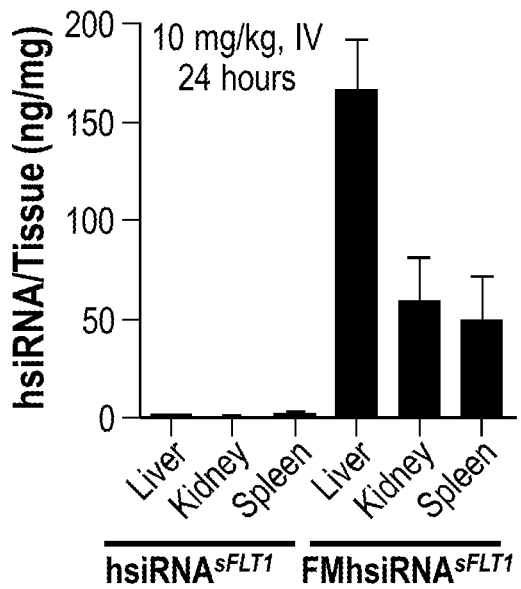
Figure 110C:
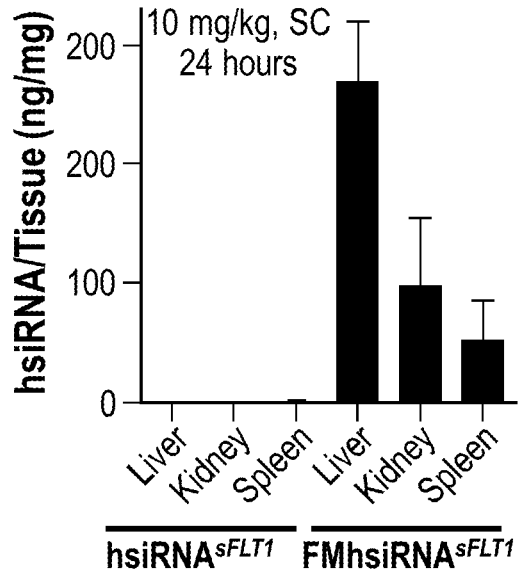
Figure 110D:
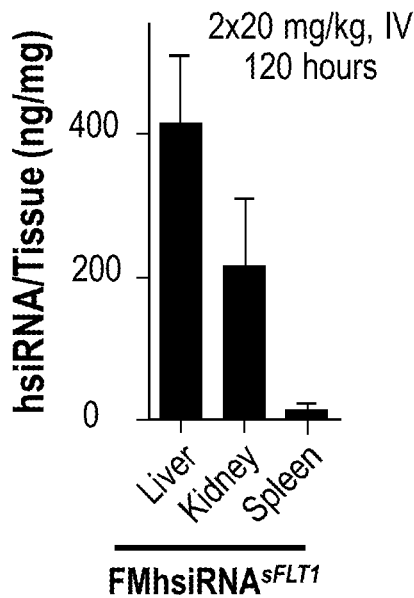
Figure 110E:
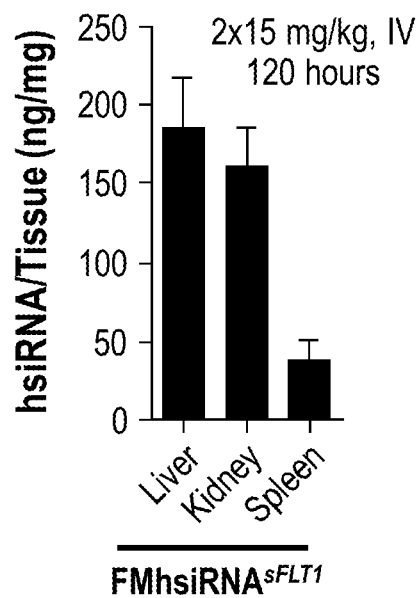
Figure 110F:
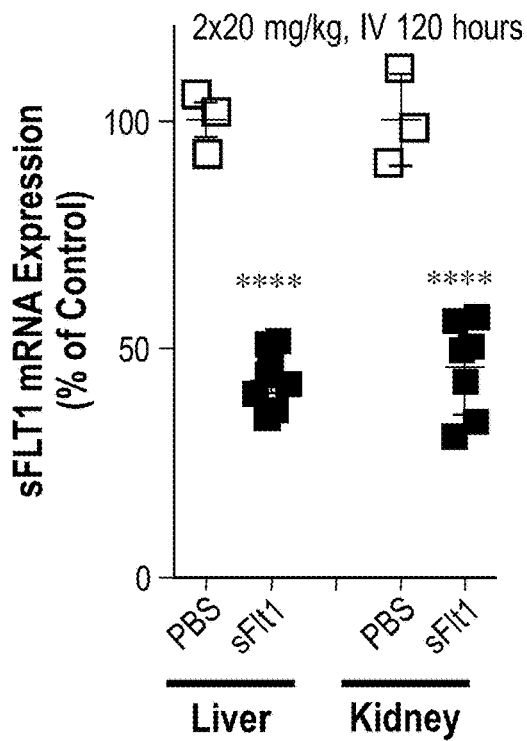
Figure 110G:
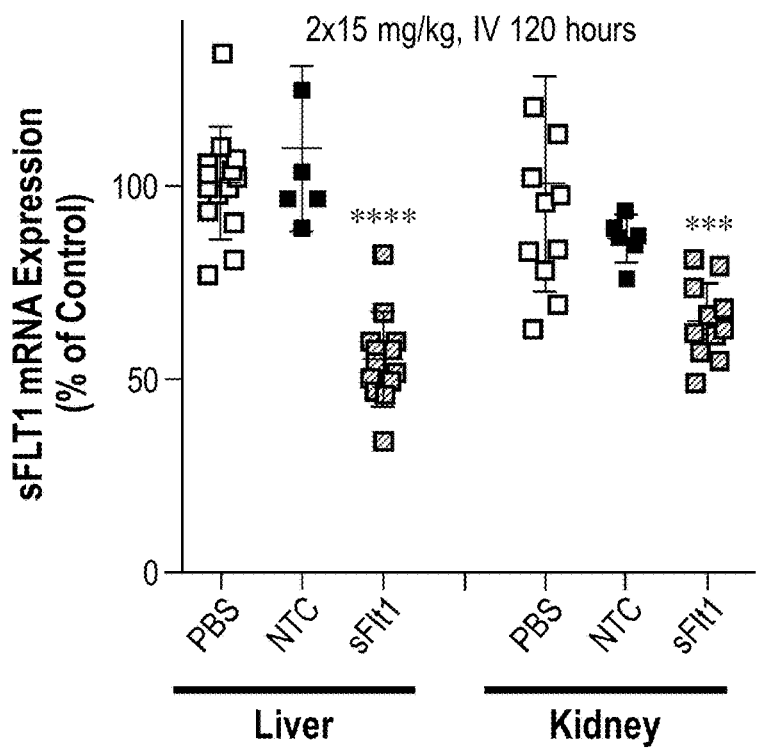
Figure 111F:
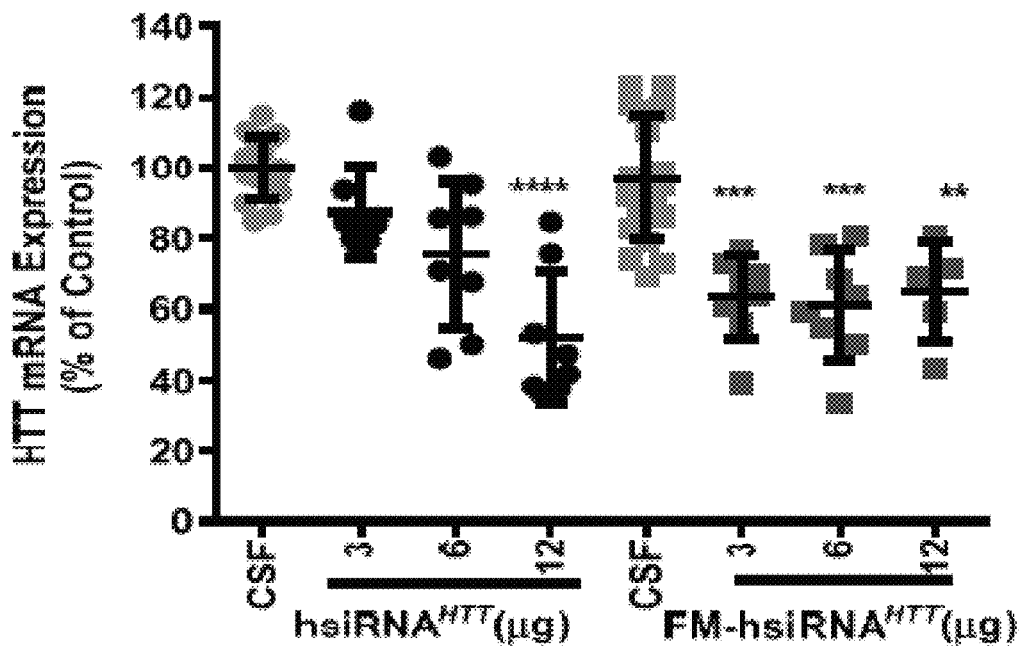
Figure 111G:
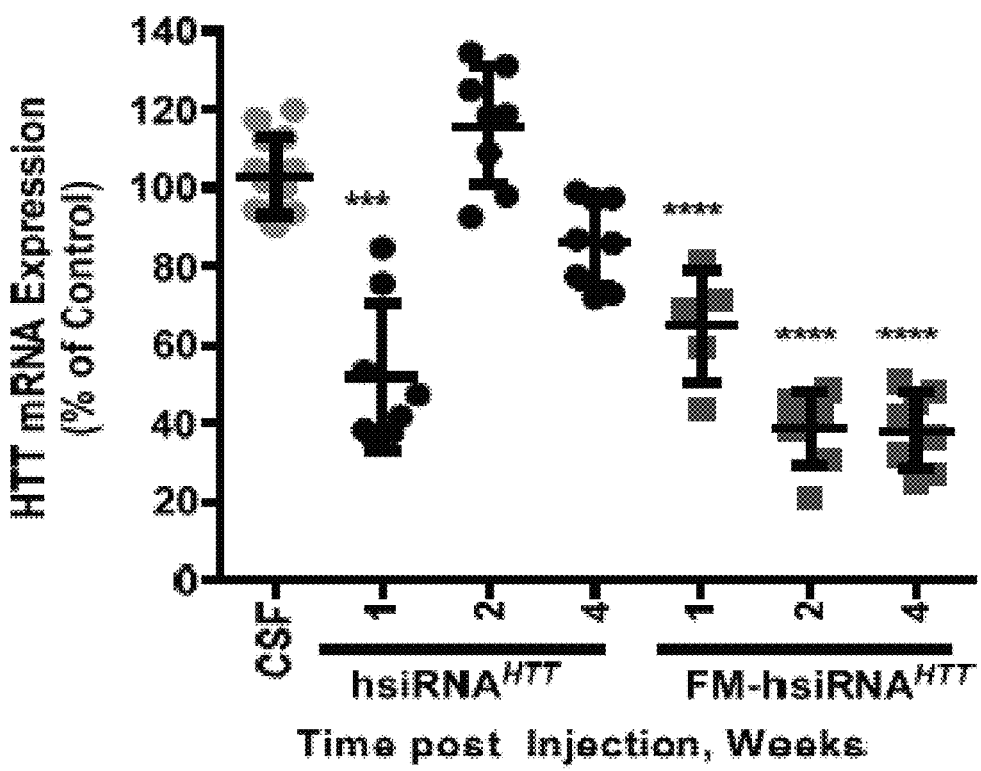

GM1-hsiRNA was efficiently internalized and induced huntingtin mRNA silencing in primary cortical neurons (FIG. 108). GM1-hsiRNA displayed limited distribution in mouse brain upon intrastriatal injection (FIG. 109).

Example 3. DHA-hsiRNA

Figure 35A:
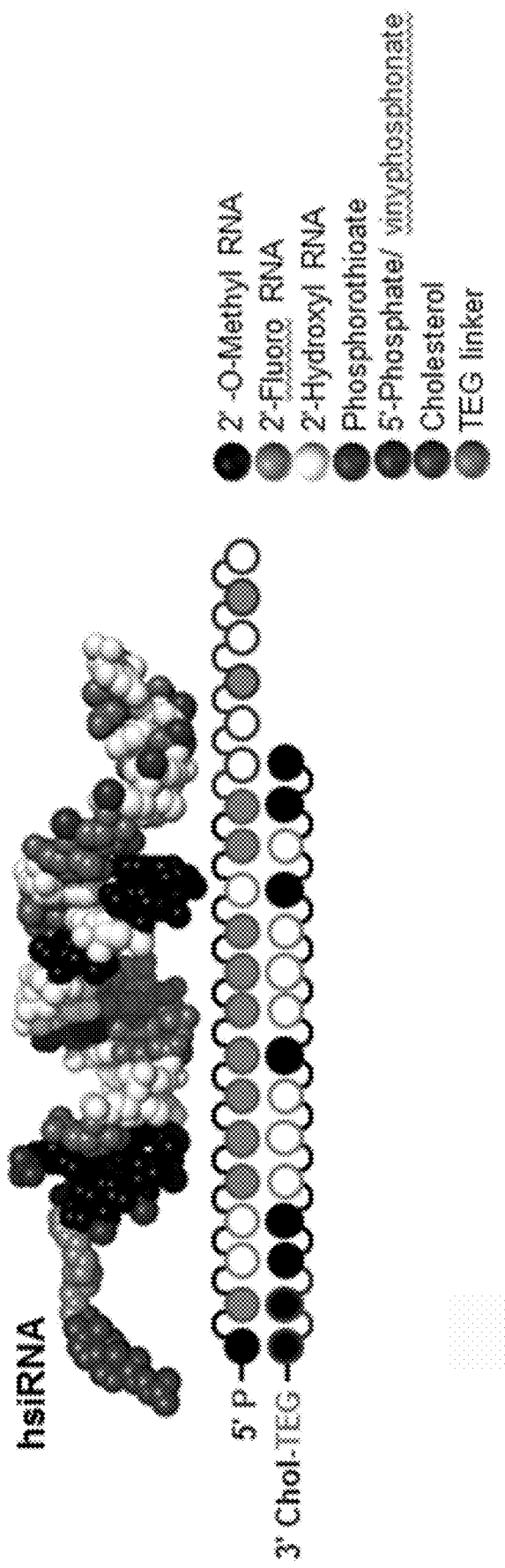
FIGS. 35A-35C show that partially modified hsiRNAs exhibit a short duration of effect and no systemic exposure.
Figure 35B:
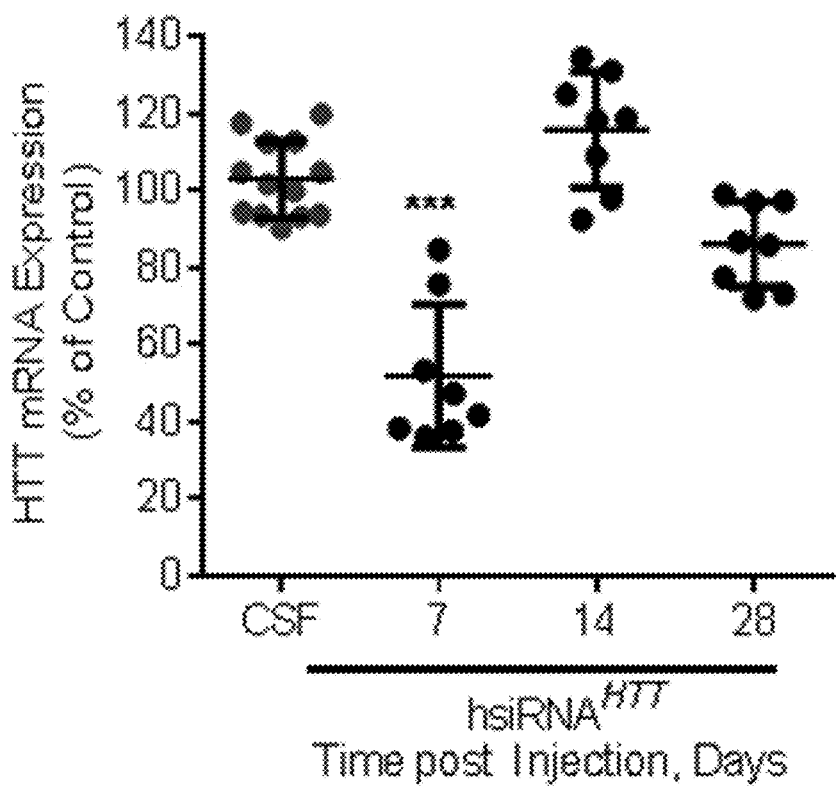
Figure 35C:
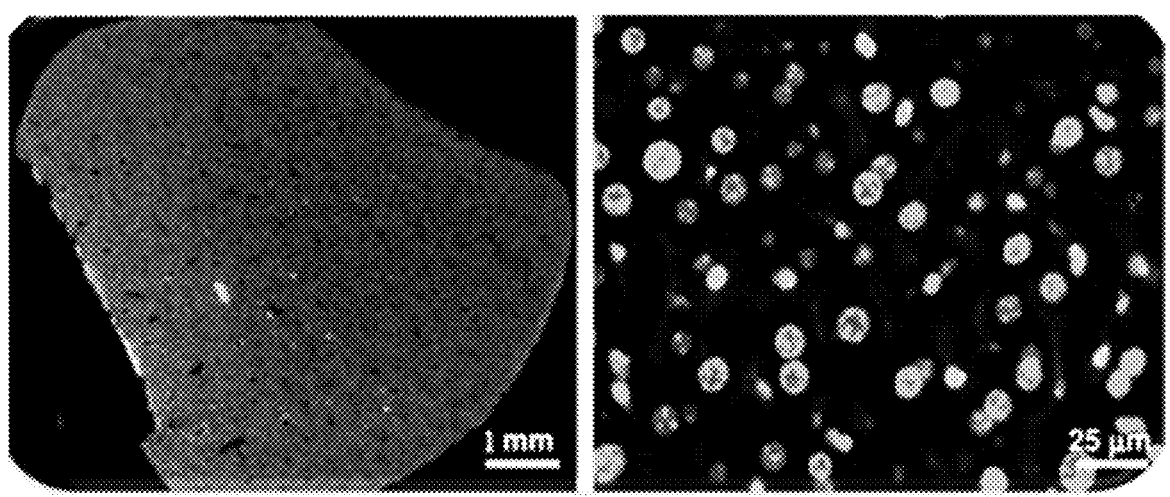
Figure 36B:
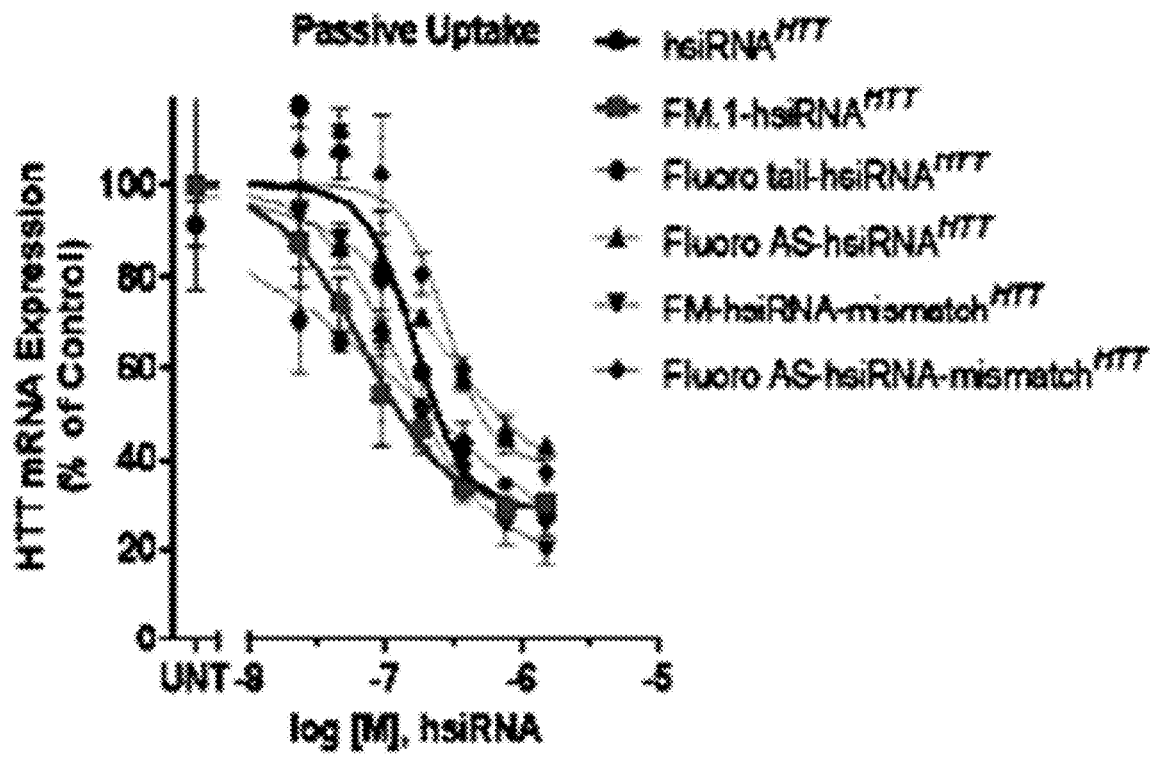
Figure 36C:
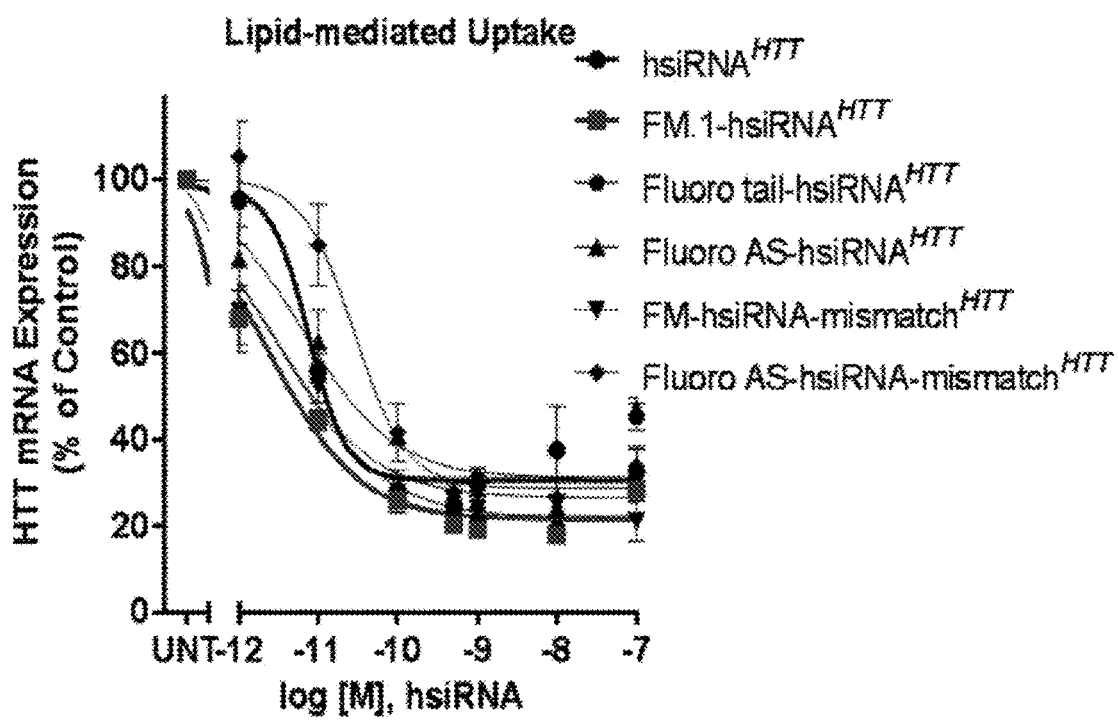
Figure 37A:
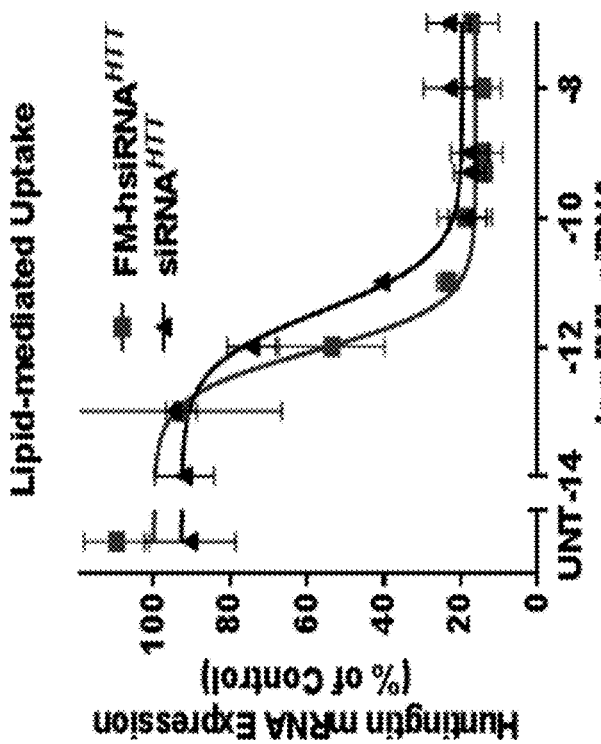
FIGS. 37A-37C show that full metabolic stabilization does not interfere with RISC entry of hsiRNAs.
Figure 37B:
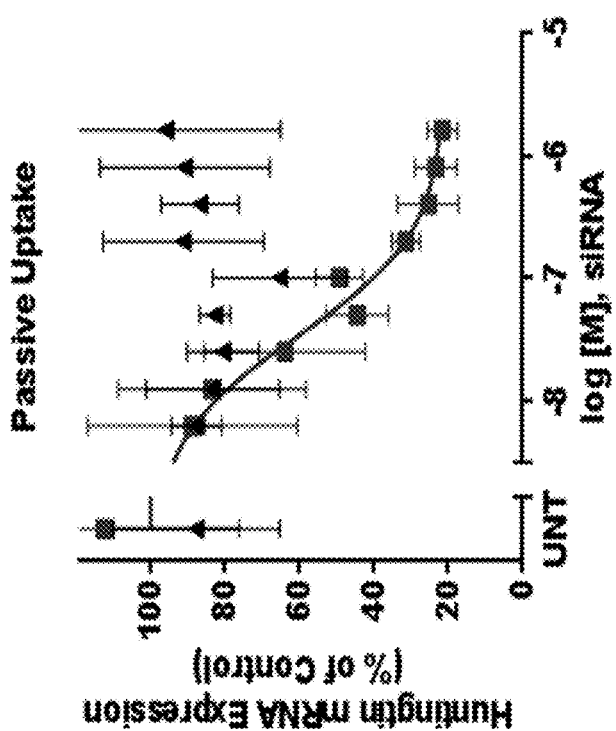
Figure 37C:
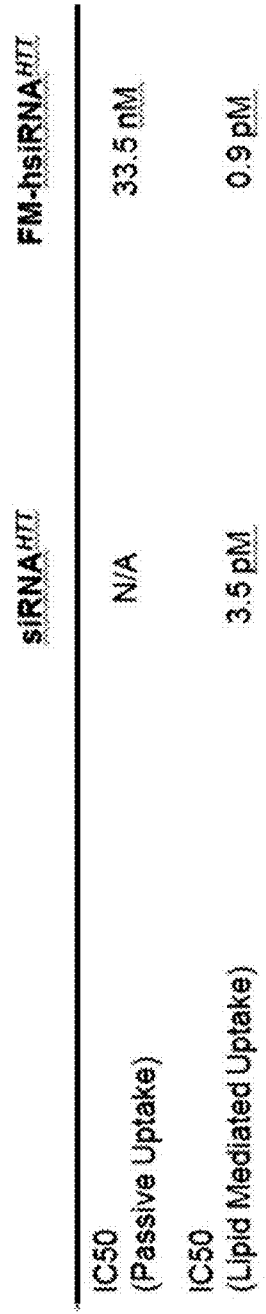
Figure 39A:
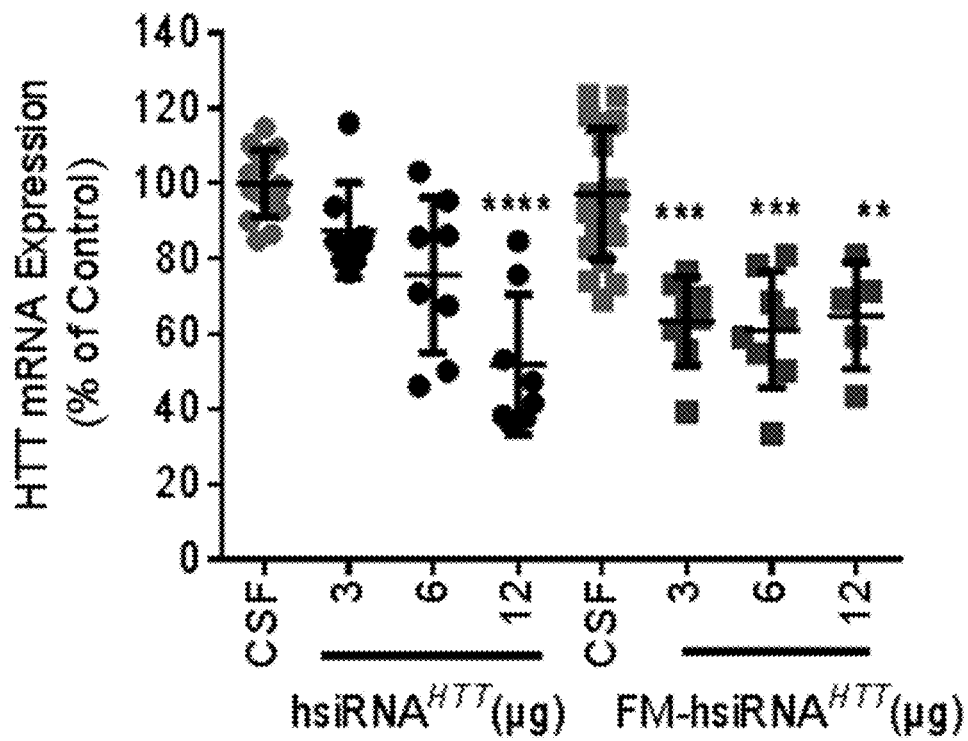
FIGS. 39A-39B depict enhanced potency and duration of effect mediated by FM-hsiRNA.
Figure 39B:
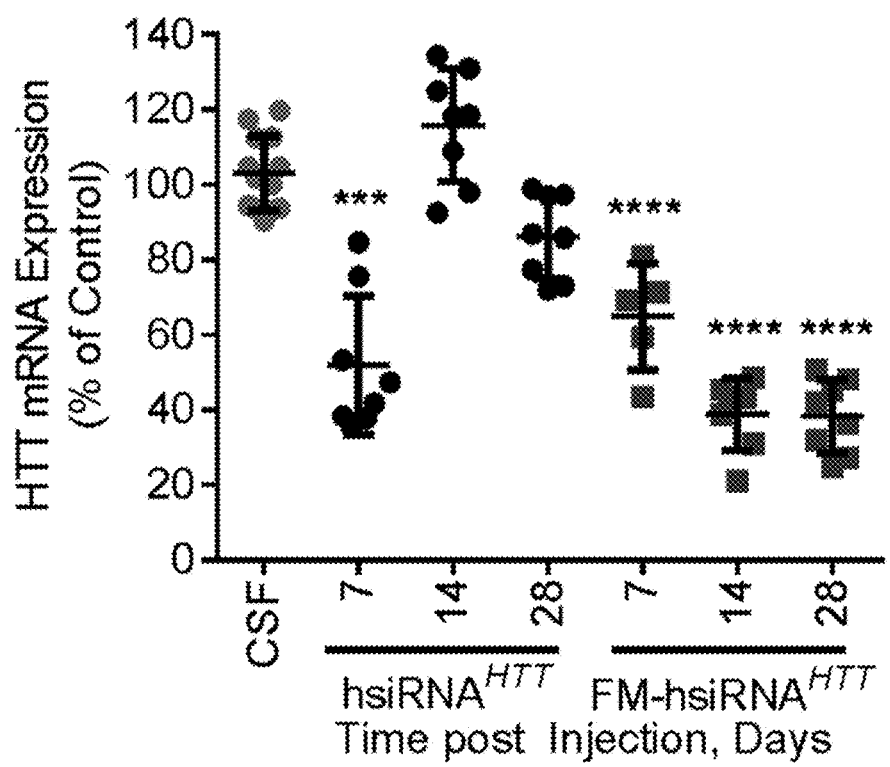

Partially-modified hsiRNAs demonstrated a short duration of effect and no systemic exposure (FIGS. 35A-C). Metabolic stabilization was further explored (FIG. 36). Full metabolic stabilization did not interfere with RISC entry of hsiRNAs (FIG. 37). Fully metabolically stabilized hsiRNA (FM-hsiRNA) enhanced local delivery and distribution and enabled a longer duration of effect (FIGS. 38, 39A-B, 91, 110 and 111 The term "nucleoside").

Figure 40A:
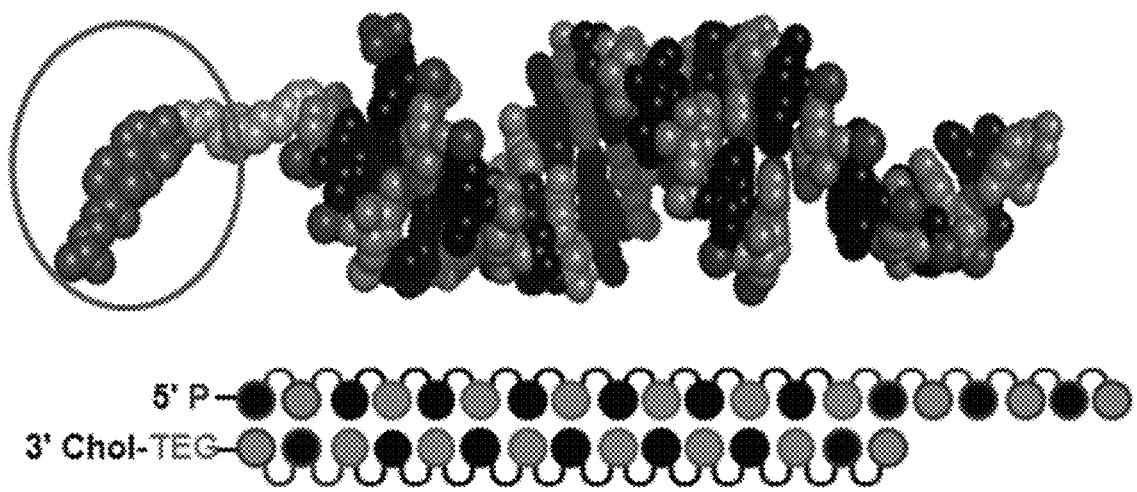
FIG. 40A-40B characterizes neuroactive, naturally occurring lipids as hsiRNA bioconjugates.
Figure 40B:
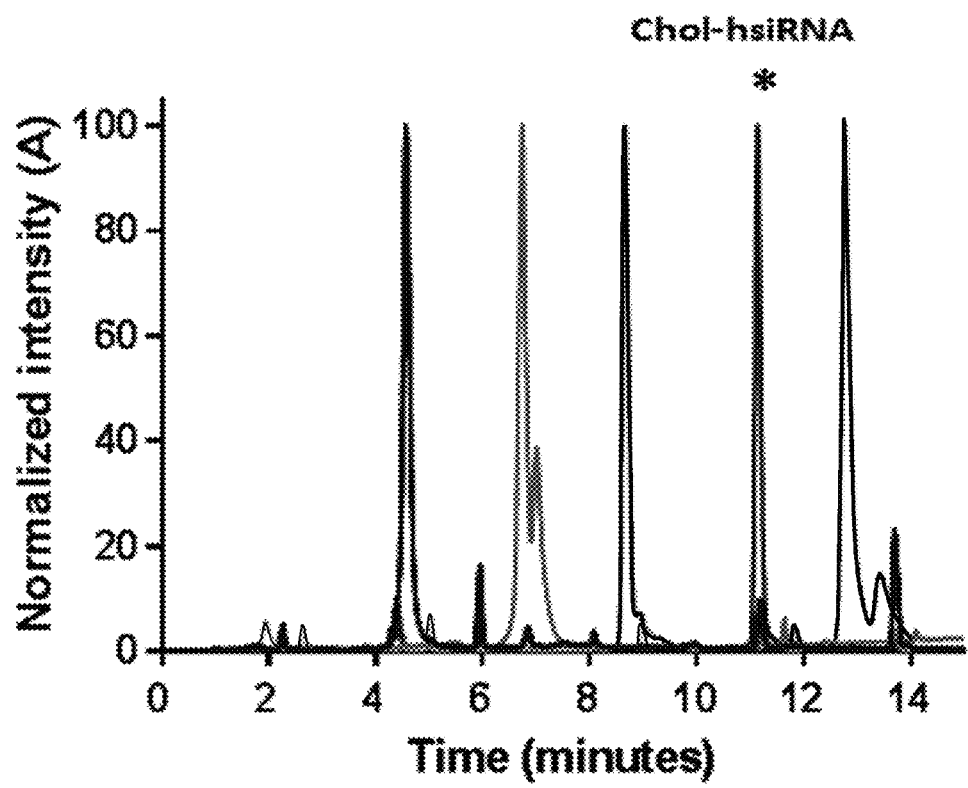

Naturally-occurring lipids (i.e., glycosphingolipids, polyunsaturated fatty acids, secosteroids, steroid hormones and sterol lipids) were investigated as hsiRNA bioconjugates (FIG. 40). Lipid bioconjugates had a pronounced effect on hsiRNAHTT sense strand hydrophobicity.

Figure 41:
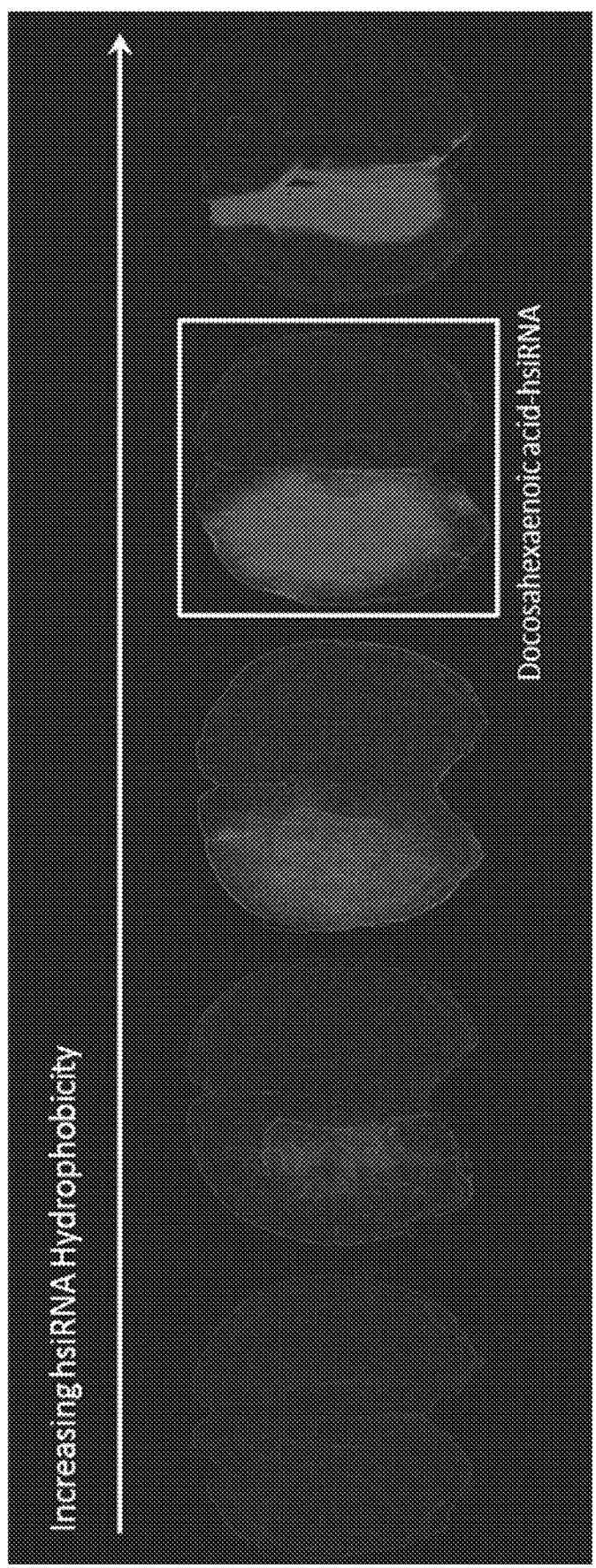
FIG. 41 depicts that hsiRNA hydrophobicity directly correlates with brain distribution and retention. Intrastriatal injection, 12.5 μg (0.5 mg/kg), t=24 hours, FVB/NJ mice (n=2).

A study was designed to explore in vivo distribution of hsiRNA conjugates. Intrastriatal unilateral injection (2 nmol/2 µl) of FVBN WT mice with P2-stabilized siRNA CY3 conjugates in aCSF was performed. 48 hours post-injection, animals were perfused with PBS and 10% formalin. Their brains were removed and post-fixed for 48 hours. 4 µm coronal and sagittal slices were prepared and stained with DAPI. Imaging was performed on a Leica DM 5500 fluorescent microscope (CY3 and DAPI). It was determined that hsiRNA hydrophobicity was directly correlated with brain distribution and retention (FIG. 41). A key property was a balance between distribution and retention.

Docosahexaenoic acid (DHA)—hsiRNAs were synthesized (FIG. 42). DHA is an omega-3 fatty acid that is a primary component of the human brain (70%). DHA crosses the bold brain barrier (BBB) and is actively internalized by neurons and other cell types. It is a non-toxic supplement clinically shown to improve cognitive function in HD and ALS patients. DHA is significantly less hydrophobic that cholesterol.

Figure 43:
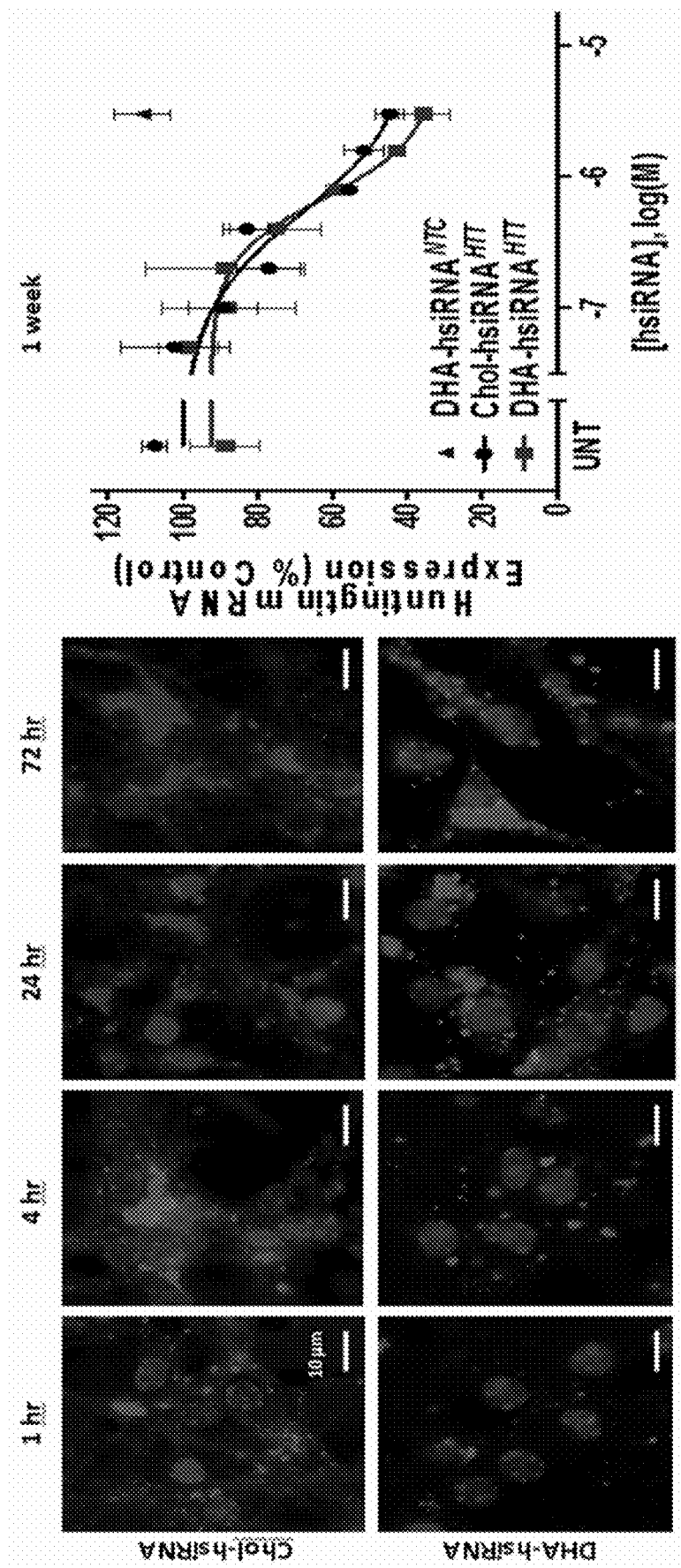
FIG. 43 depicts internalization of DHA-hsiRNA and chol-hsiRNA into primary cortical neurons. Uptake: 0.5 μM Cy3-DHA-hsiRNA (red), DAPI (blue).
Figure 44:
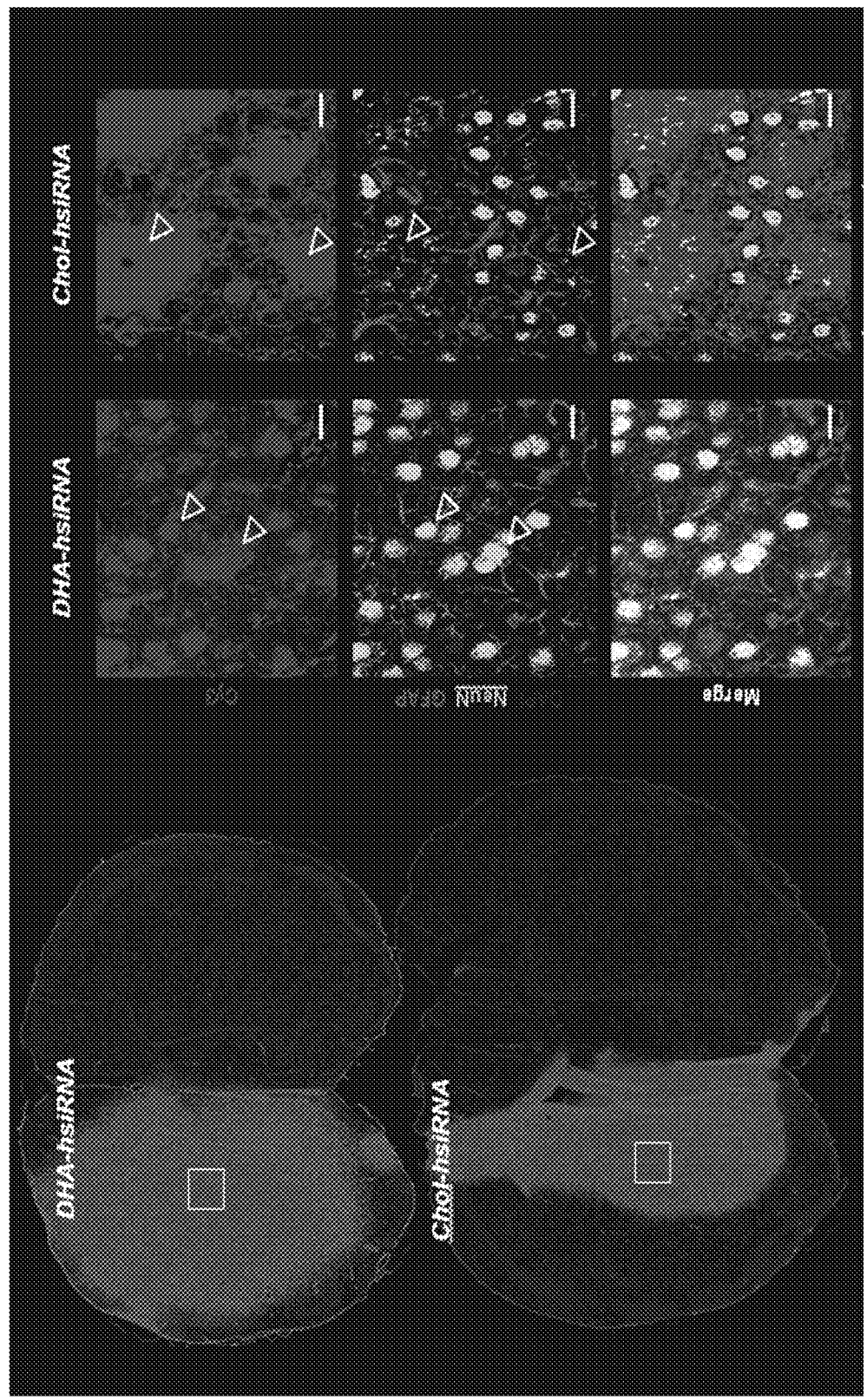
FIG. 44 depicts co-localization of DHA-hsiRNA with neurons and astrocytes. Intrastriatal injection, 12.5 μg (0.5 mg/kg), t=24 hours, FVB/NJ mice (n=2).
Figure 45:
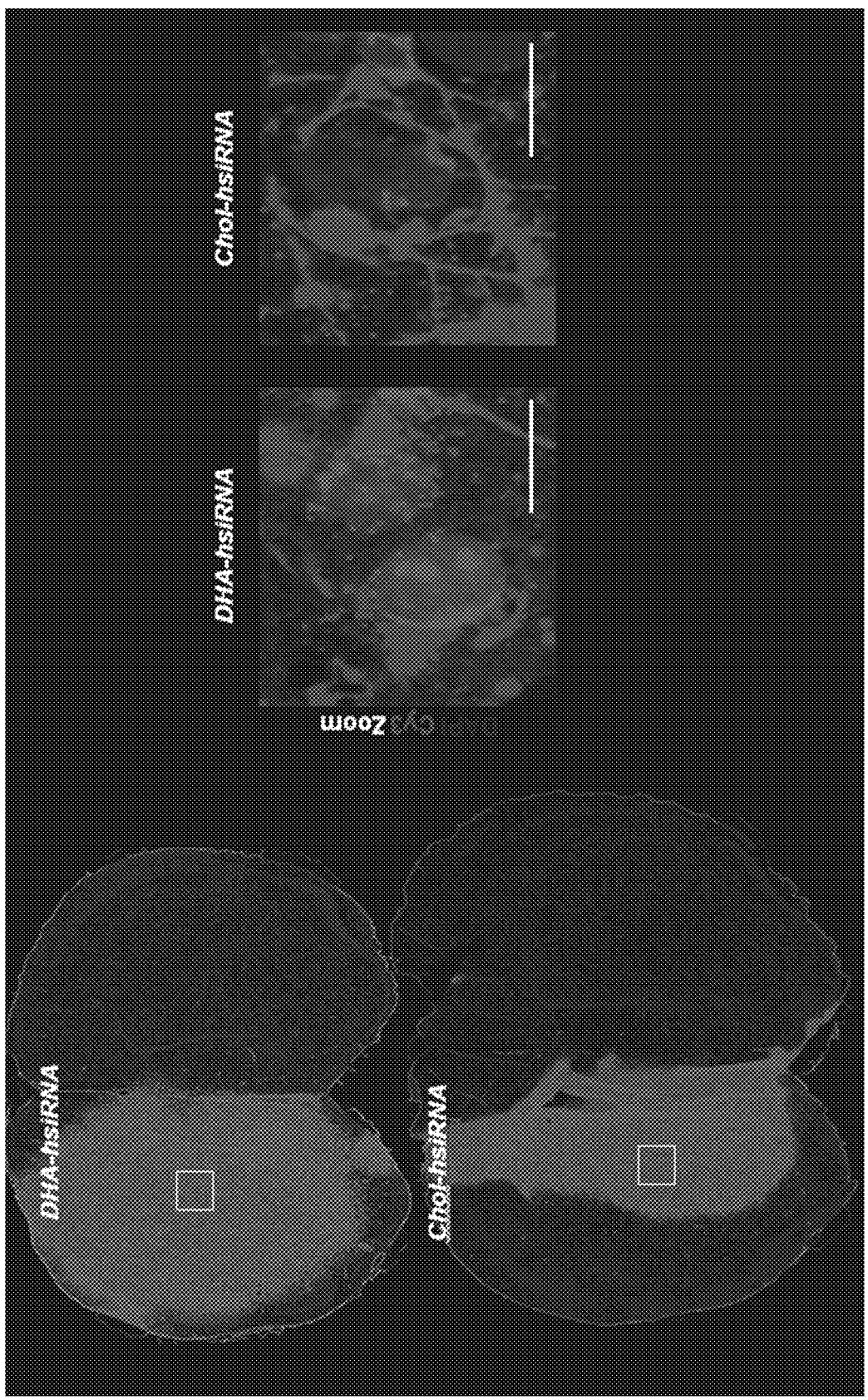
FIG. 45 depicts localization of DHA-hsiRNA to the perinuclear region in striatal neurons, while chol-hsiRNA is undetectable. Intrastriatal injection, 12.5 μg (0.5 mg/kg), t=24 hours, FVB/NJ mice (n=2).
Figure 46:
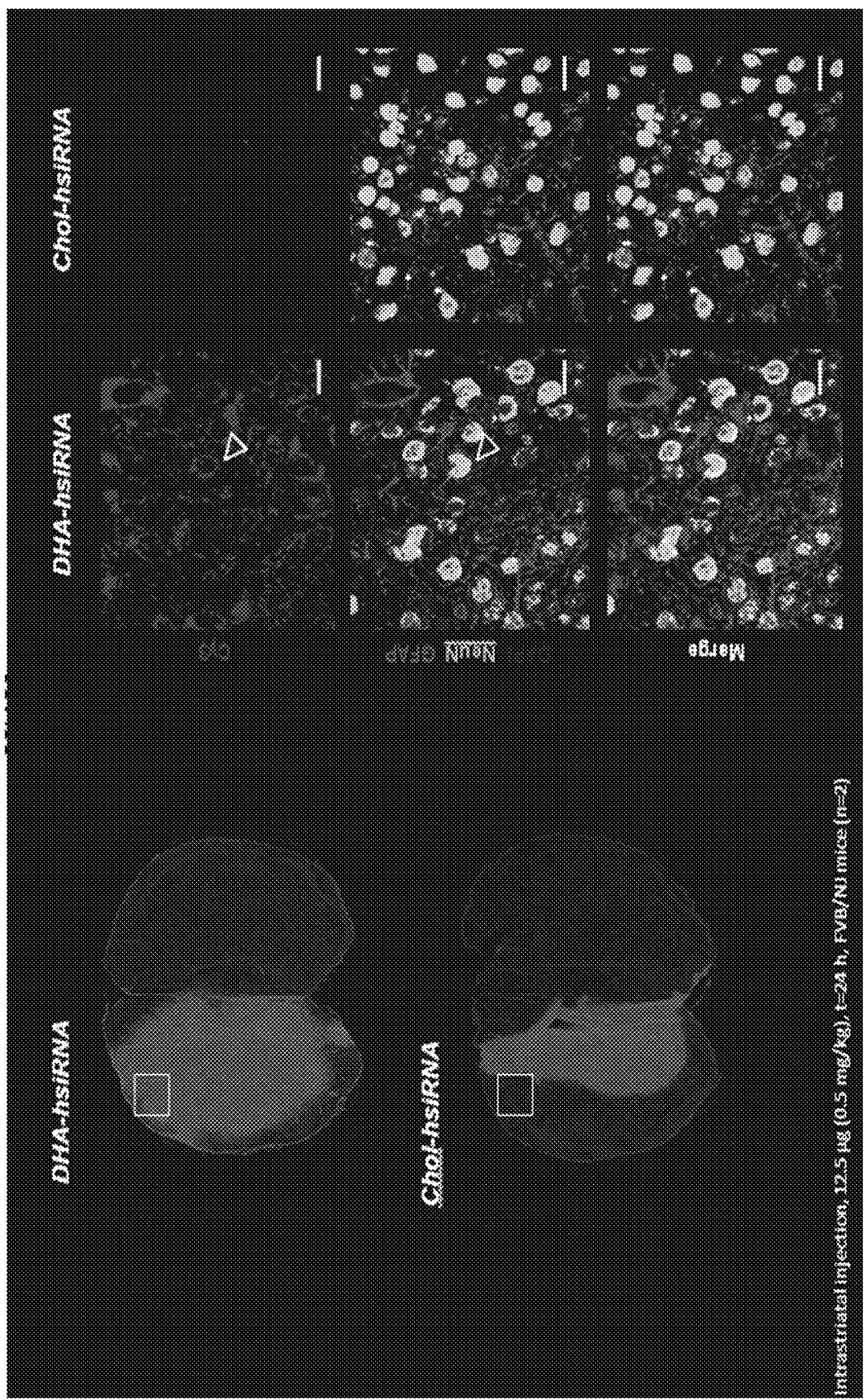
FIG. 46 depicts co-localization of DHA-hsiRNA with neurons and astrocytes in the cortex following a single intrastriatal injection. Intrastriatal injection, 12.5 μg (0.5 mg/kg), t=24 hours, FVB/NJ mice (n=2).
Figure 47:
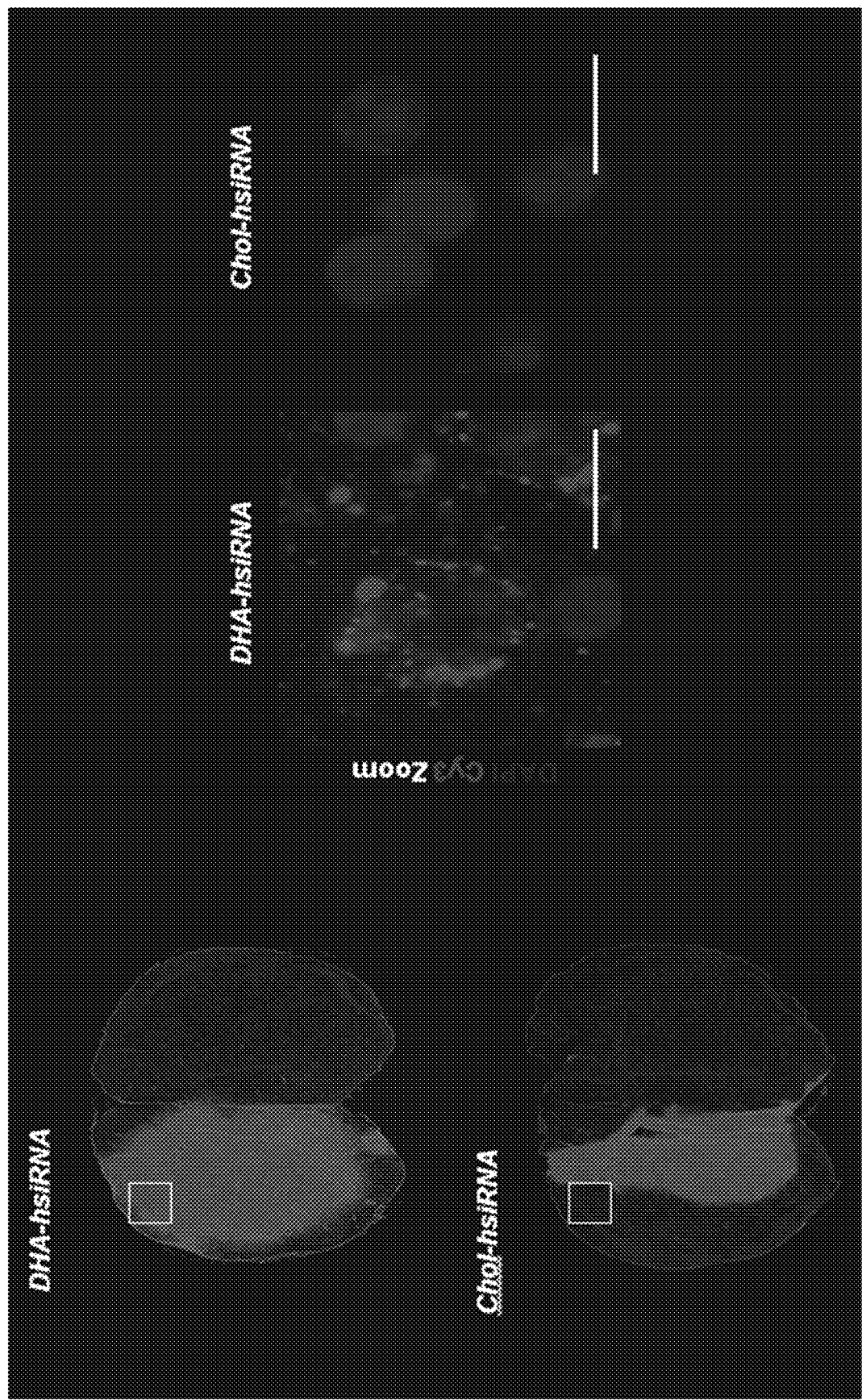
FIG. 47 depicts localization of DHA-hsiRNA to the perinuclear region in cortical neurons, while chol-hsiRNA is undetectable.
Figure 57:
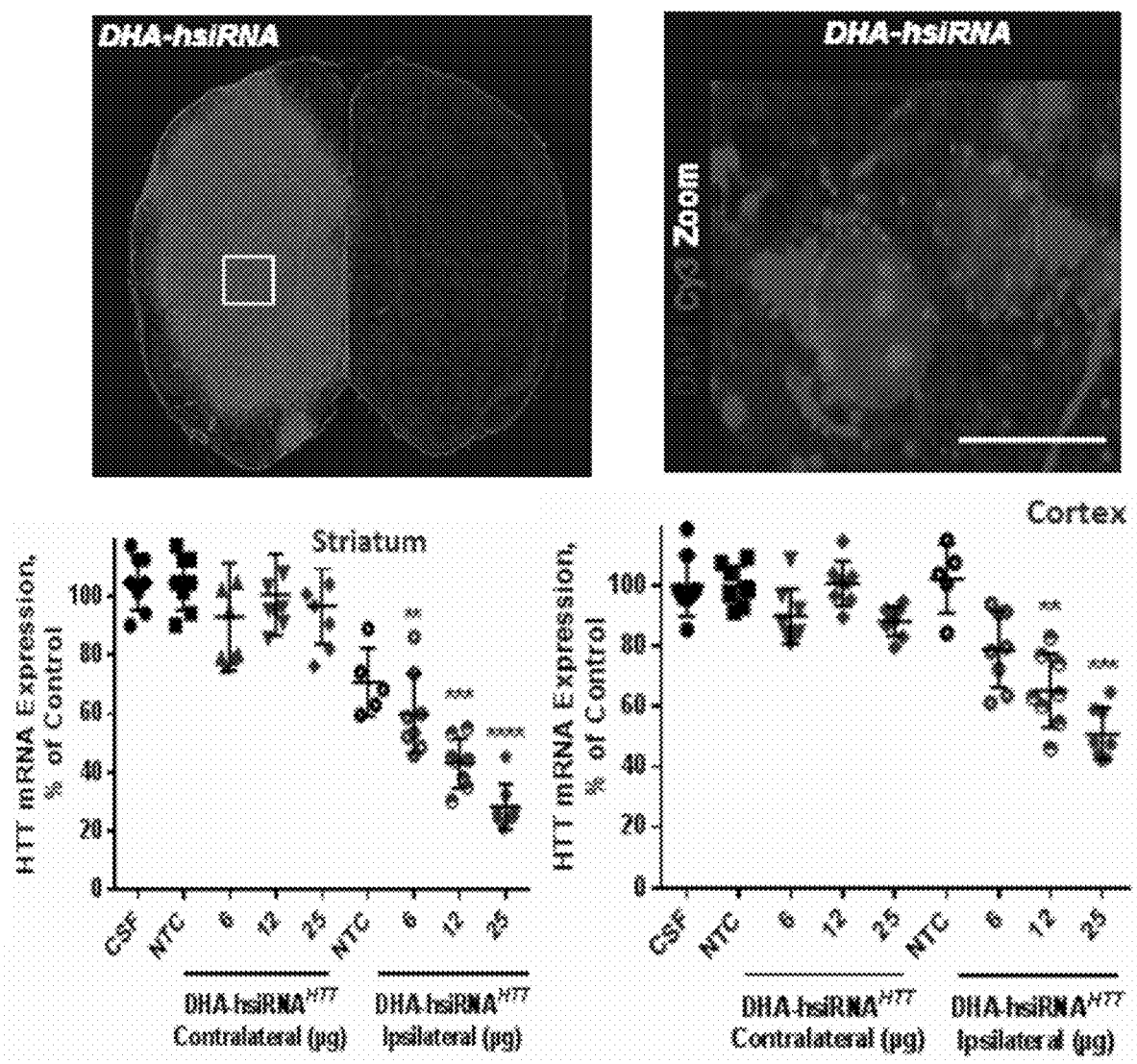
FIG. 57 shows that DHA-hsiRNA efficiently distributes throughout the brain and silences genes in both the striatum and the cortex. Intrastriatal injection, 12.5 µg (0.5 mg/kg), t=24 hours, FVB/NJ mice (n=2).

DHA-hsiRNA and chol-hsiRNA were shown to be internalized into primary cortical neurons (FIG. 43). DHA-hsiRNA co-localized with neurons and astrocytes (FIG. 44) and was localized to the perinuclear region of striatal neurons (chol-hsiRNA was undetectable in striatal neurons) (FIG. 45). DHA-hsiRNA co-localized with neurons and astrocytes in the cortex following a single intrastriatal injection (FIG. 46). DHA-hsiRNA localized to the perinuclear region in cortical neurons, while chol-hsiRNA was undetectable (FIG. 47). DHA-hsiRNA efficiently distributed throughout the brain and silenced genes in both the striatum and the cortex (FIG. 57).

Figure 48:
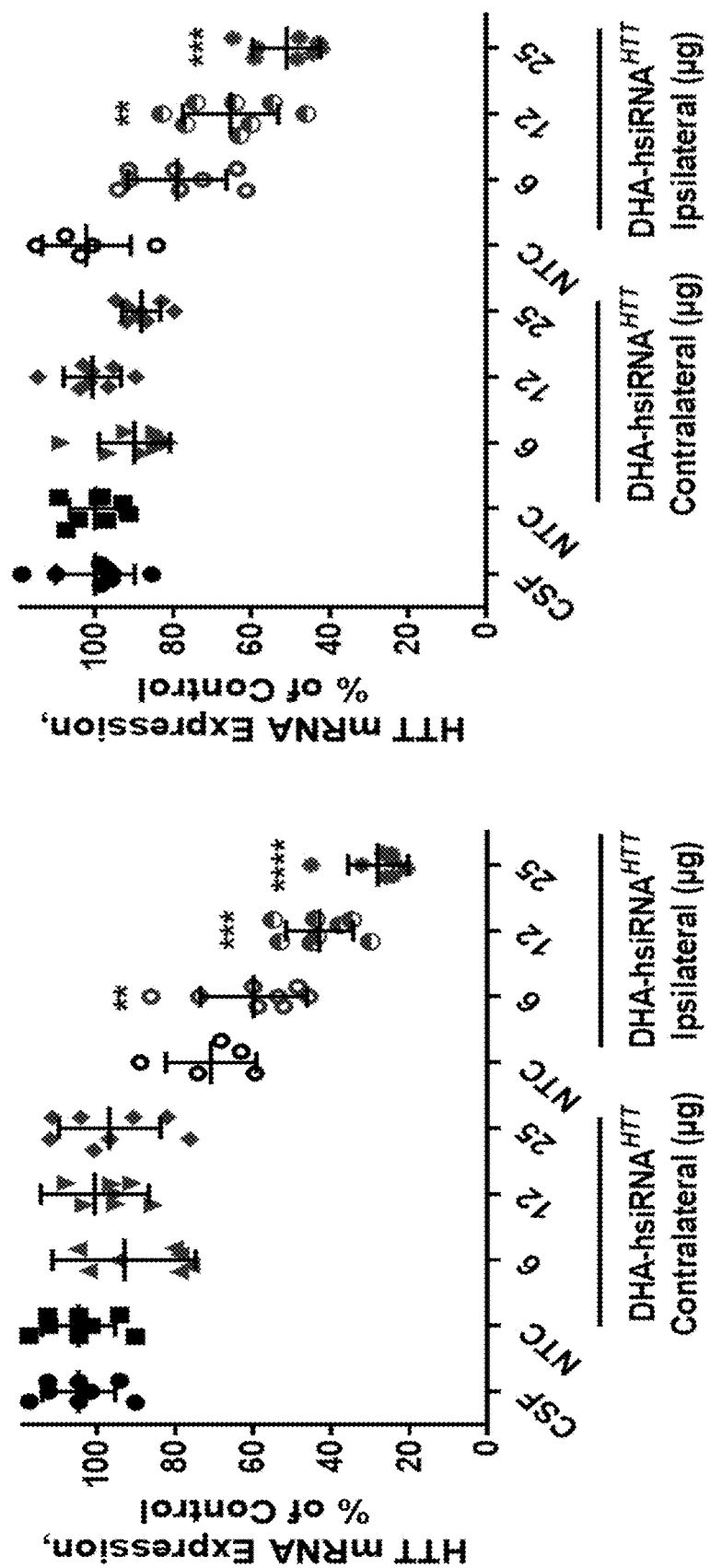
FIG. 48 depicts robust silencing efficiency of DHA-hsiRNA in the striatum and cortex. Intrastriatal injection, 6-25 μg (0.25-1 mg/kg), t=5 days, FVB/NJ mice (n=8).
Figure 49:
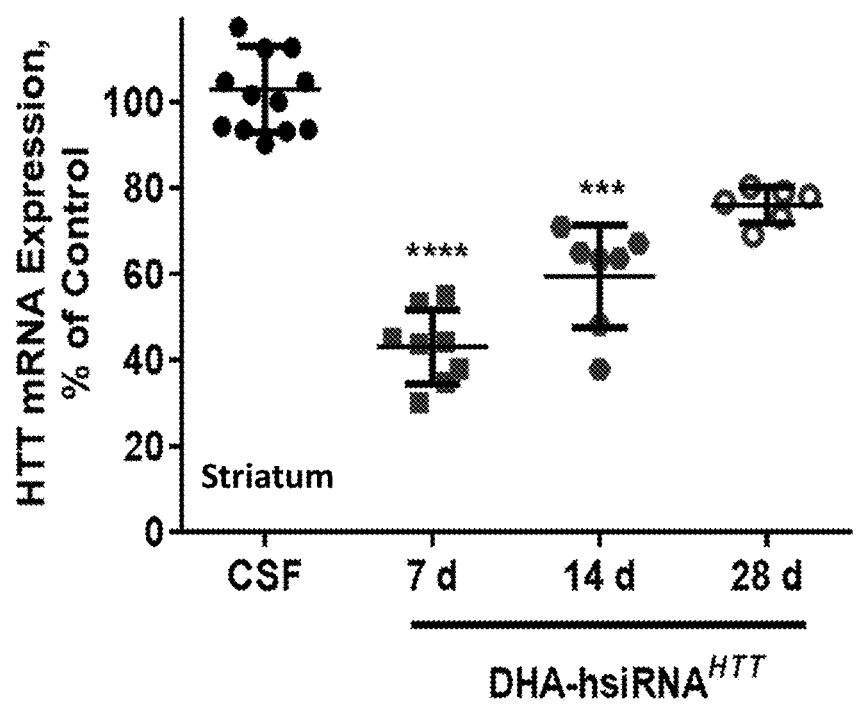
FIG. 49 depicts the duration of effect and recovery in the striatum following a single intrastriatal dose of DHA-hsiRNA.
Figure 50:
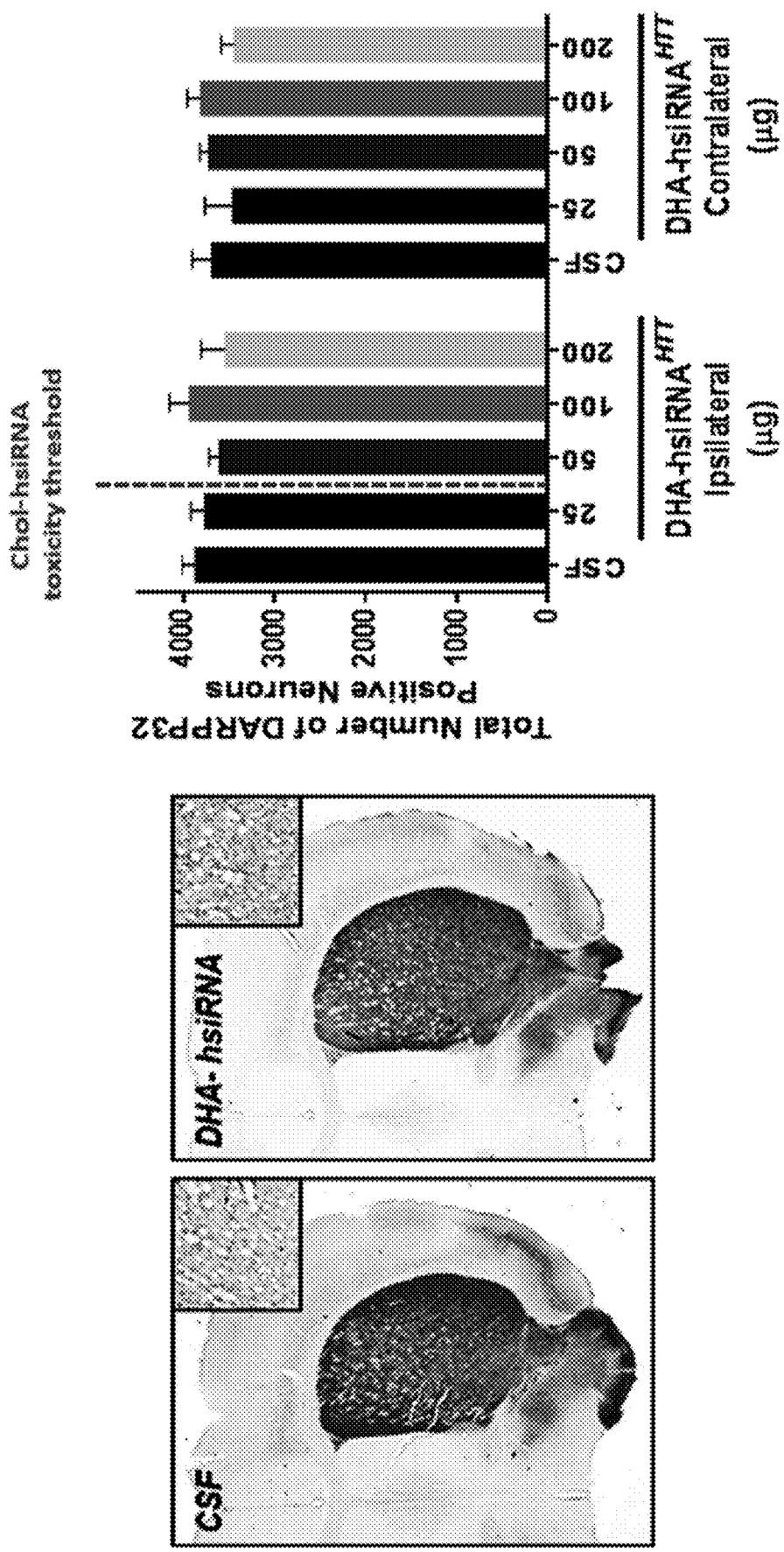
FIG. 50 depicts a pilot safety study showing that DHA-siRNA does not affect striatal neuronal integrity at greater than 20-fold over the efficacious dose.
Figure 51:
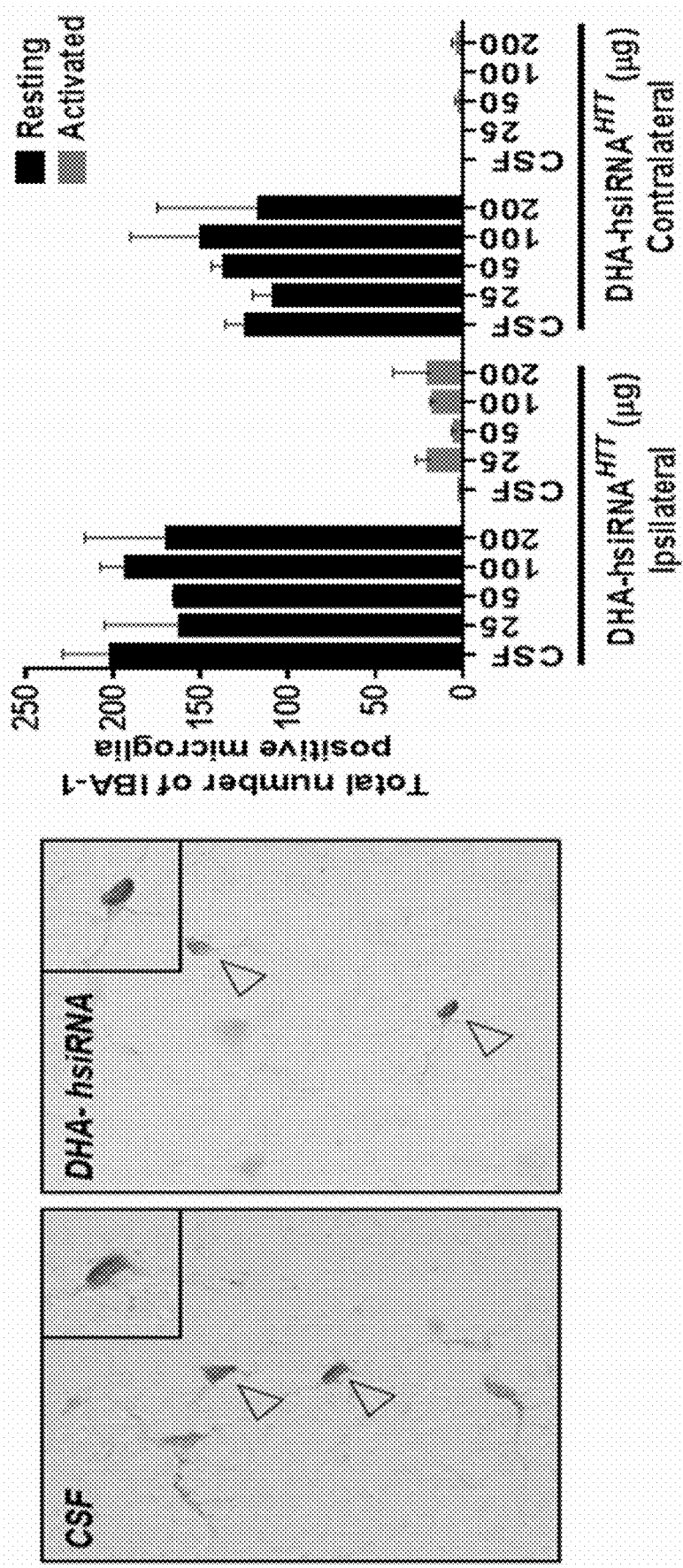
FIG. 51 depicts a pilot safety study showing that DHA-siRNA causes minimal striatal microglial activation at greater than 20-fold over the efficacious dose.
Figure 52:
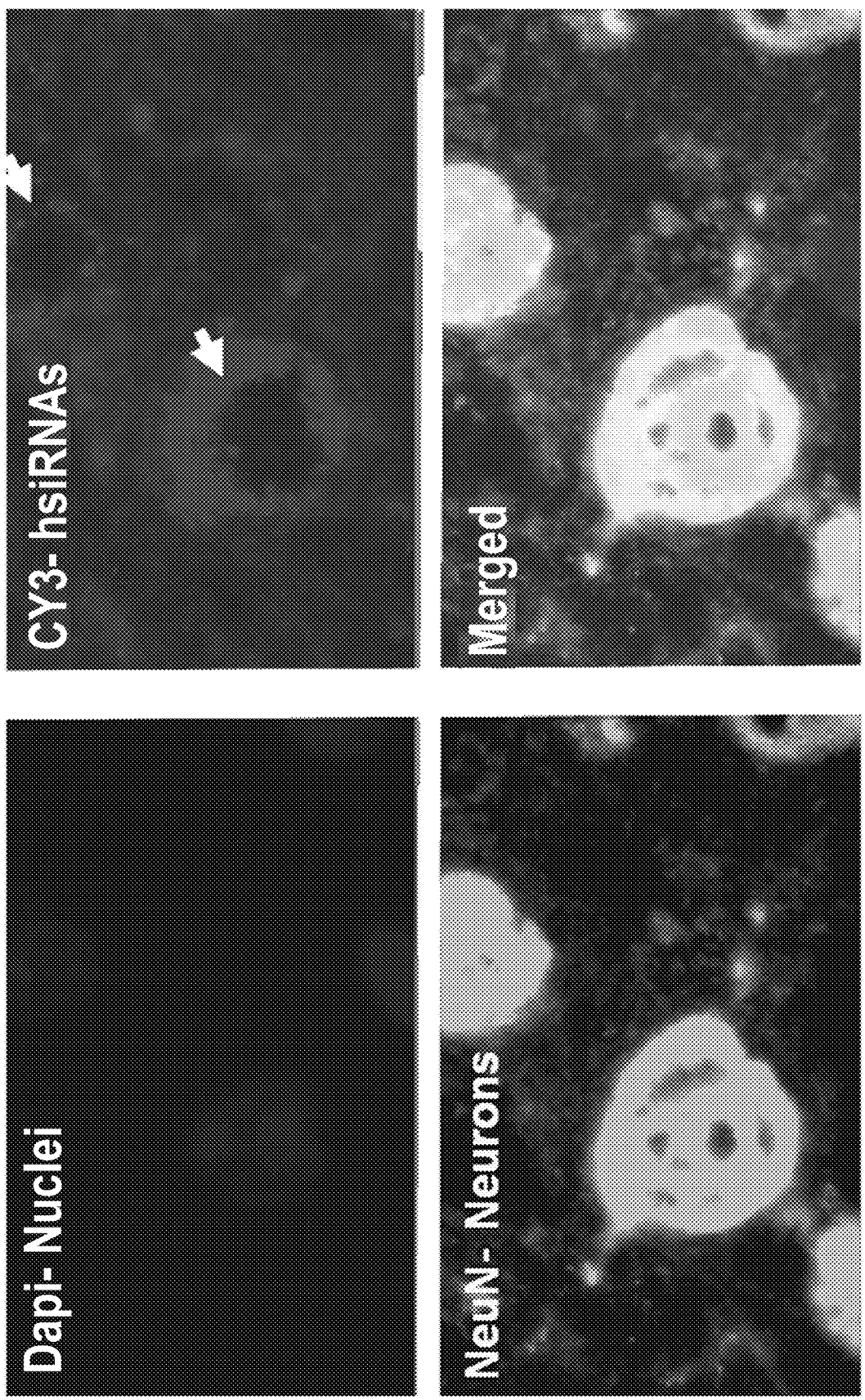
FIG. 52 depicts perinuclear localization caused by oligonucleotide chemistry.
Figure 53:
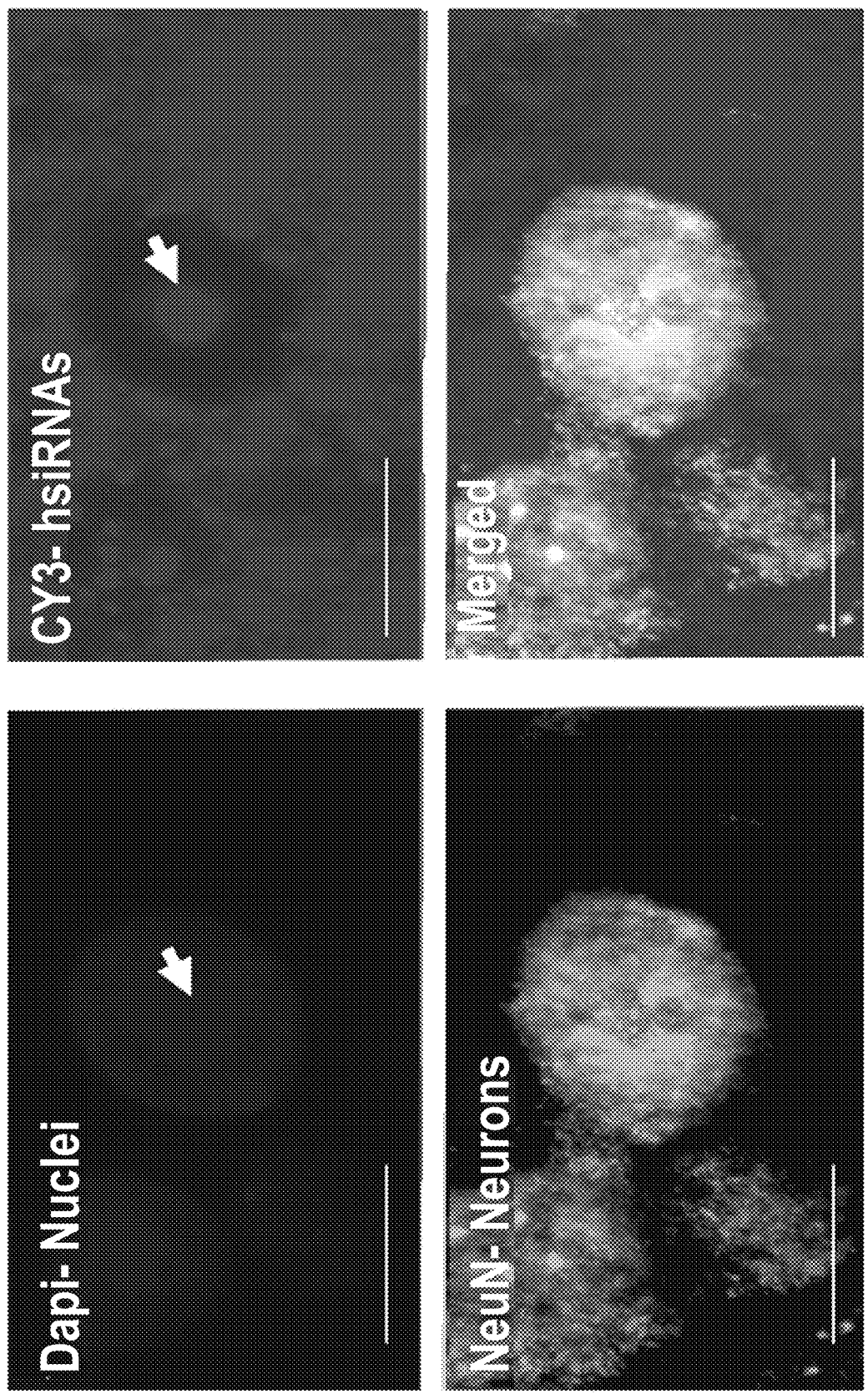
FIG. 53 depicts intra-nuclear foci distribution caused by oligonucleotide chemistry.
Figure 54:
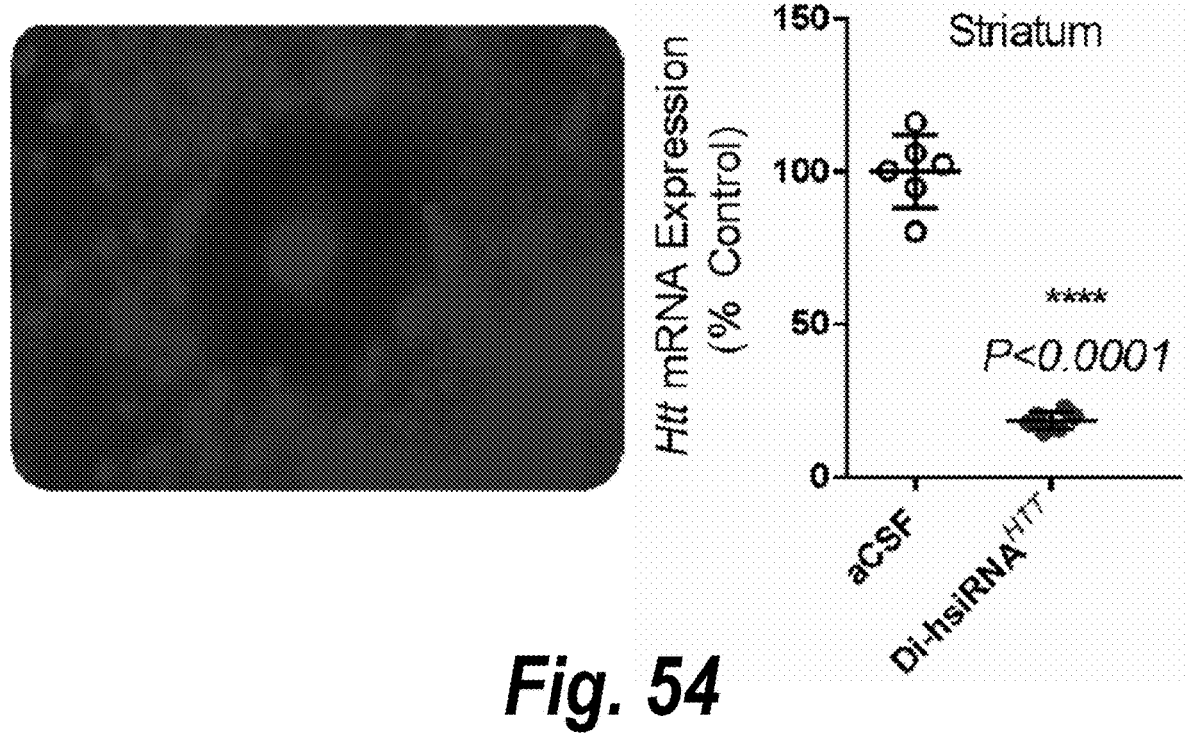
FIG. 54 shows that the degree of htt mRNA striatal silencing is effected by oligonucleotide cellular localization.
Figure 55:
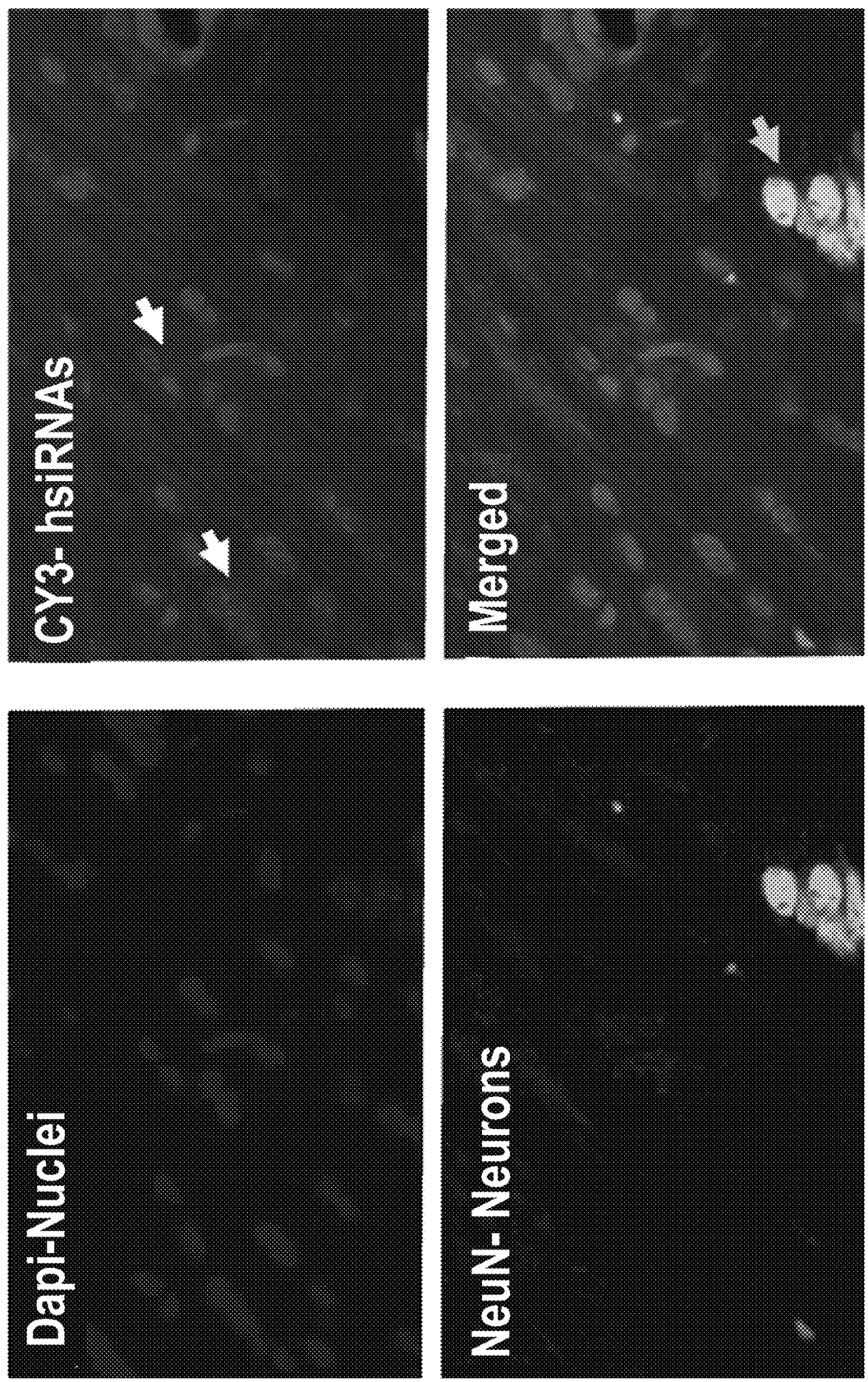
FIG. 55 depicts targeted glial delivery.
Figure 56:
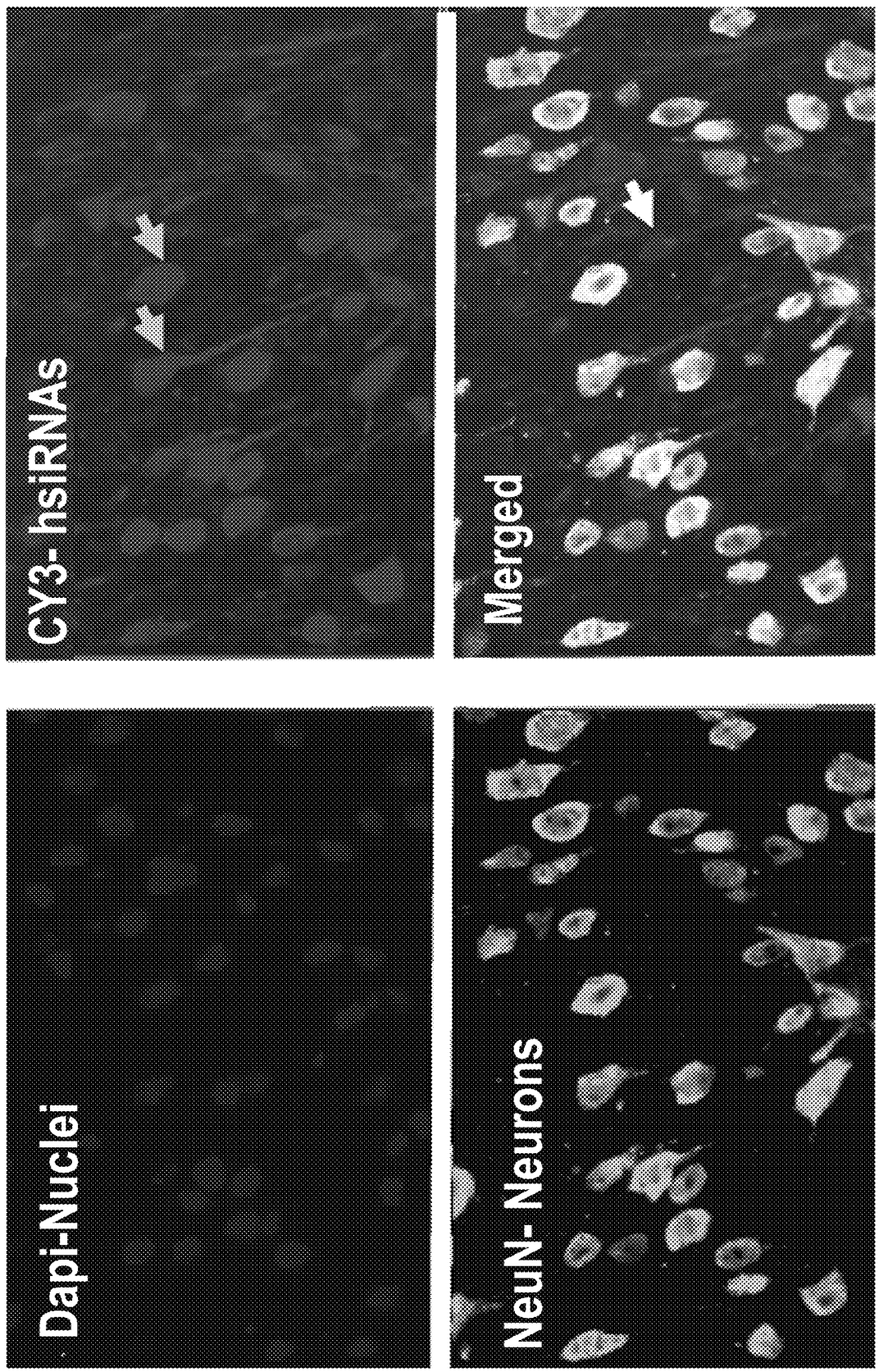
FIG. 56 depicts targeted neuronal delivery.

DHA-hsiRNA showed robust efficacy in the striatum and the cortex (FIGS. 48 and 49). Up to 200 µg DHA-hsiRNA had no effect on DARPP-32 levels, indicating compound safety (FIG. 50). In contrast, 25 µg (1 mg/kg) was the maximum tolerated intrastriatal dose of chol-hsiRNA. Up to 200 µg DHA-hsiRNA caused no significant increase in activated microglia, indicating minimal immune stimulation (FIG. 51).

hsiRNA allows for simple and efficient gene silencing in primary neurons in vivo in the brain. Oligonucleotide hydrophobicity defines brain tissue retention and distribution. Oligonucleotide chemistry was shown to impact cellular delivery and distribution (FIGS. 52-56). DHA-hsiRNA conjugates represent a new class of oligonucleotides with wide in vivo efficacy and a wide therapeutic index.

Example 4. PC-DHA-hsiRNA (PC-DHA-hsiRNA)

Encouraged by the wide therapeutic index of DHA-hsiRNAs, DHA and related conjugates were investigated in more detail. Circulating DHA is mostly present as a lysophosphatidylcholine ester, which is the only form actively trafficked through the blood-brain barrier via the specific transporter Mfsd2a (Nguyen L N, Ma D, Shui G, Wong P, Cazenave-Gassiot A, Zhang X, Wenk M R, Goh E L, Silver D L. Mfsd2a is a transporter for the essential omega-3 fatty acid docosahexaenoic acid. *Nature*. 2014; 509:503-6. PMID: 24828044).

Figure 92:
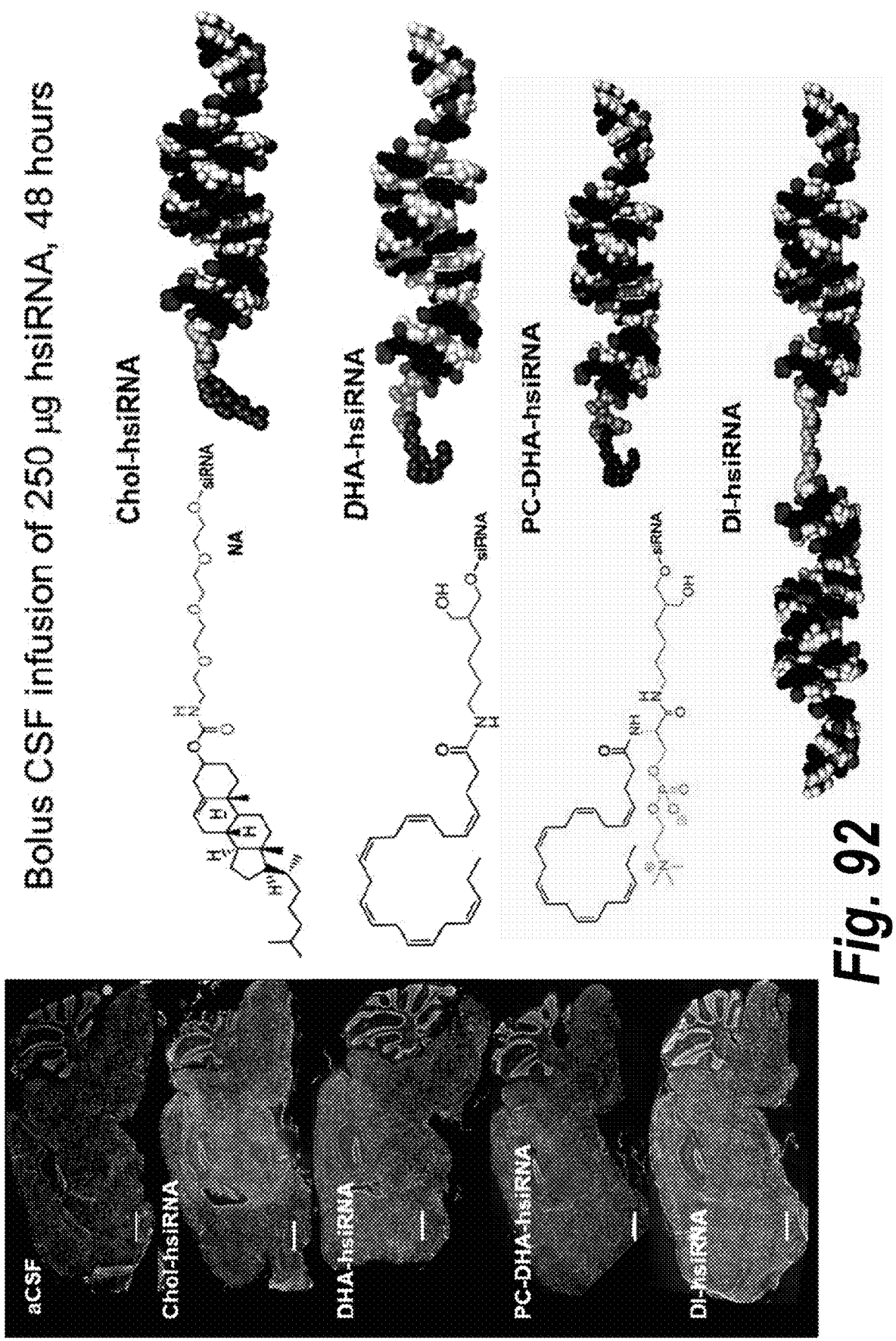
FIG. 92 depicts that the evolution of chemistry enabled wide distribution of hsiRNA in mouse brain after a bolus CSF (ICV) infusion. Images of sagittal sections (left panels) from 48 hours after ICV injection with 250 µg Cy3-labeled hsiRNA variants (right panels). Images taken with Leica tiling array microscope at 10× and at identical laser intensity. Nuclei (blue); Cy3-hsiRNA (red). Chol-hsiRNA mainly stayed around the injected ventricle with marginal distribution to the distal sides of the brain. DHA-hsiRNA shows better distribution. PC-DHA and Di-hsiRNAs shows most diffuse distribution with clear delivery to cortex, striatum, and even cerebellum. Scale bar=900 µm.

The lysophosphatidylcholine ester of DHA is unstable, so a lysophosphatidylcholine (PC) amide of DHA was synthesized (FIGS. 93, 94, 100 and 101). PC-DHA is a metabolically stable analog compatible with solid-phase oligonucleotide synthesis. Its identity was confirmed by NMR and mass spectrometry. Testing the idea that lysophosphatidylcholine should improve trafficking of DHA-hsiRNA, it was determined that that PC-DHA-hsiRNAs showed a wider distribution and increased efficacy in brain tissue than do DHA-hsiRNAs (FIGS. 92 and 103). Importantly, as a class, DHA conjugates showed a wide therapeutic index with no obvious innate immune activation or neuronal degeneration at concentrations 20-fold higher than the minimum effective dose (FIG. 92). Comparatively, Chol-hsiRNA showed significant toxicity at 25 µg injections (FIG. 92C). Lastly, a bolus CSF (ICV) infusion supported wide distribution in the brain, covering striatum, cortex and even reaching more posterior and ventral regions of the brain (FIG. 92). Due to its exceptional characteristics, PC-DHA-hsiRNA was selected as a lead chemistry to investigate.

Figure 62:
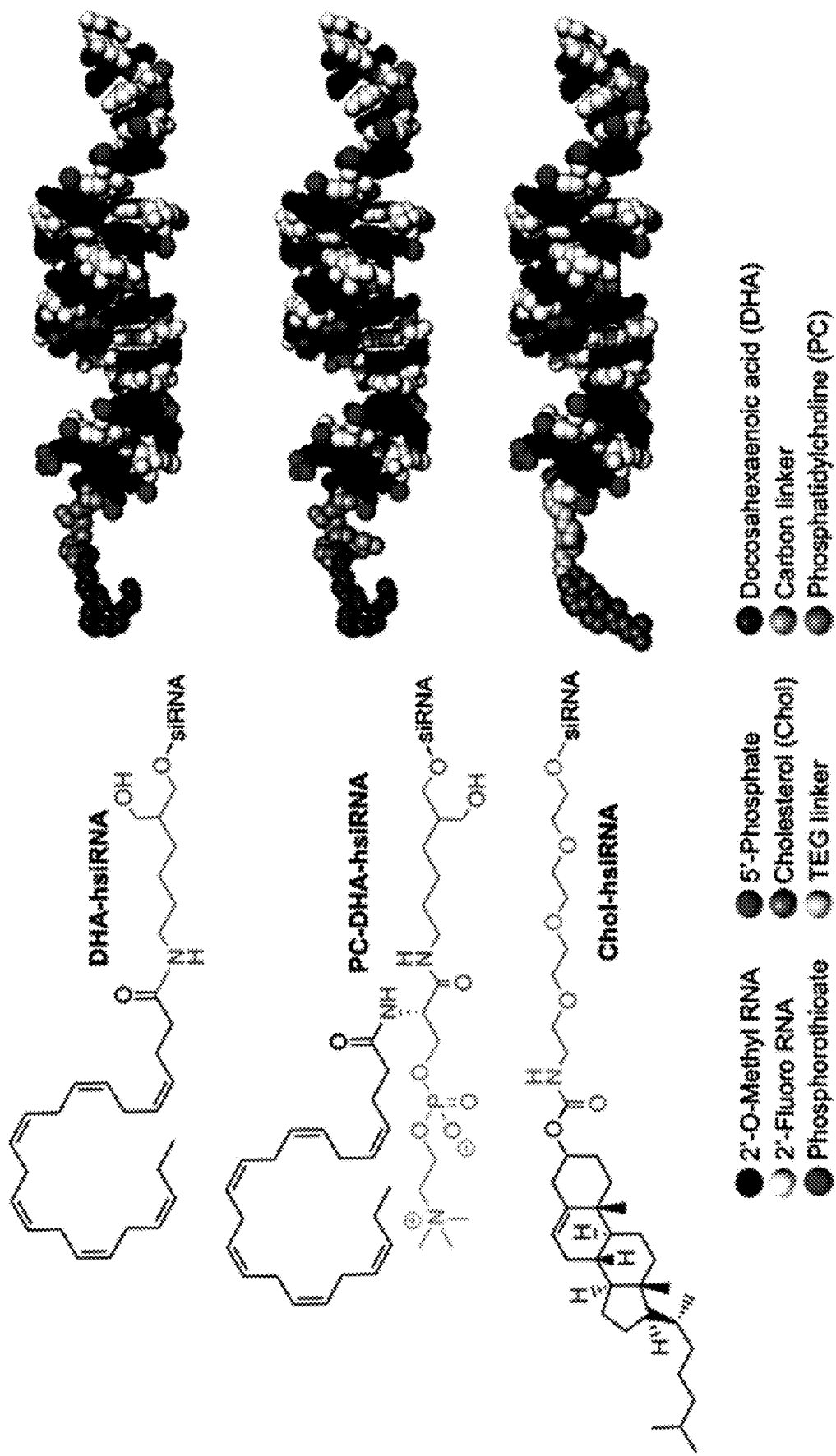
FIG. 62 describes three classes of hsiRNA chemistries: DHA-hsiRNA, PC-DHA-hsiRNA and chol-hsiRNA.

PC-DHA is a metabolically active analogue of DHA (FIG. 62). PC-DHA-hsiRNA demonstrates enhanced neuronal silencing in vitro, enhanced brain distribution and enhanced in vivo potency (with no signs of toxicity) relative to DHA-hsiRNA.

PC-DHA-hsiRNA and chol-hsiRNA were each shown to efficiently silence both mutant and wild-type htt mRNA (FIG. 61). Chol-hsiRNA demonstrated toxicity (3 out of 6 animals died). The living animals demonstrated very low (3-fold over background) human htt expression.

Figure 63A:
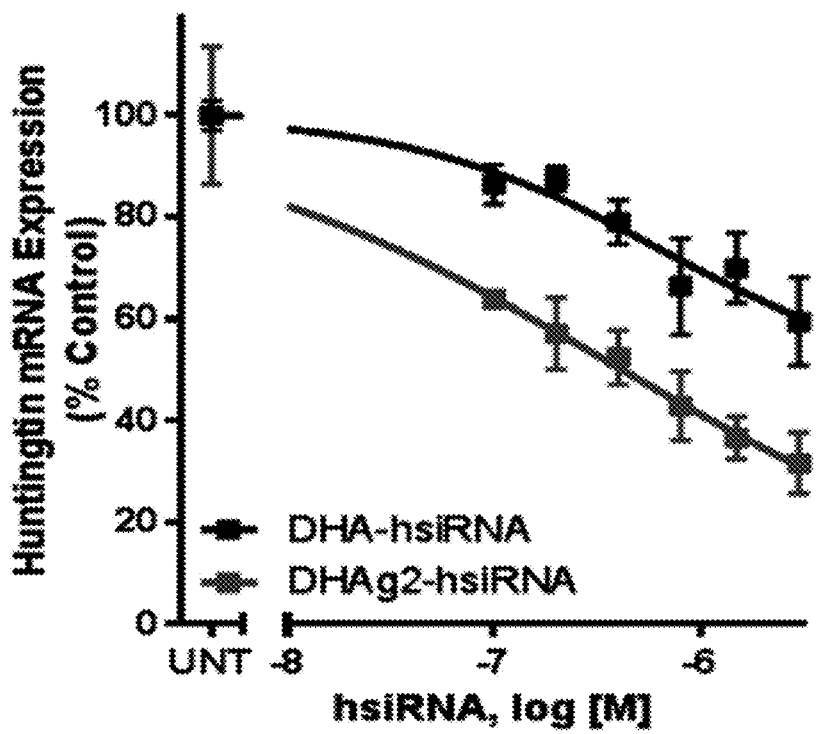
FIGS. 63A-63B graphically depict enhanced potency of PC-DHA-hsiRNA relative to DHA-hsiRNA in cortical primary neurons. 1 week, analyzed by QUANTIGENE, data normalized to PPIB.
Figure 63B:
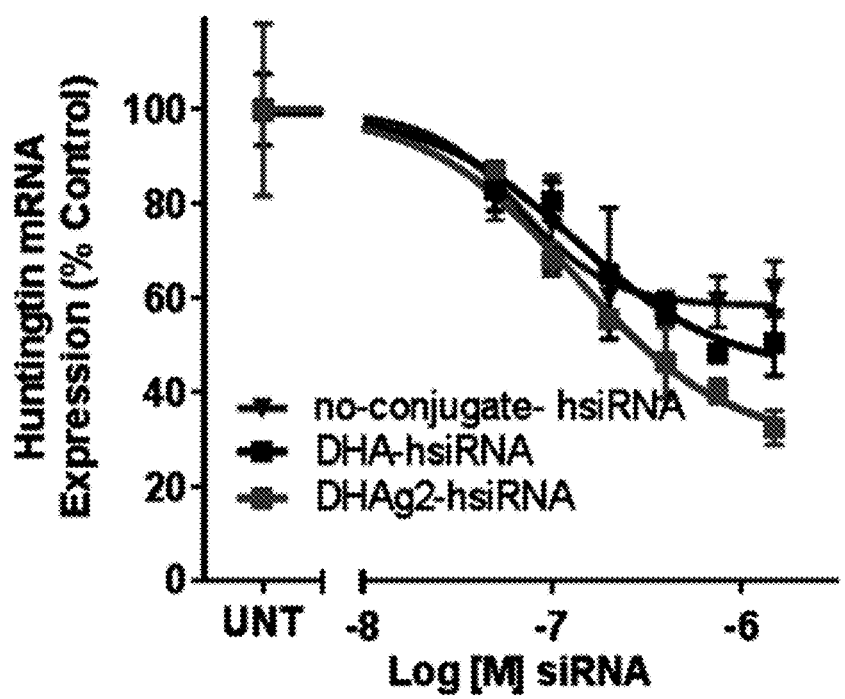
Figure 64:
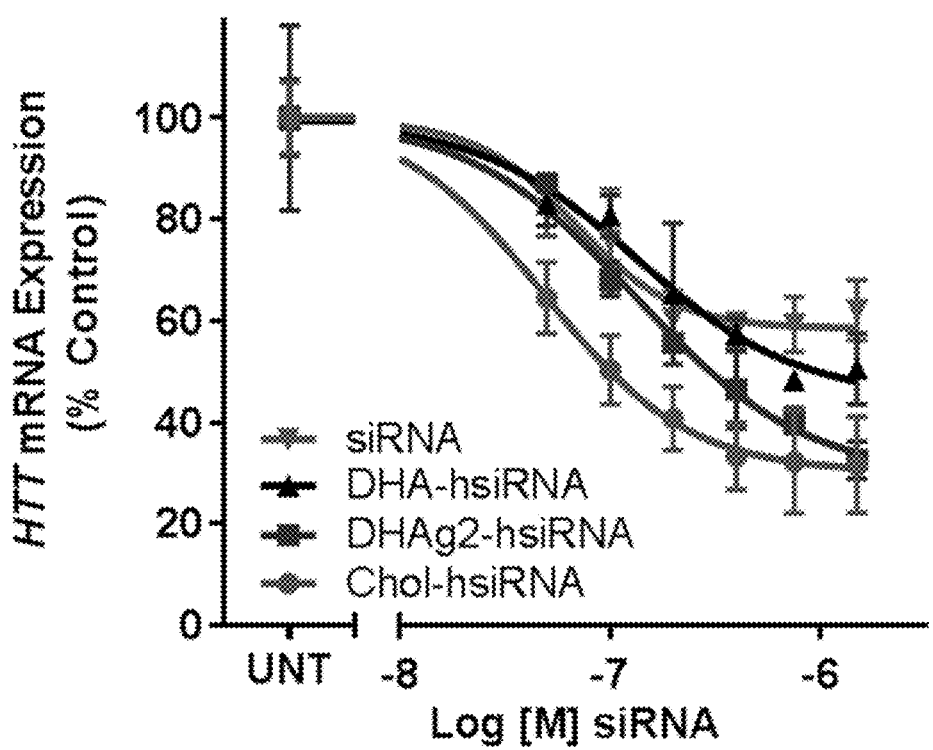
FIG. 64 illustrates that chol-hsiRNA has a more effective chemistry for gene modulation in primary cortical neurons relative to PC-DHA-hsiRNA and DHA-hsiRNA. 1 week, analyzed by QUANTIGENE, data normalized to PPIB.
Figure 65:
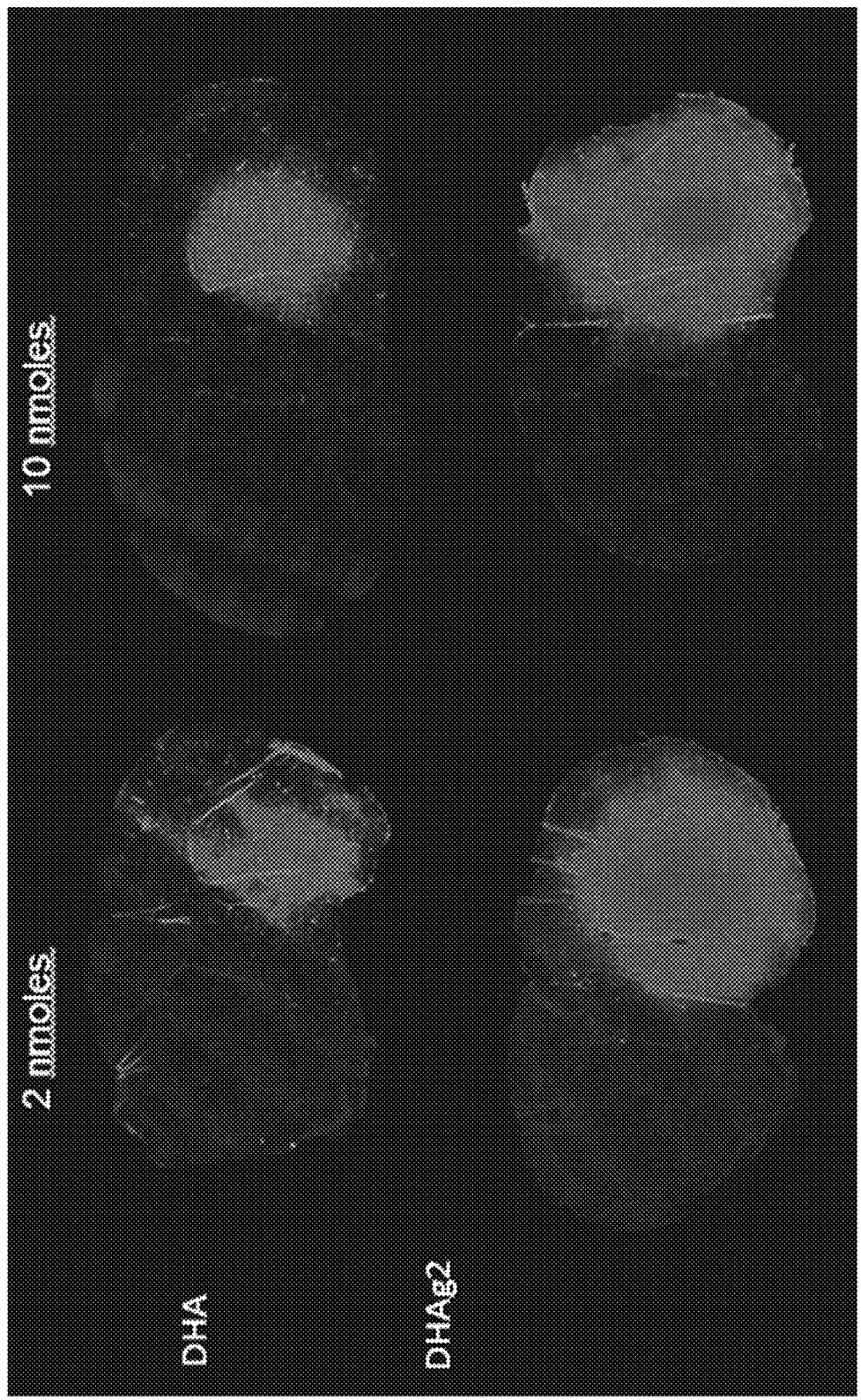
FIG. 65 shows that PC-DHA-hsiRNA shows better brain retention and wider distribution that DHA-hsiRNA. Intrastriatal injections at either 2 or 10 nmol, N=2, brains collected at 48 hours.

PC-DHA-hsiRNA, when delivered to primary neurons, demonstrated enhanced potency relative to DHA-hsiRNA (FIG. 63). Although chol-hsiRNA was more effective in decreasing htt gene expression in primary neurons (FIG. 64), PC-DHA-hsiRNA showed superior brain retention and wider distribution (FIG. 65).

PC-DHA-hsiRNA showed approximately 80% silencing in mouse striatum after a single interstitial (IS) injection (FIG. 66) and showed approximately 60% silencing in mouse cortex after a single IS injection (FIG. 67). There was no indication of toxicity. Silencing was limited to injected side of the brain.

Figure 107:
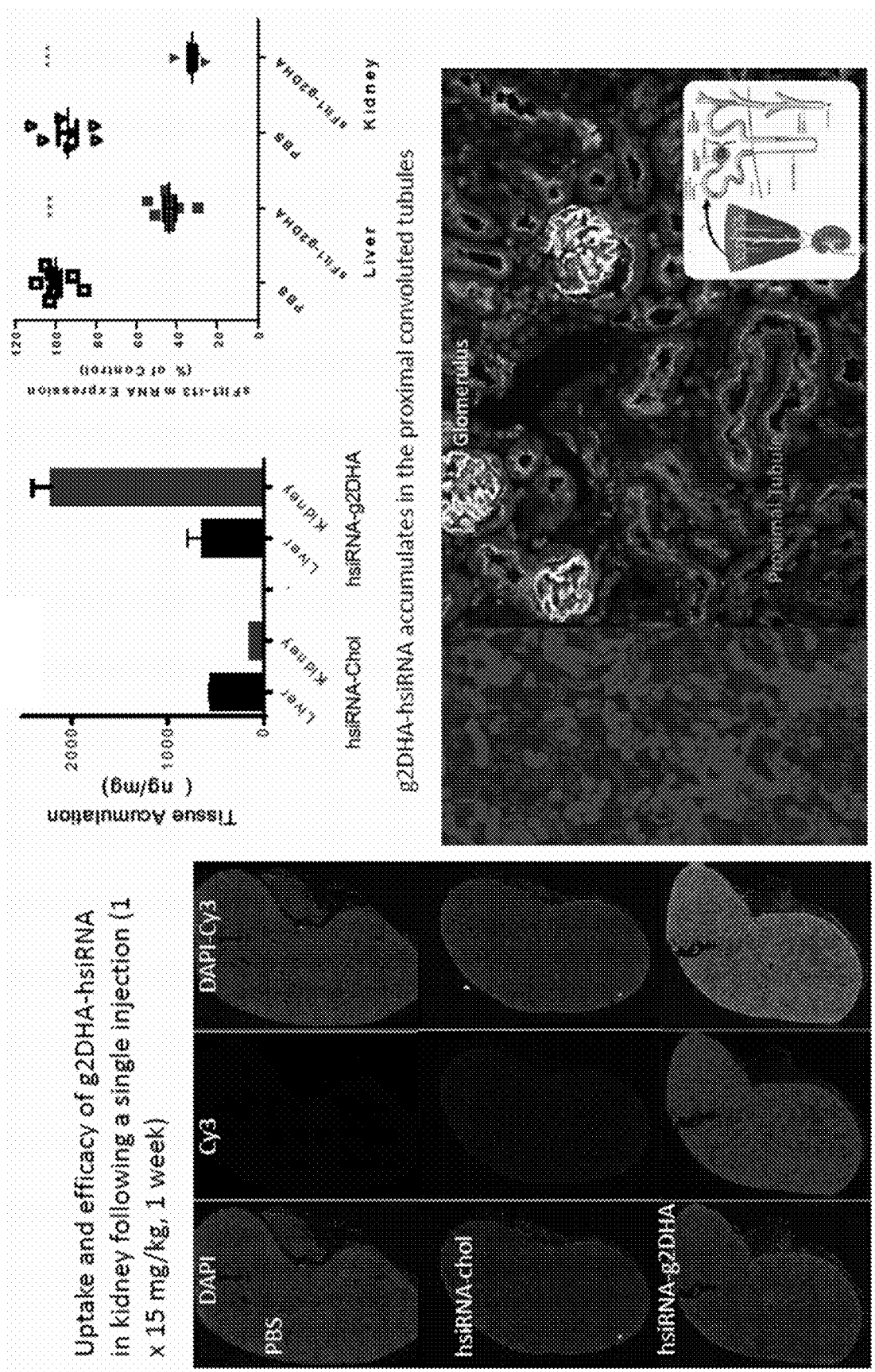
FIG. 107 depicts targeting of the kidney by PC-DHA-hsiRNA.

The kidney is the main target of PC-DHA-hsiRNA (FIG. 107). PC-DHA-hsiRNA accumulated in the proximal convoluted tubules.

Example 5. Discovery of Di-hsiRNAs

Branched oligonucleotides represent a novel class of oligonucleotide therapeutics. Two to eight oligonucleotides were attached together through a hydrophobic linker, with 2-3 oligonucleotides attached together being preferred. Substantial chemical stabilization was typically used (at least 40% bases modified, fully modified preferred. Single stranded phosphorothioated tail of 2-20 was typically used (with 8-10 preferred).

Figure 94:
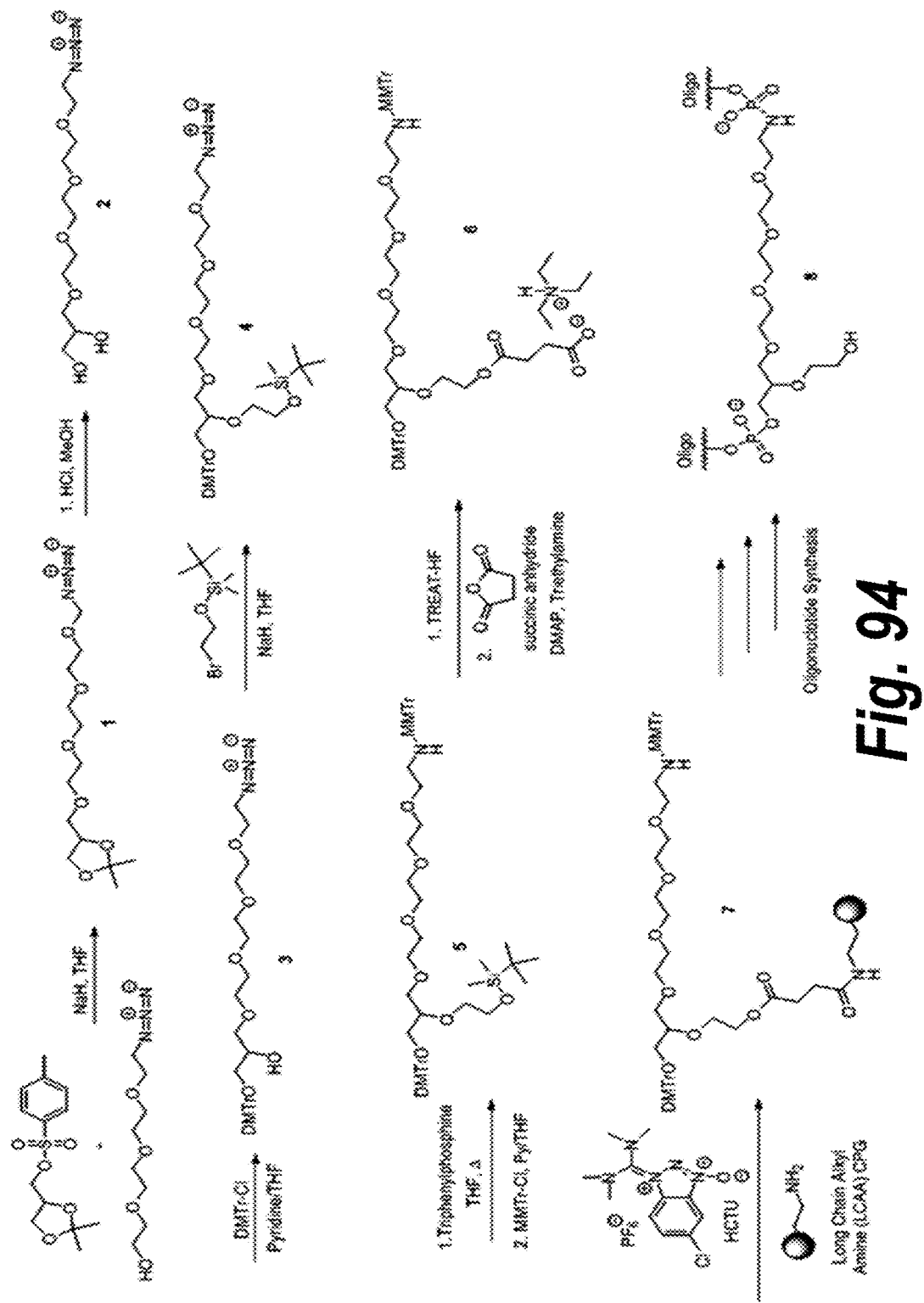
FIG. 94 depicts a synthetic protocol for DI-functionalized solid support.
Figure 95A:
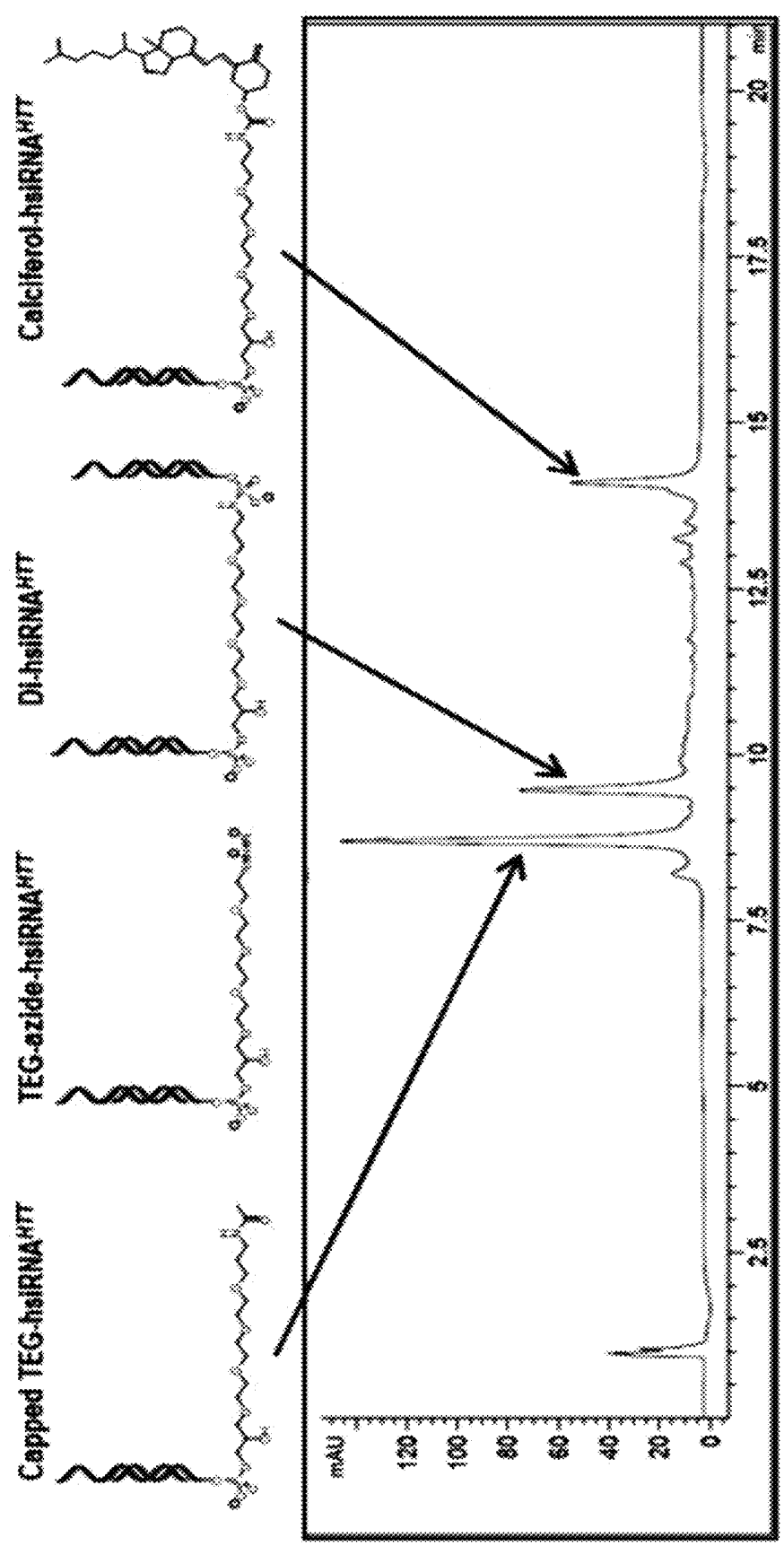
FIGS. 95A-95C depict di-hsiRNA discovery. (A) Chemical composition of the four bi-products from calciferol-hsiRNA synthesis (analytical HPLC of the crude synthesis). (B) Efficacy of bi-products in HeLa cells, 72 hours, QuantiGene®. All compounds were equally active. (C) A single, unilateral intrastriatal injection (25 µg) of each Cy3-hsiRNA bi-product, 48 hours. Only di-hsiRNAs showed broad distribution with preferential neuronal uptake.
Figure 95B:
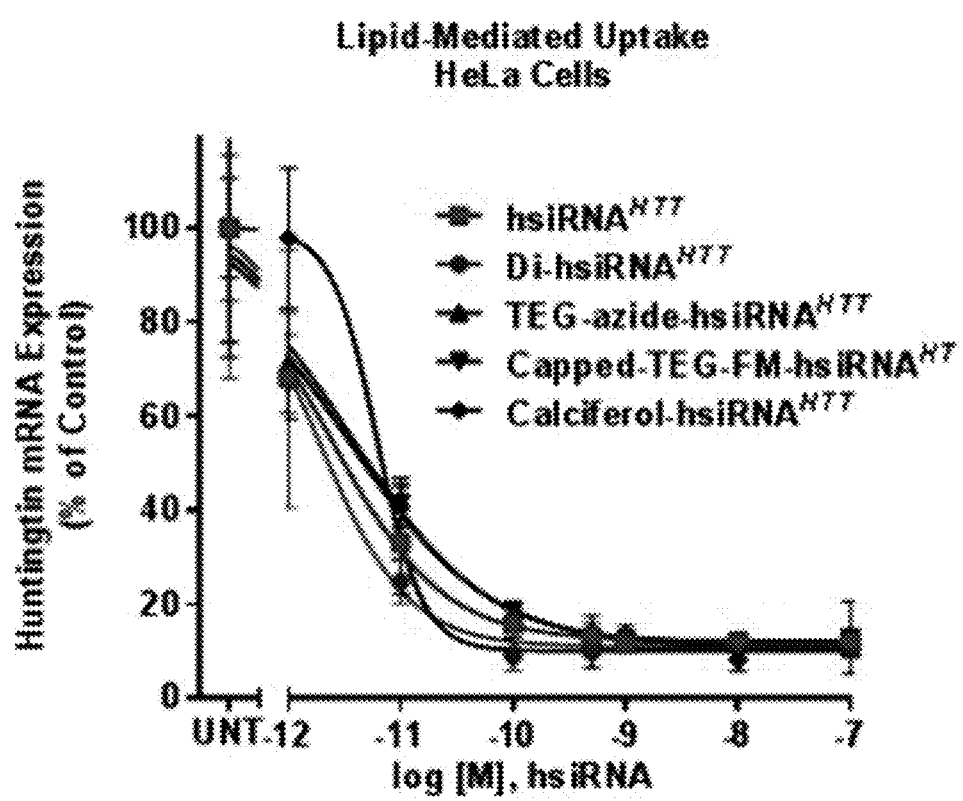
Figure 95C:
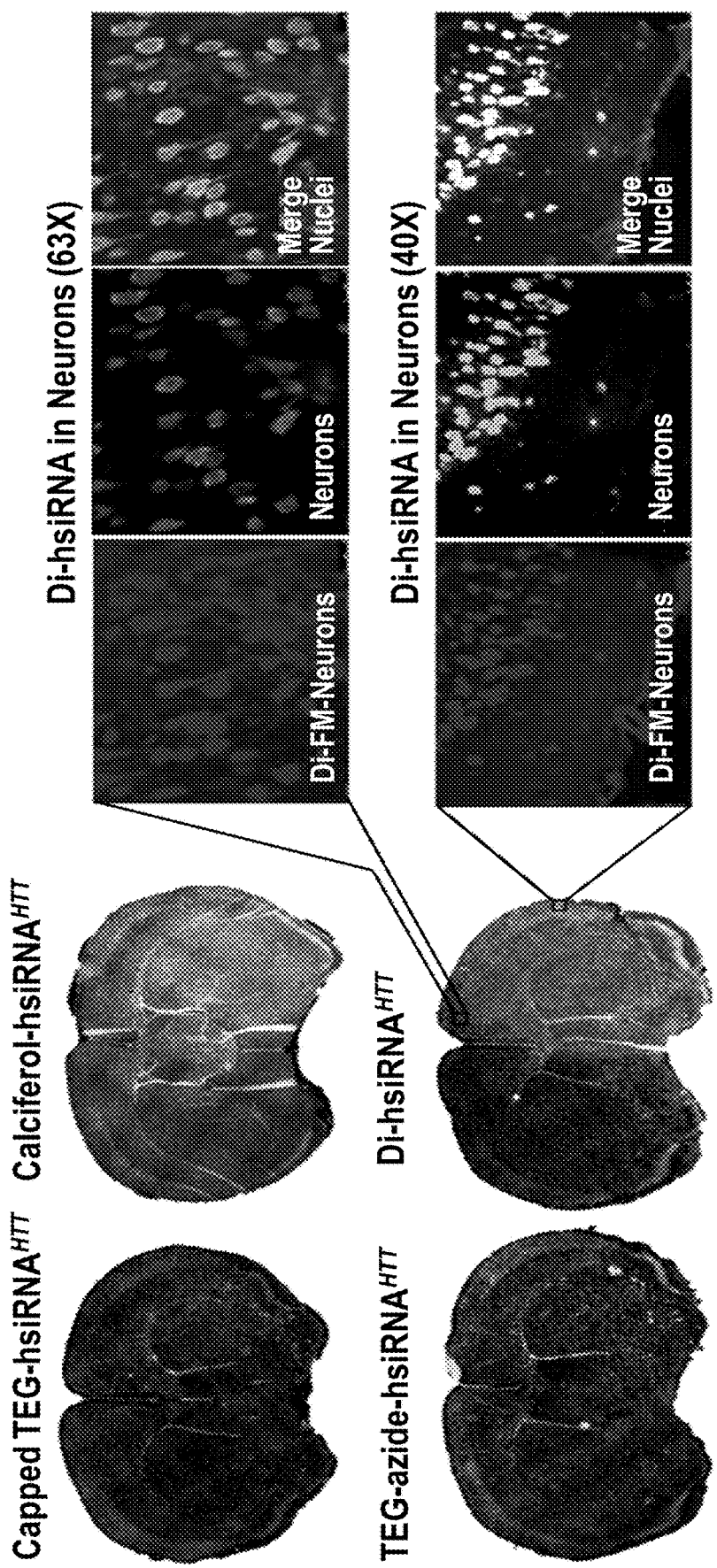
Figure 100:
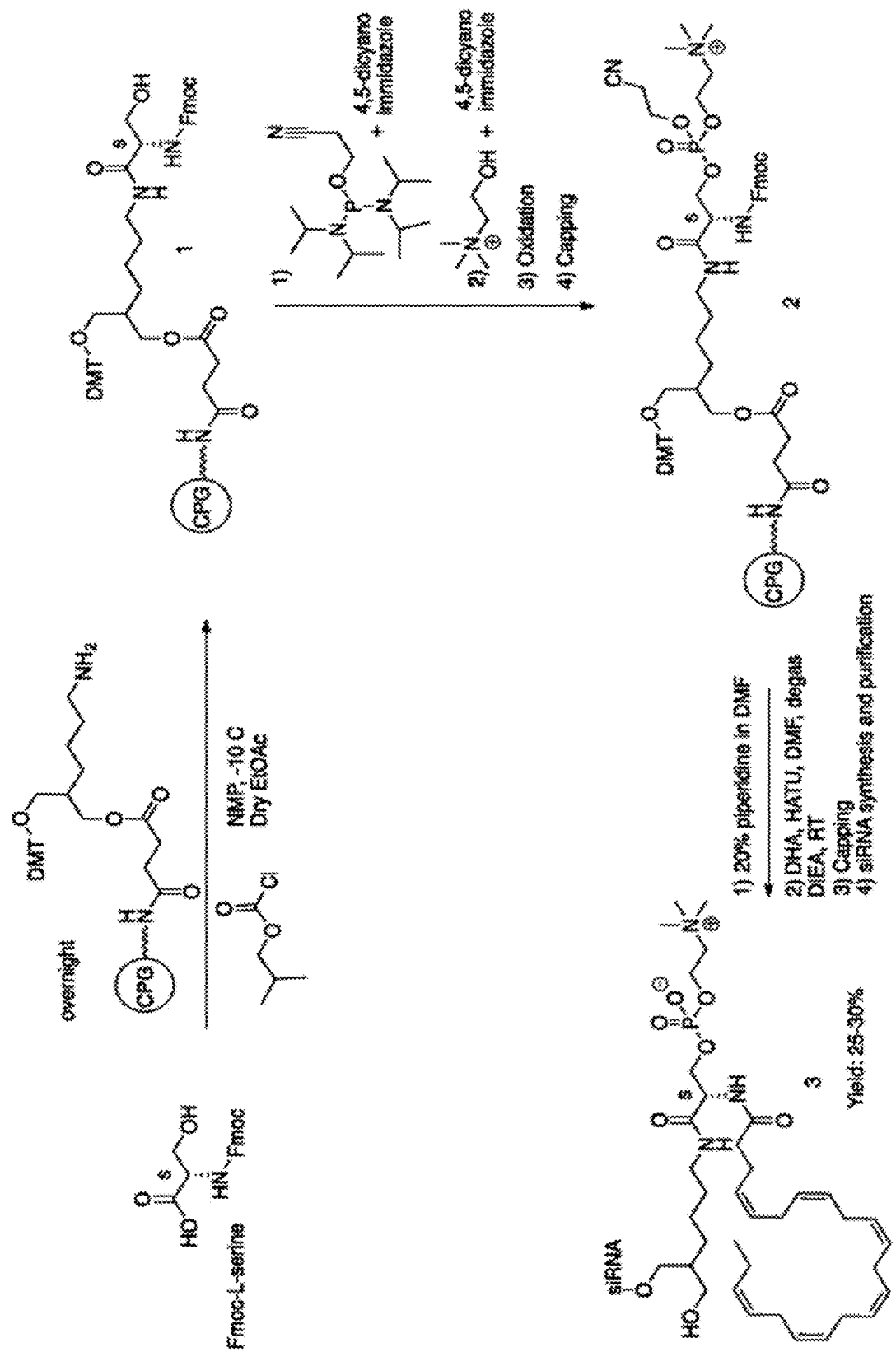
FIG. 100 depicts a solid-phase synthetic protocol for PC-DHA hsiRNA conjugates.
Figure 101:
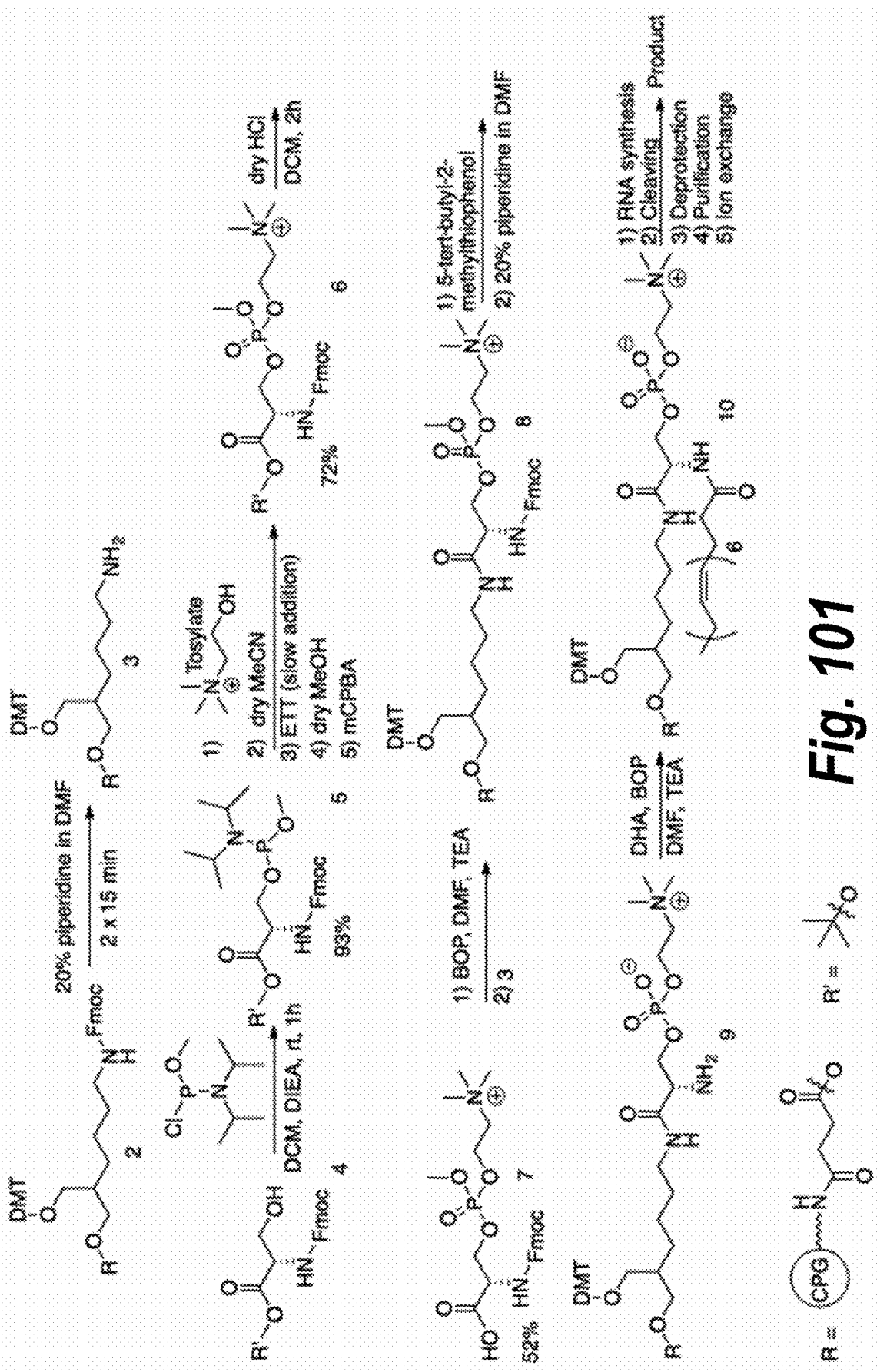
FIG. 101 depicts a solution-phase synthetic protocol for PC-DHA hsiRNA conjugates.
Figure 102B:
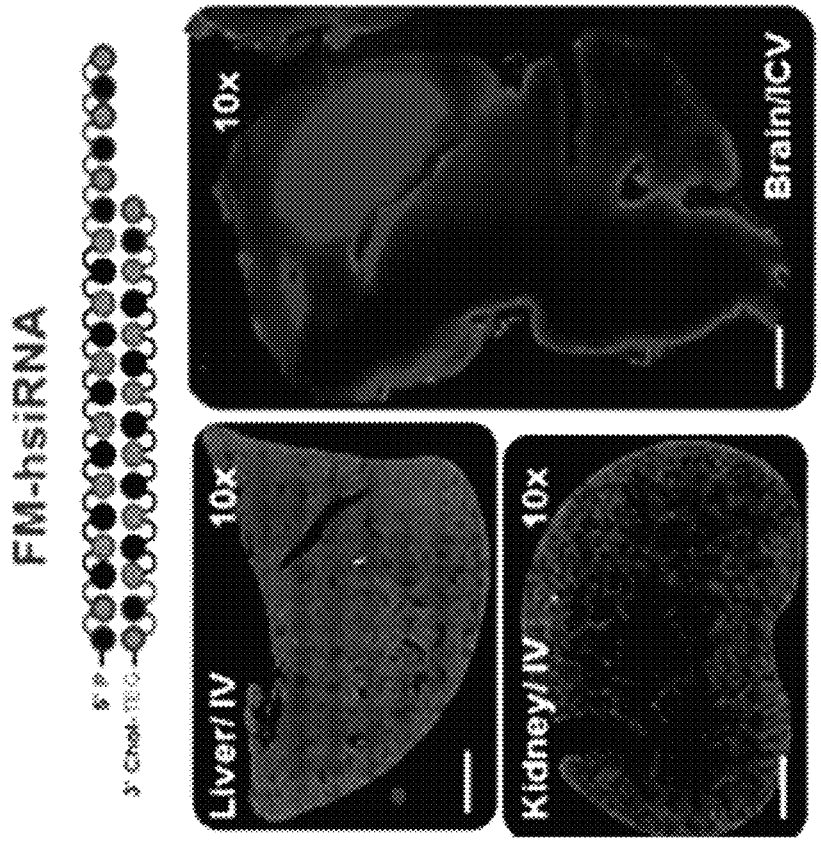
FIGS. 102A-102D depict that full metabolic stabilization was essential for conjugate mediated siRNA delivery and duration of effect in vivo. (A, B) Compared to hsiRNA (A), FM-hsiRNA (B) showed significantly enhanced distribution and retention in tissues after intravenous (IV) and CSF (ICV) administration. Wild-type pregnant mice (E15) were injected with 10 mg/kg IV or 60 µg, ICV. Tissues were imaged at 10× on a Leica tiling fluorescent microscope at identical laser intensity. HsiRNAs (red); nuclei (blue). Scale bar=900 µm. (C) Intact guide strand in tissues quantified 5 days after IV injection (n=3, mean+SEM). (D) FM-hsiRNAs silence Htt mRNA in mouse striatum one month after injection (12 µg, intrastriatal). Partially modified hsiRNAs silence for less than two weeks.
Figure 102A:
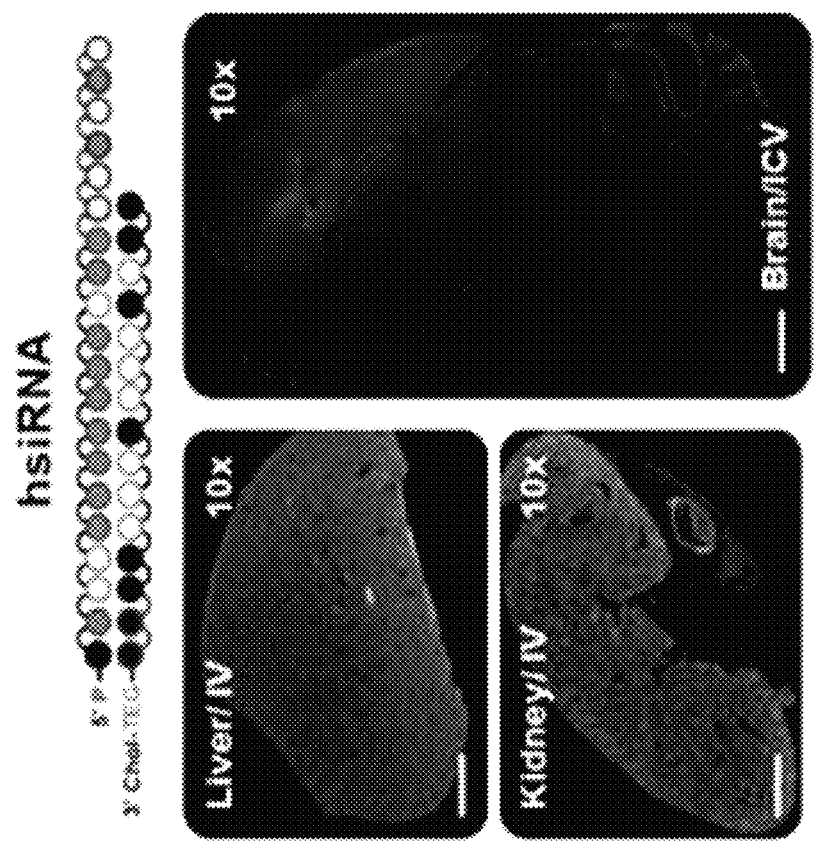
Figure 102C:
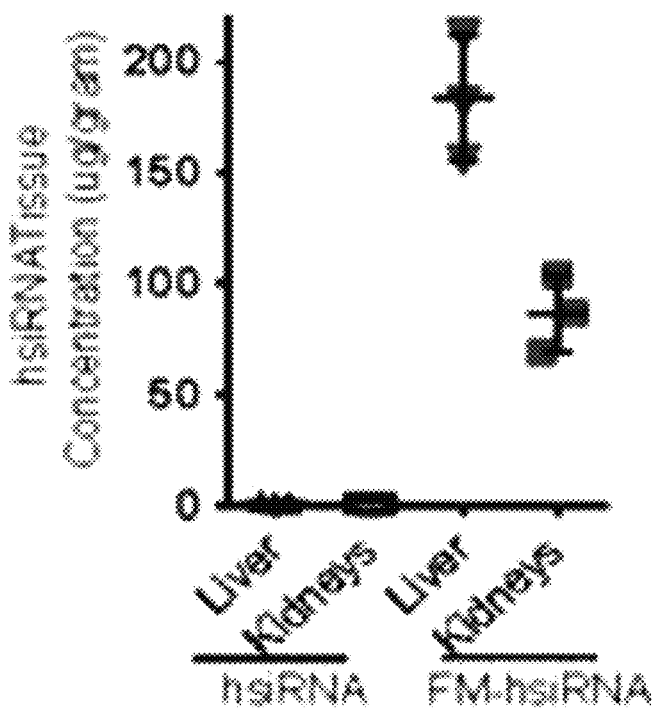
Figure 102D:
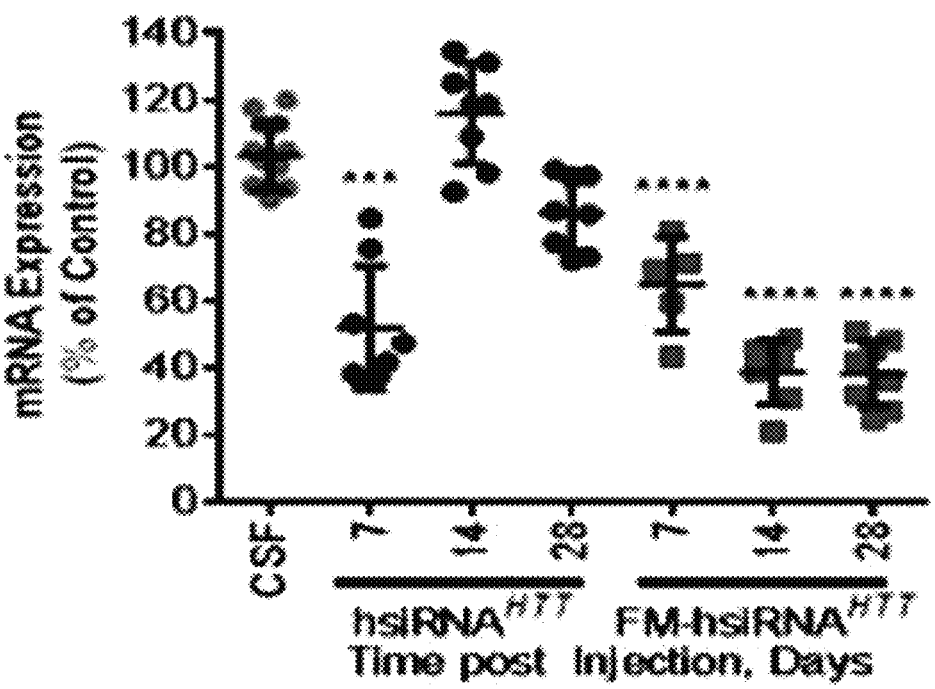

The discovery of di-branched hsiRNA (di-hsiRNA) compounds was pure serendipity. Calciferol readily oxidizes and the solid support proved to be unstable, complicating QC and purification. A pool of four major byproducts were injected into striata of wild-type mice. It performed better than any compound that had been previously injected into the CNS. The products showed wide diffusion, great retention and preferential uptake into neurons in cortex, striatum, and spinal cord, which is an almost ideal profile. Detailed characterization by HPLC and mass spectrometry identified the byproducts present in the crude mixture: the desired calciferol-hsiRNA conjugate, hsiRNA capped with a triethylene glycol linker (TEG), and two hsiRNAs connected by a TEG linker. The latter compound resulted from calciferol being cleaved off during support loading, leaving two active groups on which to grow hsiRNA passenger strands (FIG. 95A). After purifying each byproduct it was determined that each could efficiently enter RISC in vitro (FIG. 95B), but only Di-hsiRNAs showed the wide distribution and preferential neuronal uptake (FIG. 95C). A route to directly synthesize Di-hsiRNA with >70% yield (FIGS. 93 and 94), confirmed by mass spectrometry, was devised (FIGS. 100 and 101).

Figure 68:
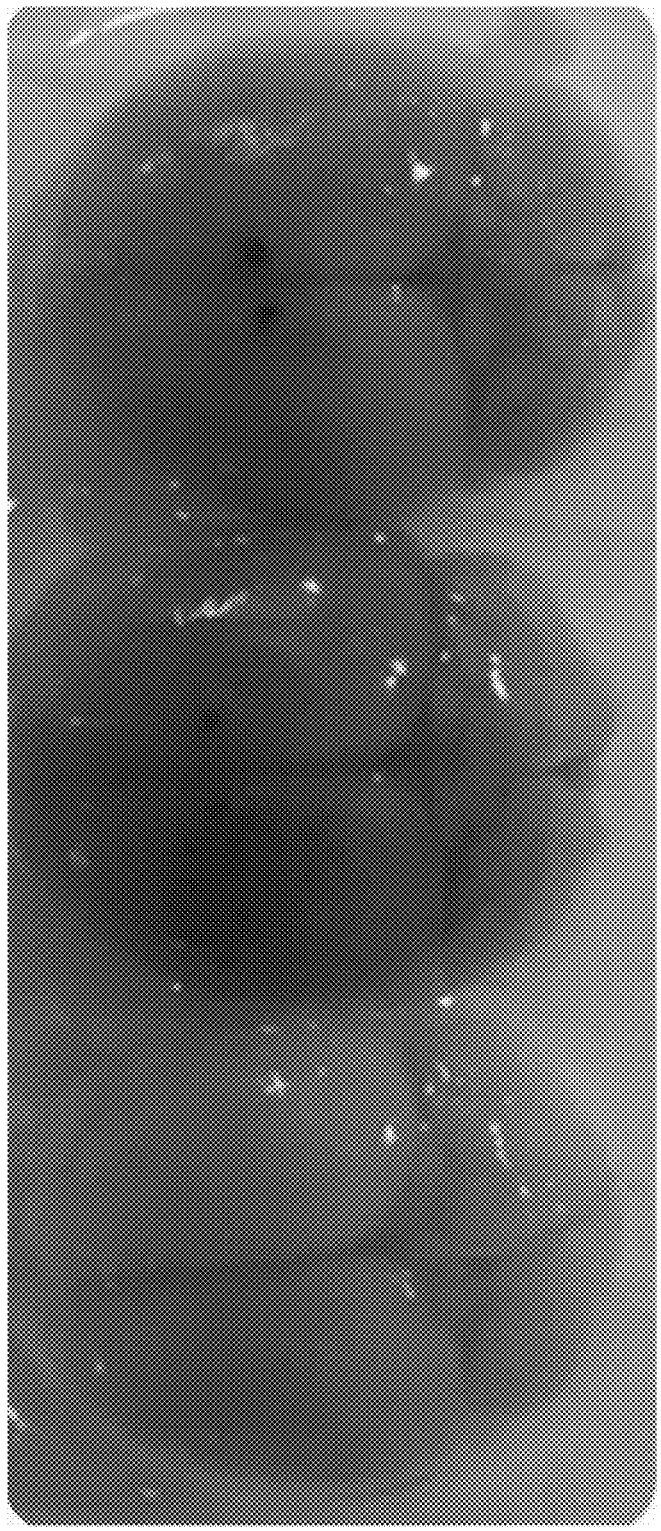
FIG. 68 depicts di-hsiRNA brain distribution after an CSF bolus injection (250 µg), 48 hours.
Figure 69:
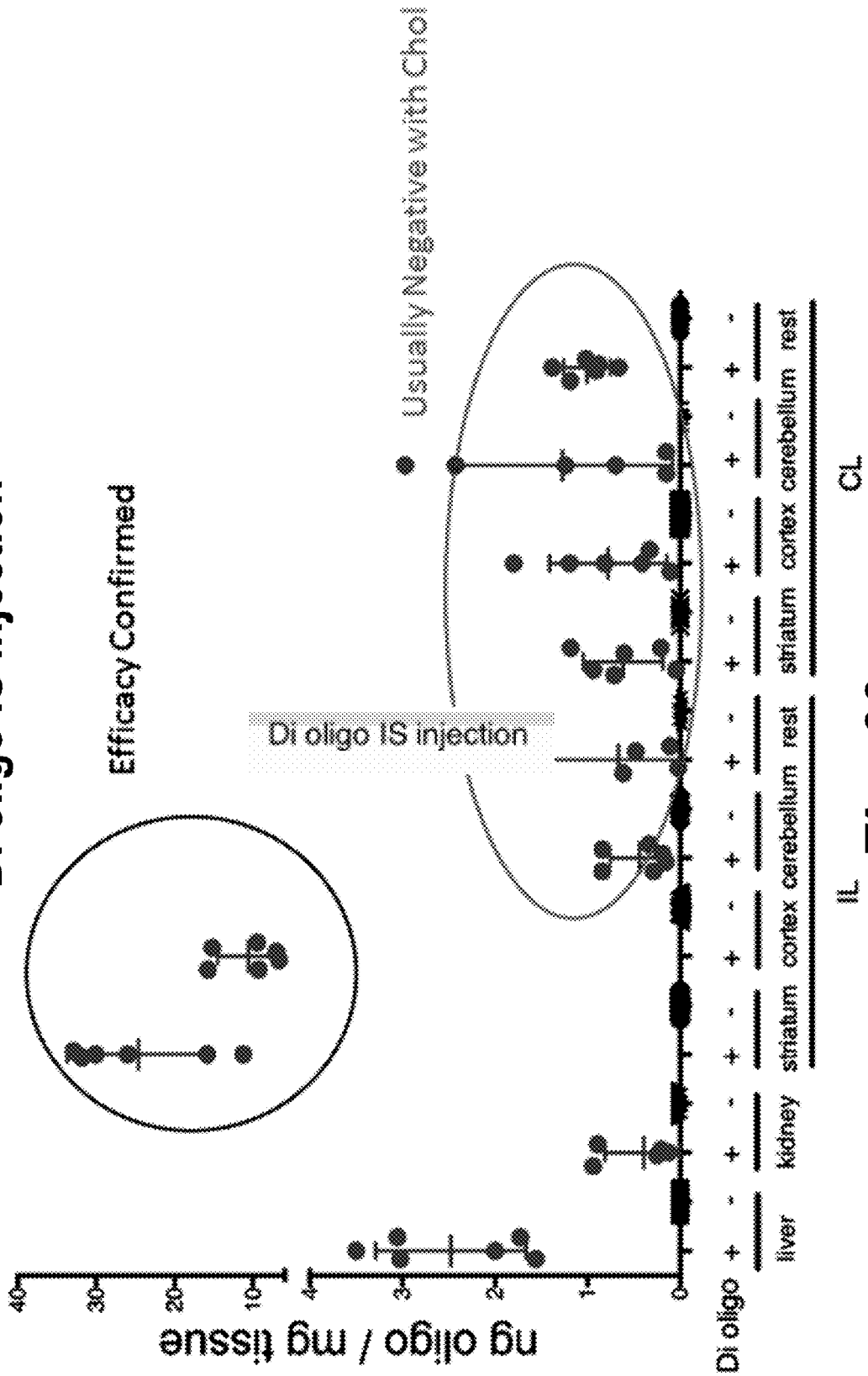
FIG. 69 depicts distribution of di-hsiRNA after a single IS injection.
Figure 104A:
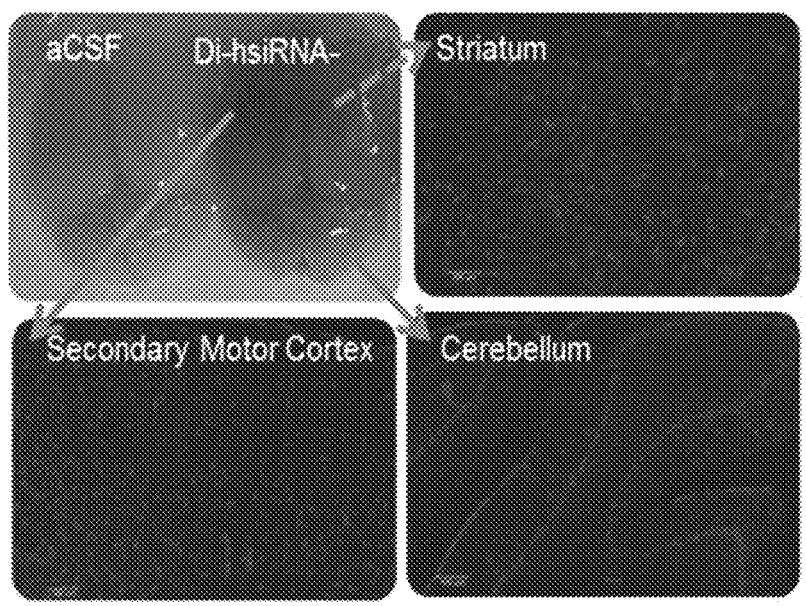
FIGS. 104A-104C show that di-hsiRNA exhibited wide distribution and efficacy in mouse brain. (A) Robust and uniform distribution of Cy3-Di-hsiRNA throughout the brain, visually and histologically, with clear neuronal uptake 48 hours after ICV injection (250 µg, CSF, both sides), scale bar=100 µm. (B) Htt mRNA silencing in cortex and striatum 7 days after single intrastriatal injection (25 µg). (C) hsiRNA accumulation in tissues 7 days after injection (PNA assay).

A bolus ICV infusion of Di-hsiRNAs supported delivery throughout the brain Di-branched hsiRNA (di-hsiRNA) compounds were determined to support wide distribution in the brain (FIGS. 68, 69 and 104A). Note the brain injected with Cy3-Di-hsiRNA in FIG. 104A is pink throughout.

Single injection of di-siRNA was detected on both ipsilateral and contralateral to injection site indicating that spread is not limited to the injected hemisphere but is also occurring across the midline into the non-injected side. The lesser degree of di-siRNA accumulation on the contralateral side, although significant, may necessitate bilateral injections for full brain silencing. Alternative methods of injection including intracerebral-ventricular may also facilitate bilateral distribution with only one injection.

Branching was determined to be essential for enhanced brain distribution (FIG. 70). Di-hsiRNA distributed throughout the injected hemisphere of the mouse brain following intrastriatal injection. While a single non-conjugated hsiRNA can silence mRNA in primary neurons, the di-hsiRNA structure was essential for enhanced tissue distribution and tissue retention of modified oligo nucleotides. Other conjugates such as cholesterol, although retained, showed a steep gradient of diffusion away from the site of injection. The subtle hydrophobicity of the two single stranded phosphorothioated tails supported tissue retention while also allowing for widespread and uniform distribution throughout the ipsilateral hemisphere of the injected brain.

Figure 71:
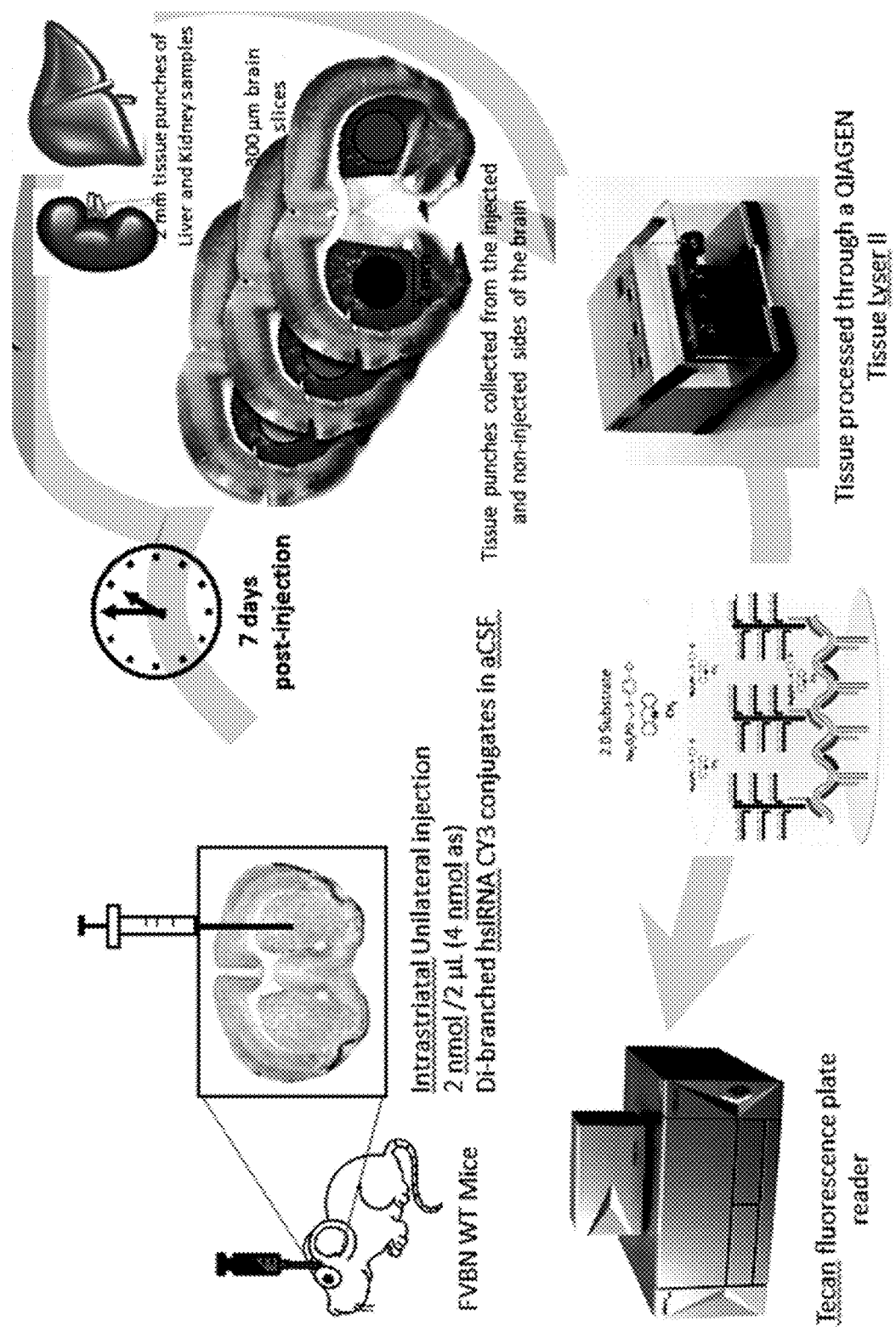
FIG. 71 depicts a study design to assay in vivo gene silencing after single IS injections of di-hsiRNA.
Figure 72:
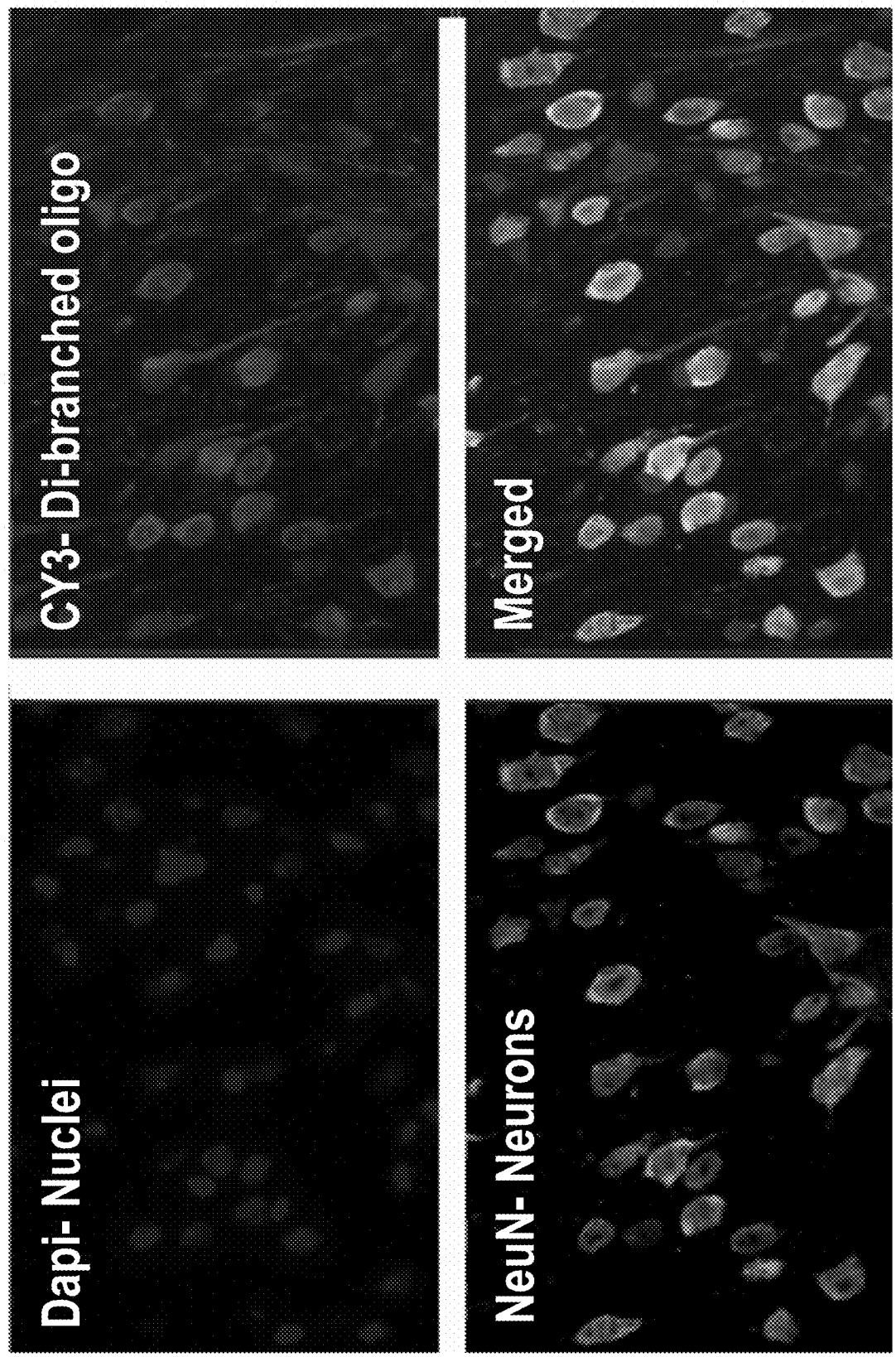
FIG. 72 depicts neuronal delivery of di-hsiRNA.
Figure 73:
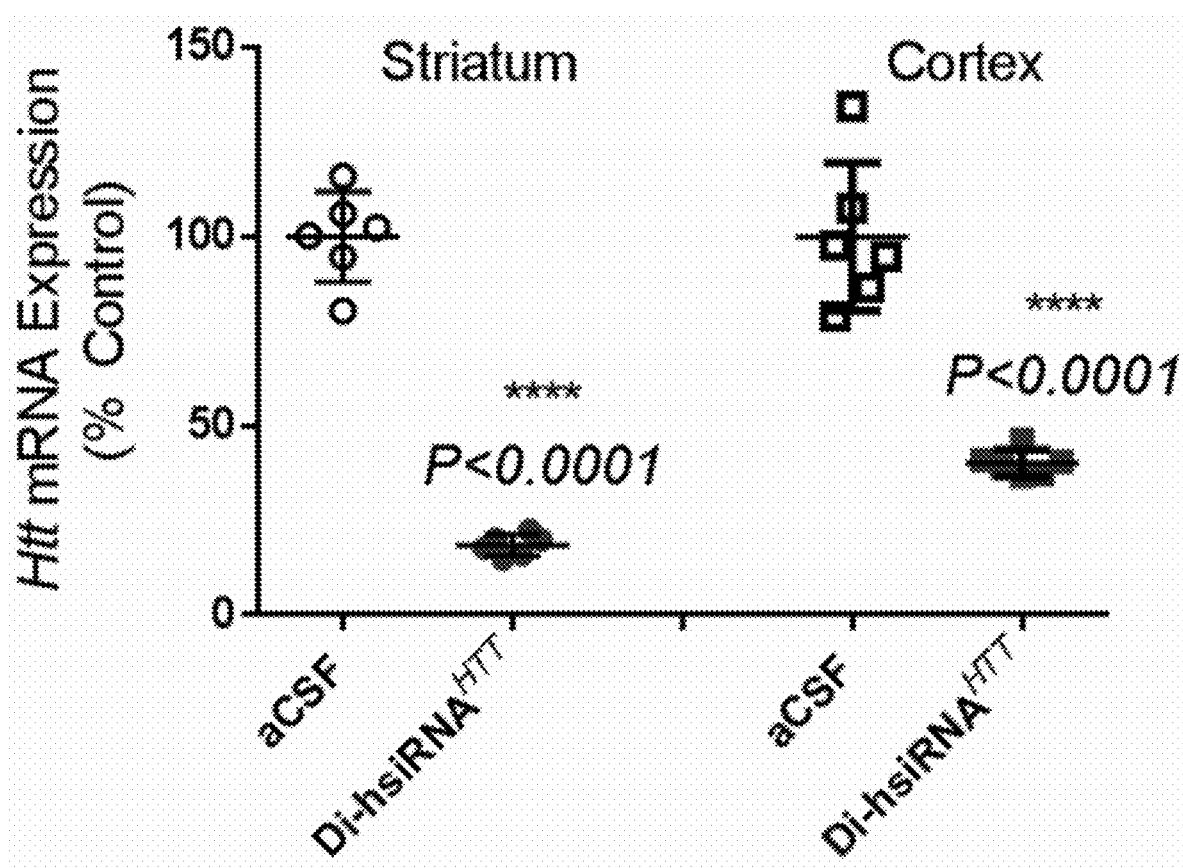
FIG. 73 depicts efficacy of di-hsiRNA in the striatum and cortex. IS injection, 2 nmol di-hsiRNA, 1 week, QuantiGene 2.0.

In vivo gene silencing after single IS injections of di-hsiRNA was studied (FIG. 71). Single injection of di-siRNA induced robust silencing in both the striatum and cortex of mouse brain (FIGS. 72 and 73). This level of efficacy has never been demonstrated previously for non-conjugated siRNAs. Although di-hsiRNA appears visually associated with fiber tracts in striatum, the efficacy observed clearly indicates that striatal neurons internalized di-siRNA to a significant degree.

Figure 74:
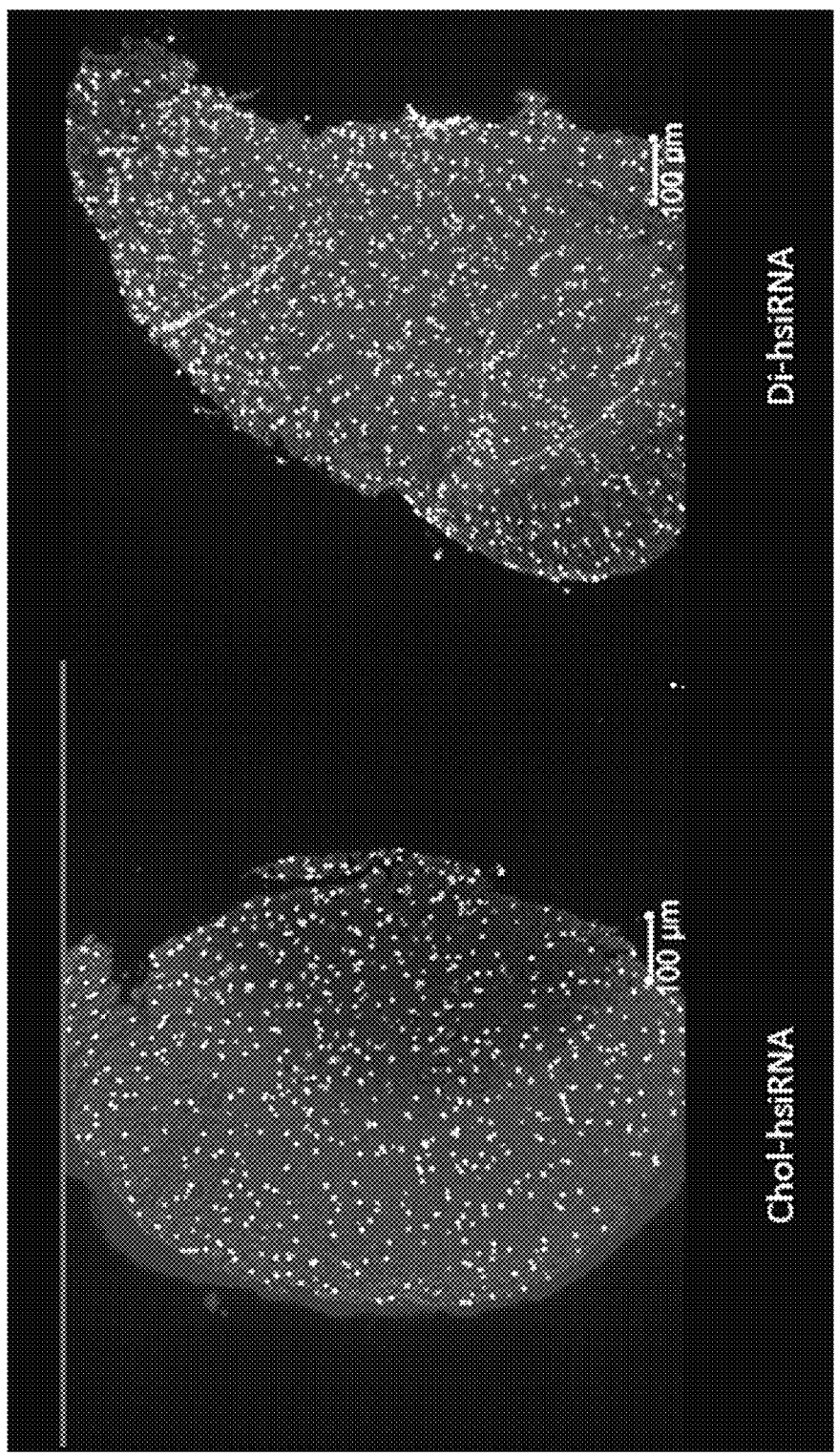
FIG. 74 depicts uniform spinal cord distribution of di-hsiRNA.
Figure 75:
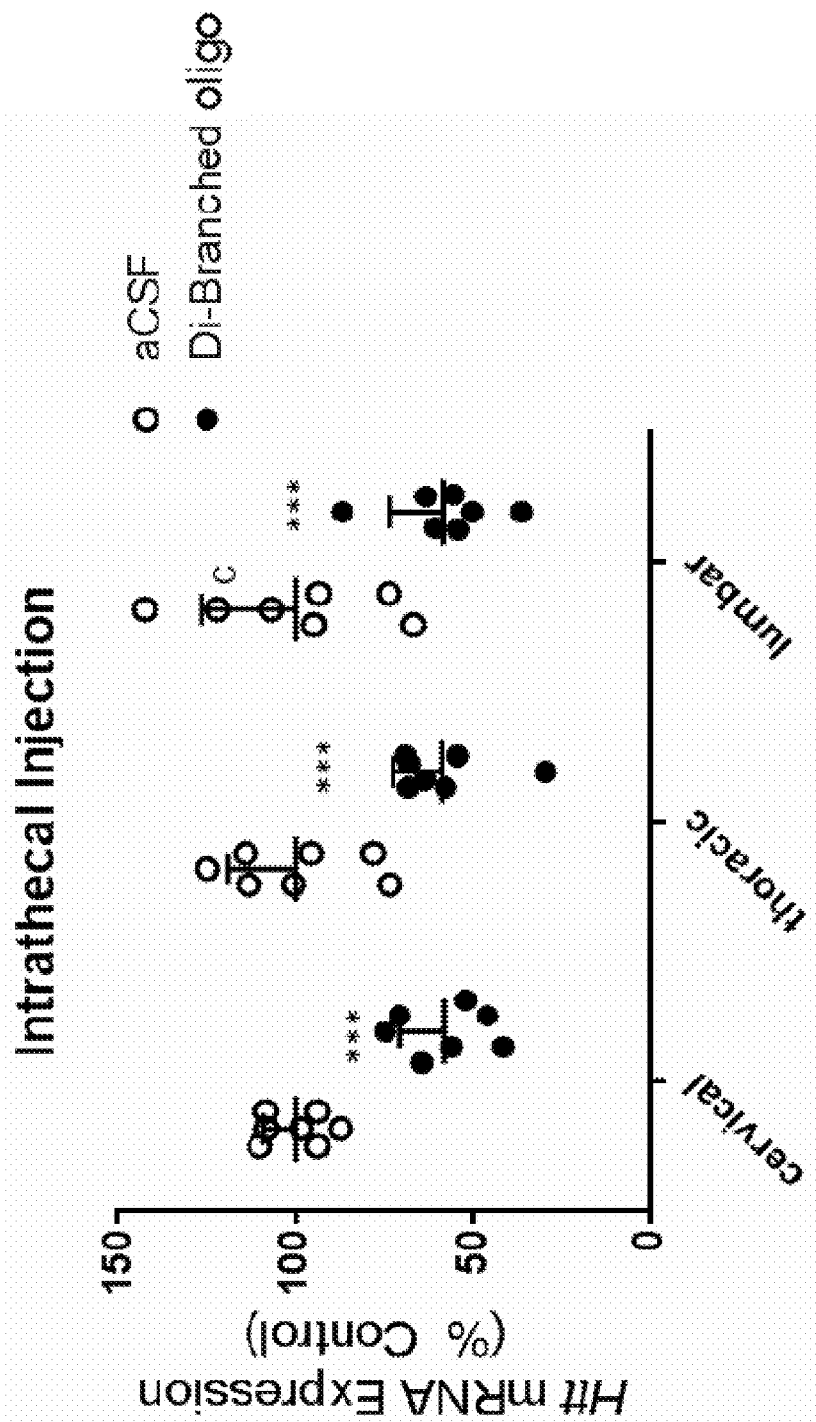
FIG. 75 depicts htt mRNA silencing in the spinal cord after administration of a di-hsiRNAH bolus. IT, 3 nmol, one week, QuantiGene.

Di-hsiRNA also supported uniform spinal cord distribution (FIG. 74). A di-hsiRNA bolus IT injection supported htt silencing in spinal cords (FIG. 75). Di-siRNA showed robust and even silencing throughout the spinal cord following intrathecal injection. A single injection of di-hsiRNA in the lumbar region of the spinal cord silenced mRNA to the same degree in the cervical, thoracic and lumbar regions indicating even and long range distribution. This accepted method of drug delivery will allow for treatment of neurodegenerative diseases affecting neurons in the spinal cord.

Figure 76A:
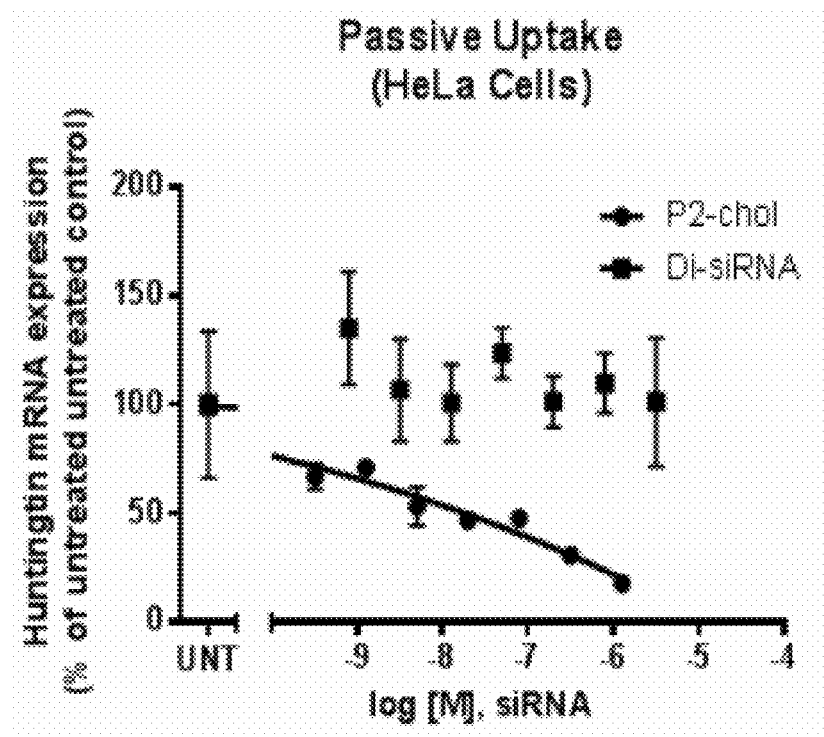
FIG. 76A-76B depicts di-hsiRNA-mediated in vitro silencing in HeLa cells and primary cortical neurons.
Figure 76B:
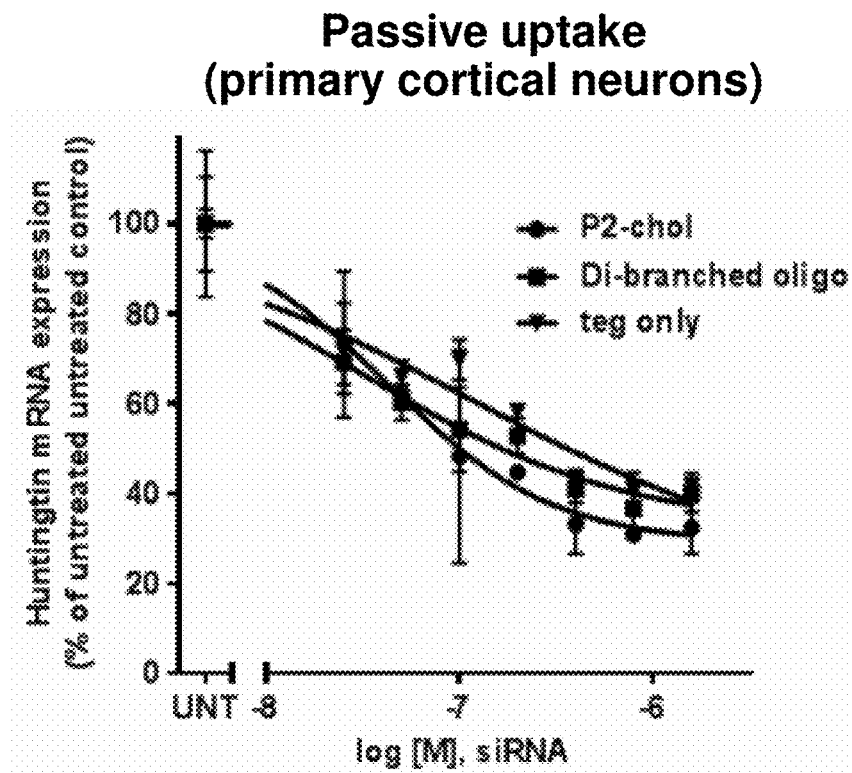

Di siRNA showed a very unique cellular distribution when injected intrastriatally into the brain (FIG. 76). Fluorescently labeled di-siRNA appeared to localize preferentially with neurons in the cortex. This selective feature was specific to these compounds and was not true for other siRNA conjugates, such as cholesterol, which showed no cell-type preference.

Figure 77:
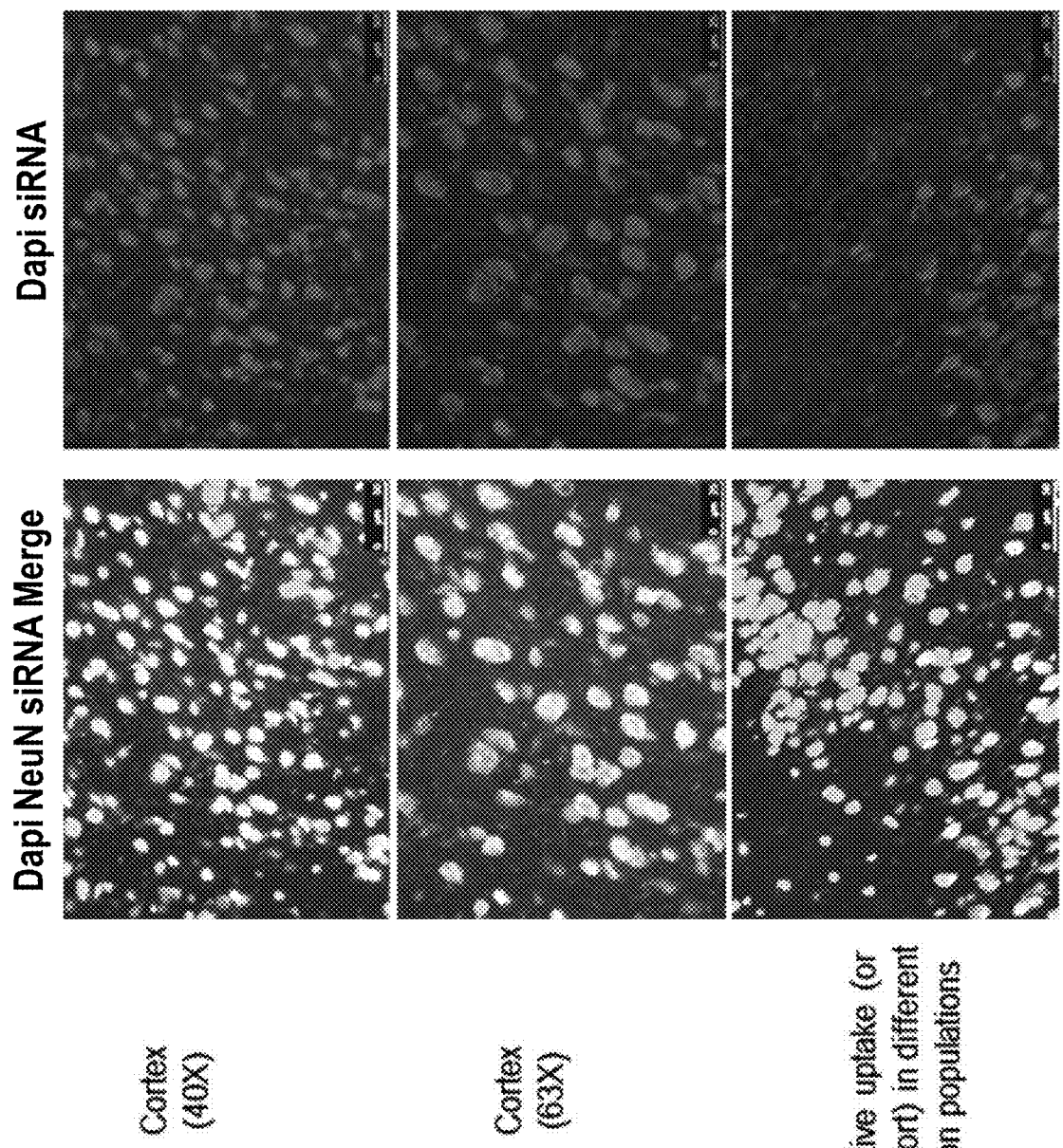
FIG. 77 depicts biodistribution of di-hsiRNA. Intrastriatal injection of 2 nmol of Di-siRNA oligo (4 nmol of corresponding antisense strand). N=2 mice per conjugate. Brains collected 48 hours later and stained with DAPI (nuclei, blue) and NeuN (neuronal marker, green). Image is representative. Red-oligo.
Figure 78:
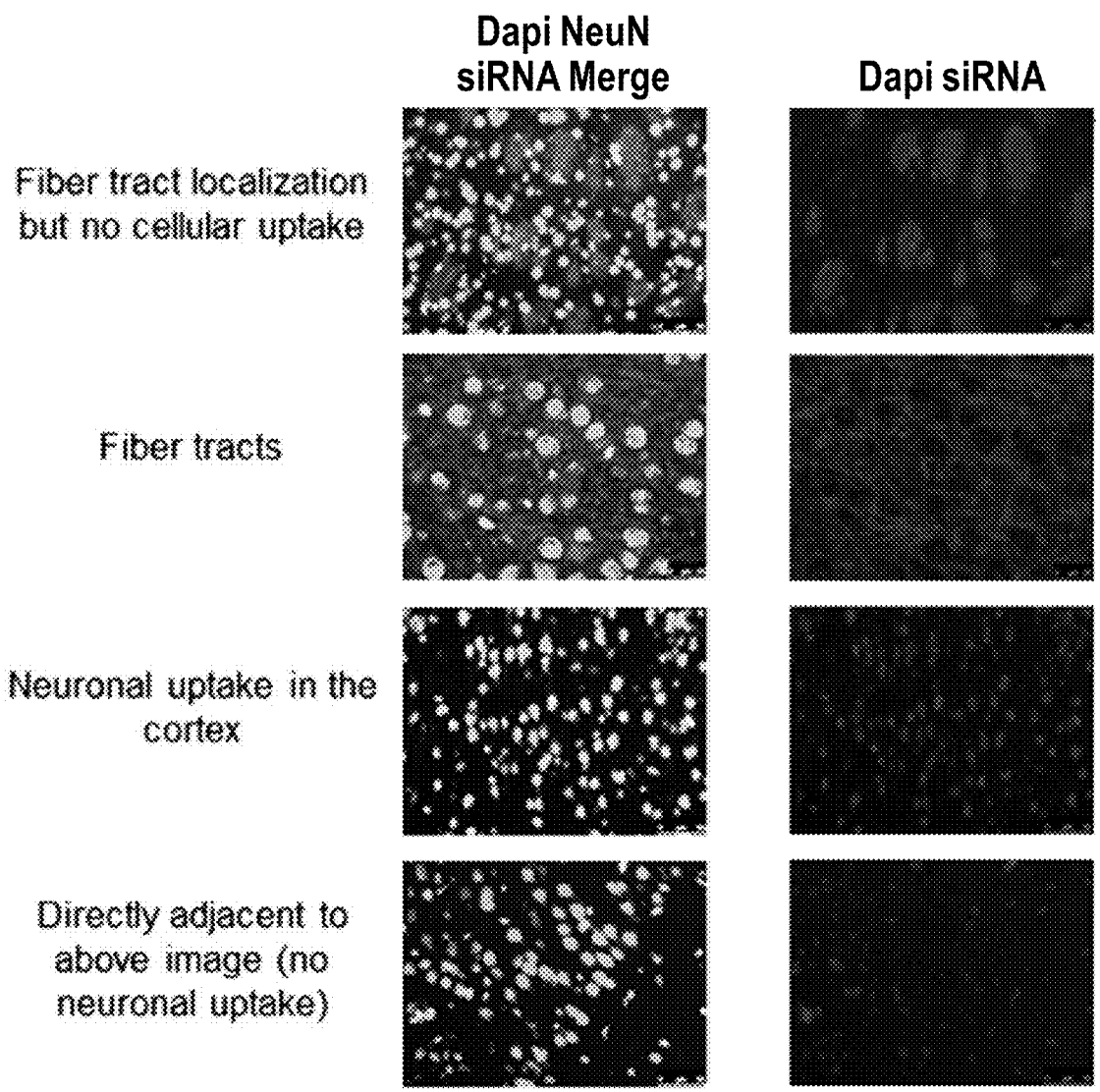
FIG. 78 depicts biodistribution of di-hsiRNA. Intrastriatal injection of 2 nmol of Di-siRNA oligo (4 nmol of corresponding antisense strand). N=2 mice per conjugate. Brains collected 48 hours later and stained with DAPI (nuclei, blue) and NeuN (neuronal marker, green). Image is representative. Red-oligo.

Di-siRNA showed localization to fiber tracts in the striatum but was present within neuronal cell bodies in the cortex (FIG. 77). Without intending to be bound by scientific theory, movement to the cortex could be through diffusion or could be the result of retrograde transport via striatal fiber tracts. The theory that retrograde transport is partially responsible is supported by the fact that some areas of the cortex showed full neuronal penetration while neurons in adjacent areas showed no di-hsiRNA association.

Figure 105A:
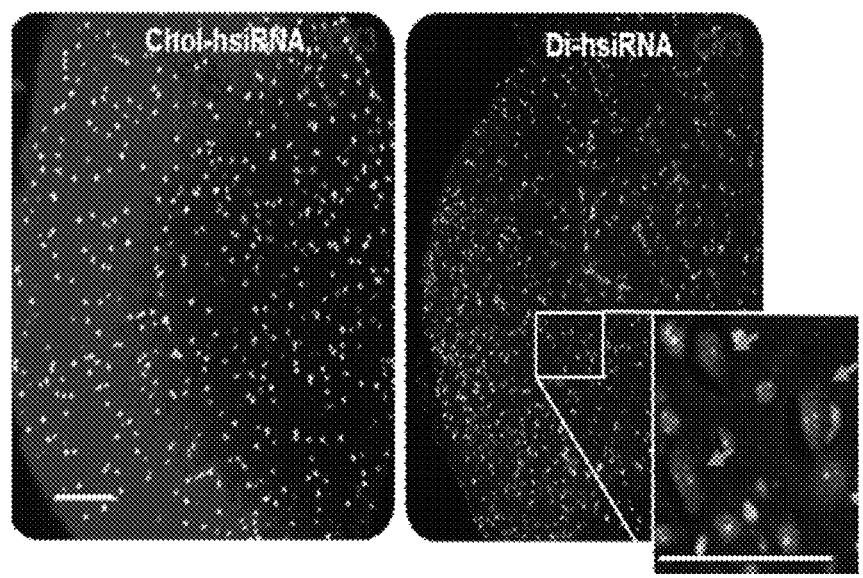
FIGS. 105A-105B show that di-hsiRNAs exhibited wide distribution and efficacy in the mouse spinal cord after a bolus lumbar intrathecal injection. (A) Chol-hsiRNAs showed a steep gradient of diffusion from outside to inside of spinal cord, but Di-hsiRNAs distribute widely throughout the spinal cord. Animals were injected intrathecally with 75 µg Cy3-Chol-hsiRNA or Cy3-Di-hsiRNA. Scale bar=100 µm. (B) Robust Htt mRNA silencing was observed in all regions of spinal cord (7 days post-injection, n=6).

Intrathecal injection of di-hsiRNA produced similarly impressive results for the spinal cord (FIG. 105A). Whereas chol-hsiRNA (the original conjugated hsiRNA) showed a steep gradient of distribution with a relatively small amount reaching grey matter and motor neurons, di-hsiRNAs uniformly distributed throughout the spinal cord and co-localized with the motor neurons (enlarged in FIG. 105A).

Figure 104B:
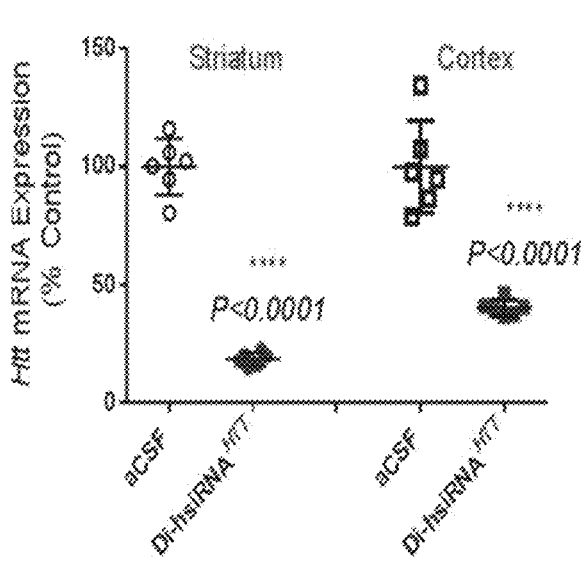
Figure 104C:
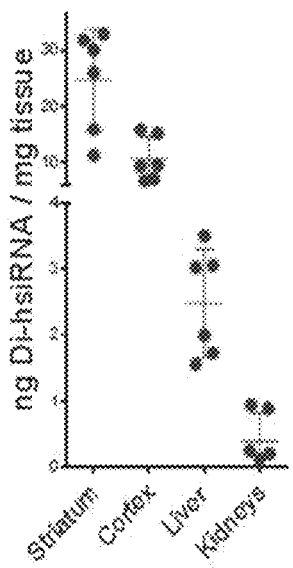
Figure 105B:
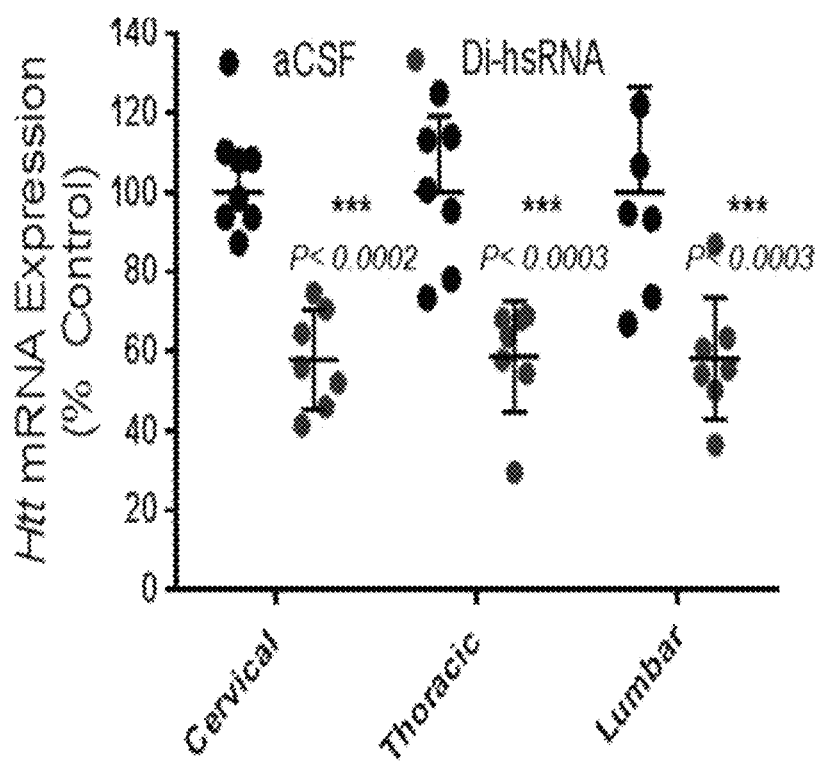

The wide distribution of di-hsiRNA after a single injection was associated with greater than 85% silencing in the striatum, 70% silencing in the in cortex (FIG. 104B) and approximately 50% silencing in the spinal cord (FIG. 105B). While significant amounts of di-hsiRNAs accumulated over time in the striatum, cortex, liver and kidneys (FIG. 104C), no evidence of inflammation or neuronal degeneration were detected at the highest doses tested (i.e., 400 µg ICV and 150 µg IT), which far exceed the minimum effective dose. At these levels, Chol-hsiRNAs are toxic. Based on these data, di-hsiRNAs have been selected as a second class of chemistry for detailed characterization, optimization, and validation. A detailed characterization of di-hsiRNAs will be performed to determine the dose-response, maximum tolerated dose and therapeutic index. Cellular, molecular and biochemical assays will be used to further measure the in vivo distribution and accumulation of compounds and the degree of target gene regulation.

Example 6. Evidence that Axonal Transport Contributes to Di-hsiRNA Distribution in Brain The preferential delivery of di-hsiRNAs to neurons, especially distal to the injection site, was encouraging. In mice intrastriatally injected with Cy3-di-hsiRNA (FIG. 95C), we detect Di-hsiRNA in every NeuN-positive cell (neurons) of the cortex but not in other non-neuronal cell types (e.g., glia). One interpretation of this observation is that di-hsiRNAs are preferentially transported along axons to distal neurons. Why would branched oligonucleotides have such a profound effect on their distribution? It is hypothesized that a role for cooperative binding, whereby one hsiRNA weakly binds to a receptor, and a second independent binding event promotes internalization (Alves I D, Ciano K A, Boguslavski V, Varga E, Salamon Z, Yamamura H I, Hruby V J, Tollin G. Selectivity, cooperativity, and reciprocity in the interactions between the delta-opioid receptor, its ligands, and G-proteins. *The Journal of biological chemistry.* 2004; 279:44673-82. PMID: 15317820). Cooperative binding by covalently linked hsiRNAs might dramatically enhance the rate of cellular uptake and consequently tissue retention. This and other hypotheses will be tested and detailed structure-activity relationship studies of di-hsiRNAs will be performed.

Example 7. Evidence PC-DHA and Di-hsiRNA Conjugates: Two Novel Classes of CNS Active Oligonucleotides As described in the data above, two novel, chemically distinct classes of therapeutic siRNAs, PC-DHA-hsiRNAs and Di-hsiRNAs, have been designed that support wide distribution and potent gene silencing in CNS tissues after CSF infusion. Di-hsiRNAs appear promising but currently lack data on safety and therapeutic index. PC-DHA-hsiRNAs have a wide therapeutic window (FIG. 103). This is important because antisense oligonucleotides in clinical trials for CNS indications have a narrow therapeutic index.

To mitigate potential risk, both classes of compounds will be evaluated in detail. The goal is to achieve greater than 70% target gene silencing at a dose of less than 200 µg/injection, greater than 10-fold therapeutic index, and 1-month to 3-month duration of effect with a bolus injection via CSF. The development of a simple technology platform that allows straightforward and long-lasting silencing in the brain and the spinal cord of a small animal will advance the field of neuroscience research significantly. It will enable direct functional analysis of a range of novel targets with suspected involvement in brain biology and neurodegenerative disease progression. The data described herein demonstrate that chemistry defines distribution, efficacy and safety of oligonucleotides. Chemical variants of PC-DHA-hsiRNA and di-hsiRNA will be evaluated to identify scaffolds with higher efficacy and wider therapeutic indices, features that are essential for future translation of this technology platform towards human therapeutics. Lastly, the performance of several compounds will be validated in established animal models of neurodegenerative disease, by silencing HTT in HD.

Figure 93:
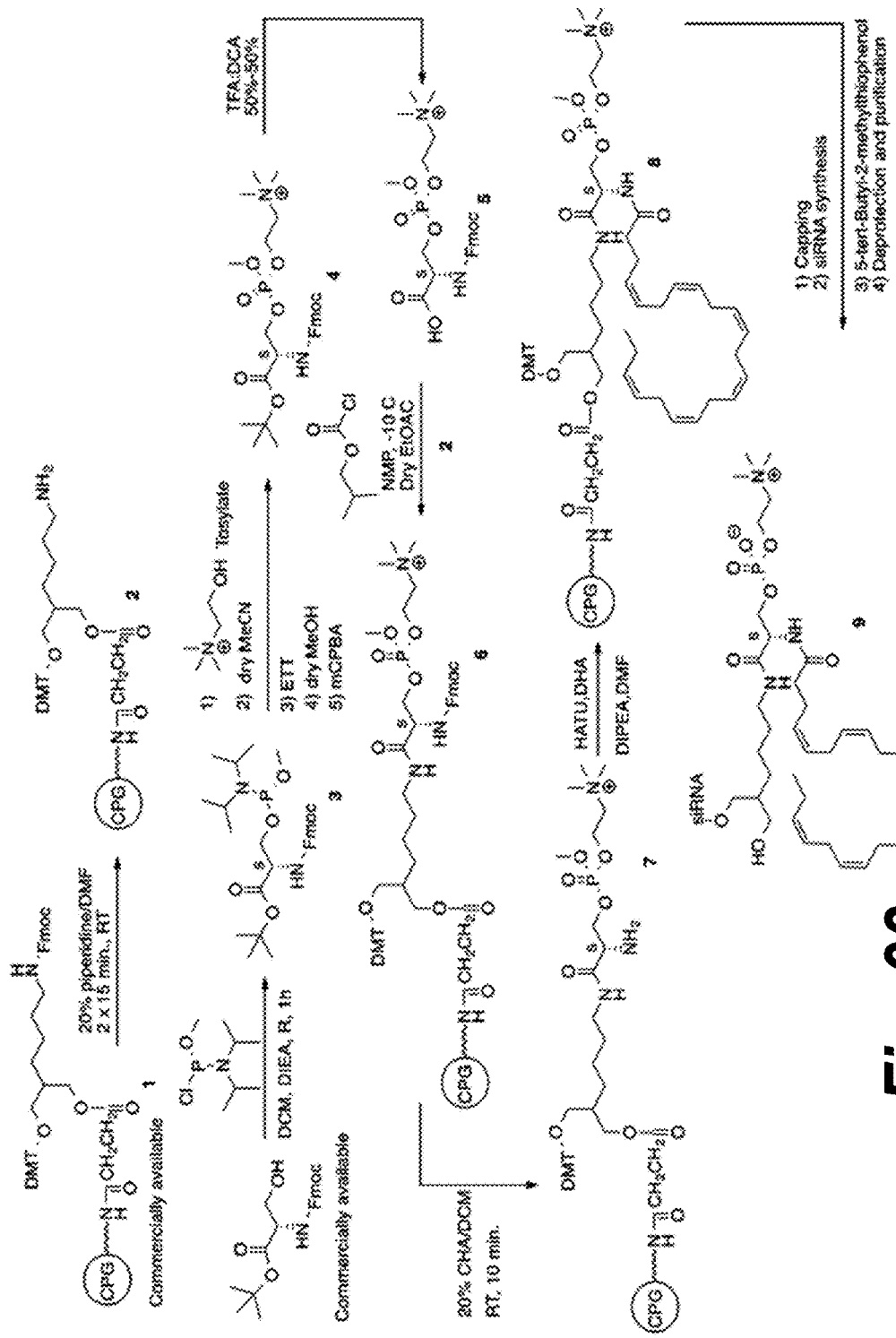
FIG. 93 depicts a synthetic protocol for PC-DHA-functionalized solid support.

Example 8. Characterization of PC-DHA and Di-hsiRNA Distribution, Efficacy and Safety in the Brain and the Spinal Cord Oligonucleotide Synthesis HsiRNA and Di-hsiRNAs will be synthesized (0.2 grams, +/−Cy3) and HPLC-purified as fully metabolically stable hsiRNAs (including 5'-E-VP as a terminal phosphate analog), followed by characterization by mass spectrometry. A variety of linkers have been screened and optimal scaffolds for PC-DHA and di-hsiRNA conjugation have been identified. The functionalized supports will be synthesized as shown in FIGS. 93 and 94. The following compounds will be used: HTT-10150 (HD) and PPIB-437 (housekeeping control). Numbers denote the position of the human mRNA targeted by the 5' nucleotide of the guide strand. All compounds have been previously identified using optimized bioinformatics parameters (Birmingham A, Anderson E, Sullivan K, Reynolds A, Boese Q, Leake D, Karpilow J, Khvorova A. A protocol for designing siRNAs with high functionality and specificity. Nature protocols. 2007; 2:2068-78. PMID: 17853862) and extensive experimental screening. Each siRNA targets and silences the corresponding human, mouse and monkey mRNAs, which will simplify future clinical development.

In addition to standard oligonucleotide synthesis systems, i.e., Mermaid12 and Expedite, a mid-scale RNA-synthesis capability (funded through an S10 grant), including an OligoPilot 100, preparative HPLCs, and high-resolution LC-MS, have been established. Large batches of novel compounds required for the in vivo studies proposed below will be synthesized.

Optimization of Administration Route

Several routes of administration were compared and it was determined that a bolus infusion via CSF (ICV and IT infusion) supports the best degree of compound retention and distribution in CNS tissues. CSF delivery via these routes is analogous to a "spinal tap," a clinically acceptable route of administration. A side-by-side comparison of tissue retention and efficacy was compared when equivalent doses were delivered by bolus injection or by ALZET pump over a period of one week. Significantly better tissue retention and efficacy were observed with bolus injections, consistent with data reported for ASOs (Rigo F, Chun S J, Norris D A, Hung G, Lee S, Matson J, Fey R A, Gaus H, Hua Y, Grundy J S, Krainer A R, Henry S P, Bennett C F. Pharmacology of a central nervous system delivered 2'-O-methoxyethyl-modified survival of motor neuron splicing oligonucleotide in mice and nonhuman primates. The Journal of pharmacology and experimental therapeutics. 2014; 350:46-55. PMID: 24784568; PMCID: PMC4056267). Without intending to be bound by scientific theory, better performance of bolus administration over pump administration could be related to the mechanism of oligonucleotide uptake. For example, non-productive oligonucleotide sinks might be saturated faster by bolus than by pump infusion, thereby allowing excess oligonucleotide to be transported more readily.

Figure 106:
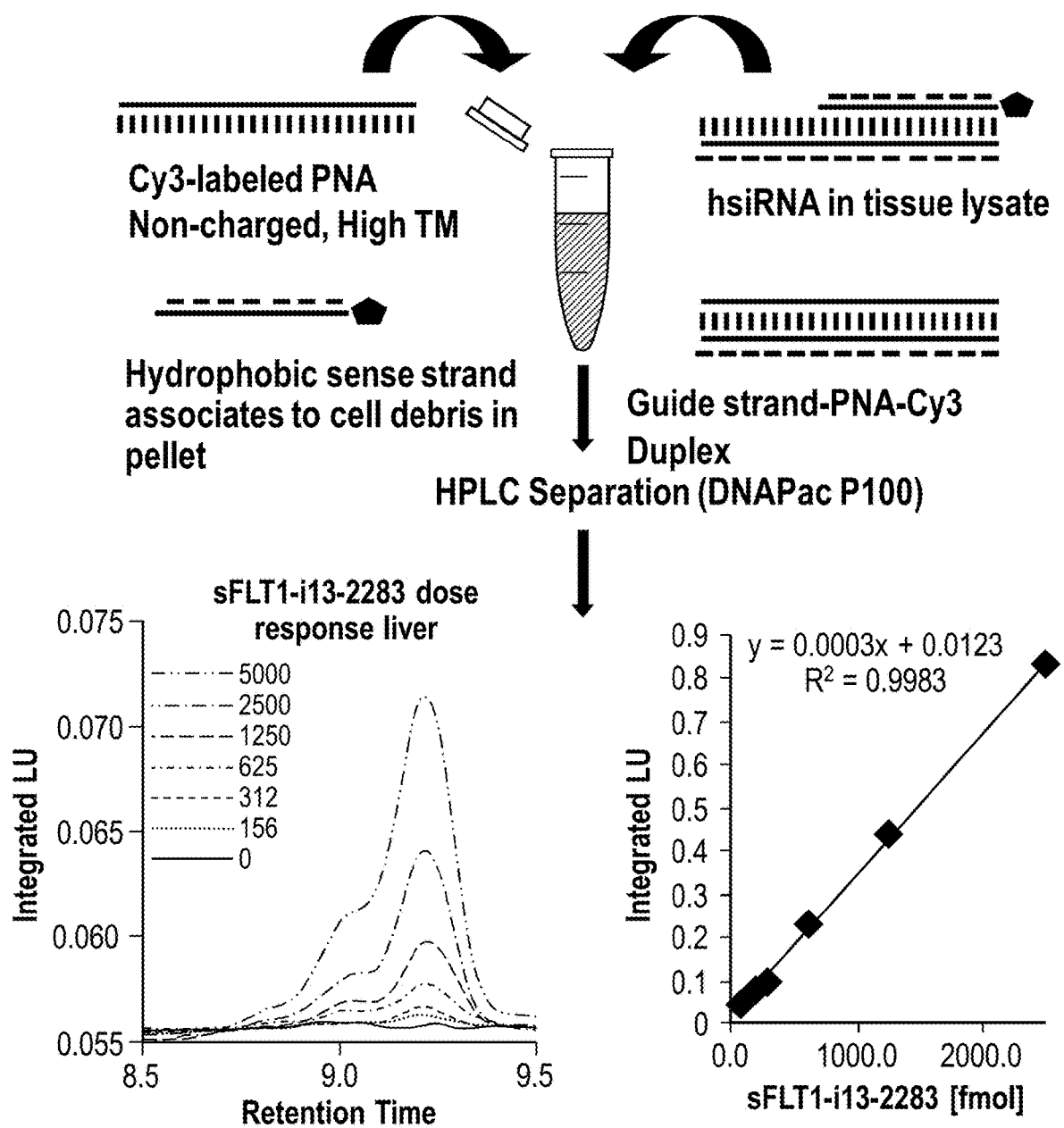
FIG. 106 depicts a PNA (Peptide Nucleic Acid)-based assay for detection of hsiRNA guide strand in mouse tissues. Tissues were lysed, debris separated by precipitation, and the PNA-guide strand duplex purified by HPLC (DNAPac P100, 50% water 50% acetonitrile, salt gradient 0-1M NaClO$_4$).

To directly quantify intact guide strand in tissues, we have developed and implemented a novel and quantitative peptide nucleic acid (PNA) hybridization assay was developed and implemented (FIG. 106). The assay was highly sensitive, with a limit of detection of less than 10 fmole hsiRNA per gram tissue. HsiRNA metabolites with full-length, partially degraded, 5'-phosphorylated and 5'-dephosphorylated guide strand could be readily quantified as separate peaks or shoulders in the HPLC trace. Using this assay the kinetics of guide strand retention in 2-mm punch biopsies taken from regions throughout spinal cord and brain will be quantified.

Based on previous experience, accumulation of 1 to 5 μg oligonucleotide per gram tissue one week after injection is usually enough to support productive target silencing (FIGS. 104B, 104C). The fluorescence and PNA assays allow mapping of the distribution and quantity of conjugated hsiRNA delivered. These studies will complement functional analyses and establish a foundation for silencing efficacy studies.

Identify the Maximum Tolerated Dose

In pilot studies, 200 μg DHA-hsiRNA and di-hsiRNA was established as a safe dose for intrastriatal injection (data for DHA is present in FIGS. 103B and 103C), 150 μg was established as a safe dose for intrathecal injection, and 400 μg was established as a safe dose for intracerebroventricular injection. Beginning at these levels, the dose will be increased in two-fold increments until animals show any indications of toxicity or until drug solubility limits of approximately 20 mM for PC-DHA-hsiRNA and approximately 50 mM for Di-hsiRNA are reached. Three weeks post-injection (optimal time required to see oligonucleotide toxicity), brain tissue will be collected and the number and viability of neurons will be assessed by staining for neuronal markers NeuN and DARPP-32 (Mullen R J, Buck C R, Smith A M. NeuN, a neuronal specific nuclear protein in vertebrates. Development (Cambridge, England). 1992; 116: 201-11. PMID: 1483388; Weyer A, Schilling K. Developmental and cell type-specific expression of the neuronal marker NeuN in the murine cerebellum. Journal of neuroscience research. 2003; 73:400-9. PMID: 12868073; Ouimet C C, Miller P E, Hemmings H C, Jr., Walaas S I, Greengard P. DARPP-32, a dopamine- and adenosine 3': 5'-monophosphate-regulated phosphoprotein enriched in dopamine-innervated brain regions. III. Immunocytochemical localization. The Journal of neuroscience: the official journal of the Society for Neuroscience. 1984; 4:111-24. PMID: 6319625). Microglial activation (innate immune activation) will also be assessed by staining for IBA1 (Judge A D, Bola G, Lee A C, MacLachlan I. Design of noninflammatory synthetic siRNA mediating potent gene silencing in vivo. Molecular therapy: the journal of the American Society of Gene Therapy. 2006; 13:494-505. PMID: 16343994; Marques J T, Williams B R. Activation of the mammalian immune system by siRNAs. Nature biotechnology. 2005; 23:1399-405. PMID: 16273073). To test whether compounds trigger a reversible, short-term inflammatory response, mice will be injected with the maximum tolerated dose and glial activation will be examined at 6 hours post-administration. Completion of this study will generate data on the maximum tolerated dose for the two new classes of therapeutic hsiRNAs described herein.

Estimate PC-DHA and Di-hsiRNAs Clearance Profiles

The residence time of RNAs in CSF and blood will be determined. A repetitive CSF withdrawal in mice is unfeasible, therefore CSF clearance studies will be performed using rats, adjusting the dose accordingly. 10 μl of CSF will be drawn at 1, 6, 12 and 24 hours and at 1 week post-administration of PC-DHA- and Di-hsiRNAs using overlapping groups of animals. Similarly, 20 μL of blood will be collected at 5 and 30 min, and at 1, 4, 12, 24, 48, 72 and 96 hours post-injection. To minimize concerns related to repetitive blood draws over short time periods, and to minimize the number of animals required to obtain precise data, jugular vein catheterization will be used.

Based on previous pharmacokinetic studies with related siRNA compounds, it is expected that biphasic clearance kinetics will be observed, with the fast phase completed within four to six hours. Based on pilot studies, it could take a month(s) for complete drug clearance. However, a one-week pilot study is enough to approximate the clearance profile. Completion of this study will generate pilot data on clearance profiles for the two new classes of therapeutic hsiRNAs described herein.

Establishing the Dose Response

Dose-response studies will be performed to determine the optimal dose for silencing in areas of the brain showing significant oligonucleotide accumulation. Experiments will be performed similarly to those presented in FIGS. 103, 104 and 105. 3-mm punch biopsies will be harvested from the brain and spinal column of mice injected with increasing doses of PC-DHA and Di-hsiRNA, the levels of HTT or control mRNAs will be measured using the QUANTI-GENE® assay.

QUANTIGENE® is a highly sensitive 96-well-based assay that uses signal amplification to detect mRNA in tissue or cell lysates directly. A protocol describing an automated, high-throughput (96-well) version of the assay that directly links TissueLyser and QUANTIGENE® was recently published (Coles A H, Osborn M F, Alterman J F, Turanov A A, Godinho B M, Kennington L, Chase K, Aronin N, Khvorova A. A High-Throughput Method for Direct Detection of Therapeutic Oligonucleotide-Induced Gene Silencing In Vivo. *Nucleic acid therapeutics.* 2015. PMID: 26595721). Thus, simultaneous quantification of HTT and housekeeping mRNAs can be performed for many tissues and/or animals. In pilot studies, it was determined that eight mice per group was sufficient to detect a 40% reduction in target gene expression with 80% confidence. Id.

HTT mRNA levels will be normalized to a control housekeeping mRNA. Artificial CSF and non-targeting controls (NTC) of the same chemical composition will be used to control for non-sequence-specific events. NTC hsiRNA will only be injected at the highest non-toxic concentration to limit the number of animals used. Though NTC is a better negative control, a second targeting hsiRNA (e.g., PPIB-targeting) will provide silencing data on two different targets with the same number of animals. Confirmation of silencing at the protein level is essential before transitioning toward animal models of disease, so Western blotting will be performed in a similar manner as has been done for chol-hsiRNAs (Alterman J F, Hall L M, Coles A H, Hassler M R, Didiot M C, Chase K, Abraham J, Sottosanti E, Johnson E, Sapp E, Osborn M F, Difiglia M, Aronin N, Khvorova A. Hydrophobically Modified siRNAs Silence Huntingtin mRNA in Primary Neurons and Mouse Brain. *Molecular therapy Nucleic acids.* 2015; 4:e266. PMID: 26623938). Completion of this study should identify doses enabling functional gene silencing in different regions of the CNS for the two new classes of therapeutic hsiRNAs described herein.

PC-DHA and Di-hsiRNA Duration of Silencing Upon Single Administration

Most neurodegenerative disorders and disease models present a late onset of symptoms (e.g., 3 to 9 months in mice). The duration of silencing from one injection and how many injections will be needed to support 6 to 9 months of silencing should be determined. In general, siRNA-induced silencing in non-dividing cells is expected to last for month(s). The half-life of loaded RISC complex is several weeks (Whitehead K A, Langer R, Anderson D G. Knocking down barriers: advances in siRNA delivery. Nature reviews Drug discovery. 2009; 8:129-38. PMID: 19180106) and less than 1,000 loaded RISC molecules per cell are sufficient to induce silencing (Stalder L, Heusermann W, Sokol L, Trojer D, Wirz J, Hean J, Fritzsche A, Aeschimann F, Pfanzagl V, Basselet P, Weiler J, Hintersteiner M, Morrissey D V, Meisner-Kober N C. The rough endoplasmatic reticulum is a central nucleation site of siRNA-mediated RNA silencing. *The EMBO journal.* 2013; 32:1115-27. PMID: 23511973; PMCID: 3630355; Pei Y, Hancock P J, Zhang H, Bartz R, Cherrin C, Innocent N, Pomerantz C J, Seitzer J, Koser M L, Abrams M T, Xu Y, Kuklin N A, Burke P A, Sachs A B, Sepp-Lorenzino L, Barnett S F. Quantitative evaluation of siRNA delivery in vivo. *Rna.* 2010; 16:2553-63. PMID: 20940339; PMCID: 2995415).

Figure 2I:
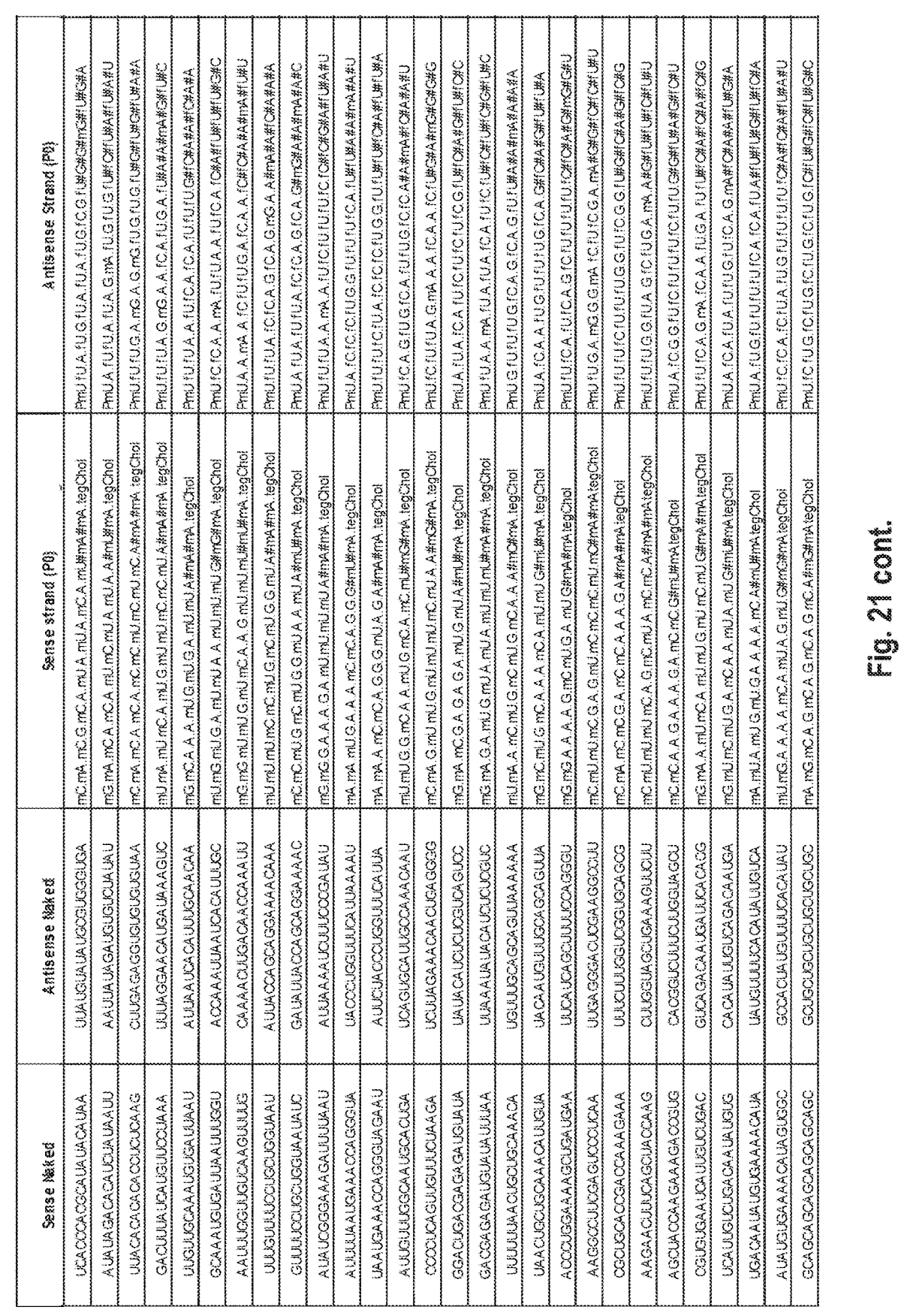
Figure 2A:
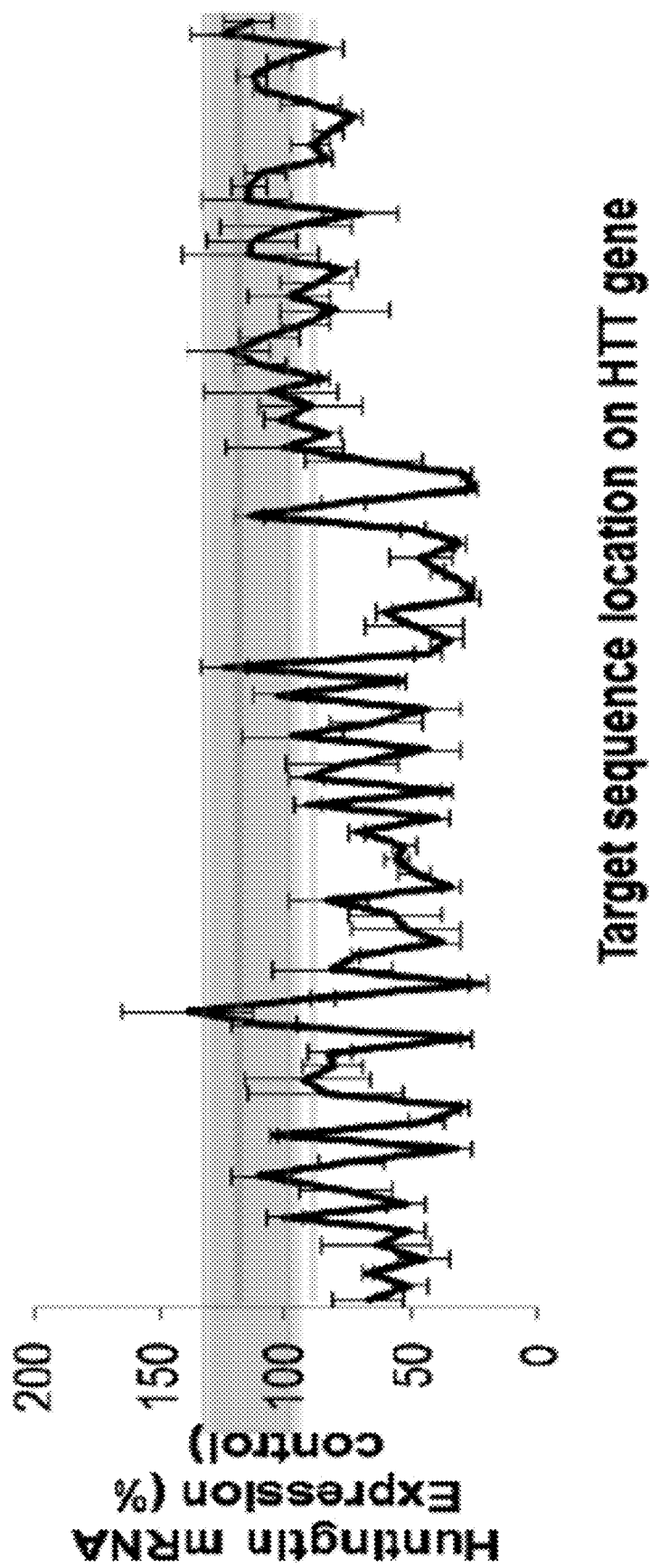
FIGS. 2A-2C depict a systematic screening of unformulated hsiRNAs targeting huntingtin mRNA plotted as a line graph (A) or a bar graphs (B) and (C). A panel of 94 hsiRNAs were added to HeLa cells at 1.5 M. Level of huntingtin mRNA was measured using QUANTIGENE (Affymetrix) at 72 hours normalized to housekeeping gene, PPIB (cyclophilin B), and presented as percent of untreated control (n=3, mean+/−SD). UNT—untreated cells, NTC—non-targeting control. Active compounds (red) were selected for further analysis.
Figure 2B:
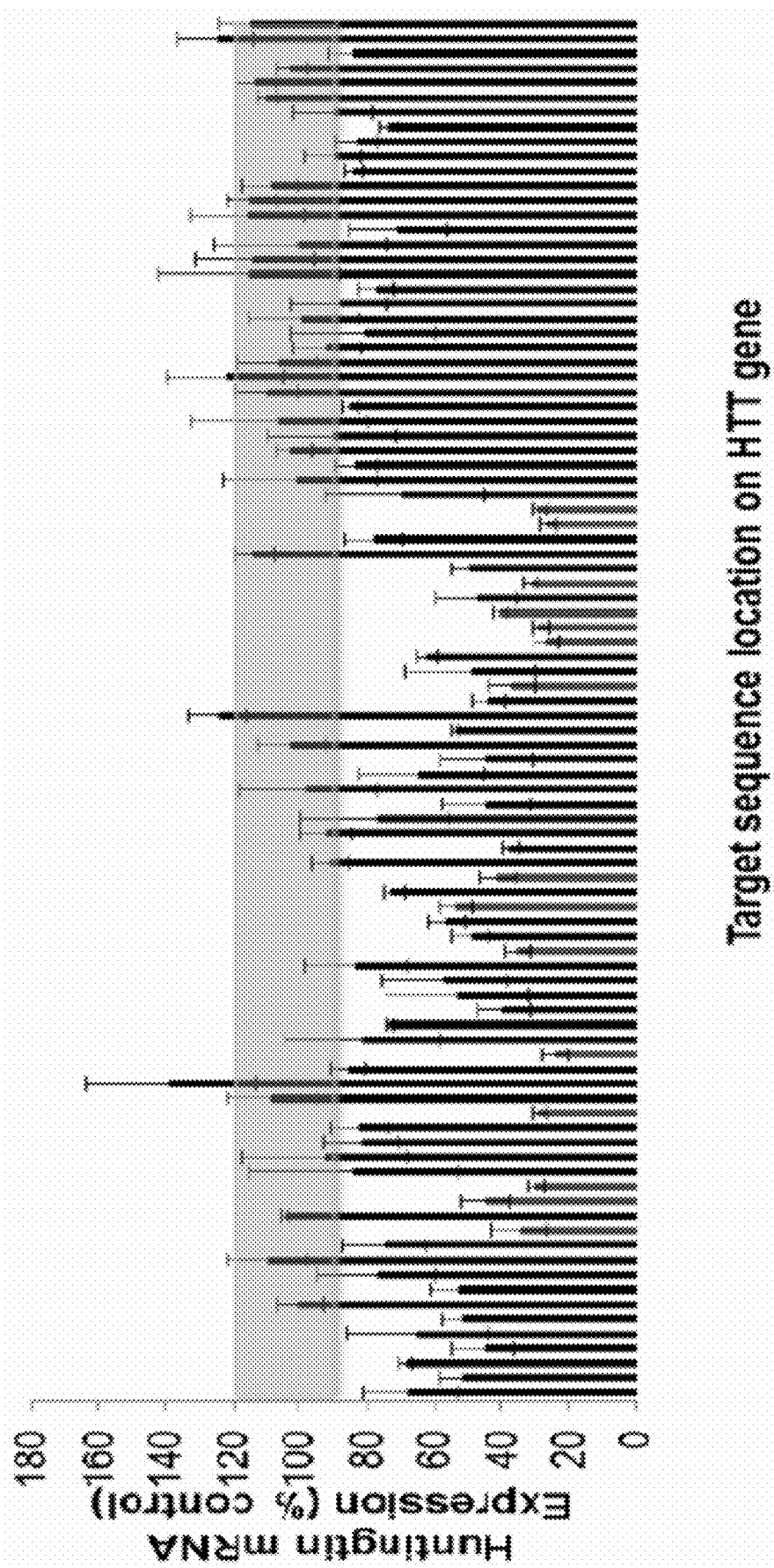
Figure 2C:
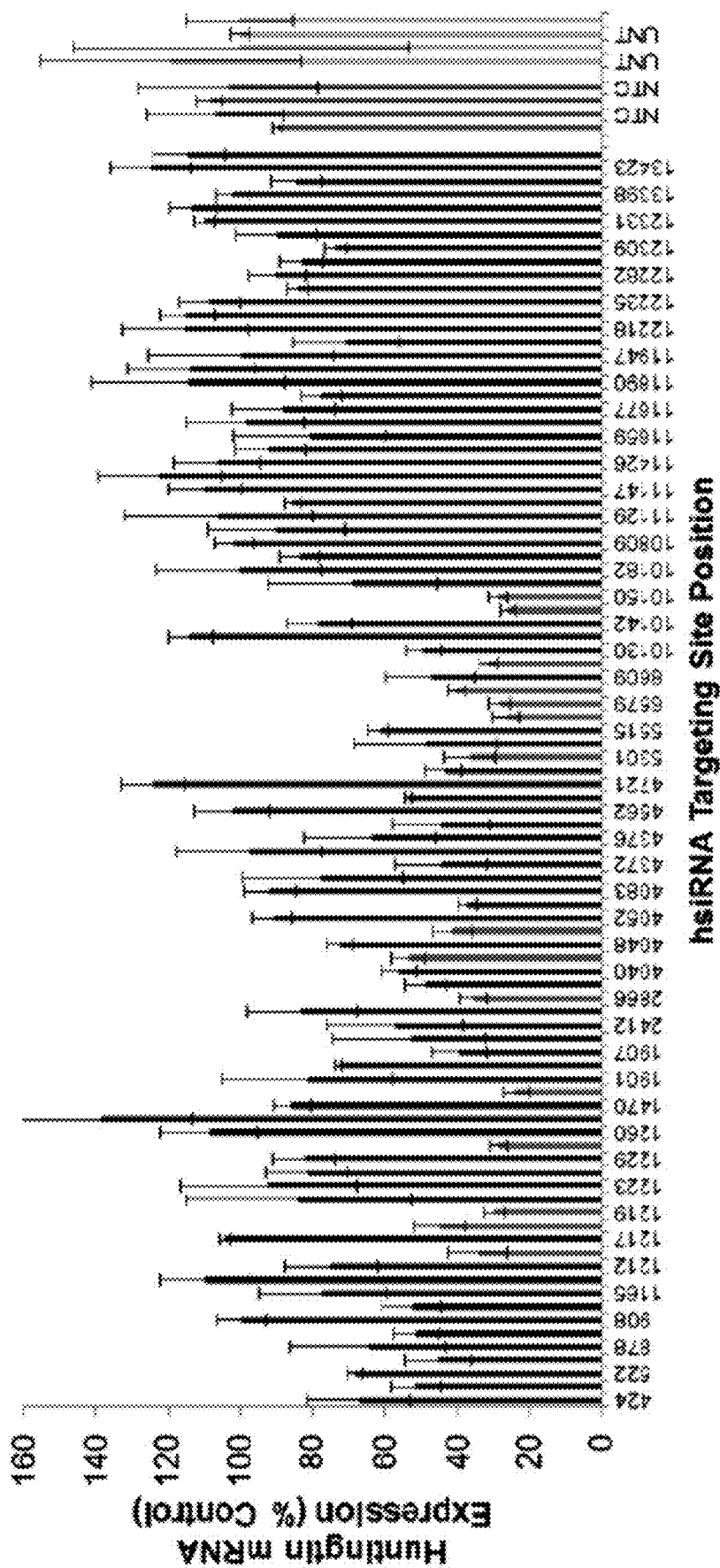

Moreover, FM-hsiRNAs may provide another advantage. A cell usually takes up millions of hsiRNAs, but the vast majority are trapped in lysosomes. Conventional, partially modified hsiRNAs entrapped in lysosomes are degraded, but FM-hsiRNAs are not. As a result, FM-hsiRNAs transiently trapped in lysosomes form an intracellular "depot" that slowly releases FM-hsiRNAs, making them available for RISC loading. Data from the Alnylam GalNAc trials indicate that optimized delivery to the liver provides up to six-month efficacy from a single subcutaneous injection. The data presented herein are in line with this observation; a single FM-hsiRNA injection provides maximal silencing for at least a month (FIG. 2D).

To measure the retention of hsiRNA and duration of silencing, three mice will be injected with the highest tolerated dose of PC-DHA- or di-hsiRNAs, and the levels of intact guide strand in tissues will be measured at 1, 2 and 4 weeks and at 2, 3, 4 and 6 months using the PNA assay (FIG. 106). As soon as intact guide strand levels fall below 1 μg hsiRNA per gram tissue, the study will be terminated. HTT mRNA levels will be measured at time points where guide strand concentration is above one g per gram tissue in a separate study powered (n=8) to reliably detect silencing effects. Though it is expected that the duration of silencing will be at least three months, experimental validation is desired.

Exploring Mechanisms of Cellular Uptake and Trafficking of Di-hsiRNAs

Di-branched hsiRNAs showed significantly enhanced retention and distribution in CNS tissues compared to an equal dose of linker-bound single siRNA, indicating that cooperative binding by the covalently linked siRNAs or receptor dimerization drive cellular uptake (FIG. 95C). Differential uptake will be visualized and characterized using a combination of TESM microscopy (time-resolved epifluorescence structure microscopy) and mass spectrometry.

Develop "Antidotes" for HTT Compounds

Gene therapy approaches (i.e., permanent gene silencing) are currently being considered for treatment of neurodegenerative disorders, so 1- to 6-month duration of silencing seems relatively safe. Nevertheless, an "antidote" to reverse the silencing would satisfy concerns about safety. An "antidote" is also be a great tool to study gene function in vivo, allowing one to test how long a gene needs to be downregulated to produce associated phenotypes.

Figure 96:
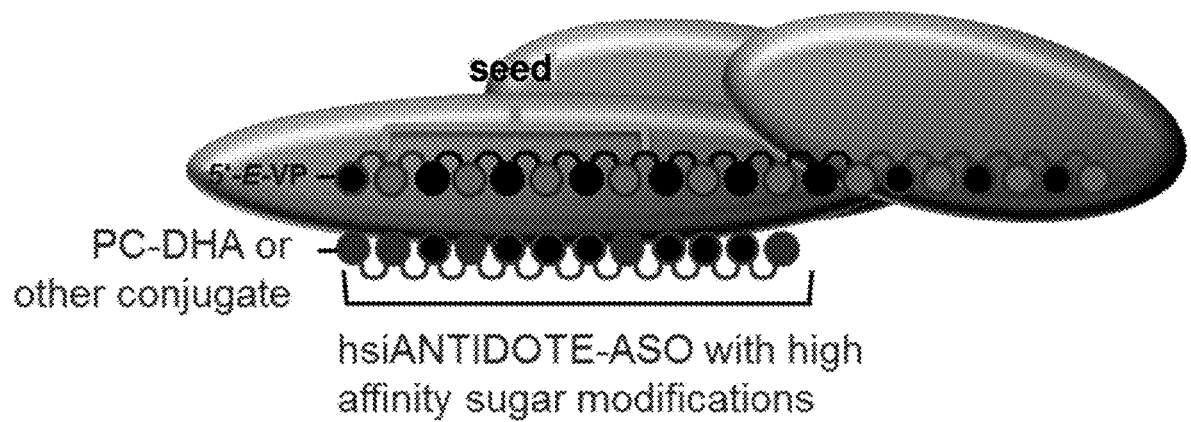
FIG. 96 depicts an hsiANTIDOTE antisense oligonucleotide carrying high affinity modification (LNA) designed to be fully complementary to the hsiRNA antisense strand seed region.

Addressing similar concerns from the FDA, Alnylam has developed a technology, called "REVERSIR®," which enables reversal of long-term silencing. The concept involves developing a high-affinity antisense (LNA and 2'-O-methyl/deoxy) MIXMER® fully complementary to the seed region of the functional hsiRNA. WA panel of hsiAN-TIDOTEs targeting HTT10150 (and eventually other compounds) will be designed and synthesized, and their ability to reverse silencing in vitro and in vivo will be assessed (FIG. 96). Antidotes will be synthesized in the context of the PC-DHA conjugate to enable similar distribution properties as the PC-DHA-hsiRNA. Completion of this study will generate antidotes against lead hsiRNA compounds to enable reversal of their in vivo activity, if desired.

Alternative Approach: Test Whether PC-DHA Conjugation and Di-Branched Structure Improve Antisense-Mediated Silencing in the Brain Antisense oligonucleotides for the treatment of neurodegenerative disorders are in clinically advanced stages of development (Evers M M, Toonen L J, van Roon-Mom W M. Antisense oligonucleotides in therapy for neurodegenerative disorders. *Advanced drug delivery reviews.* 2015. PMID: 25797014; Kordasiewicz H B, Stanek L M, Wancewicz E V, Mazur C, McAlonis M M, Pytel K A, Artates J W, Weiss A, Cheng S H, Shihabuddin L S, Hung G, Bennett C F, Cleveland D W. Sustained therapeutic reversal of Huntington's disease by transient repression of huntingtin synthesis. *Neuron.* 2012; 74:1031-44. PMID: 22726834; PMCID: PMC3383626). IONIS-HTTRx is a generation 2.5 antisense chemistry proprietary to Ionis and not generally available to the academic community.

A highly potent locked-nucleic acid (LNA) GapmeR targeting HTT has been developed, however. To test whether a PC-DHA conjugation and/or di-branching can improve the distribution and retention of antisense oligonucleotides in brain tissues and reduce their effective doses, PC-DHA- and di-LNA GapmeRs targeting HTT will be synthesized.

Completion of this example will result in the full characterization of the two novel oligonucleotide conjugates (i.e., PC-DHA and di-hsiRNAs) described herein in CNS (brain and spinal cord), including optimal delivery route, drug clearance and retention, safety, dose response and duration of effect. The experimentation described herein will enable use of these chemistries for gene silencing and target validation studies in CNS in vivo, as well as provide a solid foundation toward development of novel therapies for HD.

Example 9. Synthesis and Characterization of a Panel of PC-DHA and Di-hsiRNA Chemical Variants to Improve Distribution and Therapeutic Index The data presented herein (FIGS. 92, 103, 104 and 105) indicates that PC-DHA- and di-hsiRNA chemistry will be sufficient to reach a target of 1-month to 3-month duration of effect in spinal cord, striatum, and cortex, which is sufficient for functional genomics studies in vivo. This alone is a significant achievement, but future translation of this technology platform toward human therapeutics represents another level of complexity. Before we translate the technology, we will optimize the chemistry for (i) the widest possible therapeutic index and (ii) enhanced distribution to support delivery to large brains.

Slight changes in the chemical scaffold of a conjugate can profoundly affect tissue distribution as was demonstrated by functionalizing DHA with phosphatidylcholine (FIG. 92). Capitalizing on these synthetic platforms, a panel of PC-DHA- and di-hsiRNA variants will be synthesized to further optimize therapeutic index and wide tissue distribution.

PC-DHA Optimization

There are two essential components to the PC-DHA structure: phosphatidylcholine and DHA (see structure in FIG. 92). The synthesis approach described herein (FIGS. 93 and 94) will allow these chemistries to be varied independently. Little to no information exists in the literature on the structure-function relationship of oligonucleotide conjugates, but a large body of information exists describing how polymer structures and lipid compounds affect lipid-particle formation[48]. The studies indicate that the length of lipid has a major impact on overall formulation efficacy.

Polyunsaturated bonds are essential for enhanced hsiRNA distribution in CNS tissues. Conjugation of DCA, a fully saturated analog of DHA, does not promote wide distribution in CNS. Conjugation of EPA, two carbons shorter than DHA, leads to an interesting distribution profile, but efficacy has not yet been tested. A panel of phosphatidylcholine-modified polyunsaturated fatty acid variants, changing the length of the lipid tail from 10 to 22 carbons and the number of polyunsaturated bonds from 0 to 4 will be synthesized. The precursors for these synthesis reactions are all commercially available. These compounds will reveal how the length of the lipid tail length and number of polyunsaturated bonds affects oligonucleotide distribution in the CNS.

Second, a systematic substitution of the choline entity will be performed for a range of modifications, mostly favoring naturally occurring chemical scaffolds, e.g., phosphatidylserine, phosphatidylinositol and phosphatidyl amine. Most of these syntheses can be performed in parallel, creating a library of compounds with fixed lipid tail composition and a variety of head groups. This library will be used to define the importance of head groups on the in vivo performance of hsiRNA conjugates.

Figure 97:
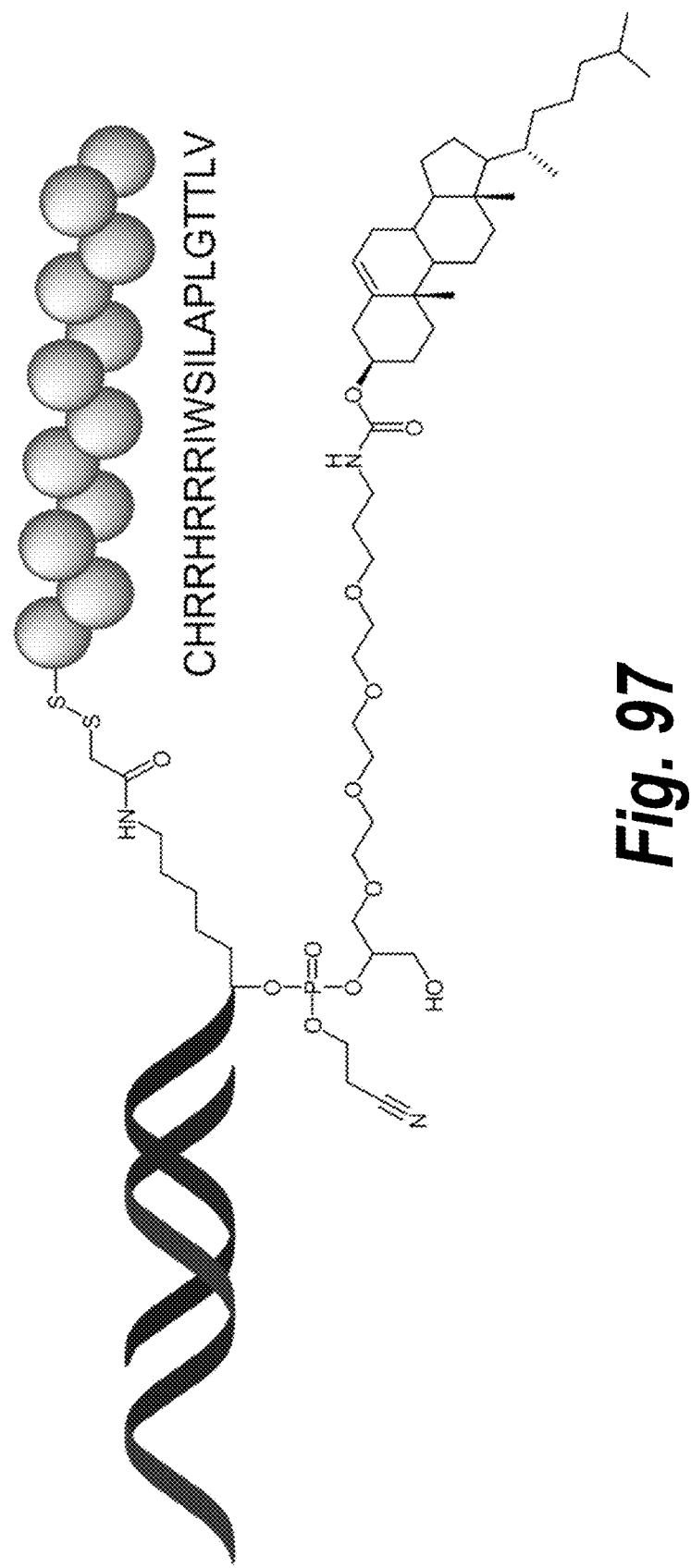
FIG. 97 depicts a cholesterol and endocytic peptide (proton sponge) conjugated hsiRNA. Fig. discloses SEQ ID NO: 1329.

It is well known that, regardless of the nature of the chemistry or formulation for delivery, the vast majority of internalized oligonucleotides are not biologically available. Endosomolytic, peptide-modified polymers have been used by Arrowhead Research Corporation (Wong S C, Klein J J, Hamilton H L, Chu Q, Frey C L, Trubetskoy V S, Hegge J, Wakefield D, Rozema D B, Lewis D L. Co-injection of a targeted, reversibly masked endosomolytic polymer dramatically improves the efficacy of cholesterol-conjugated small interfering RNAs in vivo. *Nucleic acid therapeutics.* 2012; 22:380-90. PMID: 23181701) to enhance systemic efficacy of co-administered cholesterol-modified siRNA compounds. Building on this concept, a library of linkers varying the number and composition of endosomolytic peptides was synthesized. Most variants had no impact on chol-hsiRNA efficacy, but the best lead (FIG. 97A) enhanced silencing upon passive uptake greater than 10-fold (FIG. 97B). Without intending to be bound by scientific theory, the enhanced activity likely results from the increased bioavailability of internalized chol-hsiRNA, as the modified linker did not increase the efficacy by lipid-mediated uptake (FIG. 97B) or the overall amount of oligonucleotide internalized. This linker will be combined with the most optimal combination of lipid length and head group.

Di-hsiRNA Optimization

Figure 103A:
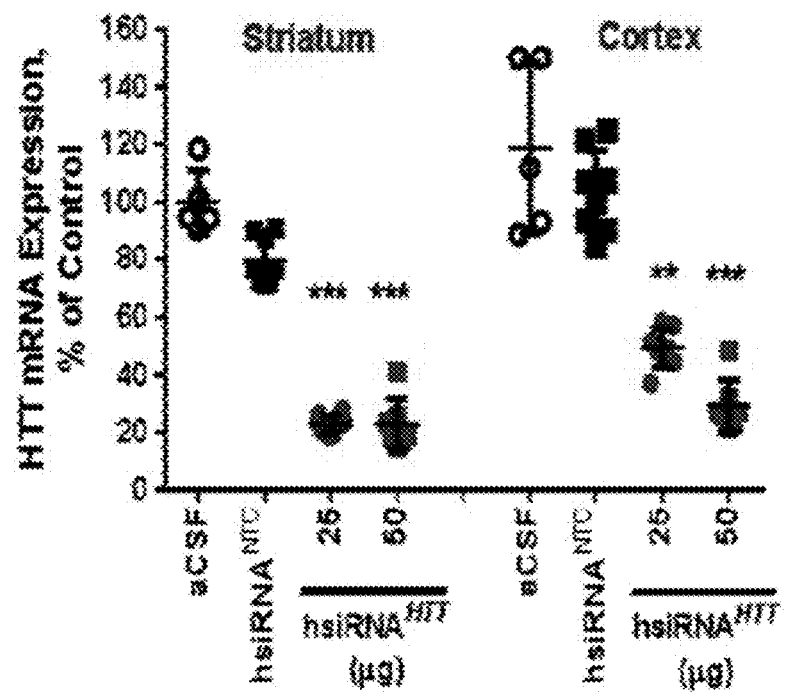
FIGS. 103A-103C depict PC-DHA-hsiRNAs efficacy and safety in mouse brain in vivo. (A) Htt mRNA levels in striatum and cortex 1 week after injecting 25 or 50 µg DHA-hsiRNA. ***P<0.0001 relative to both aCSF and NTC. (B) No detectable innate immune activation occurred at dose levels 20-fold higher than the effective dose (data shown for total microglia for DHA-hsiRNA). (C) Normal neuronal viability based on DARP32 levels. Note the toxic dose (red bar) for chol-hsiRNA.
Figure 103B:
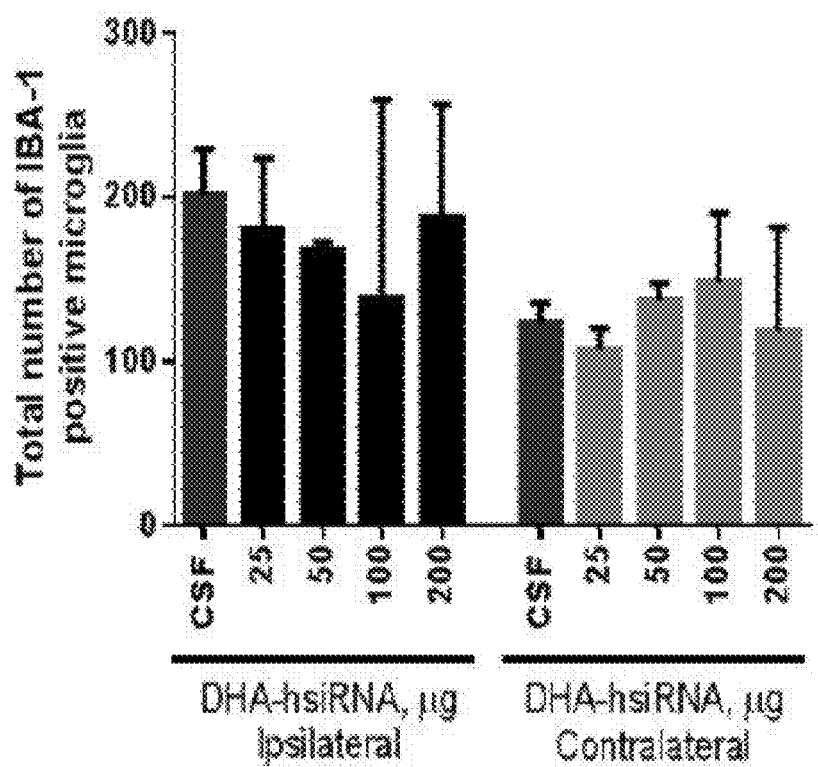
Figure 103C:
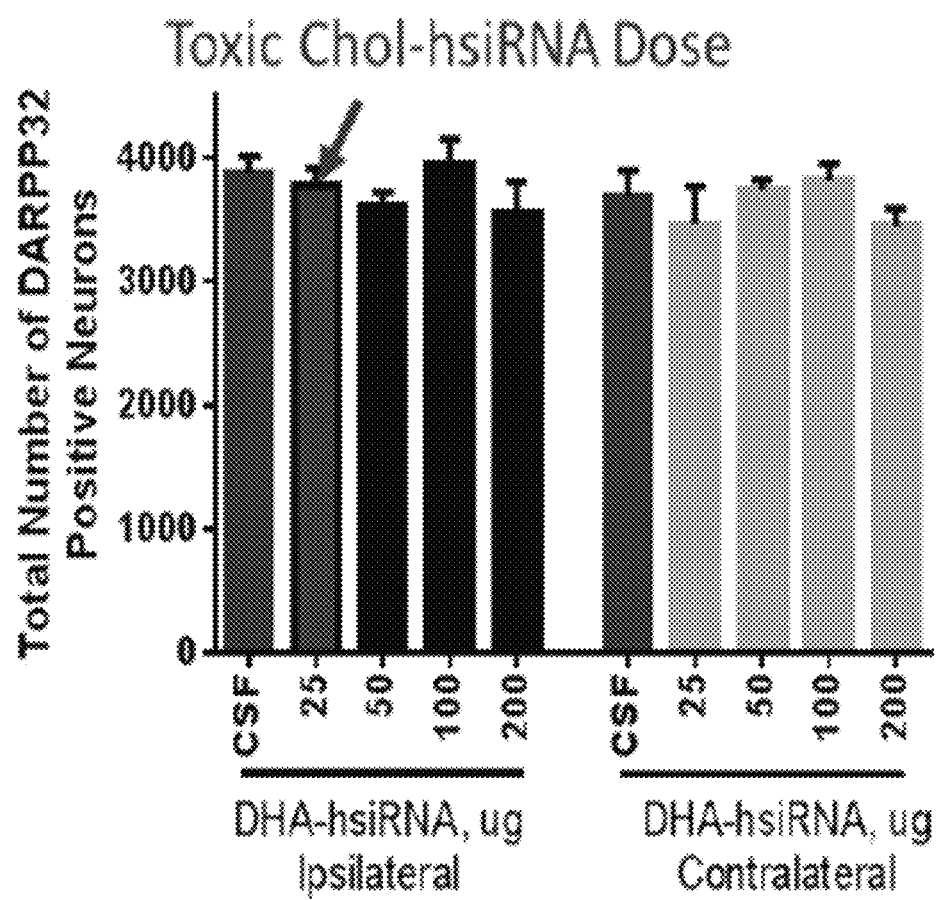

The two hsiRNAs in the di-hsiRNA compound are connected asymmetrically: one by a phosphate bond and the other by a phosphoramidate bond (FIGS. 93, 94 and 103A).

To establish whether the phosphoramidate bond is necessary, a di-branched compound in which the hsiRNAs are both connected to the linker via phosphates is being currently tested (modified synthesis scheme based on that in FIGS. 93 and 94). Showing that the phosphoramidate bond is not essential would simplify structure-activity relationship studies, as a large number of commercially available precursors can be used. Nevertheless, a requirement for the phosphoamide bond would be interesting because phosphoamide is much less stable in acidic conditions and is expected to promote release of compounds from endosomes.

A panel of variants will be synthesized, testing the following parameters: number of hsiRNAs (2, 3, 4 or 6, using two- and three-branch dividers available from Glen Research); and the chemical nature of the linker connecting the oligonucleotides (TEG, saturated and non-saturated alkyl chain, charged, non-charged, lengths from 3 to 30 carbons and proton sponges). The minimal number of phosphorothioate bonds required for uptake will also be identified. It was already determined that phosphorothioate bonds were essential for passive uptake and efficacy of hsiRNA, so it is suspected that cooperative binding of two phosphorothioate tails drives the enhanced distribution and uptake of Di-hsiRNAs. However, phosphorothioate bonds also drive the toxicity of antisense oligonucleotides (Geary R S, Norris D, Yu R, Bennett C F. Pharmacokinetics, biodistribution and cell uptake of antisense oligonucleotides. *Advanced drug delivery reviews.* 2015; 87:46-51). Thus, optimizing and reducing the number of phosphorothioates is a reasonable path toward enhancing the therapeutic index.

Evaluation of Efficacy of PC-DHA- and Di-hsiRNA Variants

Tissue culture experiments will be used to confirm safety and efficient entry into the RISC complex. Each compound will then be injected ICV at the minimum effective and maximum tolerated doses established as described herein. Compounds that are efficacious at lower concentrations or/and nontoxic at higher concentrations will be selected for detailed studies. Lastly, the ability of the most promising compounds to distribute through a large brain (e.g., sheep) will be assessed. A sheep model has been designed to evaluate the distribution of AAV-htt vectors. The PNA assay described herein will be used to measure the levels of compound in biopsies from different regions of the sheep brain after a bolus ICV infusion.

Completion of this example is expected to: (i) inform on chemical structures that define in vivo efficacy of PC-DHA- and Di-hsiRNAs; and (ii) generate versions of these compounds with enhanced distribution, efficacy and therapeutic index.

Example 10. Development of Candidate Pre-Clinical Compounds for Huntington's Disease Models Evaluation of Novel Conjugate of hsiRNA HTT10150 in Huntington's Disease Animal Models The hyper-functional, FM-hsiRNA for Htt, HTT-10150, is described herein. Multiple HD animal models currently running in his lab (Chang R, Liu X, Li S, Li X J. Transgenic animal models for study of the pathogenesis of Huntington's disease and therapy. *Drug design, development and therapy.* 2015; 9:2179-88. PMID: 25931812; PMCID: PMC4404937), including YAC128 (Hodgson J G, Agopyan N, Gutekunst C A, Leavitt B R, LePiane F, Singaraja R, Smith D J, Bissada N, McCutcheon K, Nasir J, Jamot L, Li X J, Stevens M E, Rosemond E, Roder J C, Phillips A G, Rubin E M, Hersch S M, Hayden M R. A YAC mouse model for Huntington's disease with full-length mutant huntingtin, cytoplasmic toxicity, and selective striatal neurodegeneration. *Neuron.* 1999; 23:181-92. PMID: 10402204), BACHD (Hult S, Soylu R, Bjorklund T, Belgardt B F, Mauer J, Bruning J C, Kirik D, Petersen A. Mutant huntingtin causes metabolic imbalance by disruption of hypothalamic neurocircuits. *Cell metabolism.* 2011; 13:428-39. PMID: 21459327; Hult Lundh S, Nilsson N, Soylu R, Kirik D, Petersen A. Hypothalamic expression of mutant huntingtin contributes to the development of depressive-like behavior in the BAC transgenic mouse model of Huntington's disease. *Human molecular genetics.* 2013; 22:3485-97. PMID: 23697793; Gray M, Shirasaki D I, Cepeda C, Andre V M, Wilburn B, Lu X H, Tao J, Yamazaki I, Li S H, Sun Y E, Li X J, Levine M S, Yang X W. Full-length human mutant huntingtin with a stable polyglutamine repeat can elicit progressive and selective neuropathogenesis in BACHD mice. *The Journal of neuroscience: the official journal of the Society for Neuroscience.* 2008; 28:6182-95. PMID: 18550760; PMCID: PMC2630800), and recently established allelic series including Q140 (Website: chdifoundation.org), will be used.

Based on optimal parameters identified as described herein, a bolus ICV injection of HTT-10150 will be administered into each Huntington's mouse model and the mice will be assayed for Htt silencing, Huntington's behavior and/or onset of Huntington's-associated phenotypes, and validated histological parameters. A set of validated assays have been designed to detect differential expression of YAC128 and Q140 mutant mRNAs and wild-type Htt mRNA. A panel of behavioral assays has been designed to assess motor function, including rotarod, elevated platform, and open field assays (Sah D W, Aronin N. Oligonucleotide therapeutic approaches for Huntington disease. *The Journal of clinical investigation.* 2011; 121:500-7. PMID: 21285523; PMCID: 3026739; Kordasiewicz H B, Stanek L M, Wancewicz E V, Mazur C, McAlonis M M, Pytel K A, Artates J W, Weiss A, Cheng S H, Shihabuddin L S, Hung G, Bennett C F, Cleveland D W. Sustained therapeutic reversal of Huntington's disease by transient repression of huntingtin synthesis. *Neuron.* 2012; 74:1031-44. PMID: 22726834; PMCID: PMC3383626). One group of mice will be treated at age three months to assess disease prevention, and another group of mice will be treated at age six months to assess disease reversal. HTT aggregates will be assessed by immunohistochemical staining using a commercially available anti-polyglutamine antibody (3B5H10). HTT-10150 hsiRNA conjugates will be re-administered, if necessary. Control groups will include mice injected with PBS and non-targeting control compound having identical chemistry as the HTT-10150 hsiRNA conjugate. The best lead will be re-test them independently by another group in several behavioral models of Huntington's disease.

Completion of this example, together with efficacy, safety and duration-of-effect studies, will generate a set of data sufficient to move the optimized hsiRNA HTT-10150 into pre-clinical development. Currently, the best available program for oligonucleotide-based treatment of Huntington's disease is the 2'-O-methoxyethyl GapmeR (Id.), which will be used as a benchmark. The IONIS-HTTRx compound has recently initiated Phase 1 clinical trials in which patients receive a bolus spinal tap injection and a reduction in HTT levels in CSF serves as a biomarker for proof of concept. This establishes a clinical path forward in the development of oligonucleotide therapeutics to treat Huntington's disease. Initially, it is planned to silence both mutant and wild-type Htt, similar to the IONIS approach. The scaffold described herein will also be used to generate compounds that selectively silence mutant HTT by SNP discrimination. Indeed, five SNP alleles are linked to toxic CAG expansion in 75% of Huntington's disease patient mutations (Pfister E L, Kennington L, Straubhaar J, Wagh S, Liu W, DiFiglia M, Landwehrmeyer B, Vonsattel J P, Zamore P D, Aronin N. Five siRNAs targeting three SNPs may provide therapy for three-quarters of Huntington's disease patients. *Current biology: CB*. 2009; 19:774-8. PMID: 19361997; PMCID: PMC2746439).

INCORPORATION BY REFERENCE

The contents of all cited references (including literature references, patents, patent applications, and websites) that maybe cited throughout this application are hereby expressly incorporated by reference in their entirety for any purpose, as are the references cited therein. The disclosure will employ, unless otherwise indicated, conventional techniques of immunology, molecular biology and cell biology, which are well known in the art.

The present disclosure also incorporates by reference in their entirety techniques well known in the field of molecular biology and drug delivery. These techniques include, but are not limited to, techniques described in the following publications:

Atwell et al. J. Mol. Biol. 1997, 270: 26-35;
Ausubel et al. (eds.), CURRENT PROTOCOLS IN MOLECULAR BIOLOGY, John Wiley &Sons, N Y (1993);
Ausubel, F. M. et al. eds., SHORT PROTOCOLS IN MOLECULAR BIOLOGY (4th Ed. 1999) John Wiley & Sons, NY. (ISBN 0-471-32938-X);
CONTROLLED DRUG BIOAVAILABILITY, DRUG PRODUCT DESIGN AND PERFORMANCE, Smolen and Ball (eds.), Wiley, New York (1984);
Giege, R. and Ducruix, A. Barrett, CRYSTALLIZATION OF NUCLEIC ACIDS AND PROTEINS, a Practical Approach, 2nd ea., pp. 20 1-16, Oxford University Press, New York, N.Y., (1999);
Goodson, in MEDICAL APPLICATIONS OF CONTROLLED RELEASE, vol. 2, pp. 115-138 (1984);
Hammerling, et al., in: MONOCLONAL ANTIBODIES AND T-CELL HYBRIDOMAS 563-681 (Elsevier, N.Y., 1981;
Harlow et al., ANTIBODIES: A LABORATORY MANUAL, (Cold Spring Harbor Laboratory Press, 2nd ed. 1988);
Kabat et al., SEQUENCES OF PROTEINS OF IMMUNOLOGICAL INTEREST (National Institutes of Health, Bethesda, Md. (1987) and (1991);
Kabat, E. A., et al. (1991) SEQUENCES OF PROTEINS OF IMMUNOLOGICAL INTEREST, Fifth Edition, U.S. Department of Health and Human Services, NIH Publication No. 91-3242;
Kontermann and Dubel eds., ANTIBODY ENGINEERING (2001) Springer-Verlag. New York. 790 pp. (ISBN 3-540-41354-5).
Kriegler, Gene Transfer and Expression, A Laboratory Manual, Stockton Press, N Y (1990); Lu and Weiner eds., CLONING AND EXPRESSION VECTORS FOR GENE FUNCTION ANALYSIS (2001)
BioTechniques Press. Westborough, Mass. 298 pp. (ISBN 1-881299-21-X). MEDICAL APPLICATIONS OF CONTROLLED RELEASE, Langer and Wise (eds.), CRC Pres., Boca Raton, Fla. (1974);
Old, R. W. & S. B. Primrose, PRINCIPLES OF GENE MANIPULATION: AN INTRODUCTION TO GENETIC ENGINEERING (3d Ed. 1985) Blackwell Scientific Publications, Boston. Studies in Microbiology; V.2:409 pp. (ISBN 0-632-01318-4).
Sambrook, J. et al. eds., MOLECULAR CLONING: A LABORATORY MANUAL (2d Ed. 1989) Cold Spring Harbor Laboratory Press, NY. Vols. 1-3. (ISBN 0-87969-309-6).
SUSTAINED AND CONTROLLED RELEASE DRUG DELIVERY SYSTEMS, J. R. Robinson, ed., Marcel Dekker, Inc., New York, 1978
Winnacker, E. L. FROM GENES TO CLONES: INTRODUCTION TO GENE TECHNOLOGY (1987) VCH Publishers, NY (translated by Horst Ibelgaufts). 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

What is claimed:

1. A vector comprising a regulatory sequence operably linked to a nucleotide sequence that encodes an RNA duplex comprising a sense strand and an antisense strand wherein the sense strand is between 15 and 30 nucleotides in length and comprises a nucleotide sequence which is at least 80% identical to SEQ ID NO: 1056 and wherein antisense strand comprises a nucleotide sequence which is at least 85% identical to 5'UAAGCAUGGAGCUAGCAGGC3' (SEQ ID NO: 328) and is complementary to at least 7 contiguous nucleotides of SEQ ID NO: 1056.

2. The vector of claim 1 wherein the antisense strand comprises no more than 3 mismatches with SEQ ID NO: 1056.

3. The vector of claim 1 wherein the antisense strand is complementary to at least 10 contiguous nucleotides of SEQ ID NO: 1056.

4. The vector of claim 1 wherein the antisense strand is complementary to at least 13 contiguous nucleotides of SEQ ID NO: 1056.

5. The vector of claim 4, wherein the antisense strand comprises a nucleotide sequence which is at least 90% identical to 5'UAAGCAUGGAGCUAGCAGGC3' (SEQ ID NO: 328); and wherein the sense strand is between 15 and 30 nucleotides in length and comprises a nucleotide sequence which is at least 85% identical to SEQ ID NO: 1056.

6. A recombinant adeno-associated viruses (rAAV) comprising the vector of claim 1 and an AAV capsid.

7. A pharmaceutical composition comprising the rAAV of claim 6 and a pharmaceutically acceptable carrier.

8. A vector comprising a regulatory sequence operably linked to a nucleotide sequence that encodes the RNA duplex of claim 1.

9. A recombinant adeno-associated viruses (rAAV) comprising the vector of claim 8 and an AAV capsid.

10. A pharmaceutical composition comprising the rAAV of claim 9 and a pharmaceutically acceptable carrier.

11. A method for inhibiting expression of HTT gene in a cell, the method comprising introducing into the cell the RNA duplex of claim 1 or a vector comprising a nucleotide sequence encoding the RNA duplex of claim 1.

12. A method for inhibiting expression of HTT gene in a cell, the method comprising introducing into the cell the RNA duplex of claim 1 or a vector comprising a nucleotide sequence encoding the RNA duplex of claim 1.

13. A method of treating Huntington's Disease in a patient, the method comprising administering to the patient a therapeutically effective amount of the rAAV of claim 6.

14. The method of claim 13, wherein the rAAV is administered to a putamen of the patient.

15. The method of claim 13, wherein the rAAV is administered to one or more regions of the parenchyma of the brain, with at least one region being a putamen.

16. The method of claim 13, wherein administering the rAAV to the patient causes a decrease in HTT gene mRNA in the striatum, the cortex, or both the striatum and the cortex of the patient.

17. A method of treating Huntington's Disease in a patient, the method comprising administering to the patient a therapeutically effective amount of the rAAV of claim 9.

18. The method of claim 17, wherein the rAAV is administered to a putamen of the patient.

19. The method of claim 17, wherein the rAAV is administered to one or more regions of the parenchyma of the brain, with at least one region being a putamen.

20. The method of claim 17, wherein administering the rAAV to the patient causes a decrease in HTT gene mRNA in the striatum, the cortex, or both the striatum and the cortex of the patient.

* * * * *

UNITED STATES PATENT AND TRADEMARK OFFICE
CERTIFICATE OF CORRECTION

PATENT NO. : 10,774,327 B2
APPLICATION NO. : 16/263200
DATED : September 15, 2020
INVENTOR(S) : Khvorova et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 67 days.

Signed and Sealed this
Seventh Day of February, 2023

Katherine Kelly Vidal
*Director of the United States Patent and Trademark Office*

SEQUENCE LISTING

```
<160> NUMBER OF SEQ ID NOS: 1329

<210> SEQ ID NO 1
<211> LENGTH: 15
<212> TYPE: RNA
<213> ORGANISM: Homo sapiens

<400> SEQUENCE: 1
caguaaagag auuaa                                                    15

<210> SEQ ID NO 2
<211> LENGTH: 15
<212> TYPE: RNA
<213> ORGANISM: Homo sapiens

<400> SEQUENCE: 2
auaucaguaa agaga                                                    15
```

```
<210> SEQ ID NO 3
<211> LENGTH: 15
<212> TYPE: RNA
<213> ORGANISM: Homo sapiens

<400> SEQUENCE: 3
cucaggauuu aaaau                                                     15

<210> SEQ ID NO 4
<211> LENGTH: 620
<212> TYPE: RNA
<213> ORGANISM: Homo sapiens

<400> SEQUENCE: 4
agcgccaugg ugggagagac ugugaggcgg cagcuggggc cggagccuuu ggaagucugc     60
gcccuugugc ccugccucca ccgagccagc uugguccccua ugggcuuccg cacaugccgc   120
gggcggccag gcaacgugcg ugucucugcc auguggcaga agugcucuuu guggcagugg    180
ccaggcaggg agugucugca guccuggugg ggcugagccu gaggccuucc agaaagcagg    240
agcagcugug cugcaccccca ugggguugac caggucccuuu cuccugauag ucaccugcug  300
guuguugcca gguugcagcu gcucuugcau cugggccaga aguccucccu ccugcaggcu    360
ggcuguuggc cccucugcug uccugcagua gaaggugccg ugagcaggcu uugggaacac    420
uggccugggu ucccugguug ggggugcau gccacgccccc gugucuggau gcacagaugc    480
cauggccugu gcugggccag uggcuggggg ugcuagacac ccggcaccau ucucccuucu    540
cucuuuucuu cucaggauuu aaaauuuaau uauaucagua aagagauuaa uuuuaacgua    600
acucuuucua ugcccguguga                                               620

<210> SEQ ID NO 5
<211> LENGTH: 10
<212> TYPE: RNA
<213> ORGANISM: Homo sapiens

<400> SEQUENCE: 5
gcugccggga                                                           10

<210> SEQ ID NO 6
<211> LENGTH: 20
<212> TYPE: RNA
<213> ORGANISM: Homo sapiens

<400> SEQUENCE: 6
guccagguuu augaacugac                                                20

<210> SEQ ID NO 7
<211> LENGTH: 20
<212> TYPE: RNA
<213> ORGANISM: Homo sapiens

<400> SEQUENCE: 7
agguuuauga acugacguua                                                20

<210> SEQ ID NO 8
<211> LENGTH: 20
<212> TYPE: RNA
<213> ORGANISM: Homo sapiens

<400> SEQUENCE: 8
gguuuaugaa cugacguuac                                                20
```

```
<210> SEQ ID NO 9
<211> LENGTH: 20
<212> TYPE: RNA
<213> ORGANISM: Homo sapiens

<400> SEQUENCE: 9
accacaaugu ugugaccgga                                              20

<210> SEQ ID NO 10
<211> LENGTH: 20
<212> TYPE: RNA
<213> ORGANISM: Homo sapiens

<400> SEQUENCE: 10
uguguuagac gguaccgaca                                              20

<210> SEQ ID NO 11
<211> LENGTH: 20
<212> TYPE: RNA
<213> ORGANISM: Homo sapiens

<400> SEQUENCE: 11
accgacaacc aguauuuggg                                              20

<210> SEQ ID NO 12
<211> LENGTH: 20
<212> TYPE: RNA
<213> ORGANISM: Homo sapiens

<400> SEQUENCE: 12
acgagugcuc aauaauguug                                              20

<210> SEQ ID NO 13
<211> LENGTH: 20
<212> TYPE: RNA
<213> ORGANISM: Homo sapiens

<400> SEQUENCE: 13
ugaaauccug cuuuagucga                                              20

<210> SEQ ID NO 14
<211> LENGTH: 20
<212> TYPE: RNA
<213> ORGANISM: Homo sapiens

<400> SEQUENCE: 14
ugcuuuaguc gagaaccaau                                              20

<210> SEQ ID NO 15
<211> LENGTH: 20
<212> TYPE: RNA
<213> ORGANISM: Homo sapiens

<400> SEQUENCE: 15
gggacaguac uucaacgcua                                              20

<210> SEQ ID NO 16
<211> LENGTH: 20
<212> TYPE: RNA
<213> ORGANISM: Homo sapiens

<400> SEQUENCE: 16
ggcaauucag ucucguugug                                              20
```

<210> SEQ ID NO 17
<211> LENGTH: 20
<212> TYPE: RNA
<213> ORGANISM: Homo sapiens

<400> SEQUENCE: 17
gccugcuagc uccaugcuua					20

<210> SEQ ID NO 18
<211> LENGTH: 20
<212> TYPE: RNA
<213> ORGANISM: Homo sapiens

<400> SEQUENCE: 18
gcccacugcg ugaacauuca					20

<210> SEQ ID NO 19
<211> LENGTH: 20
<212> TYPE: RNA
<213> ORGANISM: Homo sapiens

<400> SEQUENCE: 19
uucuucucag gauuuaaaau					20

<210> SEQ ID NO 20
<211> LENGTH: 20
<212> TYPE: RNA
<213> ORGANISM: Homo sapiens

<400> SEQUENCE: 20
uaauuauauc aguaaagaga					20

<210> SEQ ID NO 21
<211> LENGTH: 20
<212> TYPE: RNA
<213> ORGANISM: Homo sapiens

<400> SEQUENCE: 21
uauaucagua aagagauuaa					20

<210> SEQ ID NO 22
<211> LENGTH: 20
<212> TYPE: RNA
<213> ORGANISM: Homo sapiens

<400> SEQUENCE: 22
acuuucagcu accaagaaag					20

<210> SEQ ID NO 23
<211> LENGTH: 20
<212> TYPE: RNA
<213> ORGANISM: Homo sapiens

<400> SEQUENCE: 23
auugucugac aauaugugaa					20

<210> SEQ ID NO 24
<211> LENGTH: 20
<212> TYPE: RNA
<213> ORGANISM: Homo sapiens

<400> SEQUENCE: 24

| | |
|---|---|
| uucugggcau cgcuauggaa | 20 |

<210> SEQ ID NO 25
<211> LENGTH: 20
<212> TYPE: RNA
<213> ORGANISM: Homo sapiens

<400> SEQUENCE: 25

| | |
|---|---|
| ggcaucgcua uggaacuuuu | 20 |

<210> SEQ ID NO 26
<211> LENGTH: 20
<212> TYPE: RNA
<213> ORGANISM: Homo sapiens

<400> SEQUENCE: 26

| | |
|---|---|
| gcaaaugaca augaaauuaa | 20 |

<210> SEQ ID NO 27
<211> LENGTH: 20
<212> TYPE: RNA
<213> ORGANISM: Homo sapiens

<400> SEQUENCE: 27

| | |
|---|---|
| caaaugacaa ugaaauuaag | 20 |

<210> SEQ ID NO 28
<211> LENGTH: 20
<212> TYPE: RNA
<213> ORGANISM: Homo sapiens

<400> SEQUENCE: 28

| | |
|---|---|
| aaggccuuca uagcgaaccu | 20 |

<210> SEQ ID NO 29
<211> LENGTH: 20
<212> TYPE: RNA
<213> ORGANISM: Homo sapiens

<400> SEQUENCE: 29

| | |
|---|---|
| acuaaaugug cucuuaggcu | 20 |

<210> SEQ ID NO 30
<211> LENGTH: 20
<212> TYPE: RNA
<213> ORGANISM: Homo sapiens

<400> SEQUENCE: 30

| | |
|---|---|
| cggagugaca aggaaagaaa | 20 |

<210> SEQ ID NO 31
<211> LENGTH: 20
<212> TYPE: RNA
<213> ORGANISM: Homo sapiens

<400> SEQUENCE: 31

| | |
|---|---|
| gcagcuuguc cagguuuaug | 20 |

<210> SEQ ID NO 32
<211> LENGTH: 20
<212> TYPE: RNA
<213> ORGANISM: Homo sapiens

<400> SEQUENCE: 32

```
uuguccaggu uuaugaacug                                              20

<210> SEQ ID NO 33
<211> LENGTH: 20
<212> TYPE: RNA
<213> ORGANISM: Homo sapiens

<400> SEQUENCE: 33
cagguuuaug aacugacguu                                              20

<210> SEQ ID NO 34
<211> LENGTH: 20
<212> TYPE: RNA
<213> ORGANISM: Homo sapiens

<400> SEQUENCE: 34
guuuaugaac ugacguuaca                                              20

<210> SEQ ID NO 35
<211> LENGTH: 20
<212> TYPE: RNA
<213> ORGANISM: Homo sapiens

<400> SEQUENCE: 35
uaugaacuga cguuacauca                                              20

<210> SEQ ID NO 36
<211> LENGTH: 20
<212> TYPE: RNA
<213> ORGANISM: Homo sapiens

<400> SEQUENCE: 36
aacugacguu acaucauaca                                              20

<210> SEQ ID NO 37
<211> LENGTH: 20
<212> TYPE: RNA
<213> ORGANISM: Homo sapiens

<400> SEQUENCE: 37
cugacguuac aucauacaca                                              20

<210> SEQ ID NO 38
<211> LENGTH: 20
<212> TYPE: RNA
<213> ORGANISM: Homo sapiens

<400> SEQUENCE: 38
acaauguugu gaccggagcc                                              20

<210> SEQ ID NO 39
<211> LENGTH: 20
<212> TYPE: RNA
<213> ORGANISM: Homo sapiens

<400> SEQUENCE: 39
gggaguauug uggaacuuau                                              20

<210> SEQ ID NO 40
<211> LENGTH: 20
<212> TYPE: RNA
<213> ORGANISM: Homo sapiens
```

```
<400> SEQUENCE: 40
aaggcaaagu gcucuuagga                                            20

<210> SEQ ID NO 41
<211> LENGTH: 20
<212> TYPE: RNA
<213> ORGANISM: Homo sapiens

<400> SEQUENCE: 41
gacgguaccg acaaccagua                                            20

<210> SEQ ID NO 42
<211> LENGTH: 20
<212> TYPE: RNA
<213> ORGANISM: Homo sapiens

<400> SEQUENCE: 42
cgguaccgac aaccaguauu                                            20

<210> SEQ ID NO 43
<211> LENGTH: 20
<212> TYPE: RNA
<213> ORGANISM: Homo sapiens

<400> SEQUENCE: 43
uugaacuaca ucgaucaugg                                            20

<210> SEQ ID NO 44
<211> LENGTH: 20
<212> TYPE: RNA
<213> ORGANISM: Homo sapiens

<400> SEQUENCE: 44
ugaacuacau cgaucaugga                                            20

<210> SEQ ID NO 45
<211> LENGTH: 20
<212> TYPE: RNA
<213> ORGANISM: Homo sapiens

<400> SEQUENCE: 45
aacgagugcu caauaauguu                                            20

<210> SEQ ID NO 46
<211> LENGTH: 20
<212> TYPE: RNA
<213> ORGANISM: Homo sapiens

<400> SEQUENCE: 46
guccuguuac aacaaguaaa                                            20

<210> SEQ ID NO 47
<211> LENGTH: 20
<212> TYPE: RNA
<213> ORGANISM: Homo sapiens

<400> SEQUENCE: 47
cugaaauccu gcuuuagucg                                            20

<210> SEQ ID NO 48
<211> LENGTH: 20
<212> TYPE: RNA
<213> ORGANISM: Homo sapiens
```

```
<400> SEQUENCE: 48
cugcuuuagu cgagaaccaa                                              20

<210> SEQ ID NO 49
<211> LENGTH: 20
<212> TYPE: RNA
<213> ORGANISM: Homo sapiens

<400> SEQUENCE: 49
uuuagucgag aaccaaugau                                              20

<210> SEQ ID NO 50
<211> LENGTH: 20
<212> TYPE: RNA
<213> ORGANISM: Homo sapiens

<400> SEQUENCE: 50
agucgagaac caaugauggc                                              20

<210> SEQ ID NO 51
<211> LENGTH: 20
<212> TYPE: RNA
<213> ORGANISM: Homo sapiens

<400> SEQUENCE: 51
guguucaaca auuguugaag                                              20

<210> SEQ ID NO 52
<211> LENGTH: 20
<212> TYPE: RNA
<213> ORGANISM: Homo sapiens

<400> SEQUENCE: 52
ugaggaacau ggugcaggcg                                              20

<210> SEQ ID NO 53
<211> LENGTH: 20
<212> TYPE: RNA
<213> ORGANISM: Homo sapiens

<400> SEQUENCE: 53
ugucacaaag aaccgugcag                                              20

<210> SEQ ID NO 54
<211> LENGTH: 20
<212> TYPE: RNA
<213> ORGANISM: Homo sapiens

<400> SEQUENCE: 54
ucacaaagaa ccgugcagau                                              20

<210> SEQ ID NO 55
<211> LENGTH: 20
<212> TYPE: RNA
<213> ORGANISM: Homo sapiens

<400> SEQUENCE: 55
acaaagaacc gugcagauaa                                              20

<210> SEQ ID NO 56
<211> LENGTH: 20
<212> TYPE: RNA
```

<213> ORGANISM: Homo sapiens

<400> SEQUENCE: 56
uugaaccucu uguuauaaaa                                          20

<210> SEQ ID NO 57
<211> LENGTH: 20
<212> TYPE: RNA
<213> ORGANISM: Homo sapiens

<400> SEQUENCE: 57
uuuauuggcu uuguauugaa                                          20

<210> SEQ ID NO 58
<211> LENGTH: 20
<212> TYPE: RNA
<213> ORGANISM: Homo sapiens

<400> SEQUENCE: 58
ucauuggaau uccuaaaauc                                          20

<210> SEQ ID NO 59
<211> LENGTH: 20
<212> TYPE: RNA
<213> ORGANISM: Homo sapiens

<400> SEQUENCE: 59
ugugauggca ucauggccag                                          20

<210> SEQ ID NO 60
<211> LENGTH: 20
<212> TYPE: RNA
<213> ORGANISM: Homo sapiens

<400> SEQUENCE: 60
gauuucccag ucaacugaag                                          20

<210> SEQ ID NO 61
<211> LENGTH: 20
<212> TYPE: RNA
<213> ORGANISM: Homo sapiens

<400> SEQUENCE: 61
gagugagcag caacauacuu                                          20

<210> SEQ ID NO 62
<211> LENGTH: 20
<212> TYPE: RNA
<213> ORGANISM: Homo sapiens

<400> SEQUENCE: 62
gucuggaaug uuccggagaa                                          20

<210> SEQ ID NO 63
<211> LENGTH: 20
<212> TYPE: RNA
<213> ORGANISM: Homo sapiens

<400> SEQUENCE: 63
ugcgugaaca uucacagcca                                          20

<210> SEQ ID NO 64
<211> LENGTH: 20

```
<212> TYPE: RNA
<213> ORGANISM: Homo sapiens

<400> SEQUENCE: 64
cucaggauuu aaaauuuaau                                               20

<210> SEQ ID NO 65
<211> LENGTH: 20
<212> TYPE: RNA
<213> ORGANISM: Homo sapiens

<400> SEQUENCE: 65
ggauuuaaaa uuuaauuaua                                               20

<210> SEQ ID NO 66
<211> LENGTH: 20
<212> TYPE: RNA
<213> ORGANISM: Homo sapiens

<400> SEQUENCE: 66
aauuuaauua uaucaguaaa                                               20

<210> SEQ ID NO 67
<211> LENGTH: 20
<212> TYPE: RNA
<213> ORGANISM: Homo sapiens

<400> SEQUENCE: 67
auuuuaacgu aacucuuucu                                               20

<210> SEQ ID NO 68
<211> LENGTH: 20
<212> TYPE: RNA
<213> ORGANISM: Homo sapiens

<400> SEQUENCE: 68
ucuuucuaug cccguguaaa                                               20

<210> SEQ ID NO 69
<211> LENGTH: 20
<212> TYPE: RNA
<213> ORGANISM: Homo sapiens

<400> SEQUENCE: 69
ucuaugcccg uguaaaguau                                               20

<210> SEQ ID NO 70
<211> LENGTH: 20
<212> TYPE: RNA
<213> ORGANISM: Homo sapiens

<400> SEQUENCE: 70
cuuuuaguca ggagagugca                                               20

<210> SEQ ID NO 71
<211> LENGTH: 20
<212> TYPE: RNA
<213> ORGANISM: Homo sapiens

<400> SEQUENCE: 71 uguuugggu auugaaugug                                                20

<210> SEQ ID NO 72
```

```
<211> LENGTH: 20
<212> TYPE: RNA
<213> ORGANISM: Homo sapiens

<400> SEQUENCE: 72
gaauguggua aguggaggaa                                               20

<210> SEQ ID NO 73
<211> LENGTH: 20
<212> TYPE: RNA
<213> ORGANISM: Homo sapiens

<400> SEQUENCE: 73
ugguaagugg aggaaauguu                                               20

<210> SEQ ID NO 74
<211> LENGTH: 20
<212> TYPE: RNA
<213> ORGANISM: Homo sapiens

<400> SEQUENCE: 74
aaauguugga acucugugca                                               20

<210> SEQ ID NO 75
<211> LENGTH: 20
<212> TYPE: RNA
<213> ORGANISM: Homo sapiens

<400> SEQUENCE: 75
auguuugagg aggcccuuaa                                               20

<210> SEQ ID NO 76
<211> LENGTH: 20
<212> TYPE: RNA
<213> ORGANISM: Homo sapiens

<400> SEQUENCE: 76
ccuuaaggga agcuacugaa                                               20

<210> SEQ ID NO 77
<211> LENGTH: 20
<212> TYPE: RNA
<213> ORGANISM: Homo sapiens

<400> SEQUENCE: 77
gaauuauaac acguaagaaa                                               20

<210> SEQ ID NO 78
<211> LENGTH: 20
<212> TYPE: RNA
<213> ORGANISM: Homo sapiens

<400> SEQUENCE: 78
auguuuacau uuguaagaaa                                               20

<210> SEQ ID NO 79
<211> LENGTH: 20
<212> TYPE: RNA
<213> ORGANISM: Homo sapiens

<400> SEQUENCE: 79
cauuuguaag aaauaacacu                                               20
```

```
<210> SEQ ID NO 80
<211> LENGTH: 20
<212> TYPE: RNA
<213> ORGANISM: Homo sapiens

<400> SEQUENCE: 80
aauaacacug ugaauguaaa                                                 20

<210> SEQ ID NO 81
<211> LENGTH: 20
<212> TYPE: RNA
<213> ORGANISM: Homo sapiens

<400> SEQUENCE: 81
aauaugagcu cauuaguaaa                                                 20

<210> SEQ ID NO 82
<211> LENGTH: 20
<212> TYPE: RNA
<213> ORGANISM: Homo sapiens

<400> SEQUENCE: 82
ucacccacgc auauacauaa                                                 20

<210> SEQ ID NO 83
<211> LENGTH: 20
<212> TYPE: RNA
<213> ORGANISM: Homo sapiens

<400> SEQUENCE: 83
auauagacac aucuauaauu                                                 20

<210> SEQ ID NO 84
<211> LENGTH: 20
<212> TYPE: RNA
<213> ORGANISM: Homo sapiens

<400> SEQUENCE: 84
uuacacacac accucucaag                                                 20

<210> SEQ ID NO 85
<211> LENGTH: 20
<212> TYPE: RNA
<213> ORGANISM: Homo sapiens

<400> SEQUENCE: 85
gacuuuauca uguuccuaaa                                                 20

<210> SEQ ID NO 86
<211> LENGTH: 20
<212> TYPE: RNA
<213> ORGANISM: Homo sapiens

<400> SEQUENCE: 86
uuguugcaaa ugugauuaau                                                 20

<210> SEQ ID NO 87
<211> LENGTH: 20
<212> TYPE: RNA
<213> ORGANISM: Homo sapiens

<400> SEQUENCE: 87
gcaaauguga uuaauuggu                                                  20
```

```
<210> SEQ ID NO 88
<211> LENGTH: 20
<212> TYPE: RNA
<213> ORGANISM: Homo sapiens

<400> SEQUENCE: 88
aauuugguug ucaaguuuug                                               20

<210> SEQ ID NO 89
<211> LENGTH: 20
<212> TYPE: RNA
<213> ORGANISM: Homo sapiens

<400> SEQUENCE: 89
uuuguuuucc ugcugguaau                                               20

<210> SEQ ID NO 90
<211> LENGTH: 20
<212> TYPE: RNA
<213> ORGANISM: Homo sapiens

<400> SEQUENCE: 90 guuuccugc ugguaauauc                                                20

<210> SEQ ID NO 91
<211> LENGTH: 20
<212> TYPE: RNA
<213> ORGANISM: Homo sapiens

<400> SEQUENCE: 91
auaucgggaa agauuuuaau                                               20

<210> SEQ ID NO 92
<211> LENGTH: 20
<212> TYPE: RNA
<213> ORGANISM: Homo sapiens

<400> SEQUENCE: 92
auuuuaauga aaccagggua                                               20

<210> SEQ ID NO 93
<211> LENGTH: 20
<212> TYPE: RNA
<213> ORGANISM: Homo sapiens

<400> SEQUENCE: 93
uaaugaaacc aggguagaau                                               20

<210> SEQ ID NO 94
<211> LENGTH: 20
<212> TYPE: RNA
<213> ORGANISM: Homo sapiens

<400> SEQUENCE: 94
auuguuuggc aaugcacuga                                               20

<210> SEQ ID NO 95
<211> LENGTH: 20
<212> TYPE: RNA
<213> ORGANISM: Homo sapiens

<400> SEQUENCE: 95
ccccucaguu guuucuaaga                                               20
```

```
<210> SEQ ID NO 96
<211> LENGTH: 20
<212> TYPE: RNA
<213> ORGANISM: Homo sapiens

<400> SEQUENCE: 96
ggacugacga gagauguaua                                            20

<210> SEQ ID NO 97
<211> LENGTH: 20
<212> TYPE: RNA
<213> ORGANISM: Homo sapiens

<400> SEQUENCE: 97
gacgagagau guauauuuaa                                            20

<210> SEQ ID NO 98
<211> LENGTH: 20
<212> TYPE: RNA
<213> ORGANISM: Homo sapiens

<400> SEQUENCE: 98
uuuuuuaacu gcugcaaaca                                            20

<210> SEQ ID NO 99
<211> LENGTH: 20
<212> TYPE: RNA
<213> ORGANISM: Homo sapiens

<400> SEQUENCE: 99
uaacugcugc aaacauugua                                            20

<210> SEQ ID NO 100
<211> LENGTH: 20
<212> TYPE: RNA
<213> ORGANISM: Homo sapiens

<400> SEQUENCE: 100
acccuggaaa agcugaugaa                                            20

<210> SEQ ID NO 101
<211> LENGTH: 20
<212> TYPE: RNA
<213> ORGANISM: Homo sapiens

<400> SEQUENCE: 101
aaggccuucg agucccucaa                                            20

<210> SEQ ID NO 102
<211> LENGTH: 20
<212> TYPE: RNA
<213> ORGANISM: Homo sapiens

<400> SEQUENCE: 102
cgcugcaccg accaaagaaa                                            20

<210> SEQ ID NO 103
<211> LENGTH: 20
<212> TYPE: RNA
<213> ORGANISM: Homo sapiens

<400> SEQUENCE: 103
```

-continued aagaacuuuc agcuaccaag                                         20

<210> SEQ ID NO 104
<211> LENGTH: 20
<212> TYPE: RNA
<213> ORGANISM: Homo sapiens

<400> SEQUENCE: 104
agcuaccaag aaagaccgug                                         20

<210> SEQ ID NO 105
<211> LENGTH: 20
<212> TYPE: RNA
<213> ORGANISM: Homo sapiens

<400> SEQUENCE: 105
cgugugaauc auugucugac                                         20

<210> SEQ ID NO 106
<211> LENGTH: 20
<212> TYPE: RNA
<213> ORGANISM: Homo sapiens

<400> SEQUENCE: 106
ucauugucug acaauaugug                                         20

<210> SEQ ID NO 107
<211> LENGTH: 20
<212> TYPE: RNA
<213> ORGANISM: Homo sapiens

<400> SEQUENCE: 107
ugacaauaug ugaaaacaua                                         20

<210> SEQ ID NO 108
<211> LENGTH: 20
<212> TYPE: RNA
<213> ORGANISM: Homo sapiens

<400> SEQUENCE: 108
auaugugaaa acauaguggc                                         20

<210> SEQ ID NO 109
<211> LENGTH: 20
<212> TYPE: RNA
<213> ORGANISM: Homo sapiens

<400> SEQUENCE: 109
gcagcagcag cagcagcagc                                         20

<210> SEQ ID NO 110
<211> LENGTH: 30
<212> TYPE: RNA
<213> ORGANISM: Homo sapiens

<400> SEQUENCE: 110
agcuugucca gguuuaugaa cugacguuac                              30

<210> SEQ ID NO 111
<211> LENGTH: 30
<212> TYPE: RNA
<213> ORGANISM: Homo sapiens

<400> SEQUENCE: 111
uguccagguu uaugaacuga cguuacauca				30

<210> SEQ ID NO 112
<211> LENGTH: 30
<212> TYPE: RNA
<213> ORGANISM: Homo sapiens

<400> SEQUENCE: 112
guccagguuu augaacugac guuacaucau				30

<210> SEQ ID NO 113
<211> LENGTH: 30
<212> TYPE: RNA
<213> ORGANISM: Homo sapiens

<400> SEQUENCE: 113
ccaagaccac aauguuguga ccggagcccu				30

<210> SEQ ID NO 114
<211> LENGTH: 30
<212> TYPE: RNA
<213> ORGANISM: Homo sapiens

<400> SEQUENCE: 114
gaaauugugu uagacgguac cgacaaccag				30

<210> SEQ ID NO 115
<211> LENGTH: 30
<212> TYPE: RNA
<213> ORGANISM: Homo sapiens

<400> SEQUENCE: 115
acgguaccga caaccaguau uugggccugc				30

<210> SEQ ID NO 116
<211> LENGTH: 30
<212> TYPE: RNA
<213> ORGANISM: Homo sapiens

<400> SEQUENCE: 116
caagaacgag ugcucaauaa uguugucauc				30

<210> SEQ ID NO 117
<211> LENGTH: 30
<212> TYPE: RNA
<213> ORGANISM: Homo sapiens

<400> SEQUENCE: 117
auaccugaaa uccugcuuua gucgagaacc				30

<210> SEQ ID NO 118
<211> LENGTH: 30
<212> TYPE: RNA
<213> ORGANISM: Homo sapiens

<400> SEQUENCE: 118
aauccugcuu uagucgagaa ccaaugaugg				30

<210> SEQ ID NO 119
<211> LENGTH: 30
<212> TYPE: RNA
<213> ORGANISM: Homo sapiens

```
<400> SEQUENCE: 119 agaugggac aguacuucaa cgcuagaaga                              30

<210> SEQ ID NO 120
<211> LENGTH: 30
<212> TYPE: RNA
<213> ORGANISM: Homo sapiens

<400> SEQUENCE: 120
auccaggcaa uucagucucg uugugaaaac                             30

<210> SEQ ID NO 121
<211> LENGTH: 30
<212> TYPE: RNA
<213> ORGANISM: Homo sapiens

<400> SEQUENCE: 121
ccuaagccug cuagcuccau gcuuaagccu                             30

<210> SEQ ID NO 122
<211> LENGTH: 30
<212> TYPE: RNA
<213> ORGANISM: Homo sapiens

<400> SEQUENCE: 122
ggaucgccca cugcgugaac auucacagcc                             30

<210> SEQ ID NO 123
<211> LENGTH: 30
<212> TYPE: RNA
<213> ORGANISM: Homo sapiens

<400> SEQUENCE: 123
cucuuuucuu cucaggauuu aaaauuuaau                             30

<210> SEQ ID NO 124
<211> LENGTH: 30
<212> TYPE: RNA
<213> ORGANISM: Homo sapiens

<400> SEQUENCE: 124
aaauuuaauu auaucaguaa agagauuaau                             30

<210> SEQ ID NO 125
<211> LENGTH: 30
<212> TYPE: RNA
<213> ORGANISM: Homo sapiens

<400> SEQUENCE: 125
uuaauuauau caguaaagag auuaauuuua                             30

<210> SEQ ID NO 126
<211> LENGTH: 30
<212> TYPE: RNA
<213> ORGANISM: Homo sapiens

<400> SEQUENCE: 126
aaagaacuuu cagcuaccaa gaaagaccgu                             30

<210> SEQ ID NO 127
<211> LENGTH: 30
<212> TYPE: RNA
<213> ORGANISM: Homo sapiens
```

-continued

```
<400> SEQUENCE: 127
gaaucauugu cugacaauau gugaaaacau                                    30

<210> SEQ ID NO 128
<211> LENGTH: 30
<212> TYPE: RNA
<213> ORGANISM: Homo sapiens

<400> SEQUENCE: 128
uucugggcau cgcuauggaa cuuuuucugc                                    30

<210> SEQ ID NO 129
<211> LENGTH: 30
<212> TYPE: RNA
<213> ORGANISM: Homo sapiens

<400> SEQUENCE: 129
auuuugcaaa ugacaaugaa auuaagguuu                                    30

<210> SEQ ID NO 130
<211> LENGTH: 30
<212> TYPE: RNA
<213> ORGANISM: Homo sapiens

<400> SEQUENCE: 130
uuuugcaaau gacaaugaaa uuaagguuuu                                    30

<210> SEQ ID NO 131
<211> LENGTH: 30
<212> TYPE: RNA
<213> ORGANISM: Homo sapiens

<400> SEQUENCE: 131
uguuaaaggc cuucauagcg aaccugaagu                                    30

<210> SEQ ID NO 132
<211> LENGTH: 30
<212> TYPE: RNA
<213> ORGANISM: Homo sapiens

<400> SEQUENCE: 132
uggcuacuaa augugcucuu aggcuuacuc                                    30

<210> SEQ ID NO 133
<211> LENGTH: 30
<212> TYPE: RNA
<213> ORGANISM: Homo sapiens

<400> SEQUENCE: 133
agcuucggag ugacaaggaa agaaauggaa                                    30

<210> SEQ ID NO 134
<211> LENGTH: 30
<212> TYPE: RNA
<213> ORGANISM: Homo sapiens

<400> SEQUENCE: 134
gcagagcagc uugccaggu uuaugaacug                                     30

<210> SEQ ID NO 135
<211> LENGTH: 30
<212> TYPE: RNA
```

<213> ORGANISM: Homo sapiens

<400> SEQUENCE: 135
gcagcuuguc cagguuuaug aacugacguu            30

<210> SEQ ID NO 136
<211> LENGTH: 30
<212> TYPE: RNA
<213> ORGANISM: Homo sapiens

<400> SEQUENCE: 136 uguccaggu uuaugaacug acguuacauc            30

<210> SEQ ID NO 137
<211> LENGTH: 30
<212> TYPE: RNA
<213> ORGANISM: Homo sapiens

<400> SEQUENCE: 137
uccagguuua ugaacugacg uuacaucaua            30

<210> SEQ ID NO 138
<211> LENGTH: 30
<212> TYPE: RNA
<213> ORGANISM: Homo sapiens

<400> SEQUENCE: 138
agguuuauga acugacguua caucauacac            30

<210> SEQ ID NO 139
<211> LENGTH: 30
<212> TYPE: RNA
<213> ORGANISM: Homo sapiens

<400> SEQUENCE: 139
uuaugaacug acguuacauc auacacagca            30

<210> SEQ ID NO 140
<211> LENGTH: 30
<212> TYPE: RNA
<213> ORGANISM: Homo sapiens

<400> SEQUENCE: 140
augaacugac guuacaucau acacagcacc            30

<210> SEQ ID NO 141
<211> LENGTH: 30
<212> TYPE: RNA
<213> ORGANISM: Homo sapiens

<400> SEQUENCE: 141
agaccacaau guugugaccg gagcccugga            30

<210> SEQ ID NO 142
<211> LENGTH: 30
<212> TYPE: RNA
<213> ORGANISM: Homo sapiens

<400> SEQUENCE: 142
guagugggag uauugguggaa cuuauagcug            30

<210> SEQ ID NO 143
<211> LENGTH: 30

<212> TYPE: RNA
<213> ORGANISM: Homo sapiens

<400> SEQUENCE: 143
acaaaaaggc aaagugcucu uaggagaaga                                  30

<210> SEQ ID NO 144
<211> LENGTH: 30
<212> TYPE: RNA
<213> ORGANISM: Homo sapiens

<400> SEQUENCE: 144
uguuagacgg uaccgacaac caguauuugg                                  30

<210> SEQ ID NO 145
<211> LENGTH: 30
<212> TYPE: RNA
<213> ORGANISM: Homo sapiens

<400> SEQUENCE: 145
uuagacggua ccgacaacca guauuugggc                                  30

<210> SEQ ID NO 146
<211> LENGTH: 30
<212> TYPE: RNA
<213> ORGANISM: Homo sapiens

<400> SEQUENCE: 146
acaucuugaa cuacaucgau cauggagacc                                  30

<210> SEQ ID NO 147
<211> LENGTH: 30
<212> TYPE: RNA
<213> ORGANISM: Homo sapiens

<400> SEQUENCE: 147
caucuugaac uacaucgauc auggagaccc                                  30

<210> SEQ ID NO 148
<211> LENGTH: 30
<212> TYPE: RNA
<213> ORGANISM: Homo sapiens

<400> SEQUENCE: 148
gcaagaacga gugcucaaua auguugucau                                  30

<210> SEQ ID NO 149
<211> LENGTH: 30
<212> TYPE: RNA
<213> ORGANISM: Homo sapiens

<400> SEQUENCE: 149
cucagguccu guuacaacaa guaaauccuc                                  30

<210> SEQ ID NO 150
<211> LENGTH: 30
<212> TYPE: RNA
<213> ORGANISM: Homo sapiens

<400> SEQUENCE: 150
gauaccugaa auccugcuuu agucgagaac                                  30

<210> SEQ ID NO 151

```
<211> LENGTH: 30
<212> TYPE: RNA
<213> ORGANISM: Homo sapiens

<400> SEQUENCE: 151
aaauccugcu uuagucgaga accaaugaug                                          30

<210> SEQ ID NO 152
<211> LENGTH: 30
<212> TYPE: RNA
<213> ORGANISM: Homo sapiens

<400> SEQUENCE: 152
ccugcuuuag ucgagaacca augauggcaa                                          30

<210> SEQ ID NO 153
<211> LENGTH: 30
<212> TYPE: RNA
<213> ORGANISM: Homo sapiens

<400> SEQUENCE: 153
gcuuuagucg agaaccaaug auggcaacug                                          30

<210> SEQ ID NO 154
<211> LENGTH: 30
<212> TYPE: RNA
<213> ORGANISM: Homo sapiens

<400> SEQUENCE: 154
uguuuguguu caacaauugu ugaagacucu                                          30

<210> SEQ ID NO 155
<211> LENGTH: 30
<212> TYPE: RNA
<213> ORGANISM: Homo sapiens

<400> SEQUENCE: 155
cagccugagg aacauggugc aggcggagca                                          30

<210> SEQ ID NO 156
<211> LENGTH: 30
<212> TYPE: RNA
<213> ORGANISM: Homo sapiens

<400> SEQUENCE: 156
acgaguguca caaagaaccg ugcagauaag                                          30

<210> SEQ ID NO 157
<211> LENGTH: 30
<212> TYPE: RNA
<213> ORGANISM: Homo sapiens

<400> SEQUENCE: 157
gagugucaca aagaaccgug cagauaagaa                                          30

<210> SEQ ID NO 158
<211> LENGTH: 30
<212> TYPE: RNA
<213> ORGANISM: Homo sapiens

<400> SEQUENCE: 158
gugucacaaa gaaccgugca gauaagaaug                                          30
```

```
<210> SEQ ID NO 159
<211> LENGTH: 30
<212> TYPE: RNA
<213> ORGANISM: Homo sapiens

<400> SEQUENCE: 159
uuuguuugaa ccucuuguua uaaaagcuuu                              30

<210> SEQ ID NO 160
<211> LENGTH: 30
<212> TYPE: RNA
<213> ORGANISM: Homo sapiens

<400> SEQUENCE: 160
agguguuuau uggcuuugua uugaaacagu                              30

<210> SEQ ID NO 161
<211> LENGTH: 30
<212> TYPE: RNA
<213> ORGANISM: Homo sapiens

<400> SEQUENCE: 161
acagaucauu ggaauuccua aaaucauuca                              30

<210> SEQ ID NO 162
<211> LENGTH: 30
<212> TYPE: RNA
<213> ORGANISM: Homo sapiens

<400> SEQUENCE: 162
agcucuguga uggcaucaug gccaguggaa                              30

<210> SEQ ID NO 163
<211> LENGTH: 30
<212> TYPE: RNA
<213> ORGANISM: Homo sapiens

<400> SEQUENCE: 163
guucugauuu cccagucaac ugaagauauu                              30

<210> SEQ ID NO 164
<211> LENGTH: 30
<212> TYPE: RNA
<213> ORGANISM: Homo sapiens

<400> SEQUENCE: 164
gaaaugagug agcagcaaca uacuuucuau                              30

<210> SEQ ID NO 165
<211> LENGTH: 30
<212> TYPE: RNA
<213> ORGANISM: Homo sapiens

<400> SEQUENCE: 165
uucaagucug gaauguuccg gagaaucaca                              30

<210> SEQ ID NO 166
<211> LENGTH: 30
<212> TYPE: RNA
<213> ORGANISM: Homo sapiens

<400> SEQUENCE: 166
cccacugcgu gaacauucac agccagcagc                              30
```

```
<210> SEQ ID NO 167
<211> LENGTH: 30
<212> TYPE: RNA
<213> ORGANISM: Homo sapiens

<400> SEQUENCE: 167
uucuucucag gauuuaaaau uuaauuauau                                    30

<210> SEQ ID NO 168
<211> LENGTH: 30
<212> TYPE: RNA
<213> ORGANISM: Homo sapiens

<400> SEQUENCE: 168
ucucaggauu uaaaauuuaa uuauaucagu                                    30

<210> SEQ ID NO 169
<211> LENGTH: 30
<212> TYPE: RNA
<213> ORGANISM: Homo sapiens

<400> SEQUENCE: 169
uuuaaaauuu aauuauauca guaaagagau                                    30

<210> SEQ ID NO 170
<211> LENGTH: 30
<212> TYPE: RNA
<213> ORGANISM: Homo sapiens

<400> SEQUENCE: 170
gauuaauuuu aacguaacuc uuucuaugcc                                    30

<210> SEQ ID NO 171
<211> LENGTH: 30
<212> TYPE: RNA
<213> ORGANISM: Homo sapiens

<400> SEQUENCE: 171
guaacucuuu cuaugcccgu guaaaguaug                                    30

<210> SEQ ID NO 172
<211> LENGTH: 30
<212> TYPE: RNA
<213> ORGANISM: Homo sapiens

<400> SEQUENCE: 172
cucuuucuau gcccguguaa aguaugugaa                                    30

<210> SEQ ID NO 173
<211> LENGTH: 30
<212> TYPE: RNA
<213> ORGANISM: Homo sapiens

<400> SEQUENCE: 173
gaccccuuuu agucaggaga gugcagaucu                                    30

<210> SEQ ID NO 174
<211> LENGTH: 30
<212> TYPE: RNA
<213> ORGANISM: Homo sapiens

<400> SEQUENCE: 174
gucgauguuu uggguauuga augugguaag                                    30
```

<210> SEQ ID NO 175
<211> LENGTH: 30
<212> TYPE: RNA
<213> ORGANISM: Homo sapiens

<400> SEQUENCE: 175
guauugaaug ugguaagugg aggaaauguu                                30

<210> SEQ ID NO 176
<211> LENGTH: 30
<212> TYPE: RNA
<213> ORGANISM: Homo sapiens

<400> SEQUENCE: 176
gaauguggua aguggaggaa auguuggaac                                30

<210> SEQ ID NO 177
<211> LENGTH: 30
<212> TYPE: RNA
<213> ORGANISM: Homo sapiens

<400> SEQUENCE: 177
ggaggaaaug uuggaacucu gugcaggugc                                30

<210> SEQ ID NO 178
<211> LENGTH: 30
<212> TYPE: RNA
<213> ORGANISM: Homo sapiens

<400> SEQUENCE: 178
guccgauguu ugaggaggcc cuuaagggaa                                30

<210> SEQ ID NO 179
<211> LENGTH: 30
<212> TYPE: RNA
<213> ORGANISM: Homo sapiens

<400> SEQUENCE: 179
gaggcccuua agggaagcua cugaauuaua                                30

<210> SEQ ID NO 180
<211> LENGTH: 30
<212> TYPE: RNA
<213> ORGANISM: Homo sapiens

<400> SEQUENCE: 180
cuacugaauu auaacacgua agaaaaucac                                30

<210> SEQ ID NO 181
<211> LENGTH: 30
<212> TYPE: RNA
<213> ORGANISM: Homo sapiens

<400> SEQUENCE: 181
gcuagauguu uacauuugua agaaauaaca                                30

<210> SEQ ID NO 182
<211> LENGTH: 30
<212> TYPE: RNA
<213> ORGANISM: Homo sapiens

<400> SEQUENCE: 182

```
guuuacauuu guaagaaaua acacugugaa                               30

<210> SEQ ID NO 183
<211> LENGTH: 30
<212> TYPE: RNA
<213> ORGANISM: Homo sapiens

<400> SEQUENCE: 183
uaagaaauaa cacugugaau guaaaacaga                               30

<210> SEQ ID NO 184
<211> LENGTH: 30
<212> TYPE: RNA
<213> ORGANISM: Homo sapiens

<400> SEQUENCE: 184
agaugaauau gagcucauua guaaaaauga                               30

<210> SEQ ID NO 185
<211> LENGTH: 30
<212> TYPE: RNA
<213> ORGANISM: Homo sapiens

<400> SEQUENCE: 185
ugacuucacc cacgcauaua cauaaaguau                               30

<210> SEQ ID NO 186
<211> LENGTH: 30
<212> TYPE: RNA
<213> ORGANISM: Homo sapiens

<400> SEQUENCE: 186
ugugcauaua gacacaucua uaauuuuaca                               30

<210> SEQ ID NO 187
<211> LENGTH: 30
<212> TYPE: RNA
<213> ORGANISM: Homo sapiens

<400> SEQUENCE: 187
uaauuuuaca cacacaccuc ucaagacgga                               30

<210> SEQ ID NO 188
<211> LENGTH: 30
<212> TYPE: RNA
<213> ORGANISM: Homo sapiens

<400> SEQUENCE: 188
aggaagacuu uaucauguuc cuaaaaaucu                               30

<210> SEQ ID NO 189
<211> LENGTH: 30
<212> TYPE: RNA
<213> ORGANISM: Homo sapiens

<400> SEQUENCE: 189
aaauuuuguu gcaaauguga uuaauuuggu                               30

<210> SEQ ID NO 190
<211> LENGTH: 30
<212> TYPE: RNA
<213> ORGANISM: Homo sapiens

<400> SEQUENCE: 190
```
uuguugcaaa ugugauuaau uugguuguca                    30

<210> SEQ ID NO 191
<211> LENGTH: 30
<212> TYPE: RNA
<213> ORGANISM: Homo sapiens

<400> SEQUENCE: 191
ugauuaauuu gguugucaag uuuuggggu                     30

<210> SEQ ID NO 192
<211> LENGTH: 30
<212> TYPE: RNA
<213> ORGANISM: Homo sapiens

<400> SEQUENCE: 192
uugcuuuugu uuccugcug guaauaucgg                     30

<210> SEQ ID NO 193
<211> LENGTH: 30
<212> TYPE: RNA
<213> ORGANISM: Homo sapiens

<400> SEQUENCE: 193
cuuuuguuuu ccugcuggua auaucgggaa                    30

<210> SEQ ID NO 194
<211> LENGTH: 30
<212> TYPE: RNA
<213> ORGANISM: Homo sapiens

<400> SEQUENCE: 194
ugguaauauc gggaaagauu uuaaugaaac                    30

<210> SEQ ID NO 195
<211> LENGTH: 30
<212> TYPE: RNA
<213> ORGANISM: Homo sapiens

<400> SEQUENCE: 195
gaaagauuuu aaugaaacca ggguagaauu                    30

<210> SEQ ID NO 196
<211> LENGTH: 30
<212> TYPE: RNA
<213> ORGANISM: Homo sapiens

<400> SEQUENCE: 196 gauuuaaug aaaccagggu agaauuguuu                     30

<210> SEQ ID NO 197
<211> LENGTH: 30
<212> TYPE: RNA
<213> ORGANISM: Homo sapiens

<400> SEQUENCE: 197
guagaauugu uuggcaaugc acugaagcgu                    30

<210> SEQ ID NO 198
<211> LENGTH: 30
<212> TYPE: RNA
<213> ORGANISM: Homo sapiens

```
<400> SEQUENCE: 198 gccuucccu caguuguuuc uaagagcaga                                30

<210> SEQ ID NO 199
<211> LENGTH: 30
<212> TYPE: RNA
<213> ORGANISM: Homo sapiens

<400> SEQUENCE: 199
gggaaggacu gacgagagau guauauuuaa                               30

<210> SEQ ID NO 200
<211> LENGTH: 30
<212> TYPE: RNA
<213> ORGANISM: Homo sapiens

<400> SEQUENCE: 200
ggacugacga gagauguaua uuuaauuuuu                               30

<210> SEQ ID NO 201
<211> LENGTH: 30
<212> TYPE: RNA
<213> ORGANISM: Homo sapiens

<400> SEQUENCE: 201
uuuaauuuuu uaacugcugc aaacauugua                               30

<210> SEQ ID NO 202
<211> LENGTH: 30
<212> TYPE: RNA
<213> ORGANISM: Homo sapiens

<400> SEQUENCE: 202
uuuuuuaacu gcugcaaaca uuguacaucc                               30

<210> SEQ ID NO 203
<211> LENGTH: 30
<212> TYPE: RNA
<213> ORGANISM: Homo sapiens

<400> SEQUENCE: 203
uggcgacccu ggaaaagcug augaaggccu                               30

<210> SEQ ID NO 204
<211> LENGTH: 30
<212> TYPE: RNA
<213> ORGANISM: Homo sapiens

<400> SEQUENCE: 204
ugaugaaggc cuucgagucc cucaaguccu                               30

<210> SEQ ID NO 205
<211> LENGTH: 30
<212> TYPE: RNA
<213> ORGANISM: Homo sapiens

<400> SEQUENCE: 205
ggagccgcug caccgaccaa agaaagaacu                               30

<210> SEQ ID NO 206
<211> LENGTH: 30
<212> TYPE: RNA
<213> ORGANISM: Homo sapiens
```

```
<400> SEQUENCE: 206
aaagaaagaa cuuucagcua ccaagaaaga                                30

<210> SEQ ID NO 207
<211> LENGTH: 30
<212> TYPE: RNA
<213> ORGANISM: Homo sapiens

<400> SEQUENCE: 207
cuuucagcua ccaagaaaga ccgugugaau                                30

<210> SEQ ID NO 208
<211> LENGTH: 30
<212> TYPE: RNA
<213> ORGANISM: Homo sapiens

<400> SEQUENCE: 208
aagaccgugu gaaucauugu cugacaauau                                30

<210> SEQ ID NO 209
<211> LENGTH: 30
<212> TYPE: RNA
<213> ORGANISM: Homo sapiens

<400> SEQUENCE: 209
gugaaucauu gucugacaau augugaaaac                                30

<210> SEQ ID NO 210
<211> LENGTH: 30
<212> TYPE: RNA
<213> ORGANISM: Homo sapiens

<400> SEQUENCE: 210
uugucugaca auaugugaaa acauaguggc                                30

<210> SEQ ID NO 211
<211> LENGTH: 30
<212> TYPE: RNA
<213> ORGANISM: Homo sapiens

<400> SEQUENCE: 211
ugacaauaug ugaaaacaua guggcacagu                                30

<210> SEQ ID NO 212
<211> LENGTH: 30
<212> TYPE: RNA
<213> ORGANISM: Homo sapiens

<400> SEQUENCE: 212
cagcagcagc agcagcagca gcagcagcag                                30

<210> SEQ ID NO 213
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
guccagguuu augaacugac                                           20
```

```
<210> SEQ ID NO 214
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
agguuuauga acugacguua                                                    20

<210> SEQ ID NO 215
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
gguuuaugaa cugacguuac                                                    20

<210> SEQ ID NO 216
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 216
accacaaugu ugugaccgga                                                    20

<210> SEQ ID NO 217
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
uguguuagac gguaccgaca                                                    20

<210> SEQ ID NO 218
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
accgacaacc aguauuuggg                                                    20

<210> SEQ ID NO 219
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 219
acgagugcuc aauaauguug                                           20

<210> SEQ ID NO 220
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
ugaaauccug cuuuagucga                                           20

<210> SEQ ID NO 221
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
ugcuuuaguc gagaaccaau                                           20

<210> SEQ ID NO 222
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
gggacaguac uucaacgcua                                           20

<210> SEQ ID NO 223
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
ggcaauucag ucucguugug                                           20

<210> SEQ ID NO 224
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
gccugcuagc uccaugcuua                                           20

<210> SEQ ID NO 225
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
gcccacugcg ugaacauuca                                              20

<210> SEQ ID NO 226
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
uucuucucag gauuuaaaau                                              20

<210> SEQ ID NO 227
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
uaauuauauc aguaaagaga                                              20

<210> SEQ ID NO 228
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
uauaucagua aagagauuaa                                              20

<210> SEQ ID NO 229
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
acuuucagcu accaagaaag                                              20

<210> SEQ ID NO 230
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230 auugcugac aauaugugaa                                               20
```

```
<210> SEQ ID NO 231
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
uucugggcau cgcuauggaa                                                   20

<210> SEQ ID NO 232
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
ggcaucgcua uggaacuuuu                                                   20

<210> SEQ ID NO 233
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
gcaaaugaca augaaauuaa                                                   20

<210> SEQ ID NO 234
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
caaaugacaa ugaaauuaag                                                   20

<210> SEQ ID NO 235
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
aaggccuuca uagcgaaccu                                                   20

<210> SEQ ID NO 236
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 236
acuaaaugug cucuuaggcu                                         20

<210> SEQ ID NO 237
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
cggagugaca aggaaagaaa                                         20

<210> SEQ ID NO 238
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
gcagcuuguc cagguuuaug                                         20

<210> SEQ ID NO 239
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
uuguccaggu uuaugaacug                                         20

<210> SEQ ID NO 240
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
cagguuuaug aacugacguu                                         20

<210> SEQ ID NO 241
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
guuuaugaac ugacguuaca                                         20

<210> SEQ ID NO 242
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
uaugaacuga cguuacauca                                                     20

<210> SEQ ID NO 243
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
aacugacguu acaucauaca                                                     20

<210> SEQ ID NO 244
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
cugacguuac aucauacaca                                                     20

<210> SEQ ID NO 245
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
acaauguugu gaccggagcc                                                     20

<210> SEQ ID NO 246
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gggaguauug uggaacuuau                                                     20

<210> SEQ ID NO 247
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
```
aaggcaaagu gcucuuagga                                          20

<210> SEQ ID NO 248
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 248
gacgguaccg acaaccagua                                          20

<210> SEQ ID NO 249
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
cgguaccgac aaccaguauu                                          20

<210> SEQ ID NO 250
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
uugaacuaca ucgaucaugg                                          20

<210> SEQ ID NO 251
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
ugaacuacau cgaucaugga                                          20

<210> SEQ ID NO 252
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
aacgagugcu caauaauguu                                          20

<210> SEQ ID NO 253
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 253
guccuguuac aacaaguaaa                                              20

<210> SEQ ID NO 254
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
cugaaauccu gcuuuagucg                                              20

<210> SEQ ID NO 255
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
cugcuuuagu cgagaaccaa                                              20

<210> SEQ ID NO 256
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
uuuagucgag aaccaaugau                                              20

<210> SEQ ID NO 257
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
agucgagaac caaugauggc                                              20

<210> SEQ ID NO 258
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
guguucaaca auuguugaag                                              20

<210> SEQ ID NO 259
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
ugaggaacau ggugcaggcg                                                   20

<210> SEQ ID NO 260
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
ugucacaaag aaccgugcag                                                   20

<210> SEQ ID NO 261
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
ucacaaagaa ccgugcagau                                                   20

<210> SEQ ID NO 262
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
acaaagaacc gugcagauaa                                                   20

<210> SEQ ID NO 263
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
uugaaccucu uguuauaaaa                                                   20

<210> SEQ ID NO 264
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
```
uuuauuggcu uuguauugaa                                               20

<210> SEQ ID NO 265
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 265
ucauuggaau uccuaaaauc                                               20

<210> SEQ ID NO 266
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
ugugauggca ucauggccag                                               20

<210> SEQ ID NO 267
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
gauuucccag ucaacugaag                                               20

<210> SEQ ID NO 268
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
gagugagcag caacauacuu                                               20

<210> SEQ ID NO 269
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
gucuggaaug uuccggagaa                                               20

<210> SEQ ID NO 270
<211> LENGTH: 20
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 270
ugcgugaaca uucacagcca                                                     20

<210> SEQ ID NO 271
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
cucaggauuu aaaauuuaau                                                     20

<210> SEQ ID NO 272
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
ggauuuaaaa uuuaauuaua                                                     20

<210> SEQ ID NO 273
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
aauuuaauua uaucaguaaa                                                     20

<210> SEQ ID NO 274
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
auuuuaacgu aacucuuucu                                                     20

<210> SEQ ID NO 275
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
ucuuucuaug cccguguaaa                                                     20

```
<210> SEQ ID NO 276
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
ucuaugcccg uguaaaguau                                              20

<210> SEQ ID NO 277
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277
cuuuuaguca ggagagugca                                              20

<210> SEQ ID NO 278
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278
uguuuugggu auugaaugug                                              20

<210> SEQ ID NO 279
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279
gaauguggua aguggaggaa                                              20

<210> SEQ ID NO 280
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280
ugguaagugg aggaaauguu                                              20

<210> SEQ ID NO 281
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 281
aaauguugga acucugugca                                              20

<210> SEQ ID NO 282
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 282 auguugagg aggcccuuaa                                               20

<210> SEQ ID NO 283
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
ccuuaaggga agcuacugaa                                              20

<210> SEQ ID NO 284
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
gaauuauaac acguaagaaa                                              20

<210> SEQ ID NO 285
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
auguuuacau uuguaagaaa                                              20

<210> SEQ ID NO 286
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
cauuuguaag aaauaacacu                                              20

<210> SEQ ID NO 287
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 287
aauaacacug ugaauguaaa                                                    20

<210> SEQ ID NO 288
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
aauaugagcu cauuaguaaa                                                    20

<210> SEQ ID NO 289
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
ucacccacgc auauacauaa                                                    20

<210> SEQ ID NO 290
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
auauagacac aucuauaauu                                                    20

<210> SEQ ID NO 291
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
uuacacacac accucucaag                                                    20

<210> SEQ ID NO 292
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
gacuuuauca uguuccuaaa                                                    20
```

```
<210> SEQ ID NO 293
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
uuguugcaaa ugugauuaau                                                  20

<210> SEQ ID NO 294
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
gcaaauguga uuaauuuggu                                                  20

<210> SEQ ID NO 295
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
aauuugguug ucaaguuuug                                                  20

<210> SEQ ID NO 296
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
uuuguuuucc ugcugguaau                                                  20

<210> SEQ ID NO 297
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
guuuuccugc ugguaauauc                                                  20

<210> SEQ ID NO 298
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 298
auaucgggaa agauuuuaau                                               20

<210> SEQ ID NO 299
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 299
auuuuaauga aaccagggua                                               20

<210> SEQ ID NO 300
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
uaaugaaacc aggguagaau                                               20

<210> SEQ ID NO 301
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
auuguuuggc aaugcacuga                                               20

<210> SEQ ID NO 302
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
ccccucaguu guuucuaaga                                               20

<210> SEQ ID NO 303
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
ggacugacga gagauguaua                                               20

<210> SEQ ID NO 304
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
gacgagagau guauauuuaa                                               20

<210> SEQ ID NO 305
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
uuuuuuaacu gcugcaaaca                                               20

<210> SEQ ID NO 306
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
uaacugcugc aaacauugua                                               20

<210> SEQ ID NO 307
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
acccuggaaa agcugaugaa                                               20

<210> SEQ ID NO 308
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
aaggccuucg agucccucaa                                               20

<210> SEQ ID NO 309
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
cgcugcaccg accaaagaaa                                               20
```

```
<210> SEQ ID NO 310
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 310
aagaacuuuc agcuaccaag                                                 20

<210> SEQ ID NO 311
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
agcuaccaag aaagaccgug                                                 20

<210> SEQ ID NO 312
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
cgugugaauc auugucugac                                                 20

<210> SEQ ID NO 313
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
ucauugucug acaauaugug                                                 20

<210> SEQ ID NO 314
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
ugacaauaug ugaaaacaua                                                 20

<210> SEQ ID NO 315
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 315
auaugugaaa acauaguggc                                           20

<210> SEQ ID NO 316
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 316
gcagcagcag cagcagcagc                                           20

<210> SEQ ID NO 317
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 317
gucaguucau aaaccuggac                                           20

<210> SEQ ID NO 318
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 318
uaacgucagu ucauaaaccu                                           20

<210> SEQ ID NO 319
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 319
guaacgucag uucauaaacc                                           20

<210> SEQ ID NO 320
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 320
uccggucaca acauuguggu                                           20

<210> SEQ ID NO 321
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
ugucgguacc gucuaacaca                                              20

<210> SEQ ID NO 322
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
cccaaauacu gguugucggu                                              20

<210> SEQ ID NO 323
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
caacauuauu gagcacucgu                                              20

<210> SEQ ID NO 324
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
ucgacuaaag caggauuuca                                              20

<210> SEQ ID NO 325
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
auugguucuc gacuaaagca                                              20

<210> SEQ ID NO 326
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
```
uagcguugaa guacuguccc                                                    20

<210> SEQ ID NO 327
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
cacaacgaga cugaauugcc                                                    20

<210> SEQ ID NO 328
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
uaagcaugga gcuagcaggc                                                    20

<210> SEQ ID NO 329
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
ugaauguuca cgcagugggc                                                    20

<210> SEQ ID NO 330
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
auuuuaaauc cugagaagaa                                                    20

<210> SEQ ID NO 331
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
ucucuuuacu gauauaauua                                                    20

<210> SEQ ID NO 332
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 332
uuaaucucuu uacugauaua                                                   20

<210> SEQ ID NO 333
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
cuuucuuggu agcugaaagu                                                   20

<210> SEQ ID NO 334
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
uucacauauu gucagacaau                                                   20

<210> SEQ ID NO 335
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
uuccauagcg augcccagaa                                                   20

<210> SEQ ID NO 336
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
aaaaguucca uagcgaugcc                                                   20

<210> SEQ ID NO 337
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
uuaauuucau ugucauuugc                                                   20

<210> SEQ ID NO 338
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
cuuaauuuca uugucauuug                                              20

<210> SEQ ID NO 339
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
agguucgcua ugaaggccuu                                              20

<210> SEQ ID NO 340
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
agccuaagag cacauuuagu                                              20

<210> SEQ ID NO 341
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
uuucuuuccu ugucacuccg                                              20

<210> SEQ ID NO 342
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
cauaaaccug gacaagcugc                                              20

<210> SEQ ID NO 343
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
```
caguucauaa accuggacaa                                               20

<210> SEQ ID NO 344
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 344
aacgucaguu cauaaaccug                                               20

<210> SEQ ID NO 345
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
uguaacguca guucauaaac                                               20

<210> SEQ ID NO 346
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
ugauguaacg ucaguucaua                                               20

<210> SEQ ID NO 347
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
uguaugaugu aacgucaguu                                               20

<210> SEQ ID NO 348
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
uguguaugau guaacgucag                                               20

<210> SEQ ID NO 349
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 349
ggcuccgguc acaacauugu                                              20

<210> SEQ ID NO 350
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
auaaguucca caauacuccc                                              20

<210> SEQ ID NO 351
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
uccuaagagc acuuugccuu                                              20

<210> SEQ ID NO 352
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
uacugguugu cgguaccguc                                              20

<210> SEQ ID NO 353
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
aauacugguu gucgguaccg                                              20

<210> SEQ ID NO 354
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
ccaugaucga uguaguucaa                                              20
```

```
<210> SEQ ID NO 355
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
uccaugaucg auguaguuca                                              20

<210> SEQ ID NO 356
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
aacauuauug agcacucguu                                              20

<210> SEQ ID NO 357
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
uuuacuuguu guaacaggac                                              20

<210> SEQ ID NO 358
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
cgacuaaagc aggauuucag                                              20

<210> SEQ ID NO 359
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
uugguucucg acuaaagcag                                              20

<210> SEQ ID NO 360
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 360
aucauugguu cucgacuaaa                                              20

<210> SEQ ID NO 361
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 361
gccaucauug guucucgacu                                              20

<210> SEQ ID NO 362
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 362
cuucaacaau uguugaacac                                              20

<210> SEQ ID NO 363
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 363
cgccugcacc auguccuca                                               20

<210> SEQ ID NO 364
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 364
cugcacgguu cuuugugaca                                              20

<210> SEQ ID NO 365
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 365
aucugcacgg uucuuuguga                                              20

<210> SEQ ID NO 366
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 366
uuaucugcac gguucuuugu                                                     20

<210> SEQ ID NO 367
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
uuuuauaaca agagguucaa                                                     20

<210> SEQ ID NO 368
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
uucaauacaa agccaauaaa                                                     20

<210> SEQ ID NO 369
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
gauuuuagga auuccaauga                                                     20

<210> SEQ ID NO 370
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
cuggccauga ugccaucaca                                                     20

<210> SEQ ID NO 371
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
cuucaguuga cugggaaauc                                                     20
```

```
<210> SEQ ID NO 372
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
aaguauguug cugcucacuc                                               20

<210> SEQ ID NO 373
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
uucuccggaa cauuccagac                                               20

<210> SEQ ID NO 374
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
uggcugugaa uguucacgca                                               20

<210> SEQ ID NO 375
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
auuaaauuuu aaauccugag                                               20

<210> SEQ ID NO 376
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
uauaauuaaa uuuuaaaucc                                               20

<210> SEQ ID NO 377
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 377
uuuacugaua uaauuaaauu                                                    20

<210> SEQ ID NO 378
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 378
agaaagaguu acguuaaaau                                                    20

<210> SEQ ID NO 379
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
uuuacacggg cauagaaaga                                                    20

<210> SEQ ID NO 380
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
auacuuuaca cgggcauaga                                                    20

<210> SEQ ID NO 381
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
ugcacucucc ugacuaaaag                                                    20

<210> SEQ ID NO 382
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
cacauucaau acccaaaaca                                                    20

<210> SEQ ID NO 383
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
uuccuccacu uaccacauuc                                                   20

<210> SEQ ID NO 384
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
aacauuuccu ccacuuacca                                                   20

<210> SEQ ID NO 385
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
ugcacagagu uccaacauuu                                                   20

<210> SEQ ID NO 386
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
uuaagggccu ccucaaacau                                                   20

<210> SEQ ID NO 387
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
uucaguagcu ucccuuaagg                                                   20

<210> SEQ ID NO 388
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
uuucuuacgu guuauaauuc                                                   20
```

```
<210> SEQ ID NO 389
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 389
uuucuuacaa auguaaacau                                              20

<210> SEQ ID NO 390
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
aguguuauuu cuuacaaaug                                              20

<210> SEQ ID NO 391
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
uuuacauuca caguguuauu                                              20

<210> SEQ ID NO 392
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
uuuacuaaug agcucauauu                                              20

<210> SEQ ID NO 393
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
uuauguauau gcguggguga                                              20

<210> SEQ ID NO 394
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

```
            Synthetic oligonucleotide"

<400> SEQUENCE: 394
aauuauagau gugucuauau                                          20

<210> SEQ ID NO 395
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 395
cuugagaggu gugugugugaa                                         20

<210> SEQ ID NO 396
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
uuuaggaaca ugauaaaguc                                          20

<210> SEQ ID NO 397
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
auuaaucaca uuugcaacaa                                          20

<210> SEQ ID NO 398
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
accaaauuaa ucacauuugc                                          20

<210> SEQ ID NO 399
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
caaaacuuga caaccaaauu                                          20

<210> SEQ ID NO 400
<211> LENGTH: 20
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
auuaccagca ggaaaacaaa                                                   20

<210> SEQ ID NO 401
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
gauauuacca gcaggaaaac                                                   20

<210> SEQ ID NO 402
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
auuaaaaucu uucccgauau                                                   20

<210> SEQ ID NO 403
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
uacccugguu ucauuaaaau                                                   20

<210> SEQ ID NO 404
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
auucuacccu gguuucauua                                                   20

<210> SEQ ID NO 405
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
```
ucagugcauu gccaaacaau                                             20

<210> SEQ ID NO 406
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
ucuuagaaac aacugagggg                                             20

<210> SEQ ID NO 407
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
uauacaucuc ucgucagucc                                             20

<210> SEQ ID NO 408
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
uuaaauauac aucucucguc                                             20

<210> SEQ ID NO 409
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
uguuugcagc aguuaaaaaa                                             20

<210> SEQ ID NO 410
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
uacaauguuu gcagcaguua                                             20

<210> SEQ ID NO 411
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
uucaucagcu uuuccagggu                                                  20

<210> SEQ ID NO 412
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
uugagggacu cgaaggccuu                                                  20

<210> SEQ ID NO 413
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 413
uuucuuuggu cggugcagcg                                                  20

<210> SEQ ID NO 414
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 414
cuugguagcu gaaaguucuu                                                  20

<210> SEQ ID NO 415
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 415
cacggucuuu cuugguagcu                                                  20

<210> SEQ ID NO 416
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 416
gucagacaau gauucacacg                                                  20

<210> SEQ ID NO 417

<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 417
cacauauugu cagacaauga                                              20

<210> SEQ ID NO 418
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 418
uauguuuuca cauauuguca                                              20

<210> SEQ ID NO 419
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 419
gccacuaugu uuucacauau                                              20

<210> SEQ ID NO 420
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 420
gcugcugcug cugcugcugc                                              20

<210> SEQ ID NO 421
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 421
gguuuaugaa cugaa                                                   15

<210> SEQ ID NO 422
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 422
uaugaacuga cguua         15

<210> SEQ ID NO 423
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
augaacugac guuaa         15

<210> SEQ ID NO 424
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
aauguuguga ccgga         15

<210> SEQ ID NO 425
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
uagacgguac cgaca         15

<210> SEQ ID NO 426
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
caaccaguau uugga         15

<210> SEQ ID NO 427
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
ugcucaauaa uguua         15

<210> SEQ ID NO 428
<211> LENGTH: 15
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 428
uccugcuuua gucga                                                        15

<210> SEQ ID NO 429
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
uagucgagaa ccaaa                                                        15

<210> SEQ ID NO 430
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
aguacuucaa cgcua                                                        15

<210> SEQ ID NO 431
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
uucagucucg uugua                                                        15

<210> SEQ ID NO 432
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
cuagcuccau gcuua                                                        15

<210> SEQ ID NO 433
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 433
cugcgugaac auuca                                                        15
```

```
<210> SEQ ID NO 434
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 434
cucaggauuu aaaaa                                                    15

<210> SEQ ID NO 435
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 435
auaucaguaa agaga                                                    15

<210> SEQ ID NO 436
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 436
caguaaagag auuaa                                                    15

<210> SEQ ID NO 437
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 437
cagcuaccaa gaaaa                                                    15

<210> SEQ ID NO 438
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 438
cugacaauau gugaa                                                    15

<210> SEQ ID NO 439
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 439
ggcaucgcua uggaa                                                    15

<210> SEQ ID NO 440
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 440
cgcuauggaa cuuua                                                    15

<210> SEQ ID NO 441
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 441
ugacaaugaa auuaa                                                    15

<210> SEQ ID NO 442
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 442
gacaaugaaa uuaaa                                                    15

<210> SEQ ID NO 443
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 443
cuucauagcg aacca                                                    15

<210> SEQ ID NO 444
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 444
augugcucuu aggca                                                    15

<210> SEQ ID NO 445
<211> LENGTH: 15
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 445
ugacaaggaa agaaa                                                      15

<210> SEQ ID NO 446
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 446
uuguccaggu uuaua                                                      15

<210> SEQ ID NO 447
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 447
cagguuuaug aacua                                                      15

<210> SEQ ID NO 448
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 448
uuaugaacug acgua                                                      15

<210> SEQ ID NO 449
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 449
ugaacugacg uuaca                                                      15

<210> SEQ ID NO 450
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 450
acugacguua cauca                                                      15
```

<210> SEQ ID NO 451
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 451
acguuacauc auaca                                                    15

<210> SEQ ID NO 452
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 452
guuacaucau acaca                                                    15

<210> SEQ ID NO 453
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 453
guugugaccg gagca                                                    15

<210> SEQ ID NO 454
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 454
uauuguggaa cuuaa                                                    15

<210> SEQ ID NO 455
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 455
aaagugcucu uagga                                                    15

<210> SEQ ID NO 456
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 456
uaccgacaac cagua                                                        15

<210> SEQ ID NO 457
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 457
ccgacaacca guaua                                                        15

<210> SEQ ID NO 458
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 458
cuacaucgau cauga                                                        15

<210> SEQ ID NO 459
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 459
uacaucgauc augga                                                        15

<210> SEQ ID NO 460
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 460
gugcucaaua augua                                                        15

<210> SEQ ID NO 461
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 461
guuacaacaa guaaa                                                        15

<210> SEQ ID NO 462
<211> LENGTH: 15
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 462
auccugcuuu aguca                                                    15

<210> SEQ ID NO 463
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 463
uuagucgaga accaa                                                    15

<210> SEQ ID NO 464
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 464
ucgagaacca augaa                                                    15

<210> SEQ ID NO 465
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 465
agaaccaaug augga                                                    15

<210> SEQ ID NO 466
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 466
caacaauugu ugaaa                                                    15

<210> SEQ ID NO 467
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 467
aacauggugc aggca                                                    15
```

```
<210> SEQ ID NO 468
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 468
caaagaaccg ugcaa                                                      15

<210> SEQ ID NO 469
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 469
aagaaccgug cagaa                                                      15

<210> SEQ ID NO 470
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 470
gaaccgugca gauaa                                                      15

<210> SEQ ID NO 471
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 471
ccucuuguua uaaaa                                                      15

<210> SEQ ID NO 472
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 472
uggcuuugua uugaa                                                      15

<210> SEQ ID NO 473
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 473
ggaauuccua aaaua                                                    15

<210> SEQ ID NO 474
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 474
uggcaucaug gccaa                                                    15

<210> SEQ ID NO 475
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 475
cccagucaac ugaaa                                                    15

<210> SEQ ID NO 476
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 476
agcagcaaca uacua                                                    15

<210> SEQ ID NO 477
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 477
gaauguuccg gagaa                                                    15

<210> SEQ ID NO 478
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 478
gaacauucac agcca                                                    15

<210> SEQ ID NO 479
<211> LENGTH: 15

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
gauuuaaaau uuaaa                                                       15

<210> SEQ ID NO 480
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
uaaaauuuaa uuaua                                                       15

<210> SEQ ID NO 481
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
aauuauauca guaaa                                                       15

<210> SEQ ID NO 482
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
aacguaacuc uuuca                                                       15

<210> SEQ ID NO 483
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
cuaugcccgu guaaa                                                       15

<210> SEQ ID NO 484
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484
```
gcccguguaa aguaa 15

<210> SEQ ID NO 485
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
agucaggaga gugca 15

<210> SEQ ID NO 486
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
uggguauuga augua 15

<210> SEQ ID NO 487
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
ugguaagugg aggaa 15

<210> SEQ ID NO 488
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
aguggaggaa augua 15

<210> SEQ ID NO 489
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
uuggaacucu gugca 15

<210> SEQ ID NO 490
<211> LENGTH: 15
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 490
ugaggaggcc cuuaa                                                    15

<210> SEQ ID NO 491
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
agggaagcua cugaa                                                    15

<210> SEQ ID NO 492
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
auaacacgua agaaa                                                    15

<210> SEQ ID NO 493
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
uacauuugua agaaa                                                    15

<210> SEQ ID NO 494
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 494
guaagaaaua acaca                                                    15

<210> SEQ ID NO 495
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
cacugugaau guaaa                                                    15

<210> SEQ ID NO 496
```

```
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
gagcucauua guaaa                                                          15

<210> SEQ ID NO 497
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
cacgcauaua cauaa                                                          15

<210> SEQ ID NO 498
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498
gacacaucua uaaua                                                          15

<210> SEQ ID NO 499
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
cacacaccuc ucaaa                                                          15

<210> SEQ ID NO 500
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
uaucauguuc cuaaa                                                          15

<210> SEQ ID NO 501
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
```
gcaaauguga uuaaa                                                15

<210> SEQ ID NO 502
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
ugugauuaau uugga                                                15

<210> SEQ ID NO 503
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
gguugucaag uuuua                                                15

<210> SEQ ID NO 504
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
uuuccugcug guaaa                                                15

<210> SEQ ID NO 505
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
ccugcuggua auaua                                                15

<210> SEQ ID NO 506
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
gggaaagauu uuaaa                                                15

<210> SEQ ID NO 507
<211> LENGTH: 15
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 507
aaugaaacca gggua                                                        15

<210> SEQ ID NO 508
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
aaaccagggu agaaa                                                        15

<210> SEQ ID NO 509
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
uuggcaaugc acuga                                                        15

<210> SEQ ID NO 510
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonuclectide"

<400> SEQUENCE: 510
caguuguuuc uaaga                                                        15

<210> SEQ ID NO 511
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 511
gacgagagau guaua                                                        15

<210> SEQ ID NO 512
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
gagauguaua uuuaa                                                        15
```

```
<210> SEQ ID NO 513
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
uaacugcugc aaaca                                                     15

<210> SEQ ID NO 514
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
gcugcaaaca uugua                                                     15

<210> SEQ ID NO 515
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
ggaaaagcug augaa                                                     15

<210> SEQ ID NO 516
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
cuucgagucc cucaa                                                     15

<210> SEQ ID NO 517
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
caccgaccaa agaaa                                                     15

<210> SEQ ID NO 518
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 518
cuuucagcua ccaaa                                                          15

<210> SEQ ID NO 519
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
ccaagaaaga ccgua                                                          15

<210> SEQ ID NO 520
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
gaaucauugu cugaa                                                          15

<210> SEQ ID NO 521
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
gucugacaau augua                                                          15

<210> SEQ ID NO 522
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 522
auaugugaaa acaua                                                          15

<210> SEQ ID NO 523
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
ugaaaacaua gugga                                                          15

<210> SEQ ID NO 524
<211> LENGTH: 15
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 524
agcagcagca gcaga                                                         15

<210> SEQ ID NO 525
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
uucaguucau aaaccuggac                                                    20

<210> SEQ ID NO 526
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
uaacgucagu ucauaaaccu                                                    20

<210> SEQ ID NO 527
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
uuaacgucag uucauaaacc                                                    20

<210> SEQ ID NO 528
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 528
uccggucaca acauuguggu                                                    20

<210> SEQ ID NO 529
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
ugucgguacc gcuaacaca                                                     20
```

<210> SEQ ID NO 530
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 530
uccaaauacu gguugucggu                                              20

<210> SEQ ID NO 531
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 531
uaacauuauu gagcacucgu                                              20

<210> SEQ ID NO 532
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 532
ucgacuaaag caggauuuca                                              20

<210> SEQ ID NO 533
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 533
uuugguucuc gacuaaagca                                              20

<210> SEQ ID NO 534
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 534
uagcguugaa guacuguccc                                              20

<210> SEQ ID NO 535
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 535
uacaacgaga cugaauugcc                                           20

<210> SEQ ID NO 536
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 536
uaagcaugga gcuagcaggc                                           20

<210> SEQ ID NO 537
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 537
ugaauguuca cgcagugggc                                           20

<210> SEQ ID NO 538
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 538
uuuuuaaauc cugagaagaa                                           20

<210> SEQ ID NO 539
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 539
ucucuuuacu gauauaauua                                           20

<210> SEQ ID NO 540
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
uuaaucucuu uacugauaua                                           20

<210> SEQ ID NO 541
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
uuuucuuggu agcugaaagu                                               20

<210> SEQ ID NO 542
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
uucacauauu gucagacaau                                               20

<210> SEQ ID NO 543
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
uuccauagcg augcccagaa                                               20

<210> SEQ ID NO 544
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
uaaaguucca uagcgaugcc                                               20

<210> SEQ ID NO 545
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
uuaauuucau ugucauuugc                                               20

<210> SEQ ID NO 546
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
uuuaauuuca uugucauuug                                               20
```

<210> SEQ ID NO 547
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
ugguucgcua ugaaggccuu                                              20

<210> SEQ ID NO 548
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
ugccuaagag cacauuuagu                                              20

<210> SEQ ID NO 549
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
uuucuuuccu ugucacuccg                                              20

<210> SEQ ID NO 550
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
uauaaaccug gacaagcugc                                              20

<210> SEQ ID NO 551
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
uaguucauaa accuggacaa                                              20

<210> SEQ ID NO 552
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

```
            Synthetic oligonucleotide"

<400> SEQUENCE: 552
uacgucaguu cauaaaccug                                          20

<210> SEQ ID NO 553
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
uguaacguca guucauaaac                                          20

<210> SEQ ID NO 554
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
ugauguaacg ucaguucaua                                          20

<210> SEQ ID NO 555
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
uguaugaugu aacgucaguu                                          20

<210> SEQ ID NO 556
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 556
uguguaugau guaacgucag                                          20

<210> SEQ ID NO 557
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
ugcuccgguc acaacauugu                                          20

<210> SEQ ID NO 558
<211> LENGTH: 20
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
uuaaguucca caauacuccc                                               20

<210> SEQ ID NO 559
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
uccuaagagc acuuugccuu                                               20

<210> SEQ ID NO 560
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
uacugguugu cgguaccguc                                               20

<210> SEQ ID NO 561
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
uauacugguu gucgguaccg                                               20

<210> SEQ ID NO 562
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
ucaugaucga uguaguucaa                                               20

<210> SEQ ID NO 563
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
```
uccaugaucg auguaguuca                                              20

<210> SEQ ID NO 564
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
uacauuauug agcacucguu                                              20

<210> SEQ ID NO 565
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
uuuacuuguu guaacaggac                                              20

<210> SEQ ID NO 566
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
ugacuaaagc aggauuucag                                              20

<210> SEQ ID NO 567
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
uugguucucg acuaaagcag                                              20

<210> SEQ ID NO 568
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
uucauugguu cucgacuaaa                                              20

<210> SEQ ID NO 569
<211> LENGTH: 20
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 569
uccaucauug guucucgacu                                              20

<210> SEQ ID NO 570
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
uuucaacaau uguugaacac                                              20

<210> SEQ ID NO 571
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
ugccugcacc auguccuca                                               20

<210> SEQ ID NO 572
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
uugcacgguu cuuugugaca                                              20

<210> SEQ ID NO 573
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 573
uucugcacgg uucuuuguga                                              20

<210> SEQ ID NO 574
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
uuaucugcac gguucuuugu                                              20

<210> SEQ ID NO 575
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
uuuuauaaca agagguucaa                                                    20

<210> SEQ ID NO 576
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
uucaauacaa agccauaaa                                                     20

<210> SEQ ID NO 577
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
uauuuuagga auuccaauga                                                    20

<210> SEQ ID NO 578
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578
uuggccauga ugccaucaca                                                    20

<210> SEQ ID NO 579
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
uuucaguuga cugggaaauc                                                    20

<210> SEQ ID NO 580
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
```

-continued

```
uaguauguug cugcucacuc                                              20

<210> SEQ ID NO 581
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
uucuccggaa cauuccagac                                              20

<210> SEQ ID NO 582
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
uggcugugaa uguucacgca                                              20

<210> SEQ ID NO 583
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
uuuaaauuuu aaauccugag                                              20

<210> SEQ ID NO 584
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
uauaauuaaa uuuuaaaucc                                              20

<210> SEQ ID NO 585
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
uuuacugaua uaauuaaauu                                              20

<210> SEQ ID NO 586
<211> LENGTH: 20
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 586
ugaaagaguu acguuaaaau                                              20

<210> SEQ ID NO 587
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
uuuacacggg cauagaaaga                                              20

<210> SEQ ID NO 588
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
uuacuuuaca cgggcauaga                                              20

<210> SEQ ID NO 589
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
ugcacucucc ugacuaaaag                                              20

<210> SEQ ID NO 590
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 590
uacauucaau acccaaaaca                                              20

<210> SEQ ID NO 591
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
uuccuccacu uaccacauuc                                              20
```

```
<210> SEQ ID NO 592
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592 uacauuccu ccacuuacca                                                    20

<210> SEQ ID NO 593
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
ugcacagagu uccaacauuu                                                   20

<210> SEQ ID NO 594
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
uuaagggccu ccucaaacau                                                   20

<210> SEQ ID NO 595
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
uucaguagcu ucccuuaagg                                                   20

<210> SEQ ID NO 596
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
uuucuuacgu guuauaauuc                                                   20

<210> SEQ ID NO 597
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 597
uuucuuacaa auguaaacau                                               20

<210> SEQ ID NO 598
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
uguguuauuu cuuacaaaug                                               20

<210> SEQ ID NO 599
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
uuuacauuca caguguuauu                                               20

<210> SEQ ID NO 600
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
uuuacuaaug agcucauauu                                               20

<210> SEQ ID NO 601
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 601
uuauguauau gcguggguga                                               20

<210> SEQ ID NO 602
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
uauuauagau gugucuauau                                               20

<210> SEQ ID NO 603
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 603
uuugagaggu guguguguaa                                                  20

<210> SEQ ID NO 604
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
uuuaggaaca ugauaaaguc                                                  20

<210> SEQ ID NO 605
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
uuuaaucaca uuugcaacaa                                                  20

<210> SEQ ID NO 606
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
uccaaauuaa ucacauuugc                                                  20

<210> SEQ ID NO 607
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 607
uaaaacuuga caaccaaauu                                                  20

<210> SEQ ID NO 608
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
uuuaccagca ggaaaacaaa                                                  20
```

<210> SEQ ID NO 609
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 609
uauauuacca gcaggaaaac                    20

<210> SEQ ID NO 610
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 610
uuuaaaaucu uucccgauau                    20

<210> SEQ ID NO 611
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 611
uacccugguu ucauuaaaau                    20

<210> SEQ ID NO 612
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 612
uuucuacccu gguuucauua                    20

<210> SEQ ID NO 613
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 613
ucagugcauu gccaaacaau                    20

<210> SEQ ID NO 614
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 614
ucuuagaaac aacugagggg                                         20

<210> SEQ ID NO 615
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
uauacaucuc ucgucagucc                                         20

<210> SEQ ID NO 616
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
uuaaauauac aucucucguc                                         20

<210> SEQ ID NO 617
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
uguuugcagc aguuaaaaaa                                         20

<210> SEQ ID NO 618
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 618
uacaauguuu gcagcaguua                                         20

<210> SEQ ID NO 619
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
uucaucagcu uuuccagggu                                         20

<210> SEQ ID NO 620
<211> LENGTH: 20
<212> TYPE: RNA
```

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
uugagggacu cgaaggccuu                                                    20

<210> SEQ ID NO 621
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
uuucuuuggu cggugcagcg                                                    20

<210> SEQ ID NO 622
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
uuugguagcu gaaaguucuu                                                    20

<210> SEQ ID NO 623
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
uacggucuuu cuugguagcu                                                    20

<210> SEQ ID NO 624
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
uucagacaau gauucacacg                                                    20

<210> SEQ ID NO 625
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
uacauauugu cagacaauga                                                    20
```

```
<210> SEQ ID NO 626
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
uauguuuuca cauauuguca                                              20

<210> SEQ ID NO 627
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
uccacuaugu uuucacauau                                              20

<210> SEQ ID NO 628
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
ucugcugcug cugcugcugc                                              20

<210> SEQ ID NO 629
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
guccagguuu augaa                                                   15

<210> SEQ ID NO 630
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
agguuuauga acuga                                                   15

<210> SEQ ID NO 631
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
```

```
      Synthetic oligonucleotide"

<400> SEQUENCE: 631
gguuuaugaa cugaa                                                    15

<210> SEQ ID NO 632
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
accacaaugu uguga                                                    15

<210> SEQ ID NO 633
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
uguguuagac gguaa                                                    15

<210> SEQ ID NO 634
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
accgacaacc aguaa                                                    15

<210> SEQ ID NO 635
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 635
acgagugcuc aauaa                                                    15

<210> SEQ ID NO 636
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
ugaaauccug cuuua                                                    15

<210> SEQ ID NO 637
<211> LENGTH: 15
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
ugcuuuaguc gagaa                                                           15

<210> SEQ ID NO 638
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
gggacaguac uucaa                                                           15

<210> SEQ ID NO 639
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
ggcaauucag ucuca                                                           15

<210> SEQ ID NO 640
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
gccugcuagc uccaa                                                           15

<210> SEQ ID NO 641
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
gcccacugcg ugaaa                                                           15

<210> SEQ ID NO 642
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
```

-continued uucuucucag gauua                                              15

<210> SEQ ID NO 643
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
uaauuauauc aguaa                                              15

<210> SEQ ID NO 644
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
uauaucagua aagaa                                              15

<210> SEQ ID NO 645
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
acuuucagcu accaa                                              15

<210> SEQ ID NO 646
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
auugucugac aauaa                                              15

<210> SEQ ID NO 647
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
uucugggcau cgcua                                              15

<210> SEQ ID NO 648
<211> LENGTH: 15
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 648
ggcaucgcua uggaa                                                      15

<210> SEQ ID NO 649
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
gcaaaugaca augaa                                                      15

<210> SEQ ID NO 650
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
caaaugacaa ugaaa                                                      15

<210> SEQ ID NO 651
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
aaggccuuca uagca                                                      15

<210> SEQ ID NO 652
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
acuaaaugug cucua                                                      15

<210> SEQ ID NO 653
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
cggagugaca aggaa                                                      15

<210> SEQ ID NO 654
```

```
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
gcagcuuguc cagga                                                     15

<210> SEQ ID NO 655
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
uuguccaggu uuaua                                                     15

<210> SEQ ID NO 656
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
cagguuuaug aacua                                                     15

<210> SEQ ID NO 657
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
guuuaugaac ugaca                                                     15

<210> SEQ ID NO 658
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
uaugaacuga cguua                                                     15

<210> SEQ ID NO 659
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
```
aacugacguu acaua                                                        15

<210> SEQ ID NO 660
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
cugacguuac aucaa                                                        15

<210> SEQ ID NO 661
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
acaauguugu gacca                                                        15

<210> SEQ ID NO 662
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
gggaguauug uggaa                                                        15

<210> SEQ ID NO 663
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
aaggcaaagu gcuca                                                        15

<210> SEQ ID NO 664
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
gacgguaccg acaaa                                                        15

<210> SEQ ID NO 665
<211> LENGTH: 15
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 665
cgguaccgac aacca                                                    15

<210> SEQ ID NO 666
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
uugaacuaca ucgaa                                                    15

<210> SEQ ID NO 667
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
ugaacuacau cgaua                                                    15

<210> SEQ ID NO 668
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
aacgagugcu caaua                                                    15

<210> SEQ ID NO 669
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 669
guccuguuac aacaa                                                    15

<210> SEQ ID NO 670
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
cugaaauccu gcuua                                                    15
```

```
<210> SEQ ID NO 671
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
cugcuuuagu cgaga                                                    15

<210> SEQ ID NO 672
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
uuuagucgag aacca                                                    15

<210> SEQ ID NO 673
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
agucgagaac caaua                                                    15

<210> SEQ ID NO 674
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
guguucaaca auuga                                                    15

<210> SEQ ID NO 675
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
ugaggaacau gguga                                                    15

<210> SEQ ID NO 676
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 676
ugucacaaag aacca                                                    15

<210> SEQ ID NO 677
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
ucacaaagaa ccgua                                                    15

<210> SEQ ID NO 678
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678
acaaagaacc gugca                                                    15

<210> SEQ ID NO 679
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
uugaaccucu uguua                                                    15

<210> SEQ ID NO 680
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 680
uuuauuggcu uugua                                                    15

<210> SEQ ID NO 681
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 681
ucauuggaau uccua                                                    15

<210> SEQ ID NO 682
<211> LENGTH: 15
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 682
ugugauggca ucaua                                                    15

<210> SEQ ID NO 683
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
gauuucccag ucaaa                                                    15

<210> SEQ ID NO 684
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 684
gagugagcag caaca                                                    15

<210> SEQ ID NO 685
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
gucuggaaug uucca                                                    15

<210> SEQ ID NO 686
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 686
ugcgugaaca uucaa                                                    15

<210> SEQ ID NO 687
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
cucaggauuu aaaaa                                                    15
```

```
<210> SEQ ID NO 688
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
ggauuuaaaa uuuaa                                                      15

<210> SEQ ID NO 689
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 689
aauuuaauua uauca                                                      15

<210> SEQ ID NO 690
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
auuuuaacgu aacua                                                      15

<210> SEQ ID NO 691
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
ucuuucuaug cccga                                                      15

<210> SEQ ID NO 692
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 692
ucuaugcccg uguaa                                                      15

<210> SEQ ID NO 693
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 693
cuuuuaguca ggaga                                                    15

<210> SEQ ID NO 694
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694 uguuugggu auuga                                                     15

<210> SEQ ID NO 695
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
gaauguggua aguga                                                    15

<210> SEQ ID NO 696
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696
ugguaagugg aggaa                                                    15

<210> SEQ ID NO 697
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 697
aaauguugga acuca                                                    15

<210> SEQ ID NO 698
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698 auguugagg aggca                                                     15

<210> SEQ ID NO 699
<211> LENGTH: 15
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
ccuuaaggga agcua                                                          15

<210> SEQ ID NO 700
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700
gaauuauaac acgua                                                          15

<210> SEQ ID NO 701
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 701
auguuuacau uugua                                                          15

<210> SEQ ID NO 702
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
cauuuguaag aaaua                                                          15

<210> SEQ ID NO 703
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
aauaacacug ugaaa                                                          15

<210> SEQ ID NO 704
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
aauaugagcu cauua                                                          15
```

```
<210> SEQ ID NO 705
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
ucacccacgc auaua                                                        15

<210> SEQ ID NO 706
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
auauagacac aucua                                                        15

<210> SEQ ID NO 707
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
uuacacacac accua                                                        15

<210> SEQ ID NO 708
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
gacuuuauca uguua                                                        15

<210> SEQ ID NO 709
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
uuguugcaaa uguga                                                        15

<210> SEQ ID NO 710
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 710
gcaaauguga uuaaa                                                          15

<210> SEQ ID NO 711
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
aauuugguug ucaaa                                                          15

<210> SEQ ID NO 712
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
uuuguuuucc ugcua                                                          15

<210> SEQ ID NO 713
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713 guuuccugc uggua                                                           15

<210> SEQ ID NO 714
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 714
auaucgggaa agaua                                                          15

<210> SEQ ID NO 715
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 715
auuuuaauga aacca                                                          15

<210> SEQ ID NO 716
<211> LENGTH: 15

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 716
uaaugaaacc aggga                                                      15

<210> SEQ ID NO 717
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 717
auuguuuggc aauga                                                      15

<210> SEQ ID NO 718
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 718
ccccucaguu guuua                                                      15

<210> SEQ ID NO 719
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 719
ggacugacga gagaa                                                      15

<210> SEQ ID NO 720
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 720
gacgagagau guaua                                                      15

<210> SEQ ID NO 721
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
```
uuuuuuaacu gcuga                                            15

<210> SEQ ID NO 722
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
uaacugcugc aaaca                                            15

<210> SEQ ID NO 723
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 723
acccuggaaa agcua                                            15

<210> SEQ ID NO 724
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
aaggccuucg aguca                                            15

<210> SEQ ID NO 725
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 725
cgcugcaccg accaa                                            15

<210> SEQ ID NO 726
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
aagaacuuuc agcua                                            15

<210> SEQ ID NO 727
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 727
agcuaccaag aaaga                                                    15

<210> SEQ ID NO 728
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
cgugugaauc auuga                                                    15

<210> SEQ ID NO 729
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
ucauugucug acaaa                                                    15

<210> SEQ ID NO 730
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
ugacaauaug ugaaa                                                    15

<210> SEQ ID NO 731
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 731
auaugugaaa acaua                                                    15

<210> SEQ ID NO 732
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 732
gcagcagcag cagca                                                    15

<210> SEQ ID NO 733

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 733
uucaguucau aaaccuggac                                                 20

<210> SEQ ID NO 734
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 734
uaacgucagu ucauaaaccu                                                 20

<210> SEQ ID NO 735
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 735
uuaacgucag uucauaaacc                                                 20

<210> SEQ ID NO 736
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 736
uccggucaca acauuguggu                                                 20

<210> SEQ ID NO 737
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
ugucgguacc gucuaacaca                                                 20

<210> SEQ ID NO 738
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
```

```
uccaaauacu gguugucggu                                             20
```

<210> SEQ ID NO 739
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739

```
uaacauuauu gagcacucgu                                             20
```

<210> SEQ ID NO 740
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 740

```
ucgacuaaag caggauuuca                                             20
```

<210> SEQ ID NO 741
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741

```
uuugguucuc gacuaaagca                                             20
```

<210> SEQ ID NO 742
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 742

```
uagcguugaa guacuguccc                                             20
```

<210> SEQ ID NO 743
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743

```
uacaacgaga cugaauugcc                                             20
```

<210> SEQ ID NO 744
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 744
uaagcaugga gcuagcaggc                                                     20

<210> SEQ ID NO 745
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
ugaauguuca cgcagugggc                                                     20

<210> SEQ ID NO 746
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 746
uuuuuaaauc cugagaagaa                                                     20

<210> SEQ ID NO 747
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
ucucuuuacu gauauaauua                                                     20

<210> SEQ ID NO 748
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 748
uuaaucucuu uacugauaua                                                     20

<210> SEQ ID NO 749
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
uuuucuuggu agcugaaagu                                                     20
```

```
<210> SEQ ID NO 750
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750
uucacauauu gucagacaau                                              20

<210> SEQ ID NO 751
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751
uuccauagcg augcccagaa                                              20

<210> SEQ ID NO 752
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 752
uaaaguucca uagcgaugcc                                              20

<210> SEQ ID NO 753
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 753
uuaauuucau ugucauuugc                                              20

<210> SEQ ID NO 754
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 754
uuuaauuuca uugucauuug                                              20

<210> SEQ ID NO 755
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 755
ugguucgcua ugaaggccuu                                                    20

<210> SEQ ID NO 756
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 756
ugccuaagag cacauuuagu                                                    20

<210> SEQ ID NO 757
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 757
uuucuuuccu ugucacuccg                                                    20

<210> SEQ ID NO 758
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758
uauaaaccug gacaagcugc                                                    20

<210> SEQ ID NO 759
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 759
uaguucauaa accuggacaa                                                    20

<210> SEQ ID NO 760
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
uacgucaguu cauaaaccug                                                    20

<210> SEQ ID NO 761
<211> LENGTH: 20
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 761
uguaacguca guucauaaac                                                     20

<210> SEQ ID NO 762
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
ugauguaacg ucaguucaua                                                     20

<210> SEQ ID NO 763
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 763
uguaugaugu aacgucaguu                                                     20

<210> SEQ ID NO 764
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
uguguaugau guaacgucag                                                     20

<210> SEQ ID NO 765
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 765
ugcuccgguc acaacauugu                                                     20

<210> SEQ ID NO 766
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
uuaaguucca caauacuccc                                                     20
```

```
<210> SEQ ID NO 767
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 767
uccuaagagc acuuugccuu                                              20

<210> SEQ ID NO 768
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
uacugguugu cgguaccguc                                              20

<210> SEQ ID NO 769
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 769
uauacugguu gucgguaccg                                              20

<210> SEQ ID NO 770
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 770
ucaugaucga uguaguucaa                                              20

<210> SEQ ID NO 771
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 771
uccaugaucg auguaguuca                                              20

<210> SEQ ID NO 772
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 772
uacauuauug agcacucguu                                         20

<210> SEQ ID NO 773
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 773
uuuacuuguu guaacaggac                                         20

<210> SEQ ID NO 774
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 774
ugacuaaagc aggauuucag                                         20

<210> SEQ ID NO 775
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 775
uugguucucg acuaaagcag                                         20

<210> SEQ ID NO 776
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 776
uucauugguu cucgacuaaa                                         20

<210> SEQ ID NO 777
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 777
uccaucauug guucucgacu                                         20

<210> SEQ ID NO 778
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 778
uuucaacaau uguugaacac                                            20

<210> SEQ ID NO 779
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
ugccugcacc auguccuca                                             20

<210> SEQ ID NO 780
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 780
uugcacgguu cuuugugaca                                            20

<210> SEQ ID NO 781
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 781
uucugcacgg uucuuuguga                                            20

<210> SEQ ID NO 782
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 782
uuaucugcac gguucuuugu                                            20

<210> SEQ ID NO 783
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
uuuuauaaca agagguucaa                                            20
```

```
<210> SEQ ID NO 784
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 784
uucaauacaa agccaauaaa                                                    20

<210> SEQ ID NO 785
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 785
uauuuuagga auuccaauga                                                    20

<210> SEQ ID NO 786
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
uuggccauga ugccaucaca                                                    20

<210> SEQ ID NO 787
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
uuucaguuga cugggaaauc                                                    20

<210> SEQ ID NO 788
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 788
uaguauguug cugcucacuc                                                    20

<210> SEQ ID NO 789
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

```
      Synthetic oligonucleotide"

<400> SEQUENCE: 789
uucuccggaa cauuccagac                                              20

<210> SEQ ID NO 790
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 790
uggcugugaa uguucacgca                                              20

<210> SEQ ID NO 791
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 791
uuuaaauuuu aaauccugag                                              20

<210> SEQ ID NO 792
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 792
uauaauuaaa uuuuaaaucc                                              20

<210> SEQ ID NO 793
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 793
uuuacugaua uaauuaaauu                                              20

<210> SEQ ID NO 794
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 794
ugaaagaguu acguuaaaau                                              20

<210> SEQ ID NO 795
<211> LENGTH: 20
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 795
uuuacacggg cauagaaaga                                                   20

<210> SEQ ID NO 796
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 796
uuacuuuaca cgggcauaga                                                   20

<210> SEQ ID NO 797
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 797
ugcacucucc ugacuaaaag                                                   20

<210> SEQ ID NO 798
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 798
uacauucaau acccaaaaca                                                   20

<210> SEQ ID NO 799
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 799
uuccuccacu uaccacauuc                                                   20

<210> SEQ ID NO 800
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800
```

-continued uacauuuccu ccacuuacca                                              20

<210> SEQ ID NO 801
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801
ugcacagagu uccaacauuu                                              20

<210> SEQ ID NO 802
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 802
uuaagggccu ccucaaacau                                              20

<210> SEQ ID NO 803
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 803
uucaguagcu ucccuuaagg                                              20

<210> SEQ ID NO 804
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 804
uuucuuacgu guuauaauuc                                              20

<210> SEQ ID NO 805
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 805
uuucuuacaa auguaaacau                                              20

<210> SEQ ID NO 806
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 806
uguguuauuu cuuacaaaug                                            20

<210> SEQ ID NO 807
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 807
uuuacauuca caguguuauu                                            20

<210> SEQ ID NO 808
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 808
uuuacuaaug agcucauauu                                            20

<210> SEQ ID NO 809
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 809
uuauguauau gcguggguga                                            20

<210> SEQ ID NO 810
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 810
uauuauagau gugucuauau                                            20

<210> SEQ ID NO 811
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811
uuugagaggu guguguguaa                                            20

<210> SEQ ID NO 812
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 812
uuuaggaaca ugauaaaguc                                                  20

<210> SEQ ID NO 813
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
uuuaaucaca uuugcaacaa                                                  20

<210> SEQ ID NO 814
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 814
uccaaauuaa ucacauuugc                                                  20

<210> SEQ ID NO 815
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 815
uaaaacuuga caaccaaauu                                                  20

<210> SEQ ID NO 816
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 816
uuuaccagca ggaaaacaaa                                                  20

<210> SEQ ID NO 817
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 817
```
uauauuacca gcaggaaaac                                          20

<210> SEQ ID NO 818
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 818
uuuaaaaucu uucccgauau                                          20

<210> SEQ ID NO 819
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 819
uacccugguu ucauuaaaau                                          20

<210> SEQ ID NO 820
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 820
uuucuacccu gguuucauua                                          20

<210> SEQ ID NO 821
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
ucagugcauu gccaaacaau                                          20

<210> SEQ ID NO 822
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
ucuuagaaac aacugagggg                                          20

<210> SEQ ID NO 823
<211> LENGTH: 20
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 823
uauacaucuc ucgucagucc                                              20

<210> SEQ ID NO 824
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
uuaaauauac aucucucguc                                              20

<210> SEQ ID NO 825
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 825
uguuugcagc aguuaaaaaa                                              20

<210> SEQ ID NO 826
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 826
uacaauguuu gcagcaguua                                              20

<210> SEQ ID NO 827
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 827
uucaucagcu uuuccagggu                                              20

<210> SEQ ID NO 828
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
uugagggacu cgaaggccuu                                              20

```
<210> SEQ ID NO 829
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829
uuucuuuggu cggugcagcg                                                    20

<210> SEQ ID NO 830
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
uuugguagcu gaaaguucuu                                                    20

<210> SEQ ID NO 831
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
uacggucuuu cuugguagcu                                                    20

<210> SEQ ID NO 832
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 832
uucagacaau gauucacacg                                                    20

<210> SEQ ID NO 833
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
uacauauugu cagacaauga                                                    20

<210> SEQ ID NO 834
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 834
uauguuuuca cauauuguca                                              20

<210> SEQ ID NO 835
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835
uccacuaugu uuucacauau                                              20

<210> SEQ ID NO 836
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 836
ucugcugcug cugcugcugc                                              20

<210> SEQ ID NO 837
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 837
guccagguuu augaa                                                   15

<210> SEQ ID NO 838
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 838
agguuuauga acuga                                                   15

<210> SEQ ID NO 839
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 839
gguuuaugaa cugaa                                                   15

<210> SEQ ID NO 840
<211> LENGTH: 15
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 840
accacaaugu uguga                                                          15

<210> SEQ ID NO 841
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841
uguguuagac gguaa                                                          15

<210> SEQ ID NO 842
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842
accgacaacc aguaa                                                          15

<210> SEQ ID NO 843
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
acgagugcuc aauaa                                                          15

<210> SEQ ID NO 844
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 844
ugaaauccug cuuua                                                          15

<210> SEQ ID NO 845
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
ugcuuuaguc gagaa                                                          15
```

<210> SEQ ID NO 846
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 846
gggacaguac uucaa                                                    15

<210> SEQ ID NO 847
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 847
ggcaauucag ucuca                                                    15

<210> SEQ ID NO 848
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 848
gccugcuagc uccaa                                                    15

<210> SEQ ID NO 849
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 849
gcccacugcg ugaaa                                                    15

<210> SEQ ID NO 850
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 850
uucuucucag gauua                                                    15

<210> SEQ ID NO 851
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 851
uaauuauauc aguaa                                                  15

<210> SEQ ID NO 852
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 852
uauaucagua aagaa                                                  15

<210> SEQ ID NO 853
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 853
acuuucagcu accaa                                                  15

<210> SEQ ID NO 854
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 854
auugucugac aauaa                                                  15

<210> SEQ ID NO 855
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 855
uucugggcau cgcua                                                  15

<210> SEQ ID NO 856
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 856
ggcaucgcua uggaa                                                  15

<210> SEQ ID NO 857
<211> LENGTH: 15
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
gcaaaugaca augaa                                                    15

<210> SEQ ID NO 858
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 858
caaaugacaa ugaaa                                                    15

<210> SEQ ID NO 859
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 859
aaggccuuca uagca                                                    15

<210> SEQ ID NO 860
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 860
acuaaaugug cucua                                                    15

<210> SEQ ID NO 861
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 861
cggagugaca aggaa                                                    15

<210> SEQ ID NO 862
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 862
gcagcuuguc cagga                                                    15
```

<210> SEQ ID NO 863
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 863
uuguccaggu uuaua                                                        15

<210> SEQ ID NO 864
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 864
cagguuuaug aacua                                                        15

<210> SEQ ID NO 865
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 865
guuuaugaac ugaca                                                        15

<210> SEQ ID NO 866
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 866
uaugaacuga cguua                                                        15

<210> SEQ ID NO 867
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 867
aacugacguu acaua                                                        15

<210> SEQ ID NO 868
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 868
cugacguuac aucaa                                                15

<210> SEQ ID NO 869
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 869
acaauguugu gacca                                                15

<210> SEQ ID NO 870
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 870
gggaguauug uggaa                                                15

<210> SEQ ID NO 871
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 871
aaggcaaagu gcuca                                                15

<210> SEQ ID NO 872
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 872
gacgguaccg acaaa                                                15

<210> SEQ ID NO 873
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 873
cgguaccgac aacca                                                15

<210> SEQ ID NO 874
<211> LENGTH: 15

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 874
uugaacuaca ucgaa                                                    15

<210> SEQ ID NO 875
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 875
ugaacuacau cgaua                                                    15

<210> SEQ ID NO 876
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 876
aacgagugcu caaua                                                    15

<210> SEQ ID NO 877
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
guccuguuac aacaa                                                    15

<210> SEQ ID NO 878
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 878
cugaaauccu gcuua                                                    15

<210> SEQ ID NO 879
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879
```
cugcuuuagu cgaga                                                        15

<210> SEQ ID NO 880
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 880
uuuagucgag aacca                                                        15

<210> SEQ ID NO 881
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881
agucgagaac caaua                                                        15

<210> SEQ ID NO 882
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882
guguucaaca auuga                                                        15

<210> SEQ ID NO 883
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 883
ugaggaacau gguga                                                        15

<210> SEQ ID NO 884
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 884
ugucacaaag aacca                                                        15

<210> SEQ ID NO 885
<211> LENGTH: 15
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 885
ucacaaagaa ccgua                                                      15

<210> SEQ ID NO 886
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 886
acaaagaacc gugca                                                      15

<210> SEQ ID NO 887
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 887
uugaaccucu uguua                                                      15

<210> SEQ ID NO 888
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
uuuauuggcu uugua                                                      15

<210> SEQ ID NO 889
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 889
ucauuggaau uccua                                                      15

<210> SEQ ID NO 890
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 890
ugugauggca ucaua                                                      15

<210> SEQ ID NO 891
```

```
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 891
gauuucccag ucaaa                                                      15

<210> SEQ ID NO 892
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 892
gagugagcag caaca                                                      15

<210> SEQ ID NO 893
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 893
gucuggaaug uucca                                                      15

<210> SEQ ID NO 894
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 894
ugcgugaaca uucaa                                                      15

<210> SEQ ID NO 895
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 895
cucaggauuu aaaaa                                                      15

<210> SEQ ID NO 896
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 896
```
ggauuuaaaa uuuaa                                                       15

<210> SEQ ID NO 897
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 897
aauuuaauua uauca                                                       15

<210> SEQ ID NO 898
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 898
auuuuaacgu aacua                                                       15

<210> SEQ ID NO 899
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 899
ucuuucuaug cccga                                                       15

<210> SEQ ID NO 900
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 900
ucuaugcccg uguaa                                                       15

<210> SEQ ID NO 901
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 901
cuuuuaguca ggaga                                                       15

<210> SEQ ID NO 902
<211> LENGTH: 15
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 902 uguuugggu auuga                                                       15

<210> SEQ ID NO 903
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 903
gaauguggua aguga                                                      15

<210> SEQ ID NO 904
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 904
ugguaagugg aggaa                                                      15

<210> SEQ ID NO 905
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 905
aaauguugga acuca                                                      15

<210> SEQ ID NO 906
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 906
auguuugagg aggca                                                      15

<210> SEQ ID NO 907
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 907
ccuuaaggga agcua                                                      15

```
<210> SEQ ID NO 908
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908
gaauuauaac acgua                                                         15

<210> SEQ ID NO 909
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 909
auguuuacau uugua                                                         15

<210> SEQ ID NO 910
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910
cauuuguaag aaaua                                                         15

<210> SEQ ID NO 911
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 911
aauaacacug ugaaa                                                         15

<210> SEQ ID NO 912
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 912
aauaugagcu cauua                                                         15

<210> SEQ ID NO 913
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 913
ucacccacgc auaua                                                       15

<210> SEQ ID NO 914
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 914
auauagacac aucua                                                       15

<210> SEQ ID NO 915
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 915
uuacacacac accua                                                       15

<210> SEQ ID NO 916
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 916
gacuuuauca uguua                                                       15

<210> SEQ ID NO 917
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 917
uuguugcaaa uguga                                                       15

<210> SEQ ID NO 918
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 918
gcaaauguga uuaaa                                                       15

<210> SEQ ID NO 919
<211> LENGTH: 15
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 919
aauuugguug ucaaa                                                       15

<210> SEQ ID NO 920
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
uuuguuuucc ugcua                                                       15

<210> SEQ ID NO 921
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 921 guuuccugc uggua                                                        15

<210> SEQ ID NO 922
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 922
auaucgggaa agaua                                                       15

<210> SEQ ID NO 923
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 923
auuuuaauga aacca                                                       15

<210> SEQ ID NO 924
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 924
uaaugaaacc aggga                                                       15
```

```
<210> SEQ ID NO 925
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 925
auuguuuggc aauga                                                  15

<210> SEQ ID NO 926
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 926
ccccucaguu guuua                                                  15

<210> SEQ ID NO 927
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 927
ggacugacga gagaa                                                  15

<210> SEQ ID NO 928
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928
gacgagagau guaua                                                  15

<210> SEQ ID NO 929
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 929
uuuuuuaacu gcuga                                                  15

<210> SEQ ID NO 930
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 930
uaacugcugc aaaca                                                      15

<210> SEQ ID NO 931
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931
acccuggaaa agcua                                                      15

<210> SEQ ID NO 932
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 932
aaggccuucg aguca                                                      15

<210> SEQ ID NO 933
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
cgcugcaccg accaa                                                      15

<210> SEQ ID NO 934
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 934
aagaacuuuc agcua                                                      15

<210> SEQ ID NO 935
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 935
agcuaccaag aaaga                                                      15

<210> SEQ ID NO 936
<211> LENGTH: 15
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 936
cgugugaauc auuga                                                    15

<210> SEQ ID NO 937
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 937 ucaugucug acaaa                                                     15

<210> SEQ ID NO 938
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 938
ugacaauaug ugaaa                                                    15

<210> SEQ ID NO 939
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 939
auaugugaaa acaua                                                    15

<210> SEQ ID NO 940
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 940
gcagcagcag cagca                                                    15

<210> SEQ ID NO 941
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 941
uucaguucau aaaccuggac                                               20
```

<210> SEQ ID NO 942
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 942
uaacgucagu ucauaaaccu                                               20

<210> SEQ ID NO 943
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 943
uuaacgucag uucauaaacc                                               20

<210> SEQ ID NO 944
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 944
uccggucaca acauuguggu                                               20

<210> SEQ ID NO 945
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 945
ugucgguacc gucuaacaca                                               20

<210> SEQ ID NO 946
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 946
uccaaauacu gguugucggu                                               20

<210> SEQ ID NO 947
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 947
uaacauuauu gagcacucgu                                            20

<210> SEQ ID NO 948
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 948
ucgacuaaag caggauuuca                                            20

<210> SEQ ID NO 949
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 949
uuugguucuc gacuaaagca                                            20

<210> SEQ ID NO 950
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 950
uagcguugaa guacuguccc                                            20

<210> SEQ ID NO 951
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 951
uacaacgaga cugaauugcc                                            20

<210> SEQ ID NO 952
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 952
uaagcaugga gcuagcaggc                                            20

<210> SEQ ID NO 953
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 953
ugaauguuca cgcagugggc                                                    20

<210> SEQ ID NO 954
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 954
uuuuuaaauc cugagaagaa                                                    20

<210> SEQ ID NO 955
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 955
ucucuuuacu gauauaauua                                                    20

<210> SEQ ID NO 956
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 956
uuaaucucuu uacugauaua                                                    20

<210> SEQ ID NO 957
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 957
uuuucuuggu agcugaaagu                                                    20

<210> SEQ ID NO 958
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 958
```
uucacauauu gucagacaau                    20

<210> SEQ ID NO 959
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 959
uuccauagcg augcccagaa                    20

<210> SEQ ID NO 960
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 960
uaaaguucca uagcgaugcc                    20

<210> SEQ ID NO 961
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 961
uuaauuucau ugucauuugc                    20

<210> SEQ ID NO 962
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 962
uuuaauuuca uugucauuug                    20

<210> SEQ ID NO 963
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 963
ugguucgcua ugaaggccuu                    20

<210> SEQ ID NO 964
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 964
ugccuaagag cacauuuagu                                                    20

<210> SEQ ID NO 965
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 965
uuucuuuccu ugucacuccg                                                    20

<210> SEQ ID NO 966
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 966
uauaaaccug gacaagcugc                                                    20

<210> SEQ ID NO 967
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 967
uaguucauaa accuggacaa                                                    20

<210> SEQ ID NO 968
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 968
uacgucaguu cauaaaccug                                                    20

<210> SEQ ID NO 969
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 969
uguaacguca guucauaaac                                                    20

<210> SEQ ID NO 970
```

-continued

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 970
ugauguaacg ucaguucaua                                                    20

<210> SEQ ID NO 971
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 971
uguaugaugu aacgucaguu                                                    20

<210> SEQ ID NO 972
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 972
uguguaugau guaacgucag                                                    20

<210> SEQ ID NO 973
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 973
ugcuccgguc acaacauugu                                                    20

<210> SEQ ID NO 974
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 974
uuaaguucca caauacuccc                                                    20

<210> SEQ ID NO 975
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 975
```
uccuaagagc acuuugccuu                                              20

<210> SEQ ID NO 976
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 976
uacugguugu cgguaccguc                                              20

<210> SEQ ID NO 977
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 977
uauacugguu gucgguaccg                                              20

<210> SEQ ID NO 978
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 978
ucaugaucga uguaguucaa                                              20

<210> SEQ ID NO 979
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 979
uccaugaucg auguaguuca                                              20

<210> SEQ ID NO 980
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 980
uacauuauug agcacucguu                                              20

<210> SEQ ID NO 981
<211> LENGTH: 20
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 981
uuuacuuguu guaacaggac                                                    20

<210> SEQ ID NO 982
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 982
ugacuaaagc aggauuucag                                                    20

<210> SEQ ID NO 983
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 983
uugguucucg acuaaagcag                                                    20

<210> SEQ ID NO 984
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 984
uucauugguu cucgacuaaa                                                    20

<210> SEQ ID NO 985
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 985
uccaucauug guucucgacu                                                    20

<210> SEQ ID NO 986
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 986
uuucaacaau uguugaacac                                                    20
```

```
<210> SEQ ID NO 987
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 987
ugccugcacc auguuccuca                                              20

<210> SEQ ID NO 988
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 988
uugcacgguu cuuugugaca                                              20

<210> SEQ ID NO 989
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 989
uucugcacgg uucuuuguga                                              20

<210> SEQ ID NO 990
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 990
uuaucugcac gguucuuugu                                              20

<210> SEQ ID NO 991
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 991
uuuuauaaca agagguucaa                                              20

<210> SEQ ID NO 992
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 992
uucaauacaa agccaauaaa                                               20

<210> SEQ ID NO 993
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 993
uauuuuagga auuccaauga                                               20

<210> SEQ ID NO 994
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 994
uuggccauga ugccaucaca                                               20

<210> SEQ ID NO 995
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 995
uuucaguuga cugggaaauc                                               20

<210> SEQ ID NO 996
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 996
uaguauguug cugcucacuc                                               20

<210> SEQ ID NO 997
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 997
uucuccggaa cauuccagac                                               20

<210> SEQ ID NO 998
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 998
uggcugugaa uguucacgca                                                    20

<210> SEQ ID NO 999
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 999
uuuaaauuuu aaauccugag                                                    20

<210> SEQ ID NO 1000
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1000
uauaauuaaa uuuuaaaucc                                                    20

<210> SEQ ID NO 1001
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1001
uuuacugaua uaauuaaauu                                                    20

<210> SEQ ID NO 1002
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1002
ugaaagaguu acguuaaaau                                                    20

<210> SEQ ID NO 1003
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1003
uuuacacggg cauagaaaga                                                    20
```

```
<210> SEQ ID NO 1004
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1004
uuacuuuaca cgggcauaga                                              20

<210> SEQ ID NO 1005
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1005
ugcacucucc ugacuaaaag                                              20

<210> SEQ ID NO 1006
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1006
uacauucaau acccaaaaca                                              20

<210> SEQ ID NO 1007
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1007
uuccuccacu uaccacauuc                                              20

<210> SEQ ID NO 1008
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1008
uacauuuccu ccacuuacca                                              20

<210> SEQ ID NO 1009
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 1009
ugcacagagu uccaacauuu                                           20

<210> SEQ ID NO 1010
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1010
uuaagggccu ccucaaacau                                           20

<210> SEQ ID NO 1011
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1011
uucaguagcu ucccuuaagg                                           20

<210> SEQ ID NO 1012
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1012
uuucuuacgu guuauaauuc                                           20

<210> SEQ ID NO 1013
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1013
uuucuuacaa auguaaacau                                           20

<210> SEQ ID NO 1014
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1014
uguguuauuu cuuacaaaug                                           20

<210> SEQ ID NO 1015
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1015
uuuacauuca caguguuauu                                                   20

<210> SEQ ID NO 1016
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1016
uuuacuaaug agcucauauu                                                   20

<210> SEQ ID NO 1017
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1017
uuauguauau gcguggguga                                                   20

<210> SEQ ID NO 1018
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1018
uauuauagau gugucuauau                                                   20

<210> SEQ ID NO 1019
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1019
uuugagaggu guguguguaa                                                   20

<210> SEQ ID NO 1020
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1020
uuuaggaaca ugauaaaguc                                                   20
```

<210> SEQ ID NO 1021
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1021
uuuaaucaca uuugcaacaa                                                   20

<210> SEQ ID NO 1022
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1022
uccaaauuaa ucacauuugc                                                   20

<210> SEQ ID NO 1023
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1023
uaaaacuuga caaccaaauu                                                   20

<210> SEQ ID NO 1024
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1024
uuuaccagca ggaaaacaaa                                                   20

<210> SEQ ID NO 1025
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1025
uauauuacca gcaggaaaac                                                   20

<210> SEQ ID NO 1026
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:

```
          Synthetic oligonucleotide"

<400> SEQUENCE: 1026
uuuaaaaucu uucccgauau                                          20

<210> SEQ ID NO 1027
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1027
uacccugguu ucauuaaaau                                          20

<210> SEQ ID NO 1028
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1028
uuucuacccu gguuucauua                                          20

<210> SEQ ID NO 1029
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1029
ucagugcauu gccaaacaau                                          20

<210> SEQ ID NO 1030
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1030
ucuuagaaac aacugagggg                                          20

<210> SEQ ID NO 1031
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1031
uauacaucuc ucgucagucc                                          20

<210> SEQ ID NO 1032
<211> LENGTH: 20
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1032
uuaaauauac aucucucguc                                              20

<210> SEQ ID NO 1033
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1033
uguuugcagc aguuaaaaaa                                              20

<210> SEQ ID NO 1034
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1034
uacaauguuu gcagcaguua                                              20

<210> SEQ ID NO 1035
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1035
uucaucagcu uuuccagggu                                              20

<210> SEQ ID NO 1036
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1036
uugagggacu cgaaggccuu                                              20

<210> SEQ ID NO 1037
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1037
```
uuucuuuggu cggugcagcg          20

<210> SEQ ID NO 1038
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1038
uuugguagcu gaaaguucuu          20

<210> SEQ ID NO 1039
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1039
uacggucuuu cuugguagcu          20

<210> SEQ ID NO 1040
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1040
uucagacaau gauucacacg          20

<210> SEQ ID NO 1041
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1041
uacauauugu cagacaauga          20

<210> SEQ ID NO 1042
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1042
uauguuuuca cauauuguca          20

<210> SEQ ID NO 1043
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 1043
uccacuaugu uuucacauau                                                 20

<210> SEQ ID NO 1044
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1044
ucugcugcug cugcugcugc                                                 20

<210> SEQ ID NO 1045
<211> LENGTH: 15
<212> TYPE: RNA
<213> ORGANISM: Homo sapiens

<400> SEQUENCE: 1045
gguuuaugaa cugac                                                      15

<210> SEQ ID NO 1046
<211> LENGTH: 15
<212> TYPE: RNA
<213> ORGANISM: Homo sapiens

<400> SEQUENCE: 1046
uaugaacuga cguua                                                      15

<210> SEQ ID NO 1047
<211> LENGTH: 15
<212> TYPE: RNA
<213> ORGANISM: Homo sapiens

<400> SEQUENCE: 1047
augaacugac guuac                                                      15

<210> SEQ ID NO 1048
<211> LENGTH: 15
<212> TYPE: RNA
<213> ORGANISM: Homo sapiens

<400> SEQUENCE: 1048
aauguuguga ccgga                                                      15

<210> SEQ ID NO 1049
<211> LENGTH: 15
<212> TYPE: RNA
<213> ORGANISM: Homo sapiens

<400> SEQUENCE: 1049
uagacgguac cgaca                                                      15

<210> SEQ ID NO 1050
<211> LENGTH: 15
<212> TYPE: RNA
<213> ORGANISM: Homo sapiens

<400> SEQUENCE: 1050
```
caaccaguau uuggg                                                    15

<210> SEQ ID NO 1051
<211> LENGTH: 15
<212> TYPE: RNA
<213> ORGANISM: Homo sapiens

<400> SEQUENCE: 1051
ugcucaauaa uguug                                                    15

<210> SEQ ID NO 1052
<211> LENGTH: 15
<212> TYPE: RNA
<213> ORGANISM: Homo sapiens

<400> SEQUENCE: 1052
uccugcuuua gucga                                                    15

<210> SEQ ID NO 1053
<211> LENGTH: 15
<212> TYPE: RNA
<213> ORGANISM: Homo sapiens

<400> SEQUENCE: 1053
uagucgagaa ccaau                                                    15

<210> SEQ ID NO 1054
<211> LENGTH: 15
<212> TYPE: RNA
<213> ORGANISM: Homo sapiens

<400> SEQUENCE: 1054
aguacuucaa cgcua                                                    15

<210> SEQ ID NO 1055
<211> LENGTH: 15
<212> TYPE: RNA
<213> ORGANISM: Homo sapiens

<400> SEQUENCE: 1055
uucagucucg uugug                                                    15

<210> SEQ ID NO 1056
<211> LENGTH: 15
<212> TYPE: RNA
<213> ORGANISM: Homo sapiens

<400> SEQUENCE: 1056
cuagcuccau gcuua                                                    15

<210> SEQ ID NO 1057
<211> LENGTH: 15
<212> TYPE: RNA
<213> ORGANISM: Homo sapiens

<400> SEQUENCE: 1057
cugcgugaac auuca                                                    15

<210> SEQ ID NO 1058
<211> LENGTH: 15
<212> TYPE: RNA
<213> ORGANISM: Homo sapiens

<400> SEQUENCE: 1058

-continued

```
cagcuaccaa gaaag                                                   15

<210> SEQ ID NO 1059
<211> LENGTH: 15
<212> TYPE: RNA
<213> ORGANISM: Homo sapiens

<400> SEQUENCE: 1059
cugacaauau gugaa                                                   15

<210> SEQ ID NO 1060
<211> LENGTH: 15
<212> TYPE: RNA
<213> ORGANISM: Homo sapiens

<400> SEQUENCE: 1060
ggcaucgcua uggaa                                                   15

<210> SEQ ID NO 1061
<211> LENGTH: 15
<212> TYPE: RNA
<213> ORGANISM: Homo sapiens

<400> SEQUENCE: 1061
cgcuauggaa cuuuu                                                   15

<210> SEQ ID NO 1062
<211> LENGTH: 15
<212> TYPE: RNA
<213> ORGANISM: Homo sapiens

<400> SEQUENCE: 1062
ugacaaugaa auuaa                                                   15

<210> SEQ ID NO 1063
<211> LENGTH: 15
<212> TYPE: RNA
<213> ORGANISM: Homo sapiens

<400> SEQUENCE: 1063
gacaaugaaa uuaag                                                   15

<210> SEQ ID NO 1064
<211> LENGTH: 15
<212> TYPE: RNA
<213> ORGANISM: Homo sapiens

<400> SEQUENCE: 1064
cuucauagcg aaccu                                                   15

<210> SEQ ID NO 1065
<211> LENGTH: 15
<212> TYPE: RNA
<213> ORGANISM: Homo sapiens

<400> SEQUENCE: 1065
augugcucuu aggcu                                                   15

<210> SEQ ID NO 1066
<211> LENGTH: 15
<212> TYPE: RNA
<213> ORGANISM: Homo sapiens
```

<400> SEQUENCE: 1066
ugacaaggaa agaaa                                                        15

<210> SEQ ID NO 1067
<211> LENGTH: 15
<212> TYPE: RNA
<213> ORGANISM: Homo sapiens

<400> SEQUENCE: 1067
uuguccaggu uuaug                                                        15

<210> SEQ ID NO 1068
<211> LENGTH: 15
<212> TYPE: RNA
<213> ORGANISM: Homo sapiens

<400> SEQUENCE: 1068
cagguuuaug aacug                                                        15

<210> SEQ ID NO 1069
<211> LENGTH: 15
<212> TYPE: RNA
<213> ORGANISM: Homo sapiens

<400> SEQUENCE: 1069
uuaugaacug acguu                                                        15

<210> SEQ ID NO 1070
<211> LENGTH: 15
<212> TYPE: RNA
<213> ORGANISM: Homo sapiens

<400> SEQUENCE: 1070
ugaacugacg uuaca                                                        15

<210> SEQ ID NO 1071
<211> LENGTH: 15
<212> TYPE: RNA
<213> ORGANISM: Homo sapiens

<400> SEQUENCE: 1071
acugacguua cauca                                                        15

<210> SEQ ID NO 1072
<211> LENGTH: 15
<212> TYPE: RNA
<213> ORGANISM: Homo sapiens

<400> SEQUENCE: 1072
acguuacauc auaca                                                        15

<210> SEQ ID NO 1073
<211> LENGTH: 15
<212> TYPE: RNA
<213> ORGANISM: Homo sapiens

<400> SEQUENCE: 1073
guuacaucau acaca                                                        15

<210> SEQ ID NO 1074
<211> LENGTH: 15
<212> TYPE: RNA
<213> ORGANISM: Homo sapiens

<400> SEQUENCE: 1074
guugugaccg gagcc                                                    15

<210> SEQ ID NO 1075
<211> LENGTH: 15
<212> TYPE: RNA
<213> ORGANISM: Homo sapiens

<400> SEQUENCE: 1075
uauuguggaa cuuau                                                    15

<210> SEQ ID NO 1076
<211> LENGTH: 15
<212> TYPE: RNA
<213> ORGANISM: Homo sapiens

<400> SEQUENCE: 1076
aaagugcucu uagga                                                    15

<210> SEQ ID NO 1077
<211> LENGTH: 15
<212> TYPE: RNA
<213> ORGANISM: Homo sapiens

<400> SEQUENCE: 1077
uaccgacaac cagua                                                    15

<210> SEQ ID NO 1078
<211> LENGTH: 15
<212> TYPE: RNA
<213> ORGANISM: Homo sapiens

<400> SEQUENCE: 1078
ccgacaacca guauu                                                    15

<210> SEQ ID NO 1079
<211> LENGTH: 15
<212> TYPE: RNA
<213> ORGANISM: Homo sapiens

<400> SEQUENCE: 1079
cuacaucgau caugg                                                    15

<210> SEQ ID NO 1080
<211> LENGTH: 15
<212> TYPE: RNA
<213> ORGANISM: Homo sapiens

<400> SEQUENCE: 1080
uacaucgauc augga                                                    15

<210> SEQ ID NO 1081
<211> LENGTH: 15
<212> TYPE: RNA
<213> ORGANISM: Homo sapiens

<400> SEQUENCE: 1081
gugcucaaua auguu                                                    15

<210> SEQ ID NO 1082
<211> LENGTH: 15
<212> TYPE: RNA

```
<213> ORGANISM: Homo sapiens

<400> SEQUENCE: 1082
guuacaacaa guaaa                                                    15

<210> SEQ ID NO 1083
<211> LENGTH: 15
<212> TYPE: RNA
<213> ORGANISM: Homo sapiens

<400> SEQUENCE: 1083
auccugcuuu agucg                                                    15

<210> SEQ ID NO 1084
<211> LENGTH: 15
<212> TYPE: RNA
<213> ORGANISM: Homo sapiens

<400> SEQUENCE: 1084
uuagucgaga accaa                                                    15

<210> SEQ ID NO 1085
<211> LENGTH: 15
<212> TYPE: RNA
<213> ORGANISM: Homo sapiens

<400> SEQUENCE: 1085
ucgagaacca augau                                                    15

<210> SEQ ID NO 1086
<211> LENGTH: 15
<212> TYPE: RNA
<213> ORGANISM: Homo sapiens

<400> SEQUENCE: 1086
agaaccaaug auggc                                                    15

<210> SEQ ID NO 1087
<211> LENGTH: 15
<212> TYPE: RNA
<213> ORGANISM: Homo sapiens

<400> SEQUENCE: 1087
caacaauugu ugaag                                                    15

<210> SEQ ID NO 1088
<211> LENGTH: 15
<212> TYPE: RNA
<213> ORGANISM: Homo sapiens

<400> SEQUENCE: 1088
aacauggugc aggcg                                                    15

<210> SEQ ID NO 1089
<211> LENGTH: 15
<212> TYPE: RNA
<213> ORGANISM: Homo sapiens

<400> SEQUENCE: 1089
caaagaaccg ugcag                                                    15

<210> SEQ ID NO 1090
<211> LENGTH: 15
```

```
<212> TYPE: RNA
<213> ORGANISM: Homo sapiens

<400> SEQUENCE: 1090
aagaaccgug cagau                                                  15

<210> SEQ ID NO 1091
<211> LENGTH: 15
<212> TYPE: RNA
<213> ORGANISM: Homo sapiens

<400> SEQUENCE: 1091
gaaccgugca gauaa                                                  15

<210> SEQ ID NO 1092
<211> LENGTH: 15
<212> TYPE: RNA
<213> ORGANISM: Homo sapiens

<400> SEQUENCE: 1092
ccucuuguua uaaaa                                                  15

<210> SEQ ID NO 1093
<211> LENGTH: 15
<212> TYPE: RNA
<213> ORGANISM: Homo sapiens

<400> SEQUENCE: 1093
uggcuuugua uugaa                                                  15

<210> SEQ ID NO 1094
<211> LENGTH: 15
<212> TYPE: RNA
<213> ORGANISM: Homo sapiens

<400> SEQUENCE: 1094
ggaauuccua aaauc                                                  15

<210> SEQ ID NO 1095
<211> LENGTH: 15
<212> TYPE: RNA
<213> ORGANISM: Homo sapiens

<400> SEQUENCE: 1095
uggcaucaug gccag                                                  15

<210> SEQ ID NO 1096
<211> LENGTH: 15
<212> TYPE: RNA
<213> ORGANISM: Homo sapiens

<400> SEQUENCE: 1096
cccagucaac ugaag                                                  15

<210> SEQ ID NO 1097
<211> LENGTH: 15
<212> TYPE: RNA
<213> ORGANISM: Homo sapiens

<400> SEQUENCE: 1097
agcagcaaca uacuu                                                  15

<210> SEQ ID NO 1098
```

```
<211> LENGTH: 15
<212> TYPE: RNA
<213> ORGANISM: Homo sapiens

<400> SEQUENCE: 1098
gaauguuccg gagaa                                                    15

<210> SEQ ID NO 1099
<211> LENGTH: 15
<212> TYPE: RNA
<213> ORGANISM: Homo sapiens

<400> SEQUENCE: 1099
gaacauucac agcca                                                    15

<210> SEQ ID NO 1100
<211> LENGTH: 15
<212> TYPE: RNA
<213> ORGANISM: Homo sapiens

<400> SEQUENCE: 1100
gauuuaaaau uuaau                                                    15

<210> SEQ ID NO 1101
<211> LENGTH: 15
<212> TYPE: RNA
<213> ORGANISM: Homo sapiens

<400> SEQUENCE: 1101
uaaaauuuaa uuaua                                                    15

<210> SEQ ID NO 1102
<211> LENGTH: 15
<212> TYPE: RNA
<213> ORGANISM: Homo sapiens

<400> SEQUENCE: 1102
aauuauauca guaaa                                                    15

<210> SEQ ID NO 1103
<211> LENGTH: 15
<212> TYPE: RNA
<213> ORGANISM: Homo sapiens

<400> SEQUENCE: 1103
aacguaacuc uuucu                                                    15

<210> SEQ ID NO 1104
<211> LENGTH: 15
<212> TYPE: RNA
<213> ORGANISM: Homo sapiens

<400> SEQUENCE: 1104
cuaugcccgu guaaa                                                    15

<210> SEQ ID NO 1105
<211> LENGTH: 15
<212> TYPE: RNA
<213> ORGANISM: Homo sapiens

<400> SEQUENCE: 1105
gcccguguaa aguau                                                    15
```

```
<210> SEQ ID NO 1106
<211> LENGTH: 15
<212> TYPE: RNA
<213> ORGANISM: Homo sapiens

<400> SEQUENCE: 1106
agucaggaga gugca                                                    15

<210> SEQ ID NO 1107
<211> LENGTH: 15
<212> TYPE: RNA
<213> ORGANISM: Homo sapiens

<400> SEQUENCE: 1107
uggguauuga augug                                                    15

<210> SEQ ID NO 1108
<211> LENGTH: 15
<212> TYPE: RNA
<213> ORGANISM: Homo sapiens

<400> SEQUENCE: 1108
ugguaagugg aggaa                                                    15

<210> SEQ ID NO 1109
<211> LENGTH: 15
<212> TYPE: RNA
<213> ORGANISM: Homo sapiens

<400> SEQUENCE: 1109
aguggaggaa auguu                                                    15

<210> SEQ ID NO 1110
<211> LENGTH: 15
<212> TYPE: RNA
<213> ORGANISM: Homo sapiens

<400> SEQUENCE: 1110
uuggaacucu gugca                                                    15

<210> SEQ ID NO 1111
<211> LENGTH: 15
<212> TYPE: RNA
<213> ORGANISM: Homo sapiens

<400> SEQUENCE: 1111
ugaggaggcc cuuaa                                                    15

<210> SEQ ID NO 1112
<211> LENGTH: 15
<212> TYPE: RNA
<213> ORGANISM: Homo sapiens

<400> SEQUENCE: 1112
agggaagcua cugaa                                                    15

<210> SEQ ID NO 1113
<211> LENGTH: 15
<212> TYPE: RNA
<213> ORGANISM: Homo sapiens

<400> SEQUENCE: 1113
auaacacgua agaaa                                                    15
```

```
<210> SEQ ID NO 1114
<211> LENGTH: 15
<212> TYPE: RNA
<213> ORGANISM: Homo sapiens

<400> SEQUENCE: 1114
uacauuugua agaaa                                                    15

<210> SEQ ID NO 1115
<211> LENGTH: 15
<212> TYPE: RNA
<213> ORGANISM: Homo sapiens

<400> SEQUENCE: 1115
guaagaaaua acacu                                                    15

<210> SEQ ID NO 1116
<211> LENGTH: 15
<212> TYPE: RNA
<213> ORGANISM: Homo sapiens

<400> SEQUENCE: 1116
cacugugaau guaaa                                                    15

<210> SEQ ID NO 1117
<211> LENGTH: 15
<212> TYPE: RNA
<213> ORGANISM: Homo sapiens

<400> SEQUENCE: 1117
gagcucauua guaaa                                                    15

<210> SEQ ID NO 1118
<211> LENGTH: 15
<212> TYPE: RNA
<213> ORGANISM: Homo sapiens

<400> SEQUENCE: 1118
cacgcauaua cauaa                                                    15

<210> SEQ ID NO 1119
<211> LENGTH: 15
<212> TYPE: RNA
<213> ORGANISM: Homo sapiens

<400> SEQUENCE: 1119
gacacaucua uaauu                                                    15

<210> SEQ ID NO 1120
<211> LENGTH: 15
<212> TYPE: RNA
<213> ORGANISM: Homo sapiens

<400> SEQUENCE: 1120
cacacaccuc ucaag                                                    15

<210> SEQ ID NO 1121
<211> LENGTH: 15
<212> TYPE: RNA
<213> ORGANISM: Homo sapiens

<400> SEQUENCE: 1121
uaucauguuc cuaaa                                                    15
```

```
<210> SEQ ID NO 1122
<211> LENGTH: 15
<212> TYPE: RNA
<213> ORGANISM: Homo sapiens

<400> SEQUENCE: 1122
gcaaauguga uuaau                                                          15

<210> SEQ ID NO 1123
<211> LENGTH: 15
<212> TYPE: RNA
<213> ORGANISM: Homo sapiens

<400> SEQUENCE: 1123
ugugauuaau uuggu                                                          15

<210> SEQ ID NO 1124
<211> LENGTH: 15
<212> TYPE: RNA
<213> ORGANISM: Homo sapiens

<400> SEQUENCE: 1124
gguugucaag uuuug                                                          15

<210> SEQ ID NO 1125
<211> LENGTH: 15
<212> TYPE: RNA
<213> ORGANISM: Homo sapiens

<400> SEQUENCE: 1125
uuuccugcug guaau                                                          15

<210> SEQ ID NO 1126
<211> LENGTH: 15
<212> TYPE: RNA
<213> ORGANISM: Homo sapiens

<400> SEQUENCE: 1126
ccugcuggua auauc                                                          15

<210> SEQ ID NO 1127
<211> LENGTH: 15
<212> TYPE: RNA
<213> ORGANISM: Homo sapiens

<400> SEQUENCE: 1127
gggaaagauu uuaau                                                          15

<210> SEQ ID NO 1128
<211> LENGTH: 15
<212> TYPE: RNA
<213> ORGANISM: Homo sapiens

<400> SEQUENCE: 1128
aaugaaacca gggua                                                          15

<210> SEQ ID NO 1129
<211> LENGTH: 15
<212> TYPE: RNA
<213> ORGANISM: Homo sapiens

<400> SEQUENCE: 1129
```

-continued aaaccagggu agaau                                             15

<210> SEQ ID NO 1130
<211> LENGTH: 15
<212> TYPE: RNA
<213> ORGANISM: Homo sapiens

<400> SEQUENCE: 1130
uuggcaaugc acuga                                             15

<210> SEQ ID NO 1131
<211> LENGTH: 15
<212> TYPE: RNA
<213> ORGANISM: Homo sapiens

<400> SEQUENCE: 1131
caguuguuuc uaaga                                             15

<210> SEQ ID NO 1132
<211> LENGTH: 15
<212> TYPE: RNA
<213> ORGANISM: Homo sapiens

<400> SEQUENCE: 1132
gacgagagau guaua                                             15

<210> SEQ ID NO 1133
<211> LENGTH: 15
<212> TYPE: RNA
<213> ORGANISM: Homo sapiens

<400> SEQUENCE: 1133
gagauguaua uuuaa                                             15

<210> SEQ ID NO 1134
<211> LENGTH: 15
<212> TYPE: RNA
<213> ORGANISM: Homo sapiens

<400> SEQUENCE: 1134
uaacugcugc aaaca                                             15

<210> SEQ ID NO 1135
<211> LENGTH: 15
<212> TYPE: RNA
<213> ORGANISM: Homo sapiens

<400> SEQUENCE: 1135
gcugcaaaca uugua                                             15

<210> SEQ ID NO 1136
<211> LENGTH: 13
<212> TYPE: RNA
<213> ORGANISM: Homo sapiens

<400> SEQUENCE: 1136
acaaauacga uua                                               13

<210> SEQ ID NO 1137
<211> LENGTH: 15
<212> TYPE: RNA
<213> ORGANISM: Homo sapiens

<400> SEQUENCE: 1137

-continued gguuuaugaa cugaa                                    15

<210> SEQ ID NO 1138
<211> LENGTH: 15
<212> TYPE: RNA
<213> ORGANISM: Homo sapiens

<400> SEQUENCE: 1138
uaugaacuga cguua                                    15

<210> SEQ ID NO 1139
<211> LENGTH: 15
<212> TYPE: RNA
<213> ORGANISM: Homo sapiens

<400> SEQUENCE: 1139
augaacugac guuaa                                    15

<210> SEQ ID NO 1140
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1140
aauguuguga ccgga                                    15

<210> SEQ ID NO 1141
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1141
uagacgguac cgaca                                    15

<210> SEQ ID NO 1142
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1142
caaccaguau uugga                                    15

<210> SEQ ID NO 1143
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1143
ugcucaauaa uguua                                    15

```
<210> SEQ ID NO 1144
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1144
uccugcuuua gucga                                                          15

<210> SEQ ID NO 1145
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1145
uagucgagaa ccaaa                                                          15

<210> SEQ ID NO 1146
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1146
aguacuucaa cgcua                                                          15

<210> SEQ ID NO 1147
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1147
uucagucucg uugua                                                          15

<210> SEQ ID NO 1148
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1148
cuagcuccau gcuua                                                          15

<210> SEQ ID NO 1149
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1149
cugcgugaac auuca                                                    15

<210> SEQ ID NO 1150
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1150
cucaggauuu aaaaa                                                    15

<210> SEQ ID NO 1151
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1151
auaucaguaa agaga                                                    15

<210> SEQ ID NO 1152
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1152
caguaaagag auuaa                                                    15

<210> SEQ ID NO 1153
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1153
cagcuaccaa gaaaa                                                    15

<210> SEQ ID NO 1154
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1154
cugacaauau gugaa                                                    15

<210> SEQ ID NO 1155
<211> LENGTH: 15
<212> TYPE: RNA
```

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1155
ggcaucgcua uggaa                                                          15

<210> SEQ ID NO 1156
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1156
cgcuauggaa cuuua                                                          15

<210> SEQ ID NO 1157
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1157
ugacaaugaa auuaa                                                          15

<210> SEQ ID NO 1158
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1158
gacaaugaaa uuaaa                                                          15

<210> SEQ ID NO 1159
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1159
cuucauagcg aacca                                                          15

<210> SEQ ID NO 1160
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1160
augugcucuu aggca                                                          15

```
<210> SEQ ID NO 1161
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1161
ugacaaggaa agaaa                                                          15

<210> SEQ ID NO 1162
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1162
uuguccaggu uuaua                                                          15

<210> SEQ ID NO 1163
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1163
cagguuuaug aacua                                                          15

<210> SEQ ID NO 1164
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1164
uuaugaacug acgua                                                          15

<210> SEQ ID NO 1165
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1165
ugaacugacg uuaca                                                          15

<210> SEQ ID NO 1166
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 1166
acugacguua cauca                                                        15

<210> SEQ ID NO 1167
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1167
acguuacauc auaca                                                        15

<210> SEQ ID NO 1168
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1168
guuacaucau acaca                                                        15

<210> SEQ ID NO 1169
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1169
guugugaccg gagca                                                        15

<210> SEQ ID NO 1170
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1170
uauuguggaa cuuaa                                                        15

<210> SEQ ID NO 1171
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1171
aaagugcucu uagga                                                        15

<210> SEQ ID NO 1172
<211> LENGTH: 15

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1172
uaccgacaac cagua                                                    15

<210> SEQ ID NO 1173
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1173
ccgacaacca guaua                                                    15

<210> SEQ ID NO 1174
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1174
cuacaucgau cauga                                                    15

<210> SEQ ID NO 1175
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1175
uacaucgauc augga                                                    15

<210> SEQ ID NO 1176
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1176
gugcucaaua augua                                                    15

<210> SEQ ID NO 1177
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1177
```

```
guuacaacaa guaaa                                            15

<210> SEQ ID NO 1178
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1178
auccugcuuu aguca                                            15

<210> SEQ ID NO 1179
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1179
uuagucgaga accaa                                            15

<210> SEQ ID NO 1180
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1180
ucgagaacca augaa                                            15

<210> SEQ ID NO 1181
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1181
agaaccaaug augga                                            15

<210> SEQ ID NO 1182
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1182
caacaauugu ugaaa                                            15

<210> SEQ ID NO 1183
<211> LENGTH: 15
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 1183
aacauggugc aggca                                                    15

<210> SEQ ID NO 1184
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1184
caaagaaccg ugcaa                                                    15

<210> SEQ ID NO 1185
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1185
aagaaccgug cagaa                                                    15

<210> SEQ ID NO 1186
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1186
gaaccgugca gauaa                                                    15

<210> SEQ ID NO 1187
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1187
ccucuuguua uaaaa                                                    15

<210> SEQ ID NO 1188
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1188
uggcuuugua uugaa                                                    15

<210> SEQ ID NO 1189
```

```
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1189
ggaauuccua aaaua                                                      15

<210> SEQ ID NO 1190
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1190
uggcaucaug gccaa                                                      15

<210> SEQ ID NO 1191
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1191
cccagucaac ugaaa                                                      15

<210> SEQ ID NO 1192
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1192
agcagcaaca uacua                                                      15

<210> SEQ ID NO 1193
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1193
gaauguuccg gagaa                                                      15

<210> SEQ ID NO 1194
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1194
```

```
gaacauucac agcca                                              15
```

<210> SEQ ID NO 1195
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1195

```
gauuuaaaau uuaaa                                              15
```

<210> SEQ ID NO 1196
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1196

```
uaaaauuaa uuaua                                               15
```

<210> SEQ ID NO 1197
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1197

```
aauuauauca guaaa                                              15
```

<210> SEQ ID NO 1198
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1198

```
aacguaacuc uuuca                                              15
```

<210> SEQ ID NO 1199
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1199

```
cuaugcccgu guaaa                                              15
```

<210> SEQ ID NO 1200
<211> LENGTH: 15
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 1200
gcccguguaa aguaa                                                        15

<210> SEQ ID NO 1201
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1201
agucaggaga gugca                                                        15

<210> SEQ ID NO 1202
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1202
uggguauuga augua                                                        15

<210> SEQ ID NO 1203
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1203
ugguaagugg aggaa                                                        15

<210> SEQ ID NO 1204
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1204
aguggaggaa augua                                                        15

<210> SEQ ID NO 1205
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1205
uuggaacucu gugca                                                        15
```

```
<210> SEQ ID NO 1206
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1206
ugaggaggcc cuuaa                                                        15

<210> SEQ ID NO 1207
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1207
agggaagcua cugaa                                                        15

<210> SEQ ID NO 1208
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1208
auaacacgua agaaa                                                        15

<210> SEQ ID NO 1209
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1209
uacauuugua agaaa                                                        15

<210> SEQ ID NO 1210
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1210
guaagaaaua acaca                                                        15

<210> SEQ ID NO 1211
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 1211
cacugugaau guaaa                                                     15

<210> SEQ ID NO 1212
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1212
gagcucauua guaaa                                                     15

<210> SEQ ID NO 1213
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1213
cacgcauaua cauaa                                                     15

<210> SEQ ID NO 1214
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1214
gacacaucua uaaua                                                     15

<210> SEQ ID NO 1215
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1215
cacacaccuc ucaaa                                                     15

<210> SEQ ID NO 1216
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1216
uaucauguuc cuaaa                                                     15

<210> SEQ ID NO 1217
<211> LENGTH: 15
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 1217 gcaauguga uuaaa                                                          15

<210> SEQ ID NO 1218
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1218
ugugauuaau uugga                                                         15

<210> SEQ ID NO 1219
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1219
gguugucaag uuuua                                                         15

<210> SEQ ID NO 1220
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1220
uuuccugcug guaaa                                                         15

<210> SEQ ID NO 1221
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1221
ccugcuggua auaua                                                         15

<210> SEQ ID NO 1222
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1222
gggaaagauu uuaaa                                                         15
```

<210> SEQ ID NO 1223
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1223
aaugaaacca gggua                                                        15

<210> SEQ ID NO 1224
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1224
aaaccagggu agaaa                                                        15

<210> SEQ ID NO 1225
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1225
uuggcaaugc acuga                                                        15

<210> SEQ ID NO 1226
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1226
caguuguuuc uaaga                                                        15

<210> SEQ ID NO 1227
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1227
gacgagagau guaua                                                        15

<210> SEQ ID NO 1228
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<400> SEQUENCE: 1228
gagauguaua uuuaa                                                    15

<210> SEQ ID NO 1229
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1229
uaacugcugc aaaca                                                    15

<210> SEQ ID NO 1230
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1230
gcugcaaaca uugua                                                    15

<210> SEQ ID NO 1231
<211> LENGTH: 13
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1231
acaaauacga uua                                                      13

<210> SEQ ID NO 1232
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1232
uucaguucau aaaccuggac                                               20

<210> SEQ ID NO 1233
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1233
uaacgucagu ucauaaaccu                                               20

<210> SEQ ID NO 1234
<211> LENGTH: 20
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1234
uuaacgucag uucauaaacc                                                    20

<210> SEQ ID NO 1235
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1235
uccggucaca acauuguggu                                                    20

<210> SEQ ID NO 1236
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1236
ugucgguacc gucuaacaca                                                    20

<210> SEQ ID NO 1237
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1237
uccaaauacu gguugucggu                                                    20

<210> SEQ ID NO 1238
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1238
uaacauuauu gagcacucgu                                                    20

<210> SEQ ID NO 1239
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1239
ucgacuaaag caggauuuca                                                    20
```

```
<210> SEQ ID NO 1240
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1240
uuugguucuc gacuaaagca                                                20

<210> SEQ ID NO 1241
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1241
uagcguugaa guacuguccc                                                20

<210> SEQ ID NO 1242
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1242
uacaacgaga cugaauugcc                                                20

<210> SEQ ID NO 1243
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1243
uaagcaugga gcuagcaggc                                                20

<210> SEQ ID NO 1244
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1244
ugaauguuca cgcagugggc                                                20

<210> SEQ ID NO 1245
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 1245
uuuuuaaauc cugagaagaa                                           20

<210> SEQ ID NO 1246
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1246
ucucuuuacu gauauaauua                                           20

<210> SEQ ID NO 1247
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1247
uuaaucucuu uacugauaua                                           20

<210> SEQ ID NO 1248
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1248
uuuucuuggu agcugaaagu                                           20

<210> SEQ ID NO 1249
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1249
uucacauauu gucagacaau                                           20

<210> SEQ ID NO 1250
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1250
uuccauagcg augcccagaa                                           20

<210> SEQ ID NO 1251
<211> LENGTH: 20

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1251
uaaaguucca uagcgaugcc                                              20

<210> SEQ ID NO 1252
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1252
uuaauuucau ugucauuugc                                              20

<210> SEQ ID NO 1253
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1253
uuuaauuuca uugucauuug                                              20

<210> SEQ ID NO 1254
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1254
ugguucgcua ugaaggccuu                                              20

<210> SEQ ID NO 1255
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1255
ugccuaagag cacauuuagu                                              20

<210> SEQ ID NO 1256
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1256
```

```
uuucuuuccu ugucacuccg                                            20
```

<210> SEQ ID NO 1257
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1257

```
uauaaaccug gacaagcugc                                            20
```

<210> SEQ ID NO 1258
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1258

```
uaguucauaa accuggacaa                                            20
```

<210> SEQ ID NO 1259
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1259

```
uacgucaguu cauaaaccug                                            20
```

<210> SEQ ID NO 1260
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1260

```
uguaacguca guucauaaac                                            20
```

<210> SEQ ID NO 1261
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1261

```
ugauguaacg ucaguucaua                                            20
```

<210> SEQ ID NO 1262
<211> LENGTH: 20
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 1262
uguaugaugu aacgucaguu                                                 20

<210> SEQ ID NO 1263
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1263
uguguaugau guaacgucag                                                 20

<210> SEQ ID NO 1264
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1264
ugcuccgguc acaacauugu                                                 20

<210> SEQ ID NO 1265
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1265
uuaaguucca caauacuccc                                                 20

<210> SEQ ID NO 1266
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1266
uccuaagagc acuuugccuu                                                 20

<210> SEQ ID NO 1267
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1267
uacugguugu cgguaccguc                                                 20

<210> SEQ ID NO 1268
```

```
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1268
uauacugguu gucgguaccg                                                     20

<210> SEQ ID NO 1269
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1269
ucaugaucga uguaguucaa                                                     20

<210> SEQ ID NO 1270
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1270
uccaugaucg auguaguuca                                                     20

<210> SEQ ID NO 1271
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1271
uacauuauug agcacucguu                                                     20

<210> SEQ ID NO 1272
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1272
uuuacuuguu guaacaggac                                                     20

<210> SEQ ID NO 1273
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1273
```
ugacuaaagc aggauuucag                                              20

<210> SEQ ID NO 1274
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1274
uugguucucg acuaaagcag                                              20

<210> SEQ ID NO 1275
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1275
uucauugguu cucgacuaaa                                              20

<210> SEQ ID NO 1276
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1276
uccaucauug guucucgacu                                              20

<210> SEQ ID NO 1277
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1277
uuucaacaau uguugaacac                                              20

<210> SEQ ID NO 1278
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1278
ugccugcacc auguuccuca                                              20

<210> SEQ ID NO 1279
<211> LENGTH: 20
<212> TYPE: RNA
<213> ORGANISM: Artificial Sequence
<220> FEATURE:

-continued

```
<221> NAME/KEY: source
<223> OTHER INFORMATION: /note="Description of Artificial Sequence:
      Synthetic oligonucleotide"

<400> SEQUENCE: 1279
uugcacgguu cuuugugaca                                               20

<210> SEQ ID NO 1280
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1280
uucugcacgg uucuuuguga                                               20

<210> SEQ ID NO 1281
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1281
uuaucugcac gguucuuugu                                               20

<210> SEQ ID NO 1282
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1282
uuuuauaaca agagguucaa                                               20

<210> SEQ ID NO 1283
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1283
uucaauacaa agccaauaaa                                               20

<210> SEQ ID NO 1284
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1284
uauuuuagga auuccaauga                                               20
```

```
<210> SEQ ID NO 1285
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1285
uuggccauga ugccaucaca                                              20

<210> SEQ ID NO 1286
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1286
uuucaguuga cugggaaauc                                              20

<210> SEQ ID NO 1287
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1287
uaguauguug cugcucacuc                                              20

<210> SEQ ID NO 1288
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1288
uucuccggaa cauuccagac                                              20

<210> SEQ ID NO 1289
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1289
uggcugugaa uguucacgca                                              20

<210> SEQ ID NO 1290
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1290
uuuaaauuuu aaauccugag                                              20

<210> SEQ ID NO 1291
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1291
uauaauuaaa uuuuaaaucc                                              20

<210> SEQ ID NO 1292
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1292
uuuacugaua uaauuaaauu                                              20

<210> SEQ ID NO 1293
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1293
ugaaagaguu acguuaaaau                                              20

<210> SEQ ID NO 1294
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1294
uuuacacggg cauagaaaga                                              20

<210> SEQ ID NO 1295
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1295
uuacuuuaca cgggcauaga                                              20

<210> SEQ ID NO 1296
<211> LENGTH: 20
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 1296
ugcacucucc ugacuaaaag                                             20

<210> SEQ ID NO 1297
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1297
uacauucaau acccaaaaca                                             20

<210> SEQ ID NO 1298
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1298
uuccuccacu uaccacauuc                                             20

<210> SEQ ID NO 1299
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1299
uacauuuccu ccacuuacca                                             20

<210> SEQ ID NO 1300
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1300
ugcacagagu uccaacauuu                                             20

<210> SEQ ID NO 1301
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1301
uuaagggccu ccucaaacau                                             20
```

<210> SEQ ID NO 1302
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1302
uucaguagcu ucccuuaagg                                              20

<210> SEQ ID NO 1303
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1303
uuucuuacgu guuauaauuc                                              20

<210> SEQ ID NO 1304
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1304
uuucuuacaa auguaaacau                                              20

<210> SEQ ID NO 1305
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1305
uguguuauuu cuuacaaaug                                              20

<210> SEQ ID NO 1306
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1306
uuuacauuca caguguuauu                                              20

<210> SEQ ID NO 1307
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1307
uuuacuaaug agcucauauu                                          20

<210> SEQ ID NO 1308
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1308
uuauguauau gcguggguga                                          20

<210> SEQ ID NO 1309
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1309
uauuauagau gugucuauau                                          20

<210> SEQ ID NO 1310
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1310
uuugagaggu gugugeguaa                                          20

<210> SEQ ID NO 1311
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1311
uuuaggaaca ugauaaaguc                                          20

<210> SEQ ID NO 1312
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1312
uuuaaucaca uuugcaacaa                                          20

<210> SEQ ID NO 1313
<211> LENGTH: 20
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1313
uccaaauuaa ucacauuugc                                              20

<210> SEQ ID NO 1314
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1314
uaaaacuuga caaccaaauu                                              20

<210> SEQ ID NO 1315
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1315
uuuaccagca ggaaaacaaa                                              20

<210> SEQ ID NO 1316
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1316
uauauuacca gcaggaaaac                                              20

<210> SEQ ID NO 1317
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1317
uuuaaaaucu uucccgauau                                              20

<210> SEQ ID NO 1318
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1318
uacccugguu ucauuaaaau                                              20
```

```
<210> SEQ ID NO 1319
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1319
uuucuacccu gguuucauua                                              20

<210> SEQ ID NO 1320
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1320
ucagugcauu gccaaacaau                                              20

<210> SEQ ID NO 1321
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1321
ucuuagaaac aacugagggg                                              20

<210> SEQ ID NO 1322
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1322
uauacaucuc ucgucagucc                                              20

<210> SEQ ID NO 1323
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1323
uuaaauauac aucucucguc                                              20

<210> SEQ ID NO 1324
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 1324
uguuugcagc aguuaaaaaa                                          20

<210> SEQ ID NO 1325
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1325
uacaauguuu gcagcaguua                                          20

<210> SEQ ID NO 1326
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1326
uaaucguauu ugucaauca                                           19

<210> SEQ ID NO 1327
<211> LENGTH: 20
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1327
uuaaucucuu uacugauaua                                          20

<210> SEQ ID NO 1328
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1328
caguaaagag auuaa                                               15

<210> SEQ ID NO 1329
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 1329

Cys His Arg Arg His Arg Arg Arg Ile Trp Ser Ile Leu Ala Pro Leu
1               5                   10                  15

Gly Thr Thr Leu Val
            20
```